United States Patent
Hung et al.

(10) Patent No.: US 12,006,314 B2
(45) Date of Patent: Jun. 11, 2024

(54) ANTI-CANCER NUCLEAR HORMONE RECEPTOR-TARGETING COMPOUNDS

(71) Applicant: Nuvation Bio Inc., New York, NY (US)

(72) Inventors: David Hung, New York, NY (US); Jayakanth Kankanala, Saint Paul, MN (US); Christopher Paul Miller, San Mateo, CA (US); Jeremy David Pettigrew, Vancouver (CA); Son Minh Pham, San Francisco, CA (US); Ihab S. Darwish, San Carlos, CA (US)

(73) Assignee: NUVATION BIO INC., New York, NY (US)

( * ) Notice: Subject to any disclaimer, the term of this patent is extended or adjusted under 35 U.S.C. 154(b) by 0 days.

(21) Appl. No.: 17/735,011

(22) Filed: May 2, 2022

(65) Prior Publication Data

US 2022/0380364 A1    Dec. 1, 2022

Related U.S. Application Data

(60) Provisional application No. 63/183,569, filed on May 3, 2021.

(51) Int. Cl.
| | |
|---|---|
| *C07D 471/04* | (2006.01) |
| *C07D 403/10* | (2006.01) |
| *C07D 403/14* | (2006.01) |
| *C07D 413/14* | (2006.01) |
| *C07D 417/14* | (2006.01) |

(52) U.S. Cl.
CPC ......... *C07D 471/04* (2013.01); *C07D 403/10* (2013.01); *C07D 403/14* (2013.01); *C07D 413/14* (2013.01); *C07D 417/14* (2013.01)

(58) Field of Classification Search
CPC .. C07D 471/04; C07D 403/10; C07D 403/14; C07D 413/14; C07D 417/14; A61K 45/06; A61K 47/545; A61K 47/55; A61P 35/00
See application file for complete search history.

(56) References Cited

U.S. PATENT DOCUMENTS

| | | | |
|---|---|---|---|
| 6,074,625 A | 6/2000 | Hawthorne et al. | |
| 6,462,038 B1 | 10/2002 | Higuchi et al. | |
| 6,777,427 B2 | 8/2004 | Miyakawa et al. | |
| 7,037,919 B1 | 5/2006 | Hanada et al. | |
| 7,038,041 B2 | 5/2006 | Ray et al. | |
| 7,220,730 B2 | 5/2007 | Baranowska-Kortylewicz et al. | |
| 7,449,464 B2 | 11/2008 | Martin et al. | |
| 7,981,889 B2 | 7/2011 | Martin et al. | |
| 8,012,976 B2 | 9/2011 | Wang et al. | |
| 8,129,380 B2 | 3/2012 | Menear et al. | |
| 8,252,802 B2 | 8/2012 | Foote et al. | |
| 8,629,167 B2 | 1/2014 | Miller | |
| 8,785,501 B2 | 7/2014 | Witt-Enderby et al. | |
| 8,871,765 B2 | 10/2014 | Shrivastava | |
| 9,056,140 B2 | 6/2015 | Stoloff et al. | |
| 9,963,433 B2 | 5/2018 | Qin | |
| 10,300,143 B2 | 5/2019 | Sengupta et al. | |
| 10,723,717 B2 | 7/2020 | Crew et al. | |
| 10,730,870 B2 | 8/2020 | Crew et al. | |
| 11,034,669 B2 | 6/2021 | Chakravarty et al. | |
| 11,292,782 B2 | 4/2022 | Chakravarty et al. | |
| 2003/0059465 A1 | 3/2003 | Unger et al. | |
| 2005/0069495 A1 | 3/2005 | Baranowska-Kortylewicz et al. | |
| 2005/0096381 A1 | 5/2005 | Kohn et al. | |
| 2005/0227919 A1 | 10/2005 | Ashworth et al. | |
| 2005/0245485 A1 | 11/2005 | Lanter et al. | |
| 2005/0250741 A1 | 11/2005 | Lanter et al. | |
| 2005/0277660 A1 | 12/2005 | Miyakawa | |
| 2005/0277681 A1 | 12/2005 | Hanney et al. | |
| 2006/0063819 A1 | 3/2006 | Lanter et al. | |

(Continued)

FOREIGN PATENT DOCUMENTS

| | | |
|---|---|---|
| CN | 101948500 A | 1/2011 |
| CN | 101967172 A | 2/2011 |

(Continued)

OTHER PUBLICATIONS

Kronenberger, T., Keminer, O., Wrenger, C., & Windshügel, B. (Jun. 3, 2015). Nuclear Receptor Modulators—Current Approaches and Future Perspectives. (Year: 2015).*

(Continued)

*Primary Examiner* — Matthew P Coughlin
*Assistant Examiner* — David M Shim
(74) *Attorney, Agent, or Firm* — Morrison & Foerster LLP

(57) ABSTRACT

The disclosure relates to anti-cancer compounds derived from nuclear steroid receptor binders, such as a compound of Formula I:

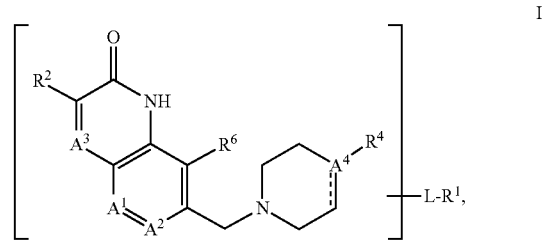

or a tautomer, stereoisomer, mixture of stereoisomers, hydrate, solvate, isotopically enriched analog, or pharmaceutically acceptable salt thereof, to products containing the same, as well as to methods of their use and preparation.

17 Claims, No Drawings

(56) References Cited

U.S. PATENT DOCUMENTS

| | | |
|---|---|---|
| 2006/0128737 A1 | 6/2006 | Miyakawa et al. |
| 2006/0142387 A1 | 6/2006 | Cadilla et al. |
| 2006/0148893 A1 | 7/2006 | Blanc et al. |
| 2006/0160845 A1 | 7/2006 | Schlienger et al. |
| 2006/0211756 A1 | 9/2006 | Zhang et al. |
| 2008/0200469 A1 | 8/2008 | Martin et al. |
| 2009/0257999 A1 | 10/2009 | Fink |
| 2010/0003192 A1 | 1/2010 | Sherman et al. |
| 2011/0028420 A1 | 2/2011 | Boulares et al. |
| 2011/0053923 A1 | 3/2011 | Foote et al. |
| 2011/0104074 A1 | 5/2011 | Kakar |
| 2011/0305631 A1 | 12/2011 | Govindan et al. |
| 2012/0046461 A1 | 2/2012 | Hanson |
| 2013/0156698 A1 | 6/2013 | Zhou et al. |
| 2013/0309170 A1 | 11/2013 | Reiner et al. |
| 2014/0080905 A1 | 3/2014 | Dalton et al. |
| 2015/0110742 A1 | 4/2015 | Spiegel et al. |
| 2015/0284416 A1 | 10/2015 | Zhao |
| 2015/0322155 A1 | 11/2015 | Zhao |
| 2016/0058872 A1 | 3/2016 | Crew et al. |
| 2016/0176916 A1 | 6/2016 | Bradner et al. |
| 2016/0214972 A1 | 7/2016 | Jin et al. |
| 2017/0008904 A1 | 1/2017 | Crew et al. |
| 2017/0217903 A1 | 8/2017 | Qin et al. |
| 2017/0233365 A1 | 8/2017 | Hilderbrand et al. |
| 2017/0319543 A1 | 11/2017 | Ashworth et al. |
| 2017/0327469 A1 | 11/2017 | Crew et al. |
| 2018/0052180 A1 | 2/2018 | Jose et al. |
| 2018/0099940 A1 | 4/2018 | Crew et al. |
| 2018/0215731 A1 * | 8/2018 | Crew .................. C07D 401/14 |
| 2018/0228907 A1 | 8/2018 | Crew et al. |
| 2018/0346461 A1 | 12/2018 | Crew et al. |
| 2019/0111010 A1 | 4/2019 | Narayanan et al. |
| 2019/0365904 A1 | 12/2019 | Low et al. |
| 2019/0375732 A1 | 12/2019 | Hung et al. |
| 2020/0055825 A1 | 2/2020 | Crew et al. |
| 2020/0155689 A1 | 5/2020 | Crew et al. |
| 2020/0155690 A1 | 5/2020 | Crew et al. |
| 2020/0172480 A1 | 6/2020 | Zhao et al. |
| 2020/0199098 A1 | 6/2020 | Chakravarty et al. |
| 2020/0239433 A1 | 7/2020 | Chakravarty et al. |
| 2020/0281955 A1 | 9/2020 | Xu et al. |
| 2020/0297725 A1 | 9/2020 | Crews et al. |
| 2020/0360523 A1 | 11/2020 | Hung et al. |
| 2020/0392131 A1 | 12/2020 | Crew et al. |
| 2021/0214316 A1 | 7/2021 | Pham et al. |
| 2022/0340587 A1 | 10/2022 | Hung et al. |
| 2023/0122310 A1 | 4/2023 | Hung et al. |

FOREIGN PATENT DOCUMENTS

| | | | |
|---|---|---|---|
| CN | 101967173 A | 2/2011 | |
| CN | 102492009 A | 6/2012 | |
| CN | 102492010 A | 6/2012 | |
| CN | 102516347 A | 6/2012 | |
| CN | 102532237 A | 7/2012 | |
| CN | 104292290 A | 1/2015 | |
| CN | 105315294 A | 2/2016 | |
| CN | 107266520 A | 10/2017 | |
| CN | 107286166 A | 10/2017 | |
| CN | WO 2022/228387 A1 * | 11/2022 | ........... C07D 471/04 |
| EP | 0699754 A1 | 3/1996 | |
| EP | 0705903 A1 | 4/1996 | |
| JP | 5934986 B2 | 3/2013 | |
| JP | 5934986 B2 | 6/2016 | |
| WO | WO 1990010638 A1 | 9/1990 | |
| WO | WO 1996000090 A1 | 1/1996 | |
| WO | 199613613 A1 | 5/1996 | |
| WO | 200127086 A1 | 4/2001 | |
| WO | WO 2003079965 A2 | 2/2003 | |
| WO | 2003034987 A2 | 5/2003 | |
| WO | 2003101995 A2 | 12/2003 | |
| WO | 2004000816 A1 | 12/2003 | |
| WO | 2004013104 A1 | 2/2004 | |
| WO | 2004035736 A2 | 4/2004 | |
| WO | 2004041277 A1 | 5/2004 | |
| WO | WO 2004080976 A1 | 9/2004 | |
| WO | 2004093807 A2 | 11/2004 | |
| WO | 2004113309 A1 | 12/2004 | |
| WO | 2005000795 A2 | 1/2005 | |
| WO | WO 2005034856 A2 | 5/2005 | |
| WO | 2005085185 A1 | 9/2005 | |
| WO | WO 2005086974 A2 | 9/2005 | |
| WO | 2005108351 A1 | 11/2005 | |
| WO | 2005115361 A2 | 12/2005 | |
| WO | 2005118612 A1 | 12/2005 | |
| WO | 2006044707 A1 | 4/2006 | |
| WO | 2006060108 A1 | 6/2006 | |
| WO | 2006124447 A2 | 11/2006 | |
| WO | 2006133216 A2 | 12/2006 | |
| WO | 2007002181 A2 | 1/2007 | |
| WO | WO 2007035927 A2 | 3/2007 | |
| WO | WO 2008090379 A1 | 7/2008 | |
| WO | WO 2009005839 A2 | 1/2009 | |
| WO | WO 2009029375 A1 | 3/2009 | |
| WO | 2009114459 A2 | 9/2009 | |
| WO | WO 2009155431 A1 | 12/2009 | |
| WO | WO 2010085747 A1 | 7/2010 | |
| WO | WO 2010108251 A2 | 9/2010 | |
| WO | 2011079245 A1 | 6/2011 | |
| WO | 2011130697 A2 | 10/2011 | |
| WO | WO 2012014221 A1 | 2/2012 | |
| WO | WO 2012050868 A1 | 4/2012 | |
| WO | WO 2012074840 A2 | 6/2012 | |
| WO | 2012123820 A1 | 9/2012 | |
| WO | 2012134446 A1 | 10/2012 | |
| WO | WO 2013028495 A1 | 2/2013 | |
| WO | 2013106643 A2 | 7/2013 | |
| WO | 2013170147 A1 | 11/2013 | |
| WO | 2014080251 A1 | 5/2014 | |
| WO | WO 2014108452 A1 | 7/2014 | |
| WO | 2014191726 A1 | 12/2014 | |
| WO | 2014201026 A2 | 12/2014 | |
| WO | 2015038649 A1 | 3/2015 | |
| WO | WO 2015095755 A1 | 6/2015 | |
| WO | 2015134464 A2 | 9/2015 | |
| WO | 2015143004 A1 | 9/2015 | |
| WO | 2015151078 A2 | 10/2015 | |
| WO | 2015151080 A2 | 10/2015 | |
| WO | 2015151081 A2 | 10/2015 | |
| WO | 2015155753 A2 | 10/2015 | |
| WO | 2016059622 A2 | 4/2016 | |
| WO | 2016077505 A2 | 5/2016 | |
| WO | 2016097072 A1 | 6/2016 | |
| WO | 2016118666 A1 | 7/2016 | |
| WO | 2016149668 A1 | 9/2016 | |
| WO | 2016196337 A1 | 12/2016 | |
| WO | 2016197032 A1 | 12/2016 | |
| WO | 2016197114 A1 | 12/2016 | |
| WO | 2017011590 A1 | 1/2017 | |
| WO | 2017059139 A1 | 4/2017 | |
| WO | 2017075495 A1 | 5/2017 | |
| WO | 2017170564 A1 | 10/2017 | |
| WO | 2017199042 A1 | 11/2017 | |
| WO | WO 2017214491 A1 | 12/2017 | |
| WO | 2018019793 A1 | 2/2018 | |
| WO | 2018038680 A1 | 3/2018 | |
| WO | 2018071606 A1 | 4/2018 | |
| WO | WO 2018111990 A1 | 6/2018 | |
| WO | 2018156815 A1 | 8/2018 | |
| WO | WO 2018185526 A1 | 10/2018 | |
| WO | 2018234636 A1 | 12/2018 | |
| WO | WO 2019023553 A1 | 1/2019 | |
| WO | WO 2019100973 A1 | 5/2019 | |
| WO | 2019123367 A1 | 6/2019 | |
| WO | 2019199634 A1 | 10/2019 | |
| WO | 2019199816 A1 | 10/2019 | |
| WO | WO 2019222272 A1 * | 11/2019 | ............. A61K 45/06 |
| WO | WO 2019222272 A1 | 11/2019 | |
| WO | WO 2019241231 A1 | 12/2019 | |
| WO | 2020023851 A1 | 1/2020 | |
| WO | WO 2020113088 A1 | 6/2020 | |
| WO | WO 2020113094 A1 | 6/2020 | |
| WO | WO 2020232119 A1 | 11/2020 | |

(56) References Cited

FOREIGN PATENT DOCUMENTS

| | | | |
|---|---|---|---|
| WO | 2020257998 A1 | 12/2020 | |
| WO | 2021013735 A1 | 1/2021 | |
| WO | WO 2021/013735 A1 * | 1/2021 | ............ C07D 471/04 |
| WO | 2021055705 A1 | 3/2021 | |
| WO | WO 2021097046 A1 | 5/2021 | |
| WO | 2021127443 A1 | 6/2021 | |
| WO | 2021212638 A1 | 10/2021 | |
| WO | 2022035818 A2 | 2/2022 | |
| WO | 2022040635 A1 | 2/2022 | |
| WO | 2022087125 A1 | 4/2022 | |
| WO | 2022098544 A1 | 5/2022 | |
| WO | 2022204184 A1 | 9/2022 | |
| WO | 2022235585 A1 | 11/2022 | |

OTHER PUBLICATIONS

Berge, S.M. et al. (Jan. 1977). "Pharmaceuticals Salts," J. Pharmaceutical Sciences 66(1):1-19.
Chekler, E.L.P. (Mar. 27, 2014, e-pub. Feb. 17, 2014). "1-(2-Hydroxy-2-methyl-3-phenoxypropanoyl) indoline-4-carbonitrile Derivatives as Potent and Tissue Selective Androgen Receptor Modulators," J. Med. Chem. 57(6):2462-2471.
Gillmore, A.T. et al. (Nov. 14, 2012). "Multkilogram Scale-Up of a Reductive Alkylation Route to a Novel PARP Inhibitor," Org. Process Res. Dev. 16(12):1897-1904.
Guo, C. et al. (Sep. 21, 2011). "Discovery of Aryloxy Tetramethylcyclobutanes as Novel Androgen Receptor Antagonists," J. Medicinal Chemistry 54:7693-7704.
Hughes-Davies, L. et al. (Nov. 26, 2003). "EMSY Links the BRCA2 Pathway to Sporadic Breast and Ovarian Cancer," Cell 115:523-535.
Huxley, M. et al. (2010). "An Androgenic Steroid Delivery Vector That Imparts Activity to a Non-Conventional Platinum(II) Metallo-Drug," Dalton Trans. 39:11353-11364.
International Preliminary Report on Patentability, dated May 17, 2022, for PCT Application No. PCT/US2020/060165, filed Nov. 12, 2020, 9 pages.
International Search Report and Written Opinion, dated May 11, 2022, regarding Application No. PCT/US2022/021390 filed Mar. 22, 2022, 12 pages.
International Search Report and Written Opinion, dated Aug. 22, 2022, PCT Application No. PCT/US2022/027334, filed May 2, 2022, 14 pages.
Jadhavar, P.S. et al. (Nov. 1, 2016, e-pub. Oct. 4, 2016). "Targeting Prostate Cancer with Compounds Possessing Dual Activity as Androgen Receptor Antagonists and HDAC6 Inhibitors," Bioorg. Med. Chem. Letter 26:5222-5228.
Janatová, M. et al. (2003). "Detection of the Most Frequent Mutations in BRCA1 Gene on Polyacrylamide Gels Containing Spreadex Polymer NAB," Neoplasma 50(4):246-250.
Jasin, M. (2002). "Homologous Repair of DNA Damage and Tumorigenesis:The BRCA Connection," Oncogene 21 (58):8981-8993.
Khanna, K.K. et al. (Mar. 2001). "DNA Double-Strand Breaks: Signaling, Repair and The Cancer Connection," Nat. Genet. 27(3):247-254.
Koseki, Y. et al. (2019). "Influence of Hydrolysis Susceptibility and Hydrophobicity of SN-38 Nano-Prodrugs on Their Anticancer Activity," Bulletin of the Chemical Society of Japan 92(8):1305-1313.
Li, X. et al. (Mar. 24, 2014). "Synthesis and Biological Activity of Some Bile Acid-Based Camptothecin Analogues," Molecules 19(3):3761-3776.
Menear, K.A. et al. (Oct. 23, 2008, e-pub. Sep. 19, 2008). "4-[3-(4-Cyclopropanecarbonylpiperazine-1-Carbonyl)-4-Fluorobenzyl]-2H-Phthalazin-1-One: A Novel Bioavailable Inhibitor of Poly(ADP-Ribose) Polymerase-1," J. Med. Chem. 51(20):6581-6591.
Mortensen, D.S. et al. (Jul. 23, 2015, e-pub. Jun. 23, 2015). "Optimization of a Series of Triazole Containing Mammalian Target of Rapamycin (mTOR) Kinase Inhibitors and the Discovery of CC-115," J. Med. Chem. 58(14):5599-5608.
Murai, J. et al. (Nov. 1, 2012, e-pub. Nov. 1, 2013). "Differential Trapping of PARP1 and PARP2 by Clinical PARP Inhibitors," Cancer Research 72(21):5588-5599, 22 pages.
Neuhausen, S.L. et al. (1992). "Mutation Testing of Early-Onset Breast Cancer Genes BRCA1 and BRCA2," Genet. Test 1(2):75-83.
Radice, P. (Sep. 2002). "Mutations of BRCA Genes in Hereditary Breast and Ovarian Cancer," J. Exp. Clin. Cancer Res. 21(Suppl. 3):9-12.
Ragozin, E. et al. (2016, e-pub. Dec. 11, 2015). "Biolabile Peptidyl Delivery Systems Toward Sequential Drug Release," Biopolymers 106(1):119-132.
Shen et al. (2013). "Synthesis and Anti-tumor Activity of Novel Steroidal Conjugates of Campothecin," Chinese Journal of New Drugs 22(5):585-589. English Abstract.
Tutt, A. et al. (Dec. 2002). "The Relationship Between The Roles of BRCA Genes in DNA Repair and Cancer Predisposition," Trends Mol. Med. 8(12):571-576.
Wood, R.D. et al. (Feb. 16, 2001). "Human DNA Repair Genes," Science 291:1284-1289.
Ahmed et al., "Synthesis, characterization, and estrogen receptor binding affinity of flavone-, indole-, and furan-estradiol conjugates," Bioorganic & Medicinal Chemistry Letters, 2007, vol. 17, pp. 3212-3216.
Beretta et al., "Androgen Receptor-Directed Molecular Conjugates for Targeting Prostate Cancer," Frontiers in Chemistry, 2019, vol. 7, Article 369, pp. 1-8.
Bertrand et al., "A Gold(III) Pincer Ligand Scaffold for the Synthesis of Binuclear and Bioconjugated Complexes: Synthesis and Anticancer Potential," Chemistry—A European Journal, 2018, vol. 24, Issue 14, pp. 3613-3622.
Biersack et al., "Metallodrug Conjugates with Steroids and Selective Estrogen Receptor Modulators (SERM)," Current Medicinal Chemistry, 2009, vol. 16, pp. 2324-2337.
Borsari et al., "Designing Chimeric Molecules for Drug Discovery by Leveraging Chemical Biology," Journal of Medicinal Chemistry, 2020, vol. 63, Issue 5, pp. 1908-1928.
Brix et al., "Androgen-linked alkylating agents: biological activity in methylnitrosourea-induced rat mammary carcinoma," Journal of Cancer Research and Clinical Oncology, 1990, vol. 116, pp. 538-549.
Burke et al., "Design, Synthesis, and Biological Evaluation of Doxorubicin-Formaldehyde Conjugates Targeted to Breast Cancer Cells," Journal of Medicinal Chemistry, 2004, vol. 47, Issue 5, pp. 1193-1206.
Cheng et al., "MicroRNA silencing for cancer therapy targeted to the tumour microenvironment," Nature, 2015, vol. 518, No. 7537, pp. 107-110.
Cogan et al., "Studies of Targeting and Intracellular Trafficking of an Anti-Androgen Doxorubicin-Formaldehyde Conjugate in PC-3 Prostate Cancer Cells Bearing Androgen Receptor-GFP Chimera," Journal of Medicinal Chemistry, 2004, vol. 47, No. 23, pp. 5690-5699.
Dao et al., "Design, Synthesis, and Initial Biological Evaluation of a Steroidal Anti-estrogen-Doxorubicin Bioconjugate for Targeting Estrogen Receptor-Positive Breast Cancer Cells," Bioconjugate Chemistry, 2012, vol. 23, No. 4, pp. 785-795.
Dao et al., "Targeting the Estrogen Receptor using Steroid-Therapeutic Drug Conjugates (Hybrids)," Bioconjugate Chemistry, 2012, vol. 23, No. 11, pp. 2139-2158.
Dawicki-McKenna et al., "PARP-1 Activation Requires Local Unfolding of an Autoinhibitory Domain," Molecular Cell, 2015, vol. 60, Issue 5, pp. 755-768.
Devraj et al., "Design, Synthesis, and Biological Evaluation of Ellipticine-Estradiol Conjugates," Journal of Medicinal Chemistry, 1996, vol. 39, No. 17, pp. 3367-3374.
Ding et al., "Design of a platinum-acridine-endoxifen conjugate targeted at hormone-dependent breast cancer," Chemical Communications, 2013, vol. 49, No. 24, pp. 2415-2417.
Dizio et al., "Progestin-Rhenium Complexes: Metal-Labeled Steroids with High Receptor Binding Affinity, Potential Receptor-

(56) References Cited

OTHER PUBLICATIONS

Directed Agents for Diagnostic Imaging or Therapy," Bioconjugate Chemistry, 1991, vol. 2, No. 5, pp. 353-366.
French et al., "A Synthesis of 7α-substituted estradiols: synthesis and biological evaluation of a 7α- pentyl-substituted BODIPY fluorescent conjugate and a fluorine-18-labeled 7α-pentylestradiol analog," Steroids, 1993, vol. 58, No. 4, pp. 157-169.
Fröhlich et al., "Synthesis of Artemisinin-Estrogen Hybrids Highly Active Against HCMV, P. Falciparum, and Cervical and Breast Cancer," ACS Medicinal Chemistry Letters, 2018, vol. 9, No. 11, pp. 1128-1133.
George et al., "Design, synthesis, and evaluation of the antiproliferative activity of hydantoin-derived antiandrogen-genistein conjugates," Bioorganic & Medicinal Chemistry, 2018, vol. 26, No. 8, pp. 1481-1487.
Gryder et al., "Histone Deacetylase Inhibitors Equipped with Estrogen Receptor Modulation Activity," Journal of Medicinal Chemistry, 2013, vol. 56, No. 14, pp. 5782-5796.
Gryder et al., "Selectively Targeting Prostate Cancer with Antiandrogen Equipped Histone Deacetylase Inhibitors," ACS Chemical Biology, 2013, vol. 8, No. 11, pp. 2550-2560.
Hanson et al., "Convergent synthesis of a steroidal antiestrogen-mitomycin C hybrid using "click" chemistry," Organic & Biomolecular Chemistry, 2012, vol. 10, No. 42, pp. 8501-8508.
Hasan et al., "Pharmacological, Mechanistic, and Pharmacokinetic Assessment of Novel Melatonin-Tamoxifen Drug Conjugates as Breast Cancer Drugs," Molecular Pharmacology, 2019, vol. 96, No. 2, pp. 272-296.
He et al., "Synthesis and Characterization of Nonsteroidal-Linked $M(CO)_3^+(M={}^{99m}Tc, Re)$ Compounds Based on the Androgen Receptor Targeting Molecule Flutamide," Bioconjugate Chemistry, 2009, vol. 20, No. 1, pp. 78-86.
Hendricks et al., "Synthesis and preliminary evaluation steroidal antiestrogen-geldanamycin conjugates," 2013, vol. 23, Issue 12, pp. 3635-3639.
Hillier et al., "DNA adducts formed by a novel antitumor agent 11ß-dichloro in vitro and in vivo," Molecular Cancer Therapies, 2006, vol. 5, No. 4, pp. 977-984.
Hödl et al., "Syntheses and Antigestagenic Activity of Mifepristone Derivatives," Journal of Medicinal Chemistry, 2009, vol. 52, No. 5, pp. 1268-1274.
Hu et al., "A study on platinum(IV) species containing an estrogen receptor modulator to reverse tamoxifen resistance of breast cancer," Metallomics, 2018, vol. 10, No. 2, pp. 346-359.
Huxley et al., An androgenic steroid delivery vector that imparts activity to a non-conventional platinum(II) metallo-drug, Dalton Transactions, 2010, vol. 39, No. 47, pp. 11353-11364.
International Preliminary Report on Patentability, dated Sep. 30, 2019 for PCT/US2019/32295, 7 pages.
International Search Report and Written Opinion, dated Sep. 30, 2019 for PCT/US2019/32295, 11 pages.
International Search Report and Written Opinion, dated Sep. 28, 2020 for PCT/US2020/032672, 11 pages.
International Search Report and Written Opinion, dated Mar. 15, 2021 for PCT/US2020/060165, 18 pages.
Ishiki et al., "Biological Properties of Conjugates of Mitomycin C with Estradiol Benzoate and Estradiol: Their Stability Characteristics in Biological Media and Their Binding Abilities to Estrogen Receptor," Biological and Pharmaceutical Bulletin, 1997, vol. 20, No. 10, pp. 1096-1102.
Jones et al., "Target Directed Enediyne Prodrugs: Cytotoxic Estrogen Conjugates," Tetrahedron Letters, 1996, vol. 37, No. 21, pp. 3643-3646.
Jones et al., "Target-Directed Enediynes: Designed Estramycins," The Journal of Organic Chemistry, 2001, vol. 66, No. 11, pp. 3688-3695.
Jurášek et al., "Trilobolide-steroid hybrids: Synthesis, cytotoxic and antimycobacterial activity," Steroids, 2017, vol. 117, pp. 97-104.
Kamal et al., "Synthesis and biological evaluation of estradiol linked pyrrolo [2,1-c][1,4] benzodiazepine (PBD) conjugates as potential anticancer agents," Bioorganic & Medicinal Chemistry, 2011, vol. 19, Issue 8, pp. 2565-2581.
Kasiotis et al., "Synthesis and biological evaluation of novel daunorubicin-estrogen conjugates," Steroids, 2001, vol. 66, No. 10, pp. 785-791.
Katzenellenbogen, "Designing Effective Hybrid Toxins," Chemistry & Biology, 2005, vol. 12, No. 7, pp. 719-724.
Keely et al., "Design, Synthesis and Biochemical Evaluation of Estrogen Receptor Ligand Conjugates as Tumour Targeting Agents," Letters in Drug Design & Discovery, 2012, vol. 9, No. 3, pp. 295-304.
Keely et al., "Design, Synthesis and Biochemical Evaluation of Novel Selective Estrogen Receptor Ligand Conjugates Incorporating an Endoxifen-Combretastatin Hybrid Scaffold," Biomedicines, 2016, vol. 4, No. 3, pp. 1-34.
Keely et al., "Targeting Tumors Using Estrogen Receptor Ligand Conjugates," Current Cancer Drug Targets, 2009, vol. 9, No. 3, pp. 370-380.
Kelly et al., "Novel Selective Estrogen Receptor Ligand Conjugates Incorporating Endoxifen-Combretastatin and Cyclofenil-Combretastatin Hybrid Scaffolds: Synthesis and Biochemical Evaluation," Molecules, 2017, vol. 22, No. 9, pp. 1-50.
Khan et al., "Synthesis and Biological Activities of Phthalocyanine-Estradiol Conjugates," Bioorganic & Medicinal Chemistry Letters, 2003, vol. 13, No. 7, pp. 1287-1290.
Kreis et al., "Unique synergism or antagonism of combinations of chemotherapeutic and hormonal agents in human prostate cancer cell lines," British Journal of Urology, 1997, vol. 79, No. 2, pp. 196-202.
Levine et al., "Targeting the Androgen Receptor with Steroid Conjugates: Miniperspective," Journal of Medicinal Chemistry, 2014, vol. 57, No. 20, pp. 8224-8237.
Liu et al., "Design, Synthesis, and Bioactivities of Steroid-Linked Taxol Analogues as Potential Targeted Drugs for Prostate and Breast Cancer," Journal of Natural Products, 2004, vol. 67, No. 2, pp. 152-159.
Lowder et al., "Testosterone conjugated DNA methylating agents targeted to prostate cancer cells," SERMACS-695, 68th Southeastern Regional Meeting of the American Chemistry Society, Meeting Abstract, 2016, AN: 2016:1708008.
Lv et al., "Enhancement of therapeutic effect in breast cancer with a steroid-conjugated ruthenium complex," New Journal of Chemistry, 2019, vol. 43, No. 8, pp. 3419-3427.
Marchal et al., "Synthesis of prodigiosene-estrogen conjugates: optimization of protecting group strategies and anticancer properties," Canadian Journal of Chemistry, 2015, vol. 93, No. 5, pp. 526-535.
Marquis et al., "Disruption of Gene Expression and Induction of Apoptosis in Prostate Cancer Cells by a DNA-Damaging Agent Tethered to an Androgen Receptor Ligand," Chemistry & Biology, 2005, vol. 12, No. 7, pp. 779-787.
Mitra et al., "A Rationally Designed Genotoxin that Selectively Destroys Estrogen Receptor-Positive Breast Cancer Cells," Journal of the American Chemical Society, 2002, vol. 124, No. 9, pp. 1862-1863.
Morioka et al., "Design, synthesis, and biological evaluation of novel estradiol-bisphosphonate conjugates as bone-specific estrogens," Bioorganic & Medicinal Chemistry, 2010, vol. 18, No. 3, pp. 1143-1148.
Narayanan et al., "Selective androgen receptor modulators in preclinical and clinical development," Nuclear Receptor Signaling, 2008, vol. 6, No. 1, pp. 1-26.
Ning et al., "Novel Hybrid Conjugates with Dual Suppression of Estrogenic and Inflammatory Activities Display Significantly Improved Potency against Breast Cancer," Journal of Medicinal Chemistry, 2018, vol. 61, No. 18, pp. 8155-8173.
O'Connor et al., "Targeting the DNA Damage Response in Cancer," Molecular Cell, 2015, vol. 60, No. 4, pp. 547-560.
Ota et al., "Targeting Cancer with PCPA-Drug Conjugates: LSD1 Inhibition-Triggered Release of 4-Hydroxytamoxifen," Angewandte Chemie International Edition, 2016, vol. 55, pp. 16115-16118.

(56) References Cited

OTHER PUBLICATIONS

Palermo et al., "Incorporation of histone deacetylase inhibitory activity into the core of tamoxifen—a new hybrid design paradigm," Bioorganic & Medicinal Chemistry, 2018, vol. 26, Issue 15, pp. 4428-4440.
Patel et al., "A Chimeric SERM-Histone Deacetylase Inhibitor Approach to Breast Cancer Therapy," ChemMedChem, 2014, vol. 9, No. 3, pp. 602-613.
Peng et al., "Selective Estrogen Receptor Modulator Delivery of Quinone Warheads to DNA Triggering Apoptosis in Breast Cancer Cells," ACS Chemical Biology, vol. 4, No. 12, pp. 1039-1049.
Powell et al., "Cyano-nilutamide conjugates with a DNA minor groove methylating agent for selective destruction of prostate cancer cells," 67th Southeast/71st Southwest Joint Regional Meeting of the American Chemical Society, 2015, SERMACS-SWRM-317, Meeting Abstract.
Premnauth et al., "Reactive oxygen species (ROS)-dependent release of an anticancer drug from a targeting peptide," Chemical Abstracts, 2019.
PubChem-CID-2375, Create Date: Mar. 25, 2005, p. 2, Fig.
PubChem-CID-11297720, Create Date: Oct. 26, 2006, p. 2, Fig.
Qin et al., "Theranostic Pt(IV) Conjugate with Target Selectivity for Androgen Receptor," Inorganic Chemistry, 2018, vol. 57, No. 9, pp. 5019-5029.
Rapozzi et al., "Androgen Receptor Targeted Conjugate for Bimodal Photodynamic Therapy of Prostate Cancer in Vitro," Bioconjugate Chemistry, 2015, vol. 26, No. 8, pp. 1662-1671.
Rink et al., "Synthesis and biological activity of DNA damaging agents that form decoy binding sites for the estrogen receptor," Proceedings of the National Academy of Sciences, 1996, vol. 93, No. 26, pp. 15063-15068.
Sadler et al., "Internalization of a C17α-alkynylestradiol-porphyrin conjugate into estrogen receptor positive MCF-7 breast cancer cells," Bioorganic & Medicinal Chemistry Letters, 2011, vol. 21, No. 15, pp. 4638-4641.
Saha et al., "Design, synthesis, cytocidal activity and estrogen receptor α affinity of doxorubicin conjugates at 16α-position of estrogen for site-specific treatment of estrogen receptor positive breast cancer," Steroids, 2012, vol. 77, Issue 11, pp. 1113-1122.
Sanchez-Cano et al., "Conjugation of testosterone modifies the interaction of mono-functional cationic platinum (II) complexes with DNA, causing significant alterations to the DNA helix," Dalton Transactions, 2010, vol. 39, No. 47, pp. 11365-11374.
Sharifi et al., "A bifunctional colchicinoid that binds to the androgen receptor," Molecular Cancer Therapeutics, 2007, vol. 6, Issue 8, pp. 2328-2336.
Sharma et al., "Design, synthesis, and evaluation of estradiol-linked genotoxicants as anti-cancer agents," Bioorganic & Medicinal Chemistry Letters, 2004, vol. 14, No. 14, pp. 3829-3833.
Shi et al., "Antitumor agents 290. Design, synthesis, and biological evaluation of new LNCaP and PC-3 cytotoxic curcumin analogs conjugated with anti-androgens," Bioorganic & Medicinal Chemistry, 2012, vol. 20, No. 13, pp. 4020-4031.
Shibata et al., "Development of Protein Degradation Inducers of Androgen Receptor by Conjugation of Androgen Receptor Ligands and Inhibitor of Apoptosis Protein Ligands," Journal of Medicinal Chemistry, 2018, vol. 61, No. 2, pp. 543-575.
Steffen et al., "Structural implications for selective targeting of PARPs," Frontiers in Oncology, 2013, vol. 3, Article 301, pp. 1-14.

Sundaram et al., "Luteinizing hormone-releasing hormone receptor-targeted deslorelin-docetaxel conjugate enhances efficacy of docetaxel in prostate cancer therapy," Molecular Cancer Therapeutics, 2009, pp. 1655-1665.
Suzuki et al., "Target-selective degradation of proteins by a light-activated 2-phenylquinoline-estradiol hybrid," Chemical Communications, 2007, pp. 4260-4262.
Swamy et al., "An Estradiol-Porphyrin Conjugate Selectively Localizes Into Estrogen Receptor-Positive Breast Cancer Cells," Bioorganic & Medicinal Chemistry, 2002, vol. 10, pp. 3237-3243.
Tang et al., "Novel Bioactive Hybrid Compound Dual Targeting Estrogen Receptor and Histone Deacetylase for the Treatment of Breast Cancer," Journal of Medicinal Chemistry, 2015, vol. 58, No. 11, pp. 4550-4572.
Teutsch et al., "Synthesis of a fluorescent steroid derivative with high affinities for the glucocorticoid and progesterone receptors," Steroids, 1994, vol. 59, No. 1, pp. 22-26.
Tikhe et al., "Design, Synthesis, and Evaluation of 3,4-Dihydro-2H-[1,4]diazepino[6,7,1-hi]indol-1-ones as Inhibitors of Poly(ADP-Ribose) Polymerase," Journal of Medicinal Chemistry, 2004, vol. 47, pp. 5467-5481.
Wang et al., "Discovery and Characterization of (8S,9R)-5-Fluoro-8-(4-fluorophenyl)-9-(1-methyl-1H-1,2,4-triazol-5-yl)-2,7,8,9-tetrahydro-3H-pyrido[4,3,2-de]phthalazin-3-one (BMN 673, Talazoparib), a Novel, Highly Potent, and Orally Efficacious Poly(ADP-ribose) Polymerase-1/2 Inhibitor, as an Anticancer Agent," Journal of Medicinal Chemistry, 2016, vol. 59, pp. 335-357.
Weinstain et al., "Fluorescent Ligand for Human Progesterone Receptor Imaging in Live Cells," Bioconjugate Chemistry, 2013, vol. 24, pp. 766-771.
Zeinyeh et al., "Progesterone-adenine hybrids as bivalent inhibitors of P-glycoprotein-mediated multidrug efflux: Design, synthesis, characterization and biological evaluation," Steroids, 2012, vol. 77, Issue 12, pp. 1177-1191.
Zhang et al., "Antagonizing the Androgen Receptor with a Biomimetic Acyltransferase," ACS Chemical Biology, 2016, vol. 11, No. 10, pp. 2797-2802.
Zhang et al., "Tamoxifen-zinc(II) phthalocyanine conjugates for target-based photodynamic therapy and hormone therapy," Journal of Porphyrins and Phthalocyanines, 2019, vol. 23, No. 10, pp. 1073-1083.
Zolottsev et al., Conjugates of 17-substituted testosterone and epitestosterone with pyropheophorbide a differing in the length of linkers, Steroids, 2018, vol. 138, pp. 82-90.
Delfosse, V. et al. (2015, e-pub. Dec. 15, 2014). "A Structural Perspective on Nuclear Receptors as Targets of Environmental Compounds," Acta Pharmacologica Sinica 36:88-101.
Extended European Search Report, dated Oct. 5, 2023, for European Patent Application No. 20806178.8, 27 pages.
International Preliminary Report on Patentability, dated Sep. 12, 2023, for PCT Application No. PCT/US2022/021390, filed Mar. 22, 2022, 9 pages.
Wang, F.-Z. et al. (2014, e-pub. Jun. 14, 2014). "The Checkpoint 1 Kinase Inhibitor LY2603618 Induces Cell Cycle Arrest, DNA Damage Response and Autophagy in Cancer Cells," Apoptosis 19(9):1389-1398.
Zhuang, C. et al. (Feb. 1, 2019, e-pub. Dec. 16, 2018). "Small Molecule-Drug Conjugates: A Novel Strategy for Cancer-Targeted Treatment," European Journal of Medicinal Chemistry 163:883-895.

* cited by examiner

ANTI-CANCER NUCLEAR HORMONE RECEPTOR-TARGETING COMPOUNDS

CROSS REFERENCE TO RELATED APPLICATIONS

This application claims the benefit under 35 U.S.C. § 119(e) to U.S. Provisional Application No. 63/183,569, filed May 3, 2021, which is hereby incorporated by reference in its entirety.

BACKGROUND

The disclosure relates to anti-cancer compounds derived from nuclear receptor binders, such as nuclear steroid receptor binders, to products containing the same, as well as to methods of their use and preparation.

PARP inhibitors are pharmacologic agents that prevent DNA repair leading to the death of cells and hence tumor growth inhibition. Inhibitors of PARP enzymes (such as olaparib, rucaparib, niraparib, and talzoparib) have been approved for the treatment of breast cancer in patients with BRCA mutations, and ovarian cancer. There are several others (e.g., velaparib) that are in clinical testing for breast, prostate and ovarian cancers. The use of PARP inhibitors is not without side effects, and one of the major road blocks to the long-term use of PARP inhibitors is the rapid and dose dependent development of neutropenia. This requires dosing holidays and/or dose reductions in clinical practice, which compromise the ability to achieve maximal efficacy. Other anticancer agents, e.g., alkylating agents such as chlorambucil, can have serious side effects, such as bone marrow suppression, an increased long term risk of further cancer, infertility, and allergic reactions. Accordingly, targeted delivery of anticancer agents would be beneficial.

It has now been suggested that only PARP1 inhibition and trapping is required for synthetic lethal efficacy in homologous recombination repair deficient (HRD) cells. Thus, combining a selective PARP1 inhibitor and a nuclear receptor-targeting epitope may improve the therapeutic index versus first-generation PARP inhibitors.

SUMMARY

Provided herein are compounds comprising a nuclear payload and a nuclear receptor-targeting epitope. Compounds described herein are designed to bind nuclear receptors within the cell and allow the compound, with its nuclear payload, to accumulate in the nucleus. Not wishing to be bound by theory, one potential mode of enhanced utility is that this approach may provide for compounds having cell-type selectivity, not merely improved potency, working toward a higher therapeutic index. However, it may be that the compounds may be active by other modes, such as, but not limited to, passive localization in the nucleus.

Further, the compounds described herein offer targeted delivery of a nuclear payload. The compounds both target and localize within tumor tissue. The transport of the compound, which comprises at least one nuclear receptor-targeting epitope, such as a nuclear steroid receptor-targeting epitope, covalently attached to at least one nuclear payload, to the nucleus allows for accumulation of the nuclear payload in the nucleus, enhancing tumor cell death. By doing so, compounds described in this disclosure may exhibit superior efficacy. In addition, the compounds described in this disclosure could, by accumulating preferentially in the nucleus of nuclear receptor positive cells, such as steroid receptor positive cells, spare cells that do not express the specific nuclear steroid receptor, and therefore reduce side effects.

In certain embodiments, provided is a compound of Formula I:

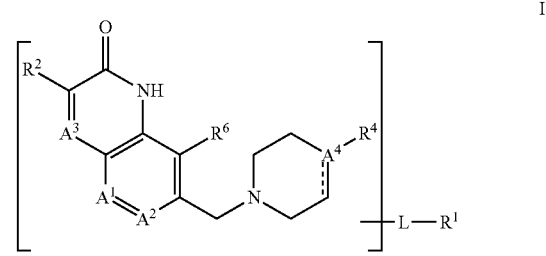

or a tautomer, stereoisomer, mixture of stereoisomers, hydrate, solvate, isotopically enriched analog, or pharmaceutically acceptable salt thereof, wherein:

$A^1$ is CH or N;
$A^2$ is CH or N;
$A^3$ is N or $CR^3$;
$A^4$ is C and $===$ is a double bond, or $A^4$ is CH and $===$ is a single bond, or $A^4$ is N and $===$ is a single bond;
L is a covalent bond or a linking moiety;
$R^1$ is a nuclear receptor-targeting epitope;
$R^2$ is hydrogen, $C_{1-6}$ alkyl, $C_{1-6}$ haloalkyl, $C_{1-6}$ alkoxy, or $C_{3-6}$ cycloalkyl;
$R^3$ is hydrogen or halo; or
$R^2$ and $R^3$ together with the atoms to which they are attached form a 6-membered heterocyclyl or 6-membered heteroaryl;
$R^4$ is hydrogen, aryl, or heteroaryl, wherein the aryl or heteroaryl is optionally substituted with one to five $R^5$;
each $R^5$ is independently halo, cyano, nitro, $-OR^{10}$, $-OC(O)R^{10}$, $-C(O)OR^{10}$, $-SR^{10}$, $-NR^{10}R^{11}$, $-NR^{10}C(O)R^{11}$, $-C(O)NR^{10}R^{11}$, $C_{1-12}$ alkyl, $C_{1-12}$ haloalkyl, $C_{2-12}$ alkenyl, or $C_{2-12}$ alkynyl; wherein each $C_{1-12}$ alkyl, $C_{1-12}$ haloalkyl, $C_{2-12}$ alkenyl, or $C_{2-12}$ alkynyl is independently optionally substituted with one to five halo, hydroxyl, or amino;
$R^6$ is hydrogen, halo, or $C_{1-6}$ alkyl; and
each $R^{10}$ and $R^{11}$ is independently hydrogen or $C_{1-12}$ alkyl optionally substituted with oxo, halo, hydroxyl, or amino as valency permits; or $R^{10}$ and $R^{11}$ are taken together with the atoms to which they are attached to form heterocyclyl optionally substituted by halo or $C_{1-12}$ alkyl optionally substituted by oxo, halo, hydroxyl, or amino;
wherein any hydrogen atom of the moiety in the brackets is replaced with -L-$R^1$.

Also provided is a compound of Table 1, or a tautomer, stereoisomer, mixture of stereoisomers, hydrate, solvate, isotopically enriched analog, or pharmaceutically acceptable salt thereof.

Also provided is a composition comprising a compound as described herein or a tautomer, stereoisomer, mixture of stereoisomers, hydrate, solvate, isotopically enriched analog, or pharmaceutically acceptable salt thereof, and a pharmaceutically acceptable excipient.

Also provided is a method of treating or preventing cancer, comprising administering an effective amount of a compound or composition as described herein to an individual in need thereof. The cancer can be a blood cancer, lung cancer, breast cancer, fallopian tube cancer, brain cancer, head and neck cancer, esophageal cancer, ovarian cancer, pancreatic cancer, peritoneal cancer, prostate cancer, or skin cancer, such as, but not limited to, liver cancer, melanoma, Hodgkin's disease, non-Hodgkin's lymphomas, acute lymphocytic leukemia, chronic lymphocytic leukemia, multiple myeloma, neuroblastoma, breast carcinoma, ovarian carcinoma, lung carcinoma, Wilms' tumor, cervical carcinoma, testicular carcinoma, soft-tissue sarcoma, chronic lymphocytic leukemia, Waldenström macroglobulinemia, primary macroglobulinemia, bladder carcinoma, chronic granulocytic leukemia, primary brain carcinoma, malignant melanoma, small-cell lung carcinoma, stomach carcinoma, colon carcinoma, malignant pancreatic insulinoma, malignant carcinoid carcinoma, malignant melanoma, choriocarcinoma, mycosis fungoides, head neck carcinoma, osteogenic sarcoma, pancreatic carcinoma, acute granulocytic leukemia, hairy cell leukemia, rhabdomyosarcoma, Kaposi's sarcoma, genitourinary carcinoma, thyroid carcinoma, esophageal carcinoma, malignant hypercalcemia, cervical hyperplasia, renal cell carcinoma, endometrial carcinoma, polycythemia vera, essential thrombocytosis, adrenal cortex carcinoma, skin cancer, trophoblastic neoplasms, prostatic carcinoma, glioma, breast cancer, or prostate cancer.

Also provided is a method of treating or preventing cancer, comprising administering an effective amount of a compound or composition as described herein, or a pharmaceutically acceptable salt or solvate thereof, in combination with an additional chemotherapeutic agent, to an individual in need thereof.

DETAILED DESCRIPTION

The following description sets forth exemplary embodiments of the present technology. It should be recognized, however, that such description is not intended as a limitation on the scope of the present disclosure but is instead provided as a description of exemplary embodiments.

1. Definitions

As used in the present specification, the following words, phrases and symbols are generally intended to have the meanings as set forth below, except to the extent that the context in which they are used indicates otherwise.

The term "about" refers to a variation of ±1%, ±3%, ±5%, or ±10% of the value specified. For example, "about 50" can in some embodiments includes a range of from 45 to 55. For integer ranges, the term "about" can include one or two integers greater than and/or less than a recited integer at each end of the range. Unless indicated otherwise herein, the term "about" is intended to include values, e.g., weight percentages, proximate to the recited range that are equivalent in terms of the functionality of the individual ingredient, the composition, or the embodiment. Also, the singular forms "a" and "the" include plural references unless the context clearly dictates otherwise. Thus, e.g., reference to "the compound" includes a plurality of such compounds and reference to "the assay" includes reference to one or more compounds and equivalents thereof known to those skilled in the art.

"Alkyl" refers to an unbranched or branched saturated hydrocarbon chain. As used herein, alkyl has 1 to 12 carbon atoms (a "$C_{1-12}$ alkyl"), 1 to 10 carbon atoms (i.e., $C_{1-10}$ alkyl), 1 to 8 carbon atoms (i.e., $C_{1-8}$ alkyl), 1 to 6 carbon atoms (i.e., $C_{1-6}$ alkyl), or 1 to 4 carbon atoms (i.e., $C_{1-4}$ alkyl). Examples of alkyl groups include methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl, and 3-methylpentyl. When an alkyl residue having a specific number of carbons is named by chemical name or identified by molecular formula, all positional isomers having that number of carbons may be encompassed; thus, for example, "butyl" includes n-butyl (i.e. —$(CH_2)_3CH_3$), sec-butyl (i.e. —$CH(CH_3)CH_2CH_3$), isobutyl (i.e. —$CH_2CH(CH_3)_2$) and tert-butyl (i.e. —$C(CH_3)_3$); and "propyl" includes n-propyl (i.e. —$(CH_2)_2CH_3$) and isopropyl (i.e. —$CH(CH_3)_2$).

"Haloalkyl" refers to an unbranched or branched alkyl group as defined above, wherein one or more hydrogen atoms are replaced by a halogen. For example, where a residue is substituted with more than one halogen, it may be referred to by using a prefix corresponding to the number of halogen moieties attached. Dihaloalkyl and trihaloalkyl refer to alkyl substituted with two ("di") or three ("tri") halo groups, which may be, but are not necessarily, the same halogen. Examples of haloalkyl include difluoromethyl (—$CHF_2$) and trifluoromethyl (—$CF_3$).

"Heteroalkyl" refers to an alkyl group in which one or more of the carbon atoms (and any associated hydrogen atoms) are each independently replaced with the same or different heteroatomic group. The term "heteroalkyl" includes unbranched or branched saturated chain having carbon and heteroatoms. By way of example, 1, 2 or 3 carbon atoms may be independently replaced with the same or different heteroatomic group. Heteroatomic groups include, but are not limited to, —NH—, —O—, —S—, —S(O)—, —$S(O)_2$—, and the like. As used herein, heteroalkyl includes 1 to 8 carbon atoms, or 1 to 4 carbon atoms; and 1 to 3 heteroatoms, 1 to 2 heteroatoms, or 1 heteroatom. "Heteroalkyl" refers to an alkyl group in which one or more of the carbon atoms (and any associated hydrogen atoms) are each independently replaced with the same or different heteroatomic group. The term "heteroalkyl" includes unbranched or branched saturated chain having carbon and heteroatoms. By way of example, 1, 2 or 3 carbon atoms may be independently replaced with the same or different heteroatomic group. Heteroatomic groups include, but are not limited to, —NH—, —O—, —S—, —S(O)—, —$S(O)_2$—. Examples of heteroalkyl groups include, e.g., ethers (e.g., —$CH_2OCH_3$, —$CH(CH_3)OCH_3$, —$CH_2CH_2OCH_3$, —$CH_2CH_2OCH_2CH_2OCH_3$, etc.), thioethers (e.g., —$CH_2SCH_3$, —$CH(CH_3)SCH_3$, —$CH_2CH_2SCH_3$, —$CH_2CH_2SCH_2CH_2SCH_3$, etc.), sulfones (e.g., —$CH_2S(O)_2CH_3$, —$CH(CH_3)S(O)_2CH_3$, —$CH_2CH_2S(O)_2CH_3$, —$CH_2CH_2S(O)_2CH_2CH_2OCH_3$, etc.), and amines (e.g., —$CH_2NHCH_3$, —$CH(CH_3)NHCH_3$, —$CH_2CH_2NHCH_3$, —$CH_2CH_2NHCH_2CH_2NHCH_3$, etc. As used herein, heteroalkyl includes 1 to 10 carbon atoms, 1 to 8 carbon atoms, or 1 to 4 carbon atoms; and 1 to 3 heteroatoms, 1 to 2 heteroatoms, or 1 heteroatom.

"Alkenyl" refers to an alkyl group containing at least one carbon-carbon double bond and having from 2 to 20 carbon atoms (i.e., $C_{2-20}$ alkenyl), 2 to 8 carbon atoms (i.e., $C_{2-8}$ alkenyl), 2 to 6 carbon atoms (i.e., $C_{2-6}$ alkenyl) or 2 to 4 carbon atoms (i.e., $C_{2-4}$ alkenyl). Examples of alkenyl groups include, e.g., ethenyl, propenyl, and butadienyl (including 1,2-butadienyl and 1,3-butadienyl).

"Alkynyl" refers to an alkyl group containing at least one carbon-carbon triple bond and having from 2 to 20 carbon atoms (i.e., $C_{2-20}$ alkynyl), 2 to 8 carbon atoms (i.e., $C_{2-8}$ alkynyl), 2 to 6 carbon atoms (i.e., $C_{2-6}$ alkynyl) or 2 to 4 carbon atoms (i.e., $C_{2-4}$ alkynyl). The term "alkynyl" also includes those groups having one triple bond and one double bond.

"Alkoxy" refers to the group "alkyl-O—". Examples of alkoxy groups include, e.g., methoxy, ethoxy, n-propoxy, iso-propoxy, n-butoxy, tert-butoxy, sec-butoxy, n-pentoxy, n-hexoxy, and 1,2-dimethylbutoxy.

"Alkoxyalkyl" refers to the group "alkyl-O-alkyl".

"Amino" refers to the group —$NR^yR^z$ wherein $R^y$ and $R^z$ are independently hydrogen, alkyl, alkenyl, alkynyl, cycloalkyl, heterocyclyl, aryl, heteroalkyl or heteroaryl; each of which may be optionally substituted, as defined herein.

"Aryl" refers to an aromatic carbocyclic group having a single ring (e.g., monocyclic) or multiple rings (e.g., bicyclic or tricyclic) including fused systems. As used herein, aryl has 6 to 20 ring carbon atoms (i.e., $C_{6-20}$ aryl), 6 to 12 carbon ring atoms (i.e., $C_{6-12}$ aryl), or 6 to 10 carbon ring atoms (i.e., $C_{6-10}$ aryl). Examples of aryl groups include, e.g., phenyl, naphthyl, fluorenyl and anthryl. Aryl, however, does not encompass or overlap in any way with heteroaryl defined below. If one or more aryl groups are fused with a heteroaryl, the resulting ring system is heteroaryl. If one or more aryl groups are fused with a heterocyclyl, the resulting ring system is heterocyclyl.

"Cycloalkyl" refers to a saturated or partially unsaturated cyclic alkyl group having a single ring or multiple rings including fused, bridged and spiro ring systems. The term "cycloalkyl" includes cycloalkenyl groups (i.e., the cyclic group having at least one double bond) and carbocyclic fused ring systems having at least one $sp^3$ carbon atom (i.e., at least one non-aromatic ring). As used herein, cycloalkyl has from 3 to 20 ring carbon atoms (i.e., $C_{3-20}$ cycloalkyl), 3 to 12 ring carbon atoms (i.e., $C_{3-12}$ cycloalkyl), 3 to 10 ring carbon atoms (i.e., $C_{3-10}$ cycloalkyl), 3 to 8 ring carbon atoms (i.e., $C_{3-8}$ cycloalkyl), or 3 to 6 ring carbon atoms (i.e., $C_{3-6}$ cycloalkyl). Monocyclic groups include, for example, cyclopropyl, cyclobutyl, cyclopentyl, cyclohexyl, cycloheptyl, and cyclooctyl. Further, the term cycloalkyl is intended to encompass any non-aromatic ring which may be fused to an aryl ring, regardless of the attachment to the remainder of the molecule. Still further, cycloalkyl also includes "spirocycloalkyl" when there are two positions for substitution on the same carbon atom.

"Heteroaryl" refers to an aromatic group having a single ring, multiple rings, or multiple fused rings, with one or more ring heteroatoms independently selected from nitrogen, oxygen, and sulfur. As used herein, heteroaryl includes 1 to 20 ring carbon atoms (i.e., $C_{1-20}$ heteroaryl), 3 to 12 ring carbon atoms (i.e., $C_{3-12}$ heteroaryl), or 3 to 8 carbon ring atoms (i.e., $C_{3-8}$ heteroaryl), and 1 to 5 ring heteroatoms, 1 to 4 ring heteroatoms, 1 to 3 ring heteroatoms, 1 to 2 ring heteroatoms, or 1 ring heteroatom independently selected from nitrogen, oxygen, and sulfur. In certain instances, heteroaryl includes 5-10 membered ring systems, 5-7 membered ring systems, or 5-6 membered ring systems, each independently having 1 to 4 ring heteroatoms, 1 to 3 ring heteroatoms, 1 to 2 ring heteroatoms, or 1 ring heteroatom independently selected from nitrogen, oxygen, and sulfur. Examples of heteroaryl groups include, e.g., acridinyl, benzimidazolyl, benzothiazolyl, benzindolyl, benzofuranyl, benzothiazolyl, benzothiadiazolyl, benzonaphthofuranyl, benzoxazolyl, benzothienyl (benzothiophenyl), benzotriazolyl, benzo[4,6]imidazo[1,2-a]pyridyl, carbazolyl, cinnolinyl, dibenzofuranyl, dibenzothiophenyl, furanyl, isothiazolyl, imidazolyl, indazolyl, indolyl, indazolyl, isoindolyl, isoquinolyl, isoxazolyl, naphthyridinyl, oxadiazolyl, oxazolyl, 1-oxidopyridinyl, 1-oxidopyrimidinyl, 1-oxidopyrazinyl, 1-oxidopyridazinyl, phenazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, thiazolyl, thiadiazolyl, triazolyl, tetrazolyl, and triazinyl. Examples of the fused-heteroaryl rings include, but are not limited to, benzo[d]thiazolyl, quinolinyl, isoquinolinyl, benzo[b]thiophenyl, indazolyl, benzo[d]imidazolyl, pyrazolo[1,5-a]pyridinyl, and imidazo[1,5-a]pyridinyl, where the heteroaryl can be bound via either ring of the fused system. Any aromatic ring, having a single or multiple fused rings, containing at least one heteroatom, is considered a heteroaryl regardless of the attachment to the remainder of the molecule (i.e., through any one of the fused rings). Heteroaryl does not encompass or overlap with aryl as defined above.

"Heterocyclyl" refers to a saturated or partially unsaturated cyclic alkyl group, with one or more ring heteroatoms independently selected from nitrogen, oxygen and sulfur. The term "heterocyclyl" includes heterocycloalkenyl groups (i.e., the heterocyclyl group having at least one double bond), bridged-heterocyclyl groups, fused-heterocyclyl groups and spiro-heterocyclyl groups. A heterocyclyl may be a single ring or multiple rings wherein the multiple rings may be fused, bridged or spiro, and may comprise one or more (e.g., 1 to 3) oxo (═O) or N-oxide (—O⁻) moieties. Any non-aromatic ring containing at least one heteroatom is considered a heterocyclyl, regardless of the attachment (i.e., can be bound through a carbon atom or a heteroatom). Further, the term heterocyclyl is intended to encompass any non-aromatic ring containing at least one heteroatom, which ring may be fused to an aryl or heteroaryl ring, regardless of the attachment to the remainder of the molecule. As used herein, heterocyclyl has 2 to 20 ring carbon atoms (i.e., $C_{2-20}$ heterocyclyl), 2 to 12 ring carbon atoms (i.e., $C_{2-12}$ heterocyclyl), 2 to 10 ring carbon atoms (i.e., $C_{2-10}$ heterocyclyl), 2 to 8 ring carbon atoms (i.e., $C_{2-8}$ heterocyclyl), 3 to 12 ring carbon atoms (i.e., $C_{3-12}$ heterocyclyl), 3 to 8 ring carbon atoms (i.e., $C_{3-8}$ heterocyclyl), or 3 to 6 ring carbon atoms (i.e., $C_{3-6}$ heterocyclyl); having 1 to 5 ring heteroatoms, 1 to 4 ring heteroatoms, 1 to 3 ring heteroatoms, 1 to 2 ring heteroatoms, or 1 ring heteroatom independently selected from nitrogen, sulfur or oxygen. The term "heterocyclyl" also includes "spiroheterocyclyl" when there are two positions for substitution on the same carbon atom. Examples of heterocyclyl groups include, e.g., azetidinyl, azepinyl, benzodioxolyl, benzo[b][1,4]dioxepinyl, 1,4-benzodioxanyl, benzopyranyl, benzodioxinyl, benzopyranonyl, benzofuranonyl, dioxolanyl, dihydropyranyl, hydropyranyl, thienyl[1,3]dithianyl, decahydroisoquinolyl, furanonyl, imidazolinyl, imidazolidinyl, indolinyl, indolizinyl, isoindolinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, oxiranyl, oxetanyl, phenothiazinyl, phenoxazinyl, piperidinyl, piperazinyl, 4-piperidonyl, pyrrolidinyl, pyrazolidinyl, quinuclidinyl, thiazolidinyl, tetrahydrofuryl, tetrahydropyranyl, trithianyl, tetrahydroquinolinyl, thiophenyl (i.e., thienyl), thiomorpholinyl, thiamorpholinyl, 1-oxo-thiomorpholinyl, and 1,1-dioxo-thiomorpholinyl. The term "heterocyclyl" also includes "spiroheterocyclyl" when there are two positions for substitution on the same carbon atom. Examples of the spiro-heterocyclyl rings include, e.g., bicyclic and tricyclic ring systems, such as oxabicyclo[2.2.2]octanyl, 2-oxa-7-azaspiro[3.5]nonanyl, 2-oxa-6-azaspiro[3.4]octanyl, and 6-oxa-1-azaspiro[3.3]heptanyl. Examples of the fused-heterocyclyl rings include, but are not limited to, 1,2,3,4- tetrahydroisoquinolinyl, 4,5,6,7-tetrahydrothieno[2,3-c]pyridinyl, indolinyl, and isoindolinyl, where the heterocyclyl can be bound via either ring of the fused system.

"Alkylene" refers to a divalent alkyl group as defined above. As used herein, alkylene has 1 to 10 carbon atoms (i.e., $C_{1-10}$ alkylene), 1 to 8 carbon atoms (i.e., $C_{1-8}$ alkylene), 1 to 6 carbon atoms (i.e., $C_{1-6}$ alkylene), or 1 to 4 carbon atoms (i.e., $C_{1-4}$ alkylene).

"Heteroalkylene" refers to an alkylene group in which one or more of the carbon atoms (and any associated hydrogen atoms) are each independently replaced with the same or different heteroatomic group. The term "heteroalkylene" includes unbranched or branched saturated chain having carbon and heteroatoms. By way of example, 1, 2, or 3 carbon atoms may be independently replaced with the same or different heteroatomic group. Heteroatomic groups include, but are not limited to, —NH—, —O—, —S—, —S(O)—, —S(O)$_2$—, and the like. As used herein, heteroalkylene includes 1 to 8 carbon atoms, or 1 to 4 carbon atoms; and 1 to 3 heteroatoms, 1 to 2 heteroatoms, or 1 heteroatom.

"Alkenylene" refers to an alkylene group containing at least one carbon-carbon double bond and having from 2 to 8 carbon atoms (i.e., $C_{2-8}$ alkenylene), 2 to 6 carbon atoms (i.e., $C_{2-6}$ alkenylene), or 2 to 4 carbon atoms (i.e., $C_{2-4}$ alkenylene).

"Heteroalkenylene" refers to a heteroalkylene group containing at least one carbon-carbon double bond and having from 2 to 8 carbon atoms, 2 to 6 carbon atoms, or 2 to 4 carbon atoms; and 1 to 3 heteroatoms, 1 to 2 heteroatoms, or 1 heteroatom. The term "heteroalkynyl" also includes those groups having one triple bond and one double bond.

"Alkynylene" refers to an alkylene group containing at least one carbon-carbon triple bond and having from 2 to 8 carbon atoms (i.e., $C_{2-8}$ alkynylene), 2 to 6 carbon atoms (i.e., $C_{2-6}$ alkynylene), or 2 to 4 carbon atoms (i.e., $C_{2-4}$ alkynylene). The term "alkynyl" also includes those groups having one triple bond and one double bond.

"Heteroalkynylene" refers to a heteroalkylene group containing at least one carbon-carbon triple bond and having from 2 to 8 carbon atoms, 2 to 6 carbon atoms, or 2 to 4 carbon atoms; and 1 to 3 heteroatoms, 1 to 2 heteroatoms, or 1 heteroatom. The term "heteroalkynyl" also includes those groups having one triple bond and one double bond.

"Cycloalkylene" refers to a divalent saturated or partially unsaturated cyclic alkyl group having a single ring or multiple rings including fused, bridged, and spiro ring systems. The term "cycloalkylene" includes cycloalkenylene groups (i.e. the cyclic group having at least one double bond). As used herein, cycloalkenylene has from 3 to 10 ring carbon atoms (i.e., $C_{3-10}$ cycloalkyl), 3 to 8 ring carbon atoms (i.e., $C_{3-8}$ cycloalkyl), or 3 to 6 ring carbon atoms (i.e., $C_{3-6}$ cycloalkyl).

"Heterocycloalkylene" refers to a cycloalkylene group in which one or more of the carbon atoms (and any associated hydrogen atoms) are each independently replaced with the same or different heteroatomic group. By way of example, 1, 2, or 3 carbon atoms may be independently replaced with the same or different heteroatomic group. Heteroatomic groups include, but are not limited to, —NH—, —O—, —S—, —S(O)—, —S(O)$_2$—, and the like. As used herein, heterocycloalkylene includes 1 to 9 carbon atoms, or 1 to 4 carbon atoms; and 1 to 3 heteroatoms, 1 to 2 heteroatoms, or 1 heteroatom.

"Oxo" refers to =O.

"Halogen" or "halo" includes fluoro, chloro, bromo, and iodo.

The terms "optional" or "optionally" means that the subsequently described event or circumstance may or may not occur. The term "optionally substituted" refers to any one or more hydrogen atoms on the designated atom or group may or may not be replaced by a moiety other than hydrogen.

"Substituted" as used herein means one or more hydrogen atoms of the group is replaced with a substituent atom or group commonly used in pharmaceutical chemistry. Each substituent can be the same or different. Examples of suitable substituents include, but are not limited to, hydrazide, halo, —CN, —NO$_2$, alkyl, alkenyl, alkynyl, cycloalkyl, aryl, heterocyclyl, heteroaryl, —OR$^{56}$, —C(O)OR$^{56}$, —C(O)R$^{56}$, —O-alkyl-OR$^{56}$, -alkyl-OR$^{56}$, haloalkyl, haloalkoxy, SR$^{56}$, S(O)R$^{56}$, SO$_2$R$^{56}$, NR$^{56}$R$^{57}$, —C(O)NR$^{56}$R$^{57}$, NR$^{56}$C(O)R$^{57}$, including seleno and thio derivatives thereof, wherein each R$^{56}$ and R$^{57}$ are independently hydrogen, alkyl, alkenyl, alkynyl, heteroalkyl, cycloalkyl, cycloalkyl-alkyl-, heterocyclyl, heterocyclyl-alkyl-, aryl, aryl-alkyl-, heteroaryl, or heteroaryl-alkyl-, and wherein each of the substituents can be optionally further substituted.

Provided are also are stereoisomers, mixture of stereoisomers, tautomers, hydrates, solvates, isotopically enriched analog, and pharmaceutically acceptable salts of the compounds described herein.

The compounds disclosed herein, or their pharmaceutically acceptable salts, may include an asymmetric center and may thus give rise to enantiomers, diastereomers, and other stereoisomeric forms that may be defined, in terms of absolute stereochemistry, as (R)- or (S)- or, as (D)- or (L)- for amino acids. The present disclosure is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high performance liquid chromatography (HPLC). When the compounds described herein contain olefinic double bonds or other centers of geometric asymmetry, and unless specified otherwise, it is intended that the compounds include both E and Z geometric isomers.

A "stereoisomer" refers to a compound made up of the same atoms bonded by the same bonds but having different three-dimensional structures, which are not interchangeable. The present disclosure contemplates various stereoisomers and mixtures thereof and includes "enantiomers," which refers to two stereoisomers whose molecules are nonsuperimposeable mirror images of one another and "diastereomers," which refers to stereoisomers that have at least two asymmetric atoms, but which are not mirror-images of each other. Thus, all stereoisomers (for example, geometric isomers, optical isomers, and the like) of the present compounds (including those of the salts, solvates, and hydrates of the compounds), such as those which may exist due to asymmetric carbons on various substituents, including enantiomeric forms (which may exist even in the absence of asymmetric carbons), rotameric forms, atropisomers, and diastereomeric forms, are contemplated.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds may be atropisomers and are considered as part of this disclosure. Stereoisomers can also be separated by use of chiral HPLC.

Some of the compounds exist as tautomers. Tautomers are in equilibrium with one another. For example, amide containing compounds may exist in equilibrium with imidic acid tautomers. Regardless of which tautomer is shown and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

The term "hydrate" refers to the complex formed by the combining of a compound described herein and water.

A "solvate" refers to an association or complex of one or more solvent molecules and a compound of the disclosure. Examples of solvents that form solvates include, but are not limited to, water, isopropanol, ethanol, methanol, dimethylsulfoxide, ethylacetate, acetic acid, and ethanolamine.

Any compound or structure given herein, is also intended to represent unlabeled forms as well as isotopically labeled forms of the compounds. These forms of compounds may also be referred to as an "isotopically enriched analog." Isotopically labeled compounds have structures depicted herein, except that one or more atoms are replaced by an atom having a selected atomic mass or mass number. Examples of isotopes that can be incorporated into the disclosed compounds include isotopes of hydrogen, carbon, nitrogen, oxygen, phosphorous, fluorine, chlorine and iodine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I, and $^{125}$I, respectively. Various isotopically labeled compounds of the present disclosure, for example those into which radioactive isotopes such as $^3$H and $^{14}$C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients. Such compounds may exhibit increased resistance to metabolism and are thus useful for increasing the half-life of any compound when administered to a mammal, particularly a human. Such compounds are synthesized by means well known in the art, for example by employing starting materials in which one or more hydrogens have been replaced by deuterium.

Certain compounds disclosed herein contain one or more ionizable groups (groups from which a proton can be removed (e.g., —COOH) or added (e.g., amines) or which can be quaternized (e.g., amines)). All possible ionic forms of such molecules and salts thereof are intended to be included individually in the disclosure herein. With regard to salts of the compounds described herein, one of ordinary skill in the art can select from among a wide variety of available counterions those that are appropriate. In specific applications, the selection of a given anion or cation for preparation of a salt may result in increased or decreased solubility of that salt.

As used herein, the term "non-biocleavable linking moiety" is intended to refer to a linking moiety which is not readily hydrolyzed under physiological conditions. As used herein, the term "biocleavable linking moiety" is intended to refer to a linking moiety which is readily hydrolyzed under physiological conditions. In certain embodiments, at least one linking moiety is hydrolyzed under intracellular conditions (e.g., low pH). In some embodiments, the biocleavable is self-cleaving and does not require physiological hydrolysis, in other embodiments, the biocleavable linker's cleavage is initiated by metabolic activation such as oxidation or pH dependent cleavage without hydrolysis such as by base or acid induced elimination, etc. More broadly speaking, a biocleavable linker may in some instances be analogous to a prodrug wherein after cleavage, one or more drugs is released. In this sense, there are many mechanisms to cleave prodrugs and release the active(s) or a precursor that yields the active and there are also many varieties of cleavage moieties known in the prodrug art and are included in our definition herein.

As used herein, the term "cancer" refers to a class of diseases of mammals characterized by uncontrolled cellular growth. The term "cancer" is used interchangeably with the terms "tumor," "solid tumor," "malignancy," "hyperproliferation," and "neoplasm." Cancer includes all types of hyperproliferative growth, hyperplasic growth, neoplastic growth, cancerous growth, or oncogenic processes, metastatic tissues or malignantly transformed cells, tissues, or organs, irrespective of histopathologic type or stage of invasiveness. Illustrative examples include, lung, prostate, head and neck, breast and colorectal cancer, melanomas and gliomas (such as a high grade glioma, including glioblastoma multiforme (GBM), the most common and deadliest of malignant primary brain tumors in adult humans).

The phrase "solid tumor" includes, for example, lung cancer, head and neck cancer, brain cancer, oral cancer, colorectal cancer, breast cancer, prostate cancer, pancreatic cancer, and liver cancer. Other types of solid tumors are named for the particular cells that form them, for example, sarcomas formed from connective tissue cells (for example, bone cartilage, fat), carcinomas formed from epithelial tissue cells (for example, breast, colon, pancreas), and lymphomas formed from lymphatic tissue cells (for example, lymph nodes, spleen, and thymus). Treatment of all types of solid tumors regardless of naming convention is within the scope of this disclosure.

"Chemotherapeutic agent" refers to any substance capable of reducing or preventing the growth, proliferation, or spread of a cancer cell, a population of cancer cells, tumor, or other malignant tissue. The term is intended also to encompass radiotherapy, or any antitumor or anticancer agent.

As used herein, "treatment" or "treating" is an approach for obtaining a beneficial or desired result, such as a clinical result. For purposes of this disclosure, beneficial or desired clinical results include, but are not limited to, alleviation of a symptom and/or diminishment of the extent of a symptom and/or preventing a worsening of a symptom associated with a disease or condition. In one variation, beneficial or desired clinical results include, but are not limited to, alleviation of a symptom and/or diminishment of the extent of a symptom and/or preventing a worsening of a symptom associated with a cognitive disorder, a psychotic disorder, a neurotransmitter-mediated disorder and/or a neuronal disorder. In one embodiment, treatment of a disease or condition with a compound of the disclosure or a pharmaceutically acceptable salt thereof is accompanied by no or fewer side effects than are associated with currently available therapies for the disease or condition and/or improves the quality of life of the individual.

The terms "inhibit," "inhibiting," and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting.

As used herein, by "combination therapy" is meant a therapy that includes two or more different compounds. Thus, in one aspect, a combination therapy comprising a compound detailed herein and anther compound is provided. In some variations, the combination therapy optionally includes one or more pharmaceutically acceptable carriers or excipients, non-pharmaceutically active compounds, and/or inert substances. In various embodiments, treatment with a combination therapy may result in an additive or even synergistic (e.g., greater than additive) result compared to administration of a single compound of the disclosure alone. In some embodiments, a lower amount of each compound is used as part of a combination therapy compared to the amount generally used for individual therapy. In one embodiment, the same or greater therapeutic benefit is achieved using a combination therapy than by using any of the individual compounds alone. In some embodiments, the same or greater therapeutic benefit is achieved using a smaller amount (e.g., a lower dose or a less frequent dosing schedule) of a compound in a combination therapy than the amount generally used for individual compound or therapy. Preferably, the use of a small amount of compound results in a reduction in the number, severity, frequency, and/or duration of one or more side-effects associated with the compound.

As used herein, the term "effective amount" intends such amount of a compound of the disclosure which in combination with its parameters of efficacy and toxicity, as well as based on the knowledge of the practicing specialist should be effective in a given therapeutic form. As is understood in the art, an effective amount may be in one or more doses, i.e., a single dose or multiple doses may be required to achieve the desired treatment endpoint. An effective amount may be considered in the context of administering one or more therapeutic agents, and a single agent may be considered to be given in an effective amount if, in conjunction with one or more other agents, a desirable or beneficial result may be or is achieved. Suitable doses of any of the co-administered compounds may optionally be lowered due to the combined action (e.g., additive or synergistic effects) of the compounds.

As used herein, the term "agonist" refers to a compound, the presence of which results in a biological activity of a protein that is the same as the biological activity resulting from the presence of a naturally occurring ligand for the protein, such as, for example, PARP.

As used herein, the term "partial agonist" refers to a compound the presence of which results in a biological activity of a protein that is of the same type as that resulting from the presence of a naturally occurring ligand for the protein, but of a lower magnitude.

As used herein, the term "antagonist" or "inhibitor" refers to a compound, the presence of which results in a decrease in the magnitude of a biological activity of a protein. In certain embodiments, the presence of an antagonist or inhibitor results in complete inhibition of a biological activity of a protein, such as, for example, the enzyme poly(ADP-ribose) polymerase (PARP). In certain embodiments, the term "inhibitor" refers to a compound, the presence of which results in a decrease in the magnitude of a biological activity of an enzyme, such as, for example, the enzyme poly(ADP-ribose) polymerase (PARP). In certain embodiments, the term "antagonist" refers to a compound, the presence of which results in a decrease in the magnitude of a biological activity of an enzyme, such as, for example, the enzyme poly(ADP-ribose) polymerase (PARP).

As used herein, the $IC_{50}$ refers to an amount, concentration or dosage of a particular test compound that achieves a 50% inhibition of a maximal response, such as modulation of PARP, in an assay that measures such response.

As used herein, $EC_{50}$ refers to a dosage, concentration or amount of a particular test compound that elicits a dose-dependent response at 50% of maximal expression of a particular response that is induced, provoked or potentiated by the particular test compound.

The term "cancer," as used herein refers to an abnormal growth of cells which tend to proliferate in an uncontrolled way and, in some cases, to metastasize (spread). The types of cancer include, but are not limited to, solid tumors (such as those of the bladder, bowel, brain, breast, endometrium, heart, kidney, lung, lymphatic tissue (lymphoma), ovary, pancreas or other endocrine organ (thyroid)), prostate, skin (melanoma) or hematological tumors (such as the leukemias).

The term "carrier," as used herein, refers to relatively nontoxic chemical compounds or agents that facilitate the incorporation of a compound into cells or tissues.

As used herein, "unit dosage form" refers to physically discrete units, suitable as unit dosages, each unit containing a predetermined quantity of active ingredient calculated to produce the desired therapeutic effect in association with the required pharmaceutical carrier. Unit dosage forms may contain a single or a combination therapy.

As used herein, the term "controlled release" refers to a drug-containing formulation or fraction thereof in which release of the drug is not immediate, i.e., with a "controlled release" formulation, administration does not result in immediate release of the drug into an absorption pool. The term encompasses depot formulations designed to gradually release the drug compound over an extended period of time. Controlled release formulations can include a wide variety of drug delivery systems, generally involving mixing the drug compound with carriers, polymers or other compounds having the desired release characteristics (e.g., pH-dependent or non-pH-dependent solubility, different degrees of water solubility, and the like) and formulating the mixture according to the desired route of delivery (e.g., coated capsules, implantable reservoirs, injectable solutions containing biodegradable capsules, and the like).

As used herein, by "pharmaceutically acceptable" or "pharmacologically acceptable" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

"Pharmaceutically acceptable salts" are those salts which retain at least some of the biological activity of the free (non-salt) compound and which can be administered as drugs or pharmaceuticals to an individual. Such salts, for example, include: (1) acid addition salts, formed with inorganic acids such as hydrochloric acid, hydrobromic acid, sulfuric acid, nitric acid, phosphoric acid, and the like; or formed with organic acids such as acetic acid, oxalic acid, propionic acid, succinic acid, maleic acid, tartaric acid, and the like; (2) salts formed when an acidic proton present in the parent compound either is replaced by a metal ion, e.g., an alkali metal ion, an alkaline earth ion, or an aluminum ion; or coordinates with an organic base. Acceptable organic bases include ethanolamine, diethanolamine, triethanolamine, and the like. Acceptable inorganic bases include aluminum hydroxide, calcium hydroxide, potassium hydroxide, sodium carbonate, sodium hydroxide, and the like. Further examples of pharmaceutically acceptable salts include those listed in Berge et al., Pharmaceutical Salts, J. Pharm. Sci. 1977 January; 66(1):1-19. Pharmaceutically acceptable salts can be prepared in situ in the manufacturing process, or by separately reacting a purified compound of the disclosure in its free acid or base form with a suitable organic or inorganic base or acid, respectively, and isolating the salt thus formed during subsequent purification. It should be understood that a reference to a pharmaceutically acceptable salt includes the solvent addition forms or crystal forms thereof, particularly solvates or polymorphs. Solvates contain either stoichiometric or non-stoichiometric amounts of a solvent, and are often formed during the process of crystallization. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

The term "excipient" as used herein means an inert or inactive substance that may be used in the production of a drug or pharmaceutical, such as a tablet containing a compound of the disclosure as an active ingredient. Various substances may be embraced by the term excipient, including without limitation any substance used as a binder, disintegrant, coating, compression/encapsulation aid, cream or lotion, lubricant, solutions for parenteral administration, materials for chewable tablets, sweetener or flavoring, suspending/gelling agent, or wet granulation agent. Binders include, e.g., carbomers, povidone, xanthan gum, etc.; coatings include, e.g., cellulose acetate phthalate, ethylcellulose, gellan gum, maltodextrin, enteric coatings, etc.; compression/encapsulation aids include, e.g., calcium carbonate, dextrose, fructose dc (directly compressible), honey dc, lactose (anhydrate or monohydrate; optionally in combination with aspartame, cellulose, or microcrystalline cellulose), starch dc, sucrose, etc.; disintegrants include, e.g., croscarmellose sodium, gellan gum, sodium starch glycolate, etc.; creams or lotions include, e.g., maltodextrin, carrageenans, etc.; lubricants include, e.g., magnesium stearate, stearic acid, sodium stearyl fumarate, etc.; materials for chewable tablets include, e.g., dextrose, fructose dc, lactose (monohydrate, optionally in combination with aspartame or cellulose), etc.; suspending/gelling agents include, e.g., carrageenan, sodium starch glycolate, xanthan gum, etc.; sweeteners include, e.g., aspartame, dextrose, fructose dc, sorbitol, sucrose dc, etc.; and wet granulation agents include, e.g., calcium carbonate, maltodextrin, microcrystalline cellulose, etc.

Compounds

Provided herein are targeted compounds for treating cancer. The compounds described herein are capable of targeting the nucleus of a cell by recognition and binding of a nuclear receptor-targeting epitope to the respective binding site and delivering the nuclear payload to the nucleus of the cell. The nuclear payload then is capable of binding to one or more target sites within the nucleus and/or disrupting one or more cellular processes, causing the cell to die. In certain embodiments, the nuclear payload is bonded to the nuclear receptor-targeting epitope(s) via a linking moiety. In certain embodiments, the linking moiety provides a single or mono-linkage, meaning that the linker is only conjugated to one atom of each of the payload and the epitope.

In certain embodiments, the compound as described herein is binds to a poly(ADP-ribose) and/or inhibits the activity of polymerase-1 (e.g., PARP-1) and/or PARP-2 with an $IC_{50}$ of less than about 500 nM, or less than about 400 nM, or less than about 350 nM, or less than about 300 nM, or less than about 200 nM, or less than about 100 nM, or less than about 50 nM. In some embodiments, a compound of this invention has higher affinity and/or enzyme inhibitory potency for PARP-1 compared to PARP-2. In some embodiments, the potency and/or affinity ratio of PARP binding and or PARP inhibitory activity indicates that its activity against PARP-1 is greater than 5 times; greater than 10 times; greater than 20 times; greater than 30 times; greater than 50 times; or 100 times the potency and/or inhibitory activity against PARP-2.

Provided herein is a compound of Formula I:

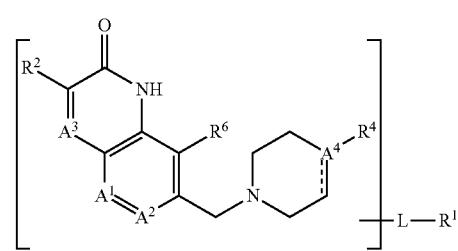

or a tautomer, stereoisomer, mixture of stereoisomers, hydrate, solvate, isotopically enriched analog, or pharmaceutically acceptable salt thereof, wherein:

$A^1$ is CH or N;

$A^2$ is CH or N;

$A^3$ is N or $CR^3$;

$A^4$ is C and === is a double bond, or $A^4$ is CH and === is a single bond, or $A^4$ is N and === is a single bond;

L is a covalent bond or a linking moiety;

$R^1$ is a nuclear receptor-targeting epitope;

$R^2$ is hydrogen, $C_{1-6}$ alkyl, $C_{1-6}$ haloalkyl, $C_{1-6}$ alkoxy, or $C_{3-6}$ cycloalkyl;

$R^3$ is hydrogen or halo; or $R^2$ and $R^3$ together with the atoms to which they are attached form a 6-membered heterocyclyl or 6-membered heteroaryl;

$R^4$ is hydrogen, aryl, or heteroaryl, wherein the aryl or heteroaryl is optionally substituted with one to five $R^5$;

each $R^5$ is independently halo, cyano, nitro, —$OR^{10}$, —$OC(O)R^{10}$, —$C(O)OR^{10}$, —$SR^{10}$, —$NR^{10}R^{11}$, —$NR^{10}C(O)R^{11}$, —$C(O)NR^{10}R^{11}$, $C_{1-12}$ alkyl, $C_{1-12}$ haloalkyl, $C_{2-12}$ alkenyl, or $C_{2-12}$ alkynyl; wherein each $C_{1-12}$ alkyl, $C_{1-12}$ haloalkyl, $C_{2-12}$ alkenyl, or $C_{2-12}$ alkynyl is independently optionally substituted with one to five halo, hydroxyl or amino;

$R^6$ is hydrogen, halo, or $C_{1-6}$ alkyl; and each $R^{10}$ and $R^{11}$ is independently hydrogen or $C_{1-12}$ alkyl optionally substituted with oxo, halo, hydroxyl, or amino as valency permits; or $R^{10}$ and $R^{11}$ are taken together with the atoms to which they are attached to form heterocyclyl optionally substituted by halo or $C_{1-12}$ alkyl optionally substituted by oxo, halo, hydroxyl, or amino;

wherein any hydrogen atom of the moiety in the brackets is replaced with -L-$R^1$.

In certain embodiments, $R^6$ is hydrogen. In certain embodiments, $R^6$ is halo. In certain embodiments, $R^6$ is fluoro. In certain embodiments, $R^6$ is $C_{1-6}$ alkyl. In certain embodiments, $R^6$ is methyl.

In certain embodiments, provided herein is a compound of Formula II:

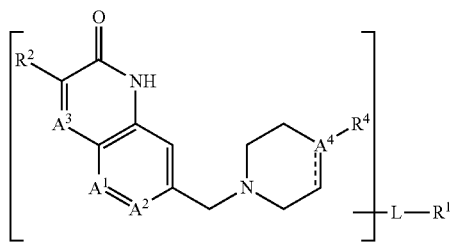

II or a tautomer, stereoisomer, mixture of stereoisomers, hydrate, solvate, isotopically enriched analog, or pharmaceutically acceptable salt thereof, wherein:

$A^1$ is CH or N;
$A^2$ is CH or N;
$A^3$ is N or $CR^3$;
$A^4$ is C and === is a double bond, or $A^4$ is CH and === is a single bond, or $A^4$ is N and === is a single bond;
L is a covalent bond or a linking moiety;
$R^1$ is a nuclear receptor-targeting epitope;
$R^2$ is $C_{1-6}$ alkyl;
$R^3$ is hydrogen; or
$R^2$ and $R^3$ together with the atoms to which they are attached form a 6-membered heterocyclyl or 6-membered heteroaryl;
$R^4$ is hydrogen, aryl, or heteroaryl, wherein the aryl or heteroaryl is optionally substituted with one to five $R^5$;
each $R^5$ is independently halo, cyano, nitro, —$OR^{10}$, —$OC(O)R^{10}$, —$C(O)OR^{10}$, —$SR^{10}$, —$NR^{10}R^{11}$, —$NR^{10}C(O)R^{11}$, —$C(O)NR^{10}R^{11}$, $C_{1-12}$ alkyl, $C_{1-12}$ haloalkyl, $C_{2-12}$ alkenyl, or $C_{2-12}$ alkynyl; wherein each $C_{1-12}$ alkyl, $C_{1-12}$ haloalkyl, $C_{2-12}$ alkenyl, or $C_{2-12}$ alkynyl is independently optionally substituted with one to five halo, hydroxyl, or amino; and each $R^{10}$ and $R^{11}$ is independently hydrogen or $C_{1-12}$ alkyl optionally substituted with oxo, halo, hydroxyl or amino as valency permits; or $R^{10}$ and $R^{11}$ are taken together with the atoms to which they are attached to form heterocyclyl optionally substituted by halo or $C_{1-12}$ alkyl optionally substituted by oxo, halo, hydroxyl, or amino;

wherein any hydrogen atom of the moiety in the brackets is replaced with -L-$R^1$.

In certain embodiments, $A^1$ is CH. In certain embodiments, $A^1$ is N.

In certain embodiments, $A^2$ is CH. In certain embodiments, $A^2$ is N.

In certain embodiments, $A^3$ is CH. In certain embodiments, $A^3$ is N.

In certain embodiments, $A^3$ is $CR^3$, and $R^2$ and $R^3$ together with the atoms to which they are attached form a 6-membered heterocyclyl or 6-membered heteroaryl.

In certain embodiments, $A^4$ is C and === is a double bond. In certain embodiments, $A^4$ is C and === is a single bond. In certain embodiments, $A^4$ is N and === is a single bond.

In certain embodiments, L is a covalent bond. In certain embodiments, a linking moiety.

In certain embodiments, $R^2$ is ethyl.

In certain embodiments, $R^4$ is hydrogen. In certain embodiments, $R^4$ is aryl optionally substituted with one to five $R^5$. In certain embodiments, $R^4$ is heteroaryl optionally substituted with one to five $R^5$. In certain embodiments, $R^4$ is a 6-10-membered aryl optionally substituted with one to five $R^5$. In certain embodiments, $R^4$ is phenyl optionally substituted with one to five $R^5$. In certain embodiments, $R^4$ is a 5-10-membered heteroaryl optionally substituted with one to five $R^5$. In certain embodiments, $R^4$ is a 6-membered heteroaryl optionally substituted with one to five $R^5$. In certain embodiments, $R^4$ is pyridyl optionally substituted with one to five $R^5$.

In certain embodiments, provided is a compound of Formula IA:

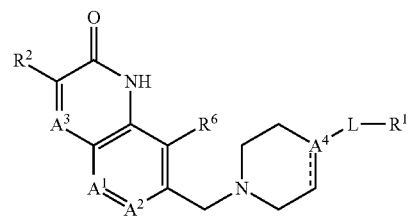

IA or a tautomer, stereoisomer, mixture of stereoisomers, hydrate, solvate, isotopically enriched analog, or pharmaceutically acceptable salt thereof, wherein each of L, $R^1$, $R^2$, $A^1$, $A^2$, $A^3$, $A^4$, and === are independently as defined herein.

In certain embodiments, provided is a compound of Formula IB:

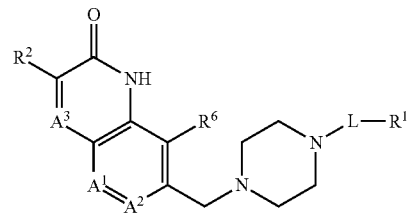

IB or a tautomer, stereoisomer, mixture of stereoisomers, hydrate, solvate, isotopically enriched analog, or pharmaceutically acceptable salt thereof, wherein each of L, $R^1$, $R^2$, $A^1$, $A^2$, and $A^3$ are independently as defined herein.

In certain embodiments, provided is a compound of Formula IIA:

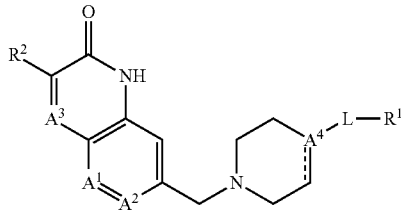

IIA or a tautomer, stereoisomer, mixture of stereoisomers, hydrate, solvate, isotopically enriched analog, or pharmaceutically acceptable salt thereof, wherein each of L, $R^1$, $R^2$, $A^1$, $A^2$, $A^3$, $A^4$, and, ≕ are independently as defined herein.

In certain embodiments, provided is a compound of Formula IIB:

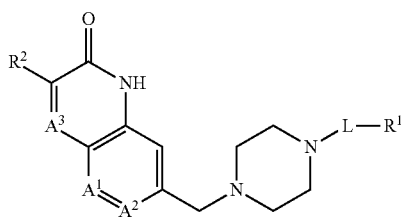

IIb or a tautomer, stereoisomer, mixture of stereoisomers, hydrate, solvate, isotopically enriched analog, or pharmaceutically acceptable salt thereof, wherein each of L, $R^1$, $R^2$, $A^1$, $A^2$, and $A^3$ are independently as defined herein.

In certain embodiments, $R^2$ is hydrogen.

In certain embodiments, $R^2$ is $C_{1-6}$ alkyl.

In certain embodiments, $R^2$ is $C_{1-6}$ alkoxy.

In certain embodiments, $R^2$ is $C_{1-6}$ haloalkyl. In certain embodiments, $R^2$ is $C_{1-6}$ fluoroalkyl. In certain embodiments, $R^2$ is $C_{1-4}$ fluoroalkyl.

In certain embodiments, $R^2$ is $C_{3-6}$ cycloalkyl.

In certain embodiments, $R^3$ is hydrogen.

In certain embodiments, $R^3$ is halo.

In certain embodiments, $R^3$ is fluoro.

In certain embodiments, $R^2$ is $C_{1-6}$ alkyl, and $R^3$ is hydrogen.

In certain embodiments, provided is a compound of Formula IC:

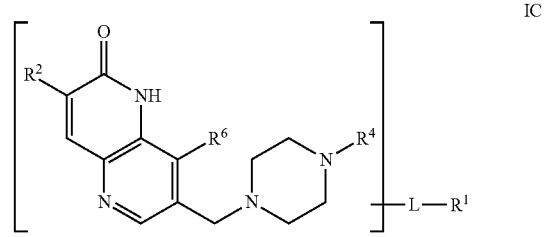

IC or a tautomer, stereoisomer, mixture of stereoisomers, hydrate, solvate, isotopically enriched analog, or pharmaceutically acceptable salt thereof, wherein each of L, $R^1$, $R^2$, and $R^4$ are independently as defined herein.

In certain embodiments, provided is a compound of Formula ID:

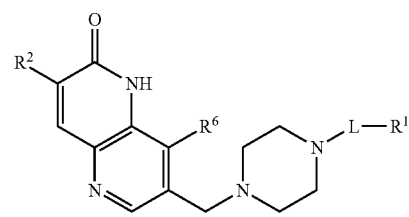

ID

Or a tautomer, stereoisomer, mixture of stereoisomers, hydrate, solvate, isotopically enriched analog, or pharmaceutically acceptable salt thereof, wherein each of L, $R^1$, and $R^2$ are independently as defined herein.

In certain embodiments, provided is a compound of Formula IE:

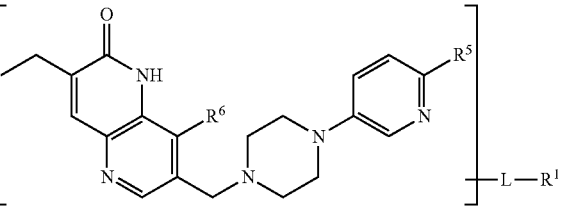

IE or a tautomer, stereoisomer, mixture of stereoisomers, hydrate, solvate, isotopically enriched analog, or pharmaceutically acceptable salt thereof, wherein each of L, $R^1$, and $R^5$ are independently as defined herein.

In certain embodiments, provided is a compound of Formula IF:

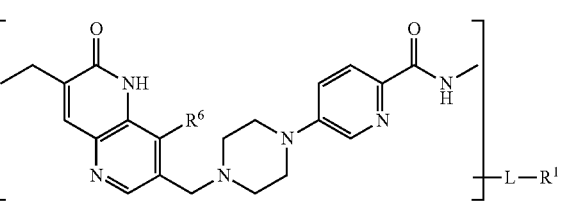

IF or a tautomer, stereoisomer, mixture of stereoisomers, hydrate, solvate, isotopically enriched analog, or pharmaceutically acceptable salt thereof, wherein each of L and R¹ are independently as defined herein.

In certain embodiments, provided is a compound of Formula IG:

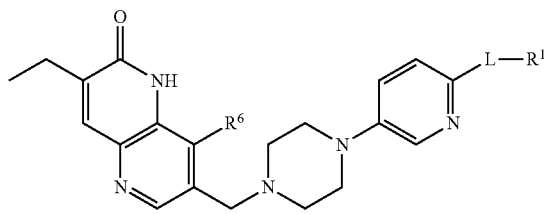

IG or a tautomer, stereoisomer, mixture of stereoisomers, hydrate, solvate, isotopically enriched analog, or pharmaceutically acceptable salt thereof, wherein each of L and R¹ are independently as defined herein.

In certain embodiments, provided is a compound of Formula IIC:

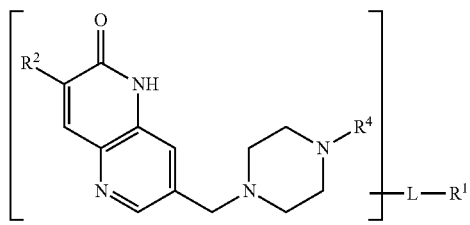

IIC or a tautomer, stereoisomer, mixture of stereoisomers, hydrate, solvate, isotopically enriched analog, or pharmaceutically acceptable salt thereof, wherein each of L, R¹, R², and R⁴ are independently as defined herein.

In certain embodiments, provided is a compound of Formula IID:

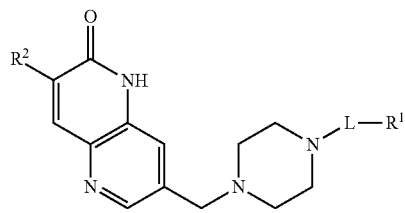

IID or a tautomer, stereoisomer, mixture of stereoisomers, hydrate, solvate, isotopically enriched analog, or pharmaceutically acceptable salt thereof, wherein each of L, R¹, and R² are independently as defined herein.

In certain embodiments, provided is a compound of Formula IIE:

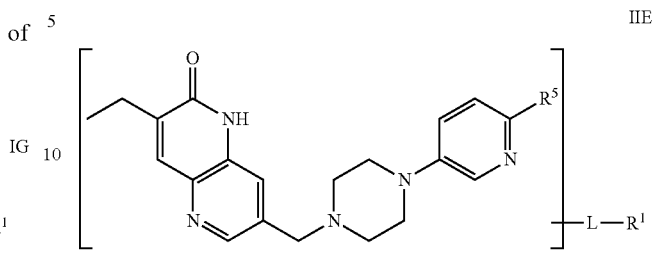

IIE or a tautomer, stereoisomer, mixture of stereoisomers, hydrate, solvate, isotopically enriched analog, or pharmaceutically acceptable salt thereof, wherein each of L, R¹, and R⁵ are independently as defined herein.

In certain embodiments, provided is a compound of Formula IIF:

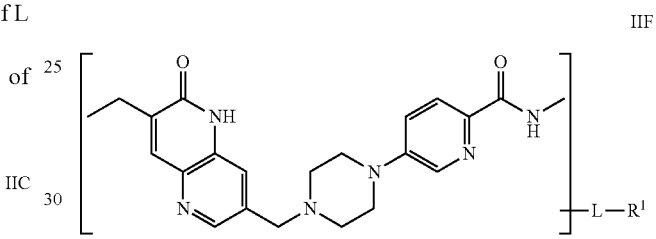

IIF or a tautomer, stereoisomer, mixture of stereoisomers, hydrate, solvate, isotopically enriched analog, or pharmaceutically acceptable salt thereof, wherein each of L and R¹ are independently as defined herein.

In certain embodiments, provided is a compound of Formula IIG:

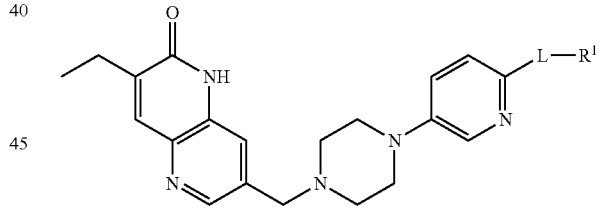

IIG or a tautomer, stereoisomer, mixture of stereoisomers, hydrate, solvate, isotopically enriched analog, or pharmaceutically acceptable salt thereof, wherein each of L and R¹ are independently as defined herein.

In certain embodiments, provided is a compound of Formula IA:

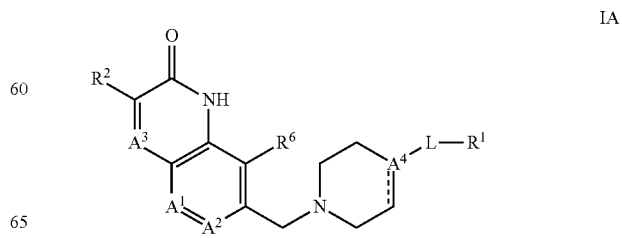

IA or a tautomer, stereoisomer, mixture of stereoisomers, hydrate, solvate, isotopically enriched analog, or pharmaceutically acceptable salt thereof, wherein:

$A^1$ is CH or N;
$A^2$ is CH or N;
$A^3$ is N or $CR^3$;
$A^4$ is C and === is a double bond, or $A^4$ is CH and === is a single bond, or $A^4$ is N and === is a single bond;
L is a covalent bond or a linking moiety;
$R^1$ is a nuclear receptor-targeting epitope;
$R^2$ is hydrogen, $C_{1-6}$ alkyl, $C_{1-6}$ haloalkyl, $C_{1-6}$ alkoxy, or $C_{3-6}$ cycloalkyl;
$R^3$ is hydrogen or halo; or
$R^2$ and $R^3$ together with the atoms to which they are attached form a 6-membered heterocyclyl or 6-membered heteroaryl;
$R^4$ is hydrogen, aryl, or heteroaryl, wherein the aryl or heteroaryl is optionally substituted with one to five $R^5$;
each $R^5$ is independently halo, cyano, nitro, $-OR^{10}$, $-OC(O)R^{10}$, $-C(O)OR^{10}$, $-SR^{10}$, $-NR^{10}R^{11}$, $-NR^{10}C(O)R^{11}$, $-C(O)NR^{10}R^{11}$, $C_{1-12}$ alkyl, $C_{1-12}$ haloalkyl, $C_{2-12}$ alkenyl, or $C_{2-12}$ alkynyl; wherein each $C_{1-12}$ alkyl, $C_{1-12}$ haloalkyl, $C_{2-12}$ alkenyl, or $C_{2-12}$ alkynyl is independently optionally substituted with one to five halo, hydroxyl or amino;
$R^6$ is hydrogen, halo, or $C_{1-6}$ alkyl; and
each $R^{10}$ and $R^{11}$ is independently hydrogen or $C_{1-12}$ alkyl optionally substituted with oxo, halo, hydroxyl, or amino as valency permits; or $R^{10}$ and $R^{11}$ are taken together with the atoms to which they are attached to form heterocyclyl optionally substituted by halo or $C_{1-12}$ alkyl optionally substituted by oxo, halo, hydroxyl, or amino;
$R^1$ is:

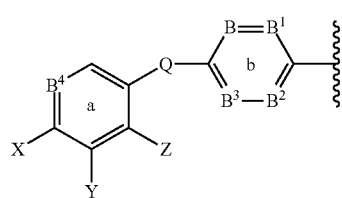

wherein:
Q is

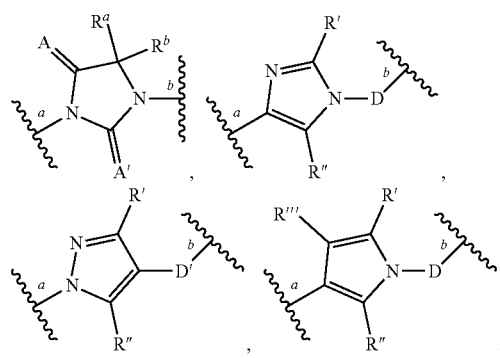

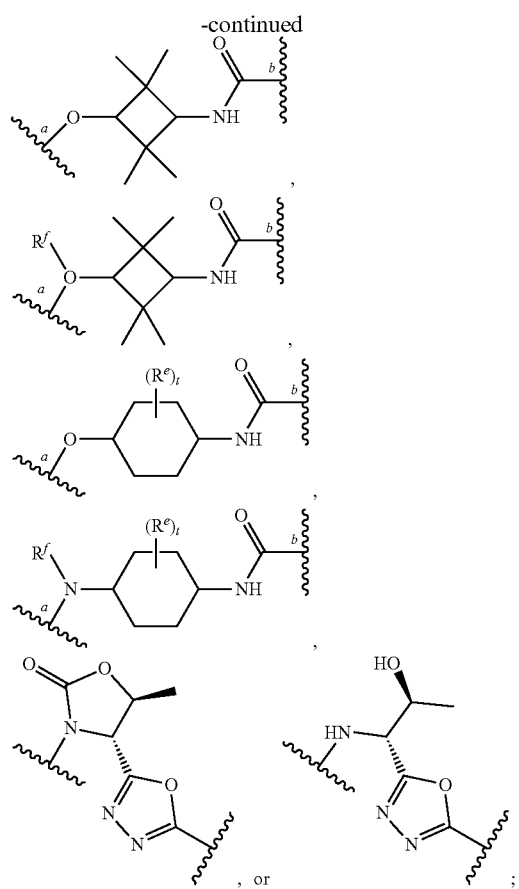

wherein bond a is attached to ring a and bond b is attached to ring b;
$R^a$ and $R^b$ are each independently $CH_3$ or $CH_2CH_3$; or $R^a$ and $R^b$ together with the atom to which they are attached form a $C_{3-5}$ cycloalkyl, oxiranyl, oxetanyl, or tetrahydrofuranyl;
A and A' are each independently O or S;
B, $B^1$, $B^2$, and $B^3$ are each independently $CR^c$ or N, and each $R^c$ is independently hydrogen, halo, CN, or methyl;
$B^4$ is CF, CH, or N;
D is a bond, $CH_2$, C=O, or (C=O)NH;
D' is NH, O, S, $CH_2$, NH(C=O), C(=O)NH, or C=O;
R', R" and R'" are each independently hydrogen, CN, or $C_{1-2}$ alkyl;
t is 0, 1, 2, 3 or 4;
each $R^e$ is independently halo, cyano, $C_{1-4}$ alkyl, or $C_{1-4}$ haloalkyl;
$R^f$ is hydrogen, $C_{1-4}$ alkyl, or $C_{3-6}$ cycloalkyl;
X is halo, CN, or $NO_2$;
Y is halo, $CH_3$, $CH_2F$, $CHF_2$, or $CF_3$; or
X and Y together form a

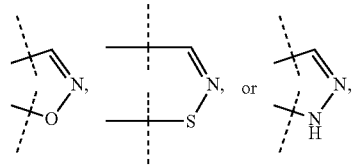

where the broken lines indicate bonds to ring a;
Z is hydrogen, halo, $C_{1-2}$ alkyl, $C_2$ alkenyl, $NO_2$, $CF_3$; or Y and Z together form a

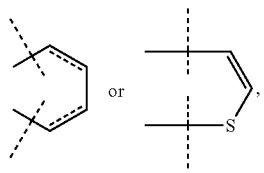

wherein each ═══ is a single or double bond, and where the broken lines indicate bonds to ring a; and L is a 1-12 chain atom alkylene or 2-12 chain atom heteroalkylene linking moiety, containing 0-3 substituted or unsubstituted cycloalkylene, 0-3 substituted or unsubstituted heterocyclylene, 0-3 substituted or unsubstituted heteroarylene, 0-3 substituted or unsubstituted arylene, and 0-2 C═O.

Nuclear Receptor-Targeting Epitopes

In certain embodiments, $R^1$ is a nuclear hormone receptor-targeting epitope. In certain embodiments, $R^1$ is a nuclear steroid receptor-targeting epitope. As used herein, "nuclear receptor-targeting epitope" refers to the portion of the compound described herein (e.g., $R^1$) which portion is derived from a nuclear targeting agent as disclosed herein and interacts with a ligand-binding domain of the target nuclear receptor, i.e., the portion of the compound which drives a ligand-binding interaction. In some embodiments, the nuclear target epitope binds to a non-ligand binding domain of the receptor. Not wishing to be bound by theory, the nuclear receptor-targeting epitope serves to associate the compound with a target nuclear receptor, e.g. a nuclear steroid receptor, facilitate the localization of compound to nuclear steroid receptor-expressing cells, and translocate the nuclear payload from the cytosol to nucleus, allowing the compound to accumulate in the nucleus. The level of accumulation can be controlled by selecting the appropriate nuclear receptor-targeting epitope. For example, the compounds described herein can accumulate in the nucleus to varying degrees, high in the case of a full agonist (e.g., dihydrotestosterone (DHT)), moderate in the case of a partial agonist (e.g., bicalutamide), and low, in the case of antagonists (e.g., enzalutamide), through nuclear translocation of the nuclear steroid receptor which happens, following epitope binding to the receptor.

The steroid receptor target can be any steroid receptor, including, but not limited to, those which are over-expressed in cancer cells. In certain embodiments, at least one nuclear steroid receptor-targeting epitope is capable of binding to a ligand binding domain of a nuclear steroid receptor, such as a ligand binding domain on an estrogen receptor, glucocorticoid receptor, progesterone receptor, or androgen receptor.

Exemplary nuclear steroid receptor-targeting epitopes include those derived from an androgen receptor agonist, an androgen receptor antagonist, a selective androgen-receptor modulator (SARM), an estrogen receptor agonist, an estrogen receptor antagonist, a selective estrogen receptor modulator (SERM), a glucocorticoid receptor antagonist, a glucocorticoid receptor agonist, a selective glucocorticoid receptor modulator (SGRM), a progesterone receptor antagonist, a progesterone receptor agonist, a selective progesterone receptor modulator (SPRM), or a combination thereof.

The nuclear steroid receptor-targeting epitopes are typically capable of binding to a nuclear steroid receptor with an $IC_{50}$ of less than about 500 nM, or less than about 400 nM, or less than about 300 nM, or less than about 200 nM, or less than about 100 nM, or with an $EC_{50}$ of less than about 1 µM, or less than about 900 nM, or less than about 800 nM, or less than about 700 nM, or less than about 600 nM, or less than about 500 nM, or less than about 400 nM, or less than about 3400 nM, or less than about 200 nM, or less than about 100 nM.

In certain embodiments, the nuclear hormone receptor binding affinity of a compound of this disclosure can be defined according to its affinity relative to a reference nuclear hormone receptor binding compound.

In certain embodiments, compounds of this disclosure can bind to a mammalian (e.g., human) androgen receptor. In some instances, a compound disclosed herein binds the human androgen receptor with an affinity of at least 0.1%, 1%, 5%, 10%, 20%, 30%, 40%, 50%, 60%, 70%, 80%, 90%, or 100% of that of dihydrotestosterone (DHT). In certain embodiments, the nuclear steroid receptor-targeting epitope (e.g., $R^1$) is an agonist at the androgen receptor. In certain embodiments, the nuclear steroid receptor-targeting epitope is an antagonist at the androgen receptor and/or partial agonist/antagonist at the androgen receptor. In certain embodiments, the AR-targeting epitope binds the androgen receptor with an affinity >1% of testosterone; >2%; >5%; >10%; >25%; >50%; >100%.

In certain embodiments, compounds of this disclosure can bind to the estrogen receptor. In some instances, a compound disclosed herein binds a mammalian (e.g., human) estrogen receptor with an affinity of at least 0.1%, 1%, 5%, 10%, 20%, 30%, 40%, 50%, 60%, 70%, 80%, 90%, or 100% of that of 17β-estradiol. In certain embodiments, the nuclear steroid receptor-targeting epitope (e.g., $R^1$) is an agonist at the estrogen receptor. In certain embodiments, the nuclear steroid receptor-targeting epitope is an antagonist and/or partial antagonist at the estrogen receptor. In certain embodiments, the ER-targeting epitope binds the estrogen receptor with an affinity >1% of 17b-estradiol; >2%; >5%; >10%; >25%; >50%; >100%. In certain embodiments, compounds of this disclosure can bind to a mammalian (e.g., human) progestin receptor. In some instances, a compound disclosed herein binds the progestin receptor with an affinity of at least 0.1%, 1%, 5%, 10%, 20%, 30%, 40%, 50%, 60%, 70%, 80%, 90%, or 100% of that of progesterone. In certain embodiments, the nuclear steroid receptor-targeting epitope (e.g., $R^1$) is an agonist at the progestin receptor. In certain embodiments, the nuclear steroid receptor-targeting epitope is an antagonist and/or partial antagonist at the progestin receptor. In certain embodiments, the PR-targeting epitope binds the progestin receptor with an affinity >1% of progesterone; >2%; >5%; >10%; >25%; >50%; >100%.

In certain embodiments, compounds of this disclosure can bind to a mammalian (e.g., human) glucocorticoid receptor. In some instances, a compound disclosed herein binds the glucocorticoid receptor with an affinity of at least 0.1%, 1%, 5%, 10%, 20%, 30%, 40%, 50%, 60%, 70%, 80%, 90%, or 100% of that of cortisone. In certain embodiments, the nuclear steroid receptor-targeting epitope (e.g., $R^1$) is an agonist at the glucocorticoid receptor. In certain embodiments, the nuclear steroid receptor-targeting epitope is an antagonist and/or partial antagonist at the glucocorticoid receptor. In certain embodiments, the GR-targeting epitope binds the glucocorticoid receptor with an affinity >1% of cortisol; >2%; >5%; >10%; >25%; >50%; >100%.

In certain embodiments, the nuclear steroid receptor-targeting epitope (e.g., R') is steroidal (e.g., dihydrotestosterone). In certain embodiments, the nuclear steroid receptor-targeting epitope is non-steroidal (e.g., enzalutamide, apalutamide, AZD9496, and bicalutamide).

The analogs are derived from the known nuclear steroid receptor-targeting epitope described herein (e.g., R') and are modified to be conjugated to at least one nuclear steroid payload, optionally via a linking moiety. The analogs, even after modification to arrive at the compounds described herein, maintain biological activity, which is comparable to that observed in the original, unmodified nuclear steroid receptor-targeting epitope. In certain embodiments, the compounds exhibit a binding activity or inhibition which is at least about 98%, about 95%, about 90%, about 85%, about 80%, about 75%, about 70%, about 65%, about 60%, about 55%, or about 50%, or about 5-50% of that observed in the original, unmodified nuclear steroid receptor-targeting epitope.

In certain embodiments, the analogs are derived from a known nuclear receptor-targeting epitope (e.g., $R^1$), such as a known nuclear steroid receptor-targeting epitope. In certain embodiments, the term "derived from" as used in reference to a nuclear receptor-targeting epitope, means that at most, one non-hydrogen atom of an original, unmodified nuclear receptor-targeting compound (i.e., a known nuclear steroid receptor-targeting compound) is replaced by a covalent bond to the nuclear payload, optionally via a linking moiety. Exemplary non-hydrogen atoms include, but are not limited to, —CH$_3$, —OH, =O, and —NH$_2$.

In certain embodiments, the term "derived from" as used in reference to a nuclear receptor-targeting epitope, means that at most, one non-hydrogen atom of an original, unmodified nuclear receptor-targeting compound (i.e., a known nuclear steroid receptor-targeting compound) is replaced by a covalent bond to the nuclear payload, optionally via a linking moiety. In certain embodiments, one hydrogen atom bound to a heteroatom (e.g., N, O, or S) of the original, unmodified nuclear receptor-targeting compound (i.e., a known nuclear steroid receptor-targeting compound) is replaced by a covalent bond to the nuclear payload, optionally via a linking moiety.

In certain embodiments, a single atom on the nuclear receptor-targeting epitope ($R^1$) as disclosed herein is replaced for attachment to the remainder of the compound (e.g., the moiety -L-$R^1$). In certain embodiments, a halogen atom on a nuclear receptor-targeting epitope disclosed herein is replaced for attachment to the remainder of the compound. In certain embodiments, a hydrogen atom on a nuclear receptor-targeting epitope disclosed herein is replaced for attachment to the remainder of the compound. In certain embodiments, the hydrogen atom is on a heteroatom. In certain embodiments, the hydrogen atom is on a nitrogen. In certain embodiments, the hydrogen atom is on an oxygen. In certain embodiments, the hydrogen atom is on a carbon.

In certain embodiments, the nuclear steroid receptor-targeting epitope (e.g., $R^1$) is an androgen receptor-targeting epitope. As used herein, the term "androgen receptor-targeting epitope" is intended to refer to the portion of the compound which binds to an androgen receptor agonist or androgen receptor antagonist (including partial androgen receptor agonists or partial androgen receptor antagonists) and which is capable of shuttling a compound from the cytoplasm into the nucleus of a cell. The "androgen receptor" (AR), also known as NR3C4 (nuclear receptor subfamily 3, group C, member 4), is a type of nuclear receptor that, when activated by binding an androgen receptor binder (e.g., an androgenic hormone such as testosterone, or dihydrotestosterone) in the cytoplasm, is capable of translocating the androgenic hormone into the nucleus.

Exemplary androgen receptor-targeting epitopes which can be used in the compounds described herein include (e.g., $R^1$) but are not limited to, an androgen receptor agonist, a selective androgen-receptor modulator (SARM) (e.g., enobosarm), an androgen receptor antagonist (e.g., bicalutamide, flutamide, nilutamide, or enzalutamide), a selective estrogen receptor modulator (SERM) (e.g., tamoxifen, toremifene, or raloxifene), an estrogen receptor antagonist (e.g., fulvestrant), a progestin (e.g., megestrol acetate), an estrogen (e.g., estramustine), ketoconazole, abiraterone, darolutamide, or an analog thereof.

In certain embodiments, the nuclear steroid receptor-targeting epitope (e.g., R') is a selective androgen receptor modulator (SARM). In certain embodiments, the compound comprises at least one nuclear steroid receptor-targeting epitope independently comprises an epitope derived from testosterone, a testosterone ester (e.g., testosterone enanthate, propionate, cypionate, etc., or an analog thereof), enobosarm, BMS-564929, PS178990, LGD-4033 (ligandrol), LGD-2941, AC-262,356, JNJ-28330835, JNJ-37654032, JNJ-26146900, LGD-2226, LGD-3303, LGD-121071, LG-120907, S-40503, S-23, testolone (RAD-140), acetothiolutamide, andarine (S-4), LG-121071, TFM-4AS-1, YK-11, MK-0773 (PF-05314882), GSK2849466, GSK2881078, GSK8698, GSK4336, ACP-105, TT701, LY2452473 (TT-701), 1-(2-hydroxy-2-methyl-3-phenoxy-propanoyl)-indoline-4-carbonitrile-derivatives (J Med Chem. 2014, 57(6), 2462-71), or an analog thereof.

In certain embodiments, $R^1$ is:

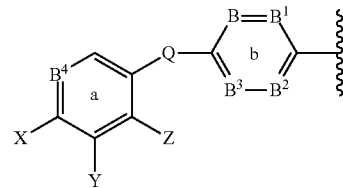

wherein:

Q is

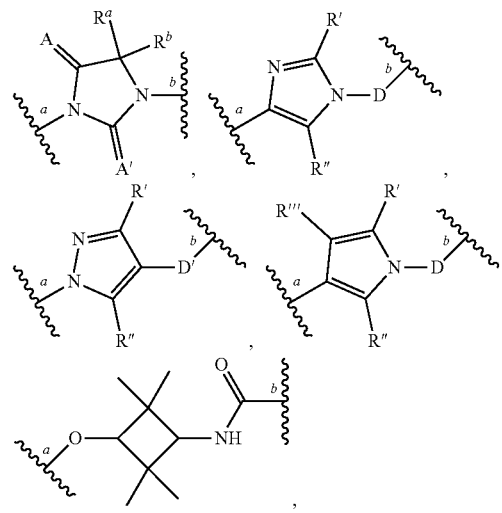

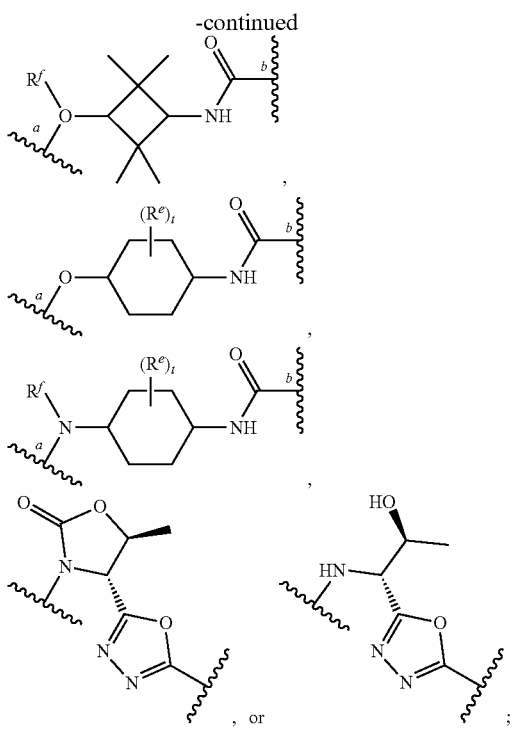

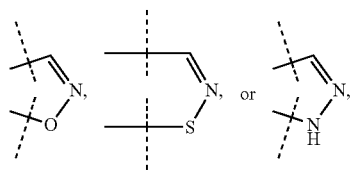

where the broken lines indicate bonds to ring a;
Z is hydrogen, halo, $C_{1-2}$ alkyl, $C_2$ alkenyl, $NO_2$, $CF_3$; or
Y and Z together form a

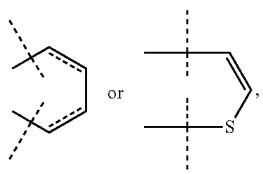

wherein each ═══ is a single or double bond, and where the broken lines indicate bonds to ring a.

In certain embodiments, $R^1$ is:

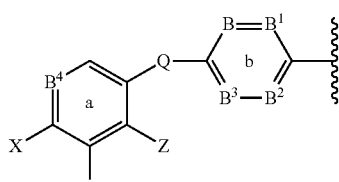

wherein:
Q is

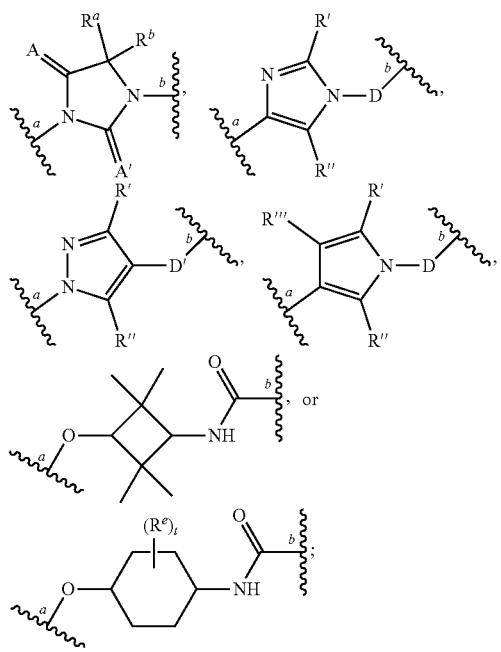

wherein bond a is attached to ring a and bond b is attached to ring b;

$R^a$ and $R^b$ are each independently $CH_3$ or $CH_2CH_3$; or $R^a$ and $R^b$ together with the atom to which they are attached form a $C_{3-5}$ cycloalkyl, oxiranyl, oxetanyl, or tetrahydrofuranyl;

A and A' are each independently O or S;

B, $B^1$, $B^2$, and $B^3$ are each independently $CR^c$ or N, and each $R^c$ is independently hydrogen, halo, CN, or methyl;

$B^4$ is CF, CH or N;

D is a bond, $CH_2$, C═O, or (C═O)NH;

D' is NH, O, S, $CH_2$, NH(C═O), C(═O)NH, or C═O;

R', R" and R'" are each independently hydrogen, CN, or $C_{1-2}$ alkyl;

wherein bond a is attached to ring a and bond b is attached to ring b;

$R^a$ and $R^b$ are each independently $CH_3$ or $CH_2CH_3$; or $R^a$ and $R^b$ together with the atom to which they are attached form a $C_{3-5}$ cycloalkyl, oxiranyl, oxetanyl, or tetrahydrofuranyl;

A and A' are each independently O or S;

B, $B^1$, $B^2$, and $B^3$ are each independently $CR^c$ or N, and each $R^c$ is independently hydrogen, halo, CN, or methyl;

$B^4$ is CF, CH, or N;

D is a bond, $CH_2$, C═O, or (C═O)NH;

D' is NH, O, S, $CH_2$, NH(C═O), C(═O)NH, or C═O;

R', R" and R'" are each independently hydrogen, CN, or $C_{1-2}$ alkyl;

t is 0, 1, 2, 3 or 4;

each $R^e$ is independently halo, cyano, $C_{1-4}$ alkyl, or $C_{1-4}$ haloalkyl;

$R^f$ is hydrogen, $C_{1-4}$ alkyl, or $C_{3-6}$ cycloalkyl;

X is halo, CN, or $NO_2$;

Y is halo, $CH_3$, $CH_2F$, $CHF_2$, or $CF_3$; or

X and Y together form a t is 0, 1, 2, 3 or 4;

each $R^e$ is independently halo, cyano, $C_{1-4}$ alkyl, or $C_{1-4}$ haloalkyl;

X is halo, CN, or $NO_2$;

Y is halo, $CH_3$, $CH_2F$, $CHF_2$, or $CF_3$; or

X and Y together form a

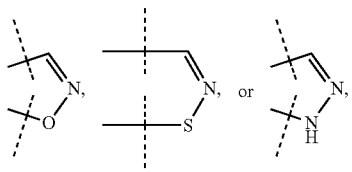

where the broken lines indicate bonds to ring a;

Z is hydrogen, halo, $C_{1-2}$ alkyl, $C_2$ alkenyl, $NO_2$, $CF_3$; or

Y and Z together form a

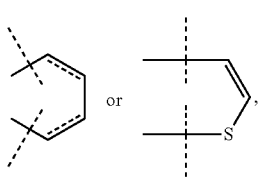

wherein each ═══ is a single or double bond, and where the broken lines indicate bonds to ring a.

In certain embodiments, $R^1$ is:

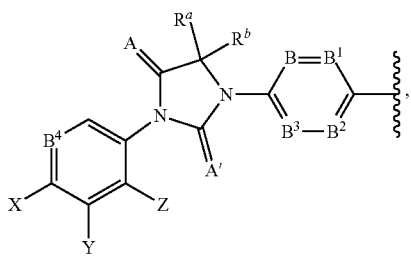

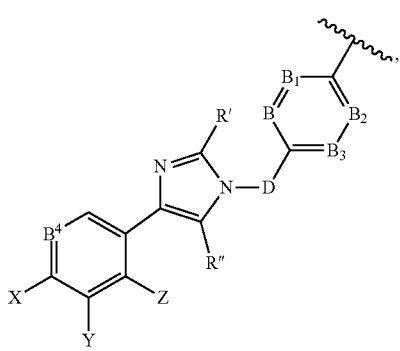

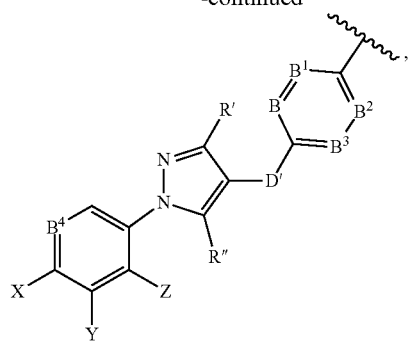

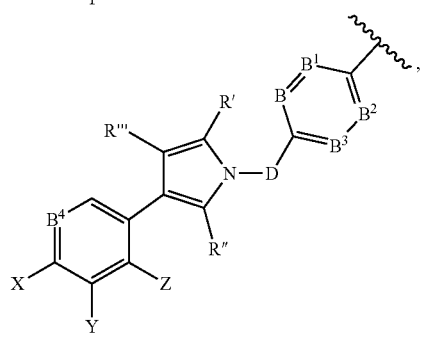

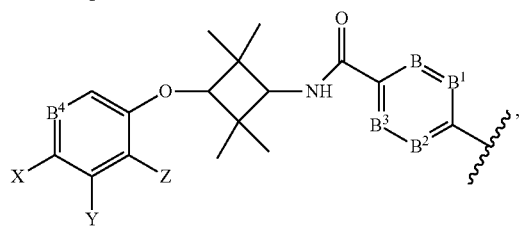

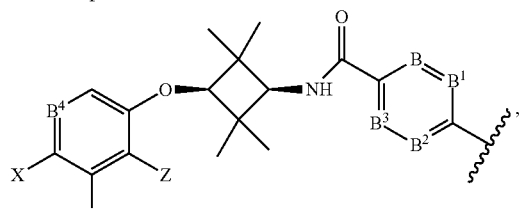

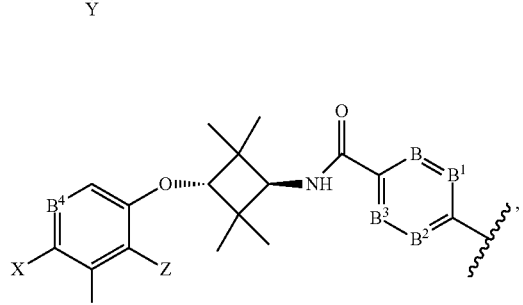

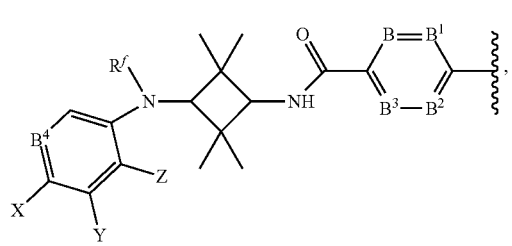

-continued
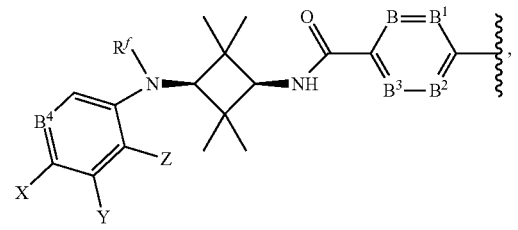
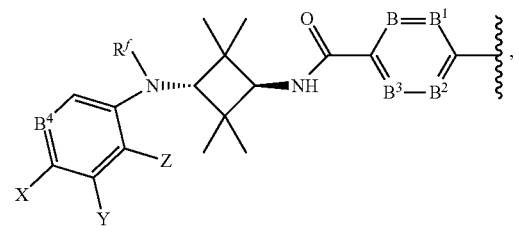
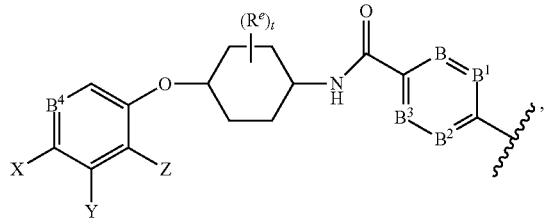
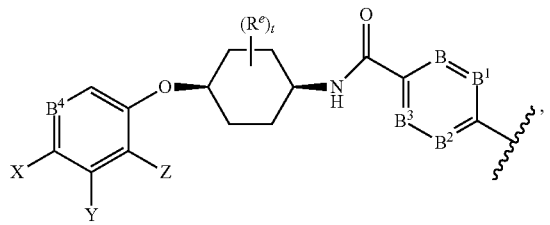
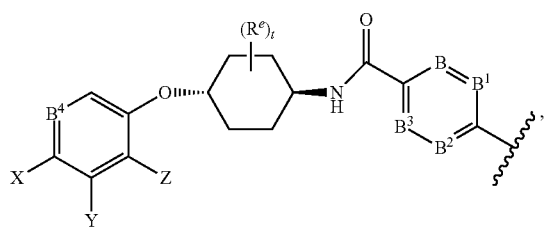
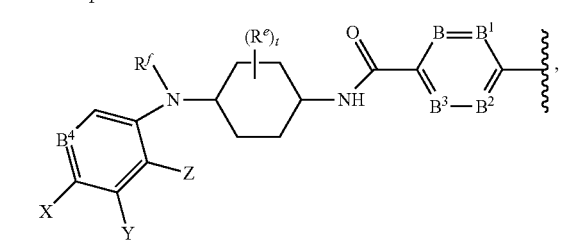
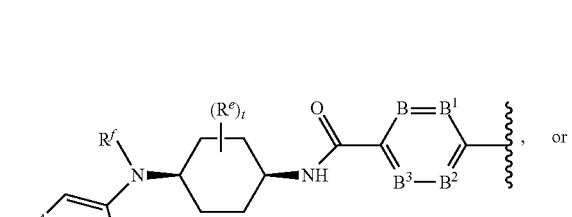
, or
-continued
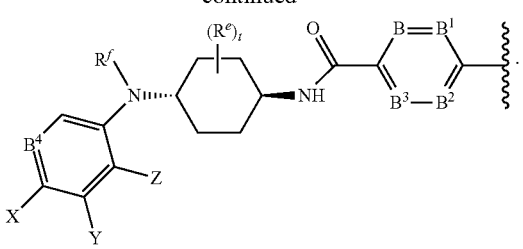
In certain embodiments, $R^1$ is:
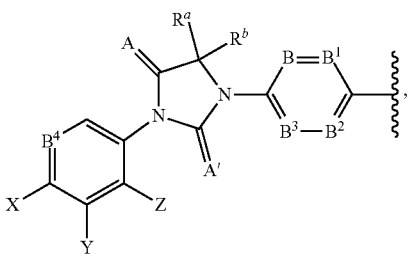
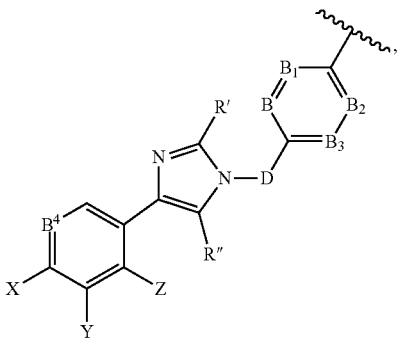
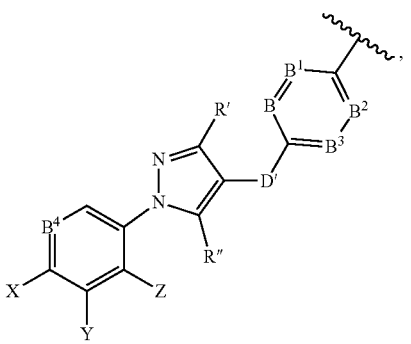
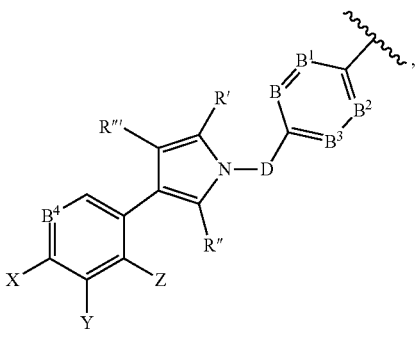

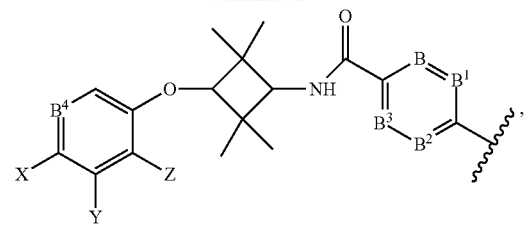

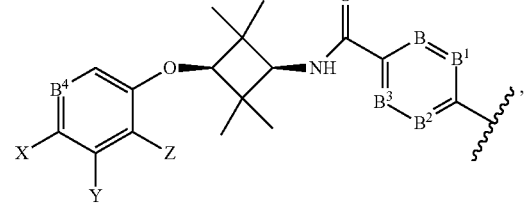

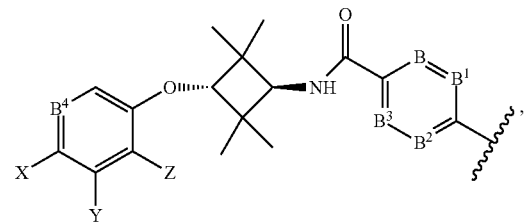

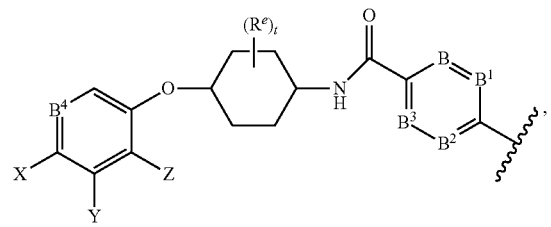

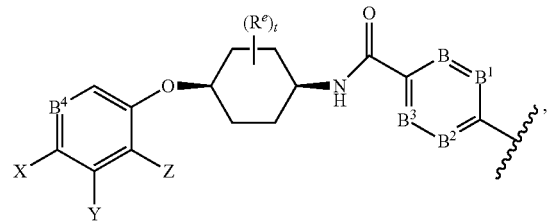

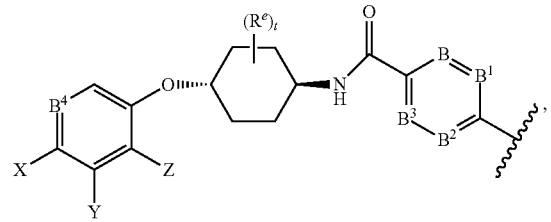

In certain embodiments, R¹ is:

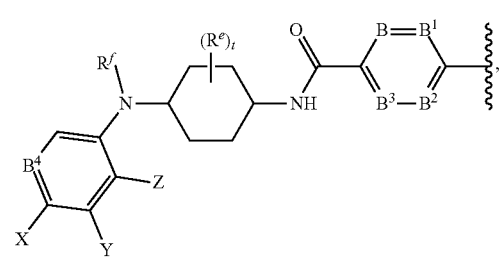

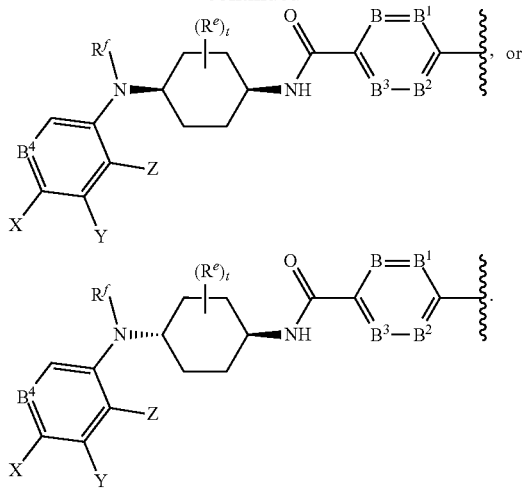

In certain embodiments, R¹ is:

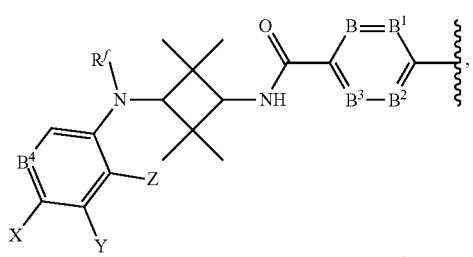

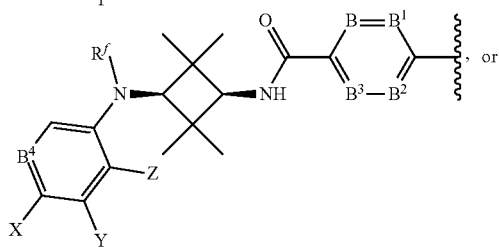

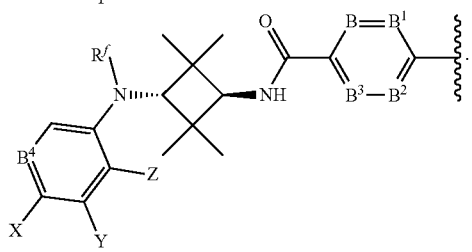

Preparation of exemplary R¹ groups can be found, for example, in US 2018/0099940.

In certain embodiments, $R^a$ and $R^b$ are each independently $CH_3$ or $CH_2CH_3$. In certain embodiments, $R^a$ and $R^b$ together with the atom to which they are attached form a $C_{3-5}$ cycloalkyl, oxiranyl, oxetanyl, or tetrahydrofuranyl.

In certain embodiments, A is O. In certain embodiments, A is S.

In certain embodiments, A' is O. In certain embodiments, A' is S.

In certain embodiments, B, B¹, B², and B³, are each independently $CR^c$.

In certain embodiments, B and B¹ are each independently $CR^c$, and B² and B³ are each N.

In certain embodiments, B is CR$^c$, and each R$^c$ is independently hydrogen, halo, CN, or methyl. In certain embodiments, B is N. In certain embodiments, B is CH.

In certain embodiments, B$^1$ is CR$^c$, and each R$^c$ is independently hydrogen, halo, CN, or methyl. In certain embodiments, B$^1$ is N. In certain embodiments, B$^1$ is CH.

In certain embodiments, B$^2$ is CR$^c$, and each R$^c$ is independently hydrogen, halo, CN, or methyl. In certain embodiments, B$^2$ is N. In certain embodiments, B$^2$ is CH.

In certain embodiments, B$^3$ is CR$^c$, and each R$^c$ is independently hydrogen, halo, CN, or methyl. In certain embodiments, B$^3$ is N. In certain embodiments, B$^3$ is CH.

In certain embodiments, B$^4$ is CF. In certain embodiments, B$^4$ is CH. In certain embodiments, B$^4$ is N.

In certain embodiments, D is a bond. In certain embodiments, D is CH$_2$. In certain embodiments, D is C=O. In certain embodiments, D is (C=O)NH.

In certain embodiments, D' is NH. In certain embodiments, D' is O. In certain embodiments, D' is S. In certain embodiments, D' is CH$_2$. In certain embodiments, D' is NH(C=O). In certain embodiments, D' is C(=O)NH. In certain embodiments, D" is C=O.

In certain embodiments, R' is hydrogen. In certain embodiments, R' is CN. In certain embodiments, R' is C$_{1-2}$ alkyl.

In certain embodiments, R''' is hydrogen. In certain embodiments, R''' is CN. In certain embodiments, R''' is C$_{1-2}$ alkyl.

In certain embodiments, R''' is hydrogen. In certain embodiments, R''' is CN. In certain embodiments, R''' is C$_{1-2}$ alkyl.

In certain embodiments, t is 0. In certain embodiments, t is 1. In certain embodiments, t is 2. In certain embodiments, t is 3, In certain embodiments, t is 4.

In certain embodiments, at least one R$^e$ is independently halo. In certain embodiments, each R$^e$ is independently halo. In certain embodiments, at least one R$^e$ is independently cyano. In certain embodiments, at least one R$^e$ is independently C$_{1-4}$ alkyl. In certain embodiments, at least one R$^e$ is independently C$_{1-4}$ haloalkyl.

In certain embodiments, X is halo. In certain embodiments, X is CN. In certain embodiments, X is NO$_2$.

In certain embodiments, Y is halo. In certain embodiments, Y is CH$_3$. In certain embodiments, Y is CH$_2$F. In certain embodiments, Y is CHF$_2$. In certain embodiments, Y is CF$_3$.

In certain embodiments, X and Y together form a

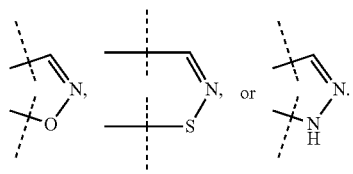

In certain embodiments, X and Y together form a

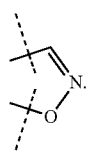

In certain embodiments, X and Y together form a

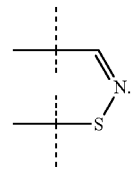

In certain embodiments, X and Y together form a

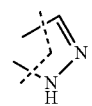

In certain embodiments, Z is hydrogen. In certain embodiments, Z is halo. In certain embodiments, Z is C$_{1-2}$ alkyl. In certain embodiments, Z is C$_2$ alkenyl. In certain embodiments, Z is NO$_2$. In certain embodiments, Z is CF$_3$.

In certain embodiments, Y and Z together form a

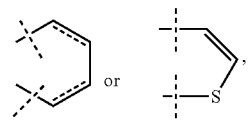

wherein each === is a single or double bond. In certain embodiments, Y and Z together form a

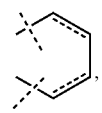

wherein each === is a single or double bond. In certain embodiments, Y and Z together form a

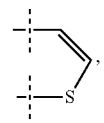

wherein each === is a single or double bond.

In certain embodiments, $R^1$ is:

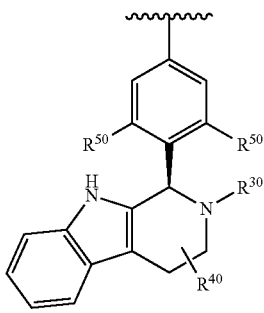

wherein:

the wavy bond refers to the point of connection to L;

$R^{30}$ is hydrogen, $C_{1-12}$ alkyl, $C_{1-12}$ haloalkyl, $C_{2-12}$ alkenyl, $C_{2-12}$ alkynyl, or $C_{3-12}$ cycloalkyl, wherein each $C_{1-12}$ alkyl, $C_{1-12}$ haloalkyl, $C_{2-12}$ alkenyl, $C_{2-12}$ alkynyl, or $C_{3-12}$ cycloalkyl is optionally independently substituted with one to five $R^{100}$ as valency permits;

$R^{40}$ is hydrogen, $C_{1-12}$ alkyl, $C_{1-12}$ haloalkyl, $C_{2-12}$ alkenyl, $C_{2-12}$ alkynyl, or $C_{3-12}$ cycloalkyl, wherein each $C_{1-12}$ alkyl, $C_{1-12}$ haloalkyl, $C_{2-12}$ alkenyl, $C_{2-12}$ alkynyl, or $C_{3-12}$ cycloalkyl is optionally independently substituted with one to five $R^{100}$ as valency permits;

each $R^{50}$ is independently halo, cyano, nitro, —$OR^{170}$, —$NR^{170}R^{180}$, $C_{1-12}$ alkyl, $C_{1-12}$ haloalkyl, $C_{2-12}$ alkenyl, or $C_{2-12}$ alkynyl; wherein each $C_{1-12}$ alkyl, $C_{1-12}$ haloalkyl, $C_{2-12}$ alkenyl, or $C_{2-12}$ alkynyl is independently optionally substituted with one to five halo, hydroxyl or amino as valency permits;

each $R^{100}$ is independently oxo, halo, cyano, nitro, —$OR^{170}$, —$SR^{170}$, —$SF_5$, —$NR^{170}R^{180}$, $C_{1-12}$ alkyl, $C_{2-12}$ alkenyl, $C_{2-12}$ alkynyl, $C_{3-10}$ cycloalkyl, heterocyclyl, aryl, heteroaryl, —$C(=O)R^{170}$, —$C(=O)OR^{170}$, —$OC(=O)OR^{170}$, —$OC(=O)R^{170}$, —$C(=O)NR^{170}R^{180}$, —$OC(=O)NR^{170}R^{180}$, —$NR^{170}C(=O)NR^{170}R^{180}$, —$S(=O)_{1-2}R^{170}$, —$S(=O)_{1-2}NR^{170}R^{180}$, —$NR^{170}S(=O)_{1-2}R^{180}$, —$NR^{170}S(=O)_{1-2}NR^{170}R^{180}$, —$NR^{170}C(=O)R^{180}$, —$NR^{170}C(=O)OR^{180}$ or —$C=NOR^{17}$, wherein each $C_{1-12}$ alkyl, $C_{2-12}$ alkenyl, $C_{2-12}$ alkynyl, $C_{3-10}$ cycloalkyl, heterocyclyl, aryl, and heteroaryl of $R^{100}$ are independently optionally substituted with one or more halo or $C_{1-12}$ alkyl optionally substituted by oxo, halo, hydroxyl or amino as valency permits; and each $R^{170}$ and $R^{180}$ is independently hydrogen or $C_{1-12}$ alkyl optionally substituted with oxo, halo, hydroxyl or amino as valency permits; or $R^{170}$ and $R^{180}$ are taken together with the atoms to which they are attached to form heterocyclyl optionally substituted by halo or $C_{1-12}$ alkyl optionally substituted by oxo, halo, hydroxyl, or amino.

In certain embodiments, $R^1$ is:

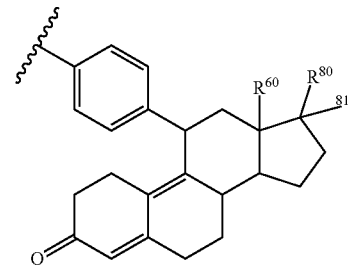

wherein:

the wavy bond refers to the point of connection to L;

$R^{60}$ is hydrogen, $C_{1-12}$ alkyl, $C_{2-12}$ alkenyl, $C_{2-12}$ alkynyl, or $C_{3-12}$ cycloalkyl, wherein each $C_{1-12}$ alkyl, $C_{2-12}$ alkenyl, $C_{2-12}$ alkynyl, or $C_{3-12}$ cycloalkyl is optionally independently substituted with one to five $R^{1\text{o}\,\text{o}}$ as valency permits;

$R^{80}$ is hydrogen, hydroxy, $C_{1-12}$ alkyl, $C_{2-12}$ alkenyl, $C_{2-12}$ alkynyl, $C_{1-12}$ alkoxy, or $C_{3-12}$ cycloalkyl, wherein each $C_{1-12}$ alkyl, $C_{2-12}$ alkenyl, $C_{2-12}$ alkynyl, or $C_{1-12}$ alkoxy, $C_{3-12}$ cycloalkyl is optionally independently substituted with one to five $R^{100}$ as valency permits;

$R^{81}$ is hydrogen, hydroxy, $C_{1-12}$ alkyl, $C_{2-12}$ alkenyl, $C_{2-12}$ alkynyl, $C_{1-12}$ alkoxy, or $C_{3-12}$ cycloalkyl, wherein each $C_{1-12}$ alkyl, $C_{2-12}$ alkenyl, $C_{2-12}$ alkynyl, $C_{1-12}$ alkoxy, or $C_{3-12}$ cycloalkyl is optionally independently substituted with one to five $R^{100}$ as valency permits;

or $R^{80}$ and $R^{81}$ are taken together with the atom to which they are attached to form heterocyclyl optionally substituted by halo or $C_{1-12}$ alkyl optionally substituted by oxo, halo, hydroxyl, or amino;

each $R^{100}$ is independently oxo, halo, cyano, nitro, —$OR^{170}$, —$SR^{170}$, —$SF_5$, —$NR^{170}R^{180}$, $C_{1-12}$ alkyl, $C_{2-12}$ alkenyl, $C_{2-12}$ alkynyl, $C_{3-10}$ cycloalkyl, heterocyclyl, aryl, heteroaryl, —$C(=O)R^{170}$, —$C(=O)OR^{170}$, —$OC(=O)OR^{170}$, —$OC(=O)R^{170}$, —$C(=O)NR^{170}R^{180}$, —$OC(=O)NR^{170}R^{180}$, —$NR^{170}C(=O)NR^{170}R^{180}$, —$S(=O)_{1-2}R^{170}$, —$S(=O)_{1-2}NR^{170}R^{180}$, —$NR^{170}S(=O)_{1-2}R^{180}$, —$NR^{170}S(=O)_{1-2}NR^{170}R^{180}$, —$NR^{170}C(=O)R^{180}$, —$NR^{170}C(=O)OR^{180}$, or —$C=NOR^{17}$, wherein each $C_{1-12}$ alkyl, $C_{2-12}$ alkenyl, $C_{2-12}$ alkynyl, $C_{3-10}$ cycloalkyl, heterocyclyl, aryl, and heteroaryl of $R^{100}$ are independently optionally substituted with one or more halo or $C_{1-12}$ alkyl optionally substituted by oxo, halo, hydroxyl, or amino as valency permits; and each $R^{170}$ and $R^{180}$ is independently hydrogen or $C_{1-12}$ alkyl optionally substituted with oxo, halo, hydroxyl or amino as valency permits; or $R^{170}$ and $R^{180}$ are taken together with the atoms to which they are attached to form heterocyclyl optionally substituted by halo or $C_{1-12}$ alkyl optionally substituted by oxo, halo, hydroxyl, or amino.

In certain embodiments, $R^1$ is:

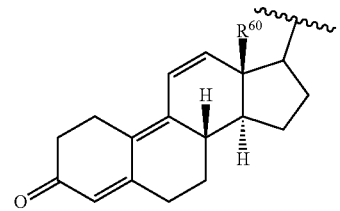

wherein:
the wavy bond refers to the point of connection to L;
$R^{60}$ is hydrogen, $C_{1-12}$ alkyl, $C_{2-12}$ alkenyl, $C_{2-12}$ alkynyl, or $C_{3-12}$ cycloalkyl, wherein each $C_{1-12}$ alkyl, $C_{2-12}$ alkenyl, $C_{2-12}$ alkynyl, or $C_{3-12}$ cycloalkyl is optionally independently substituted with one to five $R^{100}$ as valency permits;
Each $R^{100}$ is independently oxo, halo, cyano, nitro, —$OR^{170}$, —$SR^{170}$, —$SF_5$, —$NR^{170}R^{180}$, $C_{1-12}$ alkyl, $C_{2-12}$ alkenyl, $C_{2-12}$ alkynyl, $C_{3-10}$ cycloalkyl, heterocyclyl, aryl, heteroaryl, —C(=O)$R^{170}$, —C(=O)$OR^{170}$, —OC(=O)$OR^{170}$, —OC(=O)$R^{170}$, —C(=O)$NR^{170}R^{180}$, —OC(=O)$NR^{170}R^{180}$, —$NR^{170}$C(=O)$NR^{170}R^{180}$, —S(=O)$_{1-2}R^{170}$, —S(=O)$_{1-2}NR^{170}R^{180}$, —$NR^{170}$S(=O)$^{1-2}R^{180}$, —$NR^{170}$S(=O)$_{1-2}NR^{170}R^{180}$, —$NR^{170}$C(=O)$R^{180}$, —$NR^{170}$C(=O)$OR^{180}$, or —C=$NOR^{17}$, wherein each $C_{1-12}$ alkyl, $C_{2-12}$ alkenyl, $C_{2-12}$ alkynyl, $C_{3-10}$ cycloalkyl, heterocyclyl, aryl, and heteroaryl of $R^{100}$ are independently optionally substituted with one or more halo or $C_{1-12}$ alkyl optionally substituted by oxo, halo, hydroxyl, or amino as valency permits; and
each $R^{170}$ and $R^{180}$ is independently hydrogen or $C_{1-12}$ alkyl optionally substituted with oxo, halo, hydroxyl or amino as valency permits; or $R^{170}$ and $R^{180}$ are taken together with the atoms to which they are attached to form heterocyclyl optionally substituted by halo or $C_{1-12}$ alkyl optionally substituted by oxo, halo, hydroxyl, or amino.

In certain embodiments, $R^1$ is:

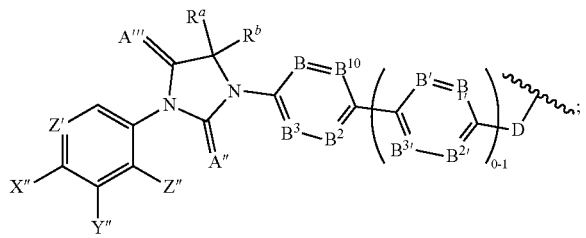

wherein:
the wavy bond refers to the point of connection to L;
A" and A''' are each independently O or S;
$R^a$ and $R^b$ are each independently $CH_3$ or $CH_2CH_3$; or $R^a$ and $R^b$ together with the atom to which they are attached form a $C_{3-5}$ cycloalkyl, oxirane, oxetane, or tetrahydrofuran;
B, $B^{10}$, $B^2$, $B^3$, B', $B^{1'}$, $B^{2'}$ and $B^{3'}$ are each independently $CR^e$ or N;
each $R^e$ is independently hydrogen, fluoro, CN, or methyl;
D is NH, O, S, $CH_2$, or C=O;
X" is CN, halo, or $NO_2$;
Y" is $CH_3$, $CH_2R^d$, $CHF_2$, or $CF_3$;
$R^d$ is halo;
Z" is hydrogen, $C_{1-2}$ alkyl, $C_2$ alkenyl, or $NO_2$; or
X" and Y" together form a

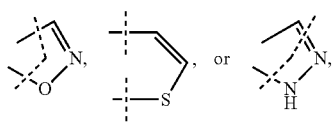

wherein the broken lines indicate bonds to the ring; or Y" and Z" together form a

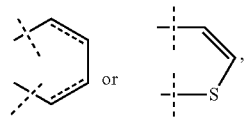

wherein each === is a single or double bond, and wherein the broken lines indicate In certain embodiments, $R^1$ is:

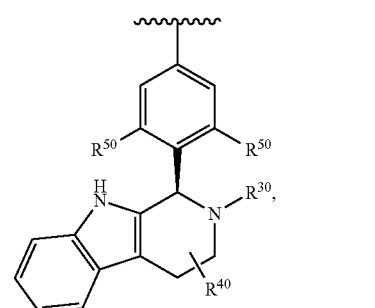

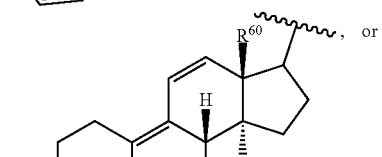

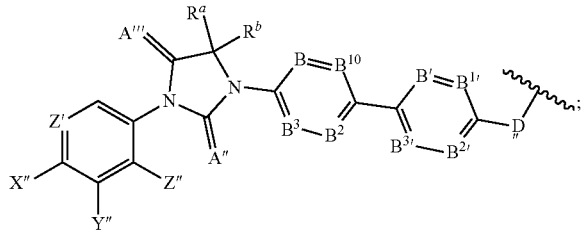

wherein:
$R^{30}$ is hydrogen, $C_{1-12}$ alkyl, $C_{1-12}$ haloalkyl, $C_{2-12}$ alkenyl, $C_{2-12}$ alkynyl, or $C_{3-12}$ cycloalkyl, wherein each $C_{1-12}$ alkyl, $C_{1-12}$ haloalkyl, $C_{2-12}$ alkenyl, $C_{2-12}$ alkynyl, or $C_{3-12}$ cycloalkyl is optionally independently substituted with one to five $R^{100}$ as valency permits;
$R^{40}$ is hydrogen, $C_{1-12}$ alkyl, $C_{1-12}$ haloalkyl, $C_{2-12}$ alkenyl, $C_{2-12}$ alkynyl, or $C_{3-12}$ cycloalkyl, wherein each $C_{1-12}$ alkyl, $C_{1-12}$ haloalkyl, $C_{2-12}$ alkenyl, $C_{2-12}$ alkynyl, or $C_{3-12}$ cycloalkyl is optionally independently substituted with one to five $R^{100}$ as valency permits;
each $R^{50}$ is independently halo, cyano, nitro, —$OR^{170}$, —$SR^{170}$, —$NR^{170}R^{180}$, $C_{1-12}$ alkyl, $C_{1-12}$ haloalkyl, $C_{2-12}$ alkenyl, or $C_{2-12}$ alkynyl; wherein each $C_{1-12}$ alkyl, $C_{1-12}$ haloalkyl, $C_{2-12}$ alkenyl, or $C_{2-12}$ alkynyl is independently optionally substituted with one to five halo, hydroxyl or amino as valency permits;
$R^{60}$ is hydrogen, $C_{1-12}$ alkyl, $C_{2-12}$ alkenyl, $C_{2-12}$ alkynyl, or $C_{3-12}$ cycloalkyl, wherein each $C_{1-12}$ alkyl, $C_{2-12}$ alkenyl, $C_{2-12}$ alkynyl, or $C_{3-12}$ cycloalkyl is optionally independently substituted with one to five $R^{100}$ as valency permits;

each $R^{100}$ is independently oxo, halo, cyano, nitro, —$OR^{170}$, —$SR^{170}$, —$SF_5$, —$NR^{170}R^{180}$, $C_{1-12}$ alkyl, $C_{2-12}$ alkenyl, $C_{2-12}$ alkynyl, $C_{3-10}$ cycloalkyl, heterocyclyl, aryl, heteroaryl, —$C(=O)R^{170}$, —$C(=O)OR^{170}$, —$OC(=O)OR^{170}$, —$OC(=O)R^{170}$, —$C(=O)NR^{170}R^{180}$, —$OC(=O)NR^{170}R^{180}$, —$NR^{170}C(=O)NR^{170}R^{180}$, —$S(=O)_{1-2}R^{170}$, —$S(=O)_{1-2}NR^{170}R^{180}$, —$NR^{170}S(=O)_{1-2}R^{180}$, —$NR^{170}S(=O)_{1-2}NR^{170}R^{180}$, —$NR^{170}C(=O)R^{180}$, —$NR^{170}C(=O)OR^{180}$ or —$C=NOR^{17}$, wherein each $C_{1-12}$ alkyl, $C_{2-12}$ alkenyl, $C_{2-12}$ alkynyl, $C_{3-10}$ cycloalkyl, heterocyclyl, aryl, and heteroaryl of $R^{100}$ are independently optionally substituted with one or more halo or $C_{1-12}$ alkyl optionally substituted by oxo, halo, hydroxyl or amino as valency permits;

each $R^{170}$ and $R^{180}$ is independently hydrogen or $C_{1-12}$ alkyl optionally substituted with oxo, halo, hydroxyl or amino as valency permits; or $R^{170}$ and $R^{180}$ are taken together with the atoms to which they are attached to form heterocyclyl optionally substituted by halo or $C_{1-12}$ alkyl optionally substituted by oxo, halo, hydroxyl or amino.

A" and A"' are each independently O or S;

$R^a$ and $R^b$ are each independently $CH_3$ or $CH_2CH_3$; or $R^a$ and $R^b$ together with the atom to which they are attached form a $C_{3-5}$ cycloalkyl, oxirane, oxetane or tetrahydrofuran;

B, $B^{10}$, $B^2$, $B^3$, B', $B^{1'}$, $B^{2'}$ and $B^{3'}$ are each independently $CR^c$ or N;

each $R^c$ is independently hydrogen, fluoro, CN, or methyl;

D" is NH, O, S, $CH_2$ or C=O;

X" is CN, halo, or $NO_2$;

Y" is $CH_3$, $CH_2R^d$, $CHF_2$, or $CF_3$;

$R^d$ is halo;

Z"' is H, $C_{1-2}$ alkyl, $C_2$ alkenyl, or $NO_2$; or

X" and Y" together form a

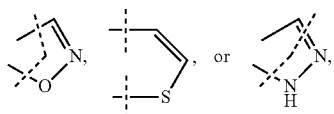

where the broken lines indicate bonds to form a fused ring; or Y" and Z" together form a

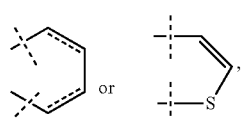

where ═ is a single or double bond and where the broken lines indicate bonds to form a fused ring;

Z' is CH or N.

In certain embodiments, $R^1$ is:

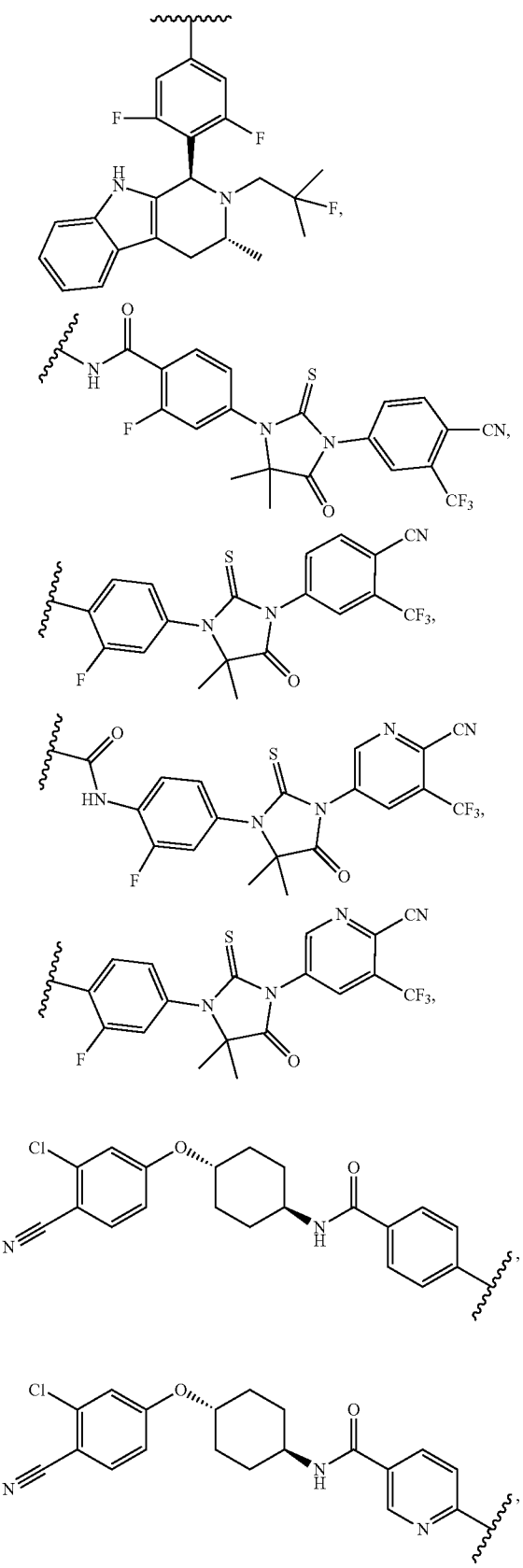

-continued
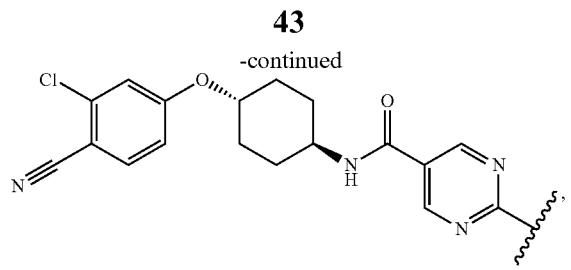
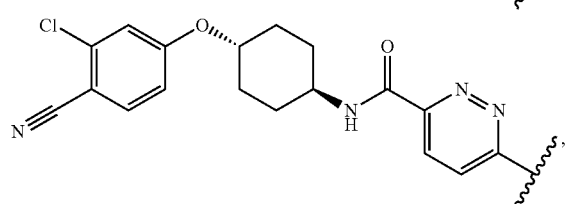
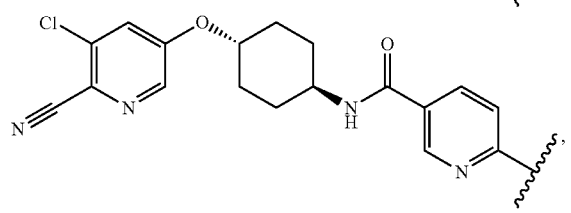
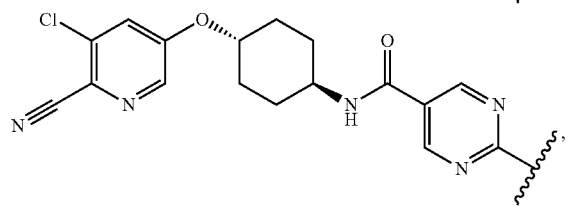
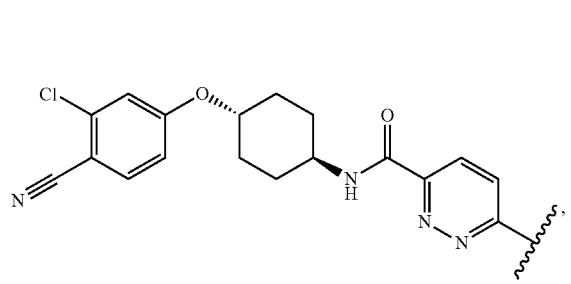
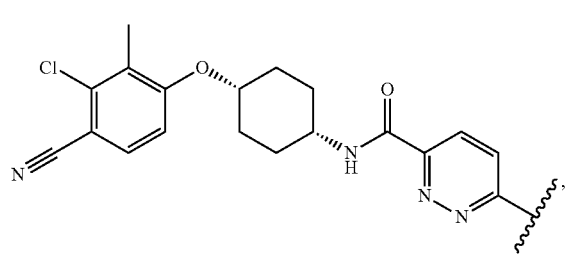
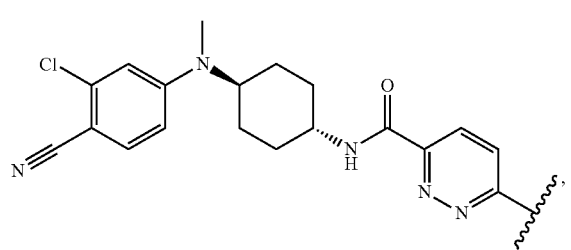
-continued
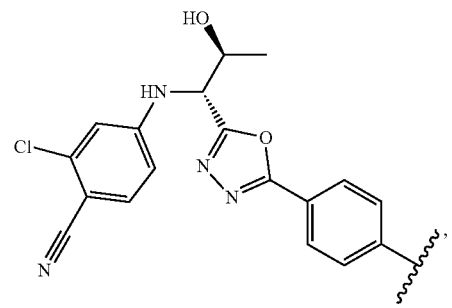
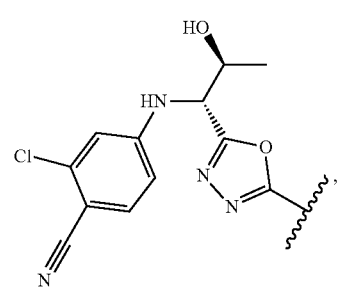
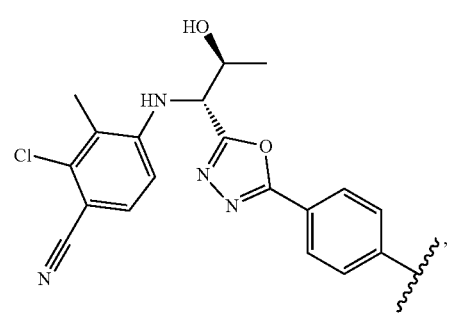
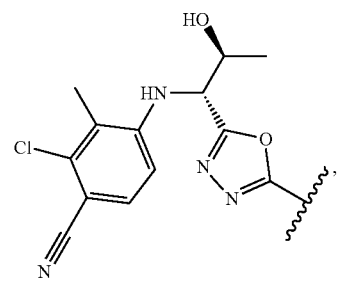
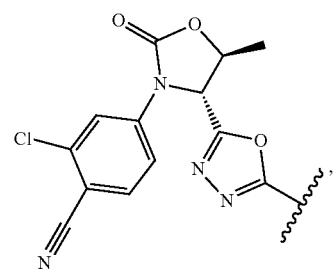

-continued

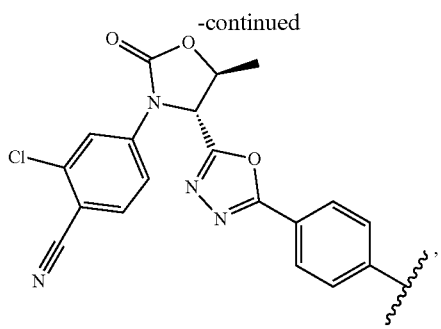

where the wavy bond refers to the point of connection to L.

In certain embodiments, $R^1$ is:

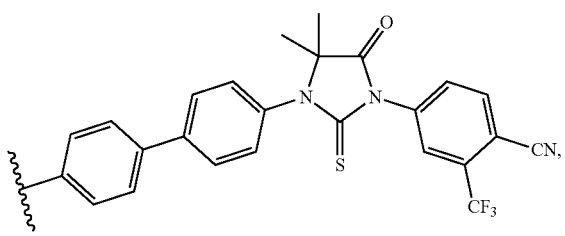

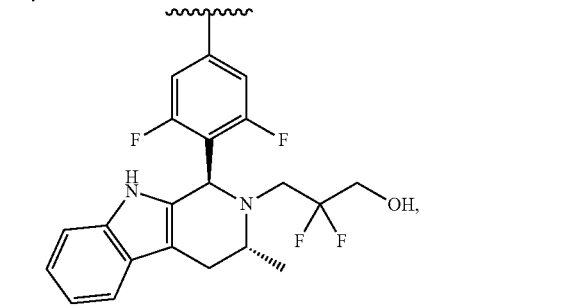

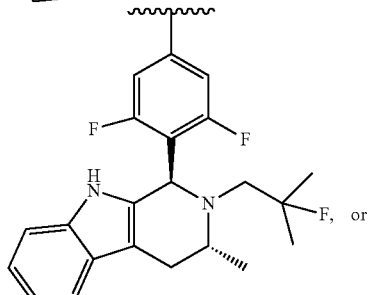

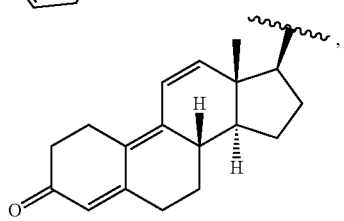

or a tautomer, stereoisomer or a mixture of stereoisomers thereof, or an analog thereof, where the wavy line indicates the point of attachment to the nuclear payload, optionally via a linking moiety.

In certain embodiments, $R^1$ is derived from, progesterone, enobosarm, bicalutamide, apalutamide, testosterone, dihydrotestosterone, testosterone, 19-nortestosterone, progesterone, andarine, cortisol, prednisone, flutamide, nilutamide, enzalutamide, tamoxifen, toremifene, raloxifene, bazedoxifene, ospemifene, megestrol acetate, estramustine, abiraterone, LGD-2941, BMS-564929, ostarine, ulipristal acetate, asoprisnil (J867), mifepristone, telapristone (CDB-4124, Proellex, Progenta), or an analog thereof.

In certain embodiments, $R^1$ is derived from, progesterone, enobosarm, bicalutamide, apalutamide, testosterone, dihydrotestosterone, flutamide, nilutamide, enzalutamide, tamoxifen, toremifene, raloxifene, bazedoxifene, ospemifene, megestrol acetate, abiraterone, LGD-2941, BMS-564929, ostarine, or an analog thereof.

In certain embodiments, the compound comprises at least one nuclear steroid receptor-targeting epitope independently comprises an epitope derived from:

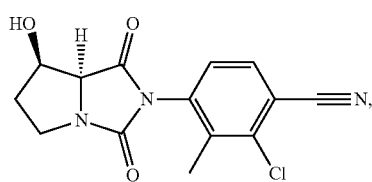

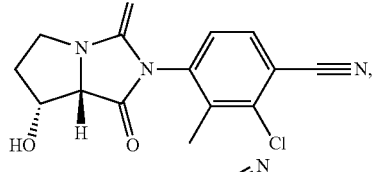

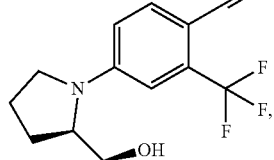

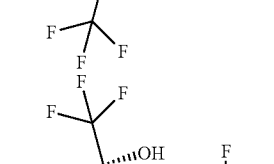

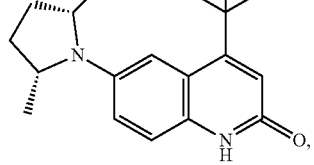

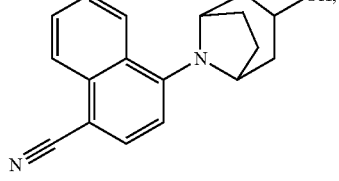

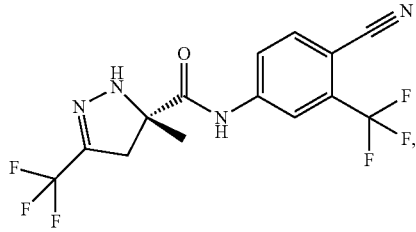

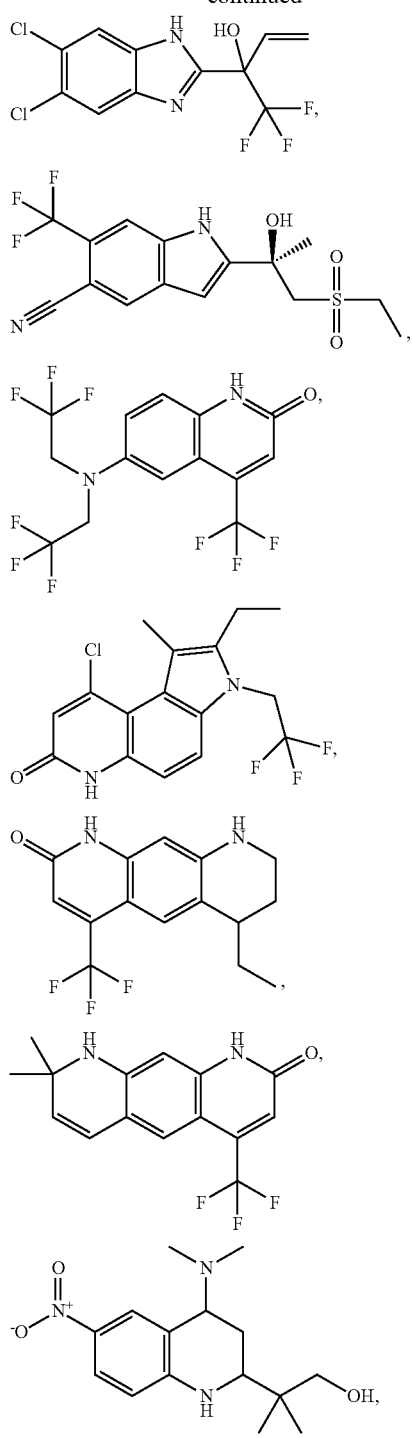
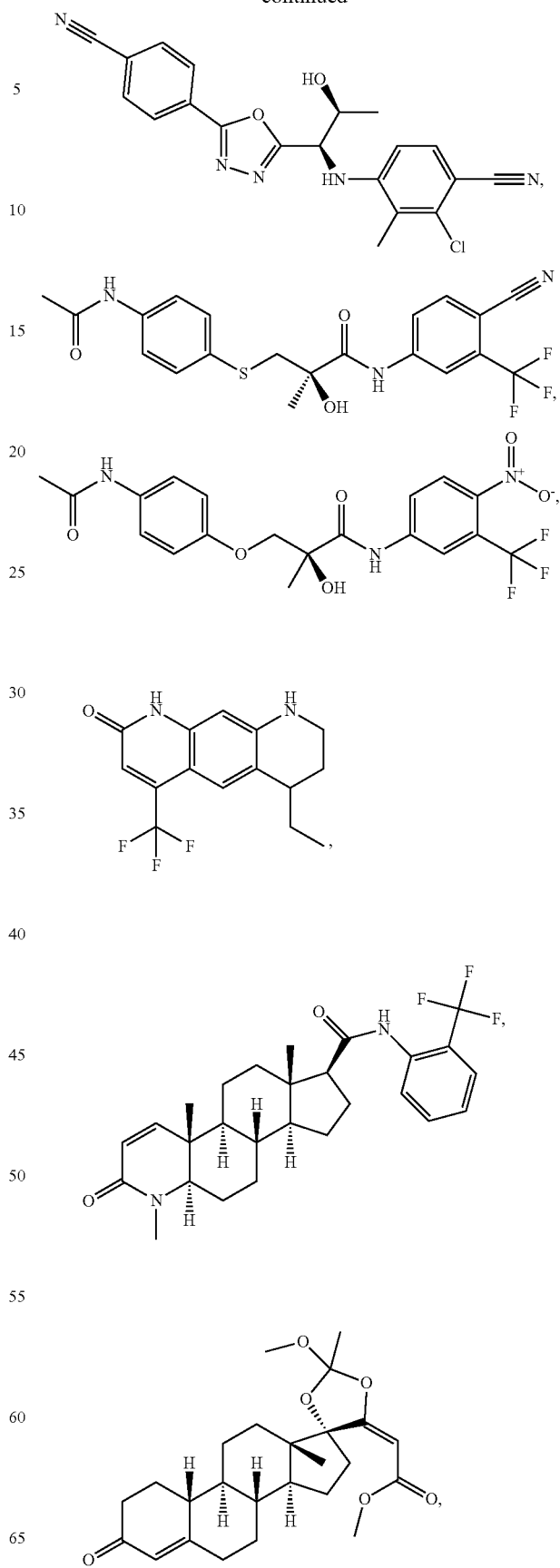

-continued
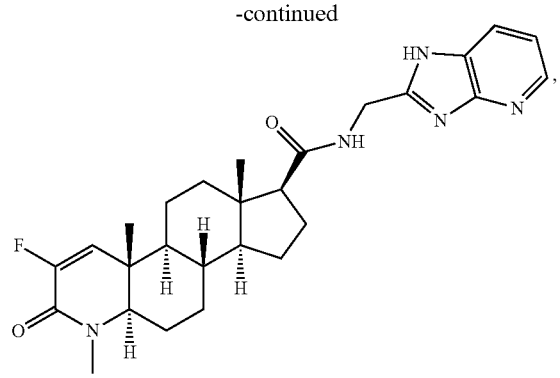
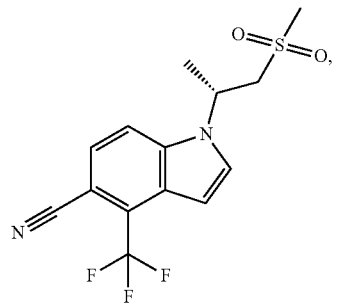
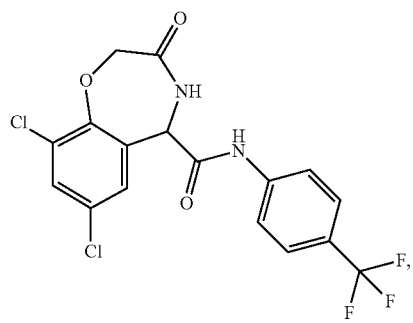
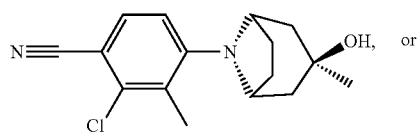
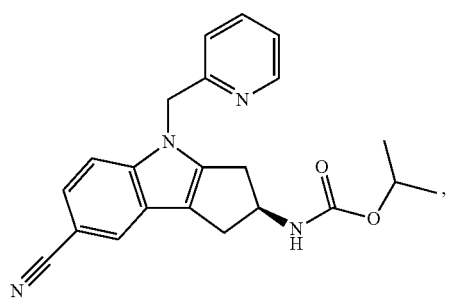
or a tautomer, stereoisomer or a mixture of stereoisomers thereof, or an analog thereof, wherein one or more atoms are replaced by a direct covalent bond to L.
In certain embodiments, $R^1$ comprises a nuclear receptor-targeting epitope derived from:
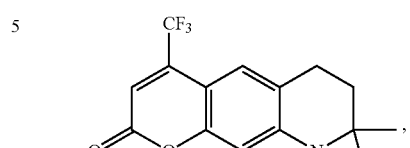
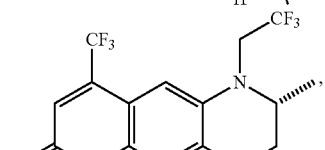
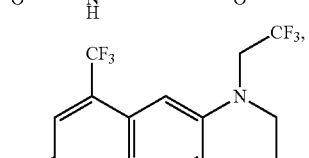
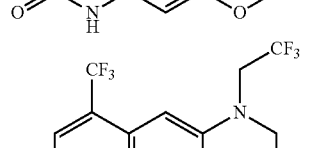
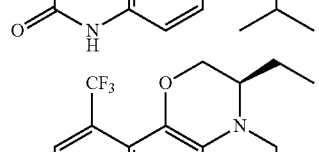
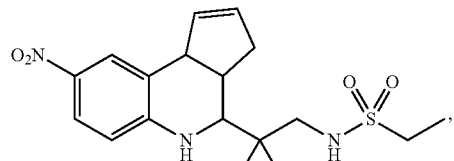
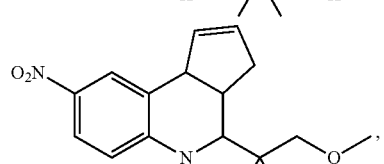
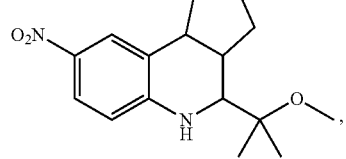
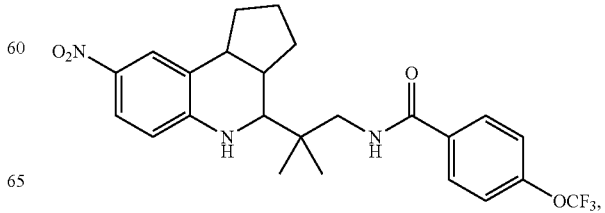

51
-continued
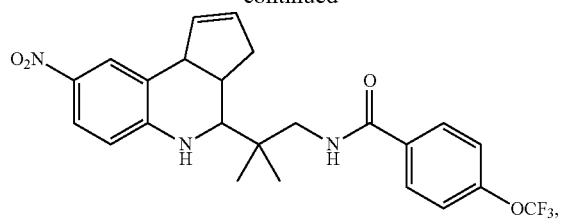
52
-continued
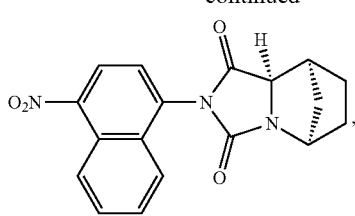
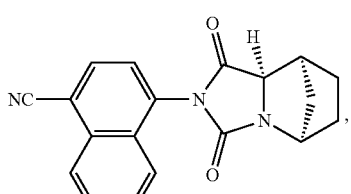
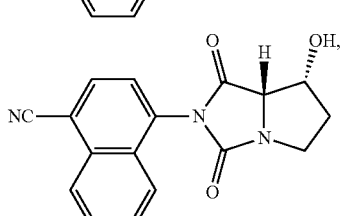
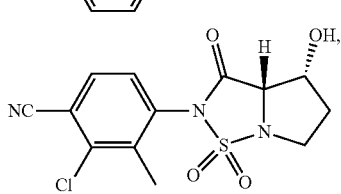
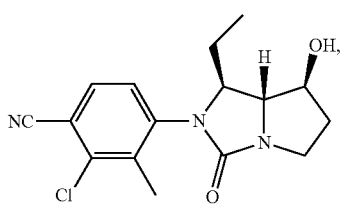
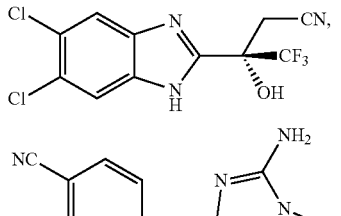
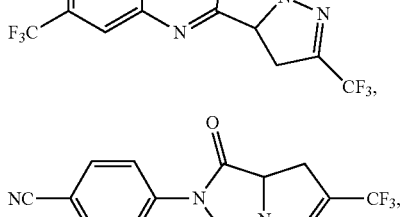
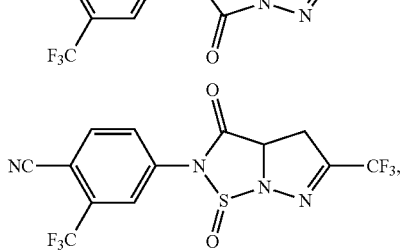

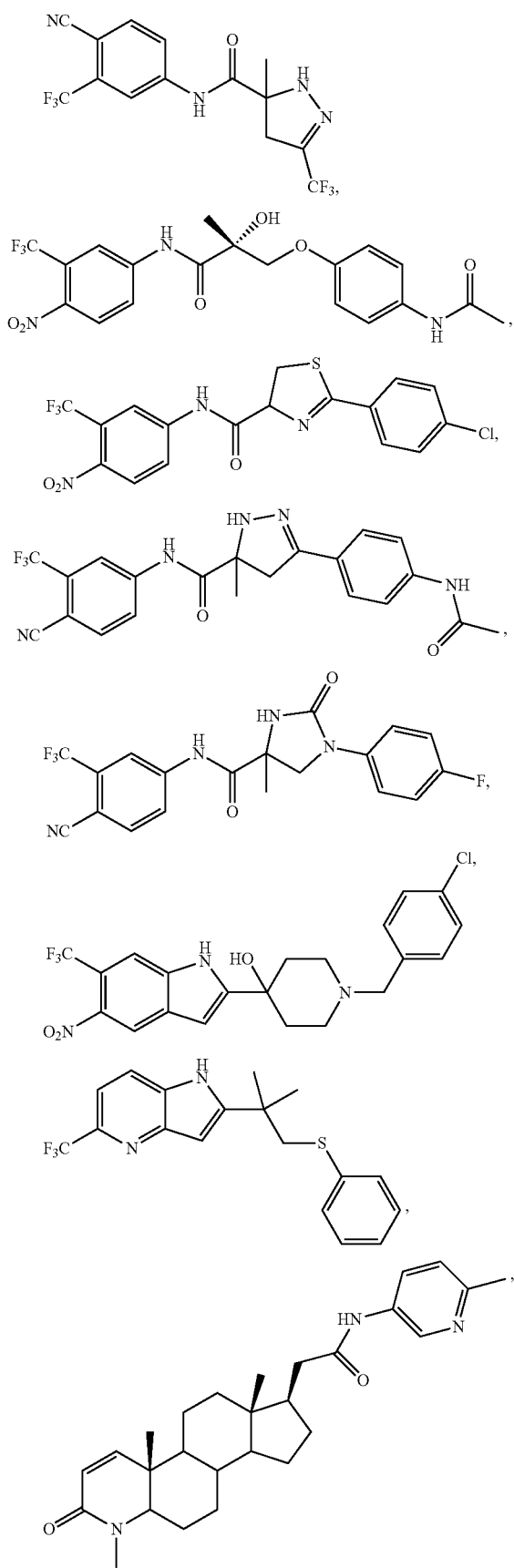
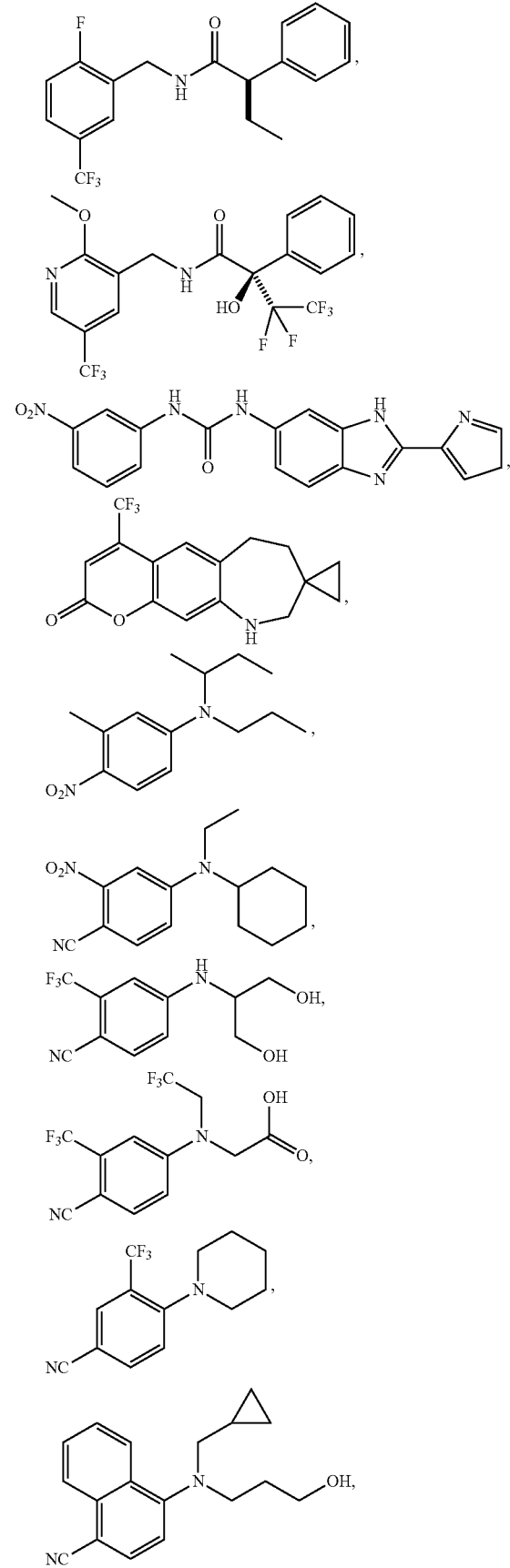

-continued

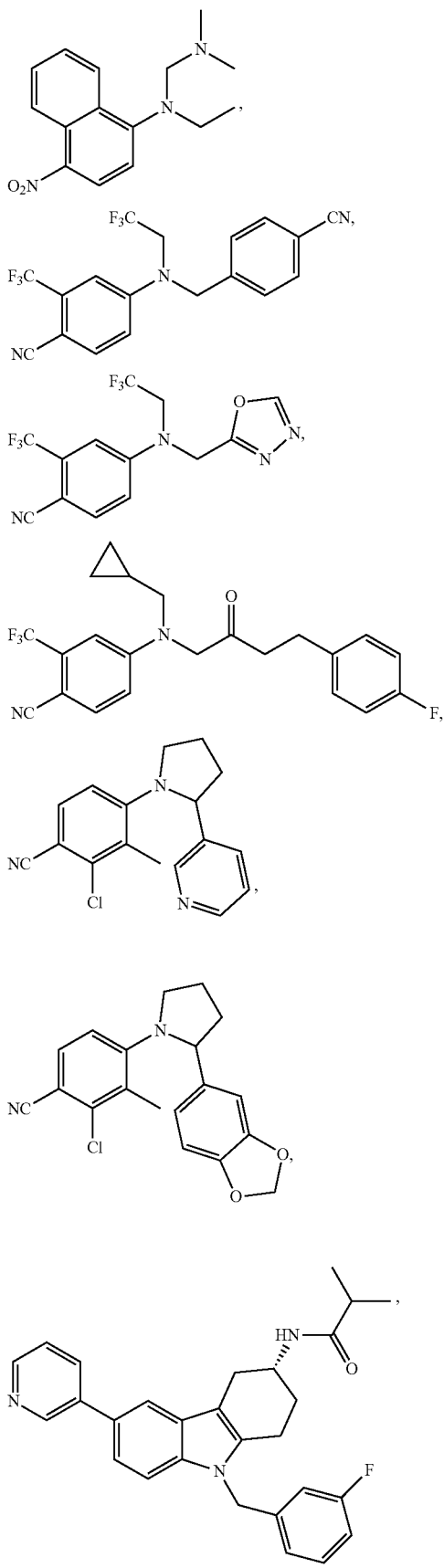

-continued

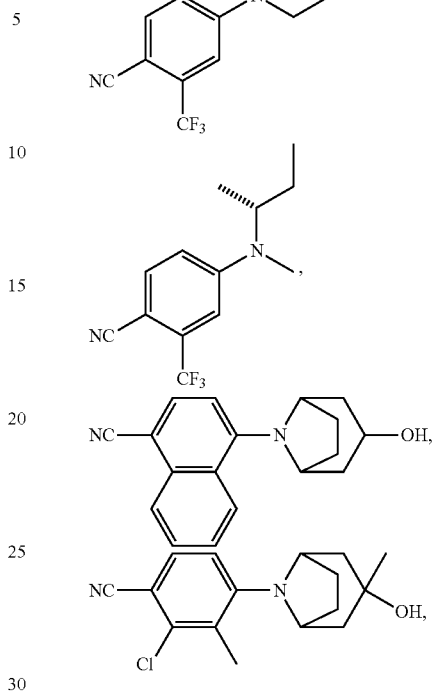

or a tautomer, stereoisomer or a mixture of stereoisomers thereof or an analog thereof, wherein at least one hydrogen atom is replaced by a direct covalent bond to L.

These and other selective androgen receptor modulator (SARMs) which can be used as a nuclear steroid receptor-targeting epitope in $R^1$ described herein can be found in U.S. Pat. Nos. 6,462,038, 6,777,427, WO2001/027086, WO2004/013104, WO2004/000816, WO2004/0113309, US2006/0211756, US2006/063819, US2005/245485, US2005/250741, US2005/277681, WO2006/060108, WO2004/041277, WO2003/034987, US2006/0148893, US2006/0142387, WO2005/000795, WO2005/085185, WO2006/133216, WO2006/044707, WO2006/124447, WO2007/002181, WO2005/108351, WO2005/115361, and US2006/0160845.

In certain embodiments, $R^1$ is a selective estrogen receptor modulator (SERM). In certain embodiments, $R^1$ comprises an epitope derived from anordrin, bazedoxifene, broparestrol (Acnestrol), clomifene (Clomid), cyclofenil (Sexovid), lasofoxifene (Fablyn), ormeloxifene (Centron, Novex, Novex-DS, Sevista), ospemifene (Osphena, deaminohydroxytoremifene), raloxifene (Evista), tamoxifen (Nolvadex), toremifene (Fareston; 4-chlorotamoxifen), acolbifene, afimoxifene (4-hydroxytamoxifen; metabolite of tamoxifen), elacestrant, enclomifene ((E)-clomifene), endoxifen (4-hydroxy-N-desmethyltamoxifen; metabolite of tamoxifen), zuclomifene ((Z)-clomifene), bazedoxifene, arzoxifene, brilanestrant, clomifenoxide (clomiphene N-oxide; metabolite of clomifene), droloxifene (3-hydroxytamoxifen), etacstil, fispemifene, GW-7604 (4-hydroxyetacstil), idoxifene (pyrrolidino-4-iodotamoxifen), levormeloxifene ((L)-ormeloxifene), miproxifene, nafoxidine, nitromifene (CI-628), panomifene, pipendoxifene (ERA-923), trioxifene, keoxifene, LY117018, onapristone, fareston (toremifine citrate), or zindoxifene (D-16726), or an analog thereof.

In certain embodiments, the SERM is classified structurally as a triphenylethylene (tamoxifen, clomifene, toremifene, droloxifene, idoxifene, ospemifene, fispemifene, afimoxifene, etc., or an analog thereof), a benzothiophene (raloxifene, arzoxifene, etc., or an analog thereof), an indole (bazedoxifene, zindoxifene, pipendoxifene, etc., or an analog thereof), a tetrahydronaphthalene (lasofoxifene, nafoxidine, etc., or an analog thereof), or a benzopyran (acolbifene, ormeloxifene, levormeloxifene, etc., or an analog thereof).

In certain embodiments, $R^1$ is a selective estrogen receptor downregulator (SERD). In certain embodiments, the compound comprises at least one nuclear steroid receptor-targeting epitope independently comprises an epitope derived from fulvestrant, brilanestrant (ARN-810), etacstil (GW5638), AZD9496, giredestrant (GDC-9545), or GW7604.

In certain embodiments, $R^1$ is a selective progesterone receptor modulator (SPRM). In certain embodiments, B comprises an epitope derived from ulipristal acetate, asoprisnil (J867), mifepristone, telapristone (CDB-4124, Proellex, Progenta), or an analog thereof.

In certain embodiments, $R^1$ comprises an epitope derived from, estrogen, estetrol, estriol, estrone, progesterone, enobosarm, bicalutamide, apalutamide, testosterone, dihydrotestosterone, estradiol, flutamide, nilutamide, enzalutamide, tamoxifen, toremifene, raloxifene, bazedoxifene, ospemifene, megestrol acetate, estramustine, abiraterone, LGD-2941, BMS-564929, ostarine, or an analog thereof.

In certain embodiments, at least one nuclear steroid receptor-targeting epitope is an androgen receptor-targeting epitope, and comprises:

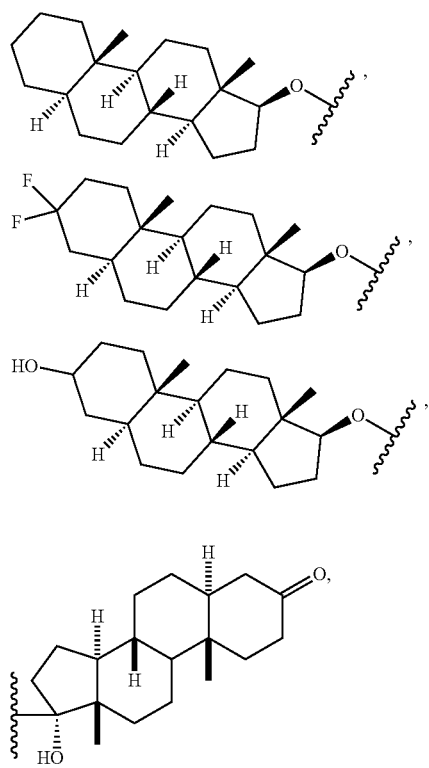

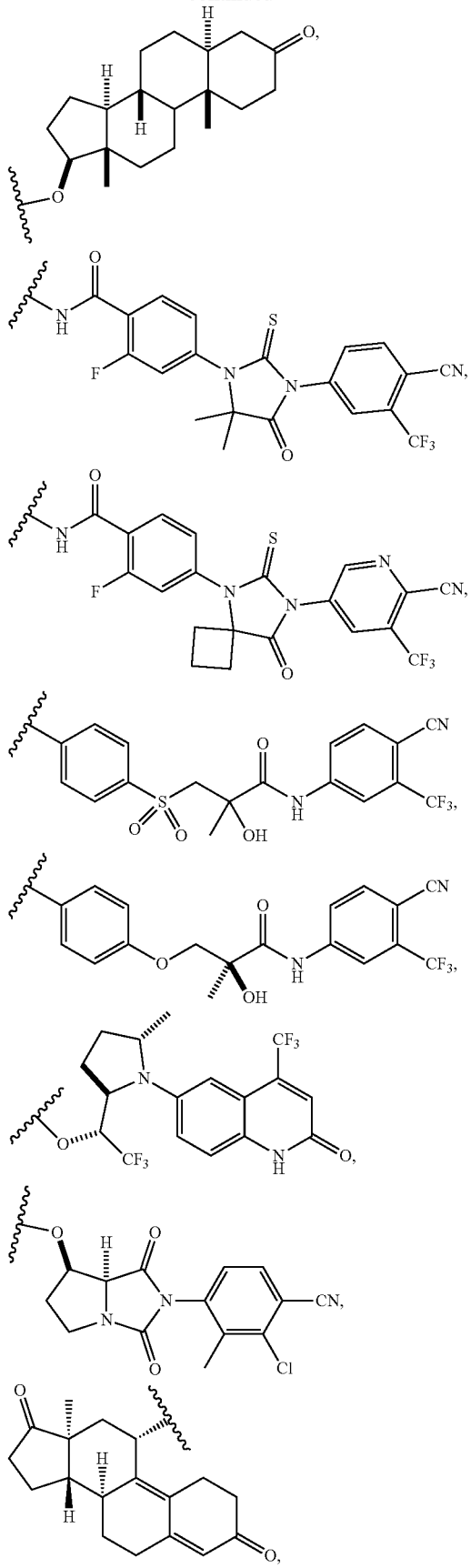

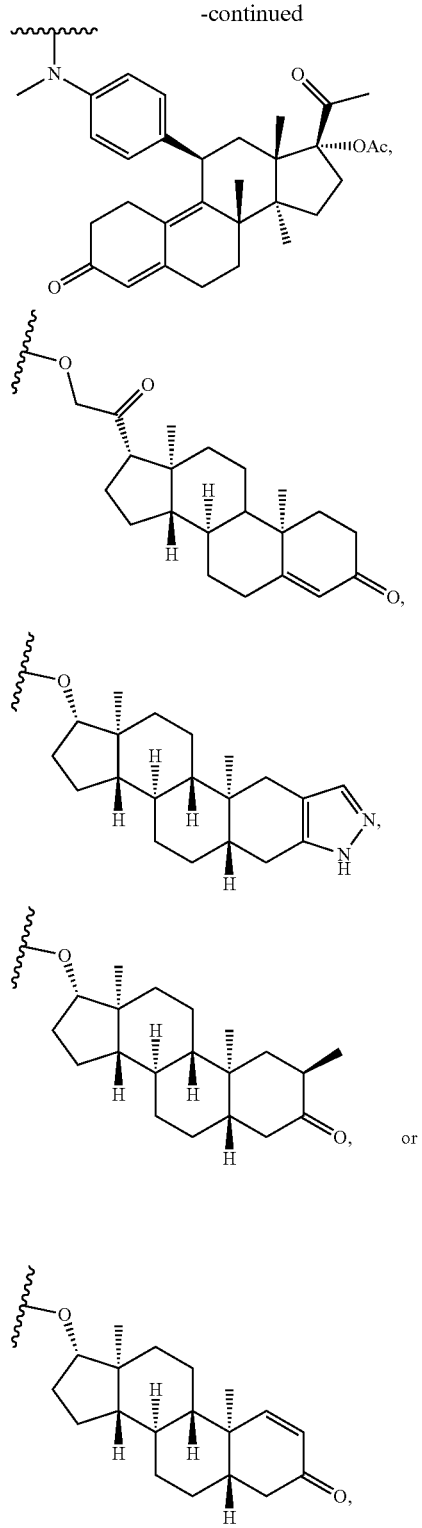
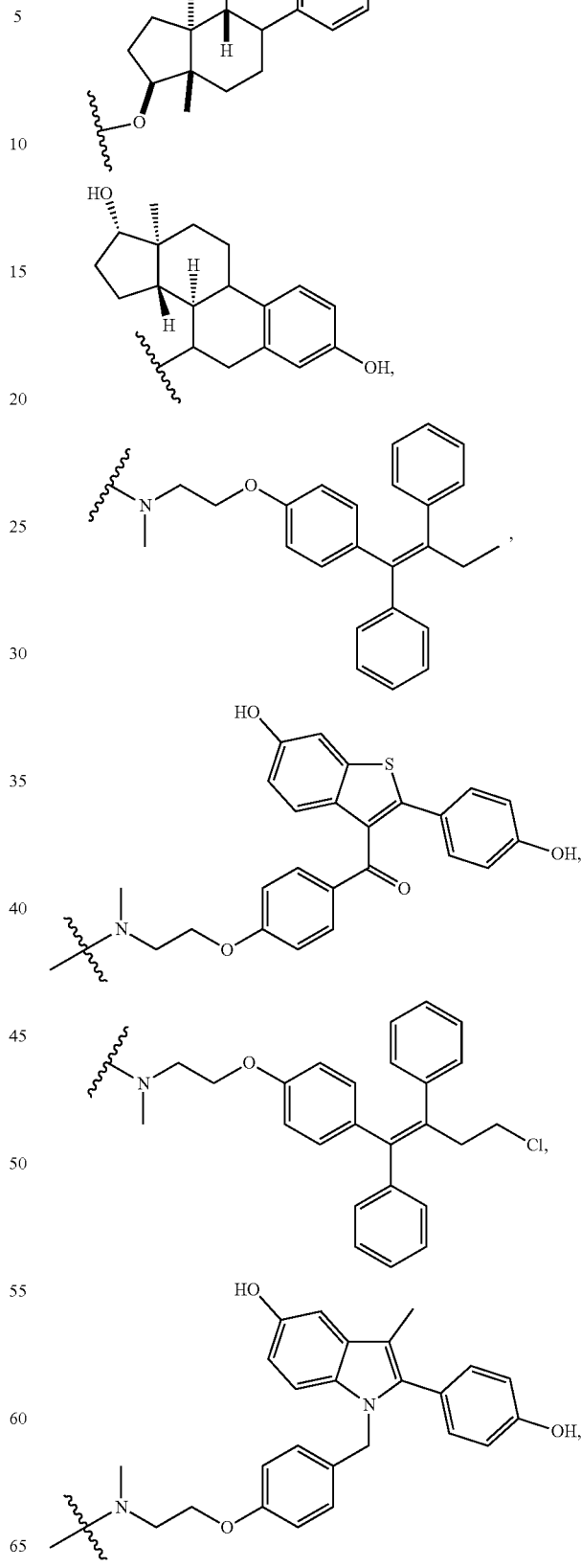
or a tautomer, stereoisomer or a mixture of stereoisomers thereof or an analog thereof, where the wavy line indicates the point of attachment to the nuclear payload, optionally via a linking moiety.
In certain embodiments, at least one nuclear steroid receptor-targeting epitope is an estrogen receptor-targeting epitope, and comprises:

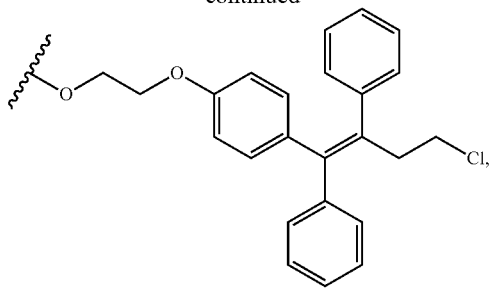
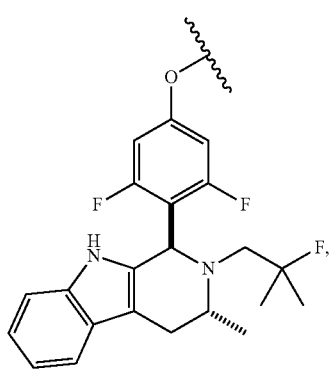
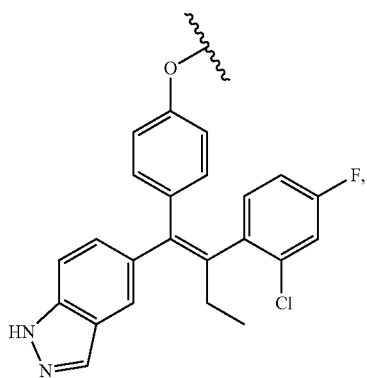
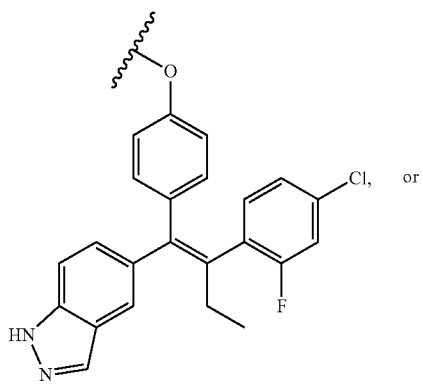
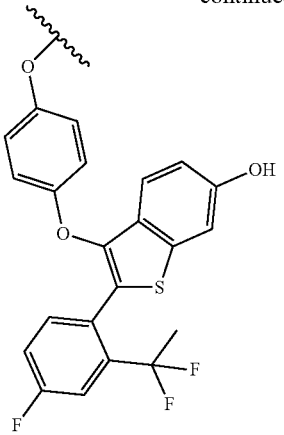
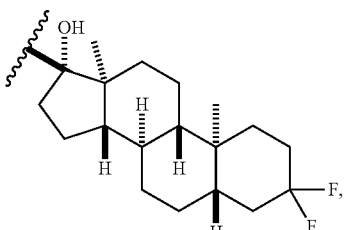
or a tautomer, stereoisomer or a mixture of stereoisomers thereof, or an analog thereof, where the wavy line indicates the point of attachment to the nuclear payload, optionally via a linking moiety.
In certain embodiments, at least one nuclear steroid receptor-targeting epitope is an estrogen receptor-targeting epitope, and comprises:
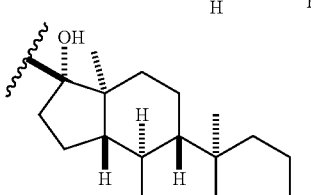
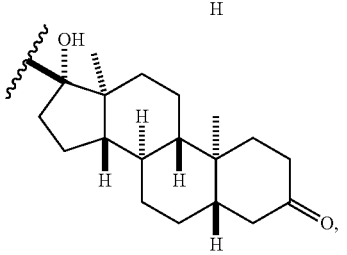
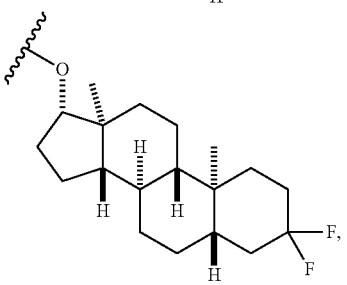

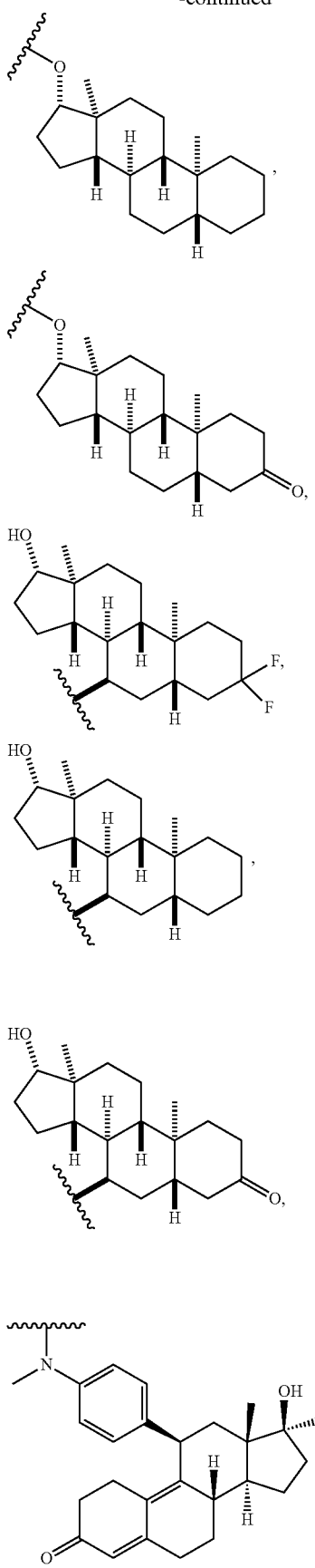
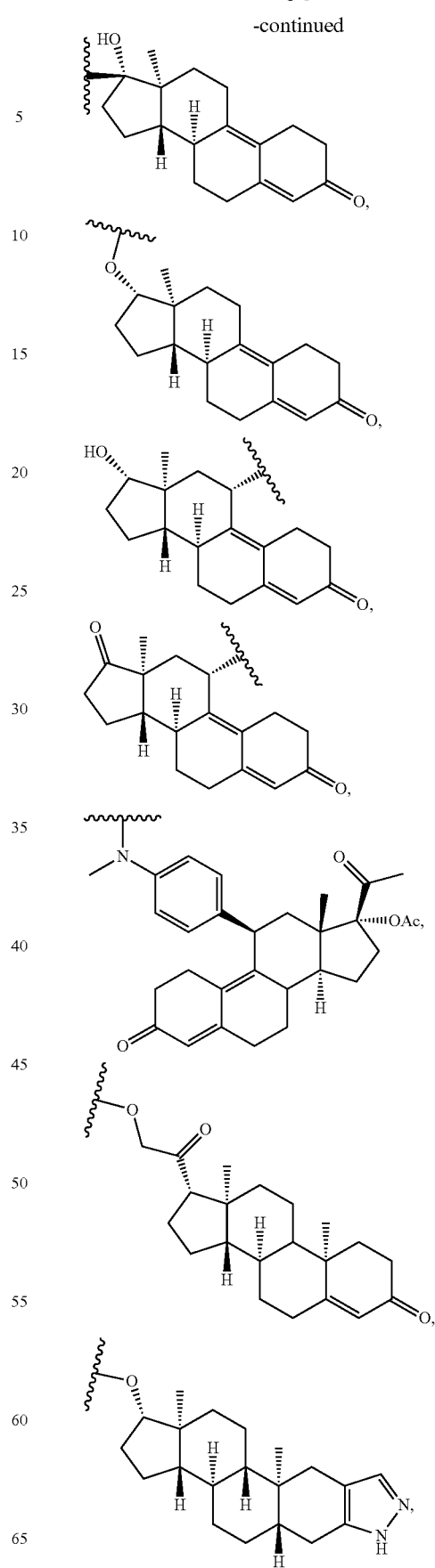

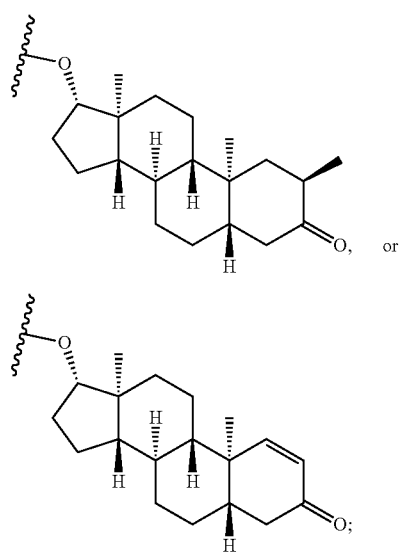
or a tautomer, stereoisomer, or a mixture of stereoisomers thereof, or an analog thereof, where the wavy line indicates the point of attachment to the nuclear payload, optionally via a linking moiety.
In certain embodiments, at least one nuclear steroid receptor-targeting epitope comprises:
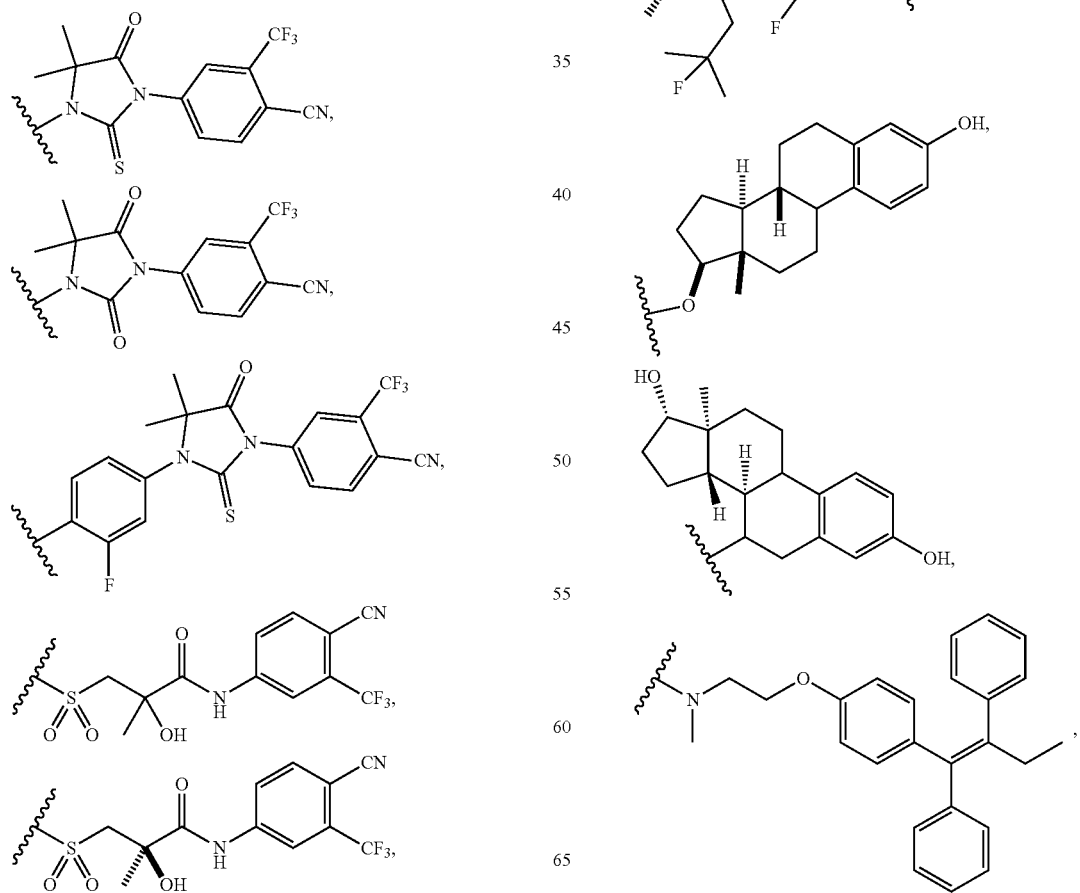

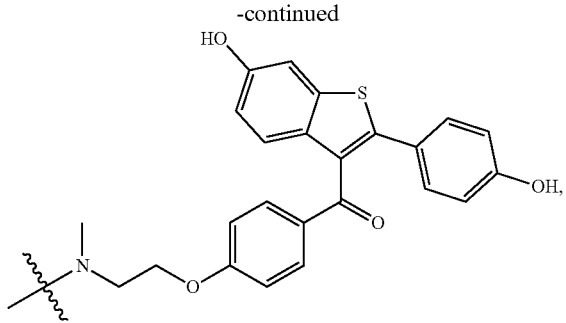
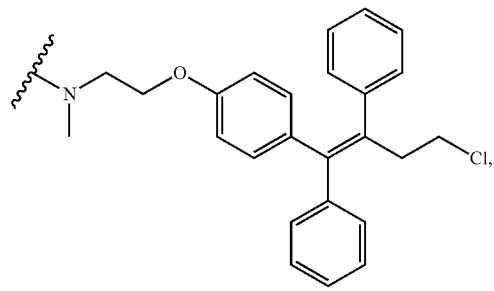
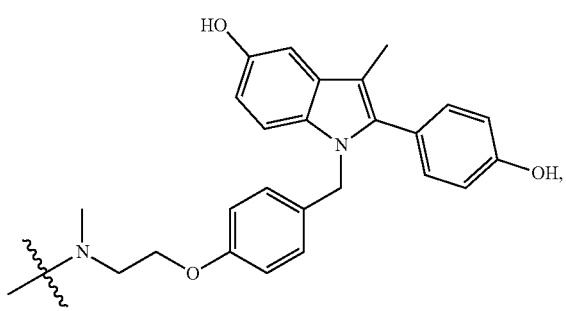
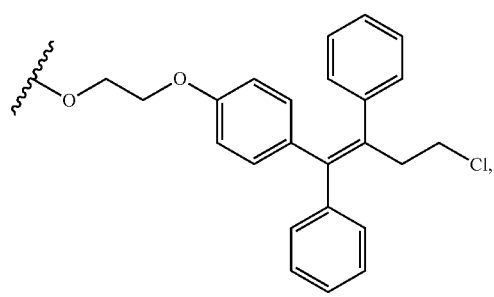
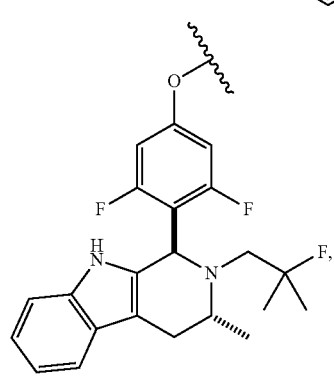
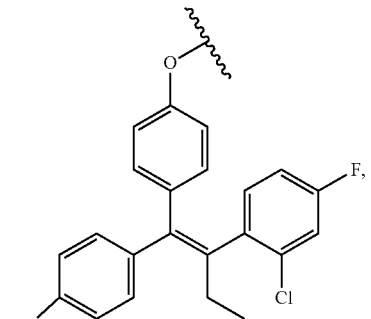
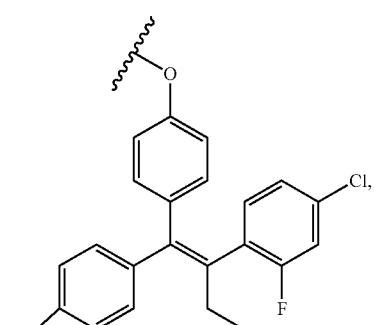
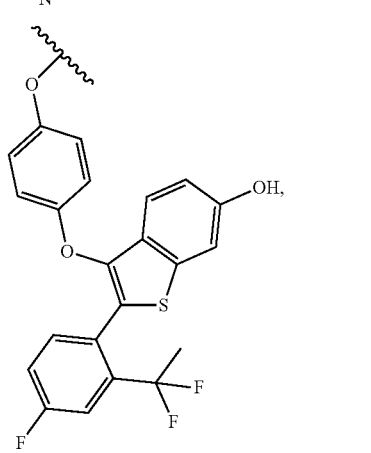
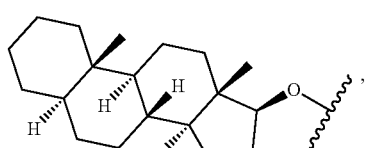
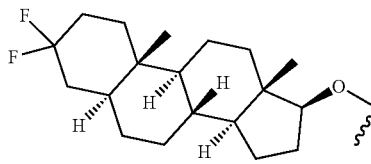
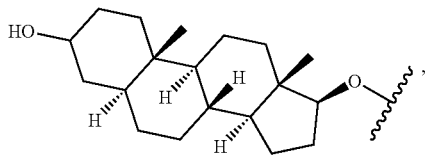

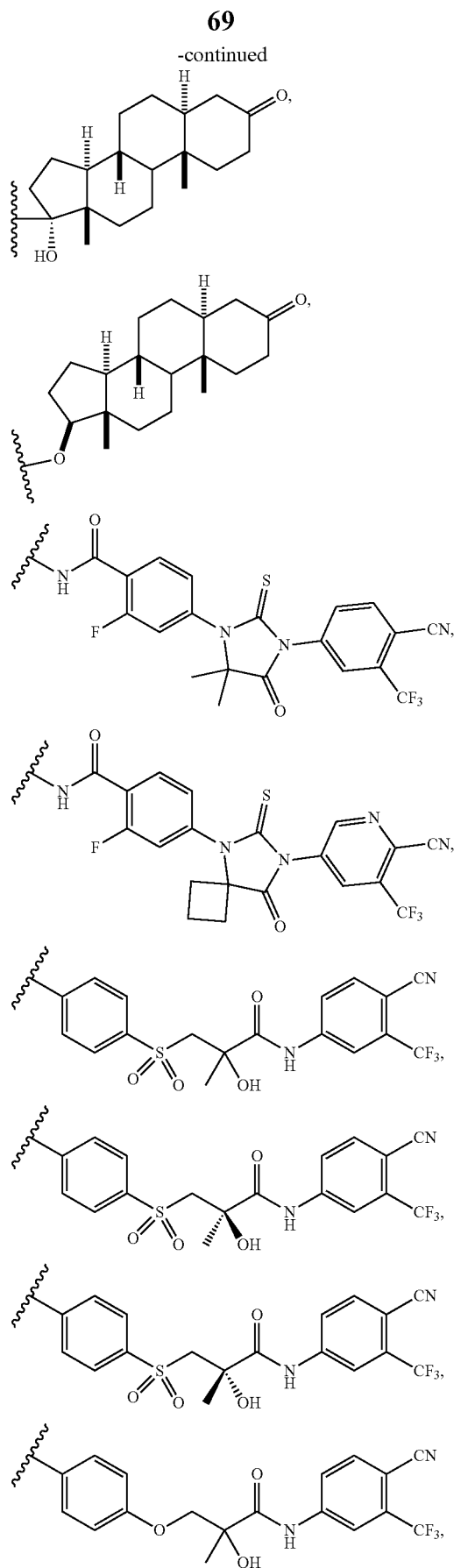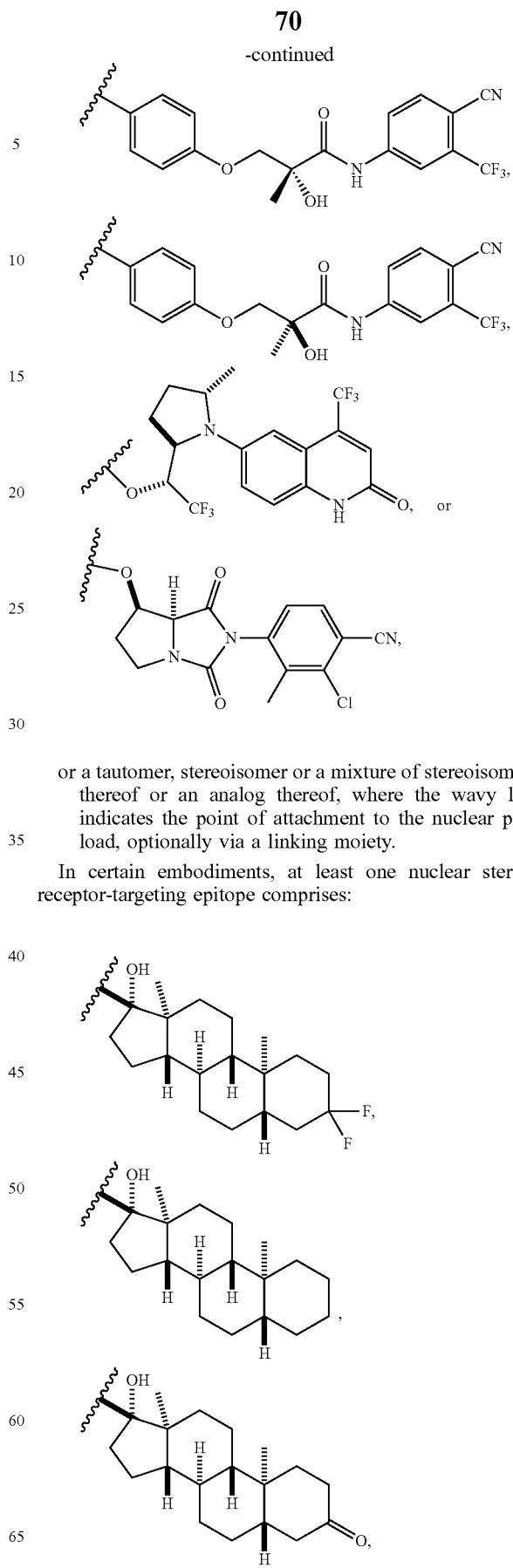
or a tautomer, stereoisomer or a mixture of stereoisomers thereof or an analog thereof, where the wavy line indicates the point of attachment to the nuclear payload, optionally via a linking moiety.
In certain embodiments, at least one nuclear steroid receptor-targeting epitope comprises:

-continued
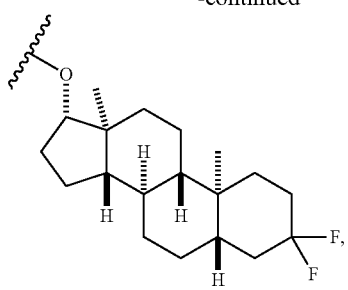
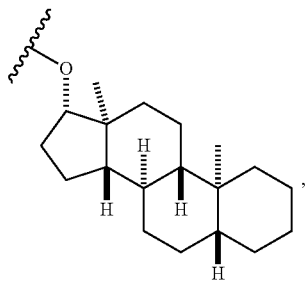
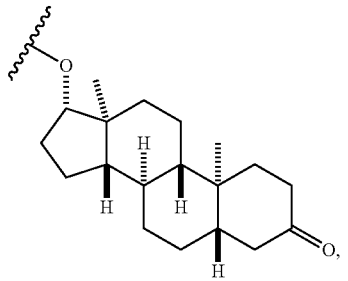
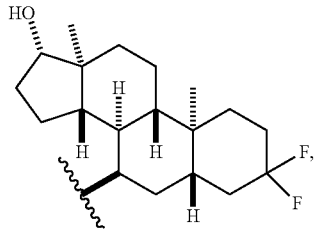
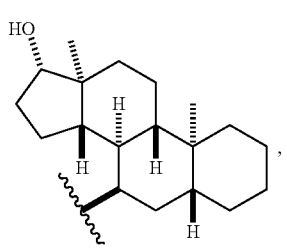
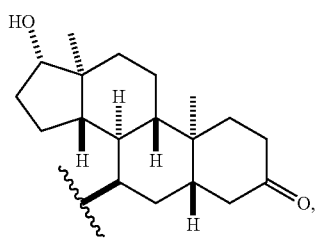
-continued
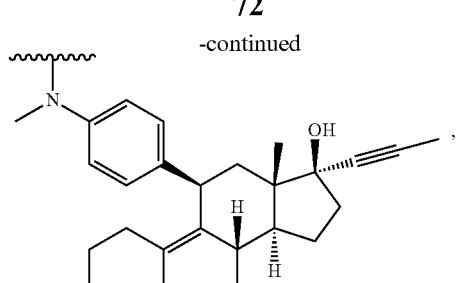
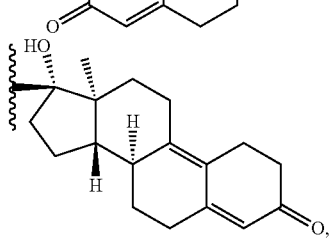
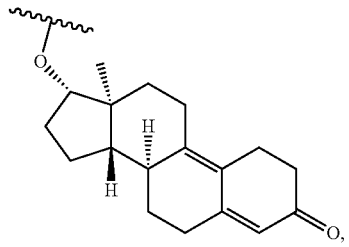
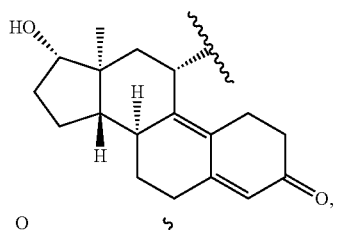
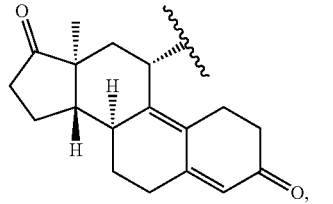
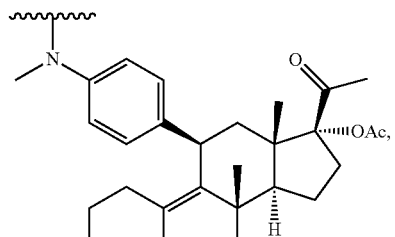
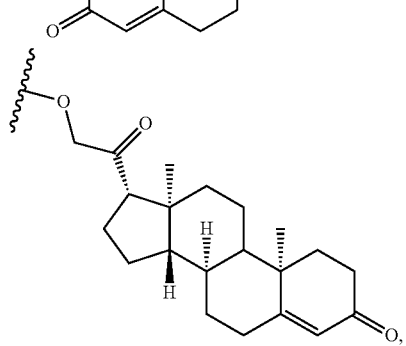

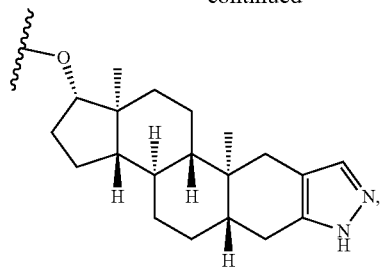

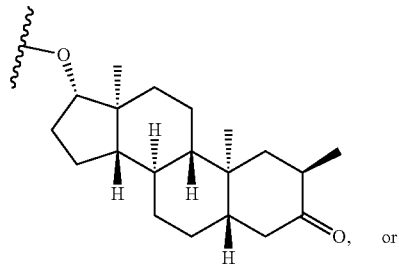

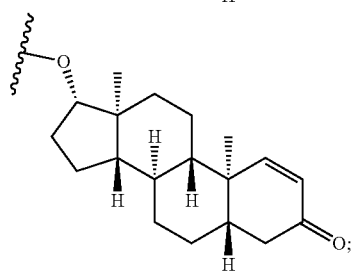

or a tautomer, stereoisomer or a mixture of stereoisomers thereof or an analog thereof, where the wavy line indicates the point of attachment to the nuclear payload, optionally via a linking moiety.

In certain embodiments, the nuclear steroid receptor-targeting epitope is not, or does not contain, a peptide, protein, nanoparticle or antibody.

Linking Moiety

The "linking moiety" of any compounds described herein can be biocleavable (e.g., acid labile) or non-biocleavable. Linking moieties can be linear, branched, saturated, unsaturated, all-carbon or heteroatomic. Linking moieties can also contain one or more rings that are fused, saturated, unsaturated, as well as be all-carbon or heteroatomic. In certain embodiments, the linking moiety is a non-biocleavable linking moiety. In certain embodiments, the linking moiety is a biocleavable linking moiety. In certain embodiments, a nuclear payload is bonded to one nuclear steroid receptor-targeting epitope via a non-biocleavable linking moiety and one or more nuclear steroid receptor-targeting epitope(s) via a biocleavable linking moiety. In certain embodiments, the biocleavable linking moiety is an acid-labile linking moiety. In some embodiments, the linking moiety comprises a hydrazone linkage.

It is contemplated that any linking moiety can be used in the compounds described herein, provided that it does not significantly interfere with or disrupt the desired binding of the nuclear payload or the nuclear receptor-targeting epitope.

In some embodiments, the linking moiety (L) is alkylene, heteroalkylene, alkenylene, heteroalkenylene, alkynylene, heteroalkynylene, arylene, heteroarylene, cycloalkylene or heterocycloalkylene; wherein each alkylene, heteroalkylene, alkenylene, heteroalkenylene, alkynylene, heteroalkynylene, arylene, heteroarylene, cycloalkylene or heteroarylene, may optionally comprise an arylene, heteroarylene, cycloalkylene or heterocycloalkylene; and further wherein each alkylene, heteroalkylene, alkenylene, heteroalkenylene, alkynylene, heteroalkynylene, arylene, heteroarylene, cycloalkylene or heterocycloalkylene is independently optionally substituted with one to five substituents independently selected from oxo, halo, $C_{1-4}$ alkyl, $C_{1-4}$ alkoxy, and $C_{1-4}$ haloalkyl.

In the linkers shown, where not directionality is specified, none is intended. Where not specified, either end of the linker can be bonded to $R^1$ or a PARP-binding portion of the compound.

In certain embodiments, the linking moiety (L) is of the formula:

$-(L^a)_q-$, wherein:

each $L^a$ is independently $-NR^{110}-$, $-O-$, $-S(O)_{0-2}-$, $-NR^{110}C(O)-$, $-C(O)NR^{110}-$, $-NR^{110}C(O)NR^{110}-$, $-NR^{110}S(O)_2-$, $-S(O)_2NR^{110}-$, $-NR^{110}S(O)_2NR^{110}-$, $-CR^{120}=N-NR^{110}-$, $-NR^{110}-N=CR^{120}-$, $-C(O)-$, $-OC(O)-$, $-OC(O)O-$, $-C(O)O-$, alkylene, alkenylene, alkynylene, arylene, or heteroarylene, wherein each alkylene, alkenylene, alkynylene, arylene, or heteroarylene is independently optionally substituted with one to five substituents independently selected from oxo, halo, $C_{1-4}$ alkyl, $C_{1-4}$ haloalkyl, $C_{1-4}$ alkoxy, $C_{1-4}$ haloalkoxy, aryl, heteroaryl, cycloalkyl, and heterocyclyl;

each $R^{110}$ is independently hydrogen, $C_{1-4}$ alkyl, $C_{1-4}$ haloalkyl, $C_{1-4}$ alkoxy, $C_{1-4}$ haloalkoxy, aryl, heteroaryl, cycloalkyl, or heterocyclyl;

each $R^{120}$ is independently hydrogen, $C_{1-4}$ alkyl, $C_{1-4}$ haloalkyl, $C_{1-4}$ alkoxy, $C_{1-4}$ haloalkoxy, aryl, heteroaryl, cycloalkyl, or heterocyclyl; and q is an integer from 0 to 20.

In certain embodiments, the linking moiety (L) is of the formula:

$-Y^{10}-(CHR^{130})_n-Y^{20}-(CHR^{140})_{n'}-Y^{30}-(CHR^{150})_{m'}-Y^{40}-$ wherein:

each of $Y^{10}$, $Y^{20}$, $Y^{30}$, and $Y^{40}$ are independently a bond, $-NR^{110}-$, $-O-$, $-S(O)_{0-2}-$, $-NR^{110}C(O)-$, $-C(O)NR^{110}-$, $-NR^{110}C(O)NR^{110}-$, $-NR^{110}S(O)_2-$, $-S(O)_2NR^{110}-$, $-NR^{110}S(O)_2NR^{110}-$, $-CR^{120}=N-NR^{110}-$, $-NR^{110}-N=CR^{120}-$, $-C(O)-$, $-OC(O)-$, $-OC(O)O-$, $-(CH_2CH_2O)_{1-5}-$, $-C(O)O-$, alkylene, alkenylene, alkynylene, arylene, and heteroarylene; wherein each alkylene, alkenylene, alkynylene, arylene, or heteroarylene is independently optionally substituted with one to five substituents independently selected from oxo, halo, $C_{1-4}$ alkyl, $C_{1-4}$ haloalkyl, $C_{1-4}$ alkoxy, or $C_{1-4}$ haloalkoxy;

each $R^{110}$ is independently hydrogen, $C_{1-4}$ alkyl, $C_{1-4}$ haloalkyl, $C_{1-4}$ alkoxy, $C_{1-4}$ haloalkoxy, aryl, heteroaryl, cycloalkyl, or heterocyclyl;

each $R^{120}$ is independently hydrogen, $C_{1-4}$ alkyl, $C_{1-4}$ haloalkyl, $C_{1-4}$ alkoxy, $C_{1-4}$ haloalkoxy, aryl, heteroaryl, cycloalkyl, or heterocyclyl;

each $R^{130}$ is independently hydrogen, $C_{1-4}$ alkyl, $C_{1-4}$ haloalkyl, $C_{1-4}$ alkoxy, $C_{1-4}$ haloalkoxy, aryl, heteroaryl, cycloalkyl, or heterocyclyl;

each $R^{140}$ is independently hydrogen, $C_{1-4}$ alkyl, $C_{1-4}$ haloalkyl, $C_{1-4}$ alkoxy, $C_{1-4}$ haloalkoxy, aryl, heteroaryl, cycloalkyl, or heterocyclyl;

each $R^{150}$ is independently hydrogen, $C_{1-4}$ alkyl, $C_{1-4}$ haloalkyl, $C_{1-4}$ alkoxy, $C_{1-4}$ haloalkoxy, aryl, heteroaryl, cycloalkyl, or heterocyclyl; and n', n", and m" are each independently 0, 1, 2, 3, 4, 5, 6, 7, or 8.

In certain embodiments, the linking moiety (L) is of the formula:

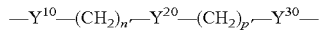
$$-Y^{10}-(CH_2)_{n'}-Y^{20}-(CH_2)_{p'}-Y^{30}-$$

wherein each of $Y^{10}$, $Y^{20}$ and $Y^{30}$ are independently a bond, optionally substituted alkylene, optionally substituted heteroalkylene, optionally substituted arylene, optionally substituted heteroarylene, optionally substituted cycloalkylene, optionally substituted heterocyclylene, $-CR^{110}R^{120}-$, $-NR^{110}-$, $-O-$, $-S(O)_{0-2}-$, $-NR^{110}C(O)-$, $-C(O)NR^{110}-$, $-NR^{110}S(O)_2-$, $-S(O)_2NR^{110}-$, $-CR^{120}=N-NR^{110}-$, $-NR^{110}-N=CR^{120}-$, $-OC(O)-$, or $-C(O)-$;

each $R^{110}$ is independently hydrogen, $C_{1-4}$ alkyl, $C_{1-4}$ haloalkyl, aryl, heteroaryl, cycloalkyl or heterocyclyl;

each $R^{120}$ is independently hydrogen, $C_{1-4}$ alkyl, $C_{1-4}$ haloalkyl, aryl, heteroaryl, cycloalkyl or heterocyclyl; and n' and p' are each independently 0, 1, 2, 3, 4, 5, 6, 7, or 8.

In certain embodiments, the linking moiety (L) is of the formula:

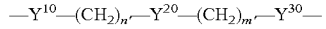
$$-Y^{10}-(CH_2)_{n'}-Y^{20}-(CH_2)_{m'}-Y^{30}-$$

wherein:

each of $Y^{10}$, $Y^{20}$, and $Y^{30}$ are independently a bond, $-NR^{110}-$, $-O-$, $-S(O)_{0-2}-$, $-NR^{110}C(O)-$, $-C(O)NR^{110}-$, $-NR^{110}S(O)_2-$, $-S(O)_2NR^{110}-$, $-CR^{120}=N-NR^{110}-$, $-NR^{110}-N=CR^{120}-$, $-C(O)-$, arylene, heteroarylene, cycloalkylene or heterocycloalkylene; wherein each alkylene, heteroalkylene, alkenylene, heteroalkenylene, alkynylene, heteroalkynylene, arylene, heteroarylene, cycloalkylene or heterocycloalkylene is independently optionally substituted with one to five substituents independently selected from oxo, halo, $C_{1-4}$ alkyl, $C_{1-4}$ alkoxy, and $C_{1-4}$ haloalkyl;

each $R^{110}$ is independently hydrogen, $C_{1-4}$ alkyl, $C_{1-4}$ haloalkyl, aryl, heteroaryl, cycloalkyl, or heterocyclyl;

each $R^{120}$ is independently hydrogen, $C_{1-4}$ alkyl, $C_{1-4}$ haloalkyl, aryl, heteroaryl, cycloalkyl, or heterocyclyl; and n' and m" are each independently 0, 1, 2, 3, 4, 5, 6, 7, or 8.

In certain embodiments, the linking moiety is not a bond. In certain embodiments, each $R^{110}$ is independently hydrogen, $C_{1-4}$ alkyl, $C_{1-4}$ haloalkyl, aryl, heteroaryl, cycloalkyl or heterocyclyl; and each $R^{120}$ is independently hydrogen, $C_{1-4}$ alkyl, $C_{1-4}$ haloalkyl, aryl, heteroaryl, cycloalkyl or heterocyclyl.

In certain embodiments, the linking moiety (L) is of the formula:

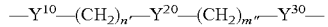
$$-Y^{10}-(CH_2)_{n'}-Y^{20}-(CH_2)_{m'}-Y^{30}-$$

wherein:

$Y^{20}$ is $-NR^{110}-$, $-O-$, $-S(O)_{0-2}-$, $-NR^{110}C(O)-$, $-C(O)NR^{110}-$, $-NR^{110}S(O)_2-$, $-S(O)_2NR^{110}-$, $-CR^{120}=N-NR^{110}-$, $-NR^{110}-N=CR^{120}-$, $-C(O)-$, arylene, heteroarylene, cycloalkylene or heterocycloalkylene; wherein each alkylene, heteroalkylene, alkenylene, heteroalkenylene, alkynylene, heteroalkynylene, arylene, heteroarylene, cycloalkylene or heterocycloalkylene is independently optionally substituted with one to five substituents independently selected from oxo, halo, $C_{1-4}$ alkyl, $C_{1-4}$ alkoxy, and $C_{1-4}$ haloalkyl;

$Y^{10}$ and $Y^{30}$ are each independently a bond, $-NR^{110}-$, $-O-$, $-S(O)_{0-2}-$, $-NR^{110}C(O)-$, $-C(O)NR^{110}-$, $-NR^{110}S(O)_2-$, $-S(O)_2NR^{110}-$, $-CR^{120}=N-NR^{110}-$, $-NR^{110}-N=CR^{120}-$, $-C(O)-$, arylene, heteroarylene, cycloalkylene or heterocycloalkylene; wherein each alkylene, heteroalkylene, alkenylene, heteroalkenylene, alkynylene, heteroalkynylene, arylene, heteroarylene, cycloalkylene or heterocycloalkylene is independently optionally substituted with one to five substituents independently selected from oxo, halo, $C_{1-4}$ alkyl, $C_{1-4}$ alkoxy, and $C_{1-4}$ haloalkyl;

each $R^{110}$ is independently hydrogen, $C_{1-4}$ alkyl, $C_{1-4}$ haloalkyl, aryl, heteroaryl, cycloalkyl, or heterocyclyl;

each $R^{120}$ is independently hydrogen, $C_{1-4}$ alkyl, $C_{1-4}$ haloalkyl, aryl, heteroaryl, cycloalkyl, or heterocyclyl; and n' and m" are each independently 0, 1, 2, 3, 4, 5, 6, 7, or 8.

In certain embodiments, the linking moiety (L) is of the formula:

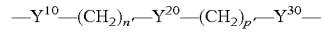
$$-Y^{10}-(CH_2)_{n'}-Y^{20}-(CH_2)_{p'}-Y^{30}-$$

wherein each of $Y^{10}$, $Y^{20}$, and $Y^{30}$ are independently a bond, optionally substituted alkylene, optionally substituted heteroalkylene, optionally substituted arylene, optionally substituted heteroarylene, optionally substituted cycloalkylene, optionally substituted heterocyclylene, $-CR^{110}R^{120}-$, $-NR^{110}-$, $-O-$, $-S(O)_{0-2}-$, $-NR^{110}C(O)-$, $-C(O)NR^{110}-$, $-NR^{110}S(O)_2-$, $-S(O)_2NR^{110}-$, $-CR^{120}=N-NR^{110}-$, $-NR^{110}-N=CR^{120}-$, or $-C(O)-$;

each $R^{110}$ is independently hydrogen, $C_{1-4}$ alkyl, $C_{1-4}$ haloalkyl, aryl, heteroaryl, cycloalkyl, or heterocyclyl;

each $R^{120}$ is independently hydrogen, $C_{1-4}$ alkyl, $C_{1-4}$ haloalkyl, aryl, heteroaryl, cycloalkyl, or heterocyclyl; and n' and p' are each independently 0, 1, 2, 3, 4, 5, 6, 7, or 8.

In certain embodiments, L comprises a non-biocleavable moiety.

In certain embodiments, L comprises an optionally substituted alkylene having 4-7 chain atoms, optionally substituted 4-7-membered heterocyclylene, or optionally substituted heteroalkylene having 4-7 chain atoms.

In certain embodiments, L comprises an optionally substituted heterocyclylene or optionally substituted heteroalkylene. In certain embodiments, L comprises an optionally substituted heterocyclylene and optionally substituted heteroalkylene.

In certain embodiments, L is optionally substituted $C_{4-10}$ atom heteroalkylene.

In certain embodiments, L is a 1-12 chain atom alkylene or 2-12 chain atom heteroalkylene linking moiety, containing 0-3 optionally substituted cycloalkylene, 0-3 optionally substituted heterocyclylene, 0-3 optionally substituted heteroarylene, 0-3 optionally substituted arylene, and 0-2 C=O. In certain embodiments, L is a 1-12 chain atom alkylene or 2-12 chain atom heteroalkylene linking moiety, containing 0-3 cycloalkylene, 0-3 heterocyclylene, 0-3 heteroarylene, 0-3 arylene, and 0-2 C=O. In certain embodiments, L is a 1-12 chain atom alkylene or 2-12 chain atom heteroalkylene linking moiety, containing 1-3 cycloalkylene, heterocyclylene, heteroarylene, or arylene rings, and 0-2 C=O.

In certain embodiments, L is a 4-12 chain atom alkylene or 4-12 chain atom heteroalkylene linking moiety containing CH$_2$ and up to 2 heteroatoms each independently selected from NH, O, or S, and optionally one C=O. In certain embodiments, L is a 4-11 chain atom alkylene or 4-11 chain atom heteroalkylene linking moiety containing CH$_2$ and up to 2 heteroatoms each independently selected from NH, O or S, and optionally one C=O. In certain embodiments, L is a 4-10 chain atom alkylene or 4-10 chain atom heteroalkylene linking moiety containing CH$_2$ and up to 2 heteroatoms each independently selected from NH, O or S, and optionally one C=O. In certain embodiments, L is a 4-9 chain atom alkylene or 4-9 chain atom heteroalkylene linking moiety containing CH$_2$ and up to 2 heteroatoms each independently selected from NH, O or S, and optionally one C=O. In certain embodiments, L is a 4-8 chain atom alkylene or 4-8 chain atom heteroalkylene linking moiety containing CH$_2$ and up to 2 heteroatoms each independently selected from NH, O or S, and optionally one C=O. In certain embodiments, L is a 4-7 chain atom alkylene or 4-7 chain atom heteroalkylene linking moiety containing CH$_2$ and up to 2 heteroatoms each independently selected from NH, O or S, and optionally one C=O. In certain embodiments, L is a 4-6 chain atom alkylene or 4-6 chain atom heteroalkylene linking moiety containing CH$_2$ and up to 2 heteroatoms each independently selected from NH, O or S, and optionally one C=O. As used herein, "chain atoms" include only those atoms making up the linking chain, and do not include hydrogen atoms or any substituent on an atom in the chain. By way of example, each of the following are linking moieties comprising 5 chain atoms:

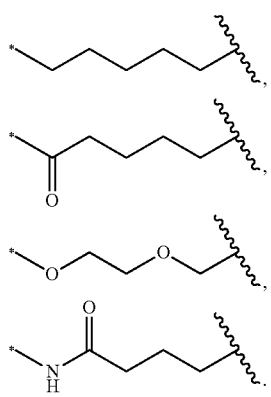

In certain embodiments, the linking moiety (L) is of the formula:

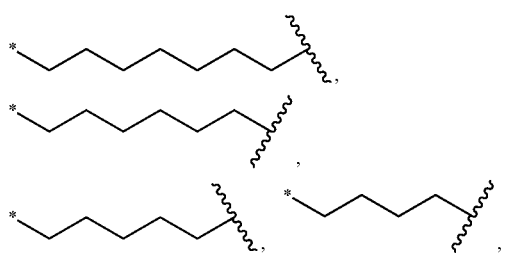

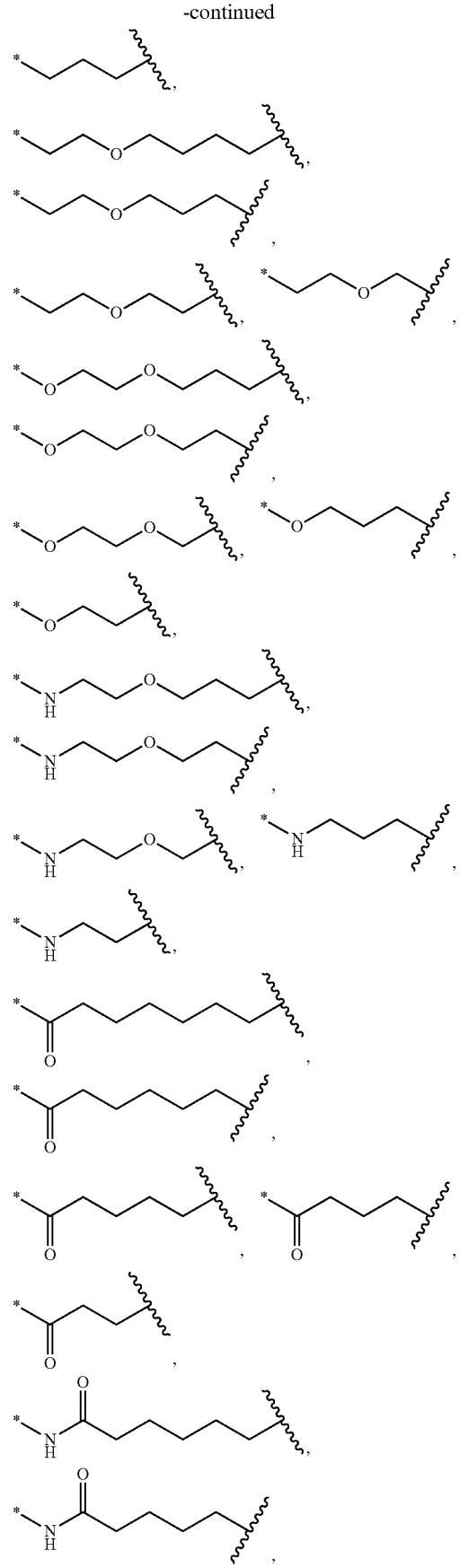

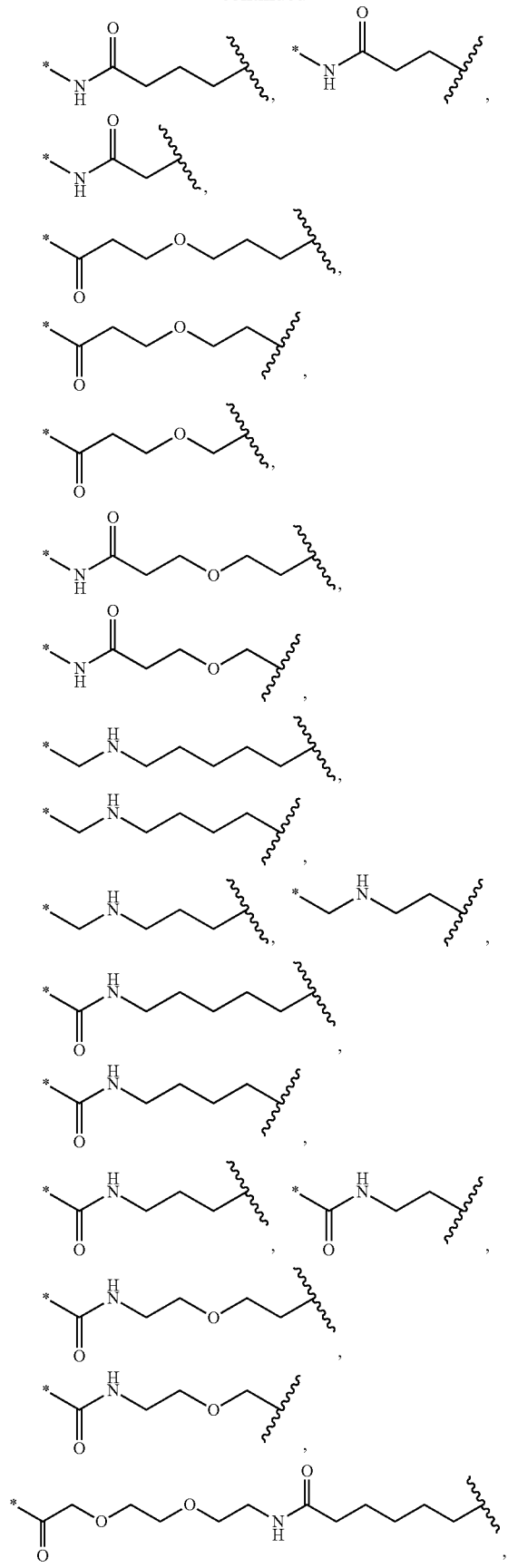
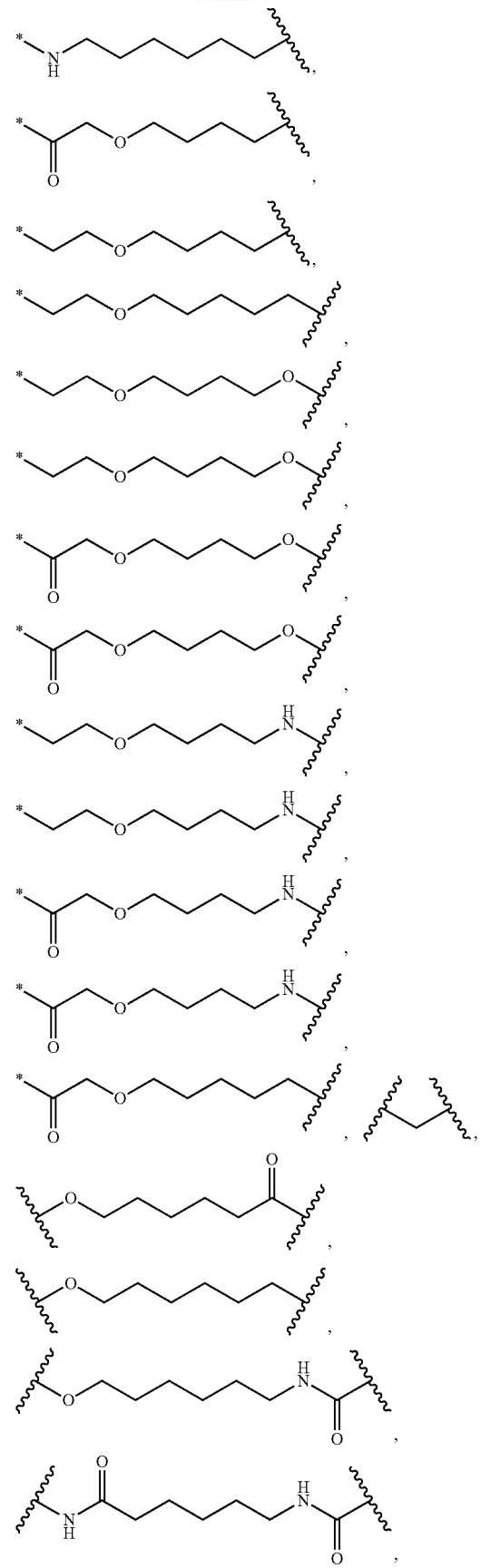

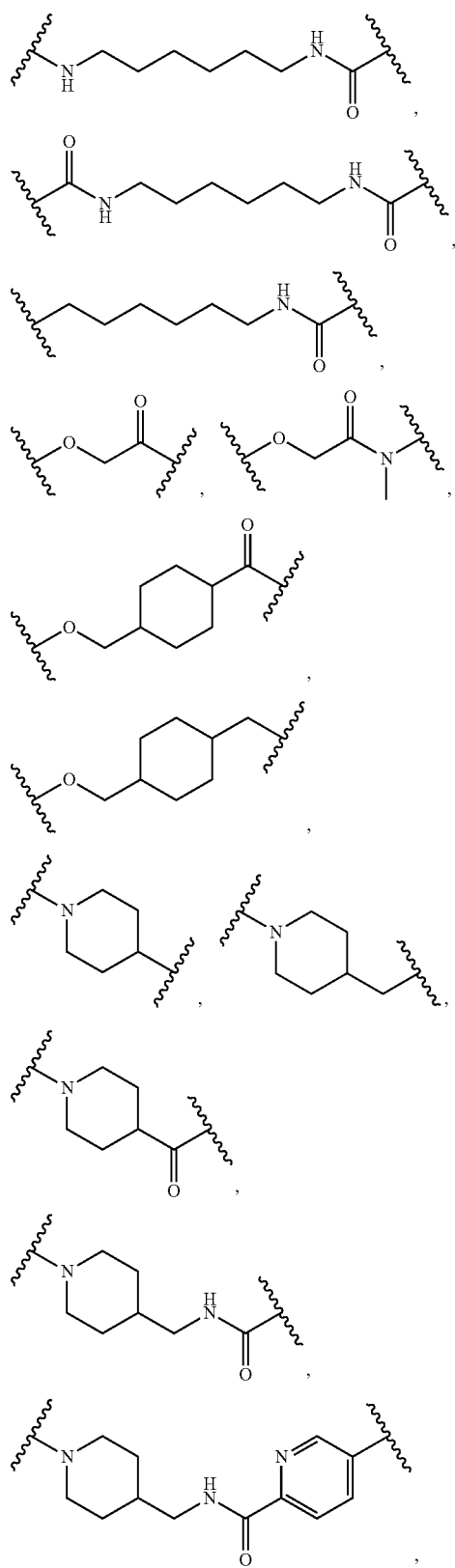
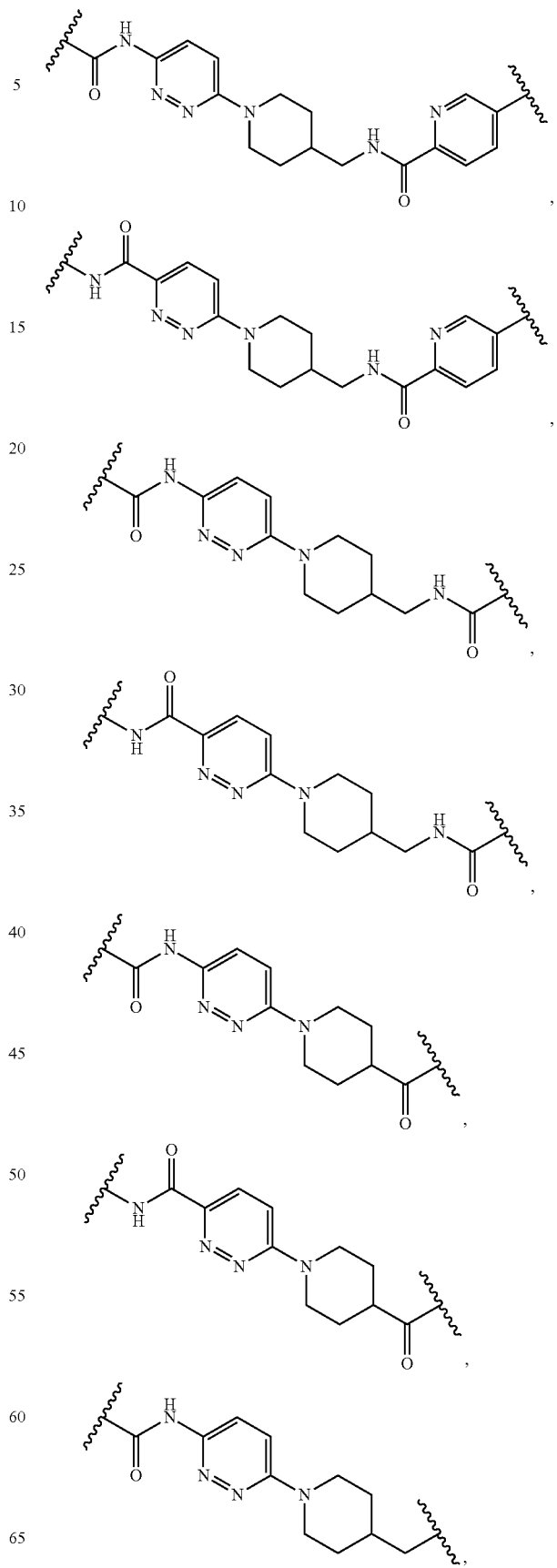

83
-continued
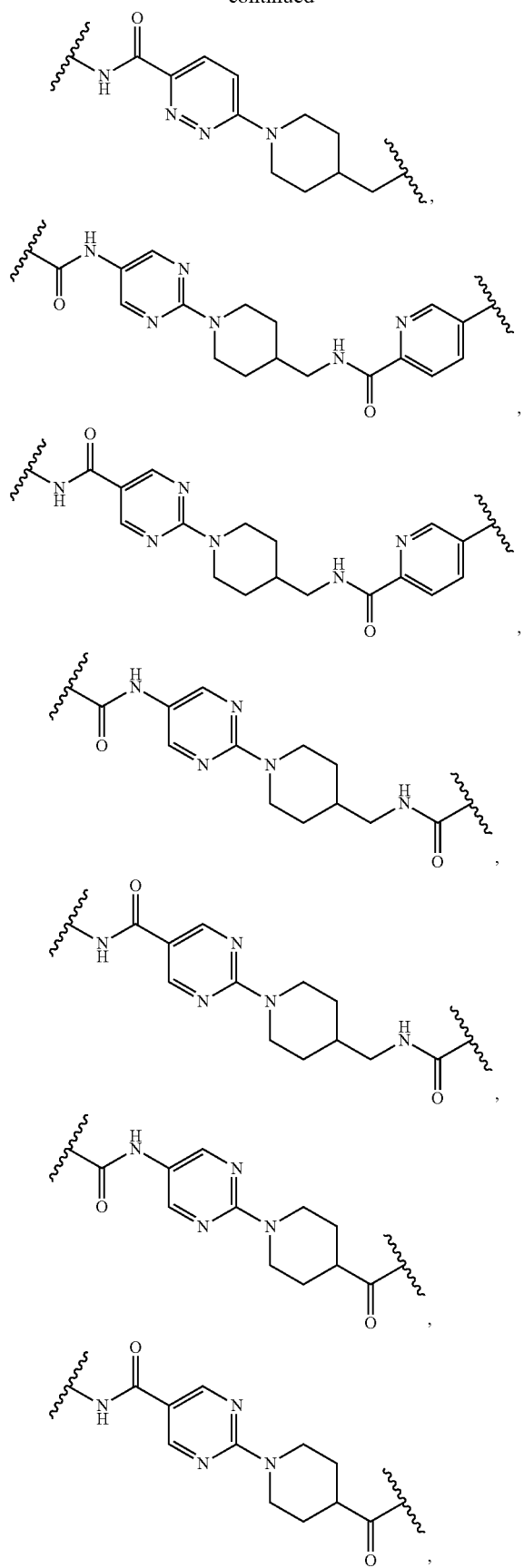
84
-continued
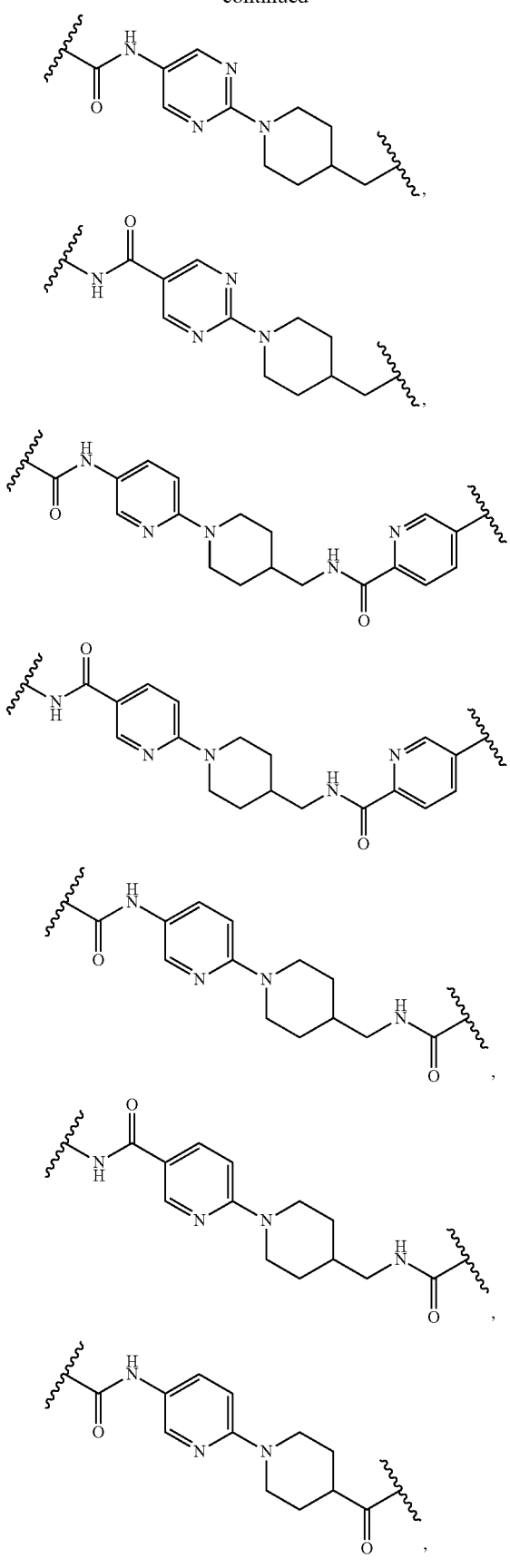

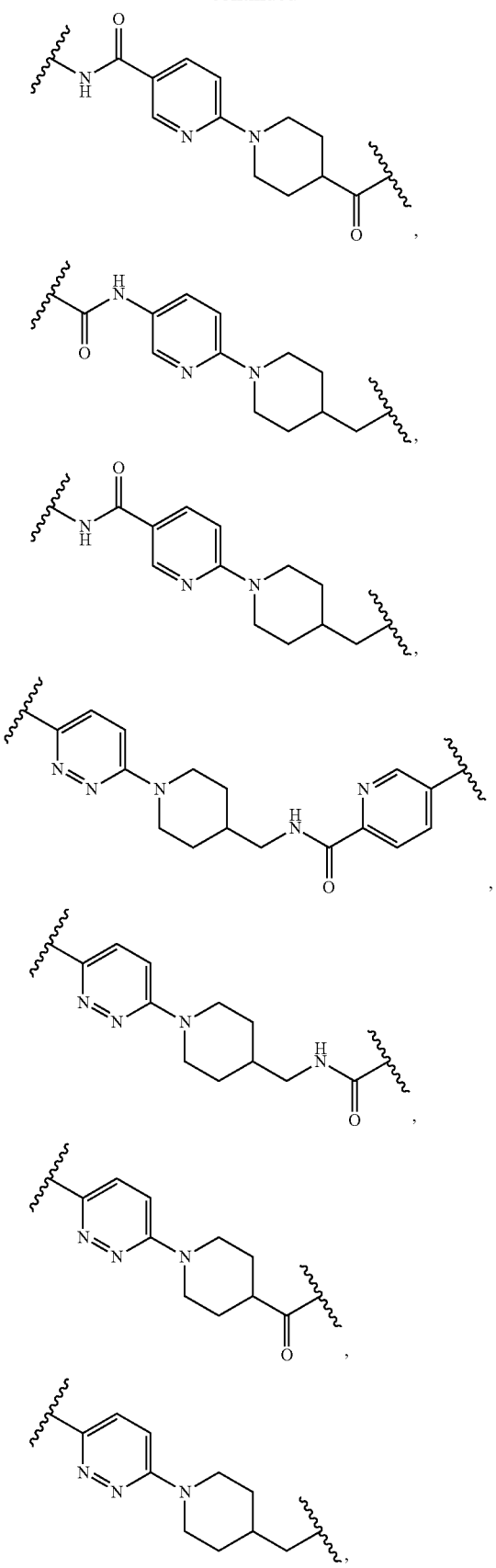
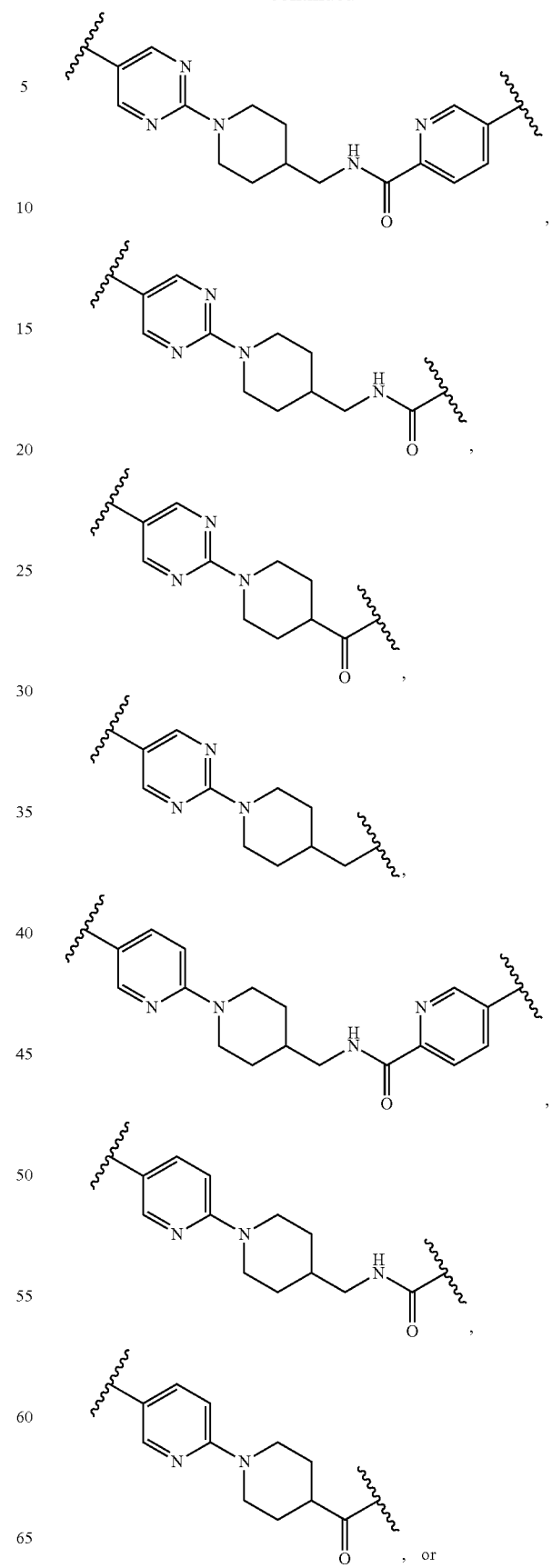

where the "*" and the wavy line represent a covalent bond to R¹ or a PARP-binding portion of the compound (e.g., as shown in Formulas I, II, etc.).

In certain embodiments, the linking moiety (L) is of the formula:

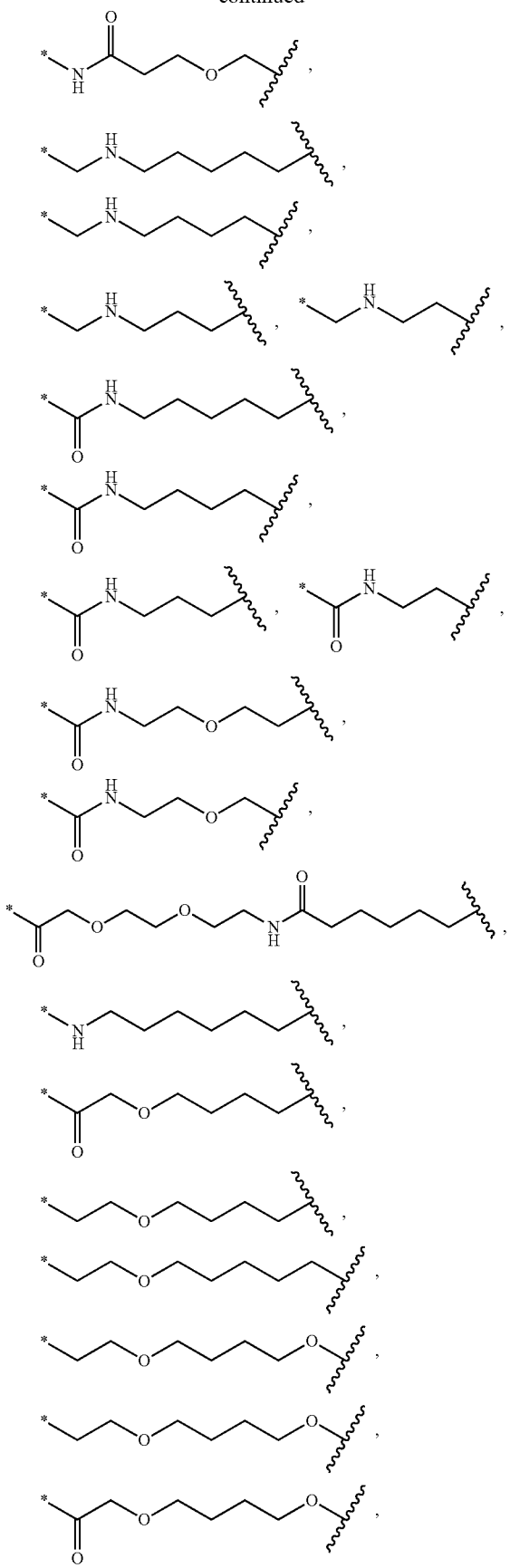
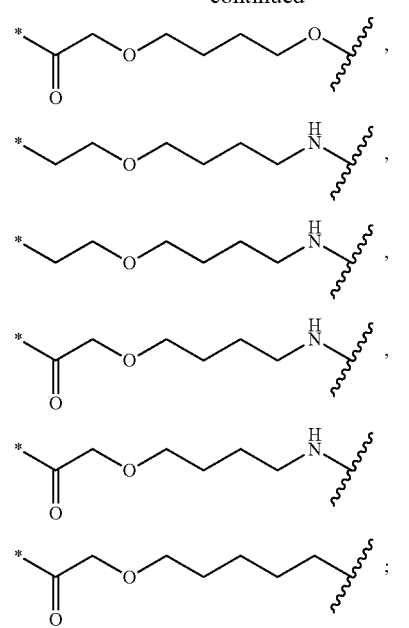
where the "*" and the wavy line represent a covalent bond.
In certain embodiments, L is
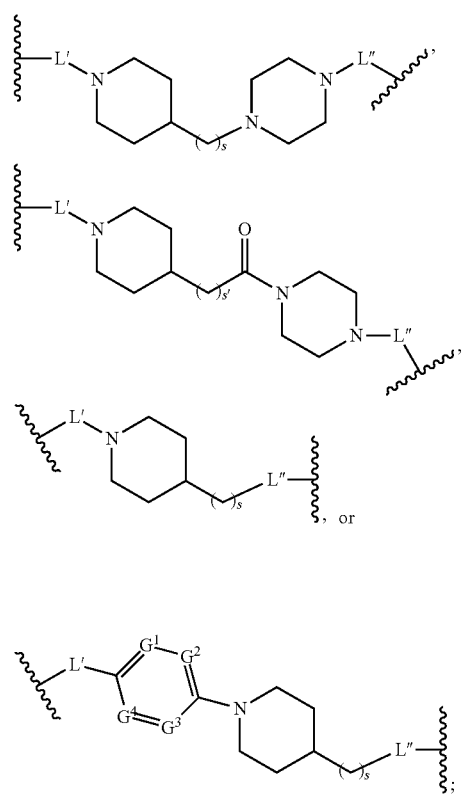
s is 1, 2, or 3; s' is 0 or 1;
$G^1$, $G^2$, $G^3$, and $G^4$ are each independently CH or N; and
L' and L" are each independently selected from a bond, $CH_2$, $CH_2CH_2$, NHC(O), or C=O.

In certain embodiments, L is
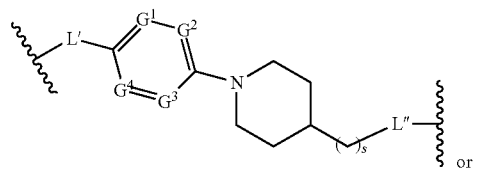
or
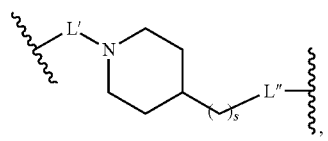
wherein L' and L" are each independently selected from a bond, $CH_2$, $CH_2CH_2$, NHC(O), or C=O; $G^1$, $G^2$, $G^3$, and $G^4$ are each independently CH or N; and s is 1, 2, or 3. In certain embodiments, s is 1 or 2. In certain embodiments, s is 1. In certain embodiments, s is 2. In certain embodiments, s is 3.
In certain embodiments, L is
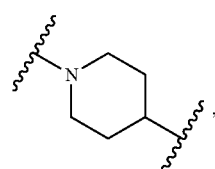, 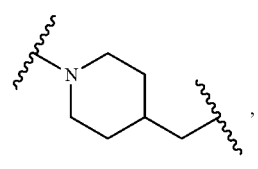,
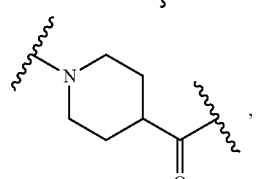,
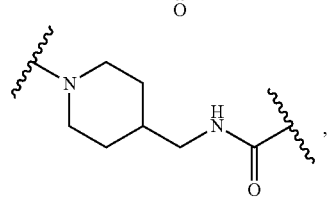,
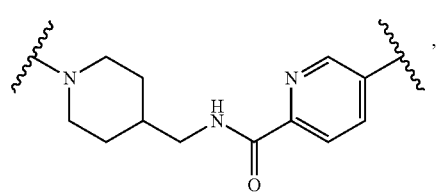,
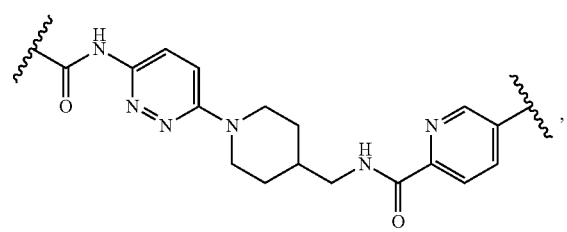,
-continued
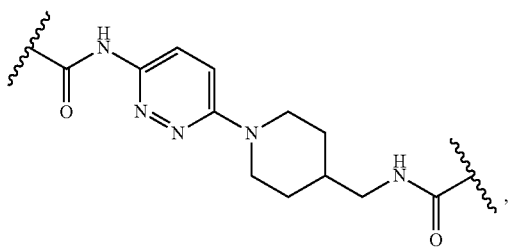,
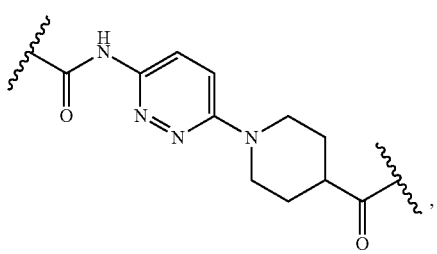,
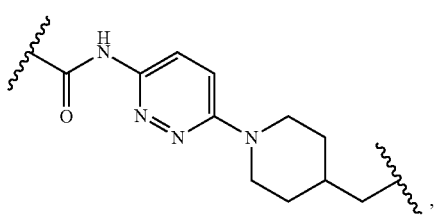,
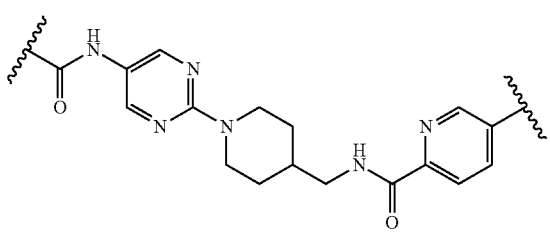,
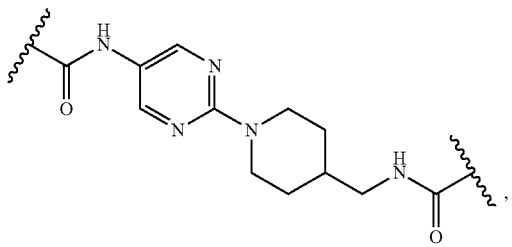,
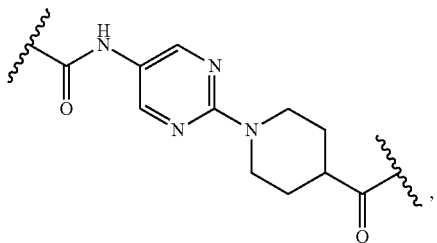,
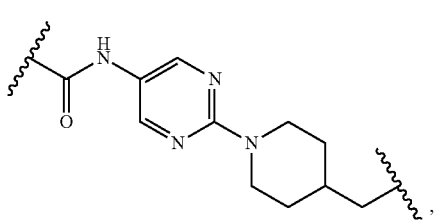, 93
-continued
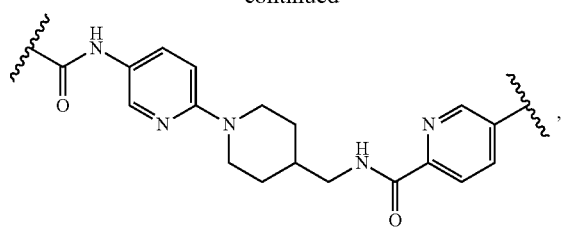
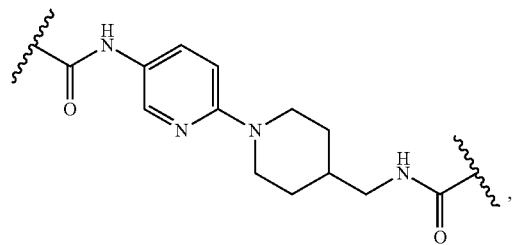
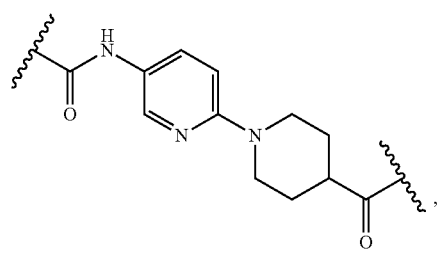
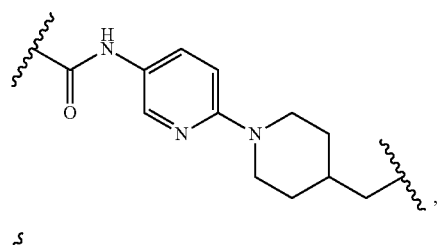
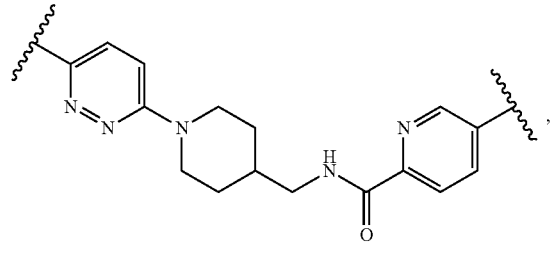
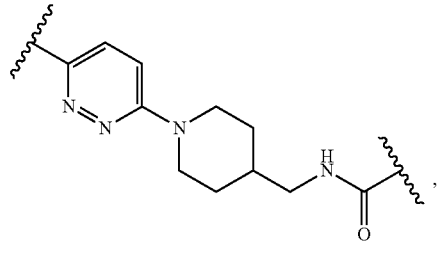
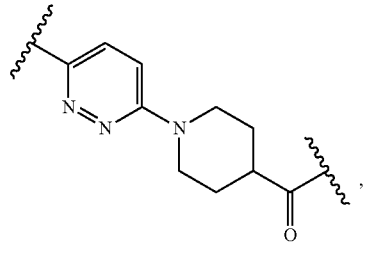
94
-continued
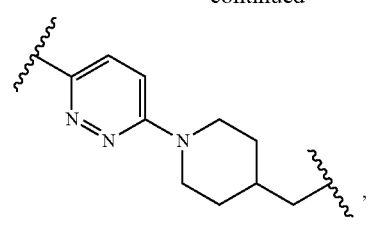
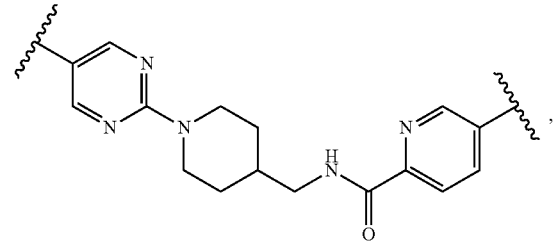
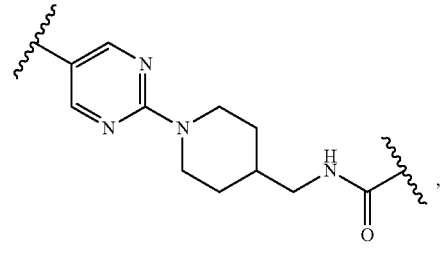
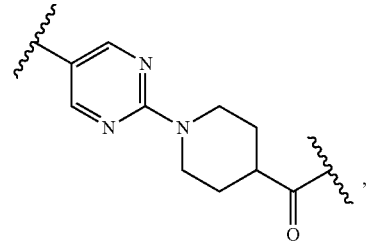
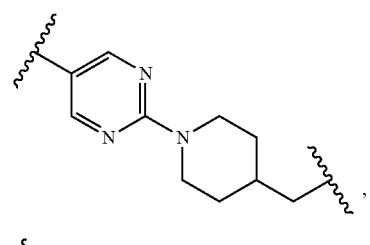
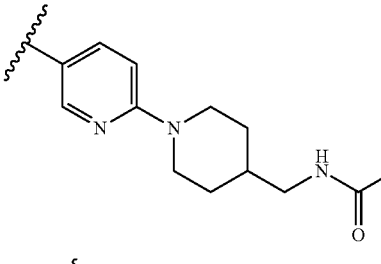
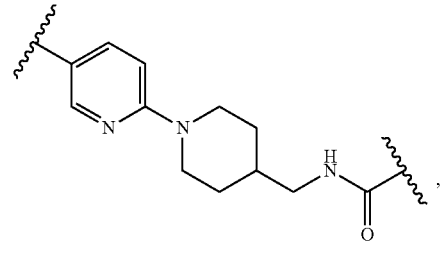

-continued

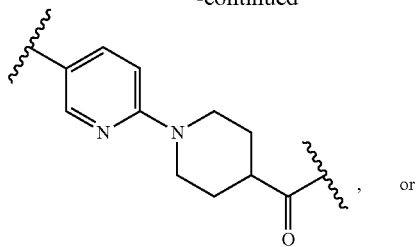, or

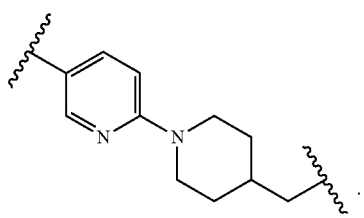.

In certain embodiments, L is

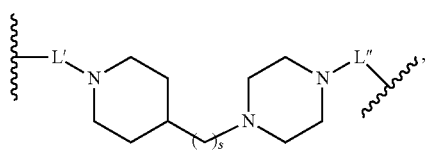, wherein L' and L" are each independently selected from a bond, $CH_2$, $CH_2CH_2$, or C=O; s is 1, 2, or 3. In certain embodiments, s is 1 or 2. In certain embodiments, s is 1. In certain embodiments, s is 2. In certain embodiments, s is 3.

In certain embodiments, L is

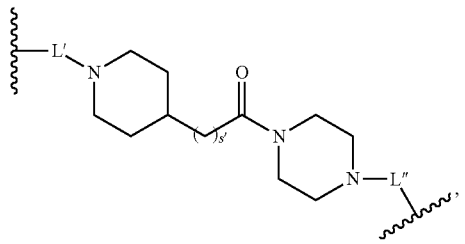, wherein L' and L" are each independently selected from a bond, $CH_2$, $CH_2CH_2$, or C=O; and s' is 0 or 1. In certain embodiments, s' is 0. In certain embodiments, s' is 1.

In certain embodiments, L is

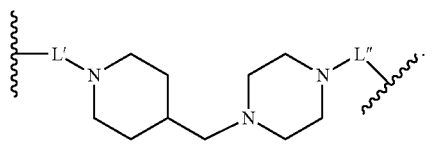.

In certain embodiments, L is

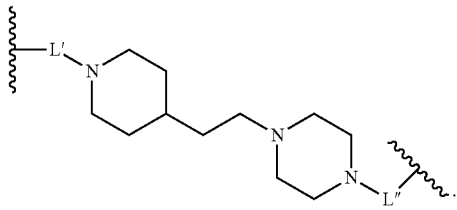

In certain embodiments, L is

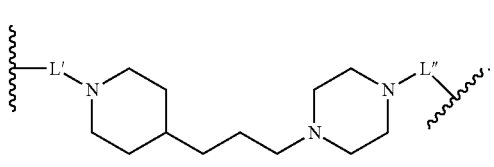

In certain embodiments, L is

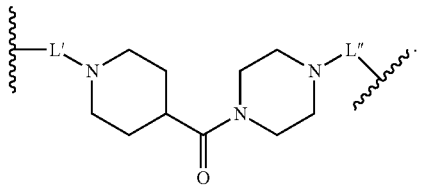

In certain embodiments, L is

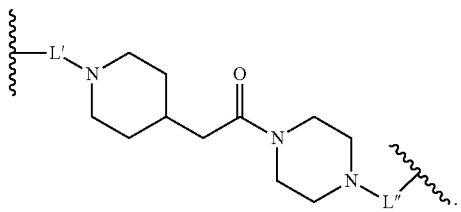

In certain embodiments, L is

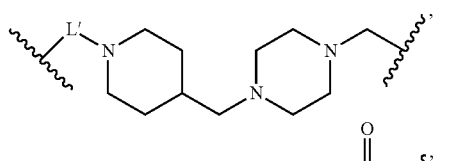

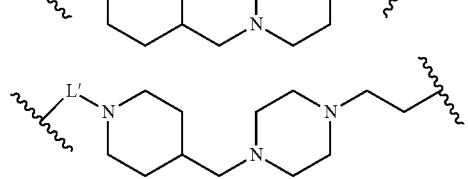

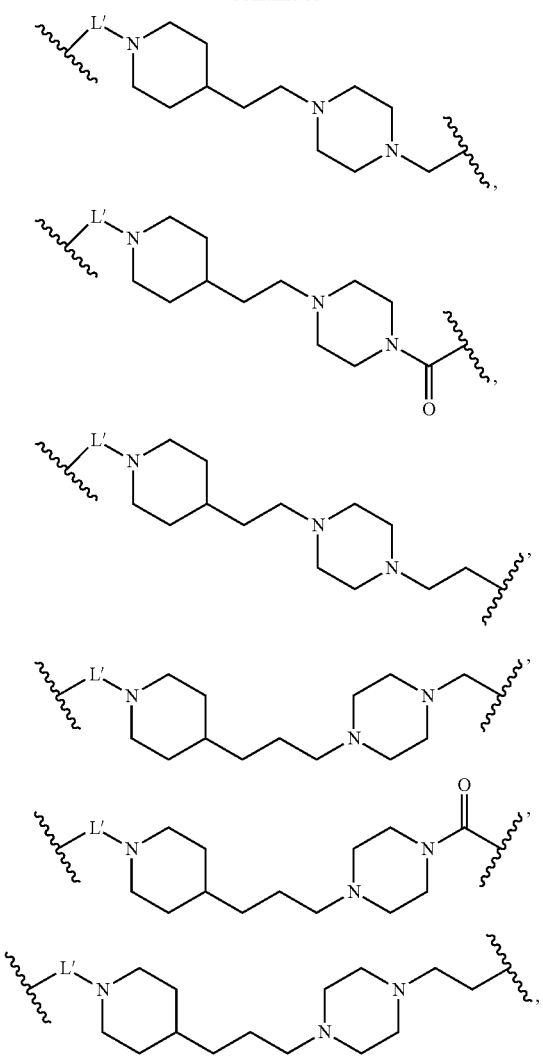

In certain embodiments, L' is a bond. In certain embodiments, L' is CH$_2$. In certain embodiments, L' is CH$_2$CH$_2$. In certain embodiments, L' is C=O.

In certain embodiments, L is

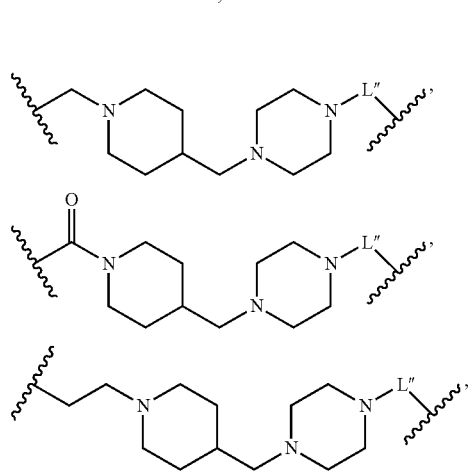

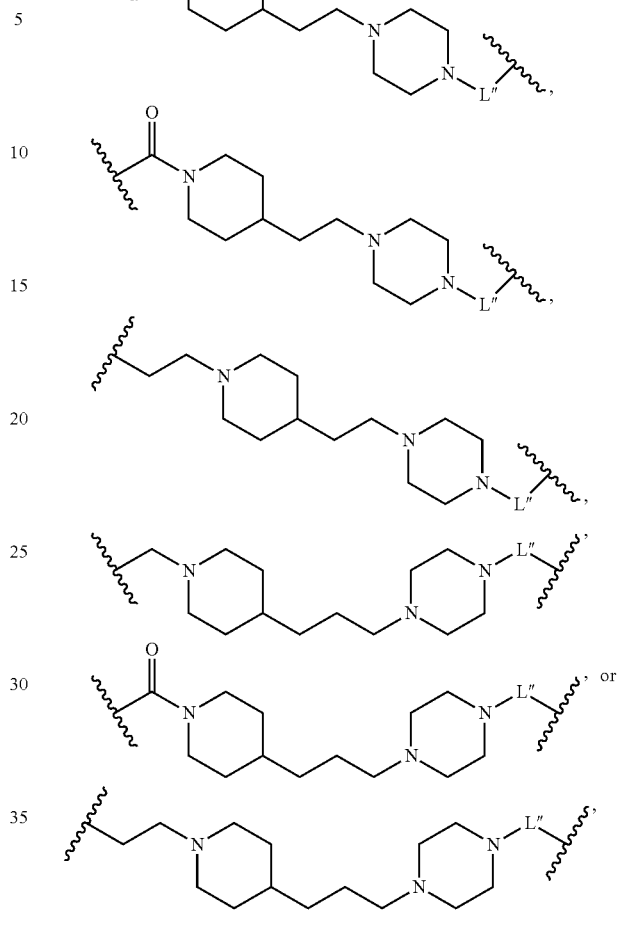

In certain embodiments, L" is a bond. In certain embodiments, L" is CH$_2$. In certain embodiments, L" is CH$_2$CH$_2$. In certain embodiments, L" is C=O.

In certain embodiments, L is

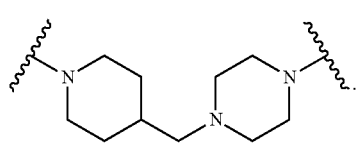 [SMILES: *N1CCC(CN2CCN(*)CC2)CC1]

In certain embodiments, L is

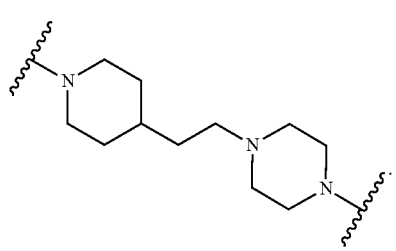 [SMILES: *N1CCC(CCN2CCN(*)CC2)CC1]

In certain embodiments, L is

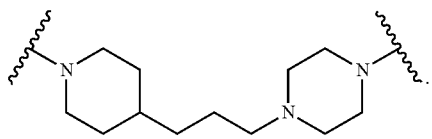 [SMILES: *N1CCC(CCCN2CCN(*)CC2)CC1]

In certain embodiments, L is

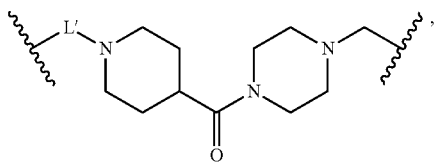

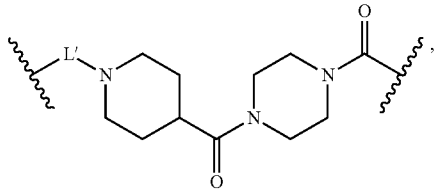

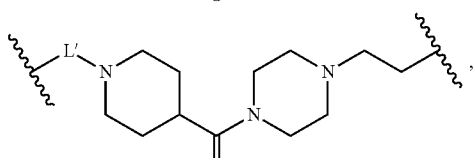

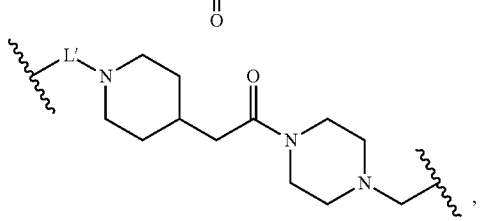

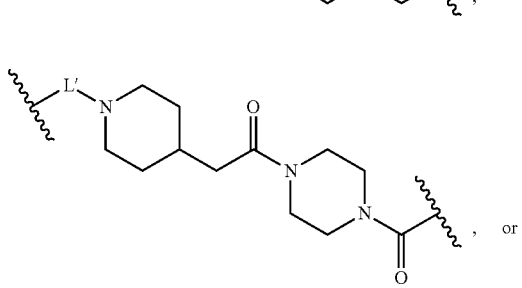, or

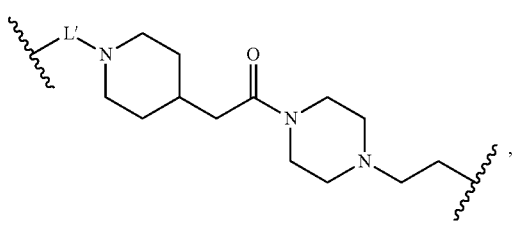

In certain embodiments, L' is a bond. In certain embodiments, L' is CH$_2$. In certain embodiments, L' is CH$_2$CH$_2$. In certain embodiments, L' is C=O.

In certain embodiments, L is

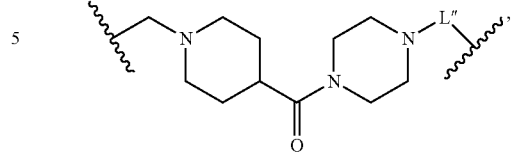

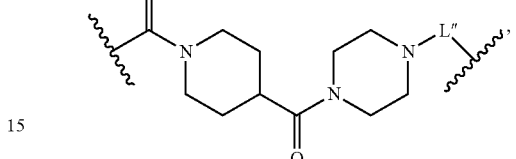

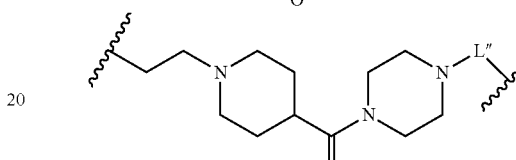

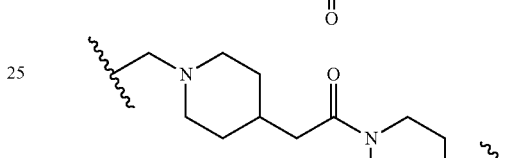

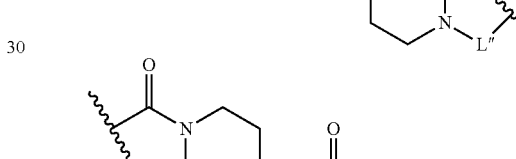

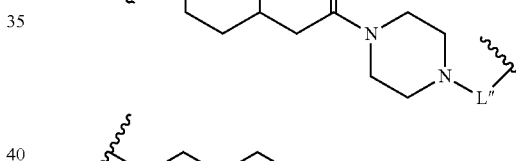, or

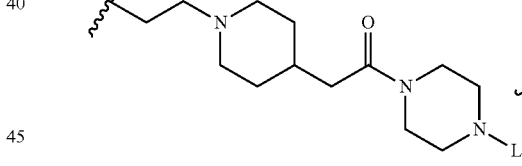

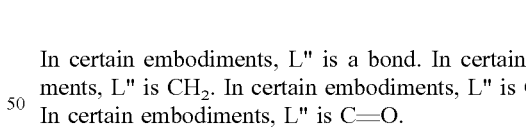

In certain embodiments, L" is a bond. In certain embodiments, L" is CH$_2$. In certain embodiments, L" is CH$_2$CH$_2$. In certain embodiments, L" is C=O.

In certain embodiments, the linking moiety L is of the formula:

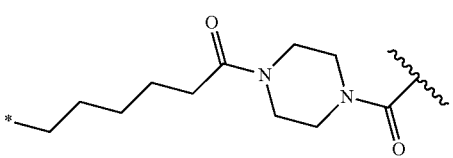

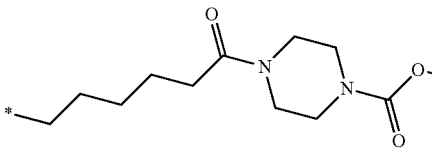

101
-continued
102
-continued
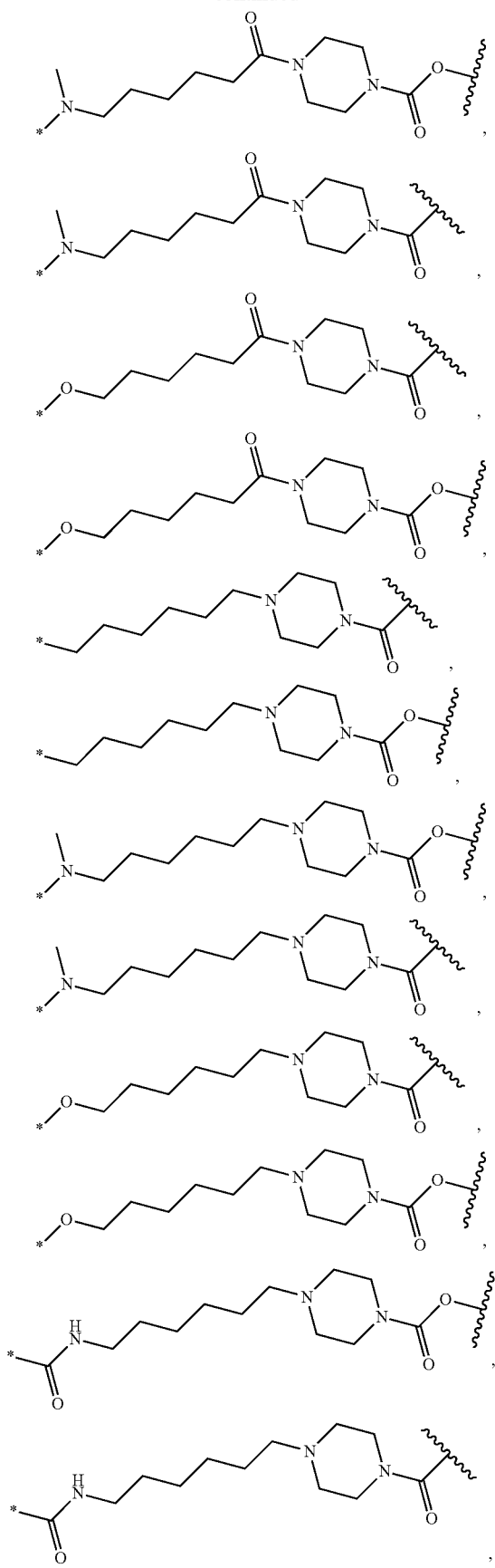
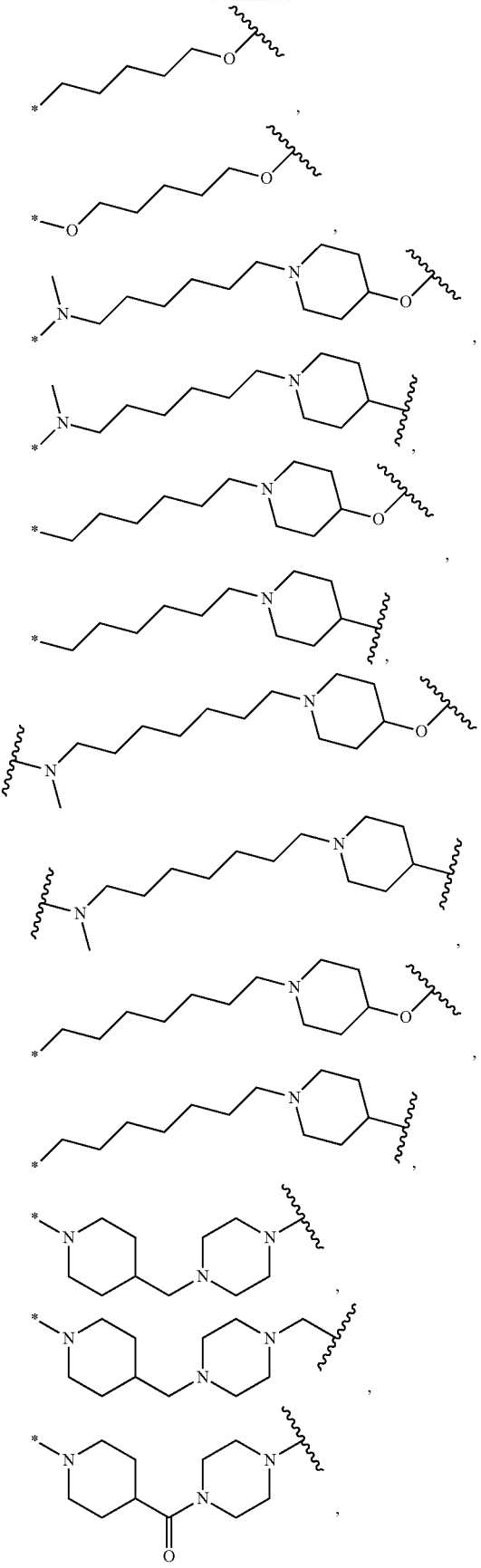

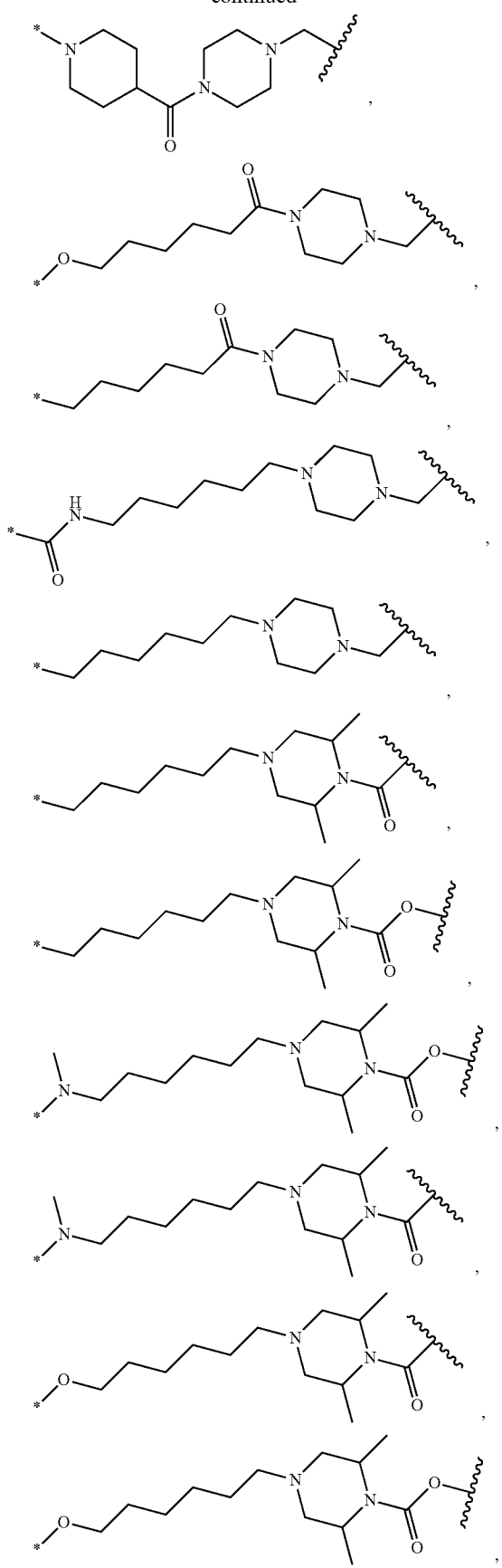
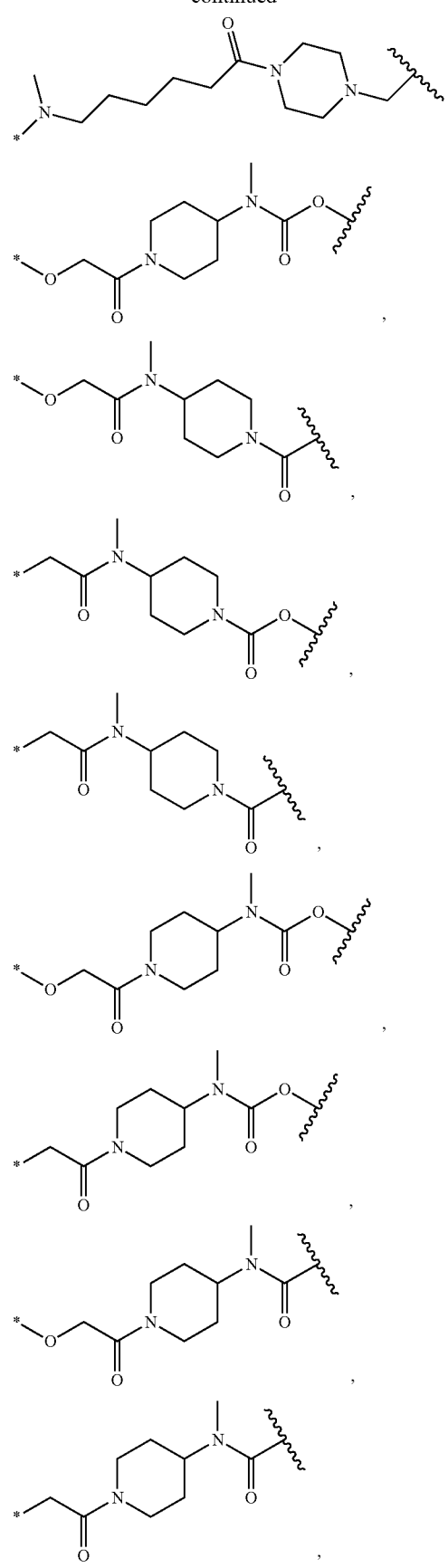

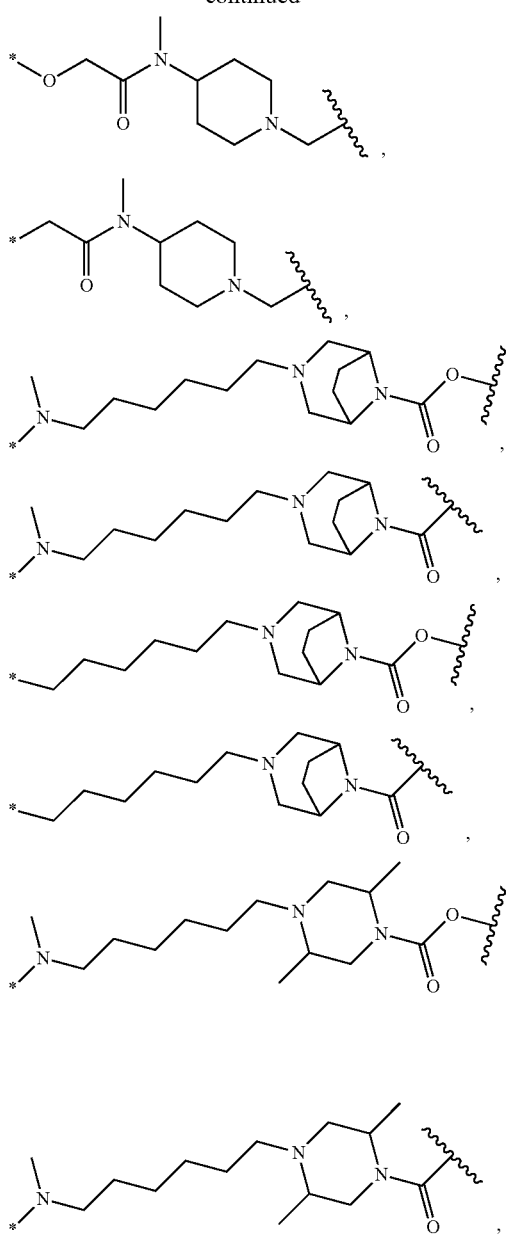
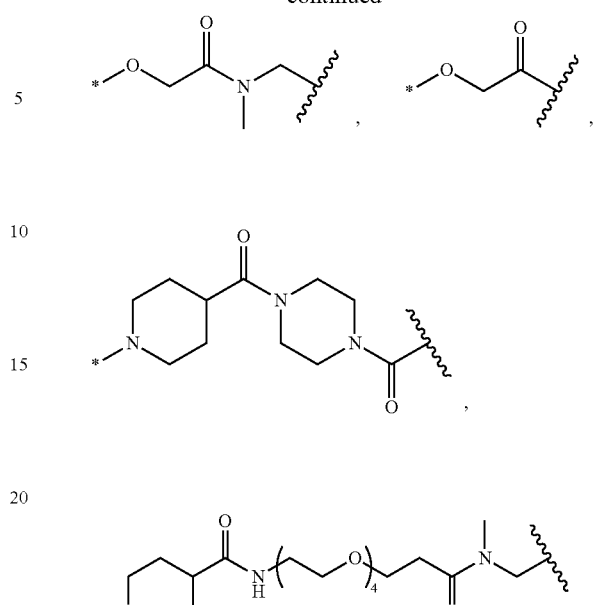
where the "*" and the wavy line represent a covalent bond.
In certain embodiments, L is
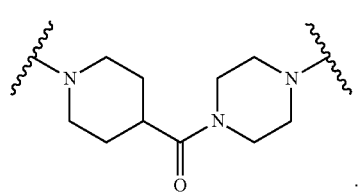 [SMILES: *N1CCC(C(=O)N2CCN(*)CC2)CC1]
In certain embodiments, L is
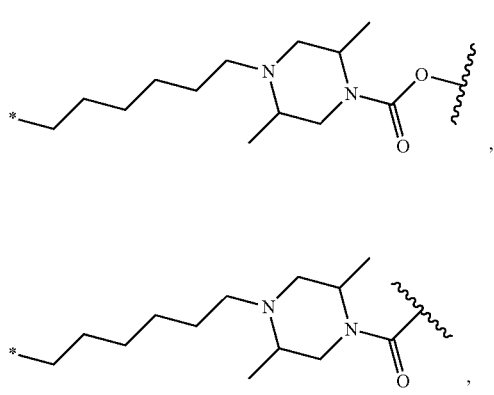
Also provided is a compound as provided in Table 1, or a tautomer, stereoisomer, mixture of stereoisomers, hydrate, solvate, isotopically enriched analog, or pharmaceutically acceptable salt thereof.

TABLE 1
| No. | Structure |
| --- | --- |
| 1 | 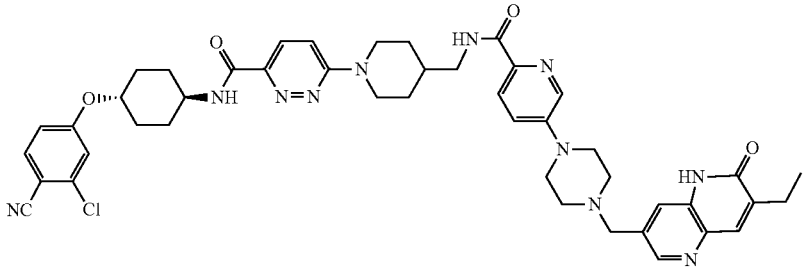 [SMILES: CCc1cc2ncc(CN3CCN(c4ccc(C(=O)NCC5CCN(c6ccc(C(=O)N[C@H]7CC[C@H](Oc8ccc(C#N)c(Cl)c8)CC7)nn6)CC5)nc4)CC3)cc2[nH]c1=O] |
| 2 | 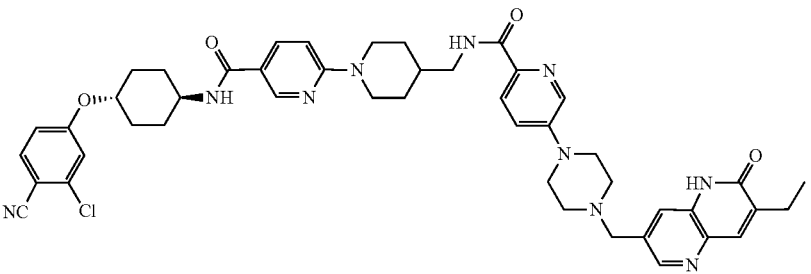 [SMILES: CCc1cc2ncc(CN3CCN(c4ccc(C(=O)NCC5CCN(c6ccc(C(=O)N[C@H]7CC[C@H](Oc8ccc(C#N)c(Cl)c8)CC7)cn6)CC5)nc4)CC3)cc2[nH]c1=O] |
| 3 | 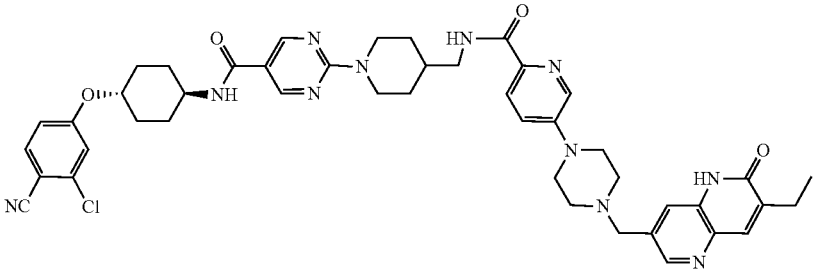 [SMILES: CCc1cc2ncc(CN3CCN(c4ccc(C(=O)NCC5CCN(c6ncc(C(=O)N[C@H]7CC[C@H](Oc8ccc(C#N)c(Cl)c8)CC7)cn6)CC5)nc4)CC3)cc2[nH]c1=O] |
| 4 | 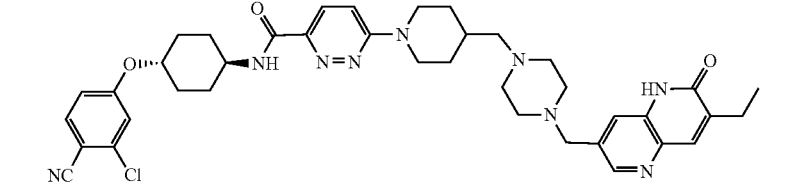 [SMILES: CCc1cc2ncc(CN3CCN(CC4CCN(c5ccc(C(=O)N[C@H]6CC[C@H](Oc7ccc(C#N)c(Cl)c7)CC6)nn5)CC4)CC3)cc2[nH]c1=O] |
| 5 | 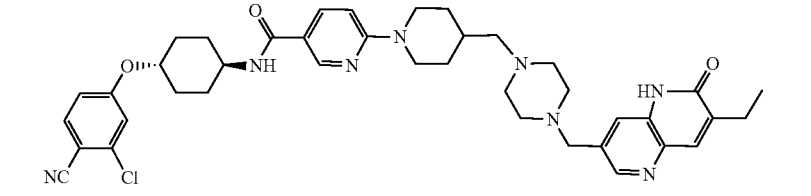 [SMILES: CCc1cc2ncc(CN3CCN(CC4CCN(c5ccc(C(=O)N[C@H]6CC[C@H](Oc7ccc(C#N)c(Cl)c7)CC6)cn5)CC4)CC3)cc2[nH]c1=O] |
| 6 | 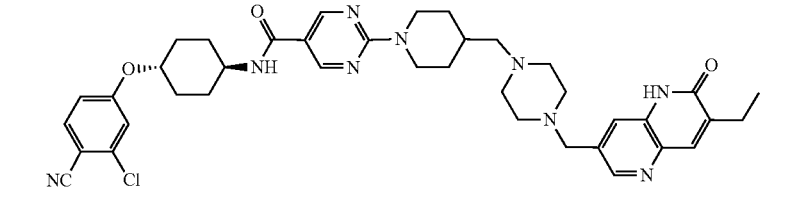 [SMILES: CCc1cc2ncc(CN3CCN(CC4CCN(c5ncc(C(=O)N[C@H]6CC[C@H](Oc7ccc(C#N)c(Cl)c7)CC6)cn5)CC4)CC3)cc2[nH]c1=O] |

TABLE 1-continued
| No. | Structure |
|---|---|
| 7 | 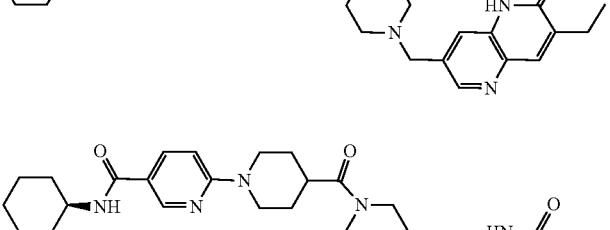 |
| 8 | 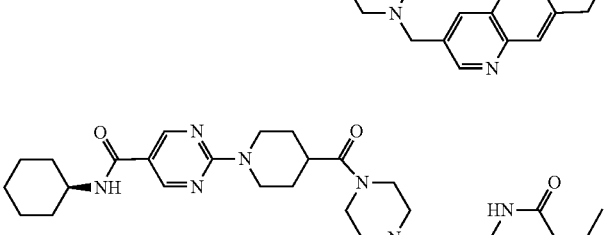 |
| 9 | 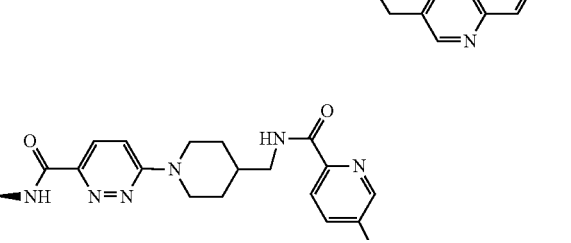 |
| 10 | 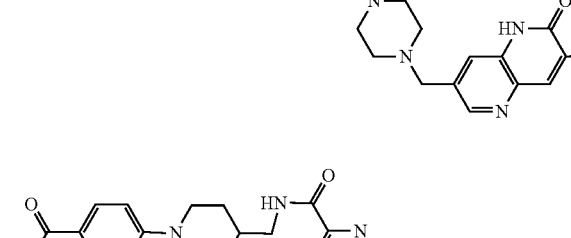 |
| 11 | 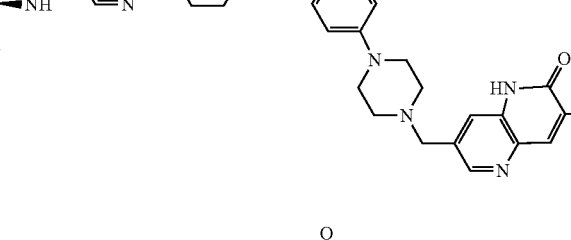 |
| 12 | 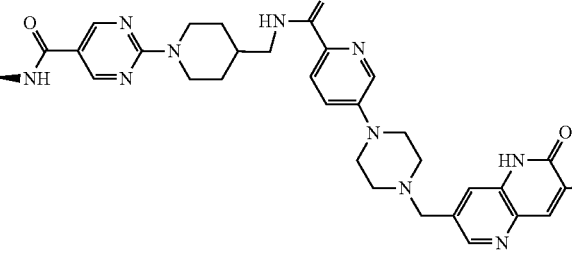 |

TABLE 1-continued

| No. | Structure |
|---|---|
| 13 | 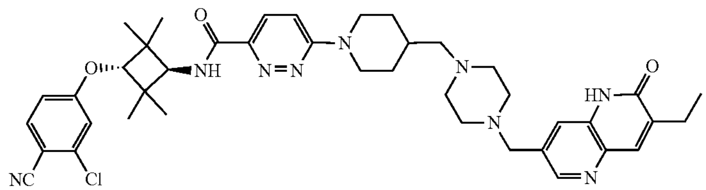 [SMILES: CCc1cc2ncc(CN3CCN(CC4CCN(c5ccc(C(=O)N[C@H]6C(C)(C)[C@H](Oc7ccc(C#N)c(Cl)c7)C6(C)C)nn5)CC4)CC3)cc2[nH]c1=O] |
| 14 | 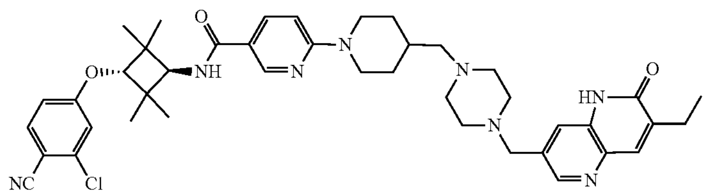 [SMILES: CCc1cc2ncc(CN3CCN(CC4CCN(c5ccc(C(=O)N[C@H]6C(C)(C)[C@H](Oc7ccc(C#N)c(Cl)c7)C6(C)C)cn5)CC4)CC3)cc2[nH]c1=O] |
| 15 | 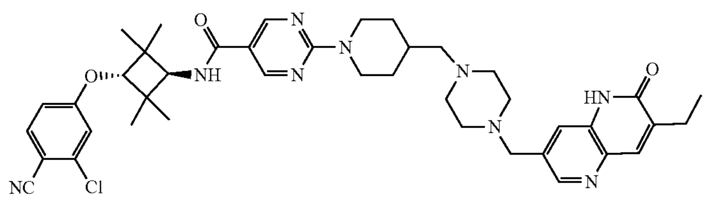 [SMILES: CCc1cc2ncc(CN3CCN(CC4CCN(c5ncc(C(=O)N[C@H]6C(C)(C)[C@H](Oc7ccc(C#N)c(Cl)c7)C6(C)C)cn5)CC4)CC3)cc2[nH]c1=O] |
| 16 | 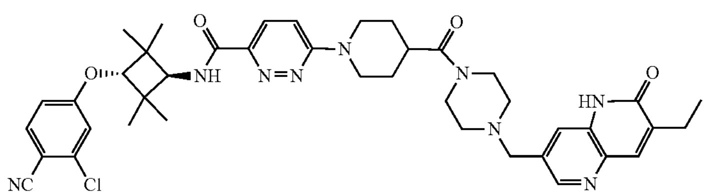 [SMILES: CCc1cc2ncc(CN3CCN(C(=O)C4CCN(c5ccc(C(=O)N[C@H]6C(C)(C)[C@H](Oc7ccc(C#N)c(Cl)c7)C6(C)C)nn5)CC4)CC3)cc2[nH]c1=O] |
| 17 | 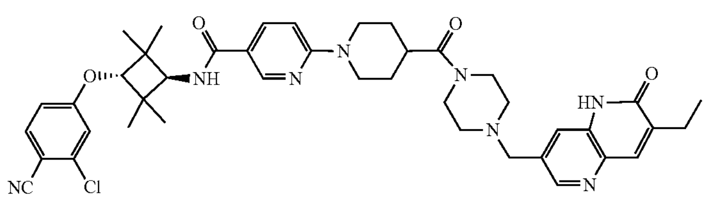 [SMILES: CCc1cc2ncc(CN3CCN(C(=O)C4CCN(c5ccc(C(=O)N[C@H]6C(C)(C)[C@H](Oc7ccc(C#N)c(Cl)c7)C6(C)C)cn5)CC4)CC3)cc2[nH]c1=O] |
| 18 | 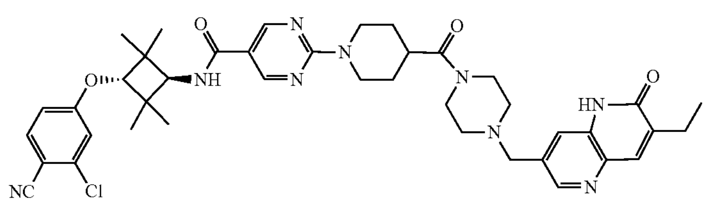 [SMILES: CCc1cc2ncc(CN3CCN(C(=O)C4CCN(c5ncc(C(=O)N[C@H]6C(C)(C)[C@H](Oc7ccc(C#N)c(Cl)c7)C6(C)C)cn5)CC4)CC3)cc2[nH]c1=O] |
| 19 | 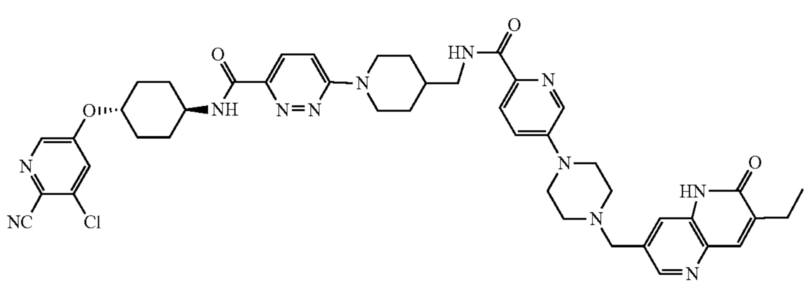 [SMILES: CCc1cc2ncc(CN3CCN(c4ccc(C(=O)NCC5CCN(c6ccc(C(=O)N[C@H]7CC[C@H](Oc8cnc(C#N)c(Cl)c8)CC7)nn6)CC5)nc4)CC3)cc2[nH]c1=O] |

TABLE 1-continued

| No. | Structure |
|---|---|
| 20 | 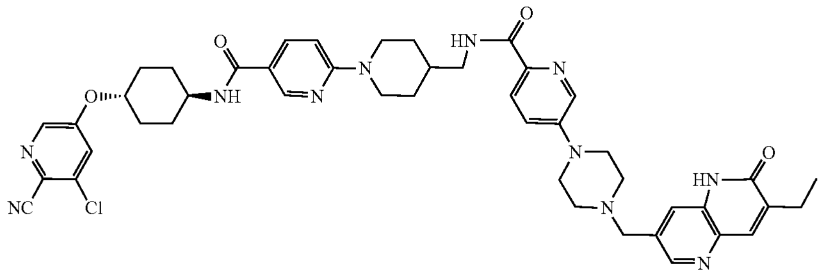 [SMILES: CCc1cc2ncc(CN3CCN(c4ccc(C(=O)NCC5CCN(c6ccc(C(=O)N[C@H]7CC[C@H](Oc8cnc(C#N)c(Cl)c8)CC7)cn6)CC5)nc4)CC3)cc2[nH]c1=O] |
| 21 | 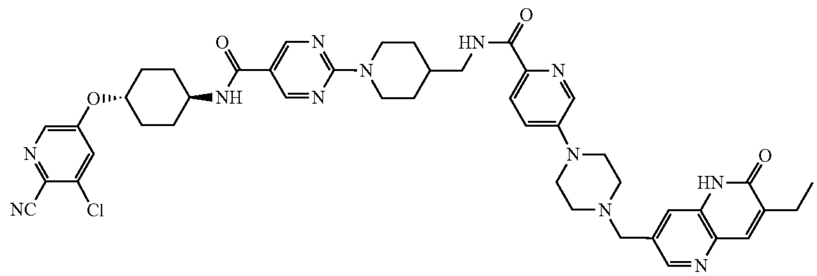 [SMILES: CCc1cc2ncc(CN3CCN(c4ccc(C(=O)NCC5CCN(c6ncc(C(=O)N[C@H]7CC[C@H](Oc8cnc(C#N)c(Cl)c8)CC7)cn6)CC5)nc4)CC3)cc2[nH]c1=O] |
| 22 | 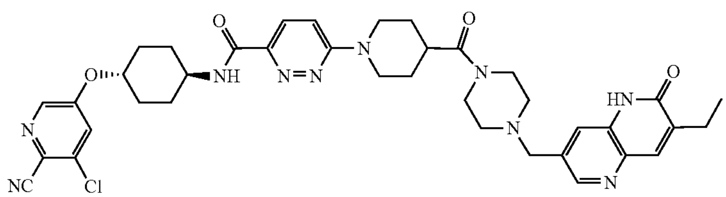 [SMILES: CCc1cc2ncc(CN3CCN(C(=O)C4CCN(c5ccc(C(=O)N[C@H]6CC[C@H](Oc7cnc(C#N)c(Cl)c7)CC6)nn5)CC4)CC3)cc2[nH]c1=O] |
| 23 | 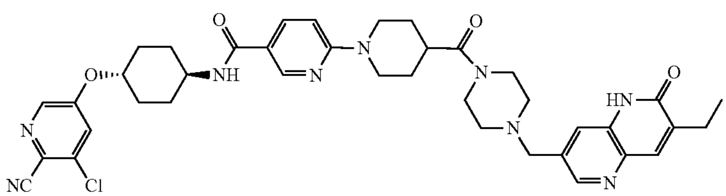 [SMILES: CCc1cc2ncc(CN3CCN(C(=O)C4CCN(c5ccc(C(=O)N[C@H]6CC[C@H](Oc7cnc(C#N)c(Cl)c7)CC6)cn5)CC4)CC3)cc2[nH]c1=O] |
| 24 | 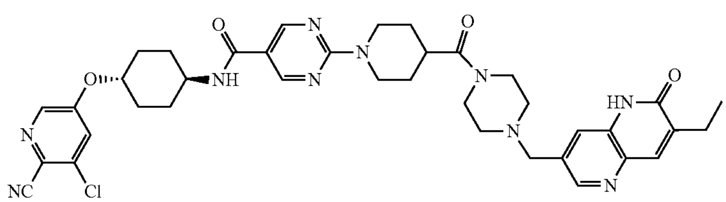 [SMILES: CCc1cc2ncc(CN3CCN(C(=O)C4CCN(c5ncc(C(=O)N[C@H]6CC[C@H](Oc7cnc(C#N)c(Cl)c7)CC6)cn5)CC4)CC3)cc2[nH]c1=O] |
| 25 | 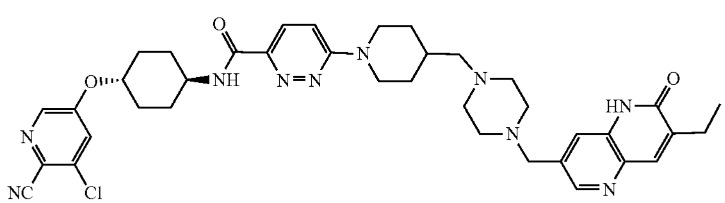 [SMILES: CCc1cc2ncc(CN3CCN(CC4CCN(c5ccc(C(=O)N[C@H]6CC[C@H](Oc7cnc(C#N)c(Cl)c7)CC6)nn5)CC4)CC3)cc2[nH]c1=O] |
| 26 | 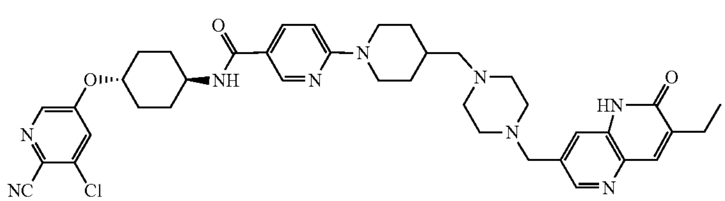 [SMILES: CCc1cc2ncc(CN3CCN(CC4CCN(c5ccc(C(=O)N[C@H]6CC[C@H](Oc7cnc(C#N)c(Cl)c7)CC6)cn5)CC4)CC3)cc2[nH]c1=O] |

TABLE 1-continued
| No. | Structure |
|---|---|
| 27 | 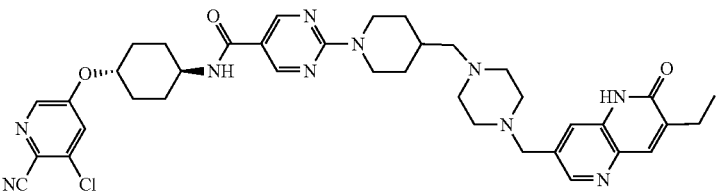 [SMILES: CCc1cc2ncc(CN3CCN(CC4CCN(c5ncc(C(=O)N[C@H]6CC[C@H](Oc7cnc(C#N)c(Cl)c7)CC6)cn5)CC4)CC3)cc2[nH]c1=O] |
| 28 | 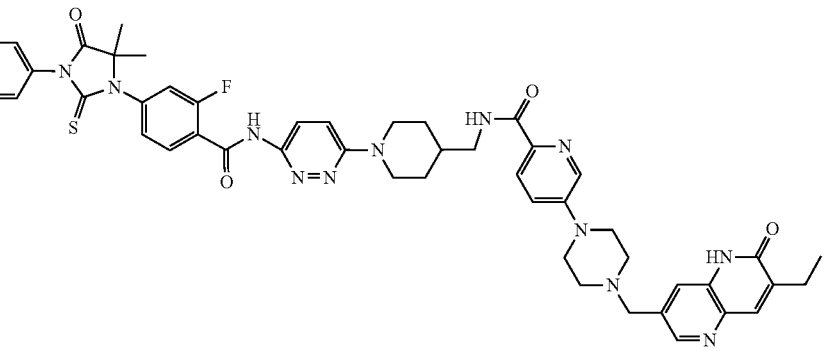 |
| 29 | 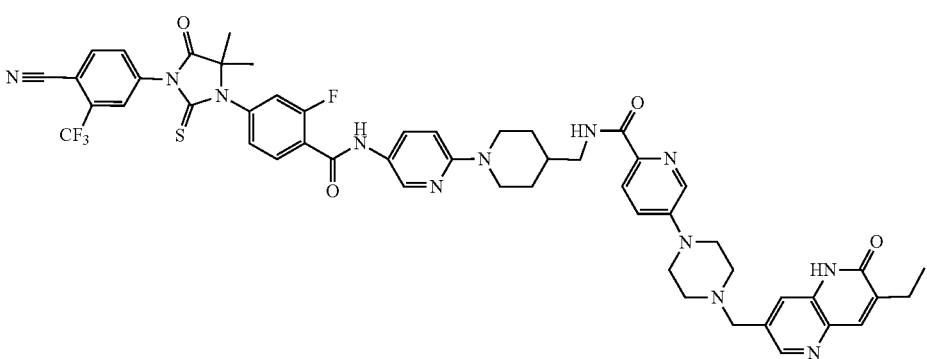 [SMILES: CCc1cc2ncc(CN3CCN(c4ccc(C(=O)NCC5CCN(c6ccc(NC(=O)c7ccc(N8C(=S)N(c9ccc(C#N)c(C(F)(F)F)c9)C(=O)C8(C)C)cc7F)cn6)CC5)nc4)CC3)cc2[nH]c1=O] |
| 30 | 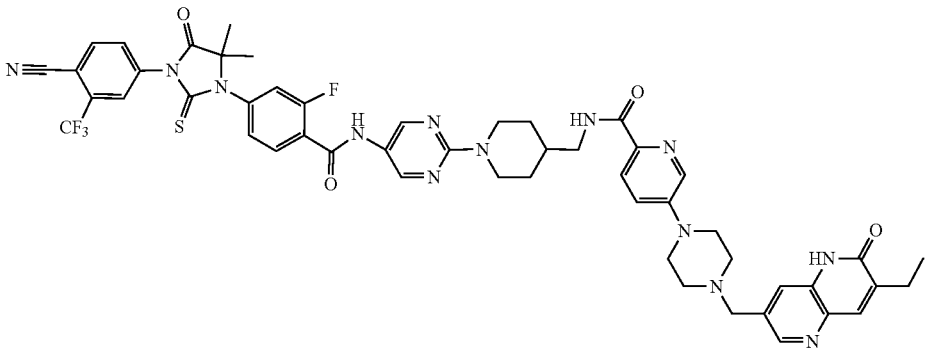 [SMILES: CCc1cc2ncc(CN3CCN(c4ccc(C(=O)NCC5CCN(c6ncc(NC(=O)c7ccc(N8C(=S)N(c9ccc(C#N)c(C(F)(F)F)c9)C(=O)C8(C)C)cc7F)cn6)CC5)nc4)CC3)cc2[nH]c1=O] |
| 31 | 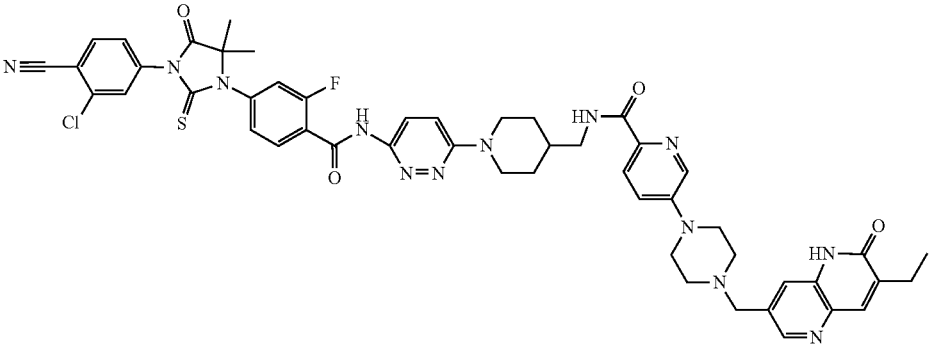 [SMILES: CCc1cc2ncc(CN3CCN(c4ccc(C(=O)NCC5CCN(c6ccc(NC(=O)c7ccc(N8C(=S)N(c9ccc(C#N)c(Cl)c9)C(=O)C8(C)C)cc7F)nn6)CC5)nc4)CC3)cc2[nH]c1=O] |

TABLE 1-continued

| No. | Structure |
| --- | --- |
| 32 | 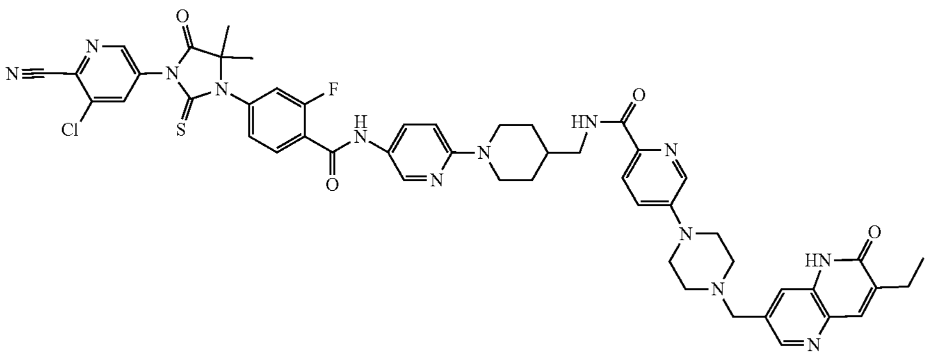 [SMILES: CCc1cc2ncc(CN3CCN(c4ccc(C(=O)NCC5CCN(c6ccc(NC(=O)c7ccc(N8C(=S)N(c9cnc(C#N)c(Cl)c9)C(=O)C8(C)C)cc7F)cn6)CC5)nc4)CC3)cc2[nH]c1=O] |
| 33 | 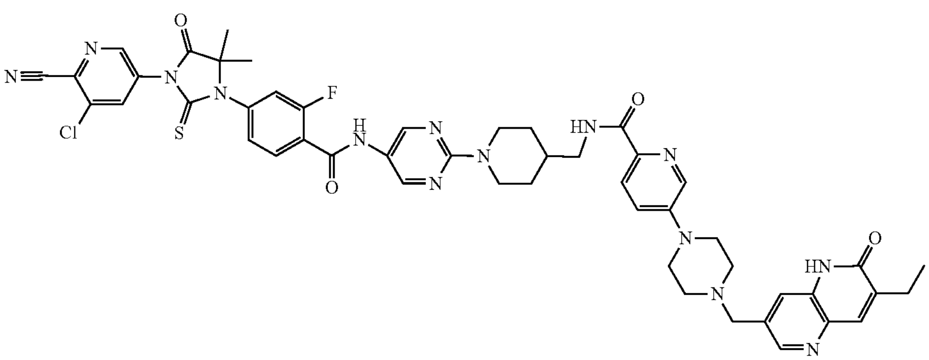 [SMILES: CCc1cc2ncc(CN3CCN(c4ccc(C(=O)NCC5CCN(c6ncc(NC(=O)c7ccc(N8C(=S)N(c9cnc(C#N)c(Cl)c9)C(=O)C8(C)C)cc7F)cn6)CC5)nc4)CC3)cc2[nH]c1=O] |
| 34 | 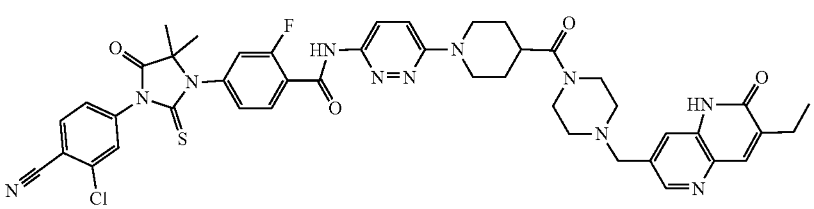 [SMILES: CCc1cc2ncc(CN3CCN(C(=O)C4CCN(c5ccc(NC(=O)c6ccc(N7C(=S)N(c8ccc(C#N)c(Cl)c8)C(=O)C7(C)C)cc6F)nn5)CC4)CC3)cc2[nH]c1=O] |
| 35 | 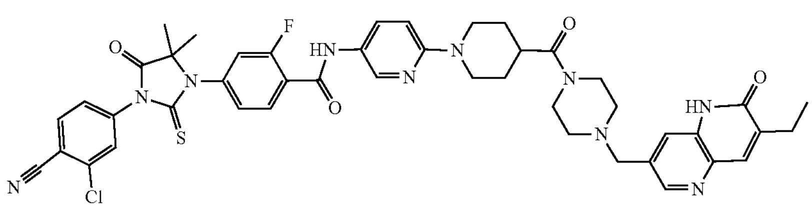 [SMILES: CCc1cc2ncc(CN3CCN(C(=O)C4CCN(c5ccc(NC(=O)c6ccc(N7C(=S)N(c8ccc(C#N)c(Cl)c8)C(=O)C7(C)C)cc6F)cn5)CC4)CC3)cc2[nH]c1=O] |
| 36 | 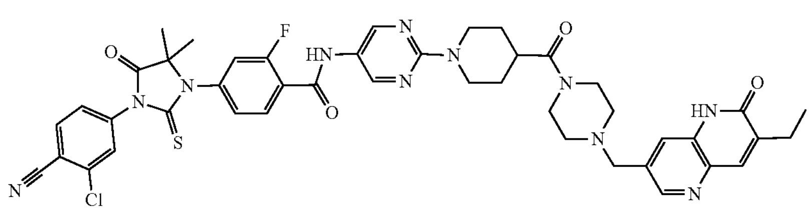 [SMILES: CCc1cc2ncc(CN3CCN(C(=O)C4CCN(c5ncc(NC(=O)c6ccc(N7C(=S)N(c8ccc(C#N)c(Cl)c8)C(=O)C7(C)C)cc6F)cn5)CC4)CC3)cc2[nH]c1=O] |
| 37 | 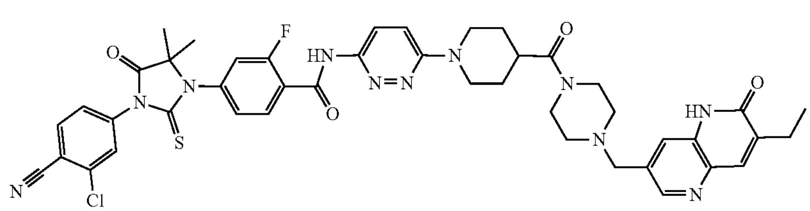 [SMILES: CCc1cc2ncc(CN3CCN(C(=O)C4CCN(c5ccc(NC(=O)c6ccc(N7C(=S)N(c8ccc(C#N)c(Cl)c8)C(=O)C7(C)C)cc6F)nn5)CC4)CC3)cc2[nH]c1=O] |

TABLE 1-continued
| No. | Structure |
|---|---|
| 38 | 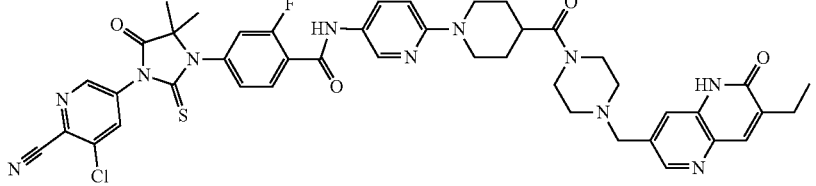 |
| 39 | 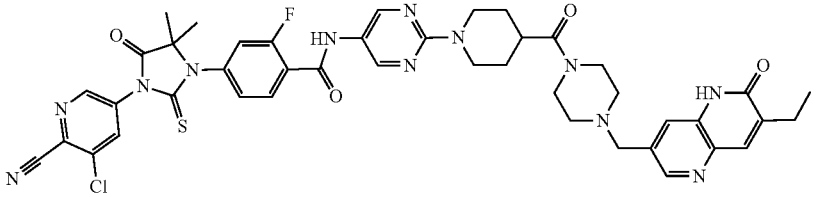 [SMILES: CCc1cc2ncc(CN3CCN(C(=O)C4CCN(c5ncc(NC(=O)c6ccc(N7C(=S)N(c8cnc(C#N)c(Cl)c8)C(=O)C7(C)C)cc6F)cn5)CC4)CC3)cc2[nH]c1=O] |
| 40 | 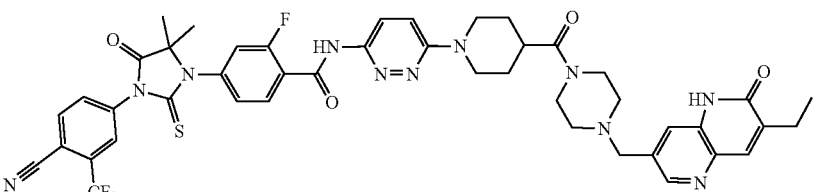 |
| 41 | 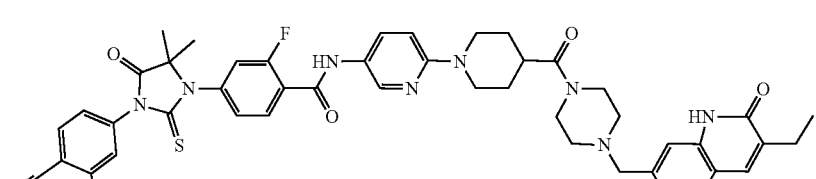 |
| 42 | 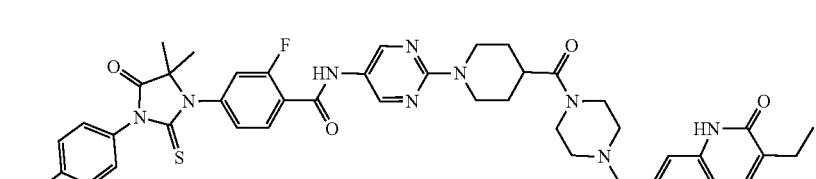 |
| 43 | 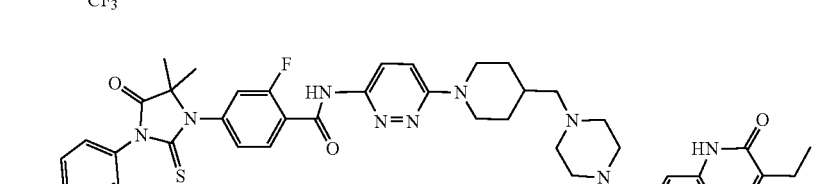 |
| 44 | 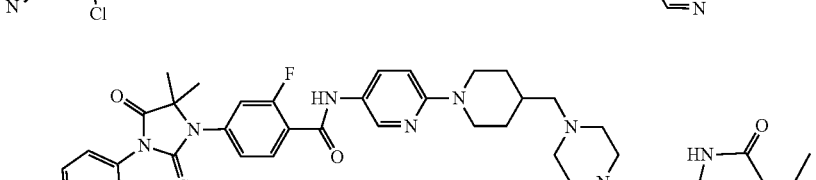 |

TABLE 1-continued

| No. | Structure |
|---|---|
| 45 | 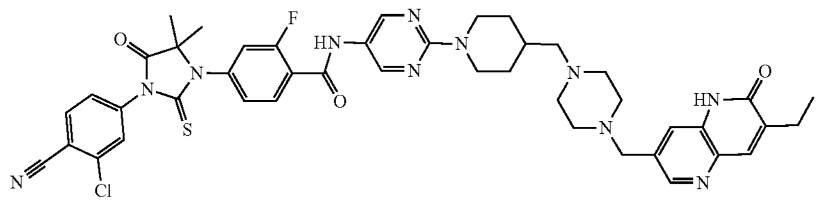 [SMILES: CCc1cc2ncc(CN3CCN(CC4CCN(c5ncc(NC(=O)c6ccc(N7C(=S)N(c8ccc(C#N)c(Cl)c8)C(=O)C7(C)C)cc6F)cn5)CC4)CC3)cc2[nH]c1=O] |
| 46 | 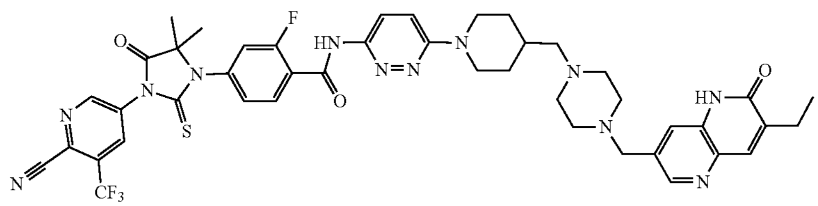 [SMILES: CCc1cc2ncc(CN3CCN(CC4CCN(c5ccc(NC(=O)c6ccc(N7C(=S)N(c8cnc(C#N)c(C(F)(F)F)c8)C(=O)C7(C)C)cc6F)nn5)CC4)CC3)cc2[nH]c1=O] |
| 47 | 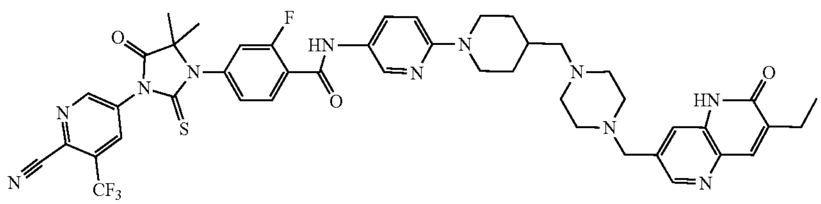 [SMILES: CCc1cc2ncc(CN3CCN(CC4CCN(c5ccc(NC(=O)c6ccc(N7C(=S)N(c8cnc(C#N)c(C(F)(F)F)c8)C(=O)C7(C)C)cc6F)cn5)CC4)CC3)cc2[nH]c1=O] |
| 48 | 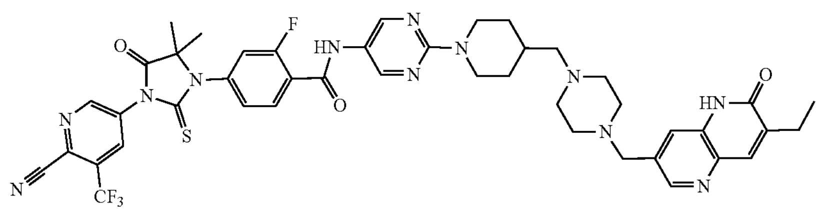 [SMILES: CCc1cc2ncc(CN3CCN(CC4CCN(c5ncc(NC(=O)c6ccc(N7C(=S)N(c8cnc(C#N)c(C(F)(F)F)c8)C(=O)C7(C)C)cc6F)cn5)CC4)CC3)cc2[nH]c1=O] |
| 49 | 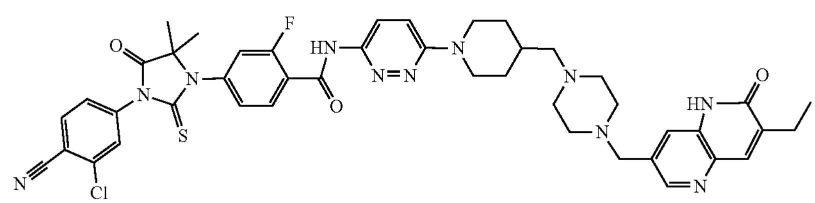 |
| 50 | 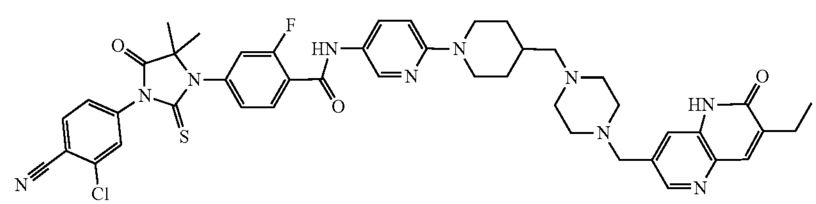 [SMILES: CCc1cc2ncc(CN3CCN(CC4CCN(c5ccc(NC(=O)c6ccc(N7C(=S)N(c8ccc(C#N)c(Cl)c8)C(=O)C7(C)C)cc6F)cn5)CC4)CC3)cc2[nH]c1=O] |
| 51 | 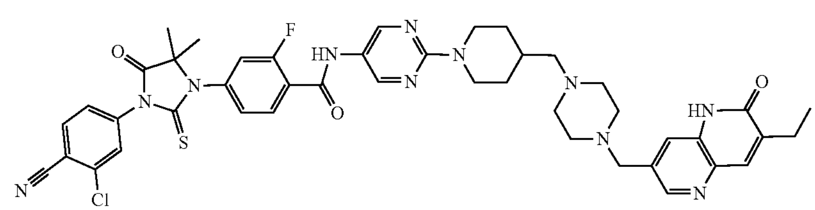 [SMILES: CCc1cc2ncc(CN3CCN(CC4CCN(c5ncc(NC(=O)c6ccc(N7C(=S)N(c8ccc(C#N)c(Cl)c8)C(=O)C7(C)C)cc6F)cn5)CC4)CC3)cc2[nH]c1=O] |

TABLE 1-continued

| No. | Structure |
|---|---|
| 52 | 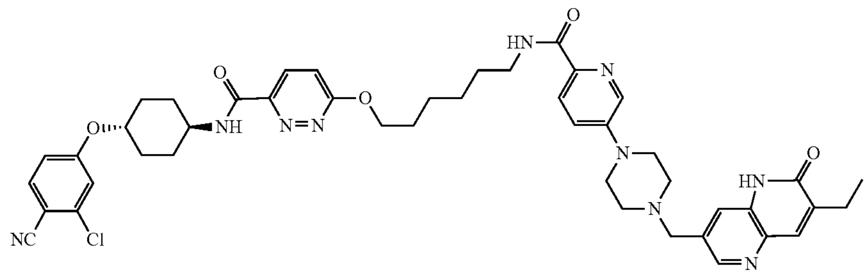 [SMILES: CCc1cc2ncc(CN3CCN(c4ccc(C(=O)NCCCCCCOc5ccc(C(=O)N[C@H]6CC[C@H](Oc7ccc(C#N)c(Cl)c7)CC6)nn5)nc4)CC3)cc2[nH]c1=O] |
| 53 | 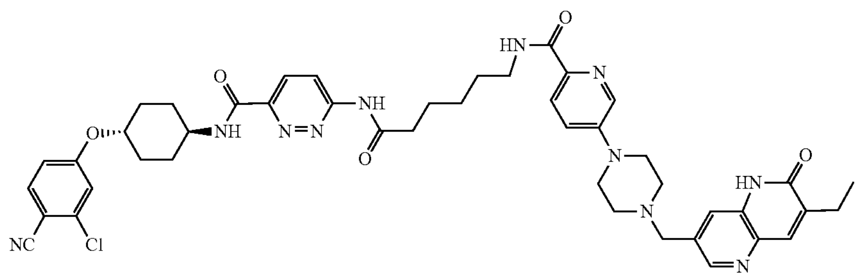 [SMILES: CCc1cc2ncc(CN3CCN(c4ccc(C(=O)NCCCCCC(=O)Nc5ccc(C(=O)N[C@H]6CC[C@H](Oc7ccc(C#N)c(Cl)c7)CC6)nn5)nc4)CC3)cc2[nH]c1=O] |
| 54 | 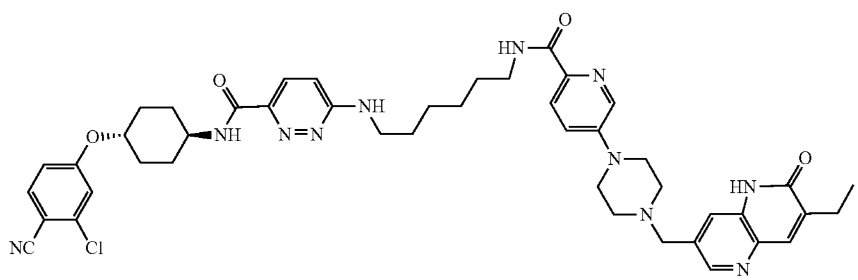 [SMILES: CCc1cc2ncc(CN3CCN(c4ccc(C(=O)NCCCCCCNc5ccc(C(=O)N[C@H]6CC[C@H](Oc7ccc(C#N)c(Cl)c7)CC6)nn5)nc4)CC3)cc2[nH]c1=O] |
| 55 | 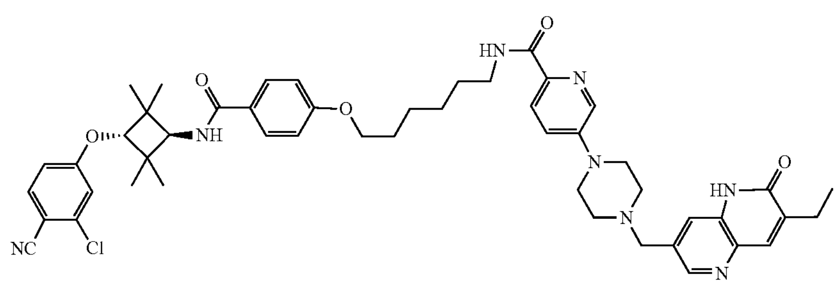 [SMILES: CCc1cc2ncc(CN3CCN(c4ccc(C(=O)NCCCCCCOc5ccc(C(=O)N[C@H]6C(C)(C)[C@H](Oc7ccc(C#N)c(Cl)c7)C6(C)C)cc5)nc4)CC3)cc2[nH]c1=O] |
| 56 | 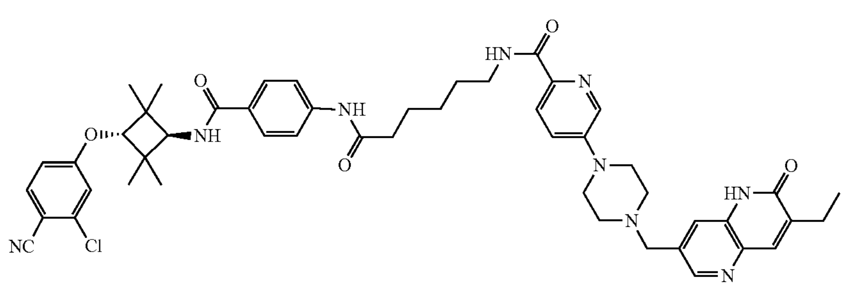 [SMILES: CCc1cc2ncc(CN3CCN(c4ccc(C(=O)NCCCCCC(=O)Nc5ccc(C(=O)N[C@H]6C(C)(C)[C@H](Oc7ccc(C#N)c(Cl)c7)C6(C)C)cc5)nc4)CC3)cc2[nH]c1=O] |

TABLE 1-continued

| No. | Structure |
|---|---|
| 57 | 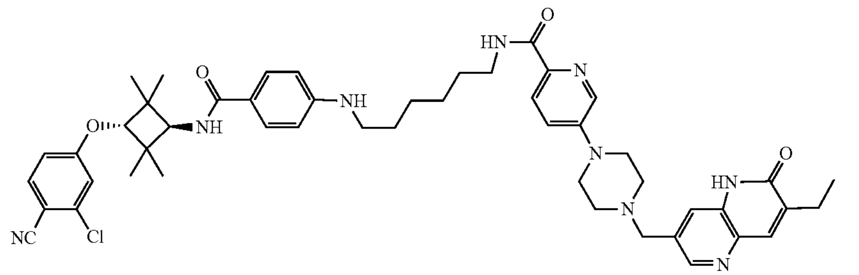 [SMILES: CCc1cc2ncc(CN3CCN(c4ccc(C(=O)NCCCCCCNc5ccc(C(=O)N[C@H]6C(C)(C)[C@H](Oc7ccc(C#N)c(Cl)c7)C6(C)C)cc5)nc4)CC3)cc2[nH]c1=O] |
| 58 | 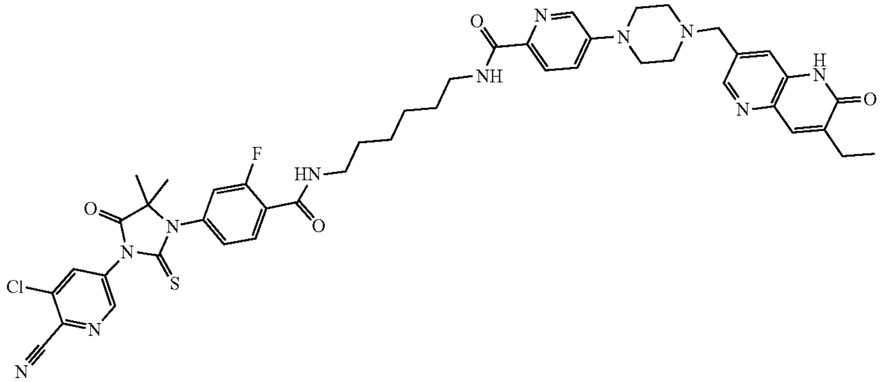 [SMILES: CCc1cc2ncc(CN3CCN(c4ccc(C(=O)NCCCCCCNC(=O)c5ccc(N6C(=S)N(c7cnc(C#N)c(Cl)c7)C(=O)C6(C)C)cc5F)nc4)CC3)cc2[nH]c1=O] |
| 59 | 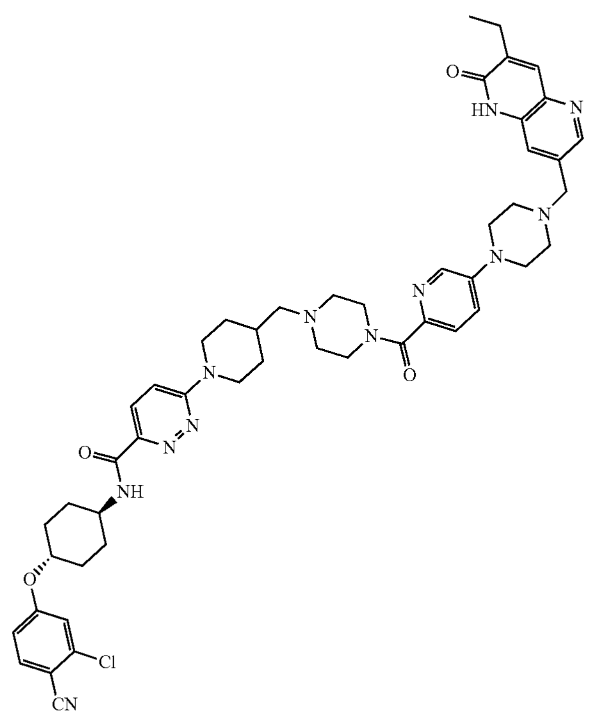 [SMILES: CCc1cc2ncc(CN3CCN(c4ccc(C(=O)N5CCN(CC6CCN(c7ccc(C(=O)N[C@H]8CC[C@H](Oc9ccc(C#N)c(Cl)c9)CC8)nn7)CC6)CC5)nc4)CC3)cc2[nH]c1=O] |
| 60 | 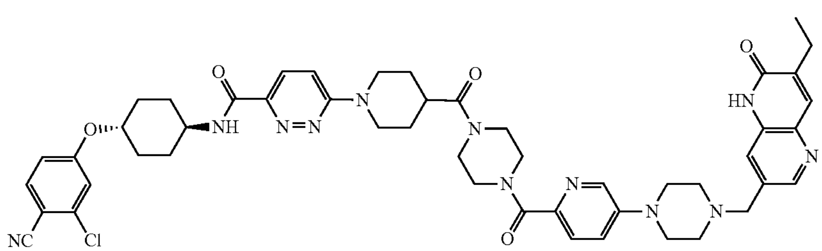 [SMILES: CCc1cc2ncc(CN3CCN(c4ccc(C(=O)N5CCN(C(=O)C6CCN(c7ccc(C(=O)N[C@H]8CC[C@H](Oc9ccc(C#N)c(Cl)c9)CC8)nn7)CC6)CC5)nc4)CC3)cc2[nH]c1=O] |

TABLE 1-continued

| No. | Structure |
|---|---|
| 61 | 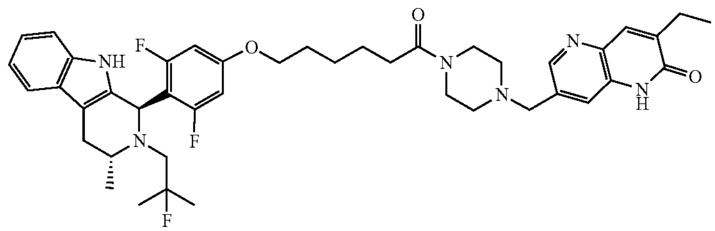 [SMILES: CCc1cc2ncc(CN3CCN(C(=O)CCCCCOc4cc(F)c([C@@H]5c6[nH]c7ccccc7c6C[C@@H](C)N5CC(C)(C)F)c(F)c4)CC3)cc2[nH]c1=O] |
| 62 | 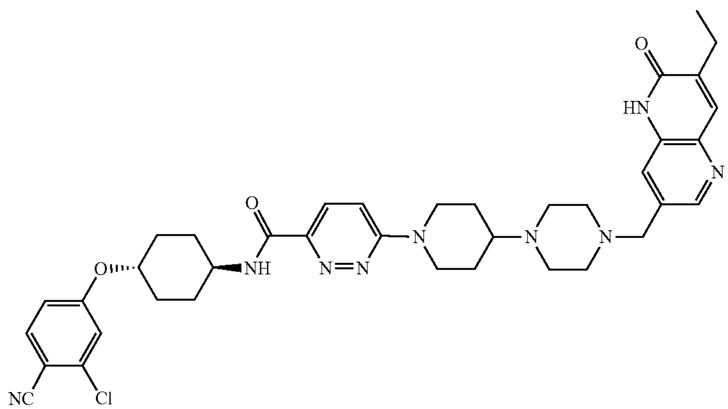 [SMILES: CCc1cc2ncc(CN3CCN(C4CCN(c5ccc(C(=O)N[C@H]6CC[C@H](Oc7ccc(C#N)c(Cl)c7)CC6)nn5)CC4)CC3)cc2[nH]c1=O] |
| 63 | 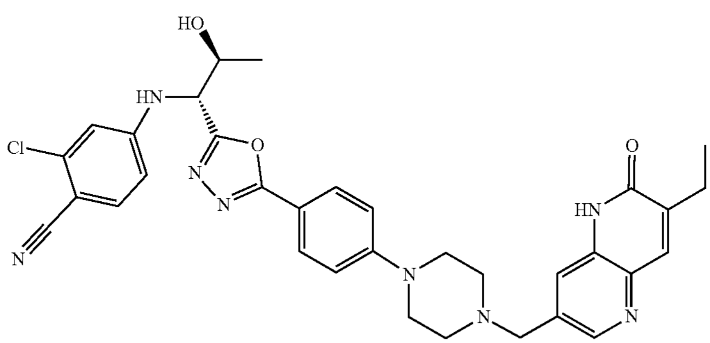 [SMILES: CCc1cc2ncc(CN3CCN(c4ccc(-c5nnc([C@H](Nc6ccc(C#N)c(Cl)c6)[C@H](C)O)o5)cc4)CC3)cc2[nH]c1=O] |
| 64 | 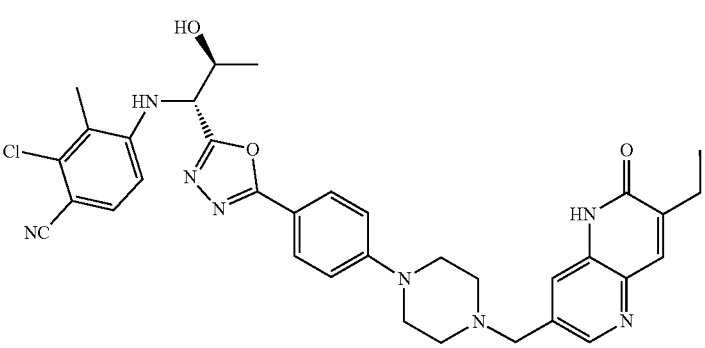 [SMILES: CCc1cc2ncc(CN3CCN(c4ccc(-c5nnc([C@H](Nc6ccc(C#N)c(Cl)c6C)[C@H](C)O)o5)cc4)CC3)cc2[nH]c1=O] |

TABLE 1-continued
| No. | Structure |
|---|---|
| 65 | 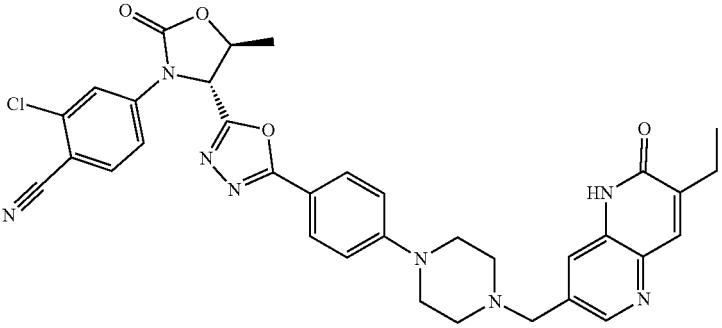 [SMILES: CCc1cc2ncc(CN3CCN(c4ccc(-c5nnc([C@H]6[C@H](C)OC(=O)N6c6ccc(C#N)c(Cl)c6)o5)cc4)CC3)cc2[nH]c1=O] |
| 66 | 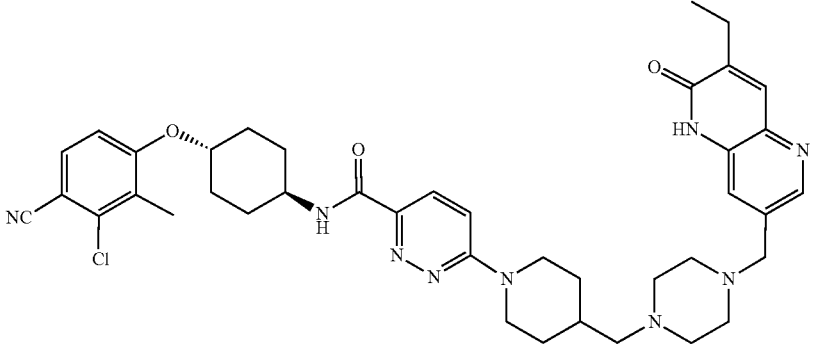 [SMILES: CCc1cc2ncc(CN3CCN(CC4CCN(c5ccc(C(=O)N[C@H]6CC[C@H](Oc7ccc(C#N)c(Cl)c7C)CC6)nn5)CC4)CC3)cc2[nH]c1=O] |
| 67 | 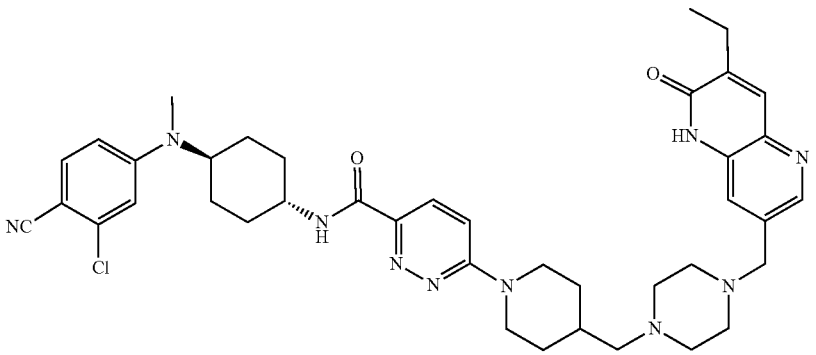 [SMILES: CCc1cc2ncc(CN3CCN(CC4CCN(c5ccc(C(=O)N[C@H]6CC[C@H](N(C)c7ccc(C#N)c(Cl)c7)CC6)nn5)CC4)CC3)cc2[nH]c1=O] |
| 68 | 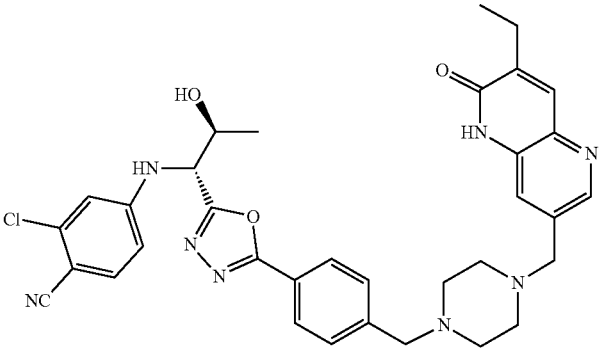 [SMILES: CCc1cc2ncc(CN3CCN(Cc4ccc(-c5nnc([C@H](Nc6ccc(C#N)c(Cl)c6)[C@H](C)O)o5)cc4)CC3)cc2[nH]c1=O] |

TABLE 1-continued

| No. | Structure |
|---|---|
| 69 | 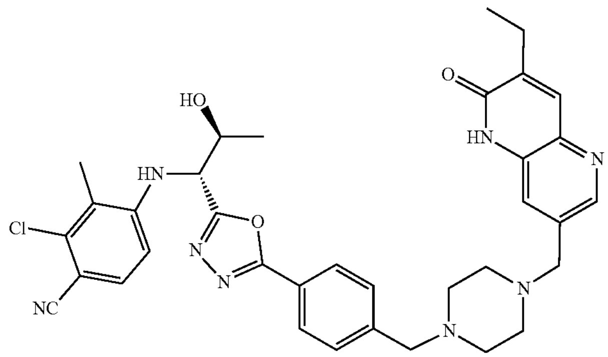 [SMILES: CCc1cc2ncc(CN3CCN(Cc4ccc(-c5nnc([C@H](Nc6ccc(C#N)c(Cl)c6C)[C@H](C)O)o5)cc4)CC3)cc2[nH]c1=O] |
| 70 | 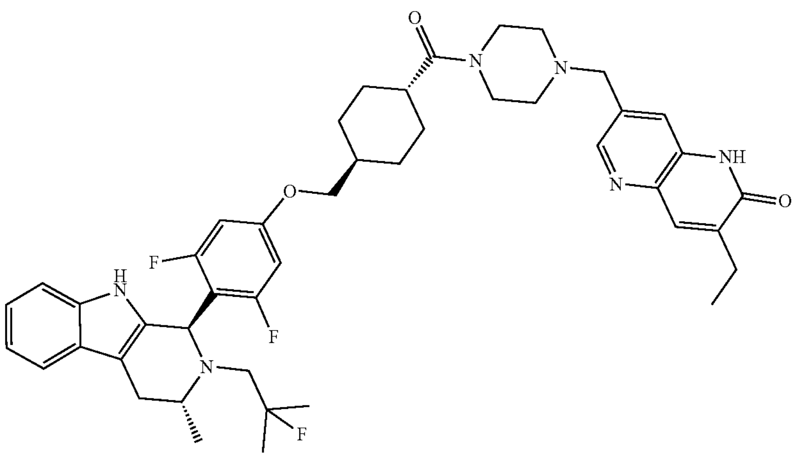 [SMILES: CCc1cc2ncc(CN3CCN(C(=O)[C@H]4CC[C@H](COc5cc(F)c([C@@H]6c7[nH]c8ccccc8c7C[C@@H](C)N6CC(C)(C)F)c(F)c5)CC4)CC3)cc2[nH]c1=O] |
| 71 | 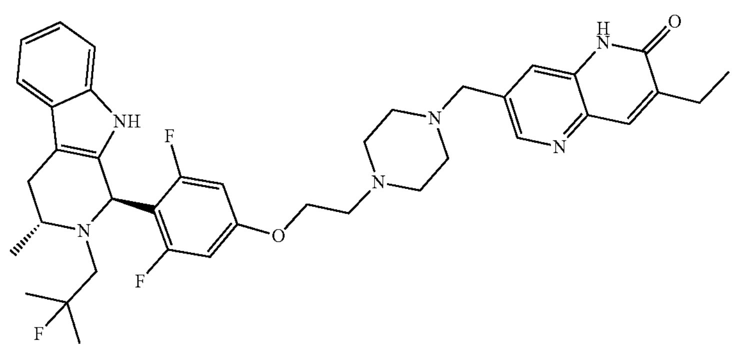 [SMILES: CCc1cc2ncc(CN3CCN(CCOc4cc(F)c([C@@H]5c6[nH]c7ccccc7c6C[C@@H](C)N5CC(C)(C)F)c(F)c4)CC3)cc2[nH]c1=O] |
| 72 | 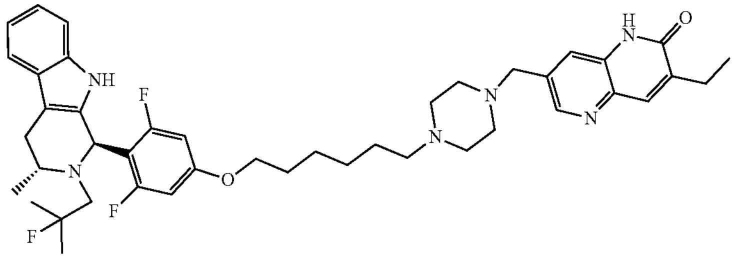 [SMILES: CCc1cc2ncc(CN3CCN(CCCCCCOc4cc(F)c([C@@H]5c6[nH]c7ccccc7c6C[C@@H](C)N5CC(C)(C)F)c(F)c4)CC3)cc2[nH]c1=O] |

TABLE 1-continued

| No. | Structure |
|---|---|
| 73 | 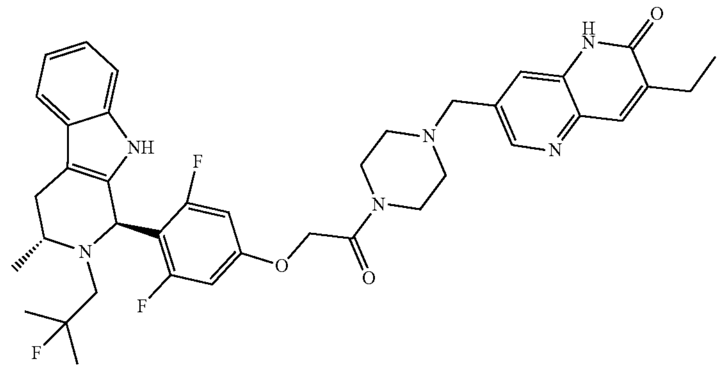 [SMILES: CCc1cc2ncc(CN3CCN(C(=O)COc4cc(F)c([C@@H]5c6[nH]c7ccccc7c6C[C@@H](C)N5CC(C)(C)F)c(F)c4)CC3)cc2[nH]c1=O] |
| 74 | 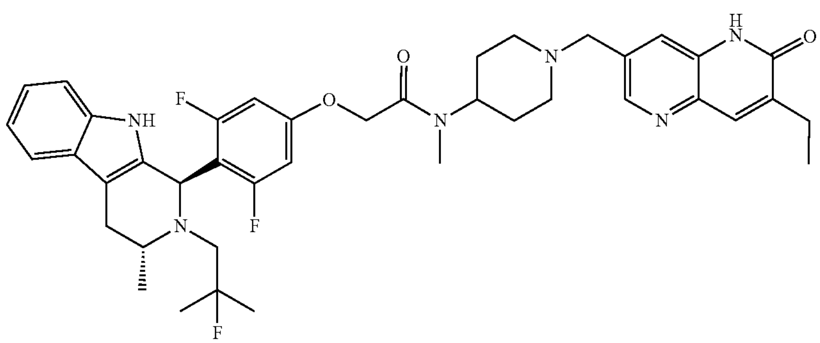 [SMILES: CCc1cc2ncc(CN3CCC(N(C)C(=O)COc4cc(F)c([C@@H]5c6[nH]c7ccccc7c6C[C@@H](C)N5CC(C)(C)F)c(F)c4)CC3)cc2[nH]c1=O] |
| 75 | 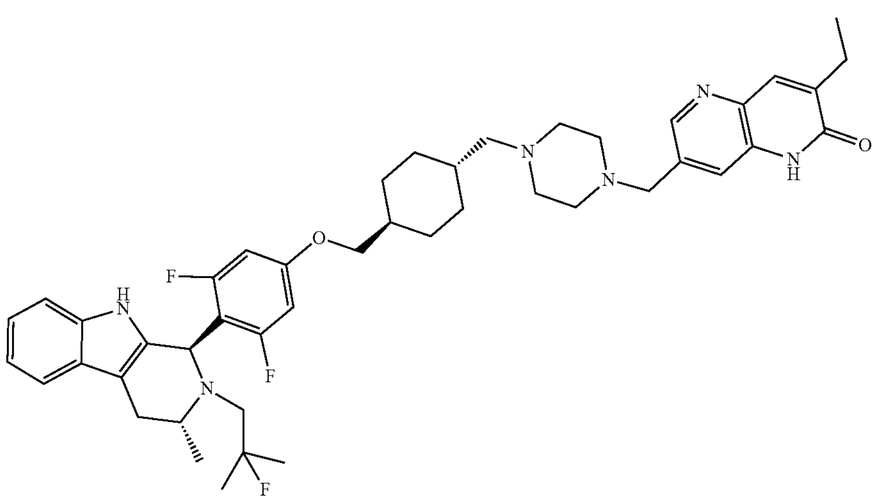 [SMILES: CCc1cc2ncc(CN3CCN(C[C@H]4CC[C@H](COc5cc(F)c([C@@H]6c7[nH]c8ccccc8c7C[C@@H](C)N6CC(C)(C)F)c(F)c5)CC4)CC3)cc2[nH]c1=O] |

TABLE 1-continued

| No. | Structure |
|---|---|
| 76 | 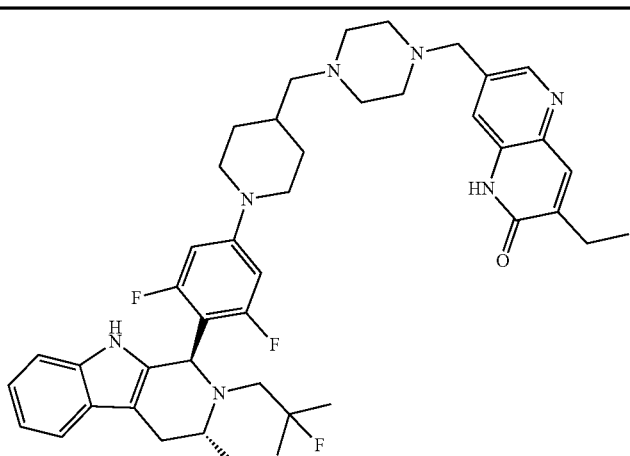 |

Methods of Treatment

Provided herein are compounds which can be used to treat, prevent, and/or delay the onset and/or development of cancer. Accordingly, in certain embodiments, provided is a method for the treatment of cancer, comprising administering to a subject in need of treatment a therapeutically-effective amount of a compound or composition described herein. Certain embodiments provide a method of potentiation of cytotoxic cancer therapy in a subject in recognized need of such treatment comprising administering to the subject a therapeutically acceptable amount of a compound or composition described herein.

It is contemplated that a patient having any cancer may benefit from being treated with the compounds and compositions described herein. Accordingly, in certain embodiments, the cancer is liver cancer, melanoma, Hodgkin's disease, non-Hodgkin's lymphomas, acute lymphocytic leukemia, chronic lymphocytic leukemia, multiple myeloma, neuroblastoma, breast carcinoma, ovarian carcinoma, lung carcinoma, Wilms' tumor, cervical carcinoma, testicular carcinoma, soft-tissue sarcoma, chronic lymphocytic leukemia, Waldenström macroglobulinemia, primary macroglobulinemia, bladder carcinoma, chronic granulocytic leukemia, primary brain carcinoma, malignant melanoma, small-cell lung carcinoma, stomach carcinoma, colon carcinoma, malignant pancreatic insulinoma, malignant carcinoid carcinoma, malignant melanoma, choriocarcinoma, mycosis fungoides, head neck carcinoma, osteogenic sarcoma, pancreatic carcinoma, acute granulocytic leukemia, hairy cell leukemia, rhabdomyosarcoma, Kaposi's sarcoma, genitourinary carcinoma, thyroid carcinoma, esophageal carcinoma, malignant hypercalcemia, cervical hyperplasia, renal cell carcinoma, endometrial carcinoma, polycythemia vera, essential thrombocytosis, adrenal cortex carcinoma, skin cancer, trophoblastic neoplasms, prostatic carcinoma, glioma, breast cancer, or prostate cancer. In certain embodiments, the cancer is bladder cancer, a blood cancer, such as leukemia (e.g., chronic leukemia, chronic lymphocytic leukemia (CLL, etc.) or lymphoma (e.g., Hodgkin lymphoma, non-Hodgkin lymphoma, low grade lymphoma, high grade lymphoma), lung cancer (e.g., small cell lung cancer), breast cancer, fallopian tube cancer, glioblastoma multiforme, head and neck cancer, esophageal cancer, ovarian cancer, pancreatic cancer, peritoneal cancer, prostate cancer, testicular cancer, skin cancer (e.g., melanoma) or uterine cancer. In certain embodiments, the cancer is bladder cancer, breast cancer, fallopian tube cancer, ovarian cancer, prostate cancer, peritoneal cancer, testicular cancer, endometrial cancer, or uterine cancer.

In certain embodiments, the cancer is chronic lymphocytic leukemia (CLL), Hodgkin lymphoma, non-Hodgkin lymphoma, Waldenström macroglobulinemia, polycythemia vera, trophoblastic neoplasms, and ovarian carcinoma.

In certain embodiments, the compounds and compositions as described herein are tailored to target cancers which overexpress a specific receptor, such as, but not limited to, androgen receptors, estrogen receptors, progesterone receptors, and/or glucocorticoid receptors by including an epitope which targets that specific nuclear receptor. The epitope can be derived from a steroid hormone or any non-steroidal drug which targets that particular receptor.

In certain embodiments, provided is a method of treating or preventing an androgen receptor overexpressing cancer, comprising administering an effective amount of a compound, or a pharmaceutically acceptable salt or solvate thereof, comprising at least one nuclear payload and at least one androgen receptor-targeting epitope to an individual in need thereof. Specific cancers which are contemplated to be treated by such methods include, but are not limited to, prostate, breast, triple negative breast cancer, bladder, or liver cancer. Also provided is a method of treating or preventing metastatic castration-resistant prostate cancer (mCRPC), comprising administering an effective amount of a compound or composition as described herein, or a pharmaceutically acceptable salt or solvate thereof, to an individual in need thereof.

In certain embodiments, provided is a method of treating or preventing an androgen receptor overexpressing cancer, comprising administering an effective amount of a compound, or a pharmaceutically acceptable salt or solvate thereof, comprising at least one nuclear payload and at least one androgen receptor-targeting epitope to an individual in need thereof. In certain embodiments, the cancer is prostate, breast, triple negative breast cancer, bladder, or liver cancer. In certain embodiments, the androgen receptor-targeting epitope comprises an androgen receptor agonist, a selective androgen-receptor modulator (SARM), an androgen receptor antagonist, a selective estrogen receptor modulator (SERM), an estrogen receptor antagonist, a progestin, or an estrogen. In certain embodiments, the androgen receptor-targeting epitope comprises enobosarm, bicalutamide, flutamide, nilutamide, enzalutamide, tamoxifen, toremifene, raloxifene, fulvestrant, megestrol acetate, estramustine, ketoconazole, abiraterone, darolutamide, or an analog thereof. In certain embodiments, the androgen receptor-targeting epitope comprises enobosarm, bicalutamide, flutamide, nilutamide, enzalutamide, tamoxifen, toremifene, raloxifene, fulvestrant, megestrol acetate, estramustine, ketoconazole, abiraterone, or an analog thereof. In certain embodiments, the nuclear payload comprises a PARP inhibitor.

In certain embodiments, provided is a method of treating or preventing an estrogen and/or progesterone receptor overexpressing cancer, comprising administering an effective amount of a compound, or a pharmaceutically acceptable salt or solvate thereof, comprising at least one nuclear payload and at least one estrogen and/or progesterone receptor-targeting epitope to an individual in need thereof. Specific cancers which are contemplated to be treated by such methods include, but are not limited to, breast, uterine, or ovarian cancer.

In certain embodiments, provided is a method of treating or preventing a glucocorticoid receptor overexpressing cancer, comprising administering an effective amount of a compound, or a pharmaceutically acceptable salt or solvate thereof, comprising at least one nuclear payload and at least one glucocorticoid receptor-targeting epitope to an individual in need thereof. Specific cancers which are contemplated to be treated by such methods include, but are not limited to, breast, uterine, or ovarian cancer. Specific cancers which are contemplated to be treated by such methods include, but are not limited to, prostate, possibly breast, uterine, ovarian.

Breast cancer includes ductal carcinoma in situ (DCIS) and invasive breast cancer. Breast cancers can occur in milk ducts, milk-producing lobules and connective tissues. Breast cancer includes estrogen receptor (ER) negative and hormone receptor (HR) negative, and also can be categorized as Group 3 (HER-2 positive) or Group 4 (basal-like).

Prostate cancer is a cancer which develops in the prostate, a gland in the male reproductive system. It occurs when cells of the prostate mutate and begin to multiply uncontrollably. These cells may metastasize (metastatic prostate cancer) from the prostate to virtually any other part of the body, particularly the bones and lymph nodes, but the kidney, bladder and even the brain, among other tissues. Prostate cancer may cause pain, difficulty in urinating, problems during sexual intercourse, erectile dysfunction. Other symptoms can potentially develop during later stages of the disease. Rates of detection of prostate cancers vary widely across the world, with South and East Asia detecting less frequently than in Europe, and especially the United States. Prostate cancer develops most frequently in men over the age of fifty and is one of the most prevalent types of cancer in men. However, many men who develop prostate cancer never have symptoms, undergo no therapy, and eventually die of other causes. This is because cancer of the prostate is, in most cases, slow-growing, and because most of those affected are over the age of 60. Hence, they often die of causes unrelated to prostate cancer. Many factors, including genetics and diet, have been implicated in the development of prostate cancer. The presence of prostate cancer may be indicated by symptoms, physical examination, prostate specific antigen (PSA), or biopsy. There is concern about the accuracy of the PSA test and its usefulness in screening. Suspected prostate cancer is typically confirmed by taking a biopsy of the prostate and examining it under a microscope. Further tests, such as CT scans and bone scans, may be performed to determine whether prostate cancer has spread. Combination with primarily surgery and radiation therapy, or other treatments such as hormonal therapy, chemotherapy, proton therapy, cryosurgery, high intensity focused ultrasound (HIFU) are also contemplated.

Certain embodiments provide a method of inhibiting PARP in a subject in recognized need of such treatment comprising administering to the subject a therapeutically acceptable amount of a compound or composition described herein. In one embodiment, provided herein is a method of treating a disease ameliorated by the inhibition of PARP comprising administering to a subject in need of treatment a therapeutically-effective amount of a compound or composition described herein.

Certain embodiments provide a method of treating leukemia, colon cancer, glioblastomas, lymphomas, melanomas, carcinomas of breast, or cervical carcinomas in a subject in recognized need of such treatment comprising administering to the subject a therapeutically acceptable amount of a compound or composition described herein.

In some embodiments, provided herein is a method of treatment of a cancer deficient in Homologous Recombination (HR) dependent DNA double strand break (DSB) repair pathway, which includes administering to a subject in need of treatment a therapeutically-effective amount of a compound or composition described herein. In certain embodiments, the cancer includes one or more cancer cells having a reduced or abrogated ability to repair DNA DSB by HR relative to normal cells. In some embodiments, the cancer cells have a BRCA1 or BRCA2 deficient phenotype. In some embodiments, the cancer cells are deficient in BRCA1 or BRCA2. In some embodiments, the methods provided herein involve treatment of an individual who is heterozygous for a mutation in a gene encoding a component of the HR dependent DNA DSB repair pathway. In certain embodiment, the individual is heterozygous for a mutation in BRCA1 and/or BRCA2. In some embodiments, the method of treatment of a cancer includes treatment of breast, ovary, pancreas and/or prostate cancer. In some embodiments, the method of treatment of a cancer further includes administration of ionizing radiation or a chemotherapeutic agent.

The primary function of the DNA mismatch repair (MMR) system is to eliminate single-base mismatches and insertion-deletion loops that may arise during DNA replication. Insertion-deletion loops result from gains or losses of short repeat units within microsatellite sequences, also known as microsatellite instability (MSI). At least six different MMR proteins are required. For mismatch recognition, the MSH2 protein forms a heterodimer with either MSH6 or MSH3 depending on the type of lesion to be repaired (MSH6 is required for the correction of single-base mispairs, whereas both MSH3 and MSH6 may contribute to the correction of insertion-deletion loops). A heterodimer of MLH1 and PMS2 coordinates the interplay between the mismatch recognition complex and other proteins necessary for MMR. These additional proteins may include at least exonuclease 1 (EXO1), possibly helicase(s), proliferating cell nuclear antigen (PCNA), single-stranded DNA-binding protein (RPA), and DNA polymerases δ and ε. In addition to PMS2, MLH1 may heterodimerize with two additional proteins, MLH3 and PMS1. Recent observations indicate that PMS2 is required for the correction of single-base mismatches, and PMS2 and MLH3 both contribute to the correction of insertion-deletion loops. Additional homologs of the human MMR proteins are known that are required for functions other than MMR. These proteins include MSH4 and MSH5 that are necessary for meiotic (and possibly mitotic) recombination but are not presumed to participate in MMR.

Germline mutations of human MMR genes cause susceptibility to hereditary nonpolyposis colon cancer (HNPCC), one of the most common cancer syndromes in humans. An excess of colon cancer and a defined spectrum of extracolonic cancers, diagnosed at an early age and transmitted as an autosomal dominant trait, constitute the clinical definition of the syndrome. MSI, the hallmark of HNPCC, occurs in approximately 15% to 25% of sporadic tumors of the colorectum and other organs as well. According to international criteria, a high degree of MSI (MSI-H) is defined as instability at two or more of five loci or ≥30% to 40% of all microsatellite loci studied, whereas instability at fewer loci is referred to as MSI-low (MSI-L). MSI occurs in a substantial proportion (2% to 50% of tumors) among non-HNPCC cancers (e.g., cancers of the breast, prostate, and lung). On the basis of the proportion of unstable markers, categories MSS, MSI-L, and MSI-H can be distinguished in these cancers in analogy to HNPCC cancers. In one embodiment is a method for treating a cancer deficient in mismatch DNA repair pathway. In another embodiment is a method for treating a cancer demonstrating microsatellite instability due to reduced or impaired DNA repair pathways. In another embodiment is a method for treating a cancer demonstrating genomic instability due to reduced or impaired DNA repair pathways.

In certain embodiments, a compound or composition described herein, may be used in the preparation of a medicament for the treatment of cancer which is deficient in Homologous Recombination (HR) dependent DNA double strand break (DSB) repair activity, or in the treatment of a patient with a cancer which is deficient in HR dependent DNA DSB repair activity, which includes administering to said patient a therapeutically-effective amount of the compound or composition.

The HR dependent DNA DSB repair pathway repairs double-strand breaks (DSBs) in DNA via homologous mechanisms to reform a continuous DNA helix. The components of the HR dependent DNA DSB repair pathway include, but are not limited to, ATM (NM_000051), RAD51 (NM_002875), RAD51L1 (NM_002877), RAD51C (NM_002876), RAD51L3 (NM_002878), DMC1 (NM_007068), XRCC2 (NM_005431), XRCC3 (NM_005432), RAD52 (NM_002879), RAD54L (NM_003579), RAD54B (NM_012415), BRCA1 (NM_007295), BRCA2 (NM_000059), RAD50 (NM_005732), MRE11A (NM_005590) and NBS11M_00248_5). Other proteins involved in the HR dependent DNA DSB repair pathway include regulatory factors such as EMSY (Wood, et al., Science, 291, 1284-1289 (2001); Khanna et al., Nat. Genet. 27(3): 247-254 (2001); and Hughes-Davies, et al., Cell, 115, pp 523-535).

In some embodiments, a cancer which is deficient in HR dependent DNA DSB repair includes one or more cancer cells which have a reduced or abrogated ability to repair DNA DSBs through that pathway, relative to normal cells, i.e. the activity of the HR dependent DNA DSB repair pathway are reduced or abolished in the one or more cancer cells.

In certain embodiments, the activity of one or more components of the HR dependent DNA DSB repair pathway is abolished in the one or more cancer cells of an individual having a cancer which is deficient in HR dependent DNA DSB repair. Components of the HR dependent DNA DSB repair pathway include the components listed above.

In some embodiments, the cancer cells have a BRCA1 and/or a BRCA2 deficient phenotype, i.e., BRCA1 and/or BRCA2 activity is reduced or abolished in the cancer cells. In certain embodiments, cancer cells with this phenotype are deficient in BRCA1 and/or BRCA2, i.e., expression and/or activity of BRCA1 and/or BRCA2 is reduced or abolished in the cancer cells, for example by means of mutation or polymorphism in the encoding nucleic acid, or by means of amplification, mutation or polymorphism in a gene encoding a regulatory factor, for example the EMSY gene which encodes a BRCA2 regulatory factor or by an epigenetic mechanism such as gene promoter methylation.

BRCA1 and BRCA2 are tumor suppressors whose wild-type alleles are frequently lost in tumors of heterozygous carriers. BRCA1 and/or BRCA2 mutations are associated with breast cancer. Amplification of the EMSY gene, which encodes a BRCA2 binding factor, is associated with breast and ovarian cancer (Jasin M., Oncogene, 21(58), 8981-93 (2002); Tutt, et al, Trends Mol. Med., 8(12), 571-6, (2002); and Radice, P. J., Exp Clin Cancer Res., 21(3 Suppl), 9-12 (2002)).

Carriers of mutations in BRCA1 and/or BRCA2 are also at elevated risk of cancer of the ovary, prostate, and pancreas.

In some embodiments, the individual is heterozygous for one or more variations, such as mutations and polymorphisms, in BRCA1 and/or BRCA2 or a regulator thereof. The detection of variation in BRCA1 and BRCA2 is described, for example in EP 699 754, EP 705 903, Neuhausen, S. L. and Ostrander, E. A., Genet. Test, 1, 75-83 (1992); Janatova M., et al, Neoplasma, 50(4), 246-50 (2003). Determination of amplification of the BRCA2 binding factor EMSY is described in Hughes-Davies, et al., Cell, 115, 523-535.

In certain instances, mutations and polymorphisms associated with cancer are detected at the nucleic acid level by detecting the presence of a variant nucleic acid sequence or at the protein level by detecting the presence of a variant (i.e. a mutant or allelic variant) polypeptide.

In certain embodiments, it is contemplated that the compounds described herein are useful for patients who have relapsed or become refractory. The term "relapsed" refers to disease (or cancer) that reappears or grows again after a period of remission. The term "refractory" is used to describe when the cancer does not respond to treatment or when the response to treatment does not last very long. For example, the compounds herein may be useful for treating cancer in patients who have previously been treated with the cancer therapies described herein, e.g. enzalutamide.

Compositions

Compositions, including pharmaceutical compositions, of any of the compounds detailed herein are embraced by this disclosure. Thus, provided herein are pharmaceutical compositions comprising a compound of the disclosure, or a pharmaceutically acceptable salt thereof, and a pharmaceutically acceptable carrier or excipient. The pharmaceutical compositions provided herein may take a form suitable for oral, buccal, parenteral (e.g., intravenous, intramuscular, infusion or subcutaneous injection), nasal, topical or rectal administration, or a form suitable for administration by inhalation.

A compound as described herein may, in one aspect, be in a purified form. Compositions comprising a compound as described herein, or a salt thereof, are provided, such as compositions of substantially pure compounds. In some embodiments, a composition comprising a compound as described herein, or a salt thereof, is in substantially pure form. Unless otherwise stated, "substantially pure" refers to a composition which contains no more than 35% impurity, wherein the impurity denotes a compound other than the desired compound, or a salt thereof, which comprises the majority of the composition. In one variation, a composition of substantially pure compound, or a salt thereof, is provided wherein the composition contains no more than 25% impurity. In another variation, a composition of substantially pure compound, or a salt thereof, is provided wherein the composition contains or no more than 20% impurity. In still another variation, a composition of substantially pure compound, or a salt thereof, is provided wherein the composition contains or no more than 10% impurity. In a further variation, a composition of substantially pure compound, or a salt thereof, is provided wherein the composition contains or no more than 5% impurity. In another variation, a composition of substantially pure compound, or a salt thereof, is provided wherein the composition contains or no more than 3% impurity. In still another variation, a composition of substantially pure compound, or a salt thereof, is provided wherein the composition contains or no more than 1% impurity. In a further variation, a composition of substantially pure compound, or a salt thereof, is provided wherein the composition contains or no more than 0.5% impurity.

In certain embodiments, pharmaceutical compositions are formulated in any manner, including using one or more physiologically acceptable carriers comprising excipients and/or auxiliaries which facilitate processing of the active compounds into pharmaceutical compositions. In some embodiments, proper formulation is dependent upon the route of administration chosen. In various embodiments, any techniques, carriers, and excipients are used as suitable.

Provided herein are pharmaceutical compositions that include a compound described herein and a pharmaceutically acceptable diluent(s), excipient(s), and/or carrier(s). In addition, in some embodiments, the compounds described herein are administered as pharmaceutical compositions in which compounds described herein are mixed with other active ingredients, as in combination therapy.

A pharmaceutical composition, as used herein, refers to a mixture of a compound described herein with other chemical components, such as carriers, stabilizers, diluents, dispersing agents, suspending agents, thickening agents, and/or excipients. In certain embodiments, a pharmaceutical composition facilitates administration of the compound to an organism. In some embodiments, practicing the methods of treatment or use provided herein, includes administering or using a pharmaceutical composition comprising a therapeutically effective amount of a compound provided herein. In specific embodiments, the methods of treatment provided for herein include administering such a pharmaceutical composition to a mammal having a disease or condition to be treated. In one embodiment, the mammal is a human. In some embodiments, the therapeutically effective amount varies widely depending on the severity of the disease, the age and relative health of the subject, the potency of the compound used and other factors. In various embodiments, the compounds described herein are used singly or in combination with one or more therapeutic agents as components of mixtures.

In certain embodiments, the pharmaceutical compositions provided herein are formulated for intravenous injections. In certain aspects, the intravenous injection formulations provided herein are formulated as aqueous solutions, and, in some embodiments, in physiologically compatible buffers such as Hank's solution, Ringer's solution, or physiological saline buffer. In certain embodiments, the pharmaceutical compositions provided herein are formulated for transmucosal administration. In some aspects, transmucosal formulations include penetrants appropriate to the barrier to be permeated. In certain embodiments, the pharmaceutical compositions provided herein are formulated for other parenteral injections, appropriate formulations include aqueous or nonaqueous solutions, and in one embodiment, with physiologically compatible buffers or excipients.

In certain embodiments, the pharmaceutical compositions provided herein are formulated for oral administration. In certain aspects, the oral formulations provided herein comprise compounds described herein that are formulated with pharmaceutically acceptable carriers or excipients. Such carriers enable the compounds described herein to be formulated as tablets, powders, pills, dragees, capsules, liquids, gels, syrups, elixirs, slurries, suspensions and the like, for oral ingestion by a patient to be treated.

In some embodiments, pharmaceutical compositions for oral use are obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients include, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents are optionally added, such as the cross-linked croscarmellose sodium, polyvinylpyrrolidone, agar, or alginic acid or a salt thereof such as sodium alginate.

In certain embodiments, provided herein is a pharmaceutical composition formulated as dragee cores with suitable coatings. In certain embodiments, concentrated sugar solutions are used in forming the suitable coating, and optionally contain gum arabic, talc, polyvinylpyrrolidone, carbopol gel, polyethylene glycol, and/or titanium dioxide, lacquer solutions, and suitable organic solvents or solvent mixtures. In some embodiments, dyestuffs and/or pigments are added to tablets, dragees and/or the coatings thereof for, e.g., identification or to characterize different combinations of active compound doses.

In certain embodiments, pharmaceutical compositions which are used include orally include push-fit capsules made of gelatin, as well as soft, sealed capsules made of gelatin and a plasticizer, such as glycerol or sorbitol. In some embodiments, the push-fit capsules contain the active ingredients in admixture with filler such as lactose, binders such as starches, and/or lubricants such as talc or magnesium stearate and, optionally, stabilizers. In certain embodiments, in soft capsules, the active compounds are dissolved or suspended in suitable liquids, such as fatty oils, liquid paraffin, or liquid polyethylene glycols. In addition, stabilizers are optionally added. In certain embodiments, the formulations for oral administration are in dosages suitable for such administration.

In certain embodiments, the pharmaceutical compositions provided herein are formulated for buccal or sublingual administration. In certain embodiments, buccal or sublingual compositions take the form of tablets, lozenges, or gels formulated in a conventional manner. In certain embodiments, parenteral injections involve bolus injection or continuous infusion. In some embodiments, formulations for injection are presented in unit dosage form, e.g., in ampoules or in multi-dose containers, with an added preservative. In some embodiments, the pharmaceutical composition described herein is in a form suitable for parenteral injection as a sterile suspensions, solutions or emulsions in oily or aqueous vehicles, and optionally contains formulatory agents such as suspending, stabilizing and/or dispersing agents. Pharmaceutical formulations for parenteral administration include aqueous solutions of the active compounds in water-soluble form. In some embodiments, suspensions of the active compounds are prepared as appropriate oily injection suspensions. Suitable lipophilic solvents or vehicles include fatty oils such as sesame oil, or synthetic fatty acid esters, such as ethyl oleate or triglycerides, or liposomes. In certain embodiments, aqueous injection suspensions contain substances which increase the viscosity of the suspension, such as sodium carboxymethyl cellulose, sorbitol, or dextran. Optionally, the suspensions also contain suitable stabilizers or agents which increase the solubility of the compounds to allow for the preparation of highly concentrated solutions. In alternative embodiments, the active ingredient is in powder form for constitution with a suitable vehicle, e.g., sterile pyrogen-free water, before use.

In some embodiments, the compounds described herein are administered topically. In specific embodiments, the compounds described herein are formulated into a variety of topically administrable compositions, such as solutions, suspensions, lotions, gels, pastes, medicated sticks, balms, creams or ointments. Such pharmaceutical compounds optionally contain solubilizers, stabilizers, tonicity enhancing agents, buffers and/or preservatives.

In certain embodiments, the pharmaceutical compositions provided herein are formulated for transdermal administration of compounds described herein. In some embodiments, administration of such compositions employs transdermal delivery devices and transdermal delivery patches. In certain embodiments, the compositions are lipophilic emulsions or buffered, aqueous solutions, dissolved and/or dispersed in a polymer or an adhesive. Such patches include those constructed for continuous, pulsatile, or on demand delivery of pharmaceutical agents. In some embodiments, transdermal delivery of the compounds described herein is accomplished by use of iontophoretic patches and the like. In certain embodiments, the rate of absorption is slowed by using rate-controlling membranes or by trapping the compound within a polymer matrix or gel. Conversely, absorption enhancers are optionally used to increase absorption. Absorption enhancer and carrier include absorbable pharmaceutically acceptable solvents that assist in passage of the compound through the skin. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

In certain embodiments, the pharmaceutical compositions provided herein are formulated for administration by inhalation. In certain embodiments, in such pharmaceutical compositions formulated for inhalation, the compounds described herein are in a form as an aerosol, a mist or a powder. In some embodiments, pharmaceutical compositions described herein are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In certain aspects of a pressurized aerosol, the dosage unit is determined by providing a valve to deliver a metered amount. In certain embodiments, capsules and cartridges of, such as, by way of example only, gelatin for use in an inhaler or insufflator is formulated containing a powder mix of the compound described herein and a suitable powder base such as lactose or starch.

In some embodiments, the compounds described herein are formulated in rectal compositions such as enemas, rectal gels, rectal foams, rectal aerosols, suppositories, jelly suppositories, or retention enemas. In certain embodiments, rectal compositions optionally contain conventional suppository bases such as cocoa butter, or other glycerides, as well as synthetic polymers such as polyvinylpyrrolidone, PEG, and the like. In certain suppository forms of the compositions, a low-melting wax such as, but not limited to, a mixture of fatty acid glycerides, optionally in combination with cocoa butter is first melted.

In various embodiments provided herein, the pharmaceutical compositions are formulated in a conventional manner using one or more physiologically acceptable carriers comprising excipients and auxiliaries which facilitate processing of the active compounds into pharmaceutically acceptable preparations. In certain embodiments, proper formulation is dependent upon the route of administration chosen. In various embodiments, any of the techniques, carriers, and excipients is used as suitable. In some embodiments, pharmaceutical compositions comprising a compound described herein are manufactured in a conventional manner, such as, by way of example only, by means of conventional mixing, dissolving, granulating, dragee-making, levigating, emulsifying, encapsulating, entrapping or compression processes.

In certain embodiments, the pharmaceutical compositions include at least one pharmaceutically acceptable carrier, diluent or excipient and a compound described herein described herein as an active ingredient in free-acid or free-base form, or in a pharmaceutically acceptable salt form. In addition, the methods and pharmaceutical compositions described herein include the use of N-oxides, crystalline forms (also known as polymorphs), as well as active metabolites of these compounds having the same type of activity. In some situations, compounds described herein exist as tautomers. All tautomers are included within the scope of the compounds presented herein. Additionally, included herein are the solvated and unsolvated forms of the compounds described herein. Solvated compounds include those that are solvated with pharmaceutically acceptable solvents such as water, ethanol, and the like. The solvated forms of the compounds presented herein are also considered to be disclosed herein. In some embodiments, the pharmaceutical compositions described herein include other medicinal or pharmaceutical agents, carriers, adjuvants, such as preserving, stabilizing, wetting or emulsifying agents, solution promoters, salts for regulating the osmotic pressure, and/or buffers. In additional embodiments, the pharmaceutical compositions described herein also contain other therapeutically valuable substances.

Methods for the preparation of compositions containing the compounds described herein include formulating the compounds with one or more inert, pharmaceutically acceptable excipients or carriers to form a solid, semi-solid or liquid. Solid compositions include, but are not limited to, powders, tablets, dispersible granules, capsules, cachets, and suppositories. Liquid compositions include solutions in which a compound is dissolved, emulsions comprising a compound, or a solution containing liposomes, micelles, or nanoparticles comprising a compound as disclosed herein. Semi-solid compositions include, but are not limited to, gels, suspensions and creams. In various embodiments, the compositions are in liquid solutions or suspensions, solid forms suitable for solution or suspension in a liquid prior to use, or as emulsions. These compositions optionally contain minor amounts of nontoxic, auxiliary substances, such as wetting or emulsifying agents, pH buffering agents, and so forth.

In some embodiments, a composition comprising a compound described herein takes the form of a liquid where the agents are present in solution, in suspension or both. In some embodiments, when the composition is administered as a solution or suspension a first portion of the agent is present in solution and a second portion of the agent is present in particulate form, in suspension in a liquid matrix. In some embodiments, a liquid composition includes a gel formulation. In other embodiments, the liquid composition is aqueous.

Useful aqueous suspension optionally contain one or more polymers as suspending agents. Useful polymers include water-soluble polymers such as cellulosic polymers, e.g., hydroxypropyl methylcellulose, and water-insoluble polymers such as cross-linked carboxyl-containing polymers. Useful compositions optionally comprise an mucoadhesive polymer, selected for example from carboxymethylcellulose, carbomer (acrylic acid polymer), poly (methylmethacrylate), polyacrylamide, polycarbophil, acrylic acid/butyl acrylate copolymer, sodium alginate and dextran.

Useful compositions optionally include solubilizing agents to aid in the solubility of a compound described herein. The term "solubilizing agent" generally includes agents that result in formation of a micellar solution or a true solution of the agent. Solubilizing agents include certain acceptable nonionic surfactants, for example polysorbate 80, and ophthalmologically acceptable glycols, polyglycols, e.g., polyethylene glycol 400, and glycol ethers.

Useful compositions optionally include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Useful compositions optionally include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate, or bisulfite anions; suitable salts include sodium chloride, potassium chloride, sodium thiosulfate, sodium bisulfite, and ammonium sulfate.

Certain useful compositions optionally include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide, and cetylpyridinium chloride.

Some useful compositions optionally include one or more surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10 and octoxynol 40.

Certain useful compositions optionally one or more antioxidants to enhance chemical stability where required. Suitable antioxidants include, by way of example only, ascorbic acid, and sodium metabisulfite.

In some embodiments, aqueous suspension compositions are packaged in single-dose non-reclosable containers. In alternative embodiments, multiple-dose reclosable containers are used, in which case it is typical to include a preservative in the composition.

In various embodiments, any delivery system for hydrophobic pharmaceutical compounds is employed. Liposomes and emulsions are examples of delivery vehicles or carriers for hydrophobic drugs. In certain embodiments, certain organic solvents such as N-methylpyrrolidone are employed. In some embodiments, the compounds are delivered using a sustained-release system, such as semipermeable matrices of solid hydrophobic polymers containing the therapeutic agent. Various sustained-release materials are utilized in the embodiments herein. In certain embodiments, sustained-release capsules release the compounds for a few weeks up to over 100 days. In some embodiments, depending on the chemical nature and the biological stability of the therapeutic reagent, additional strategies for protein stabilization are employed.

In certain embodiments, the formulations or compositions described herein benefit from and/or optionally comprise antioxidants, metal chelating agents, thiol containing compounds and other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

Dosing and Treatment Regimens

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest the symptoms of the disease or condition. In some embodiments, amounts effective for this use will depend on the severity and course of the disease or condition, previous therapy, the patient's health status, weight, and response to the drugs, and the judgment of the treating physician. In certain instances, it is considered appropriate for the caregiver to determine such therapeutically effective amounts by routine experimentation (including, but not limited to, a dose escalation clinical trial).

In certain prophylactic applications, compositions containing the compounds described herein are administered to a patient susceptible to or otherwise at risk of a particular disease, disorder or condition. In some embodiments, the amount administered is defined to be a "prophylactically effective amount or dose." In certain embodiments of this use, the precise amounts of compound administered depend on the patient's state of health, weight, and the like. In some embodiments, it is considered appropriate for the caregiver to determine such prophylactically effective amounts by routine experimentation (e.g., a dose escalation clinical trial). In certain embodiments, when used in a patient, effective amounts for this use will depend on the severity and course of the disease, disorder or condition, previous therapy, the patient's health status and response to the drugs, and the judgment of the treating physician.

In certain instances, a patient's condition does not improve or does not significantly improve following administration of a compound or composition described herein and, upon the doctor's discretion the administration of the compounds is optionally administered chronically, that is, for an extended period of time, including throughout the duration of the patient's life in order to ameliorate or otherwise control or limit the symptoms of the patient's disease or condition.

In certain cases wherein the patient's status does improve or does not substantially improve, upon the doctor's discretion the administration of the compounds are optionally given continuously; alternatively, the dose of drug being administered is optionally temporarily reduced or temporarily suspended for a certain length of time (i.e., a "drug holiday"). In certain embodiments, the length of the drug holiday varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes a reduction from about 10% to about 100%, including, by way of example only, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

In certain embodiments, once improvement of the patient's conditions has occurred, a maintenance dose is administered if necessary. In some embodiments, the dosage, e.g., of the maintenance dose, or the frequency of administration, or both, are reduced, as a function of the symptoms, to a level at which the improved disease, disorder or condition is retained. In certain embodiments, however, patients are optionally given intermittent treatment on a long-term basis upon any recurrence of symptoms.

In certain embodiments, the amount of a given agent that corresponds to an effective amount varies depending upon factors such as the particular compound, disease or condition and its severity, the identity (e.g., weight) of the subject or host in need of treatment. In some embodiments, the effective amount is, nevertheless, determined according to the particular circumstances surrounding the case, including, e.g., the specific agent that is administered, the route of administration, the condition being treated, and the subject or host being treated. In certain embodiments, however, doses employed for adult human treatment is in the range of about 0.02 to about 5000 mg per day, in a specific embodiment about 1 to about 1500 mg per day. In various embodiments, the desired dose is conveniently presented in a single dose or as divided doses administered simultaneously (or over a short period of time) or at appropriate intervals, for example as two, three, four or more sub-doses per day.

In some embodiments, the pharmaceutical compositions described herein are in a unit dosage form suitable for single administration of precise dosages. In some instances, in unit dosage form, the formulation is divided into unit doses containing appropriate quantities of one or more compound. In certain embodiments, the unit dosage is in the form of a package containing discrete quantities of the formulation. Non-limiting examples are packaged tablets or capsules, and powders in vials or ampoules. In some embodiments, aqueous suspension compositions are packaged in single-dose non-reclosable containers. In alternative embodiments, multiple-dose reclosable containers are used, in which case it is typical to include a preservative in the composition. By way of example only, formulations for parenteral injection are, in some embodiments, presented in unit dosage form, which include, but are not limited to ampoules, or in multi-dose containers, with an added preservative.

In certain embodiments, the daily dosages appropriate for the compounds described herein described herein are from about 0.01 to about 2.5 mg/kg per body weight. In some embodiments, an indicated daily dosage in the larger subject, including, but not limited to, humans, is in the range from about 0.5 mg to about 100 mg, conveniently administered in divided doses, including, but not limited to, up to four times a day or in extended release form. In certain embodiments, suitable unit dosage forms for oral administration comprise from about 1 to about 50 mg active ingredient. The foregoing ranges are merely suggestive, as the number of variables in regard to an individual treatment regime is large, and considerable excursions from these recommended values are not uncommon. In certain embodiments, the dosages are altered depending on a number of variables, not limited to the activity of the compound used, the disease or condition to be treated, the mode of administration, the requirements of the individual subject, the severity of the disease or condition being treated, and the judgment of the practitioner.

In certain embodiments, toxicity and therapeutic efficacy of such therapeutic regimens are determined by standard pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. In certain embodiments, compounds exhibiting high therapeutic indices are preferred. In some embodiments, the data obtained from cell culture assays and animal studies is used in formulating a range of dosage for use in human. In specific embodiments, the dosage of such compounds lies within a range of circulating concentrations that include the $ED_{50}$ with minimal toxicity. In certain embodiments, the dosage varies within this range depending upon the dosage form employed and the route of administration utilized.

In certain embodiments, the disclosed compounds exhibit an increased affinity for a nuclear target, increased potency or increased therapeutic index as compared to an unmodified nuclear payload from which the compound was derived. In certain embodiments, this higher affinity, potency or therapeutic index may provide benefits, such as allowing for the administration of lower doses and thus reduced potential for toxicity, improvement in therapeutic index and decreased overall cost of therapy. In certain embodiments, the daily dosages appropriate for administration of the compounds described herein is less than 100% of the recommended daily dose of the unmodified nuclear payload, or less than about 90%, or less than about 80% or less than about 70%, or less than about 60%, or less than about 50%, or less than about 40%, or from about 20% to about 90%, or from about 30% to about 90%, or from about 40% to about 90%, or from about 50% to about 90%, or from about 60% to about 90%, or from about 70% to about 90%, or from about 20% to about 80%, or from about 30% to about 80%, or from about 40% to about 80%, or from about 50% to about 80%, or from about 60% to about 80%, or from about 70% to about 80%, or from about 20% to about 70%, or from about 30% to about 70%, or from about 40% to about 70%, or from about 50% to about 70%, or from about 60% to about 70%, of the recommended daily dose of the unmodified nuclear payload.

In certain embodiments, the compounds described herein are used in the preparation or manufacture of medicaments for the treatment of diseases or conditions that are mediated by the enzyme poly(ADP-ribose)polymerase (PARP) or in which inhibition of the enzyme poly(ADP-ribose)polymerase (PARP) ameliorates the disease or condition. In some embodiments, a method for treating any of the diseases or conditions described herein in a subject in need of such treatment, involves administration of pharmaceutical compositions containing at least one compound described herein, or a pharmaceutically acceptable salt, pharmaceutically acceptable N-oxide, pharmaceutically active metabolite, pharmaceutically acceptable prodrug, or pharmaceutically acceptable solvate thereof, in therapeutically effective amounts to said subject.

Combination Therapy

Compounds described herein can also be used in combination with other active ingredients. Such combinations are selected based on the condition to be treated, cross-reactivities of ingredients and pharmaco-properties of the combination. In one embodiment, the disclosure provides a use of a compound as described herein used in combination with another agent or therapy method, such as another cancer treatment. For example, when treating cancer, the compositions can be combined with other anti-cancer compounds (such as paclitaxel or rapamycin).

It is also possible to combine a compound of the disclosure with one or more other active ingredients in a unitary dosage form for simultaneous or sequential administration to a patient. The combination therapy may be administered as a simultaneous or sequential regimen. When administered sequentially, the combination may be administered in two or more administrations.

The combination therapy may provide "synergy" and "synergistic," i.e. the effect achieved when the active ingredients used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g. in separate tablets, pills or capsules, or by different injections in separate syringes. In general, during alternation therapy, an effective dosage of each active ingredient is administered sequentially, i.e. serially, whereas in combination therapy, effective dosages of two or more active ingredients are administered together. A synergistic anti-cancer effect denotes an anti-cancer effect that is greater than the predicted purely additive effects of the individual compounds of the combination.

Administration of the compounds and compositions of the present disclosure to a patient will follow general protocols for the administration of chemotherapeutics, taking into account the toxicity, if any. It is expected that the treatment cycles would be repeated as necessary. It is also contemplated that various standard therapies or adjunct cancer therapies, as well as surgical intervention, may be applied in combination with the described active agent(s). These therapies include but are not limited to chemotherapy, radiotherapy, immunotherapy, gene therapy and surgery.

In some embodiments, provided herein is a method for the treatment of cancer, comprising administering to a subject in need of treatment a therapeutically-effective amount of a compound or composition described herein in combination with ionizing radiation or one or more chemotherapeutic agents. In some embodiments, the compound described herein is administered simultaneously with ionizing radiation or one or more chemotherapeutic agents. In other embodiments, the compound described herein is administered sequentially with ionizing radiation or one or more chemotherapeutic agents.

In certain embodiments, provided herein is a method for the treatment of cancer, which includes administering to a subject in need of treatment a therapeutically-effective amount of a compound or composition described herein in combination with ionizing radiation and one or more chemotherapeutic agents. In some embodiments, the compound described herein is administered simultaneously with ionizing radiation and one or more chemotherapeutic agents. In other embodiments, the compound described herein is administered sequentially with ionizing radiation and one or more chemotherapeutic agents.

In certain embodiments, provided herein is a method for the treatment of cancer, which includes administering to a subject in need of treatment a therapeutically-effective amount of a compound or composition described herein in combination with ionizing radiation. In certain embodiments, the radiation is administered at a dose of less than about 2.5 Gy per day, or about 2.0 Gy per day, or about 1.8 Gy per day, or about 1.6 Gy per day, or about 1.4 Gy per day, or about 1.2 Gy per day. In certain embodiments, a dose of less than about 2.5 Gy, or about 2.0 Gy, or about 1.8 Gy, or about 1.6 Gy, or about 1.4 Gy, or about 1.2 Gy is administered about 5 times per week. In certain embodiments, the radiation is administered at a dose of less than about 2.5 Gy per day, or about 2.0 Gy per day, or about 1.8 Gy per day, or about 1.6 Gy per day, or about 1.4 Gy per day, or about 1.2 Gy per day. In certain embodiments, a dose of less than about 2.5 Gy, or about 2.0 Gy, or about 1.8 Gy, or about 1.6 Gy, or about 1.4 Gy, or about 1.2 Gy is administered about 6 times per week. It is contemplated that by administering radiation in combination with a compound or composition described herein, prostate specific chemical prostatectomy can be achieved while avoiding detrimental side effects, such as the impotence and incontinence of surgical prostatectomy due to disruption of vessels and nerves.

Cancer therapies can also include a variety of combination therapies with both chemical and radiation based treatments. Combination chemotherapies include the use of chemotherapeutic agents such as, cisplatin, etoposide, irinotecan, camptostar, topotecan, paclitaxel, docetaxel, epothilones, taxotere, tamoxifen, 5-fluorouracil, methotrexate, temozolomide, cyclophosphamide, SCH 66336, R115777, L778,123, BMS 214662, IRESSA® (gefitinib), TARCEVAR® (erlotinib hydrochloride), antibodies to EGFR, GLEEVEC® (imatinib), intron, ara-C, adriamycin, cytoxan, gemcitabine, uracil mustard, chlormethine, ifosfamide, melphalan, chlorambucil, pipobroman, triethylenemelamine, triethylenethiophosphoramine, busulfan, carmustine, lomustine, streptozocin, dacarbazine, floxuridine, cytarabine, 6-mercaptopurine, 6-thioguanine, fludarabine phosphate, pentostatine, vinblastine, vincristine, vindesine, bleomycin, doxorubicin, dactinomycin, daunorubicin, epirubicin, idarubicin, mithramycin, deoxycoformycin, Mitomycin-C, L-Asparaginase, teniposide, 17α-Ethinylestradiol, Diethylstilbestrol, testosterone, prednisone, fluoxymesterone, dromostanolone propionate, testolactone, megestrolacetate, methylprednisolone, methyltestosterone, prednisolone, triamcinolone, chlorotrianisene, hydroxyprogesterone, aminoglutethimide, estramustine, medroxyprogesterone acetate, leuprolide, flutamide, toremifene, goserelin, carboplatin, hydroxyurea, amsacrine, procarbazine, mitotane, mitoxantrone, levamisole, navelbene, anastrazole, letrazole, capecitabine, reloxafine, droloxafine, hexamethylmelamine, Avastin, herceptin, Bexxar, Velcade, Zevalin, Trisenox, Xeloda, Vinorelbine, Porfimer, Erbitux® (cetuximab), Liposomal, Thiotepa, Altretamine, Melphalan, Trastuzumab, Lerozole, Fulvestrant, Exemestane, Ifosfomide, Rituximab, C225, Campath, carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP 16), tamoxifen, raloxifene, estrogen receptor binding agents, paclitaxel, gemcitabine, navelbine, farnesylprotein transferase inhibitors, transplatinum, 5-fluorouracil, vincristine, vinblastine and methotrexate, or any analog or derivative variant of the foregoing.

Other factors that cause DNA damage, such as radiotherapy, have been used extensively include what are commonly known as gamma-rays, X-rays, and/or the directed delivery of radioisotopes to tumor cells. Other forms of DNA damaging factors are also contemplated such as microwaves and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (e.g., 3 to 4 weeks), to single doses of 2000 to 6000 roentgens. Dosage ranges for radioisotopes vary widely, and depend on the half-life of the isotope, the strength and type of radiation emitted, and the uptake by the neoplastic cells. The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionucleotide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Immunotherapy, thus, could be used as part of a combined therapy, in conjunction with gene therapy. The general approach for combined therapy is discussed below. Generally, the tumor cell must bear some marker that is amenable to targeting, i.e., is not present on the majority of other cells. Many tumor markers exist and any of these may be suitable for targeting in the context of the present disclosure. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

In yet another embodiment, the secondary treatment is a secondary gene therapy in which a therapeutic polynucleotide is administered before, after, or at the same time a first chemotherapeutic agent. Delivery of the chemotherapeutic agent in conjunction with a vector encoding a gene product will have a combined anti-hyperproliferative effect on target tissues.

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present disclosure, chemotherapy, radiotherapy, hormonal therapy, gene therapy, immunotherapy and/or alternative therapies. Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present disclosure may be used in conjunction with removal of superficial cancers, precancers, or incidental amounts of normal tissue.

Administration of the compound or composition as described herein may precede or follow the other anti-cancer agent or treatment by intervals ranging from minutes to weeks. In embodiments where the other anti-cancer agent and expression construct are applied separately, one would generally ensure that a significant period of time did not elapse between the time of each delivery, such that the agent and expression construct would still be able to exert an advantageously combined effect on a cell. For example, in such instances, it is contemplated that one may contact a cell, tissue or organism with two, three, four or more modalities substantially simultaneously (i.e., within less than about a minute) with the active agent(s). In other aspects, one or more agents may be administered within about 1 minute, about 5 minutes, about 10 minutes, about 20 minutes about 30 minutes, about 45 minutes, about 60 minutes, about 2 hours, about 3 hours, about 4 hours, about 6 hours, about 8 hours, about 9 hours, about 12 hours, about 15 hours, about 18 hours, about 21 hours, about 24 hours, about 28 hours, about 31 hours, about 35 hours, about 38 hours, about 42 hours, about 45 hours, to about 48 hours or more prior to and/or after administering the active agent(s). In certain other embodiments, an agent may be administered within from about 1 day, about 2 days, about 3 days, about 4 days, about 5 days, about 6 days, about 8 days, about 9 days, about 12 days, about 15 days, about 16 days, about 18 days, about 20 days, to about 21 days prior to and/or after administering the active agent(s). In some situations, it may be desirable to extend the time period for treatment significantly, however, where several weeks (e.g., about 1, about 2, about 3, about 4, about 6, or about 8 weeks or more) lapse between the respective administrations.

Kits

Kits for use to achieve anti-cancer effects comprising a compound or composition described herein are provided. In certain embodiments, the kit comprises a unit dose of a compound or composition described herein and instructions for administering the same. In certain aspects, the kit further comprises a second drug suitable for anti-cancer therapy, or instructions for co-administering an additional anti-cancer therapy (such as radiation or gene therapy). In another aspect, kits for use to achieve anti-cancer effects comprise a low dose (e.g., less than about 500 mg/day, or less than about 400 mg/day, or less than about 300 mg/day, or less than about 200 mg/day) of a compound or composition described herein and a second drug suitable for anti-cancer therapy. In yet another variation, kits for use to achieve anti-cancer effects comprise a high dose (e.g., greater than about 500 mg/day) of a compound or composition as described herein and a second drug suitable for anti-cancer therapy.

Methods of Manufacturing a Medicament

In a further aspect of the disclosure, use of the compounds and compositions described herein in the manufacture of a medicament is provided. In particular, the manufacture of a medicament for use in the treatment of cancer, or diseases or conditions which can be mediated, at least in part, by blocking DNA repair and/or transcription activation, such as by inhibition of PARP, are provided. Further, pharmaceutical compositions of a compound described herein are also intended for use in the manufacture of a medicament for use in treatment of diseases or conditions which can be mediated, at least in part, by inhibition of PARP.

Numbered Embodiments

Embodiment 1. A compound of Formula II:

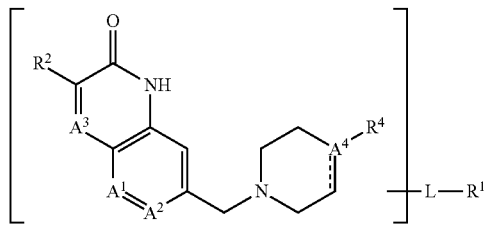

II or a tautomer, stereoisomer, mixture of stereoisomers, hydrate, solvate, isotopically enriched analog, or pharmaceutically acceptable salt thereof, wherein:

$A^1$ is CH or N;

$A^2$ is CH or N;

$A^3$ is N or $CR^3$;

$A^4$ is C and $\equiv$ is a double bond, or $A^4$ is CH and $\equiv$ is a single bond, or $A^4$ is N and $\equiv$ is a single bond;

L is a covalent bond or a linking moiety;

$R^1$ is a nuclear receptor-targeting epitope;

$R^2$ is $C_{1-6}$ alkyl;

$R^3$ is hydrogen; or $R^2$ and $R^3$ together with the atoms to which they are attached form a 6-membered heterocyclyl or 6-membered heteroaryl;

$R^4$ is hydrogen, aryl or heteroaryl, wherein the aryl or heteroaryl is optionally substituted with one to five $R^5$;

each $R^5$ is independently halo, cyano, nitro, $-OR^{10}$, $-OC(O)R^{10}$, $-C(O)OR^{10}$, $-SR^{10}$, $-NR^{10}R^{11}$, $-NR^{10}C(O)R^{11}$, $-C(O)NR^{10}R^{11}$, $C_{1-12}$ alkyl, $C_{1-12}$ haloalkyl, $C_{2-12}$ alkenyl, or $C_{2-12}$ alkynyl; wherein each $C_{1-12}$ alkyl, $C_{1-12}$ haloalkyl, $C_{2-12}$ alkenyl, or $C_{2-12}$ alkynyl is independently optionally substituted with one to five halo, hydroxyl or amino; and each $R^{10}$ and $R^{11}$ is independently hydrogen or $C_{1-12}$ alkyl optionally substituted with oxo, halo, hydroxyl or amino as valency permits; or $R^{10}$ and $R^{11}$ are taken together with the atoms to which they are attached to form heterocyclyl optionally substituted by halo or $C_{1-12}$ alkyl optionally substituted by oxo, halo, hydroxyl or amino;

wherein any hydrogen atom of the compound of Formula I is replaced with attachment to $L-R^1$.

Embodiment 2. The compound of embodiment 1, wherein the compound is represented by Formula IIA:

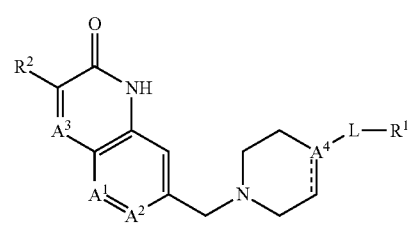

IIA or a tautomer, stereoisomer, mixture of stereoisomers, hydrate, solvate, isotopically enriched analog, or pharmaceutically acceptable salt thereof.

Embodiment 3. The compound of embodiment 1, wherein the compound is represented by Formula IIB:

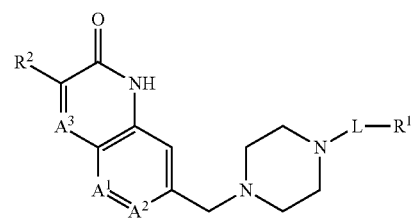

IIB or a tautomer, stereoisomer, mixture of stereoisomers, hydrate, solvate, isotopically enriched analog, or pharmaceutically acceptable salt thereof.

Embodiment 4. The compound of embodiment 1, wherein the compound is represented by Formula IIC:

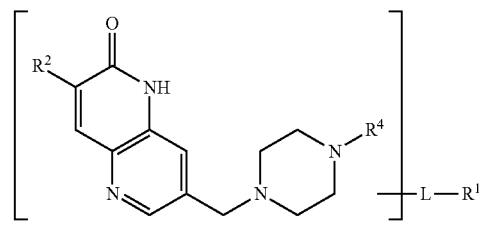

IIC or a tautomer, stereoisomer, mixture of stereoisomers, hydrate, solvate, isotopically enriched analog, or pharmaceutically acceptable salt thereof.

Embodiment 5. The compound of embodiment 1, wherein the compound is represented by Formula IID:

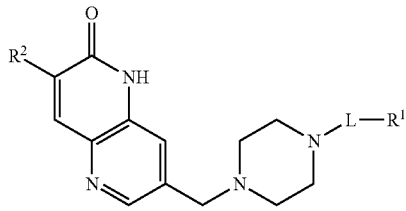

IID or a tautomer, stereoisomer, mixture of stereoisomers, hydrate, solvate, isotopically enriched analog, or pharmaceutically acceptable salt thereof.

Embodiment 6. The compound of embodiment 1, wherein the compound is represented by Formula IIE

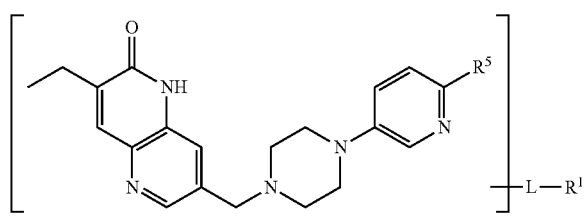

IIE or a tautomer, stereoisomer, mixture of stereoisomers, hydrate, solvate, isotopically enriched analog, or pharmaceutically acceptable salt thereof.

Embodiment 7. The compound of embodiment 1, wherein the compound is represented by Formula IIF

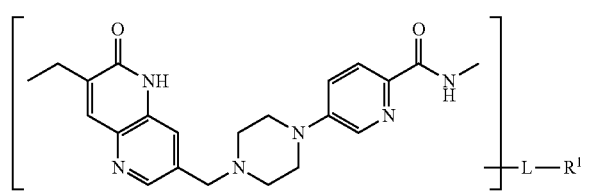

IIF or a tautomer, stereoisomer, mixture of stereoisomers, hydrate, solvate, isotopically enriched analog, or pharmaceutically acceptable salt thereof.

Embodiment 8. The compound of embodiment 1, wherein the compound is represented by Formula IIG

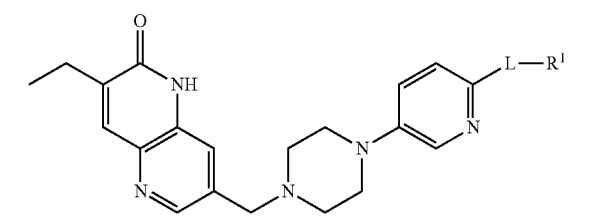

IIG or a tautomer, stereoisomer, mixture of stereoisomers, hydrate, solvate, isotopically enriched analog, or pharmaceutically acceptable salt thereof.

Embodiment 9. The compound of any preceding embodiment, wherein L is of the formula:

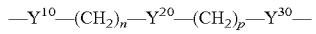

wherein each of $Y^{10}$, $Y^{20}$, and $Y^{30}$ are independently a bond, optionally substituted alkylene, optionally substituted heteroalkylene, optionally substituted arylene, optionally substituted heteroarylene, optionally substituted cycloalkylene, optionally substituted heterocyclylene, —$CR^{110}R^{120}$—, —$NR^{110}$—, —O—, —$S(O)_{0-2}$—, —$NR^{110}C(O)$—, —$C(O)NR^{110}$—, —$NR^{110}S(O)_2$—, —$S(O)_2NR^{110}$—, —$CR^{120}$=N—$NR^{110}$—, —$NR^{110}$—N=$CR^{120}$—, or —$C(O)$—;

each $R^{110}$ is independently hydrogen, $C_{1-4}$ alkyl, $C_{1-4}$ haloalkyl, aryl, heteroaryl, cycloalkyl or heterocyclyl;

each $R^{120}$ is independently hydrogen, $C_{1-4}$ alkyl, $C_{1-4}$ haloalkyl, aryl, heteroaryl, cycloalkyl or heterocyclyl; and n and p are each independently 0, 1, 2, 3, 4, 5, 6, 7, or 8.

Embodiment 10. The compound of any preceding embodiment, wherein L comprises a non-biocleavable moiety.

Embodiment 11. The compound of any preceding embodiment, wherein L is an optionally substituted alkylene or optionally substituted heteroalkylene.

Embodiment 12. The compound of any preceding embodiment, wherein L comprises an optionally substituted alkylene having 4-7 chain atoms, optionally substituted 4-7-membered heterocyclylene, or optionally substituted heteroalkylene having 4-7 chain atoms.

Embodiment 13. The compound of any preceding embodiment, wherein L is alkylene having 4-7 chain atoms or heteroalkylene having 4-7 chain atoms linking moiety containing $CH_2$ and up to 2 heteroatoms each independently selected from NH, O or S, and optionally one C=O.

Embodiment 14. The compound of any preceding embodiment, wherein the linking moiety is of the formula:

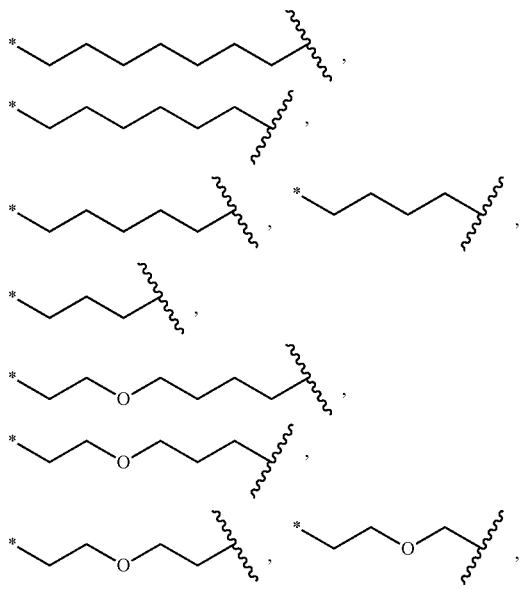

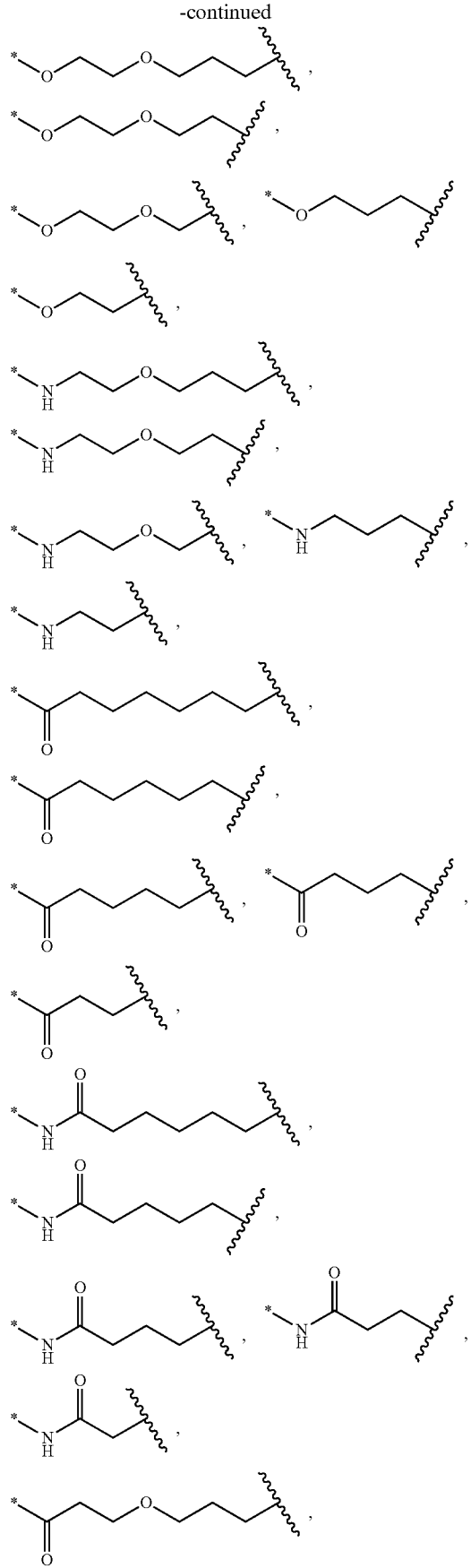
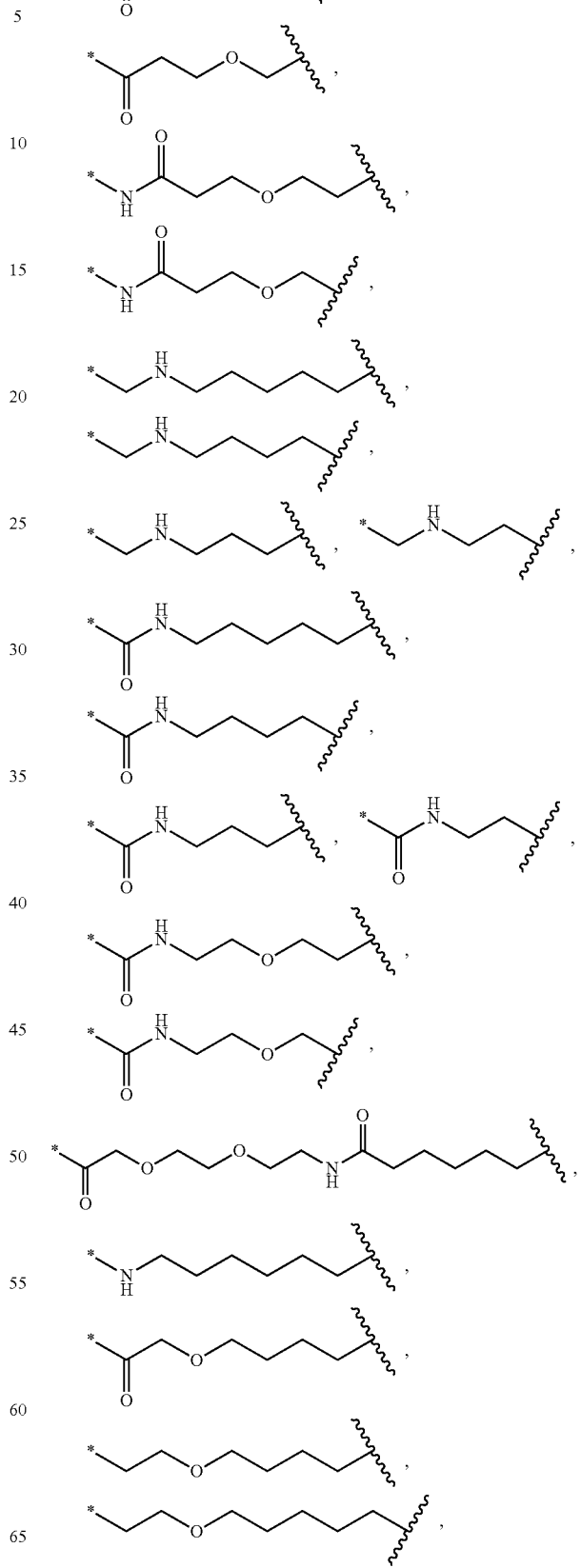

-continued

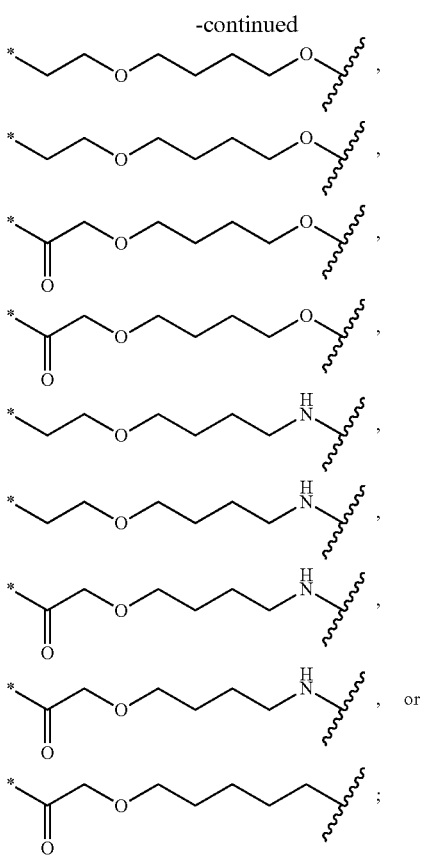

where the "*" and the wavy line represent a covalent bond.

Embodiment 11. The compound of any one of embodiments 1-9, wherein L is

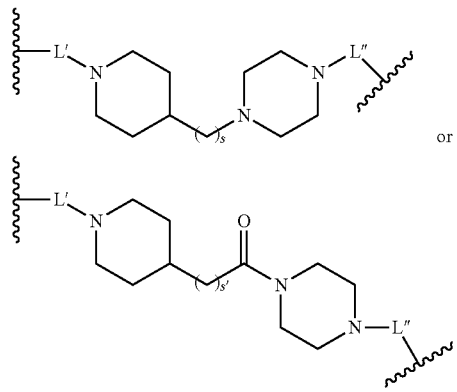

and s is 1, 2, or 3; s' is 0 or 1; and

L' and L" are each independently selected from a bond, $CH_2$, $CH_2CH_2$, or $C=O$.

Embodiment 12. The compound of any preceding embodiment, wherein $R^1$ is derived from DHT, testosterone, dienolone, trienolone, drostanolol, stanzolol, JNJ-37654032, LGD-2226, LGD-3303, enzalutamide, apalutamide, darolutamide, bicalutamide, flutamide, nilutamide, enobosarm, BMS-564929, PS178990, LGD-4033 (ligandrol), LGD-2941, JNJ-28330835, JNJ-26146900, LGD-121071, LG-120907, S-40503, RAD-140, acetothiolutamide, andarine (S-4), TFM-4AS-1, YK-11, MK-0773 (PF-05314882), GSK2849466, GSK2881078, GSK8698, GSK4336, ACP-105, TT701, LY2452473, estradiol, fulvestrant, ARN-810 (GDC-810), GW5638, AZD9496, tamoxifen, toremifene, raloxifene, GW7604, bazedoxifene, ospemifene, droloxifene, clomifene, idoxifene, fispemifene, afimoxifene, arzoxifene, zindoxifene, pipendoxifene, GDC9545, lasofoxifene, endoxifen, ormeloxifene, cyclofenil, broparoestrol, anordrin, toremifene, mapracorat, flumethasone, loteprednol etabonate, mometasone furoate, methylprednisolone, OP-3633, LLY-2707, CORT-108279, ORIC-101, AL082D06, dagrocorat, fosdagrocorat, megestrol acetate, progesterone, mifepristone (RU-486), telapristone, ulipristal acetate, anordrin, toremifene, or ketodarolutamide, or a stereoisomer or a mixture of stereoisomers thereof or an analog thereof.

Embodiment 13. The compound of any preceding embodiment, wherein $R^1$ is

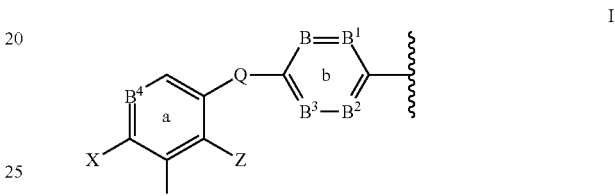

wherein:

Q is

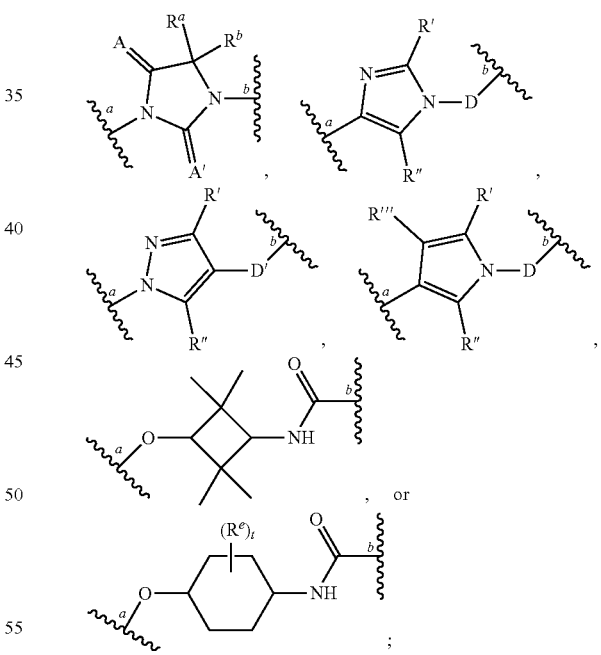

wherein bond a is attached to ring a and bond b is attached to ring b;

$R^a$ and $R^b$ are each independently $CH_3$ or $CH_2CH_3$; or $R^a$ and $R^b$ together with the atom to which they are attached form a $C_{3-5}$ cycloalkyl, oxiranyl, oxetanyl, or tetrahydrofuranyl;

A and A' are each independently O or S;

B, $B^1$, $B^2$, and $B^3$ are each independently $CR^c$ or N, and each $R^c$ is independently hydrogen, halo, CN, or methyl;

$B^4$ is CF, CH or N;
D is a bond, $CH_2$, C=O, or (C=O)NH;
D' is NH, O, S, $CH_2$, NH(C=O), C(=O)NH, or C=O;
R', R" and R'" are each independently hydrogen, CN, or $C_{1-2}$ alkyl;
t is 0, 1, 2, 3 or 4;
each $R^e$ is independently halo, cyano, $C_{1-4}$ alkyl, or $C_{1-4}$ haloalkyl;
X is halo, CN, or $NO_2$;
Y is halo, $CH_3$, $CH_2F$, $CHF_2$, or $CF_3$; or
X and Y together form a

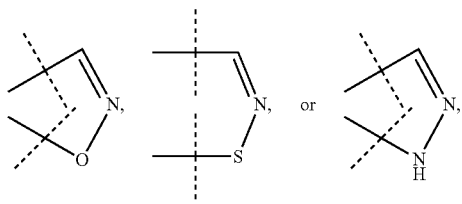

where the broken lines indicate bonds to ring a;
Z is hydrogen, halo, $C_{1-2}$ alkyl, $C_2$ alkenyl, $NO_2$, $CF_3$; or Y and Z together form a

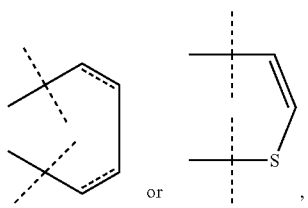

wherein each === is a single or double bond, and where the broken lines indicate bonds to ring a.

Embodiment 14. A compound selected from compound 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, and 58, as provided in Table 1, or tautomer, stereoisomer, mixture of stereoisomers, hydrate, solvate, isotopically enriched analog, or pharmaceutically acceptable salt thereof.

Embodiment 15. A pharmaceutical composition comprising a compound as in any preceding embodiment, or a tautomer, stereoisomer, mixture of stereoisomers, hydrate, solvate, isotopically enriched analog, or pharmaceutically acceptable salt thereof, and a pharmaceutically acceptable excipient.

Embodiment 16. A method of treating or preventing cancer, comprising administering an effective amount of the pharmaceutical composition embodiment 15 to an individual in need thereof.

Embodiment 17. The method of embodiment 15, wherein the administering comprises oral administration.

Embodiment 18. The method of embodiment 15, further comprising administering an additional chemotherapeutic agent.

Embodiment 19. The method of embodiment 18, wherein the additional chemotherapeutic agent is cisplatin, etoposide, irinotecan, camptothecin, topotecan, paclitaxel, docetaxel, epothilones, taxotere, tamoxifen, 5-fluorouracil, methotrexate, temozolomide, cyclophosphamide, SCH 66336, R115777, L778123, BMS 214662, gefitinib, erlotinib hydrochloride, antibodies to EGFR, matinib, intron, cytarabine, adriamycin, cytoxan, gemcitabine, uracil mustard, chlormethine, ifosfamide, melphalan, chlorambucil, pipobroman, triethylenemelamine, triethylenethiophosphoramine, busulfan, carmustine, lomustine, streptozocin, dacarbazine, floxuridine, 6-mercaptopurine, 6-thioguanine, fludarabine phosphate, pentostatine, vinblastine, vincristine, vindesine, bleomycin, doxorubicin, dactinomycin, daunorubicin, epirubicin, idarubicin, mithramycin, deoxycoformycin, mitomycin-C, L-asparaginase, teniposide, 17α-ethinylestradiol, diethylstilbestrol, testosterone, prednisone, fluoxymesterone, drostanolone propionate, testolactone, megestrolacetate, methylprednisolone, methyltestosterone, prednisolone, triamcinolone, chlorotrianisene, hydroxyprogesterone, aminoglutethimide, estramustine, medroxyprogesterone acetate, leuprolide, flutamide, toremifene, goserelin, carboplatin, hydroxyurea, amsacrine, procarbazine, mitotane, mitoxantrone, levamisole, navelbene, anastrazole, letrazole, capecitabine, droloxifenehexamethylmelamine, avastin, herceptin, bexxar, velcade, zevalin, trisenox, xeloda, vinorelbine, porfimer, cetuximab, liposomal cytarabine, thiotepa, altretamine, trastuzumab, letrozole, fulvestrant, exemestane, ifosfomide, rituximab, C225, campath, procarbazine, mechlorethamine, nitrosurea, plicomycin, mitomycin, raloxifene, estrogen receptor binding agents, navelbine, farnesyl-protein transferase inhibitors, transplatinum, and methotrexate, or an analog or derivative thereof.

Embodiment 20. The method of embodiment 18, wherein the additional chemotherapeutic agent is carboplatin.

Embodiment 21. The method of embodiment 18, wherein the additional chemotherapeutic agent is paclitaxel.

Embodiment 22. The method of embodiment 20, further comprising administering carboplatin.

Embodiment 23. The method of any one of embodiments 16-22, further comprising administering radiotherapy to the patient.

Embodiment 24. The method of any one of embodiments 16-23, wherein the cancer is a BRCA positive cancer.

Embodiment 25. The method of any one of embodiments 16-24, wherein the cancer is a solid tumor.

Embodiment 26. The method of any one of embodiments 16-25, wherein the cancer is a cancer affecting B cells.

Embodiment 27. The method of any one of embodiments 16-26, wherein the cancer is liver cancer, melanoma, Hodgkin's disease, non-Hodgkin's lymphomas, acute lymphocytic leukemia, chronic lymphocytic leukemia, multiple myeloma, neuroblastoma, breast carcinoma, ovarian carcinoma, lung carcinoma, Wilms' tumor, cervical carcinoma, testicular carcinoma, soft-tissue sarcoma, chronic lymphocytic leukemia, Waldenström macroglobulinemia, primary macroglobulinemia, bladder carcinoma, chronic granulocytic leukemia, primary brain carcinoma, malignant melanoma, small-cell lung carcinoma, stomach carcinoma, colon carcinoma, malignant pancreatic insulinoma, malignant carcinoid carcinoma, malignant melanoma, choriocarcinoma, mycosis fungoides, head neck carcinoma, osteogenic sarcoma, pancreatic carcinoma, acute granulocytic leukemia, hairy cell leukemia, rhabdomyosarcoma, Kaposi's sarcoma, genitourinary carcinoma, thyroid carcinoma, esophageal carcinoma, malignant hypercalcemia, cervical hyperplasia, renal cell carcinoma, endometrial carcinoma, polycythemia vera, essential thrombocytosis, adrenal cortex carcinoma, skin cancer, trophoblastic neoplasms, prostatic carcinoma, glioma, breast cancer, or prostate cancer.

Embodiment 28. The method of embodiment 16, wherein the cancer is a glioma, breast cancer, or prostate cancer.

EXAMPLES

The disclosure is further illustrated by the following examples. The examples below are non-limiting are merely representative of various aspects of the disclosure. Solid and dotted wedges within the structures herein disclosed illustrate relative stereochemistry, with absolute stereochemistry depicted only when specifically stated or delineated.

Where it is desired to obtain a particular enantiomer of a compound, this may be accomplished from a corresponding mixture of enantiomers using any suitable conventional procedure for separating or resolving enantiomers. Thus, for example, diastereomeric derivatives may be produced by reaction of a mixture of enantiomers, e.g., a racemate, and an appropriate chiral compound. The diastereomers may then be separated by any convenient means, for example by crystallization and the desired enantiomer recovered.

In another resolution process, a racemate may be separated using chiral High Performance Liquid Chromatography. Alternatively, if desired a particular enantiomer may be obtained by using an appropriate chiral intermediate in one of the processes described.

Compounds described herein can be prepared according to, but not limited to, the specific and generic protocols described in WO2019/222272 and WO2020/232119. Exemplary protocols for specific compounds exemplified herein are shown in the following schemes.

Scheme I illustrates a general methods which can be employed for the synthesis of compounds described herein, where each of $A^1$, $A^2$, $A^3$, $A^4$, $R^2$, $R^4$, $R^6$, L, and $R^1$ are each independently as defined herein, and LG is a leaving group (e.g., hydroxy, alkoxy, halo, etc.).

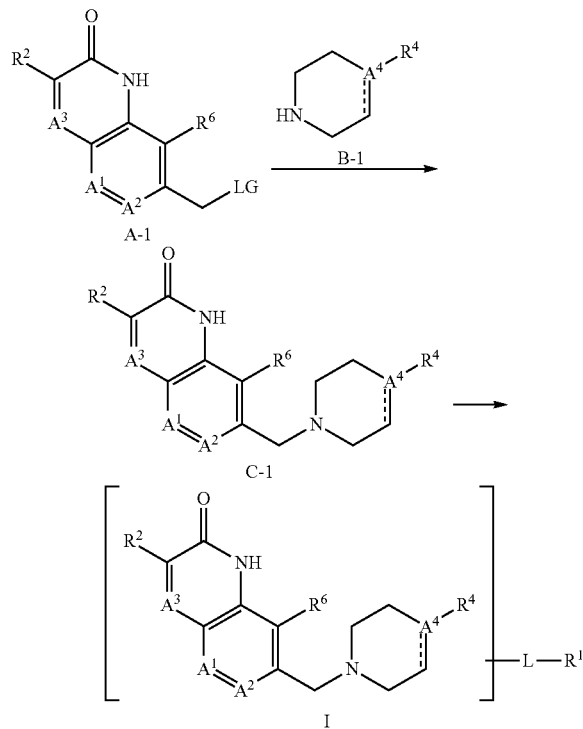

In Scheme I, compounds of formula C-1 can be prepared from suitably substituted compound of formula A-1 by coupling with a suitable suitably substituted compound of formula B-1. Coupling of compound C-1 with an appropriately substituted compound of formula C provides compound D, which can then be taken on to provide a compound of formula I by coupling with a suitable L-$R^1$ moiety, either convergently or sequentially (i.e., either an L-$R^1$ moiety or first a precursor for L followed by $R^1$). Upon each reaction completion, each of the intermediate or final compounds can be recovered, and optionally purified, by conventional techniques such as neutralization, extraction, precipitation, chromatography, filtration and the like. Exemplary methods for the preparation of compounds of formula A-1 can be found in the literature (see, e.g., WO 2021/013735).

Scheme II illustrates a general methods which can be employed for the synthesis of compounds described herein, where each of B, $B^1$, $B^2$, $B^3$, $B^4$, X, Y, and Z are each independently as defined herein, each of LG and LG' are independently a leaving group (e.g., hydroxy, alkoxy, halo, etc.) or complimentary functional group suitable for coupling to the appropriate moiety as outlined below, and Q' is a suitable synthetic precursor to the Q groups defined herein. It should be understood that derivatization of any one or more of compounds of Scheme II, or any product obtained by the process outlined in Scheme II, can be performed to provide various compounds of Formula I.

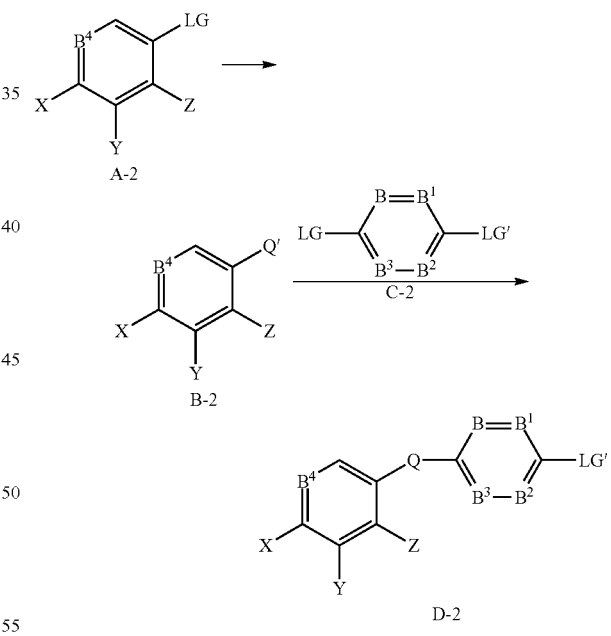

In Scheme II, compounds of formula B-2 can be prepared from suitably substituted compound A-2 by coupling with a suitable synthetic precursor to the Q groups defined herein (exemplary groups are shown below in Scheme III). For compounds comprising a Q moiety having one or more chain atoms connecting the ring portion of Q to ring b (e.g., compounds where D or D' is other than a bond, or wherein the ring portion of Q is connected to ring b via an amide bond) a portion of the LG moiety can comprise a functional group, which after coupling with compound B-2, remains in the product. Coupling of compound B-2 with an appropriately substituted compound of formula C-2 provides compound D-2, which can then be taken on to provide a compound of formula I. Upon each reaction completion, each of the intermediate or final compounds can be recovered, and optionally purified, by conventional techniques such as neutralization, extraction, precipitation, chromatography, filtration and the like.

Scheme III illustrates exemplary synthetic precursors to the Q groups defined herein, where each of A, A', $R^a$, $R^b$, R', R", R''', $R^e$, and t are each independently as defined herein, PG is a protecting group (e.g., as defined below), and M is a nucleophilic moiety (e.g., a metal or boron group) or complimentary functional group suitable for coupling to the appropriate starting material as outlined above in Scheme II. Exemplary Q groups can be found, for example, in US 2018/0099940.

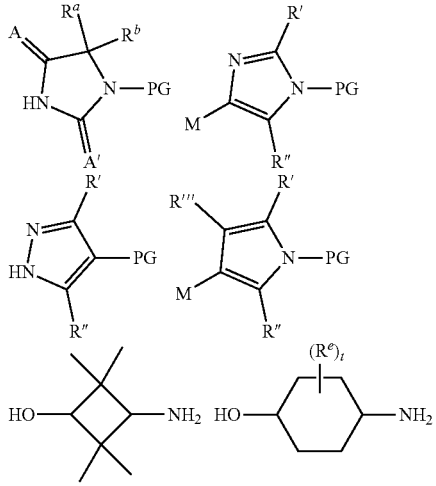

Scheme III

It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in Wuts, P. G. M., Greene, T. W., & Greene, T. W. (2006). Greene's protective groups in organic synthesis. Hoboken, N.J., Wiley-Interscience, and references cited therein. For example, protecting groups for alcohols, such as hydroxy, include silyl ethers (including trimethylsilyl (TMS), tert-butyldimethylsilyl (TBDMS), tri-iso-propylsilyloxymethyl (TOM), and triisopropylsilyl (TIPS) ethers), which can be removed by acid or fluoride ion, such as NaF, TBAF (tetra-n-butylammonium fluoride), HF-Py, or HF-NEt$_3$. Other protecting groups for alcohols include acetyl, removed by acid or base, benzoyl, removed by acid or base, benzyl, removed by hydrogenation, methoxyethoxymethyl ether, removed by acid, dimethoxytrityl, removed by acid, methoxymethyl ether, removed by acid, tetrahydropyranyl or tetrahydrofuranyl, removed by acid, and trityl, removed by acid. Examples of protecting groups for amines include carbobenzyloxy, removed by hydrogenolysis p-methoxybenzyl carbonyl, removed by hydrogenolysis, tert-butyloxycarbonyl, removed by concentrated strong acid (such as HCl or CF$_3$COOH), or by heating to greater than about 80° C., 9-fluorenylmethyloxycarbonyl, removed by base, such as piperidine, acetyl, removed by treatment with a base, benzoyl, removed by treatment with a base, benzyl, removed by hydrogenolysis, carbamate group, removed by acid and mild heating, p-methoxybenzyl, removed by hydrogenolysis, 3,4-dimethoxybenzyl, removed by hydrogenolysis, p-methoxyphenyl, removed by ammonium cerium(IV) nitrate, tosyl, removed by concentrated acid (such as HBr or H$_2$SO$_4$) and strong reducing agents (sodium in liquid ammonia or sodium naphthalenide), troc (trichloroethyl chloroformate), removed by Zn insertion in the presence of acetic acid, and sulfonamides (Nosyl & Nps), removed by samarium iodide or tributyltin hydride.

Nomenclature was derived from ChemDraw Professional v18.2 and/or Chemdraw Professional v 21. If there are any structural ambiguities based on nomenclature, the corresponding structure shown in the scheme (and context of the synthetic scheme) should be referred to.

Intermediate Procedure 1: Preparation of 7-(Chloromethyl)-3-ethyl-1,5-naphthyridin-2(1H)-one (Int-B)

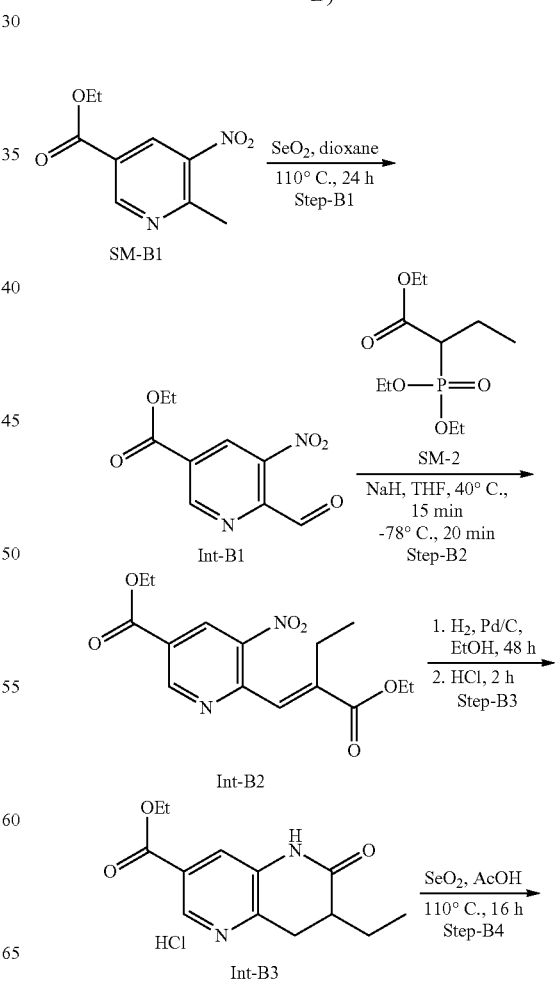

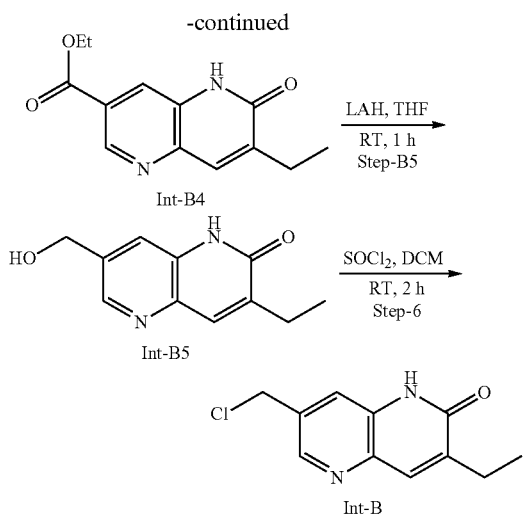

Step-B1 Preparation of Ethyl 6-formyl-5-nitronicotinate (Int-B1)

A flask was charged with ethyl 6-methyl-5-nitronicotinate (SM-B1, 50 g, 0.23 mol, 1.0 eq), SeO$_2$ (39.6 g, 0.35 mol, 1.5 eq) and Dioxane (250 mL, 5 vol). The reaction mixture was stirred under nitrogen atmosphere at 110° C. until TLC indicated complete consumption of starting material. The reaction mixture was then cooled to ambient temperature, filtered through celite and the filtrate was concentrated under reduced pressure and purified by flash column (Silica, 50-60% ethyl acetate in hexane). The pure fractions were combined and concentrated under reduced pressure to obtain ethyl 6-formyl-5-nitronicotinate (48 g, 90%).

$^1$H NMR (400 MHz, DMSO-d$_6$) δ 10.21 (s, 1H), 9.44 (d, J=1.47 Hz, 1H), 8.89 (d, J=1.47 Hz, 1H), 4.42 (q, J=7.01 Hz, 2H), 1.37 (t, J=7.01 Hz, 3H). LCMS: 225.0 [M+H]$^+$.

Step-B2: Preparation of Ethyl (E/Z)-6-(2-(Ethoxycarbonyl)but-1-en-1-yl)-5-nitronicotinate (Int-B2)

To a suspension of NaH (12.85 g, 0.32 mol, 2.0 eq, 60%) in dry THF (180 mL, 5 vol), ethyl 2-(diethoxyphosphoryl)butanoate (60 g, 0.48 mol, 1.5 eq) in dry THF (180 mL, 5 vol) solution was added dropwise at 0° C. under argon atmosphere. The reaction mixture was stirred at 40° C. for 15 min, cooled down to −78° C. and a solution of ethyl 6-formyl-5-nitronicotinate (Int-B1, 36 g, 0.32 mol, 1.0 eq) in dry THF (180 mL, 5 vol) was added dropwise at −78° C. under argon atmosphere. The reaction mixture was then allowed to stir under argon atmosphere at same temperature until TLC indicated complete consumption of starting material. The reaction mixture was quenched with saturated ammonium chloride solution (500 mL) and the aqueous layer was extracted with ethyl acetate (2×500 mL). The combined organic layer was washed with brine solution (300 mL) and dried over sodium sulfate, filtered and concentrated under reduced pressure. The crude obtained was purified on a flash column (Silica, 20-30% ethyl acetate in hexane) and the pure fractions were combined and concentrated under reduced pressure to obtain a mixture of E/Z isomers of ethyl 6-(2-(ethoxycarbonyl)but-1-en-1-yl)-5-nitronicotinate (40 g, 77%).

LCMS: 323.2 [M+H]$^+$.

Step-B3: Preparation of Ethyl 7-Ethyl-6-oxo-5,6,7,8-tetrahydro-1,5-naphthyridine-3-carboxylate Hydrochloride Salt (Int-B3)

A flask was charged with ethyl (E/Z)-6-(2-(ethoxycarbonyl)but-1-en-1-yl)-5-nitronicotinate (Int-B2, 40 g, 0.12 mmol, 1.0 eq), 10% Pd—C (12 g, 30% w/w) in EtOAc (400 mL, 10 vol). The reaction mixture was stirred under hydrogen atmosphere (100 PSI) at ambient temperature until TLC indicated complete consumption of starting material. The reaction mixture was filtered through celite, and the filtrate was concentrated under reduced pressure. The crude material was suspended in 4M HCl in Dioxane (200 mL, 5 vol) and allowed to stir for 2 h at ambient temperature. The reaction mixture was evaporated under reduced pressure, washed with diethyl ether (100 mL), filtered and dried to obtain ethyl 7-ethyl-6-oxo-5,6,7,8-tetrahydro-1,5-naphthyridine-3-carboxylate hydrochloride salt (22 g, 62%).

LCMS: 249.2 [M+H]$^+$.

Step-B4: Preparation of Ethyl 7-ethyl-6-oxo-5,6-dihydro-1,5-naphthyridine-3-carboxylate (Int-B4)

A flask was charged with ethyl 7-ethyl-6-oxo-5,6,7,8-tetrahydro-1,5-naphthyridine-3-carboxylate (Int-B3, 60 g, 0.24 mol, 1.0 eq), SeO$_2$ (39.9 g, 0.36 mol, 1.5 eq) and AcOH (600 mL, 10 vol). Reaction mixture was stirred under a nitrogen atmosphere at 110° C. until TLC indicated complete consumption of starting material. Reaction mixture was cool to ambient temperature, Reaction mixture was quenched with saturated ammonium bicarbonate solution and compound was extracted with ethyl acetate (2×1 L), combined organic layer was washed with brine solution (500 mL) and dried over sodium sulfate. Filtered organic solvent and concentrated under reduced pressure obtained ethyl 7-ethyl-6-oxo-5,6-dihydro-1,5-naphthyridine-3-carboxylate (25 g, 42%).

$^1$H NMR (400 MHz, DMSO-d$_6$) δ 12.04 (br s, 1H), 8.86 (s, 1H), 8.12 (d, J=3.91 Hz, 1H), 7.79 (s, 1H), 4.36 (q, J=7.34 Hz, 2H), 2.55 (q, J=7.17 Hz, 2H), 1.33 (t, J=7.09 Hz, 2H), 1.15 (t, J=7.09 Hz, 3H). LCMS: 247.2 [M+H]$^+$.

Step-B5: Preparation of 3-Ethyl-7-(hydroxymethyl)-1,5-naphthyridin-2(1H)-one (Int-B5)

To a flask charged with ethyl 7-ethyl-6-oxo-5,6-dihydro-1,5-naphthyridine-3-carboxylate (Int-B4, 7 g, 28.45 mmol, 1.0 eq) and dry THF (350 mL, 50 vol), LAH (28.4 mL, 56.8 mmol, 2.0 eq, 2M in THF) was added at 0° C. under nitrogen atmosphere. The reaction mixture was allowed to warm up to ambient temperature and allowed to stir under nitrogen atmosphere until TLC indicated complete consumption of starting material. The reaction mixture was quenched with saturated sodium sulfate solution, filtered and evaporated under reduced pressure to obtain 3-ethyl-7-(hydroxymethyl)-1,5-naphthyridin-2(1H)-one (4.1 g, 70%).

LCMS: 205.1 [M+H]$^+$.

Step-B6: Preparation of 7-(Chloromethyl)-3-ethyl-1,5-naphthyridin-2(1H)-one (Int-B)

A flask was charged with 3-ethyl-7-(hydroxymethyl)-1,5-naphthyridin-2(1H)-one (Int-B5, 4 g, 19.60 mmol, 1.0 eq), SOCl$_2$ (14 g, 117 mmol, 6.0 eq), DMF (0.4 mL, 0.1 vol, catalytic amount) and DCM (120 mL, 30 vol). The reaction mixture was stirred under nitrogen atmosphere at ambient temperature until TLC indicated complete consumption of starting material, diluted with water (100 mL) and extracted with DCM (2×200 mL). The combined organic layer was washed with saturated bicarbonate solution (100 mL), brine solution (100 mL) and dried over sodium sulfate. The organic Layer was filtered and concentrated under reduced pressure to obtain 7-(chloromethyl)-3-ethyl-1,5-naphthyridin-2(1H)-one (Int-8, 2 g, 46%).

$^1$H NMR (400 MHz, DMSO-d$_6$) δ 12.23 (br s, 1H), 8.56 (s, 1H), 7.90 (s, 1H), 7.82 (s, 1H), 4.94 (s, 2H), 2.55 (d, J=7.34 Hz, 2H), 1.17 (t, J=7.34 Hz, 3H). LCMS: 223.0 [M+H]$^+$.

Procedure 1: Preparation of N-((1r,4r)-4-(3-Chloro-4-cyanophenoxy)cyclohexyl)-6-(4-((4-((7-ethyl-6-oxo-5,6-dihydro-1,5-naphthyridin-3-yl)methyl)piperazin-1-yl)methyl)piperidin-1-yl)pyridazine-3-carboxamide (4)

mmol, 1.0 eq) in DCM (20 mL) was added Dess-Martin periodinane (2.2 g, 5.33 mmol, and 2.5 eq) at 0° C. slowly and the mixture was stirred at RT for 2 h. The reaction was monitored by TLC. After completion, the mixture was diluted with DCM (100 mL) and washed with saturated NaHCO$_3$ solution (100 mL×2), water (100 mL), dried over anhydrous sodium sulfate, filtered and concentrated under reduced pressure to afford the crude residue which was purified by CombiFlash Chromatography to afford title compound (0.5 g, 52%).

LCMS: 468 [M+H]$^+$.

Step-2: Preparation of N-((1r,4r)-4-(3-Chloro-4-cyanophenoxy)cyclohexyl)-6-(4-((4-((7-ethyl-6-oxo-5,6-dihydro-1,5-naphthyridin-3-yl)methyl)piperazin-1-yl)methyl)piperidin-1-yl)pyridazine-3-carboxamide (4)

To a solution of N-((1r,4r)-4-(3-chloro-4-cyanophenoxy)cyclohexyl)-6-(4-formylpiperidin-1-yl)pyridazine-3-carboxamide (0.3 g, 0.63 mmol, 1.0 eq) and 3-ethyl-7-(piperazin-1-ylmethyl)-1,5-naphthyridin-2(1H)-one

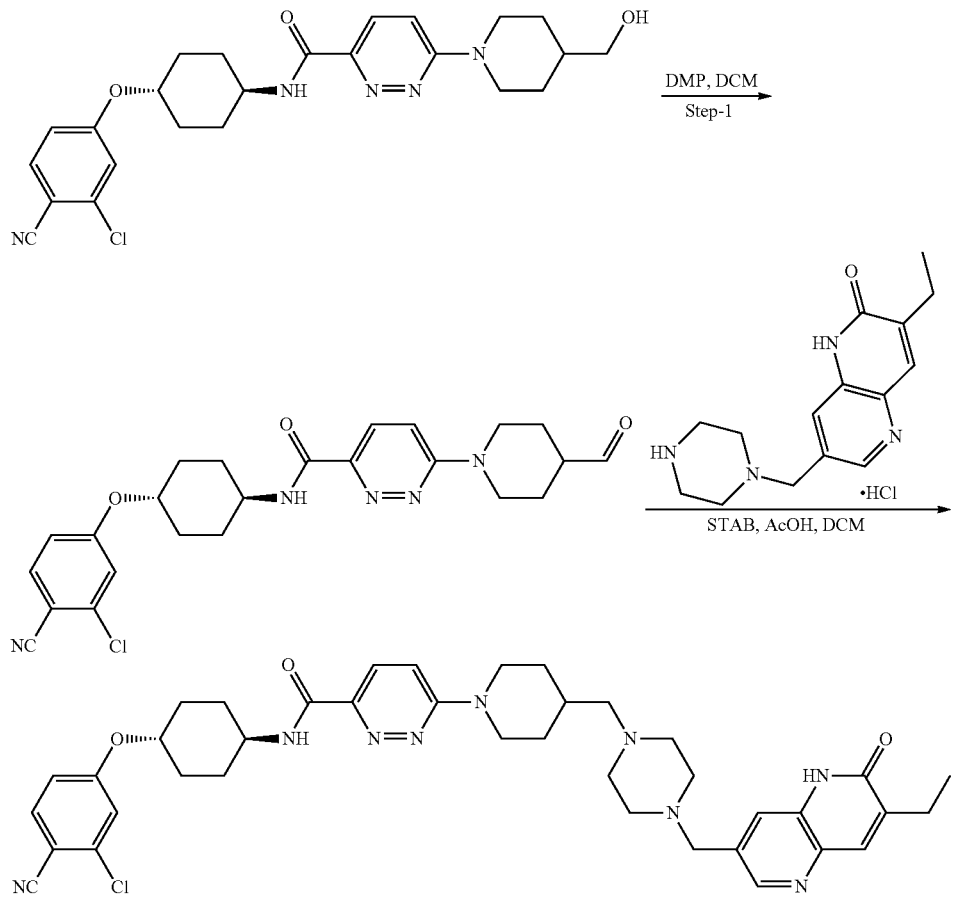

Step-1: Preparation of N-((1r,4r)-4-(3-Chloro-4-cyanophenoxy)cyclohexyl)-6-(4-formylpiperidin-1-yl)pyridazine-3-carboxamide To a stirred solution of N-((1r,4r)-4-(3-chloro-4-cyanophenoxy)cyclohexyl)-6-(4-(hydroxymethyl) piperidin-1-yl) pyridazine-3-carboxamide (CAS #2222114-20-5) (1 g, 2.13 hydrochloride (0.26 g, 0.95 mmol, 1.0 eq) in DCM (10 mL) was added catalytic amount of acetic acid (0.1 mL) and the mixture was stirred at RT for 16 h. Sodium triacetoxyborohydride (0.27 g, 1.27 mmol, 2.0 eq) was then added to the mixture slowly at RT and the resultant mixture was stirred at RT for 1 h. The reaction was monitored by TLC. After completion, the mixture was concentrated under reduced pressure and the residue obtained was diluted with H$_2$O (50 mL) and extracted with EtOAc (200 mL×2). The combined organic layer was washed with water (100 mL×2), brine (100 mL), dried over anhydrous sodium sulfate, filtered and concentrated under reduced pressure to obtain a crude residue which was purified by CombiFlash Chromatography and then re-purified by Reverse Phase HPLC to afford the title compound (32 mg, 7%).

$^1$H NMR (400 MHz, DMSO-d$_6$) δ 11.9 (s, 1H), 8.58 (d, J=7.89 Hz, 1H), 8.36 (s, 1H), 7.85 (d, J=8.77 Hz, 1H), 7.79 (d, J=10.09 Hz, 1H), 7.74 (s, 1H), 7.58 (s, 1H), 7.39 (s, 1H), 7.30 (s, 1H), 7.33 (s, 1H), 4.53 (m, 1H), 4.46 (d, J=12.72 Hz, 2H), 3.86 (m, 1H), 3.56 (s, 2H), 2.99 (t, J=12.06 Hz, 3H), 2.67 (m, 2H), 2.39 (m, 6H), 2.33 (m, 2H), 2.14 (d, J=7.02 Hz, 4H), 1.87 (m, 3H), 1.81-1.77 (m, 3H), 1.70-1.56 (m, 2H), 1.53-1.50 (m, 3H), 1.24 (m, 1H), 1.18 (t, J=7.45 Hz, 1H), 1.1-1.07 (m, 1H). LCMS: 724.8 [M+H]$^+$.

Procedure 2: Preparation of N-((1r,4r)-4-(3-Chloro-4-cyanophenoxy)cyclohexyl)-6-(4-((4-(5-(4-((7-ethyl-6-oxo-5,6-dihydro-1,5-naphthyridin-3-yl)methyl)piperazin-1-yl)picolinoyl)piperazin-1-yl)methyl)piperidin-1-yl)pyridazine-3-carboxamide (59)

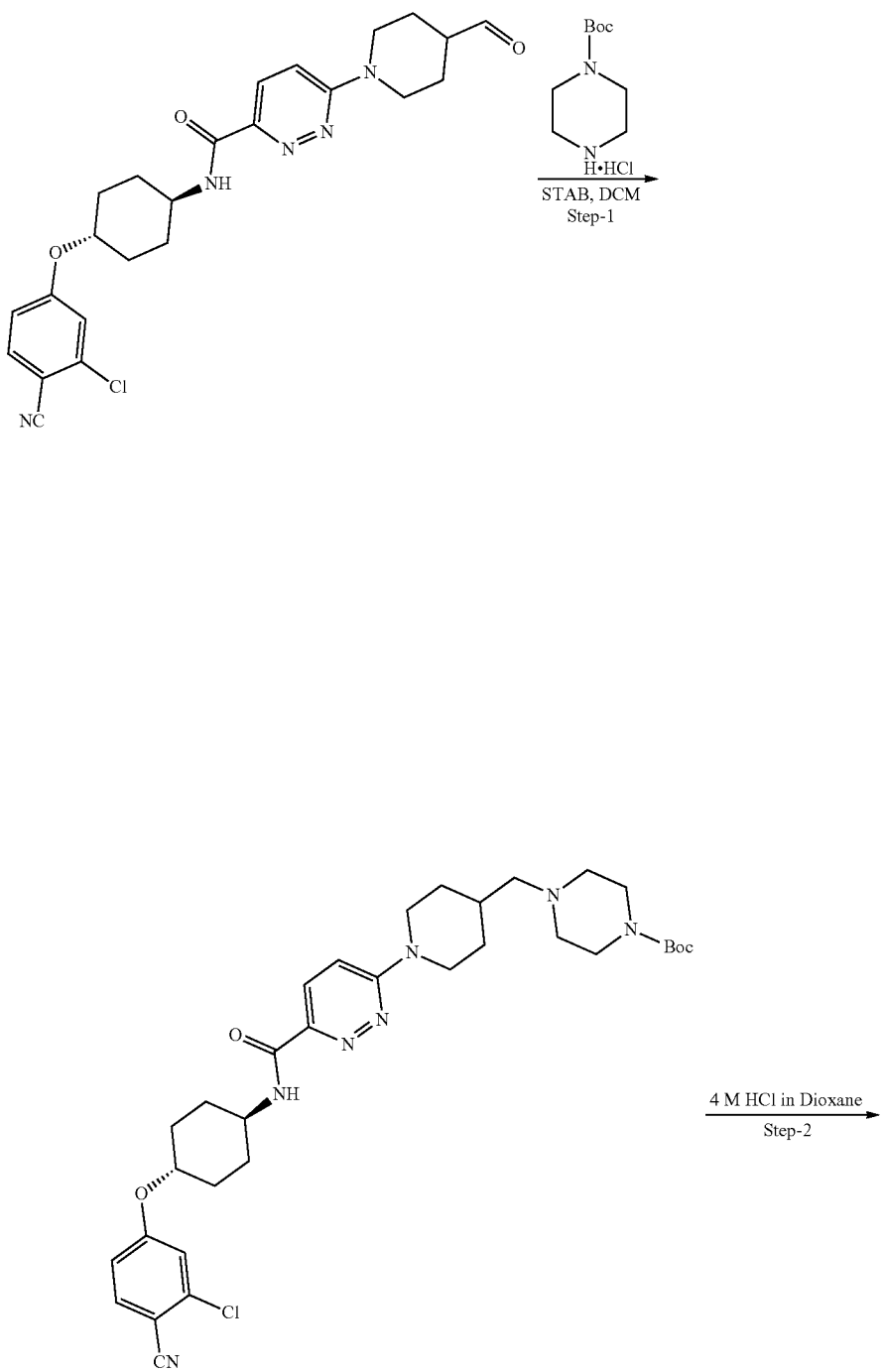

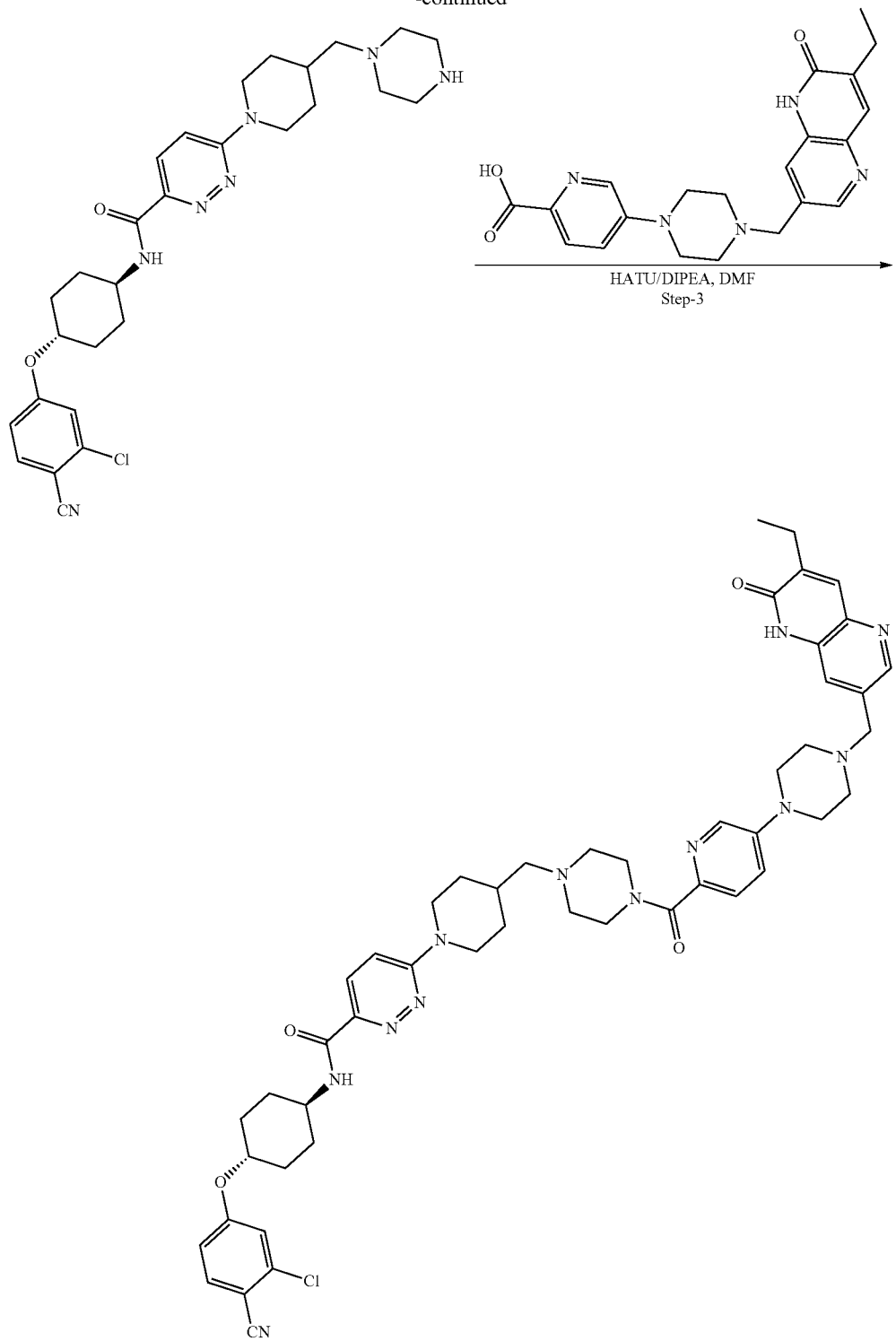

Step-1: Preparation of tert-Butyl 4-((1-(6-((1r,4r)-4-(3-Chloro-4-cyanophenoxy)cyclohexyl carbamoyl)pyridazin-3-yl)piperidin-4-yl)methyl)piperazine-1-carboxylate To a stirred solution of N-((1r,4r)-4-(3-chloro-4-cyanophenoxy)cyclohexyl)-6-(4-formylpiperidin-1-yl)pyridazine-3-carboxamide (0.9 g, 1.92 mmol, 1.0 eq) and tert-butyl piperazine-1-carboxylate hydrochloride (0.51 g, 2.31 mmol, 1.2 eq) in THF:Methanol (2:1; 20 mL) was added catalytic amount of acetic acid (0.1 mL) and the mixture was stirred at RT for 16 h. Sodium cyanoborohydride (0.26 g, 3.85 mmol, 2.0 eq) was then added to the mixture slowly at RT and the resultant mixture was stirred at RT for 1 h. The reaction was monitored by TLC. After completion, the mixture was concentrated under reduced pressure and the residue obtained was diluted with H₂O (50 mL) and extracted with EtOAc (200 mL×2). The combined organic layer was washed with water (100 mL×2), brine (100 mL), dried over anhydrous sodium sulfate, filtered and concentrated under reduced pressure to afford crude which was purified by CombiFlash Chromatography to afford title compound (0.32 g, 26%).

LCMS: 638 [M+H]⁺.

Step-2: Preparation of N-((1r,4r)-4-(3-Chloro-4-cyanophenoxy)cyclohexyl)-6-(4-(piperazin-1-ylmethyl)piperidin-1-yl)pyridazine-3-carboxamide To a stirred solution of tert-butyl 4-((1-(6-(((1r,4r)-4-(3-chloro-4-cyanophenoxy) cyclohexyl carbamoyl)pyridazin-3-yl)piperidin-4-yl)methyl)piperazine-1-carboxylate (1.4 g, 2.56 mmol, 1 eq) in 1,4-dioxane (5 mL) was added 4N HCl in 1,4-dioxane (8 mL) at 0° C. and the mixture was stirred at RT for 1 h. The reaction was monitored by TLC. Upon completion, the mixture was diluted with water (150 mL) and basified using with saturated NaHCO₃ solution (pH~8). The aqueous layer was then extracted with EtOAc (200 mL×3) and resulting organic layer was washed with saturated NaHCO₃ solution (100 mL), water (100 mL), brine (100 mL), dried over anhydrous sodium sulfate, filtered and concentrated under reduced pressure to obtain the crude product which was purified by CombiFlash Chromatography to afford the title compound (1.1 g, 93%).

LCMS: 538.4 [M+H]⁺.

Step-3: Preparation of N-((1r,4r)-4-(3-Chloro-4-cyanophenoxy)cyclohexyl)-6-(4-((4-(5-(4-((7-ethyl-6-oxo-5,6-dihydro-1,5-naphthyridin-3-yl)methyl)piperazin-1-yl)picolinoyl)piperazin-1-yl)methyl)piperidin-1-yl)pyridazine-3-carboxamide (59)

To a stirred solution of 5-(4-(7-ethyl-6-oxo-5,6-dihydro-1,5-naphthyridin-3-yl)methyl)piperazin-1-yl)picolinic acid (0.2 g, 0.50 mmol, 1.0 eq) in DMF (8 mL) was added HATU (0.39 g, 1.0 mmol, 2.0 eq) at 0° C. and the resulting mixture was stirred at same temperature for 10 min. DIPEA (0.4 mL, 2.54 mmol, 5.0 eq) and N-((1r,4r)-4-(3-chloro-4-cyanophenoxy) cyclohexyl)-6-(4-(piperazin-1-ylmethyl)piperidin-1-yl)pyridazine-3-carboxamide (0.22 g, 0.40 mmol, 0.8 eq) were then successively added to the mixture and the mixture was stirred at RT for 1 h. The reaction was monitored by TLC & LCMS. After completion, water (10 mL) was added, and the resulting precipitate was filtered over Büchner funnel. The solid obtained was washed with water (5 mL×2) and n-pentane (5 mL×2), dried under vacuum to obtain the crude product which was purified by CombiFlash Chromatography to afford the title compound (0.1 g, 29%).

¹H NMR (400 MHz, DMSO-d₆) δ 11.85 (s, 1H), 8.57 (d, J=8.33 Hz, 1H), 8.40 (s, 1H), 8.25 (m, 1H), 7.85 (d, J=8.77 Hz, 1H), 7.79 (d, J=9.65 Hz, 1H), 7.75 (s, 1H), 7.62 (s, 1H), 7.48 (d, J=8.77 Hz, 1H), 7.40-7.34 (m, 3H), 7.13 (dd, J=8.77, 2.19 Hz, 1H), 4.53 (m, 3H), 4.47 (d, J=12.28 Hz, 2H), 3.86 (m, 2H), 3.61 (s, 3H), 3.65 (s, 3H), 3.00 (t, J=12.06 Hz, 2H), 2.67 (m, 1H), 2.55 (m, 4H), 2.40 (m, 3H), 2.33 (m, 3H), 2.17 (d, J=7.45 Hz, 2H), 1.89-1.73 (m, 5H), 1.66-1.57 (m, 2H), 1.51 (d, J=11.84 Hz, 2H), 1.18 (t, J=7.45 Hz, 4H), 1.10 (d, J=11.84 Hz, 3H). LCMS: 913.8 [M+H]⁺.

Procedure 3: Preparation of N-((1r,4r)-4-(3-Chloro-4-cyanophenoxy)cyclohexyl)-6-(4-(4-(5-(4-((7-ethyl-6-oxo-5,6-dihydro-1,5-naphthyridin-3-yl)methyl)piperazin-1-yl)picolinoyl)piperazine-1-carbonyl)piperidin-1-yl)pyridazine-3-carboxamide (60)

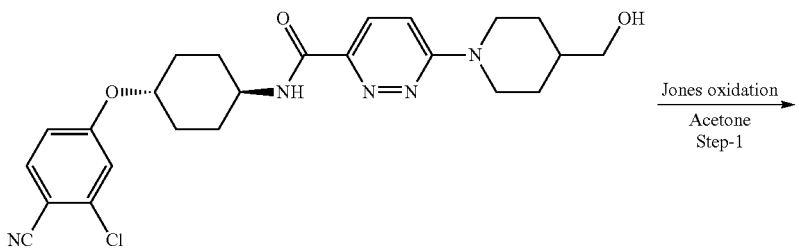

Jones oxidation
Acetone
Step-1

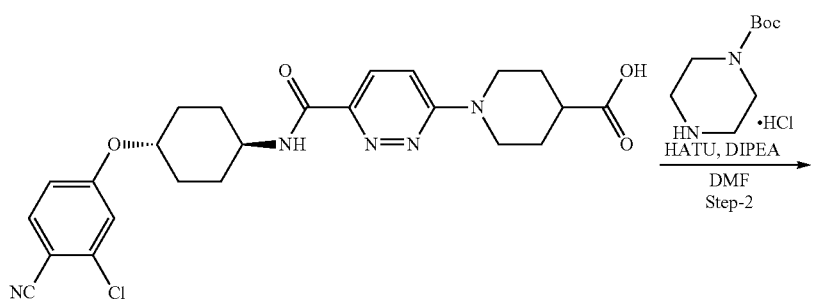

HATU, DIPEA
DMF
Step-2

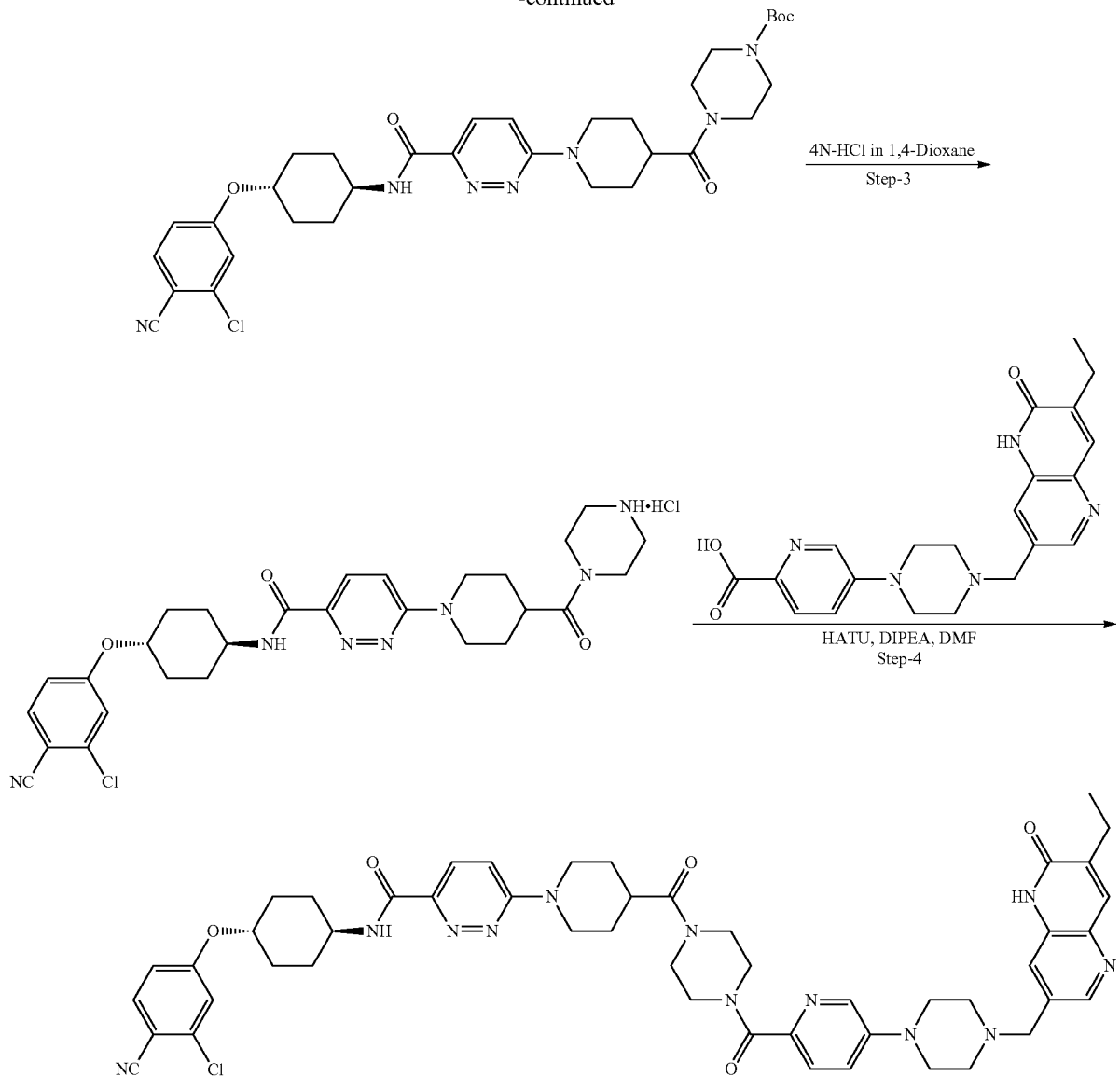

Step-1: Preparation of 1-(6-((1r,4r)-4-(3-Chloro-4-cyanophenoxy)cyclohexylcarbamoyl)pyridazin-3-yl)piperidine-4-carboxylic Acid Step-2: Preparation of tert-Butyl 4-(1-(6-((1r,4r)-4-(3-Chloro-4-cyanophenoxy)cyclohexylcarbamoyl)-pyridazin-3-yl)piperidine-4-carbonyl)piperazine-1-carboxylate To a stirred solution of N-((1r,4r)-4-(3-chloro-4-cyanophenoxy)cyclohexyl)-6-(4-(hydroxymethyl) piperidin-1-yl)pyridazine-3-carboxamide (CAS #2222114-20-5) (1.0 g, 2.13 mmol, 1 eq) in acetone (30 mL) was added Jones reagent (2 mL) at 0° C. dropwise over a period of 20 min. The resultant mixture was stirred at 0° C. for 10 min. The reaction was monitored by TLC. After completion, water (100 mL) was added, and the resulting precipitate was filtered over Büchner funnel. The solid obtained was washed with water (30 mL×2) and n-pentane (50 mL×2), dried under vacuum to afford the title compound (0.7 g, 70%).

LCMS: 484 [M+H]$^+$.

To a stirred solution of 1-(6-((1r,4r)-4-(3-chloro-4-cyanophenoxy)cyclohexylcarbamoyl)pyridazin-3-yl)piperidine-4-carboxylic acid (0.70 g, 1.44 mmol, 1.0 eq) in DMF (10 mL) were added HATU (0.83 g, 2.17 mmol, 1.5 eq) and DIPEA (1.0 mL, 5.77 mmol, 1.0 eq) successively at 0° C. and the resultant mixture was stirred at same temperature for 10 min. tert-Butyl piperazine-1-carboxylate hydrochloride (0.48 g, 2.17 mmol, 1.5 eq) was then added and the mixture was stirred at RT for 10 min. The reaction was monitored by TLC & LCMS. After completion, water (70 mL) was added, and the resulting precipitate was filtered over Buchner funnel. The solid obtained was washed with water (20 mL×2) and n-pentane (20 mL×2), dried under vacuum to obtain a crude product which was purified by Combiflash Chromatography to afford the title compound (0.020 g, 21%).

LCMS: 652 [M+H]$^+$.

Step-3: Preparation of N-((1r,4r)-4-(3-Chloro-4-cyanophenoxy)cyclohexyl)-6-(4-(piperazine-1-carbonyl)-piperidin-1-yl)pyridazine-3-carboxamide Hydrochloride To a stirred solution of tert-butyl 4-(1-(6-(((1r,4r)-4-(3-chloro-4-cyanophenoxy)cyclohexylcarbamoyl)-pyridazin-3-yl)piperidine-4-carbonyl)piperazine-1-carboxylate (0.2 g, 0.31 mmol, 1 eq) in 1,4-dioxane (4 mL) was added 4N HCl in 1,4-dioxane (2 mL) at RT and the mixture was stirred at RT for 1 h. The reaction was monitored by TLC. Upon completion, the mixture was concentrated under reduced pressure and the residue obtained was washed with diethyl ether (20 mL) and n-pentane (20 mL) to afford the title compound (0.15 g, 83%).

LCMS: 552 [M+H]$^+$.

Step-4: Preparation of N-((1r,4r)-4-(3-Chloro-4-cyanophenoxy)cyclohexyl)-6-(4-(4-(5-(4-((7-ethyl-6-oxo-5,6-dihydro-1,5-naphthyridin-3-yl)methyl) piperazin-1-yl)picolinoyl)piperazine-1-carbonyl) piperidin-1-yl)pyridazine-3-carboxamide (60)

To a stirred solution of 5-(44(7-ethyl-6-oxo-5,6-dihydro-1,5-naphthyridin-3-yl)methyl)piperazin-1-yl)picolinic acid (0.1 g, 0.25 mmol, 1.0 eq) in DMF (4 mL) were added HATU (0.2 g, 0.2 mmol, 2.0 eq) and DIPEA (0.23 mL g, 1.27 mmol, 5 eq) successively at 0° C. and the mixture was stirred at same temperature for 10 min. N-((1r,4r)-4-(3-Chloro-4-cyanophenoxy)cyclohexyl)-6-(4-(piperazine-1-carbonyl)piperidin-1-yl)pyridazine-3-carboxamide hydrochloride (0.18 g, 0.30 mmol, 1.2 eq) was then added and the mixture was stirred at RT for 10 min. The reaction was monitored by TLC & LCMS. After completion, water (20 mL) was added, and the resulting precipitate was filtered over Büchner funnel. The solid obtained was washed with water (10 mL×2) and n-pentane (10 mL×2), dried under vacuum to obtain a crude product which was purified by Combiflash Chromatography to afford the title compound (0.025 g, 10.6%).

$^1$H NMR (400 MHz, DMSO-d$_6$) δ 11.86 (s, 1H), 8.60 (d, J=8.33 Hz, 1H), 8.41 (s, 1H) 8.27 (br s, 1H) 7.85-7.82 (d, J=8.77 Hz, 2H), 7.75 (s, 1H), 7.62 (s, 1H) 7.55 (d, J=7.89 Hz, 1H), 7.45-7.26 (m, 3H), 7.14 (dd, J=8.77, 2.19 Hz, 1H), 4.58-4.43 (m, 2H), 3.85 (m, 1H), 3.65 (m, 6H), 3.49 (m, 4H), 3.09 (m, 2H), 2.97 (m, 2H), 2.67 (m, 2H), 2.54 (d, J=7.45 Hz, 4H), 2.33 (m, 2H), 2.10 (d, J=11.84 Hz, 2H), 1.88 (m, 2H), 1.73 (m, 2H), 1.68-1.46 (m, 6H), 1.27-1.22 (m, 2H) 1.22-1.13 (m, 3H). LCMS: 927 [M+H]$^+$.

Procedure 4: Preparation of N-((1r,4r)-4-(3-Chloro-4-cyanophenoxy)cyclohexyl)-6-(4-((5-(4-((7-ethyl-6-oxo-5,6-dihydro-1,5-naphthyridin-3-yl)methyl) piperazin-1-yl)picolinamido)methyl)piperidin-1-yl) pyridazine-3-carboxamide (1)

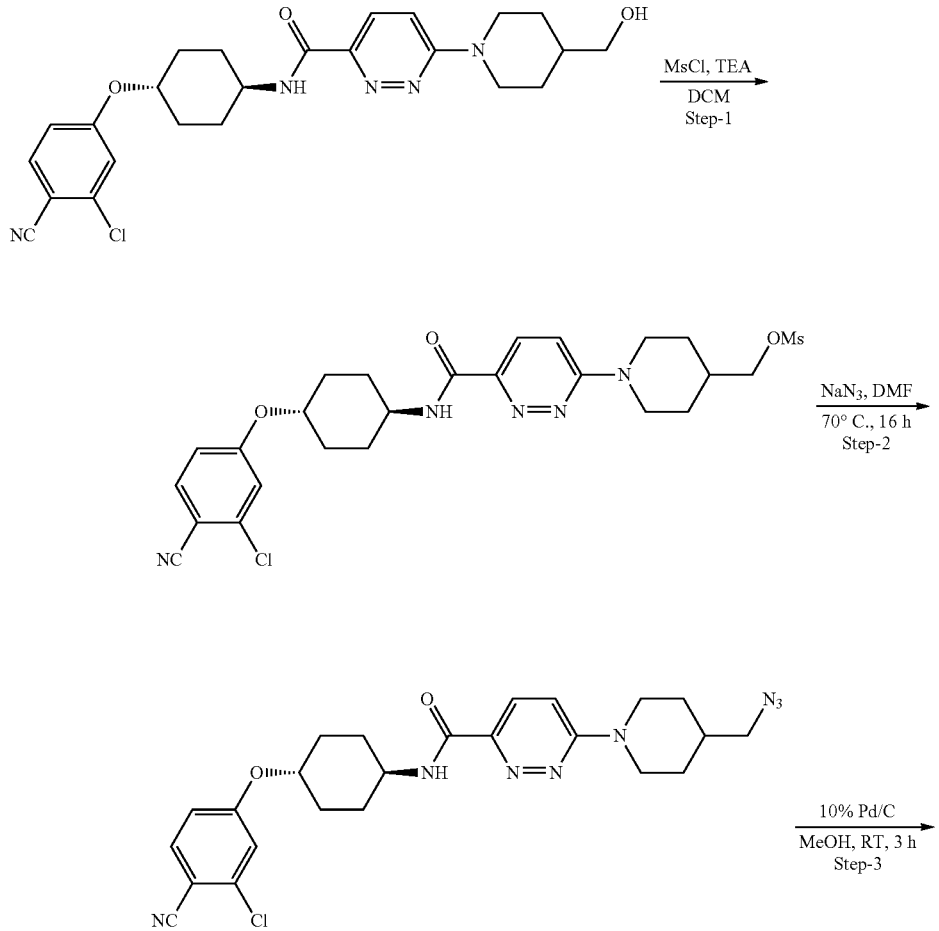

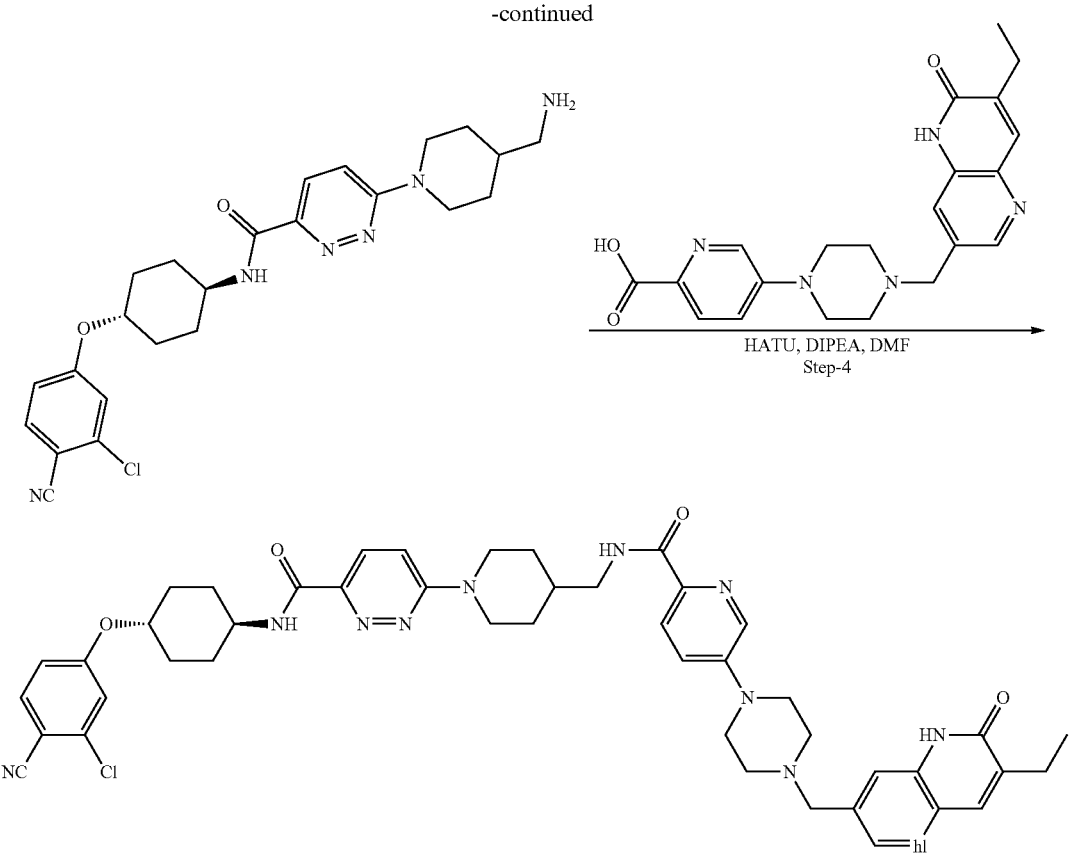

Step-1: Preparation of (1-(6-(((1r,4r)-4-(3-Chloro-4-cyanophenoxy)cyclohexyl)carbamoyl)pyridazin-3-yl)piperidin-4-yl)methyl Methanesulfonate To a stirred solution of N-((1 r,4r)-4-(3-chloro-4-cyanophenoxy)cyclohexyl)-6-(4-(hydroxymethyl)-piperidin-1-yl)pyridazine-3-carboxamide (1 g, 2.13 mmol, 1 eq) in DCM (30 mL) were added triethylamine (0.9 mL, 6.4 mmol, 3.0 eq) and methanesulfonyl chloride (0.19 mL, 2.55 mmol, 1.2 eq) at 0° C. and the mixture was stirred at RT for 2 h. Upon completion, the mixture was diluted with water (200 mL) and extracted with EtOAc (200 mL×3). The combined organic layer was washed with saturated NaHCO$_3$ (200 mL) solution, water (100 mL), brine (100 mL), dried over anhydrous sodium sulfate, filtered and concentrated under reduced pressure to obtain a title compound (1 g, 86%).
LCMS: 548 [M+H]$^+$.

Step-2: Preparation of 6-(4-(Azidomethyl)piperidin-1-yl)-N-((1r,4r)-4-(3-chloro-4-cyanophenoxy)cyclohexyl)-pyridazine-3-carboxamide To a stirred solution of (1-(6-(((1r,4r)-4-(3-chloro-4-cyanophenoxy)cyclohexyl)carbamoyl)pyridazin-3-yl)piperidin-4-yl)methyl methanesulfonate (1 g, 1.82 mmol, 1 eq) in DMF (10 mL) was added sodium azide (0.13 g, 2.01 mmol, 1.1 eq) and the mixture was heated at 70° C. for 16 h. The reaction was monitored by TLC. After completion, ice cold water (50 mL) was added, and the resulting precipitate was filtered over Buchner funnel. The solid obtained was washed with n-pentane (50 mL×2), dried under vacuum to obtain a title compound (0.59 g, 65%).
LCMS: 495 [M+H]$^+$.

Step-3: Preparation of 6-(4-(Aminomethyl)piperidin-1-yl)-N-((1r,4r)-4-(3-chloro-4-cyanophenoxy)-cyclohexyl)pyridazine-3-carboxamide To a solution of 6-(4-(azidomethyl)piperidin-1-yl)-N-((1r,4r)-4-(3-chloro-4-cyanophenoxy)-cyclohexyl)pyridazine-3-carboxamide (0.500 g, 1.01 mmol, 1.0 eq) in MeOH (20 mL) was added Pd/C (80 mg) and the mixture was hydrogenated using a H$_2$ bladder at RT for 3 h. The progress of the reaction was monitored by TLC. After completion, the mixture was filtered through a pad of celite over Büchner funnel, washed with MeOH and concentrated under reduced pressure to afford the title compound (0.40 g, 85%), which was taken to next step without further purification.
LCMS: 469 [M+H]$^+$.

Step-4: Preparation of N-((1r,4r)-4-(3-Chloro-4-cyanophenoxy)cyclohexyl)-6-(4-((5-(4-((7-ethyl-6-oxo-5,6-dihydro-1,5-naphthyridin-3-yl)methyl)piperazin-1-yl)picolinamido)methyl)piperidin-1-yl)pyridazine-3-carboxamide (1)

To a stirred solution of 5-(44(7-ethyl-6-oxo-5,6-dihydro-1,5-naphthyridin-3-yl)methyl)piperazin-1-yl)picolinic acid (0.2 g, 0.50 mmol, 1.0 eq) in DMF (8 mL) was added HATU (0.29 g, 0.75 mmol, 1.5 eq) at 0° C. and the resulting mixture was stirred at same temperature for 10 min. DIPEA (0.26 mL, 1.5 mmol, 3.0 eq) and 6-(4-(aminomethyl)piperidin-1-yl)-N-((1r,4 r)-4-(3-chloro-4-cyanophenoxy)cyclohexyl)pyridazine-3-carboxamide (0.234 g, 0.50 mmol, 1 eq) were then successively added and the mixture was stirred at RT for 2 h. The reaction was monitored by TLC & LCMS. After completion, water (20 mL) was added, and the resulting precipitate was filtered over Büchner funnel. The solid obtained was washed with water (10 mL×2) and n-pentane (10 mL×2), dried under vacuum to obtain a crude product which was purified by CombiFlash Chromatography and then re-purified by Reverse Phase HPLC to afford the title compound (0.045 g, 10%).

$^1$H NMR (400 MHz, DMSO-d$_6$) δ 11.85 (br s, 1H), 8.58 (d, J=7.9 Hz, 1H), 8.50 (t, J=6.1 Hz, 1H), 8.41 (d, J=1.3 Hz, 1H), 8.28 (d, J=2.6 Hz, 1H), 7.91-7.69 (m, 3H), 7.63 (s, 1H), 7.42-7.36 (m, 2H), 7.33 (d, J=9.6 Hz, 1H), 7.13 (dd, J=2.2, 8.8 Hz, 1H), 4.53-4.46 (m, 3H), 3.84 (s, 1H), 3.65 (s, 2H), 3.31 (s, 4H), 3.20 (t, J=6.6 Hz, 2H), 2.99 (t, J=12.1 Hz, 2H), 2.54 (d, J=7.9 Hz, 6H), 2.10 (s, 2H), 2.01-1.82 (m, 3H), 1.77-1.58 (m, 3H), 1.56-1.46 (m, 3H), 1.18 (t, J=7.5 Hz, 6H). LCMS: 844 [M+H]$^+$.

Procedure 5: Preparation of 7-((4-(6-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)hexanoyl)piperazin-1-yl)methyl)-3-ethyl-1,5-naphthyridin-2(1H)-one (61)

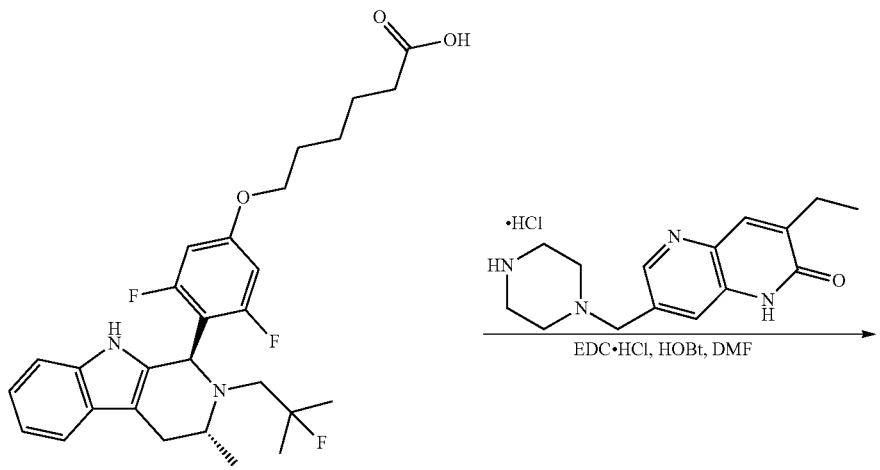

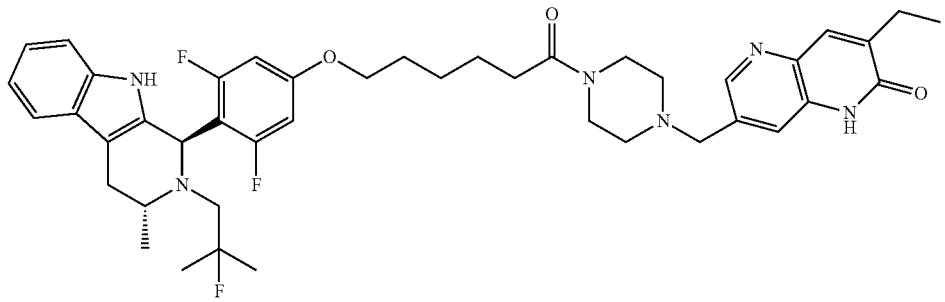

To a stirred solution of 6-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)hexanoic acid (0.130 g, 0.25 mmol, 1 eq) in DMF (5 mL) were added EDC·HCl (0.047 g, 0.31 mmol, 1.2 eq) and HOBT (0.041 g, 0.31 mmol, 1.2 eq) at 0° C. and the resulting mixture was stirred at same temperature for 20 min. DIPEA (0.2 mL, 1.03 mmol, 4.0 eq) and 3-ethyl-7-(piperazin-1-ylmethyl)-1,5-naphthyridin-2(1H)-one hydrochloride (0.095 g, 0.31 mmol, 1.2 eq) were then successively added and the mixture was stirred at RT for 16 h. The reaction was monitored by TLC & LCMS. After completion, water (10 mL) was added, and the resulting precipitate was filtered over Büchner funnel. The solid obtained was washed with water (5 mL×2) and n-pentane (5 mL×2), dried under vacuum to obtain a crude product which was purified by Reverse Phase HPLC to afford the title compound (0.040 g, 21%).

$^1$H NMR (400 MHz, DMSO-d6) δ 11.86 (br s, 1H), 10.51 (s, 1H), 8.41-8.31 (m, 1H), 7.74 (s, 1H), 7.59 (s, 1H), 7.38 (d, J=7.5 Hz, 1H), 7.17 (d, J=7.9 Hz, 1H), 7.03-6.87 (m, 2H), 6.62 (s, 1H), 6.65 (s, 1H), 5.11 (s, 1H), 3.96 (t, J=6.4 Hz, 2H), 3.59 (s, 2H), 3.50 (d, J=6.1 Hz, 1H), 3.47-3.38 (m, 4H), 2.95-2.79 (m, 2H), 2.61-2.53 (m, 2H), 2.41-2.24 (m, 7H), 1.75 (s, 1H), 1.73-1.64 (m, 2H), 1.59-1.47 (m, 2H), 1.46-1.33 (m, 2H), 1.25-1.13 (m, 6H), 1.10 (s, 2H), 1.03 (d, J=6.6 Hz, 3H). LCMS: 757 [M+H]$^+$.

Procedure 6: Preparation of N-((1r, 4r)-4-(3-chloro-4-cyanophenoxy)cyclohexyl)-6-(4-(4-((7-ethyl-6-oxo-5,6-dihydro-1,5-naphthyridin-3-yl)methyl)piperazin-1-yl)piperidin-1-yl)pyridazine-3-carboxamide (62)

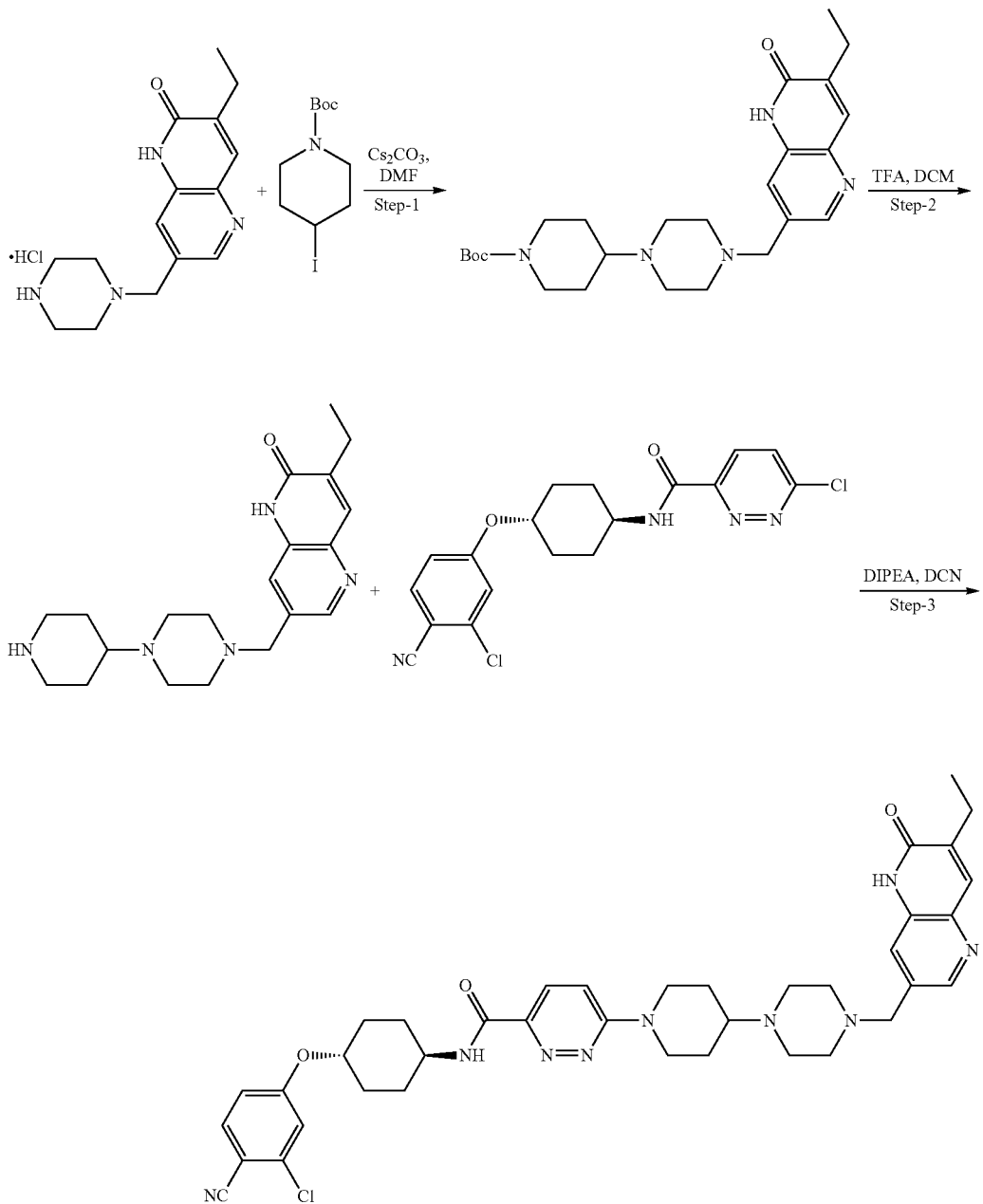

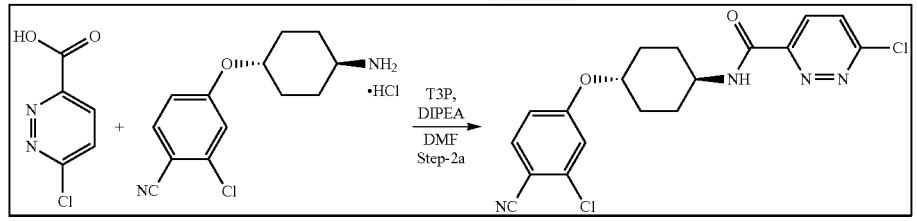

Step-1: Preparation of tert-Butyl 4-(4-(7-Ethyl-6-oxo-5,6-dihydro-1,5-naphthyridin-3-yl)methyl)piperazin-1-yl)piperidine-1-carboxylate To a stirred solution of 3-ethyl-7-(piperazin-1-ylmethyl)-1,5-naphthyridin-2(1H)-one hydrochloride (1.0 g, 3.67 mmol, 1 eq) in DMF (10 mL) was added $Cs_2CO_3$ (3.58 g, 11.02 mmol, 3 eq) and the mixture was stirred for 30 min at RT. TBAI (0.135 g, 0.36 mmol, 0.1 eq) and tert-butyl 4-iodopiperidine-1-carboxylate (3.43 g, 11.02 mmol, 3 eq) was added and the mixture was stirred at 70° C. for 16 h. Progress of the reaction was monitored by TLC and LCMS. Upon completion, the mixture was diluted with water (60 mL) and extracted with ethyl acetate (30 mL×3). The combined organic layer was washed with water (50 mL), dried over anhydrous sodium sulphate, filtered and concentrated under reduced pressure to afford a crude residue which was purified by CombiFlash Chromatography to obtain the title compound (0.100 g, 5.9%).

LCMS: 456 $[M+H]^+$.

Step-2: Preparation of 3-Ethyl-7-((4-(piperidin-4-yl)piperazin-1-yl)methyl)-1,5-naphthyridin-2(1H)-one To a stirred solution of tert-butyl 4-(4-(7-ethyl-6-oxo-5,6-dihydro-1,5-naphthyridin-3-yl)methylipiperazin-1-yl)piperidine-1-carboxylate (0.100 g, 0.44 mmol, 1 eq) in DCM (10 mL) was added TFA (0.5 mL) at 0° C. dropwise and the mixture was stirred at RT for 2 h. The reaction was monitored by TLC & LCMS. Upon completion, the mixture was concentrated under reduced pressure to afford the crude product which was triturated with diethyl ether (50 mL) to afford the desired compound (0.070 g, 89%).

LCMS: 356 $[M+H]^+$.

Step-2a: Preparation of 6-Chloro-N-((1r,4r)-4-(3-chloro-4-cyanophenoxy)cyclohexyl)pyridazine-3-carboxamide To a stirred solution of 6-chloropyridazine-3-carboxylic acid (0.400 g, 2.54 mmol, 1 eq) in DMF (8 mL) was added T3P (3.24 g, 10.18 mmol, 4 eq) at 0° C. and the resulting mixture was stirred at 0° C. for 10 min. DIPEA (4.4 mL, 25.4 mmol, 10 eq) and 4-(((1r,4r)-4-aminocyclohexyl)oxy)-2-chlorobenzonitrile hydrochloride (0.636 g, 2.54 mmol, 1 eq) were then successively added and the mixture was stirred at RT for 1 h. The reaction was monitored by TLC & LCMS. After completion, the mixture was diluted with $H_2O$ (30 mL) and extracted with EtOAc (30 mL×3). The combined organic layer was washed with water (20 mL×2), brine (30 mL), dried over anhydrous $Na_2SO_4$, filtered and concentrated under reduced pressure to obtain a crude residue which was purified by CombiFlash Chromatography to afford the title compound (0.450 g, 40%).

LCMS: 391 $[M+H]^+$.

Step-3: Preparation of N-((1r,4r)-4-(3-Chloro-4-cyanophenoxy)cyclohexyl)-6-(4-(4-((7-ethyl-6-oxo-5,6-dihydro-1,5-naphthyridin-3-yl)methyl)piperazin-1-yl)piperidin-1-yl)pyridazine-3-carboxamide (62)

To a stirred solution of 3-ethyl-74(4-(piperidin-4-yl)piperazin-1-yl)methyl)-1,5-naphthyridin-2(1H)-one (0.070 g, 0.190 mmol, 1 eq) in ACN (8 mL) was added DIPEA (0.1 mL, 0.59 mmol, 3 eq) and 6-chloro-N-((1r,4r)-4-(3-chloro-4-cyanophenoxy)cyclohexyl)pyridazine-3-carboxamide (0.076 g, 0.190 mmol, 1 eq) and the resulting mixture was stirred at 70° C. for 16 h. The reaction was monitored by TLC & LCMS. After completion, the mixture was concentrated under reduced pressure to obtain a crude residue which was purified by column chromatography followed by Reverse Phase HPLC to obtain the title compound (15 mg, 10%).

$^1$H NMR (400 MHz, DMSO-$d_6$) δ 11.82 (s, 1H), 8.60 (d, J=8.1 Hz, 1H), 8.34 (s, 1H), 7.85 (d, J=9.1 Hz, 1H), 7.80 (d, J=9.5 Hz, 1H), 7.73 (s, 1H), 7.57 (s, 1H), 7.44-7.29 (m, 2H), 7.13 (dd, J=2.1, 8.8 Hz, 1H), 4.58-4.38 (m, 3H), 3.85 (d, J=7.2 Hz, 1H), 3.54 (s, 2H), 3.00-2.97 (m, 3H), 2.67 (s, 1H), 2.54 (s, 4H), 2.39 (s, 3H), 2.33 (s, 2H), 2.10 (s, 2H), 1.87-1.80 (m, 4H), 1.72-1.46 (m, 4H), 1.46-1.33 (m, 2H), 1.25-1.04 (m, 3H). LCMS: 710.8 $[M+H]^+$.

Procedure 7: Preparation of 2-Chloro-4-(((1R,2S)-1-(5-(4-(4-((7-ethyl-6-oxo-5,6-dihydro-1,5-naphthyridin-3-yl)methyl)piperazin-1-yl)phenyl)-1,3,4-oxadiazol-2-yl)-2-hydroxypropyl)amino)benzonitrile (63)
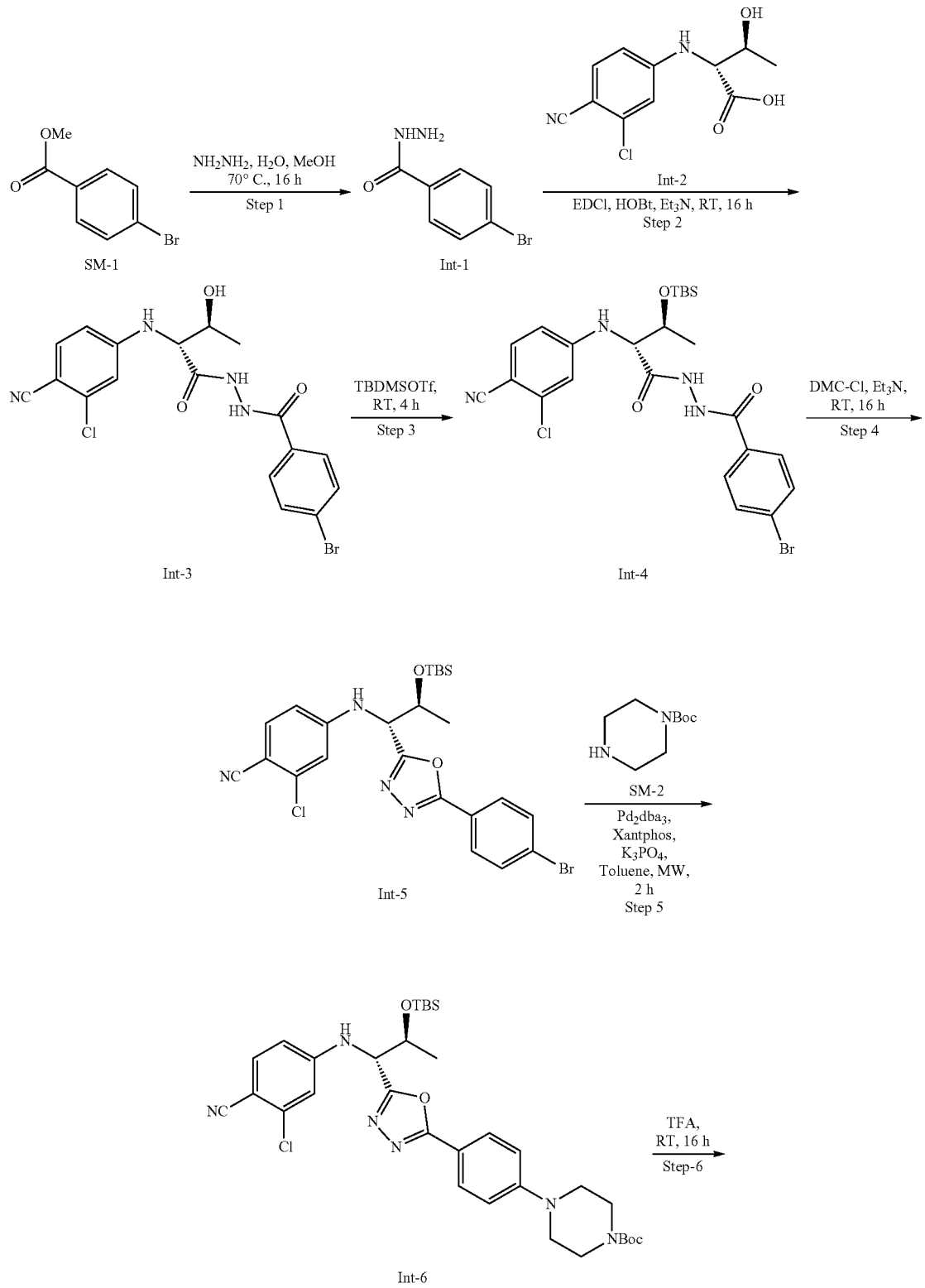

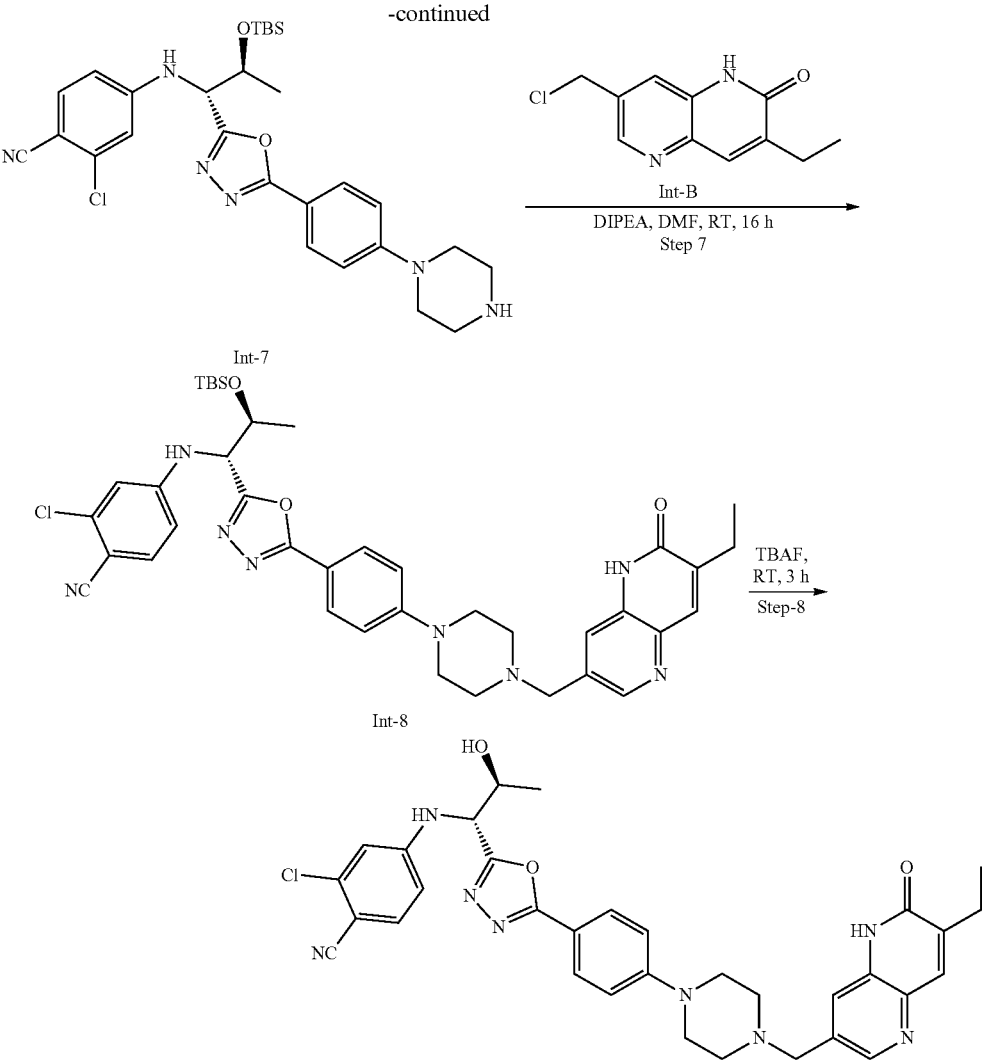

Step-1: Preparation of 4-Bromobenzohydrazide (Int-1)

A flask was charged with methyl 4-bromobenzoate (SM-1, 7.5 g, 35.04 mmol, 1.0 eq), hydrazine hydrate (17.5 mL, 350.4 mmol, 10.0 eq) and MeOH (75 mL, 10 vol). The reaction mixture was stirred at 70° C. until TLC indicated complete consumption of starting material. Reaction mixture was cooled to ambient temperature and concentrated under reduced pressure and the resulting crude was washed with diethyl ether (50 mL) and dried to obtain 4-bromobenzohydrazide (7 g, 73%).

$^1$H NMR (400 MHz, DMSO-$d_6$) δ 9.85 (br s, 1H), 7.76 (d, J=8.31 Hz, 2H), 7.66 (d, J=8.31 Hz, 2H), 4.51 (br s, 2H). LCMS: 215.0 [M+H]$^+$.

Step-1a: Preparation of (3-Chloro-4-cyanophenyl)-D-threonine (Int-2)

A flask was charged with 2-chloro-4-fluorobenzonitrile (2 g, 12.90 mmol, 1.0 eq), D-threonine (1.84 g, 15.48 mmol, 1.2 eq), $K_2CO_3$ (3.56 g, 25.80 mmol, 2.0 eq) and DMSO (20 mL, 10 vol). The reaction mixture was stirred under a nitrogen atmosphere at ambient temperature until TLC indicated complete consumption of starting material. Reaction mixture was then diluted with water (250 mL), acidified with citric acid (pH~5) and extracted with DCM (2×500 mL). The combined organic layer was washed with brine (200 mL) and dried over sodium sulfate. The organic layer was filtered, concentrated under reduced pressure and purified by flash column (Silica, 50-60% ethyl acetate in hexane). The pure fractions were combined, and the solvent evaporated under reduced pressure to give (3-chloro-4-cyanophenyl)-D-threonine (2 g, 61%).

$^1$H NMR (400 MHz, DMSO-$d_6$) δ 12.72 (br s, 1H), 7.52 (d, J=8.67 Hz, 1H), 6.85-6.94 (m, 2H), 6.73 (d, J=8.09 Hz, 1H), 5.17 (br s, 1H), 4.20 (dd, J=6.36, 3.47 Hz, 1H), 4.07 (dd, J=8.90, 3.47 Hz, 1H), 1.14 (d, J=6.36 Hz, 3H). LCMS: 255.1[M+H]$^+$.

Step-2: Preparation of 4-Bromo-N'-((3-chloro-4-cyanophenyl)-D-threonyl)benzohydrazide (Int-3)

A flask was charged with (3-chloro-4-cyanophenyl)-D-threonine (Int-2, 3 g, 11.81 mmol, 1.0 eq), 4-bromobenzohydrazide (Int-1, 2.79 g, 12.99 mmol, 1.1 eq), DIPEA (4.3 mL, 23.62 mmol, 2.0 eq), EDC·HCl (3.3 g, 17.71 mmol, 1.5 eq), HOBt (2.39 g, 17.71 mmol, 1.5 eq), DMAP (288 mg, 2.36 mmol, 0.2 eq) and DMF (30 mL, 10 vol). The reaction mixture was stirred under a nitrogen atmosphere at ambient temperature until TLC indicated complete consumption of starting material. Reaction mixture was then diluted with water (100 mL), extracted with ethyl acetate (2×200 mL) and the combined organic layer was washed with brine solution (100 mL) and dried over sodium sulfate. The organic layer was filtered, concentrated under reduced pressure and purified by flash column (Silica, 50-100% ethyl acetate in hexane). The pure fractions were combined and the solvent was evaporated under reduced pressure to obtain 4-bromo-N'-((3-chloro-4-cyanophenyl)-D-threonyl)benzohydrazide (3 g, 56%).

$^1$H NMR (400 MHz, DMSO-$d_6$) δ 10.57 (br s, 1H), 10.26 (br s, 1H), 7.81 (d, J=8.80 Hz, 2H), 7.71 (d, J=8.80 Hz, 2H), 7.56 (d, J=8.80 Hz, 1H), 7.09 (d, J=7.60 Hz, 1H), 6.93 (br s, 1H), 6.78 (d, J=8.40 Hz, 1H), 5.01 (br s, 1H), 3.90-3.96 (m, 2H), 1.25 (d, J=5.38 Hz, 3H). LCMS: 451.0 [M+H]$^+$.

Step-3: Preparation of 4-Bromo-N'—(O-(tert-butyldimethylsilyl)-N-(3-chloro-4-cyanophenyl)-D-threonyl)benzohydrazide (Int-4)

A flask was charged with 4-bromo-N'-((3-chloro-4-cyanophenyl)-D-threonyl)benzohydrazide (Int-3, 1 g, 2.21 mmol, 1.0 eq), TBDMSOTf (700 mg, 2.65 mmol, 1.2 eq), 2,6-lutidine (0.39 mL, 3.3 mmol, 1.5 eq) and DCM (10 mL, 10 vol). The reaction mixture was stirred under nitrogen atmosphere at ambient temperature until TLC indicated complete consumption of starting material. Reaction mixture was then diluted with water (200 mL), extracted with DCM (2×400 mL), and the combined organic layer was washed with brine solution (200 mL) and dried over sodium sulfate. The organic layer was filtered, concentrated under reduced pressure and purified by flash column (Silica, 20-50% ethyl acetate in hexane). The pure fractions were combined and concentrated under reduced pressure to obtain 4-bromo-N'—(O-(tert-butyldimethylsilyl)-N-(3-chloro-4-cyanophenyl)-D-threonyl)benzohydrazide (800 mg, 64%).

$^1$H NMR (400 MHz, DMSO-$d_6$) δ 10.58 (br s, 1H), 10.35 (br s, 1H), 7.81 (d, J=8.40 Hz, 2H), 7.73 (d, J=8.40 Hz, 2H), 7.54 (d, J=8.80 Hz, 1H), 7.22 (d, J=9.29 Hz, 1H), 6.93 (s, 1H), 6.73-6.83 (m, 1H), 3.94-4.17 (m, 2H), 1.14-1.36 (m, 3H), 0.75 (s, 9H), 0.06 (s, 3H), −0.08 (s, 3H). LCMS: 565.2 [M−H]$^+$.

Step-4: Preparation of 4-(((1R,2S)-1-(5-(4-Bromophenyl)-1,3,4-oxadiazol-2-yl)-2-((tert-butyldimethylsilyl)-oxy)propyl)amino)-2-chlorobenzonitrile (Int-5)

A flask was charged with 4-bromo-N'—(O-(tert-butyldimethylsilyl)-N-(3-chloro-4-cyanophenyl)-D-threonyl)benzohydrazide (Int-4, 900 mg, 1.59 mmol, 1.0 eq), DMC-Cl (269 mg, 1.59 mmol, 1.0 eq), TEA (0.46 mL, 3.19 mmol, 2.0 eq) and DCM (15 mL, 10 vol). The reaction mixture was stirred under nitrogen atmosphere at ambient temperature until TLC indicated complete consumption of starting material. Reaction mixture was then diluted with water (100 mL), extracted with DCM (2×200 mL) and the combined organic layer was washed with brine (100 mL) and dried over sodium sulfate. The organic layer was filtered, concentrated under reduced pressure and purified by flash column (Silica, 20-30% ethyl acetate in hexane). Pure fractions were combined and concentrated under reduced pressure to obtain 4-(((1R,2S)-1-(5-(4-bromophenyl)-1,3,4-oxadiazol-2-yl)-2-((tert-butyldimethylsilyl)oxy)propyl)amino)-2-chlorobenzonitrile (500 mg, 57%).

$^1$H NMR (400 MHz, DMSO-$d_6$) δ 7.83-7.91 (m, 2H), 7.77-7.83 (m, 2H), 7.55 (d, J=8.31 Hz, 1H), 7.05-7.17 (m, 2H), 6.87 (d, J=8.31 Hz, 1H), 5.72 (s, 1H), 5.19 (dd, J=9.05, 3.67 Hz, 1H), 4.40-4.49 (m, 1H), 1.24 (d, J=5.87 Hz, 3H), 0.69 (s, 9H), −0.15 (m, 3H), −0.20 (s, 3H). LCMS: 547.2 [M+H]$^+$.

Step-5: Preparation of tert-Butyl 4-(4-(5-((1R,2S)-2-((tert-Butyldimethylsilyl)oxy)-1-(3-chloro-4-cyanophenyl)amino)propyl)-1,3,4-oxadiazol-2-yl)phenyl)piperazine-1-carboxylate (Int-6)

A flask was charged with 4-(((1R,2S)-1-(5-(4-bromophenyl)-1,3,4-oxadiazol-2-yl)-2-((tert-butyldimethylsilyl)oxy)propyl)amino)-2-chlorobenzonitrile (Int-5, 500 mg, 0.91 mmol, 1.0 eq), tert-butyl piperazine-1-carboxylate (SM-2, 203 mg, 1.09 mmol, 1.2 eq), Pd$_2$dba$_3$ (83 mg, 0.09 mmol, 10 mol %), Xantphos (105 mg, 0.18 mmol, 20 mol %), K$_3$PO$_4$ (580 mg, 2.73 mmol, 3.0 eq) and Toluene (10 mL, 20 vol). The resulting mixture was purged with nitrogen for 10 min and stirred in μW at 110° C. for 2 h. TLC indicated complete consumption of starting material. The reaction mixture was then cooled to room temperature and filtered through celite pad. The filtrate was diluted with ice cold water and extracted with ethyl acetate (2×100 mL). The combined organic layer was washed with brine solution (100 mL) and dried over sodium sulfate. The organic layer was filtered and concentrated under reduced pressure. Purification by column chromatography (SiO2, hexanes/EtOAc gradient), afforded tert-butyl 4-(4-(5-((1R,2S)-2-((tert-butyldimethylsilyl)oxy)-1-((3-chloro-4-cyanophenyl)amino)propyl)-1,3,4-oxadiazol-2-yl)phenyl)piperazine-1-carboxylate (450 mg, 75% yield).

$^1$H NMR (400 MHz, DMSO-$d_6$) δ 7.78 (d, J=8.80 Hz, 2H), 7.58 (d, J=8.80 Hz, 1H), 7.02-7.20 (m, 4H), 6.89 (d, J=7.83 Hz, 1H), 5.17 (dd, J=9.29, 3.91 Hz, 1H), 4.46 (dd, J=5.87, 3.91 Hz, 1H), 3.43-3.49 (m, 4H), 3.29-3.31 (m, 4H), 1.42 (s, 9H), 1.26 (d, J=5.87 Hz, 3H), 0.74 (s, 9H), 0.02 (s, 3H), −0.16 (s, 3H). LCMS: 653.2 [M+H]$^+$.

Step-6: Preparation of 4-(((1R,2S)-2-((tert-Butyldimethylsilyl)oxy)-1-(5-(4-(piperazin-1-yl)phenyl)-1,3,4-oxadiazol-2-yl)propyl)amino)-2-chlorobenzonitrile (Int-7)

A flask was charged with tert-butyl 4-(4-(5-((1R,2S)-2-((tert-butyldimethylsilyl)oxy)-1-((3-chloro-4-cyanophenyl)amino)propyl)-1,3,4-oxadiazol-2-yl)phenyl)piperazine-1-carboxylate (Int-6, 450 mg, 0.69 mmol, 1.0 eq), DCM (9 mL, 20 vol) and TFA (0.26 mL, 3.4 mmol, 5.0 eq). The resulting mixture was stirred under a nitrogen atmosphere at room temperature until TLC indicated complete consumption of starting material. The reaction mixture was concentrated under reduced pressure, basified with saturated bicarbonate solution (pH~8) and extracted with DCM (2×100 mL). The combined organic layer was washed with brine solution (100 mL), dried over sodium sulfate. The organic layer was filtered and concentrated under reduced pressure. Purification by column chromatography (SiO2, DCM/MeOH gradient), afforded 4-(((1R,2S)-2-((tert-butyldimethylsilyl)oxy)-1-(5-(4-(piperazin-1-yl)phenyl)-1,3,4-oxadiazol-2-yl)propyl)amino)-2-chlorobenzonitrile (300 mg, 78% yield).

¹H NMR (400 MHz, DMSO-d₆) δ 7.77 (d, J=8.80 Hz, 2H), 7.58 (d, J=8.80 Hz, 2H), 7.04-7.17 (m, 4H), 6.89 (d, J=8.80 Hz, 1H), 5.16 (dd, J=9.29, 3.91 Hz, 1H), 4.40-4.51 (m, 1H), 3.22-3.31 (m, 4H), 2.83-2.92 (m, 4H), 1.26 (d, J=5.87 Hz, 3H), 0.74 (s, 9H), 0.02 (s, 3H), −0.16 (s, 3H). LCMS: 553.3 [M+H]⁺.

Step-7: Preparation of 4-(((1R,2S)-2-((tert-Butyldimethylsilyl)oxy)-1-(5-(4-(4-((7-ethyl-6-oxo-5,6-dihydro-1,5-naphthyridin-3-yl)methyl)piperazin-1-yl)phenyl)-1,3,4-oxadiazol-2-yl)propyl)amino)-2-chlorobenzonitrile (Int-8)

A flask was charged with 4-(((1R,2S)-2-((tert-butyldimethylsilyl)oxy)-1-(5-(4-(piperazin-1-yl)phenyl)-1,3,4-oxadiazol-2-yl)propyl)amino)-2-chlorobenzonitrile (Int-7, 300 mg, 0.54 mmol, 1.0 eq), 7-(chloromethyl)-3-ethyl-1,5-naphthyridin-2(1H)-one (Int-B, 210 mg, 0.81 mmol, 1.5 eq), DIPEA (0.3 mL, 1.6 mmol, 3.0 eq) and DMF (6 mL, 20 vol). The reaction mixture was stirred under nitrogen atmosphere at ambient temperature until TLC indicated complete consumption of starting material, concentrated under reduced pressure, diluted with water (100 mL) and extracted with ethyl acetate (2×200 mL). The combined organic layer was washed with brine solution (100 mL), dried over sodium sulfate, filtered and concentrated under reduced pressure to obtain 4-(((1R,2S)-2-((tert-butyldimethylsilyl)oxy)-1-(5-(4-(4-((7-ethyl-6-oxo-5,6-dihydro-1,5-naphthyridin-3-yl)methyl)piperazin-1-yl)phenyl)-1,3,4-oxadiazol-2-yl)propyl)amino)-2-chlorobenzonitrile (350 mg, 87%).

¹H NMR (400 MHz, DMSO-d₆) δ 11.84 (br s, 1H), 8.41 (d, J=1.38 Hz, 1H), 7.72-7.81 (m, 3H), 7.51-7.67 (m, 2H), 7.01-7.19 (m, 4H), 6.89 (d, J=8.63 Hz, 1H), 5.16 (dd, J=9.13, 3.75 Hz, 1H), 4.45 (br dd, J=5.88, 4.25 Hz, 1H), 3.65 (s, 2H), 3.33-3.35 (m, 4H), 2.49-2.55 (m, 6H), 1.22-1.29 (m, 3H), 1.18 (t, J=7.38 Hz, 3H), 0.74 (s, 9H), 0.02 (s, 3H), −0.15 (s, 3H). LCMS: 739.6 [M+H]⁺.

Step-8: Preparation of 2-Chloro-4-(((1R,2S)-1-(5-(4-(4-((7-ethyl-6-oxo-5,6-dihydro-1,5-naphthyridin-3-yl)methyl)piperazin-1-yl)phenyl)-1,3,4-oxadiazol-2-yl)-2-hydroxypropyl)amino)benzonitrile (63)

A flask was charged with 4-(((1R,2S)-2-((tert-butyldimethylsilyl)oxy)-1-(5-(4-(4-((7-ethyl-6-oxo-5,6-dihydro-1,5-naphthyridin-3-yl)methyl)piperazin-1-yl)phenyl)-1,3,4-oxadiazol-2-yl)propyl)amino)-2-chlorobenzonitrile (Int-8, 350 mg, 0.47 mmol, 1.0 eq), THF (7 mL, 20 vol) and TBAF (0.94 mL, 0.94 mmol, 2.0 eq, 1 M). The resulting mixture was stirred under a nitrogen atmosphere at room temperature until TLC indicated complete consumption of starting material, concentrated under reduced pressure, basified with saturated bicarbonate solution (pH~8) and extracted with DCM (2×100 mL). The combined organic layer was washed with brine solution (100 mL), dried over sodium sulfate, filtered and concentrated under reduced pressure. Purification by column chromatography (SiO2, DCM/MeOH gradient), afforded 2-chloro-4-(((1R,2S)-1-(5-(4-(4-((7-ethyl-6-oxo-5,6-dihydro-1,5-naphthyridin-3-yl)methyl)piperazin-1-yl)phenyl)-1,3,4-oxadiazol-2-yl)-2-hydroxypropyl)amino)benzonitrile (150 mg, 50% yield).

¹H NMR (400 MHz, DMSO-d₆) δ 11.84 (s, 1H), 8.41 (d, J=1.75 Hz, 1H), 7.72-7.82 (m, 3H), 7.63 (s, 1H), 7.56 (d, J=8.75 Hz, 1H), 7.37 (d, J=8.63 Hz, 1H), 7.08 (d, J=9.26 Hz, 3H), 6.86 (dd, J=8.76, 1.88 Hz, 1H), 5.34 (d, J=5.00 Hz, 1H), 4.99 (dd, J=8.63, 4.25 Hz, 1H), 4.24-4.35 (m, 1H), 3.65 (s, 2H), 3.32-3.34 (m, 4H), 2.53-2.55 (m, 6H), 1.15-1.23 (m, 6H). LCMS: 625.4 [M+H]⁺.

Procedure 8: Preparation of 2-Chloro-4-(((1R,2S)-1-(5-(4-(4-((7-ethyl-6-oxo-5,6-dihydro-1,5-naphthyridin-3-yl)methyl)piperazin-1-yl)phenyl)-1,3,4-oxadiazol-2-yl)-2-hydroxypropyl)amino)-3-methyl Benzonitrile (64)

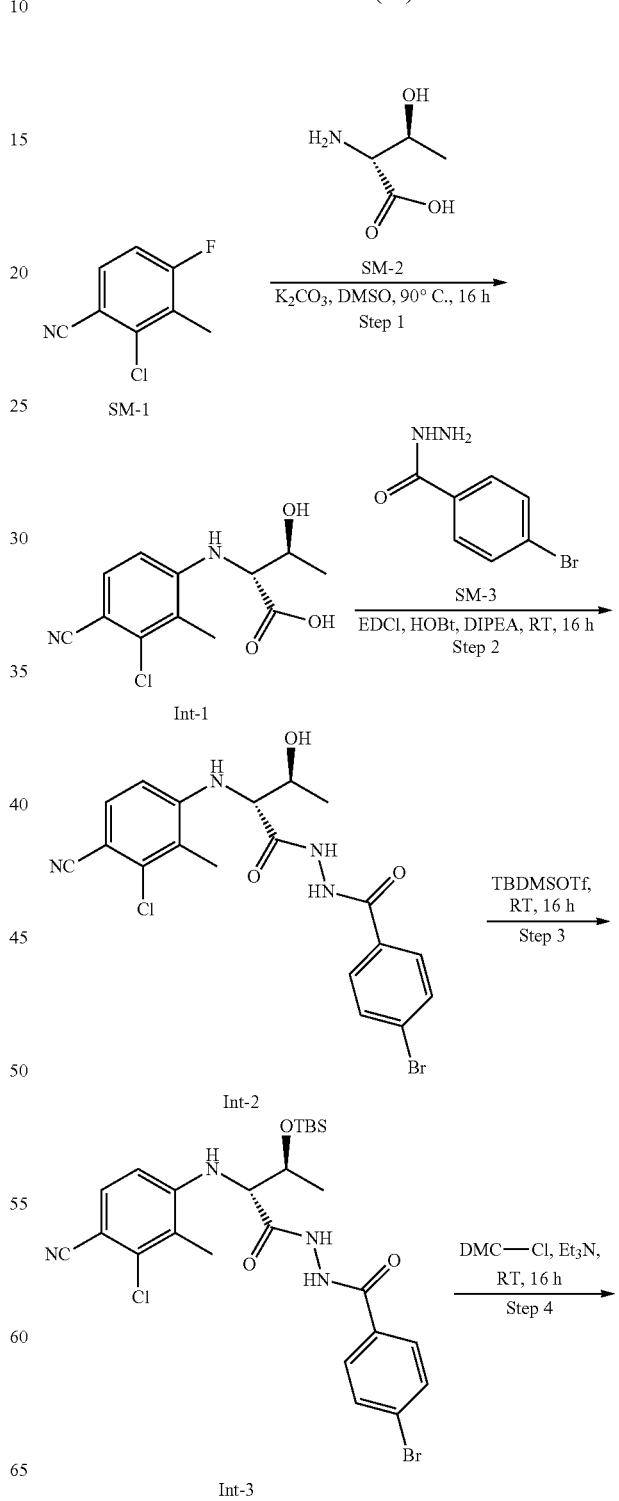

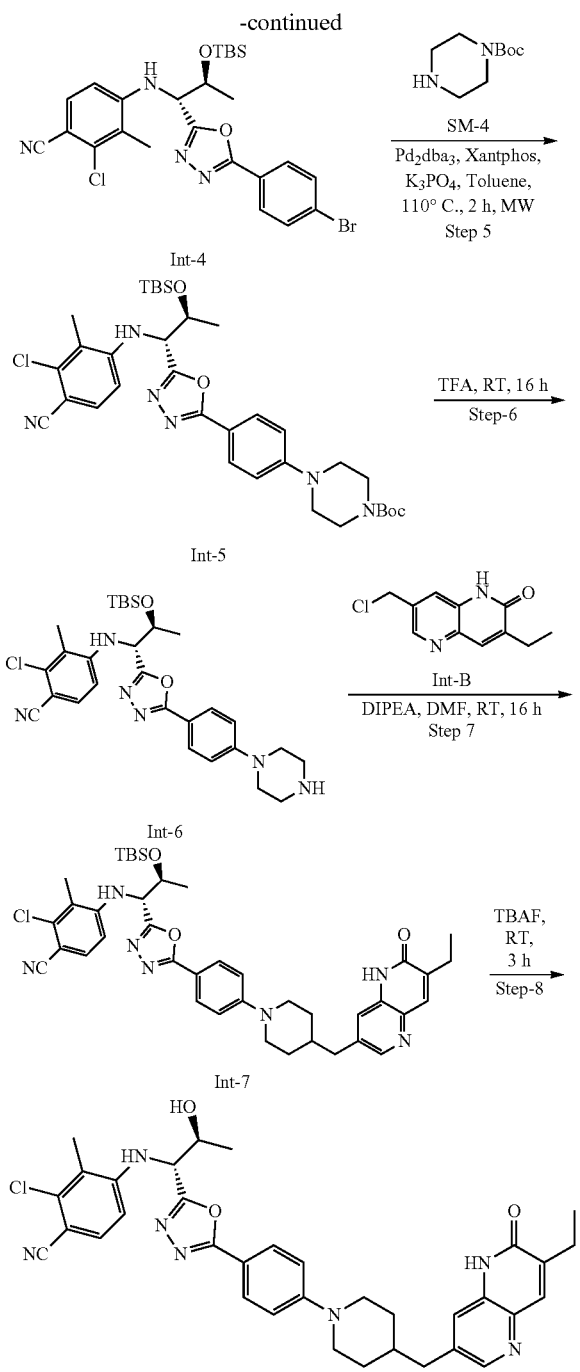

was filtered, concentrated under reduced pressure and purified by a flash column (Silica, 50-60% ethyl acetate in hexane). The pure fractions were combined and concentrated under reduced pressure to obtain (3-chloro-4-cyano-2-methylphenyl)-D-threonine (15 g, 96%).

$^1$H NMR (400 MHz, DMSO-$d_6$) δ 12.77 (br s, 1H), 7.54 (d, J=8.63 Hz, 1H), 6.58 (d, J=8.88 Hz, 1H), 5.45 (d, J=8.76 Hz, 1H), 4.22-4.29 (m, 1H), 4.13 (dd, J=8.69, 3.31 Hz, 1H), 2.27 (s, 3H), 1.19 (d, J=6.38 Hz, 3H). LCMS: 269.2 [M+H]$^+$.

Step-2: Preparation of 4-Bromo-N'-((3-chloro-4-cyano-2-methylphenyl)-D-threonyl)benzohydrazide (Int-2)

A flask was charged with (3-chloro-4-cyano-2-methylphenyl)-D-threonine (Int-1, 4 g, 14.9 mmol, 1.0 eq), 4-bromobenzohydrazide (SM-3, 3.19 g, 14.9 mmol, 1.0 eq), DIPEA (8.2 mL, 44.7 mmol, 3.0 eq), EDC·HCl (4.2 g, 22.3 mmol, 1.5 eq), HOBt (3.0 g, 22.3 mmol, 1.5 eq), DMAP (181 mg, 1.49 mmol, 0.1 eq) and DMF (80 mL, 20 vol). The reaction mixture was stirred under nitrogen atmosphere at ambient temperature until TLC indicated complete consumption of starting material, diluted with water (100 mL), extracted with ethyl acetate (2×200 mL). The combined organic layer was washed with brine solution (100 mL), dried over sodium sulfate, filtered, concentrated under reduced pressure, and purified by flash column (Silica, 50-60% ethyl acetate in hexane). The pure fractions were combined and concentrated under reduced pressure to obtain 4-bromo-N'-((3-chloro-4-cyano-2-methylphenyl)-D-threonyl)benzohydrazide (2.25 g, 32%).

$^1$H NMR (400 MHz, DMSO-$d_6$) δ 10.53 (br s, 1H), 10.21 (br s, 1H), 7.75-7.85 (m, 2H), 7.66-7.74 (m, 2H), 7.59 (d, J=8.80 Hz, 1H), 6.65 (d, J=8.80 Hz, 1H), 5.65 (d, J=7.34 Hz, 1H), 5.28 (d, J=5.38 Hz, 1H), 4.07-4.17 (m, 1H), 3.88-3.97 (m, 1H), 2.29 (m, 3H), 1.27 (d, J=6.36 Hz, 3H). LCMS: 464.8 [M+H]$^+$.

Step-3: Preparation of 4-Bromo-N'—(O-(tert-butyldimethylsilyl)-N-(3-chloro-4-cyano-2-methylphenyl)-D-threonyl)benzohydrazide (Int-3)

A flask was charged with 4-bromo-N'-((3-chloro-4-cyano-2-methylphenyl)-D-threonyl)benzohydrazide (Int-2, 3 g, 6.46 mmol, 1.0 eq), tert-butyldimethylsilyl triflate (4.4 mL, 19.3 mmol, 3.0 eq), 2,6-Lutidine (2.97 mL, 25.84 mmol, 4.0 eq) and DCM (30 mL, 10 vol). The reaction mixture was stirred under nitrogen atmosphere at ambient temperature until TLC indicated complete consumption of starting material, diluted with water (100 mL) and extracted with DCM (2×200 mL). The combined organic layer was washed with brine solution (100 mL), dried over sodium sulfate, filtered, concentrated under reduced pressure and purified by flash column (Silica, 20-30% ethyl acetate in hexane). The pure fractions were combined and concentrated under reduced pressure to obtain 4-bromo-N'—(O-(tert-butyldimethylsilyl)-N-(3-chloro-4-cyano-2-methylphenyl)-D-threonyl)benzohydrazide (1.75 g, 47%).

$^1$H NMR (400 MHz, DMSO-$d_6$) δ 10.53 (s, 1H), 10.28 (s, 1H), 7.77-7.82 (m, 2H), 7.69-7.74 (m, 2H), 7.60 (d, J=8.80 Hz, 1H), 6.69 (d, J=8.80 Hz, 1H), 5.61 (d, J=8.80 Hz, 1H), 4.30-4.39 (m, 1H), 4.11 (dd, J=8.80, 4.89 Hz, 1H), 2.26 (s, 3H), 1.22-1.32 (m, 3H), 0.83 (s, 9H), 0.02-0.12 (m, 6H). LCMS: 579.2 [M+H]$^+$.

Step-1: Preparation of (3-Chloro-4-cyano-2-methylphenyl)-D-threonine (Int-1)

A flask was charged with 2-chloro-4-fluoro-3-methylbenzonitrile (SM-1, 10 g, 58.96 mmol, 1.0 eq), D-threonine (SM-2, 8.43 g, 70.76 mmol, 1.2 eq), $K_2CO_3$ (16.3 g, 117.9 mmol, 2.0 eq) and DMSO (100 mL, 10 vol). The reaction mixture was stirred under nitrogen atmosphere at ambient temperature until TLC indicated complete consumption of starting material, diluted with water (250 mL), acidified with citric acid (pH~5) and extracted with DCM (2×500 mL). The combined organic layer was washed with brine solution (200 mL) and dried over sodium sulfate. The organic layer

Step-4: Preparation of 4-(((1R,2S)-1-(5-(4-Bromophenyl)-1,3,4-oxadiazol-2-yl)-2-((tert-butyldimethyl silyl)oxy)propyl)amino)-2-chloro-3-methylbenzonitrile (Int-4)

A flask was charged with 4-bromo-N'—(O-(tert-butyldimethylsilyl)-N-(3-chloro-4-cyano-2-methylphenyl)-D-threonyl)benzohydrazide (Int-3, 1.7 g, 3.02 mmol, 1.0 eq), DMC-Cl (765 mg, 4.53 mmol, 1.0 eq), TEA (1.31 mL, 9.06 mmol, 3.0 eq) and DCM (35 mL, 20 vol). The reaction mixture was stirred under nitrogen atmosphere at ambient temperature until TLC indicated complete consumption of starting material, diluted with water (100 mL) and extracted with DCM (2×200 mL). The combined organic layer was washed with brine solution (100 mL), dried over sodium sulfate, filtered, concentrated under reduced pressure and purified by flash column (Silica, 20-30% ethyl acetate in hexane). Pure fractions were combined and concentrated under reduced pressure to obtain 4-(((1R,2S)-1-(5-(4-bromophenyl)-1,3,4-oxadiazol-2-yl)-2-((tert-butyldimethyl silyl)oxy)propyl)amino)-2-chloro-3-methyl benzonitrile (1.0 g, 59%).

$^1$H NMR (400 MHz, DMSO-d$_6$) δ 7.87-7.95 (m, 2H), 7.78-7.87 (m, 2H), 7.58 (d, J=8.56 Hz, 1H), 6.85 (d, J=8.80 Hz, 1H), 5.60 (d, J=9.05 Hz, 1H), 5.31 (dd, J=9.05, 2.69 Hz, 1H), 4.62 (dd, J=5.99, 2.57 Hz, 1H), 2.31 (s, 3H), 1.33 (d, J=6.11 Hz, 3H), 0.76 (s, 9H), 0.04 (s, 3H), −0.25 (s, 3H). LCMS: 561.2 [M+H]$^+$.

Step-5: Preparation of tert-Butyl 4-(4-(5-((1R,2S)-2-((tert-butyldimethylsilyl)oxy)-1-((3-chloro-4-cyano-2-methylphenyl)amino)propyl)-1,3,4-oxadiazol-2-yl)phenyl)piperazine-1-carboxylate (Int-5)

A flask was charged with 4-(((1R,2S)-1-(5-(4-bromophenyl)-1,3,4-oxadiazol-2-yl)-2-((tert-butyldimethyl silyl)oxy)propyl)amino)-2-chloro-3-methyl benzonitrile (Int-4, 400 mg, 0.71 mmol, 1.0 eq), tert-butyl piperazine-1-carboxylate (SM-4, 146 mg, 0.78, 1.1 eq), Pd$_2$dba$_3$ (65 mg, 0.07 mmol, 10 mol %), Xantphos (82 mg, 0.14 mmol, 20 mol %), K$_3$PO$_4$ (450 mg, 2.13 mmol, 3.0 eq) and toluene (8 mL, 20 vol). The resulting mixture was purged with nitrogen for 10 min and stirred in μW at 110° C. for 2 h. TLC indicated complete consumption of starting material and the reaction mixture was then cooled to room temperature. Filtered the reaction mixture through celite pad and the filtrate was diluted with ice cold water and extracted with ethyl acetate (2×100 mL). The combined organic layer was washed with brine solution (100 mL), dried over sodium sulfate, filtered, concentrated under reduced pressure and purified by column chromatography (Silica, hexanes/EtOAc gradient) to afford tert-butyl 4-(4-(5-((1R,2S)-2-((tert-butyldimethylsilyl)oxy)-1-((3-chloro-4-cyano-2-methylphenyl)amino)propyl)-1,3,4-oxadiazol-2-yl)phenyl)piperazine-1-carboxylate (400 mg, 95% yield).

$^1$H NMR (400 MHz, DMSO-d$_6$) δ 7.76 (d, J=8.80 Hz, 2H), 7.57 (d, J=8.31 Hz, 1H), 7.08 (d, J=8.80 Hz, 2H), 6.84 (d, J=8.80 Hz, 1H), 5.57 (d, J=8.80 Hz, 1H), 5.26 (dd, J=9.05, 2.20 Hz, 1H), 4.59 (dd, J=6.11, 2.69 Hz, 1H), 3.46 (br s, 4H), 3.32 (br s, 4H), 2.31 (s, 3H), 1.42 (s, 9H), 1.33 (d, J=5.87 Hz, 3H), 0.77 (s, 9H), 0.04 (s, 3H), −0.24 (s, 3H). LCMS: 667.2 [M+H]$^+$.

Step-6: Preparation of 4-(((1R,2S)-2-((tert-Butyldimethylsilyl)oxy)-1-(5-(4-(piperazin-1-yl)phenyl)-1,3,4-oxadiazol-2-yl)propyl)amino)-2-chloro-3-methylbenzonitrile (Int-6)

A flask was charged with tert-butyl 4-(4-(5-((1R,2S)-2-((tert-butyldimethylsilyl)oxy)-1-((3-chloro-4-cyano-2-methylphenyl)amino)propyl)-1,3,4-oxadiazol-2-yl)phenyl)piperazine-1-carboxylate (Int-5, 300 mg, 0.45 mmol, 1.0 eq), DCM (6 mL, 20 vol) and TFA (0.17 mL, 2.25 mmol, 5.0 eq). The resulting mixture was stirred under nitrogen atmosphere at room temperature until TLC indicated complete consumption of starting material, concentrated under reduced pressure, basified with saturated bicarbonate solution (pH~8) and extracted with DCM (2×100 mL). The combined organic layer was washed with brine solution (100 mL), dried over sodium sulfate, filtered and concentrated under reduced pressure. Purification by column chromatography (Silica, DCM/MeOH gradient), afforded 4-(((1R,2S)-2-((tert-butyldimethylsilyl)oxy)-1-(5-(4-(piperazin-1-yl)phenyl)-1,3,4-oxadiazol-2-yl)propyl)amino)-2-chloro-3-methylbenzonitrile (190 mg, 76% yield).

$^1$H NMR (400 MHz, DMSO-d$_6$) δ 7.76 (d, J=8.80 Hz, 2H), 7.57 (d, J=8.80 Hz, 1H), 7.08 (d, J=8.80 Hz, 2H), 6.83 (d, J=8.80 Hz, 1H), 5.57 (d, J=9.29 Hz, 1H), 5.26 (dd, J=9.05, 2.69 Hz, 1H), 4.59 (dd, J=6.36, 2.93 Hz, 1H), 3.32 (br s, 4H), 2.98 (br s, 4H), 2.31 (s, 3H), 1.33 (d, J=5.87 Hz, 3H), 0.78 (s, 9H), 0.04 (s, 3H), −0.24 (s, 3H). LCMS: 567.4 [M+H]$^+$.

Step-7: Preparation of 4-(((1R,2S)-2-((tert-butyldimethylsilyl)oxy)-1-(5-(4-(4-((7-ethyl-6-oxo-5,6-dihydro-1,5-naphthyridin-3-yl)methyl)piperazin-1-yl)phenyl)-1,3,4-oxadiazol-2-yl)propyl)amino)-2-chloro-3-methylbenzonitrile (Int-7)

A flask was charged with 4-(((1R,2S)-2-((tert-butyldimethylsilyl)oxy)-1-(5-(4-(piperazin-1-yl)phenyl)-1,3,4-oxadiazol-2-yl)propyl)amino)-2-chloro-3-methylbenzonitrile (Int-6, 190 mg, 0.33 mmol, 1.0 eq), 7-(chloromethyl)-3-ethyl-1,5-naphthyridin-2(1H)-one (Int-B, 129 mg, 0.49 mmol, 1.5 eq), DIPEA (0.18 mL, 0.99 mmol, 3.0 eq) and DMF (3.8 mL, 10 vol). The reaction mixture was stirred under a nitrogen atmosphere at ambient temperature until TLC indicated complete consumption of starting material, cooled to ambient temperature, evaporated under reduced pressure, diluted with water (100 mL) and compound was extracted with ethyl acetate (2×200 mL), combined organic layer was washed with brine solution (100 mL) and dried over sodium sulfate. Filtered organic solvent and concentrated under reduced pressure to obtained 4-(((1R,2S)-2-((tert-butyldimethylsilyl)oxy)-1-(5-(4-(4-((7-ethyl-6-oxo-5,6-dihydro-1,5-naphthyridin-3-yl)methyl)piperazin-1-yl)phenyl)-1,3,4-oxadiazol-2-yl)propyl)amino)-2-chloro-3-methylbenzonitrile (200 mg, 80%).

LCMS: 753.6 [M+H]$^+$.

Step-8: Preparation of 2-Chloro-4-(((1R,2S)-1-(5-(4-(4-((7-ethyl-6-oxo-5,6-dihydro-1,5-naphthyridin-3-yl)methyl)piperazin-1-yl)phenyl)-1,3,4-oxadiazol-2-yl)-2-hydroxypropyl)amino)-3-methyl Benzonitrile (64)

A flask charged with 4-(((1R,2S)-2-((tert-butyldimethylsilyl)oxy)-1-(5-(4-(4-((7-ethyl-6-oxo-5,6-dihydro-1,5-naphthyridin-3-yl)methyl)piperazin-1-yl)phenyl)-1,3,4-oxadiazol-2-yl)propyl)amino)-2-chloro-3-methylbenzonitrile (Int-7, 200 mg, 0.26 mmol, 1.0 eq) in THF (4 mL, 20 vol) and TBAF (0.53 mL, 0.52 mmol, 2.0 eq, 1M in THF) was allowed to stir under a nitrogen atmosphere at 0° C. The reaction mixture was stirred under a nitrogen atmosphere at ambient temperature until TLC indicated complete consumption of starting material, quenched with water (100 mL) and extracted with ethyl acetate (2×200 mL). The combined organic layer was washed with brine solution (100 mL), dried over sodium sulfate, filtered, concentrated under reduced pressure and purified by flash column (Silica, 0-5% MeOH in DCM). Pure fractions were combined and concentrated under reduced pressure to obtain 2-chloro-4-(((1R, 2S)-1-(5-(4-(4-(((7-ethyl-6-oxo-5,6-dihydro-1,5-naphthyridin-3-yl)methyl)piperazin-1-yl)phenyl)-1,3,4-oxadiazol-2-yl)-2-hydroxypropyl)amino)-3-methyl benzonitrile (76 mg, 88%).

$^1$H NMR (400 MHz, DMSO-$d_6$) δ 11.84 (s, 1H), 8.40 (d, J=1.63 Hz, 1H), 7.71-7.78 (m, 3H), 7.62 (s, 1H), 7.55 (d, J=8.63 Hz, 1H), 7.07 (d, J=9.01 Hz, 2H), 6.78 (d, J=8.76 Hz, 1H), 5.86 (d, J=8.25 Hz, 1H), 5.46 (d, J=6.00 Hz, 1H), 5.02 (dd, J=8.32, 4.57 Hz, 1H), 4.32-4.42 (m, 1H), 3.65 (s, 2H), 3.32-3.34 (m, 4H), 2.52-2.55 (m, 6H), 2.33 (s, 3H), 1.24 (d, J=6.25 Hz, 3H), 1.18 (t, J=7.38 Hz, 3H). LCMS: 639.4 [M+H]$^+$.

Procedure 9: Preparation of N-((1r,3r)-3-(3-Chloro-4-cyanophenoxy)-2,2,4,4-tetramethylcyclobutyl)-6-(4-((4-((7-ethyl-6-oxo-5,6-dihydro-1,5-naphthyridin-3-yl)methyl)piperazin-1-yl)methyl)piperidin-1-yl) pyridazine-3-carboxamide (13)

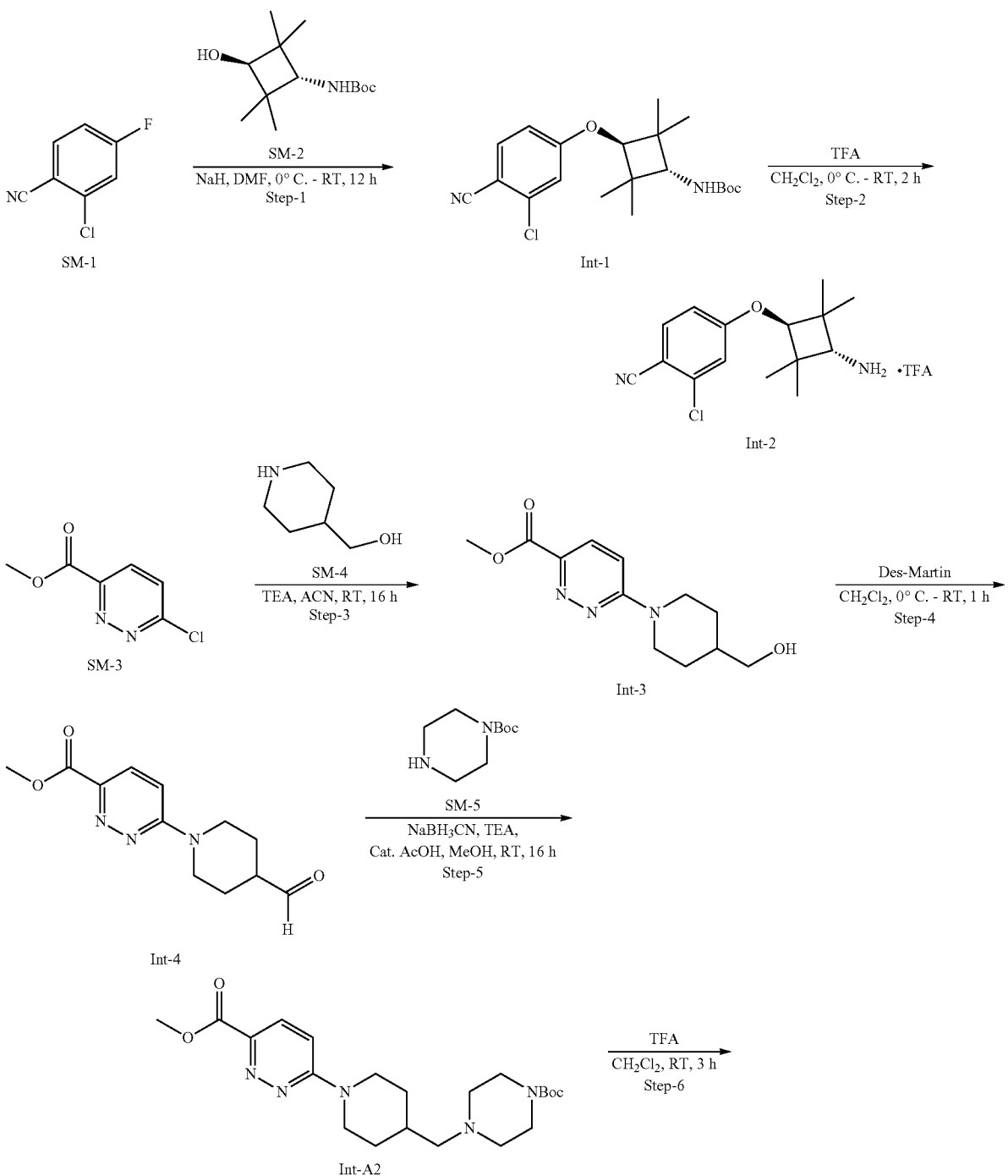

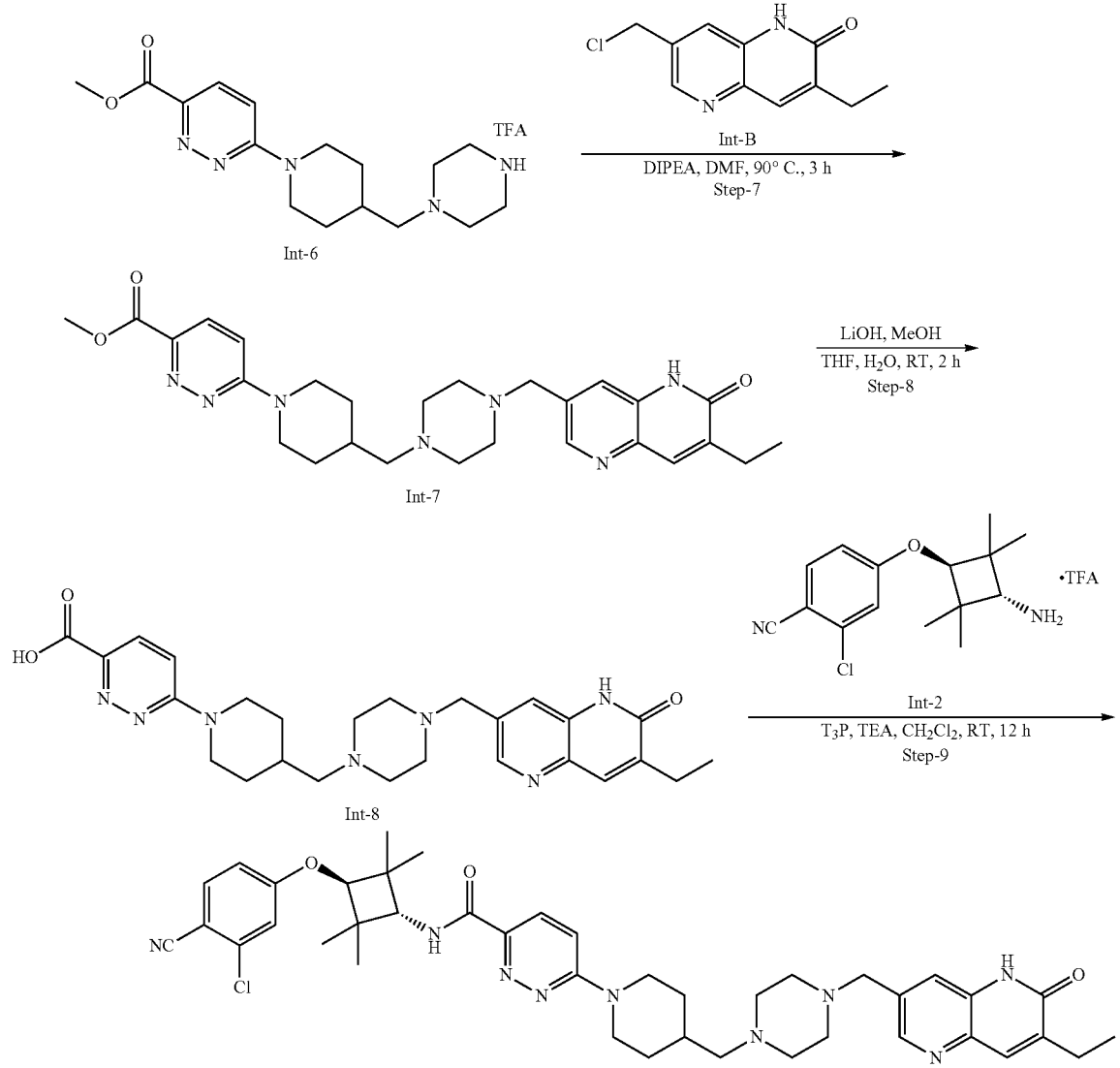

Step-1: Preparation of (1r,3r)-3-(3-Chloro-4-cyano-phenoxy)-2,2,4,4-tetramethylcyclobutyl tert-Butyl-carbamate (Int-1)

To a stirred solution of tert-butyl ((1r,3r)-3-hydroxy-2,2,4,4-tetramethylcyclobutyl)carbamate (SM-2, 500 mg, 2.05 mmol, 1.0 eq) in DMF (12 mL) was added 63% of NaH (157 mg, 4.11 mmol, 2 eq) portion wise at 0° C. and stirred for 1 h. To this reaction mixture was added 2-chloro-4-fluorobenzonitrile (SM-1, 318 mg, 2.05 mmol, 1.0 eq) in DMF (3 mL) at 0° C. The reaction mixture was allowed warm up to room temperature and stir for 12 h. Progress of the reaction was monitored by TLC. After completion of the reaction, saturated ammonium chloride (50 mL) was added, and the aqueous layer was extracted with ethyl acetate (2×100 mL). The combined organic extracts was washed with water (100 mL), brine (100 mL) and dried over anhydrous sodium sulphate, filtered and concentrated under vacuum to obtain the crude product. The crude product was purified by combiflash column eluting with 40% ethyl acetate in heptane in afford the desired product (400 mg, 51%).

$^1$H NMR (400 MHz, DMSO-d$_6$) δ 7.87 (d, J=8.80 Hz, 1H), 7.17 (d, J=2.45 Hz, 1H), 6.96 (dd, J=8.80, 2.45 Hz, 1H), 6.70 (br s, 1H), 4.17 (s, 1H), 3.54 (br d, J=9.29 Hz, 1H), 1.40 (s, 9H), 1.12 (s, 6H), 1.04 (s, 6H).

Step-2: Preparation of 4-((1r,3r)-3-Amino-2,2,4,4-tetramethylcyclobutoxy)-2-chlorobenzonitrile TFA Salt (Int-2)

To a stirred solution of tert-butyl ((1r,3r)-3-(3-chloro-4-cyanophenoxy)-2,2,4,4-tetramethylcyclo-butyl)carbamate (Int-1, 400 mg, 1.05 mmol, 1.0 eq) in DCM (8 mL) under nitrogen atmosphere was added TFA (0.4 mL, 4 vol) at 0° C. The reaction mixture was allowed to warm up to room temperature and stir for 2 h. Progress of the reaction was monitored by TLC. After completion of the reaction, solvents were evaporated under reduced pressure and the crude residue was triturated with diethyl ether (2×60 mL) and dried under vacuum to afford the product (300 mg, 75%).

$^1$H NMR (400 MHz, DMSO-d$_6$) δ 8.08 (br s, 3H), 7.86 (d, J=8.69 Hz, 1H), 7.20 (d, J=2.27 Hz, 1H), 6.97 (dd, J=8.88, 2.45 Hz, 1H), 4.34 (s, 1H), 3.11 (br s, 1H), 1.23 (s, 6H), 1.04 (s, 6H). LCMS: 279.2 [M+H]+.

Step-3: Preparation of Methyl 6-(4-(Hydroxymethyl)piperidin-1-yl)pyridazine-3-carboxylate (Int-3)

To a stirred solution of methyl 6-chloropyridazine-3-carboxylate (SM-3, 5 g, 28 mmol, 1.0 eq) and piperidin-4-ylmethanol (SM-4, 3.6 g, 31 mmol, 1.1 eq) in Acetonitrile (150 mL) was added triethylamine (6 mL, 43 mmol, 1.5 eq). The reaction mixture was allowed to stir at room temperature for 16 h. Progress of the reaction was monitored by TLC. After completion of the reaction, solvents were evaporated under reduced pressure to obtain the crude product, which was purified on a combiflash column, eluting with 80% ethyl acetate in heptane, to afford the title compound (5.9 g, 80%).

$^1$H NMR (400 MHz, DMSO-d$_6$) δ 7.79 (d, J=9.29 Hz, 1H), 7.27 (d, J=9.78 Hz, 1H), 4.55 (br s, 1H), 4.51-4.54 (m, 2H), 3.86 (s, 3H), 3.27 (t, J=5.14 Hz, 2H), 3.00 (br t, J=11.98 Hz, 2H), 1.72-1.80 (m, 3H), 1.08-1.21 (m, 2H). LCMS: 251.95 [M+H]+.

Step-4: Preparation of Methyl 6-(4-formylpiperidin-1-yl)pyridazine-3-carboxylate (Int-4)

To a stirred solution of methyl 6-(4-(hydroxymethyl)piperidin-1-yl)pyridazine-3-carboxylate (Int-3, 1 g, 3.98 mmol, 1.0 eq) in DCM (50 mL) was added Dess-Martin periodinane (2.7 g, 5.97 mmol, 1.5 eq) at 0° C. The reaction mixture was allowed to warm up to room temperature and stir for 1 h. Progress of the reaction was monitored by TLC. After completion of the reaction, Na$_2$S$_2$O$_3$ saturated solution 60 mL) was added and extracted with DCM (2×60 mL). The combined organic extracts was washed with sat. NaHCO$_3$ (60 mL), brine (60 mL), dried over anhydrous sodium sulphate, filtered and concentrated under reduced pressure to afford the crude product (930 mg) which was used without further purification.

$^1$H NMR (400 MHz, DMSO-d$_6$) δ 9.63 (s, 1H), 7.82 (d, J=9.78 Hz, 1H), 7.31 (d, J=9.78 Hz, 1H), 4.34 (br d, J=13.69 Hz, 2H), 3.86 (s, 3H), 3.23-3.30 (m, 2H), 2.90-3.11 (m, 1H), 2.64-2.75 (m, 1H), 1.88-2.03 (m, 3H), 1.45-1.61 (m, 2H). LCMS: 250.2 [M+H]+.

Step-5: Preparation of Methyl 6-(4-((4-(tert-Butoxycarbonyl)piperazin-1-yl)methyl)piperidin-1-yl)pyridazine-3-carboxylate (Int-2A)

To a stirred solution of methyl 6-(4-formylpiperidin-1-yl)pyridazine-3-carboxylate (Int-4, 900 mg, 3.61 mmol, 1.0 eq) and tert-butyl piperazine-1-carboxylate (SM-5, 670 mg, 3.61 mmol, 1.0 eq) in methanol (30 mL) was added triethylamine (1.5 mL, 10.83 mmol, 3 eq) at room temperature and stirred for 10 min. To this reaction mixture was added cat. acetic acid (0.4 mL) and stirred for 1 h followed by addition of sodium cyanoborohydride (450 mg, 7.22 mmol, 2.0 eq) at room temperature and the resulting reaction was allowed to stir for 16 h. Progress of the reaction was monitored by TLC. After completion of the reaction, water (100 mL) was added and extracted with DCM (2×100 mL). The combined organic extracts was washed with water (100 mL), brine (100 mL), dried over anhydrous sodium sulphate, filtered and concentrated under vacuum to obtain the crude product which was purified using a combiflash column, eluting with 80% ethyl acetate in heptane, to afford the titled product (750 mg, 50%).

$^1$H NMR (400 MHz, DMSO-d$_6$) δ 7.80 (d, J=9.78 Hz, 1H), 7.26 (d, J=9.78 Hz, 1H), 4.51 (br d, J=13.21 Hz, 2H), 3.86 (s, 3H), 3.30-3.35 (m, 4H), 3.01 (br t, J=11.74 Hz, 2H), 2.20-2.29 (m, 4H), 2.15 (br d, J=7.34 Hz, 2H), 1.76-1.91 (m, 3H), 1.39 (s, 9H), 0.99-1.18 (m, 2H). LCMS: 420.4 [M+H]+.

Step-6: Preparation of Methyl 6-(4-(piperazin-1-ylmethyl)piperidin-1-yl)pyridazine-3-carboxylate TFA Salt (Int-6)

To a stirred solution of methyl 6-(4-((4-(tert-butoxycarbonyl)piperazin-1-yl) methyl)piperidin-1-yl)pyridazine-3-carboxylate (Int-2A, 1 g, 2.3 mmol, 1.0 eq) in DCM (20 mL) under nitrogen atmosphere was added TFA (1 mL, 1 vol) at 0° C. The reaction mixture was allowed to warm up to room temperature and stir for 3 h. Progress of the reaction was monitored by TLC. After completion of the reaction, solvents were evaporated under reduced pressure, washed with diethyl ether (2×60 mL) and dried under vacuum to afford (790 mg, 79%).

$^1$H NMR (400 MHz, DMSO-d$_6$) δ 9.18 (br s, 2H), 7.83 (dd, J=9.78, 0.98 Hz, 1H), 7.33 (d, J=9.78 Hz, 1H), 4.54 (br d, J=13.21 Hz, 2H), 3.86 (s, 3H), 3.30-3.35 (m, 4H), 2.92-3.13 (m, 4H), 2.10-2.12 (m, 3H), 1.80-1.86 (m, 3H), 1.11-1.28 (m, 3H). LCMS: 320.4 [M+H]+.

Step-7: Preparation of Methyl 6-(4-((4-(7-Ethyl-6-oxo-5,6-dihydro-1,5-naphthyridin-3-yl)methyl)piperazin-1-yl)methyl)piperidin-1-yl)pyridazine-3-carboxylate (Int-7)

To a stirred solution of methyl 6-(4-(piperazin-1-ylmethyl)piperidin-1-yl)pyridazine-3-carboxylate TFA salt (Int-6, 800 mg, 1.91 mmol, 1.0 eq) and 7-(chloromethyl)-3-ethyl-1,5-naphthyridin-2(1H)-one (Int-B, 466 mg, 2.10 mmol, 1.0 eq) in DMF (10 mL) was added DIPEA (2 mL, 7.67 mmol, 4 eq) at RT. The reaction mixture was allowed to stir at 90° C. for 3 h. Progress of the reaction was monitored by TLC. After completion of the reaction, the reaction mixture was cooled down to room temperature, filtered, washed with diethyl ether (30 mL) and dried under vacuum to afford the titled product (350 mg, 36%).

LCMS: 506.2 [M+H]+.

Step-8: Preparation of 6-(4-((4-((7-Ethyl-6-oxo-5,6-dihydro-1,5-naphthyridin-3-yl)methyl)piperazin-1-yl)methyl)piperidin-1-yl)pyridazine-3-carboxylic Acid (Int-8)

To a stirred solution of methyl 6-(4-((4-((7-ethyl-6-oxo-5,6-dihydro-1,5-naphthyridin-3-yl)methylipiperazin-1-yl) methyl)piperidin-1-yl)pyridazine-3-carboxylate (Int-7, 350 mg, 0.69 mmol, 1.0 eq) in methanol (6 mL) and THF (6 mL) was added LiOH (83 mg, 3.46 mmol, 5 eq) in water (6 mL) at RT. The reaction mixture was stirred at room temperature for 2 h. Progress of the reaction was monitored by TLC. After completion of the reaction, the organic solvents were evaporated under reduced pressure and the aqueous solution was extracted with ethyl acetate (2×60 mL). The aqueous layer was acidified with 1N HCl (15 mL) and concentrated under reduced pressure to afford the titled compound (200 mg, 58%), which was used in next step without further purification.

$^1$H NMR (400 MHz, DMSO-d$_6$) δ 12.21 (br s, 1H), 8.69 (s, 1H), 7.89-7.91 (m, 1H), 7.87 (s, 1H), 7.81 (s, 1H), 7.50 (br d, J=9.78 Hz, 1H), 4.49 (br d, J=12.72 Hz, 2H), 3.69-3.78 (m, 6H), 3.50-3.54 (m, 6H), 3.03-3.14 (m, 4H), 2.57 (br d,

J=7.83 Hz, 2H), 2.01 (br d, J=11.74 Hz, 2H), 1.19-1.21 (m, 1H), 1.18 (br t, J=7.34 Hz, 3H) (1H exchangeable was not seen in spectra). LCMS: 492.35 [M+H]+.

Step-9: Preparation of N-((1r,3r)-3-(3-Chloro-4-cyanophenoxy)-2,2,4,4-tetramethylcyclobutyl)-6-(4-((4-((7-ethyl-6-oxo-5,6-dihydro-1,5-naphthyridin-3-yl)methyl)piperazin-1-yl)methyl)piperidin-1-yl)pyridazine-3-carboxamide (13)

To a stirred solution of 6-(4-((4-((7-ethyl-6-oxo-5,6-dihydro-1,5-naphthyridin-3-yl)methyl)piperazin-1-yl)methyl)piperidin-1-yl)pyridazine-3-carboxylic acid (Int-8, 130 mg, 0.26 mmol, 1.0 eq) and 4-((1r,3r)-3-amino-2,2,4,4-tetramethylcyclobutoxy)-2-chlorobenzonitrile TFA salt (Int-2, 100 mg, 0.26 mmol, 1.0 eq) in DCM (12 mL) were added T$_3$P (50% in Ethyl acetate, 0.32 mL, 0.53 mmol, 2 eq) and triethylamine (0.1 mL, 0.79 mmol, 3 eq) at RT. The reaction mixture was stirred at room temperature for 12 h. Progress of the reaction was monitored by TLC. After completion of the reaction, water (60 mL) was added and extracted with DCM (2×60 mL). The combined organic extracts was washed with water (100 mL), brine (100 mL), dried over anhydrous sodium sulphate, filtered and concentrated under vacuum to obtain the crude product. Purification using a combiflash column, eluting with 10% methanol in DCM, afforded the titled product (118 mg, 59%).

$^1$H NMR (400 MHz, DMSO-d$_6$) δ 11.94 (s, 1H), 9.48 (br s, 1H), 8.41 (s, 1H), 8.23 (br d, J=9.29 Hz, 1H), 7.91 (d, J=8.80 Hz, 1H), 7.76 (s, 1H), 7.56 (s, 1H), 7.41 (br d, J=9.78 Hz, 1H), 7.25 (d, J=1.96 Hz, 1H), 6.98-7.06 (m, 1H), 4.50-4.55 (m, 2H), 4.45 (s, 1H), 4.00 (d, J=8.80 Hz, 1H), 3.70-3.72 (m, 2H), 3.48 (br d, J=11.25 Hz, 2H), 3.00-3.05 (m, 7H), 2.90-2.92 (m, 3H), 2.50-2.54 (m, 3H), 2.18 (br d, J=18.59 Hz, 2H), 1.84-1.87 (m, 2H), 1.23 (s, 6H), 1.18 (br t, J=7.34 Hz, 3H), 1.05 (s, 6H). HPLC Purity: 98.6%. LCMS: 752.4 [M+H]+.

Procedure 10: Preparation of 2-Chloro-4-((4R,5S)-4-(5-(4-(4-((7-ethyl-6-oxo-5,6-dihydro-1,5-naphthyridin-3-yl)methyl)-piperazin-1-yl)phenyl)-1,3,4-oxadiazol-2-yl)-5-methyl-2-oxooxazolidin-3-yl)benzonitrile (65)

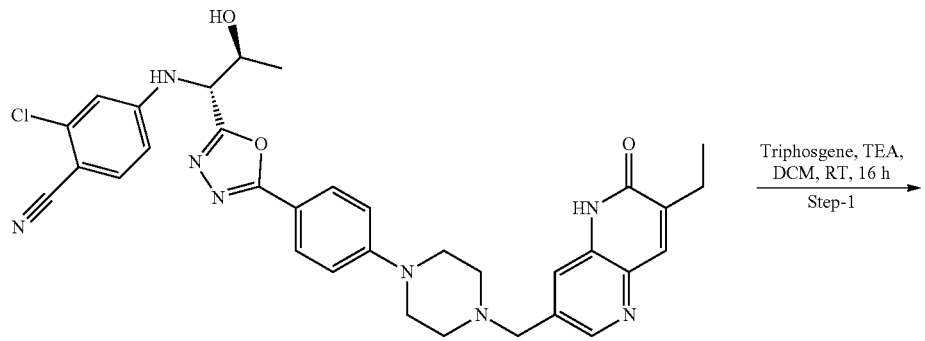

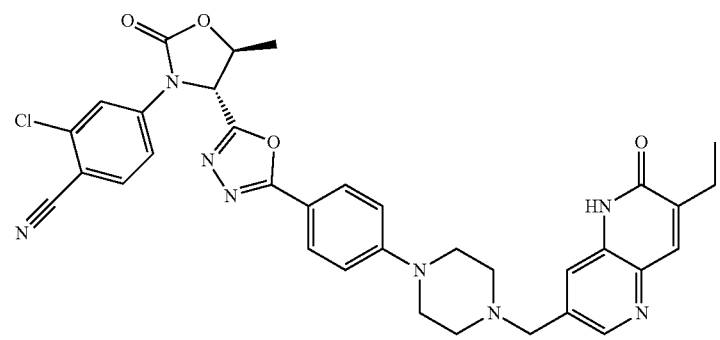

A RB flask was charged with 2-chloro-4-(((1R,2S)-1-(5-(4-(44(7-ethyl-6-oxo-5,6-dihydro-1,5-naphthyridin-3-yl)methyl)piperazin-1-yl)phenyl)-1,3,4-oxadiazol-2-yl)-2-hydroxypropyl)amino)benzonitrile (63) (90 mg, 0.14 mmol, 1 eq), triphosgene (85 mg, 0.28 mmol, 2.0 eq), TEA (0.08 mL, 0.576 mmol, 4.0 eq) and DCM (1.8 mL, 20 vol) at 0° C. under argon atmosphere. Reaction mixture was stirred at ambient temperature until TLC indicated complete consumption of starting material. The reaction mixture was diluted with water (100 mL), extracted with DCM (2×200 mL) and the combined organic layer was washed with brine solution (100 mL) and dried over sodium sulfate. The organic layer was filtered, concentrated under reduced pressure and the resulting residue was purified by flash column (Silica, 0-5% MeOH in DCM). The pure fractions were combined and the volatiles were evaporated under reduced pressure to afford 2-chloro-4-((4R,5S)-4-(5-(4-(4-((7-ethyl-6-oxo-5,6-dihydro-1,5-naphthyridin-3-yl)methyl)piperazin-1-yl)phenyl)-1,3,4-oxadiazol-2-yl)-5-methyl-2-oxooxazolidin-3-yl)benzonitrile (15 mg, 16%).

$^1$H NMR (400 MHz, DMSO-$d_6$) δ 11.84 (s, 1H), 8.40 (d, J=1.75 Hz, 1H), 8.04 (d, J=2.13 Hz, 1H), 8.00 (d, J=8.76 Hz, 1H), 7.69-7.78 (m, 4H), 7.62 (s, 1H), 7.07 (d, J=9.13 Hz, 2H), 6.06 (d, J=3.75 Hz, 1H), 5.13-5.21 (m, 1H), 3.65 (s, 2H), 3.31-3.33 (m, 4H), 2.52-2.57 (m, 6H), 1.59 (d, J=6.38 Hz, 3H), 1.18 (t, J=7.44 Hz, 3H). LCMS: 651.2 [M+H]$^+$.

Procedure 11: Preparation of N-((1r,4r)-4-(3-Chloro-4-cyano-2-methylphenoxy)cyclohexyl)-6-(4-((4-((7-ethyl-6-oxo-5,6-dihydro-1,5-naphthyridin-3-yl)methyl)piperazin-1-yl)methyl)piperidin-1-yl)pyridazine-3-carboxamide (66)

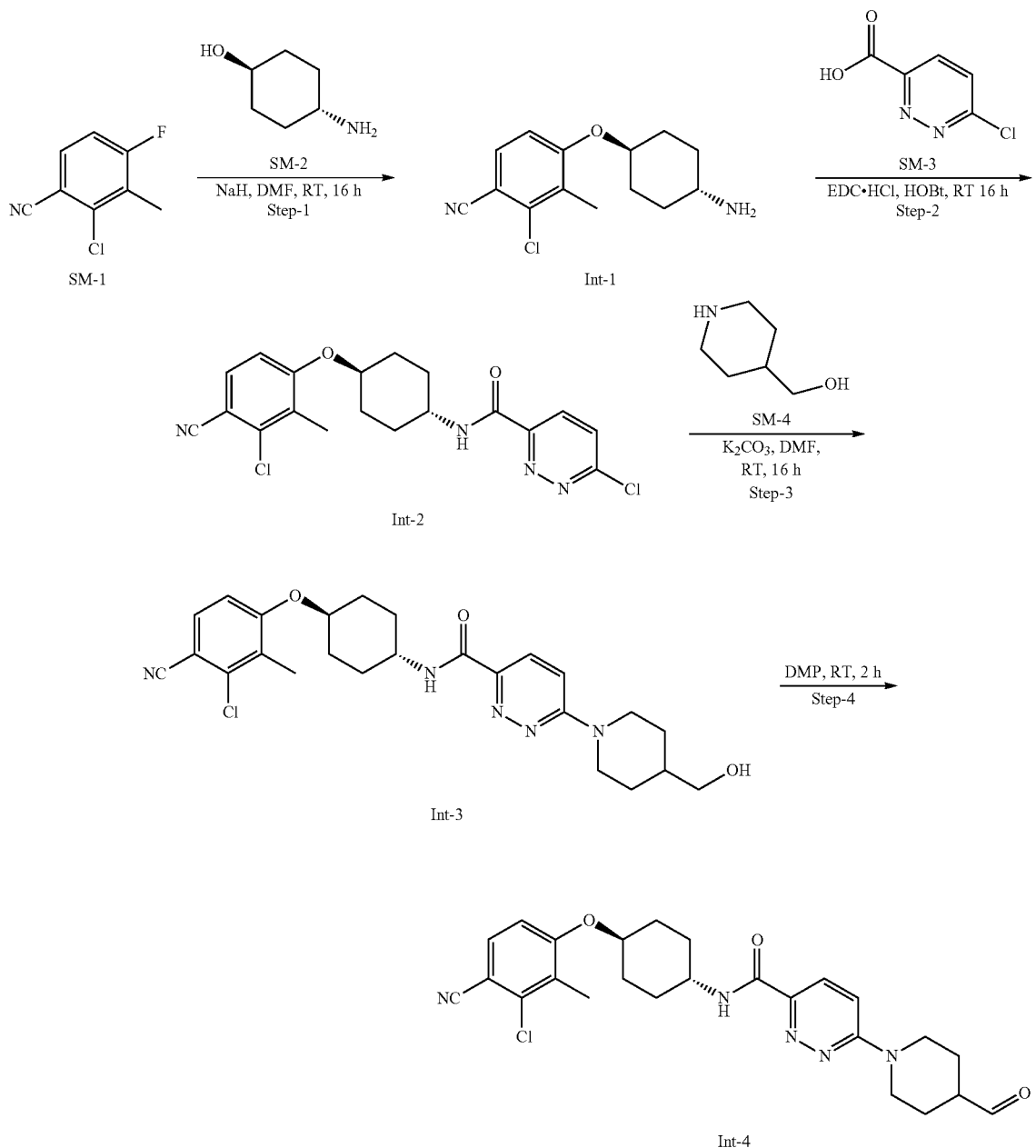

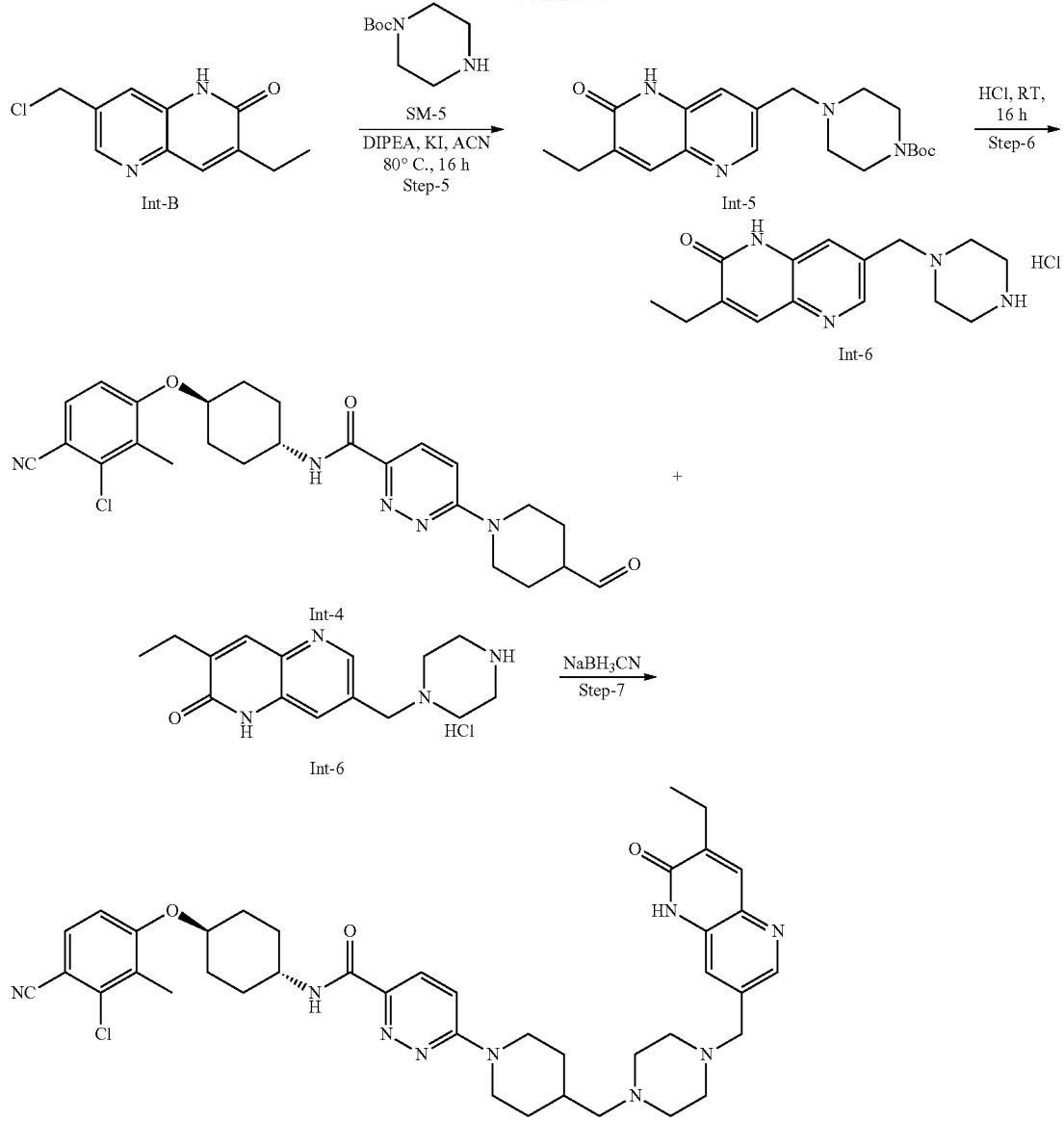

Step-1: Preparation of 4-(((1r,4r)-4-Aminocyclohexyl)oxy)-2-chloro-3-methylbenzonitrile (Int-1)

To a flask was charged with NaH (2.11 g, 53 mmol, 2.0 eq, 60%), DMF (45 mL, 10 vol) and 2-chloro-4-fluoro-3-methylbenzonitrile (SM-1, 4.5 g, 26.5 mmol, 1 eq), (1r,4r)-4-aminocyclohexan-1-ol (SM-2, 3.04 g, 26.5 mmol, 1.0 eq) was added under a nitrogen atmosphere at ambient temperature. The resulting reaction mixture was stirred at ambient temperature until TLC indicated complete consumption of starting material, diluted with water (100 mL) and extracted with ethyl acetate (2×200 mL). The aqueous layer was acidified with 1N HCl (pH~4-5) and concentrated under reduced pressure to obtain 4-(((1r,4r)-4-aminocyclohexyl)oxy)-2-chloro-3-methylbenzonitrile (6.5 g, 92%).

$^1$H NMR (400 MHz, DMSO-d$_6$) δ 7.87-8.18 (br s, 2H), 7.76 (d, J=8.80 Hz, 1H), 7.28 (d, J=8.80 Hz, 1H), 4.44-4.54 (m, 1H), 2.95-3.06 (m, 1H), 2.21 (s, 3H), 2.05-2.12 (m, 2H), 1.95-2.02 (m, 2H), 1.44-1.57 (m, 4H). LCMS: 265.0 [M+H]$^+$.

Step-2: Preparation of 6-Chloro-N-((1r,4r)-4-(3-chloro-4-cyano-2-methylphenoxy)cyclohexyl) pyridazine-3-carboxamide (Int-2)

A flask was charged with 4-(((1r,4r)-4-aminocyclohexyl)oxy)-2-chloro-3-methylbenzonitrile (Int-1, 4 g, 15.15 mmol, 1.0 eq), 6-chloropyridazine-3-carboxylic acid (SM-3, 2.3 g, 15.15 mmol, 1.0 eq), DIPEA (7.9 mL, 45.45 mmol, 3.0 eq), EDC·HCl (4.3 g, 22.72 mmol, 1.5 eq), HOBt (3 g, 22.72 mmol, 1.5 eq), DMAP (184 mg, 1.51 mmol, 0.1 eq) and DMF (40 mL, 10 vol). The reaction mixture was stirred under a nitrogen atmosphere at ambient temperature until TLC indicated complete consumption of starting material, diluted with water (100 mL) and extracted with ethyl acetate (2×200 mL). The combined organic layer was washed with brine solution (100 mL), dried over sodium sulfate, filtered and concentrated under reduced pressure. The crude residue was purified by flash column (Silica, 50-60% ethyl acetate in hexane) and the pure fractions were combined and concentrated under reduced pressure to provide 6-chloro-N-((1r,4r)-4-(3-chloro-4-cyano-2-methylphenoxy) cyclohexyl) pyridazine-3-carboxamide (1.1 g, 18%).

$^1$H NMR (400 MHz, DMSO-d$_6$) δ 9.14 (d, J=8.31 Hz, 1H), 8.22 (d, J=8.80 Hz, 1H), 8.10 (d, J=8.80 Hz, 1H), 7.77 (d, J=8.31 Hz, 1H), 7.27 (d, J=8.80 Hz, 1H), 4.43-4.57 (m, 1H), 3.86-4.01 (m, 1H), 2.23 (s, 3H), 2.13 (d, J=9.78 Hz, 2H), 1.91 (d, J=9.78 Hz, 2H), 1.63-1.77 (m, 2H), 1.48-1.62 (m, 2H). LCMS: 405.2 [M+H]$^+$.

Step-3: Preparation of N-((1r,4r)-4-(3-Chloro-4-cyano-2-methylphenoxy)cyclohexyl)-6-(4-(hydroxyl methyl)piperidin-1-yl)pyridazine-3-carboxamide (Int-3)

A flask was charged with 6-chloro-N-((1r,4r)-4-(3-chloro-4-cyano-2-methylphenoxy)cyclohexyl)-pyridazine-3-carboxamide (Int-2, 1 g, 2.46 mmol, 1.0 eq), piperidin-4-ylmethanol (SM-4, 425 mg, 3.70 mmol, 1.5 eq), K$_2$CO$_3$ (1 g, 7.40 mmol, 3.0 eq) and DMF (10 mL, 10 vol). The reaction mixture was allowed to stir under a nitrogen atmosphere at ambient temperature until TLC indicated complete consumption of starting material. The reaction mixture was then diluted with water (100 mL), extracted with ethyl acetate (2×200 mL) and the combined organic layer was washed with brine solution (100 mL) and dried over sodium sulfate. The organic solvent was filtered, concentrated under reduced pressure and purified by flash column (Silica, 50-60% ethyl acetate in hexane). The pure fractions were combined and the solvent evaporated under reduced pressure to obtain N-((1r,4r)-4-(3-chloro-4-cyano-2-methylphenoxy)cyclohexyl)-6-(4-(hydroxyl methyl)piperidin-1-yl) pyridazine-3-carboxamide (1 g, 84%).

$^1$H NMR (400 MHz, DMSO-d$_6$) δ 8.58 (d, J=8.31 Hz, 1H), 7.95 (s, 1H), 7.78 (t, J=9.05 Hz, 2H), 7.33 (d, J=9.78 Hz, 1H), 7.26 (d, J=8.80 Hz, 1H), 4.42-4.55 (m, 5H), 3.81-3.94 (m, 1H), 3.27 (t, J=5.14 Hz, 2H), 2.23 (s, 3H), 2.11 (d, J=10.76 Hz, 2H), 1.90 (d, J=10.27 Hz, 2H), 1.46-1.81 (m, 7H), 1.06-1.22 (m, 2H). LCMS: 484.4 [M+H]+.

Step-4: Preparation of N-((1r,4r)-4-(3-Chloro-4-cyano-2-methylphenoxy)cyclohexyl)-6-(4-formylpiperidin-1-yl)pyridazine-3-carboxamide (Int-4)

A flask was charged with N-((1r,4r)-4-(3-chloro-4-cyano-2-methylphenoxy)cyclohexyl)-6-(4-(hydroxyl methyl)piperidin-1-yl)pyridazine-3-carboxamide (Int-3, 800 mg, 1.65 mmol, 1.0 eq), Dess-Martin periodinane (1 g, 2.47 mmol, 1.5 eq) and DCM (10 mL, 10 vol). The reaction mixture was allowed to stir under a nitrogen atmosphere at ambient temperature until TLC indicated complete consumption of starting material. The reaction mixture was then quenched with saturated bicarbonate solution (100 mL) and the aqueous layer was extracted with DCM (2×200 mL). The combined organic layer was washed with brine solution (100 mL), dried over sodium sulfate, filtered and concentrated under reduced pressure to obtain N-((1 r,4 r)-4-(3-chloro-4-cyano-2-methylphenoxy)cyclohexyl)-6-(4-formylpiperidin-1-yl)pyridazine-3-carboxamide (750 mg, 94%).

$^1$H NMR (400 MHz, DMSO-d$_6$) δ 9.62 (s, 1H), 8.60 (d, J=7.83 Hz, 1H), 7.8 (d, J=8.40 Hz, 1H), 7.37 (d, J=9.78 Hz, 1H), 7.26 (d, J=8.80 Hz, 1H), 4.48-4.50 (m, 1H), 4.31 (d, J=13.21 Hz, 2H), 3.86-3.89 (m, 1H), 3.26 (t, J=11.98 Hz, 2H), 2.61-2.76 (m, 1H), 2.20-2.30 (m, 4H), 2.10-2.12 (m, 2H), 1.81-2.00 (m, 4H), 1.46-1.70 (m, 6H). LCMS: 482.4 [M+H]$^+$.

Step-5: Preparation of tert-Butyl 4-((7-Ethyl-6-oxo-5,6-dihydro-1,5-naphthyridin-3-yl)methyl) piperazine-1-carboxylate (Int-5)

A flask was charged with 7-(chloromethyl)-3-ethyl-1,5-naphthyridin-2(1H)-one (Int-B, 2.4 g, 9.30 mmol, 1.0 eq), tert-butyl piperazine-1-carboxylate (SM-5, 1.7 g, 9.30 mmol, 1.0 eq), DIPEA (8.5 mL, 46.5 mmol, 5.0 eq), KI (166 mg, 1.8 mmol, 0.2 eq) and acetonitrile (24 mL, 10 vol). The reaction mixture was allowed to stir under a nitrogen atmosphere at 80° C. until TLC indicated complete consumption of starting material, cooled down to ambient temperature, concentrated under reduced pressure, diluted with water (100 mL) and extracted with ethyl acetate (2×200 mL). The combined organic layer was washed with brine solution (100 mL), dried over sodium sulfate, filtered, concentrated under reduced pressure and purified by flash chromatography (Silica, 0-3% % MeOH in DCM). The pure fractions were combined and the volatiles were evaporated under reduced pressure to provide tert-butyl 4-((7-ethyl-6-oxo-5,6-dihydro-1,5-naphthyridin-3-yl)methyl) piperazine-1-carboxylate (1.7 g, 50%).

$^1$H NMR (400 MHz, DMSO-d$_6$) δ 11.84 (s, 1H), 8.36 (d, J=1.17 Hz, 1H), 7.74 (s, 1H), 7.58 (s, 1H), 3.58 (s, 2H), 3.33 (s, 4H), 2.50 (d, J=1.57 Hz, 2H), 2.34 (t, J=4.30 Hz, 4H), 1.39 (s, 9H), 1.17 (t, J=7.43 Hz, 3H). LCMS: 373.3 [M+H]$^+$.

Step-6: Preparation of 3-Ethyl-7-(piperazin-1-ylmethyl)-1,5-naphthyridin-2(1H)-one Hydrochloride Salt (Int-6)

A flask was charged with tert-butyl 4-((7-ethyl-6-oxo-5,6-dihydro-1,5-naphthyridin-3-yl)methyl) piperazine-1-carboxylate (Int-5, 1.7 g, 4.56 mmol, 1.0 eq), 1,4-dioxane·HCl (17 mL, 10 vol, 4M) and DCM (17 mL, 10 vol). The reaction mixture was allowed to stir under a nitrogen atmosphere at ambient temperature until TLC indicated complete consumption of starting material. Reaction mixture was then evaporated under reduced pressure, washed with diethyl ether (50 mL) and dried obtained 3-ethyl-7-(piperazin-1-ylmethyl)-1,5-naphthyridin-2(1H)-one hydrochloride salt (1.37 g, 97%).

$^1$H NMR (400 MHz, DMSO-d$_6$) δ 12.28 (br s, 1H), 9.88 (br s, 2H), 8.74 (s, 1H), 7.94 (s, 1H), 7.83 (s, 1H), 4.56 (br s, 2H), 3.43-3.54 (m, 8H), 2.57 (q, J=7.17 Hz, 2H), 1.18 (t, J=7.34 Hz, 3H). LCMS: 273.2 [M+H]$^+$.

Step-7: Preparation of N-((1r,4r)-4-(3-Chloro-4-cyano-2-methylphenoxy)cyclohexyl)-6-(4-((4-((7-ethyl-6-oxo-5,6-dihydro-1,5-naphthyridin-3-yl) methyl)piperazin-1-yl)methyl)piperidin-1-yl) pyridazine-3-carboxamide (66)

A flask was charged with N-((1r,4r)-4-(3-chloro-4-cyano-2-methylphenoxy)cyclohexyl)-6-(4-formylpiperidin-1-yl) pyridazine-3-carboxamide (Int-4, 700 mg, 1.45 mmol, 1.0 eq), 3-ethyl-7-(piperazin-1-ylmethyl)-1,5-naphthyridin-2 (1H)-one hydrochloride salt (Int-6, 536 mg, 1.74 mmol, 1.2 eq, free base), AcOH (0.35 mL, 0.5 vol) and IPA (14 mL, 20 vol). The reaction mixture was stirred under a nitrogen atmosphere at 80° C. for 16 h, allowed to cool down to ambient temperature and added NaCNBH$_3$ (174 mg, 2.90 mmol, 2.0 eq). The resulting reaction mixture was stirred at ambient temperature until TLC indicated complete consumption of starting material. The reaction mixture was then quenched with saturated ammonium chloride (100 mL), extracted with ethyl acetate (2×200 mL) and the combined organic layer was washed with brine solution (100 mL) and dried over sodium sulfate. The organic solvent was filtered, concentrated under reduced pressure and purified by Prep. HPLC. The pure fractions were combined and lyophilized to obtain N-((1r,4r)-4-(3-chloro-4-cyano-2-methylphenoxy)-cyclohexyl)-6-(4-((4-((7-ethyl-6-oxo-5,6-dihydro-1,5-naphthyridin-3-yl)methyl)piperazin-1-yl)methyl)-piperidin-1-yl)pyridazine-3-carboxamide (25 mg, 2.5%).

$^1$H NMR (400 MHz, DMSO-d$_6$) δ 11.83 (br s, 1H), 8.58 (d, J=8.32 Hz, 1H), 8.35 (d, J=4.40 Hz, 1H), 7.77 (dd, J=16.87, 9.54 Hz, 3H), 7.57 (d, J=4.40 Hz, 1H), 7.20-7.36 (m, 2H), 4.58-4.62 (m, 1H), 4.37-4.59 (m, 2H), 3.70-3.96 (m, 2H), 3.49-3.68 (m, 3H), 3.34-3.42 (m, 2H), 2.99 (t, J=11.49 Hz, 1H), 2.48-2.53 (m, 4H), 2.29-2.44 (m, 8H), 2.24 (s, 3H), 2.06-2.18 (m, 2H), 1.89-191 (m, 2H), 1.37-1.71 (m, 6H), 1.15-1.25 (m, 3H). LCMS: 738.6 [M+H]$^+$.

Procedure 12: Preparation of N-((1R,4R)-4-((3-Chloro-4-cyanophenyl)(methyl)amino)cyclohexyl)-6-(4-((4-((7-ethyl-6-oxo-5,6-dihydro-1,5-naphthyridin-3-yl)methyl)piperazin-1-yl)methyl)piperidin-1-yl)pyridazine-3-carboxamide (67)

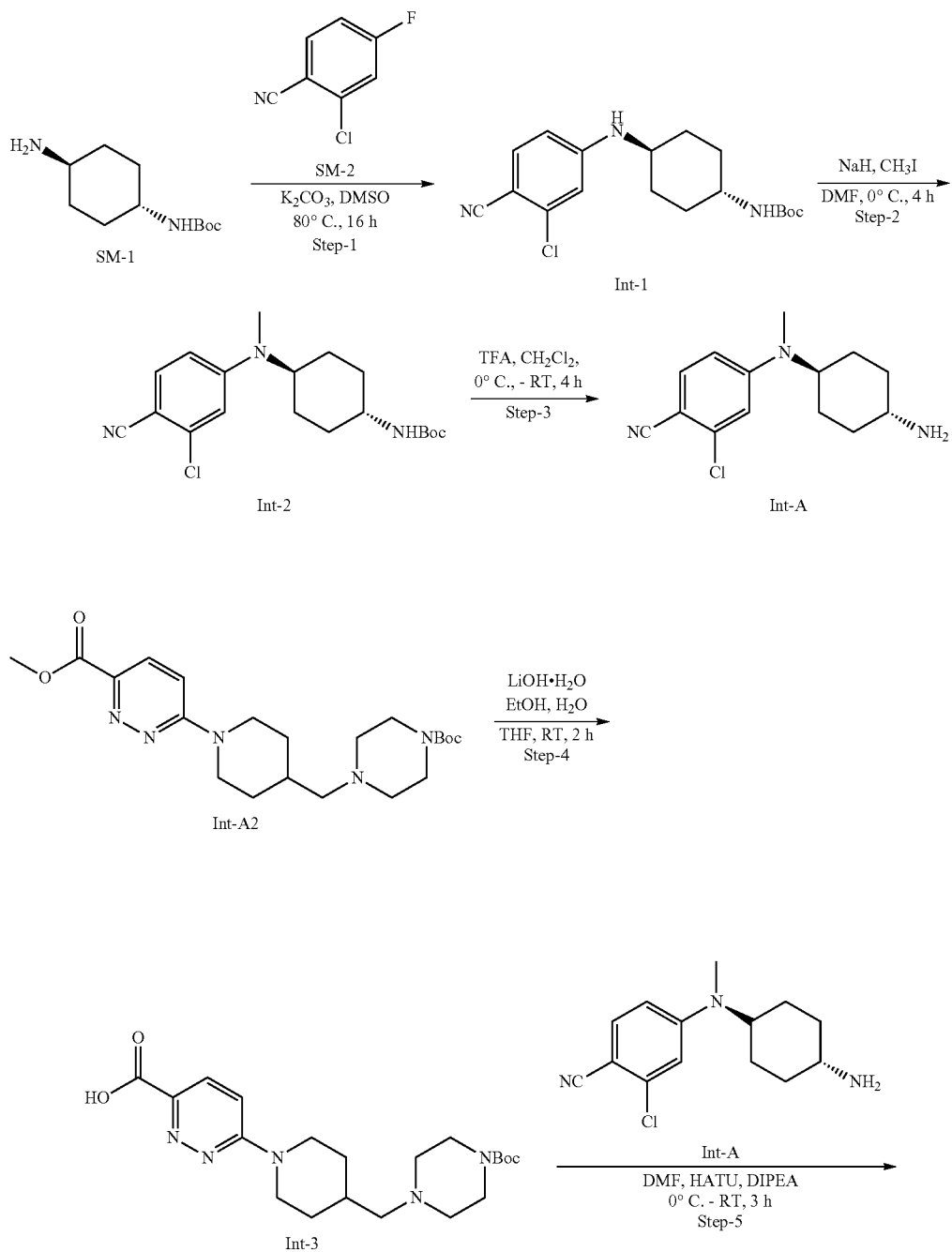

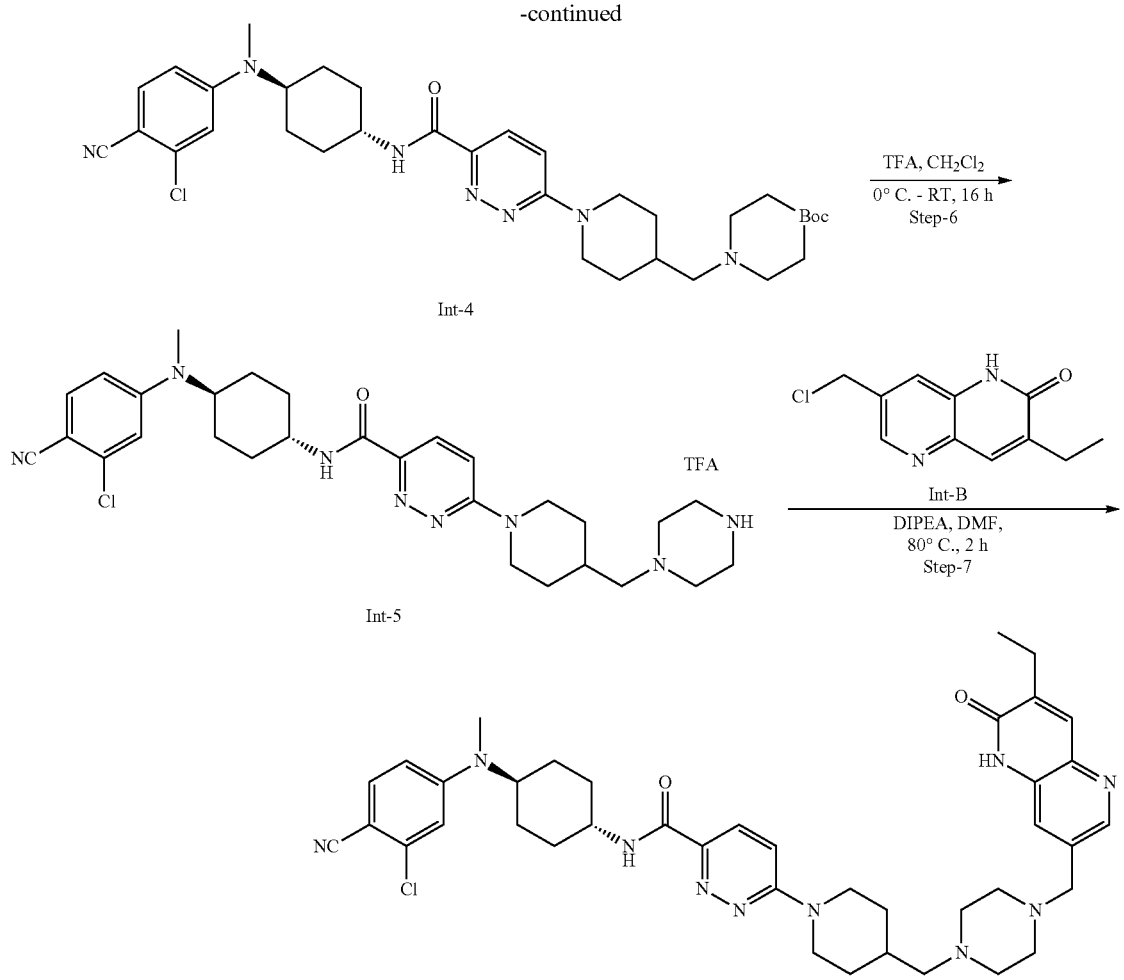

Step-1: Preparation of tert-Butyl((1R,4R)-4-(3-Chloro-4-cyanophenyl)amino)cyclohexyl)carbamate (Int-1)

To a stirred solution of tert-butyl ((1R,4R)-4-aminocyclohexyl)carbamate (SM-1, 3.0 g, 19.2 mmol, 1.0 eq) and 2-chloro-4-fluorobenzonitrile (SM-2, 5.37 g, 25 mmol, 1.3 eq) in DMSO (30 mL) was added potassium carbonate (5.30 g, 38.4 mmol, 2.0 eq) at room temperature. The reaction mixture was heated to 80° C. and stirred for 16 h. Progress of the reaction was monitored by TLC. After completion of the reaction, the reaction mixture was diluted with ice cold water (120 mL), filtered the solid and again washed with cold water and dried under reduced pressure to obtain a solid. The solid material was recrystallized from ethanol to afford the desired product (5.1 g, 75%).

LCMS: 350.2 [M+H]$^+$.

Step-2: Preparation of tert-Butyl((1R,4R)-4-((3-Chloro-4-cyanophenyl)(methyl)amino)cyclohexyl) carbamate (Int-2)

To a stirred solution of tert-butyl ((1R,4R)-4-((3-chloro-4-cyanophenyl)amino)cyclohexyl)carbamate (Int-1, 5.1 g, 14.6 mmol, 1.0 eq) and NaH (60% in mineral oil) (615 mg, 16.0 mmol, 1.1 eq) in DMF (51 mL) was added methyl iodide (0.9 mL, 14.6 mmol, 1.0 eq) dropwise over a period of 10 min at 0° C. and stirred for 4 h. Progress of the reaction was monitored by TLC. After completion of the reaction, the reaction mixture was diluted with ice cold water (120 mL), filtered the solid and again washed with cold water and dried under reduced pressure to obtain a solid compound. The solid compound was recrystallized from ethanol to afford the desired product (3.5 g, 67%).

LCMS: 364.2 [M+H]$^+$.

Step-3: Preparation of 4-(((1R,4R)-4-Aminocyclohexyl)(methyl)amino)-2-chlorobenzonitrile (Int-A)

To a stirred solution of tert-butyl ((1R,4R)-4-((3-chloro-4-cyanophenyl)(methyl)amino)cyclohexyl)-carbamate Int-2 (3.5 g, 9.64 mmol, 1.0 eq) in DCM (35 mL) under nitrogen atmosphere was added TFA (7.8 mL, 96.4 mmol, 10 eq) at 0° C. The reaction mixture was allowed to room temperature and stirred for 4 h. Progress of the reaction was monitored by TLC. After completion of the reaction, solvents were evaporated under reduced pressure to obtain crude compound. The crude compound obtained was washed with diethyl ether (3×30 mL) and dried under vacuum to afford the desired product (3.0 g, 86%).

$^1$H NMR (400 MHz, DMSO-d$_6$) δ 7.82 (br s, 3H), 7.60 (d, J=8.80 Hz, 1H), 6.97 (d, J=2.45 Hz, 1H), 6.84 (dd, J=9.05, 2.20 Hz, 1H), 3.69-3.91 (m, 1H), 3.02 (br d, J=4.40 Hz, 1H), 2.81 (s, 3H), 1.96 (br d, J=11.25 Hz, 2H), 1.67 (br d, J=7.34 Hz, 3H), 1.52 (br dd, J=10.76, 5.87 Hz, 2H). LCMS: 264.1 [M+H]+.

Step-4: Preparation of 6-(4-((4-(tert-Butoxycarbonyl)piperazin-1-yl)methyl)piperidin-1-yl)pyridazine-3-carboxylic Acid (Int-3)

To a stirred solution of methyl 6-(4-((4-(tert-butoxycarbonyl)piperazin-1-yl)methyl)piperidin-1-yl)pyridazine-3-carboxylate (Int-A2, 950 mg, 2.0 mmol, 1.0 eq) in THF (5 mL), ethanol (5 mL) and water (5 mL) was added lithium hydroxide monohydrate (250 mg, 5.97 mmol, 5 eq) at room temperature and the reaction mixture was stirred for 2 h. Progress of the reaction was monitored by TLC. After completion of the reaction, volatiles were removed under reduced pressure and the crude reaction mixture was diluted with water (30 mL) and acidified using 1N HCl until the pH reached ~5. The aqueous layer was extracted with ethyl acetate (2×30 mL) and 10% methanol in dichloromethane (2×30 mL). The combined organic extracts was washed with brine (70 mL), dried over anhydrous sodium sulfate, filtered and concentrated under reduced pressure to afford the desired product (600 mg, crude), which was used in next step without further purification.

$^1$H NMR (400 MHz, DMSO-$d_6$) δ 11.78 (br d, J=6.36 Hz, 1H), 11.28 (br s, 1H), 10.14 (br s, 1H), 7.81 (br d, J=9.29 Hz, 1H), 7.35 (br d, J=9.78 Hz, 1H), 4.51 (br d, J=12.72 Hz, 2H), 3.94 (br d, J=12.72 Hz, 1H), 3.70 (br s, 1H), 3.33 (br s, 2H), 2.91-3.14 (m, 5H), 2.21 (br s, 1H), 2.02 (br d, J=11.25 Hz, 2H), 1.42 (s, 3H), 1.22 (br d, J=7.34 Hz, 2H), 1.10 (s, 1H). LCMS: 406.2 [M+H]+.

Step-5: Preparation of tert-Butyl 4-((1-(6-(((1R,4R)-4-((3-Chloro-4-cyanophenyl)(methyl)amino)cyclohexyl)-carbamoyl)pyridazin-3-yl)piperidin-4-yl)methyl)piperazine-1-carboxylate (Int-4)

To a stirred solution of 6-(4-((4-(tert-butoxycarbonyl)piperazin-1-yl)methyl)piperidin-1-yl)pyridazine-3-carboxylic acid (Int-3, 310 mg, 0.86 mmol, 1.0 eq) and 4-0(1s,4s)-4-aminocyclohexyl)(methyl)amino)-2-chlorobenzonitrile (Int-A, 297 mg, 1.09 mmol, 1.3 eq) in DMF (6 mL) were added HATU (491 mg, 1.29 mmol, 1.5 eq) and DIPEA (334 mg, 2.59 mmol, 3 eq) at 0° C. The reaction mixture was allowed to warm up to room temperature and stir for 3 h. Progress of the reaction was monitored by TLC. After completion of the reaction, the reaction mixture was diluted with water (60 mL), filtered the precipitate and dried under vacuum to obtain the crude product. The crude obtained was purified by column chromatography by eluting with 3-6% methanol in dichloromethane to afford the desired product (400 mg, 54%).

LCMS: 651.4 [M+H]+.

Step-6: Preparation of N-((1R,4R)-4-((3-Chloro-4-cyanophenyl)(methyl)amino)cyclohexyl)-6-(4-(piperazin-1-ylmethyl)piperidin-1-yl)pyridazine-3-carboxamide TFA Salt (Int-5)

To a stirred solution of tert-butyl 4-((1-(6-(((1R,4R)-4-((3-chloro-4-cyanophenyl)(methyl)amino)-cyclohexyl)carbamoyl)pyridazin-3-yl)piperidin-4-yl)methyl)piperazine-1-carboxylate (Int-4, 400 mg, 0.615 mmol, 1.0 eq) in DCM (4 mL) under nitrogen atmosphere was added TFA (1 mL, 2.5 vol) at 0° C. The reaction mixture was allowed to warm up to room temperature and stir for 16 h. Progress of the reaction was monitored by TLC. After completion of the reaction, solvents were evaporated under reduced pressure to obtain the crude product. The crude obtained was washed with diethyl ether (3×20 mL), dried under vacuum to afford the desired product (420 mg, 89%).

$^1$H NMR (400 MHz, DMSO-$d_6$) δ 8.97 (br s, 1H), 8.48 (br d, J=8.31 Hz, 1H), 7.84 (br d, J=9.29 Hz, 1H), 7.61 (br d, J=8.80 Hz, 1H), 7.38 (br d, J=9.29 Hz, 1H), 6.94 (br s, 1H), 6.82 (br d, J=8.80 Hz, 1H), 4.50 (br d, J=12.72 Hz, 2H), 3.70-3.95 (m, 2H), 3.17-3.46 (m, 6H), 3.02 (br t, J=12.23 Hz, 3H), 2.85 (s, 5H), 2.07 (br s, 1H), 1.57-1.97 (m, 11H), 1.11-1.27 (m, 2H), 1.09 (br t, J=7.09 Hz, 2H).

Step-7: Preparation of N-((1R,4R)-4-((3-Chloro-4-cyanophenyl)(methyl)amino)cyclohexyl)-6-(4-((4-((7-ethyl-6-oxo-5,6-dihydro-1,5-naphthyridin-3-yl)methyl)piperazin-1-yl)methyl)piperidin-1-yl)pyridazine-3-carboxamide (67)

To a stirred solution of N-((1R,4R)-4-((3-chloro-4-cyanophenyl)(methyl)amino)cyclohexyl)-6-(4-(piperazin-1-ylmethyl)piperidin-1-yl)pyridazine-3-carboxamide (Int-5, 400 mg, 0.618 mmol, 1.0 eq) in DMF (4 mL) were added DIPEA (239 mg, 1.85 mmol, 3 eq) and 7-(chloromethyl)-3-ethyl-1,5-naphthyridin-2(1H)-one (Int-B, 165 mg, 0.714 mmol, 1.2 eq) at room temperature. The reaction mixture was heated to 80° C. and stirred for 2 h. Progress of the reaction was monitored by TLC. After completion of the reaction, the reaction mixture was diluted with water (60 mL), filtered the precipitate and dried under reduced pressure to obtain the crude product. The crude obtained was purified by column chromatography by eluting with 5-10% methanol in dichloromethane to afford the desired product (130 mg, 28.5%).

$^1$H NMR (400 MHz, DMSO-$d_6$) δ 11.81 (s, 1H), 8.46 (br d, J=8.31 Hz, 1H), 8.34 (s, 1H), 7.68-7.83 (m, 2H), 7.53-7.63 (m, 2H), 7.30 (br d, J=9.78 Hz, 1H), 6.93 (s, 1H), 6.81 (br d, J=8.80 Hz, 1H), 4.44 (br d, J=13.21 Hz, 2H), 3.67-3.88 (m, 2H), 3.55 (br s, 2H), 2.97 (br t, J=11.98 Hz, 2H), 2.83 (s, 3H), 2.51 (br s, 4H), 2.38 (br s, 7H), 2.12 (br d, J=5.87 Hz, 2H), 1.57-1.95 (m, 11H), 1.16 (br t, J=7.34 Hz, 4H). HPLC Purity: 95.1%. LCMS: 737.09 [M+H]+.

Procedure 13: Preparation of 2-Chloro-4-(((1R,2S)-1-(5-(4-((4-((7-ethyl-6-oxo-5,6-dihydro-1,5-naphthyridin-3-yl)-methyl)piperazin-1-yl)methyl)phenyl)-1,3,4-oxadiazol-2-yl)-2-hydroxypropyl)amino)benzonitrile (68)

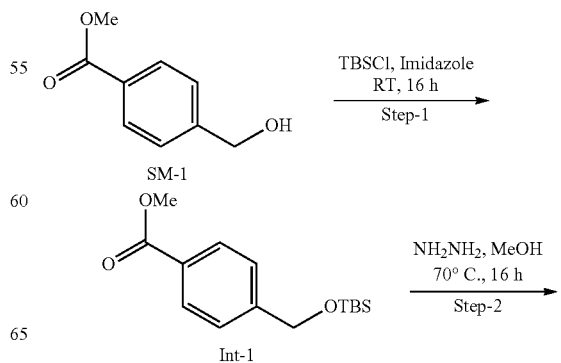

-continued

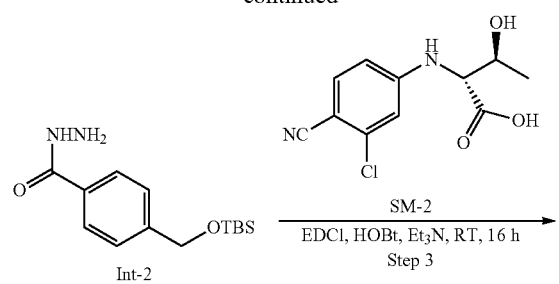

Int-3

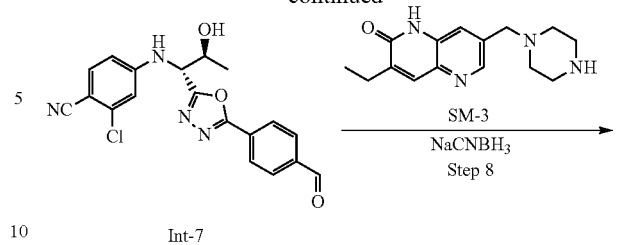

Int-7

Step-1: Preparation of Methyl 4-(((tert-Butyldimethylsilyl)oxy)methyl)benzoate A flask was charged with methyl 4-(hydroxymethyl)benzoate (SM-1, 10 g, 60.24 mmol, 1.0 eq), imidazole (6.1 g, 90.3 mmol, 1.5 eq), TBSCl (13.5 g, 90.3 mmol, 1.5 eq) and DCM (100 mL, 10 vol). The reaction mixture was stirred under nitrogen atmosphere at ambient temperature until TLC indicated complete consumption of starting material. Reaction mixture was then diluted with water (200 mL), extracted with DCM (2×400 mL) and the combined organic layer was washed with brine solution (200 mL) and dried over sodium sulfate. The organic solvent was filtered and concentrated under reduced pressure to give the crude product which was purified using a flash column (Silica, 0-20% ethyl acetate in hexane). The pure fractions were combined and concentrated under reduced pressure to obtain methyl 4-(((tert-butyldimethylsilyl)oxy)-methyl)benzoate (15 g, 88%).

$^1$H NMR (400 MHz, DMSO-$d_6$) δ 7.95 (d, J=7.34 Hz, 2H), 7.45 (d, J=7.34 Hz, 2H), 4.79 (s, 2H), 3.84 (s, 3H), 0.91 (s, 9H), 0.08 (s, 6H). LCMS: 281.2 [M+H]$^+$.

Step-2: Preparation of 4-(((tert-Butyldimethylsilyl)oxy)methyl)benzohydrazide (Int-2)

A flask was charged with methyl 4-(((tert-butyldimethylsilyl)oxy)methyl)benzoate (Int-1, 15 g, 53.57 mmol, 1.0 eq), hydrazine hydrate (26.7 g, 535.7 mmol, 1.5 eq) and MeOH (150 mL, 10 vol). The reaction mixture was allowed to stir at 70° C. until TLC indicated complete consumption of starting material. Reaction mixture was then cooled to ambient temperature and concentrated under reduced pressure and the resulting crude product was triturated with diethyl ether (50 mL), dried to afford 4-(((tert-butyldimethylsilyl)oxy)methyl)-benzohydrazide (15 g, 100%).

$^1$H NMR (400 MHz, DMSO-$d_6$) δ 9.72 (br s, 1H), 7.79 (d, J=7.83 Hz, 2H), 7.36 (d, J=7.83 Hz, 2H), 4.75 (s, 2H), 4.43 (br s, 2H) 0.91 (s, 9H), 0.08 (s, 6H). LCMS: 281.2 [M+H]$^+$.

Step-3: Preparation of 4-(((tert-Butyldimethylsilyl)oxy)methyl)-N'-chloro-4-cyanophenyl)-D-threonyl)benzohydrazide (Int-3)

A flask was charged with (3-chloro-4-cyanophenyl)-D-threonine (SM-2, 3 g, 11.81 mmol, 1.0 eq), 4-(((tert-butyldimethylsilyl)oxy)methyl)benzohydrazide (Int-2, 3.3 g, 11.81 mmol, 1.0 eq), DIPEA (6.5 mL, 45.4 mmol, 3.0 eq), EDC·HCl (3.3 g, 17.71 mmol, 1.5 eq), HOBt (2.39 g, 17.71 mmol, 1.5 eq), DMAP (143 mg, 1.18 mmol, 0.1 eq) and DMF (60 mL, 20 vol). The reaction mixture was stirred under nitrogen atmosphere at ambient temperature until TLC indicated complete consumption of starting material. Reaction mixture was then diluted with water (100 mL) and extracted with ethyl acetate (2×200 mL) and the combined organic layer was washed with brine solution (100 mL) and dried over sodium sulfate. The organic layer was concentrated under reduced pressure to obtain crude 4-(((tert-butyldimethylsilyl)oxy)methyl)-N'-((3-chloro-4-cyanophenyl)-D-threonyl)benzohydrazide (3 g, 50%) (used without purification).

LCMS: 517.2 [M+H]$^+$.

Step-4: Preparation of N'—(O-(tert-Butyldimethyl-silyl)-N-(3-chloro-4-cyanophenyl)-D-threonyl)-4-(((tert-butyldimethylsilyl)oxy)methyl)benzohydrazide (Int-4)

A flask was charged with 4-(((tert-butyldimethylsilyl)oxy)methyl)-N'-((3-chloro-4-cyanophenyl)-D-threonyl)benzohydrazide (Int-3, 3 g, 7.46 mmol, 1.0 eq), imidazole (2.5 g, 37.3 mmol, 5 eq), TBSCl (5.5 g, 37.3 mmol, 5 eq) and DCM (30 mL, 10 vol). The reaction mixture was allowed to stir under a nitrogen atmosphere at ambient temperature until TLC indicated complete consumption of starting material. Reaction mixture was then diluted with water (200 mL), extracted with DCM (2×400 mL) and the combined organic layer was washed with brine solution (200 mL) and dried over sodium sulfate. The organic layer was filtered, concentrated under reduced pressure and the resulting residue was purified by flash column (Silica, 20-50% ethyl acetate in hexane). The pure fractions were combined and concentrated under reduced pressure to provide N'—(O-(tert-butyldimethylsilyl)-N-(3-chloro-4-cyanophenyl)-D-threonyl)-4-(((tert-butyldimethyl silyl)oxy)methyl)benzohydrazide (3 g, 63%).

$^1$H NMR (400 MHz, DMSO-d$_6$) δ 10.43 (s, 1H), 10.31 (s, 1H), 7.85 (d, J=12.0 Hz, 2H), 7.55 (d, J=8.0 Hz, 1H), 7.42 (d, J=8.0 Hz, 2H), 7.25 (d, J=8.0 Hz, 1H), 6.92 (s, 1H), 6.79 (d, J=12.0 Hz, 1H), 4.77 (s, 2H), 3.98-4.09 (m, 2H), 1.30 (d, J=6.0 Hz, 3H), 0.90 (s, 9H), 0.74 (s, 9H), 0.08 (s, 6H), 0.05 (s, 3H), −0.89 (s, 3H). LCMS: 629.2 [M−H]+.

Step-4: Preparation of 4-(((1R,2S)-2-((tert-Butyldimethylsilyl)oxy)-1-(5-(4-(((tert-butyldimethyl silyl)oxy)methyl)phenyl)-1,3,4-oxadiazol-2-yl)propyl)amino)-2-chlorobenzonitrile (Int-5)

A flask was charged with N'—(O-(tert-butyldimethylsilyl)-N-(3-chloro-4-cyanophenyl)-D-threonyl)-4-(((tert-butyldimethylsilyl)oxy)methyl)benzohydrazide (Int-4, 3 g, 4.76 mmol, 1.0 eq), DMC-Cl (965 mg, 5.74 mmol, 1.2 eq), TEA (1.37 mL, 9.52 mmol, 2.0 eq) and DCM (30 mL, 10 vol). The reaction mixture was stirred under nitrogen atmosphere at ambient temperature until TLC indicated complete consumption of starting material. Reaction mixture was then diluted with water (100 mL), extracted with DCM (2×200 mL) and the combined organic layer was washed with brine solution (100 mL) and dried over sodium sulfate. The organic layer was filtered, concentrated under reduced pressure and the resulting crude product was purified by flash column (Silica, 20-30% ethyl acetate in hexane). The pure fractions were combined and concentrated under reduced pressure to afford 4-(((1R,2S)-2-((tert-butyldimethylsilyl)oxy)-1-(5-(4-(((tert-butyldimethyl silyl)oxy)-methyl)phenyl)-1,3,4-oxadiazol-2-yl)propyl)amino)-2-chlorobenzonitrile (2.3 g, 79%).

$^1$H NMR (400 MHz, DMSO-d$_6$) δ 7.95 (d, J=8.38 Hz, 2H), 7.47-7.64 (m, 3H), 7.07-7.20 (m, 2H), 6.91 (dd, J=8.63, 2.00 Hz, 1H), 5.21 (dd, J=9.19, 3.94 Hz, 1H), 4.80 (s, 2H), 4.48 (dd, J=6.13, 4.00 Hz, 1H), 1.28 (d, J=6.25 Hz, 3H), 0.91 (s, 9H), 0.73 (s, 9H), 0.10 (s, 6H), 0.02 (s, 3H), −0.16 (s, 3H). LCMS: 613.3 [M+H]$^+$.

Step-6: Preparation of 2-Chloro-4-(((1R,2S)-2-hydroxy-1-(5-(4-(hydroxymethyl)phenyl)-1,3,4-oxadiazol-2-yl)propyl)amino)benzonitrile (Int-6)

A flask was charged with 4-(((1R,2S)-2-((tert-butyldimethylsilyfloxy)-1-(5-(4-(((tert-butyldimethyl silyl) oxy) methyl) phenyl)-1,3,4-oxadiazol-2-yl)propyl)amino)-2-chlorobenzonitrile (Int-5, 2.3 g, 3.75 mmol, 1.0 eq), THF (23 mL, 10 vol) and TBAF (9.3 mL, 9.3 mmol, 2.5 eq, 1 M). The resulting mixture was stirred under a nitrogen atmosphere at room temperature until TLC indicated complete consumption of starting material. The reaction mixture was concentrated under reduced pressure, basified with saturated bicarbonate solution (pH~8) and extracted with DCM (2×100 mL). The combined organic layer was washed with brine solution (100 mL), dried over sodium sulfate and filtered. The organic solvent and concentrated under reduced pressure and the crude product was purified by column chromatography (SiO$_2$, DCM/MeOH gradient) to afford 2-chloro-4-(((1R,2S)-2-hydroxy-1-(5-(4-(hydroxymethyl)phenyl)-1,3,4-oxadiazol-2-yl)propyl)amino)-benzonitrile (1 g, 69% yield).

$^1$H NMR (400 MHz, DMSO-d$_6$) δ 7.93 (d, J=7.83 Hz, 2H), 7.50-7.61 (m, 3H), 7.37 (d, J=8.80 Hz, 1H), 7.09 (s, 1H), 6.88 (d, J=8.80 Hz, 1H), 5.39 (t, J=5.62 Hz, 1H), 5.33 (d, J=4.89 Hz, 1H), 5.06 (dd, J=8.56, 3.18 Hz, 1H), 4.59 (d, J=5.87 Hz, 2H), 4.28-4.37 (m, 1H), 1.23 (d, J=5.87 Hz, 3H). LCMS: 385.2 [M+H]$^+$.

Step-7: Preparation of 2-Chloro-4-(((1R,2S)-1-(5-(4-formylphenyl)-1,3,4-oxadiazol-2-yl)-2-hydroxypropyl)-amino)benzonitrile (Int-7)

A flask was charged with 2-chloro-4-(((1R,2S)-2-hydroxy-1-(5-(4-(hydroxymethyl)phenyl)-1,3,4-oxadiazol-2-yl)propyl)amino)benzonitrile (Int-6, 1 g, 2.6 mmol, 1.0 eq), MnO$_2$ (1.2 g, 13.0 mmol, 5.0 eq) and DCM (10 mL, 10 vol). The reaction mixture was stirred under nitrogen atmosphere at ambient temperature until TLC indicated complete consumption of starting material. Reaction mixture was filtered through celite pad and the filtrate was concentrated under reduced pressure and purified by flash column (Silica, 70-90% ethyl acetate in hexane). The pure fractions were combined and concentrated under reduced pressure to obtain 2-chloro-4-(((1R,2S)-1-(5-(4-formylphenyl)-1,3,4-oxadiazol-2-yl)-2-hydroxy propyl)amino)benzonitrile (750 mg, 75%).

$^1$H NMR (400 MHz, DMSO-d$_6$) δ 10.11 (s, 1H), 8.15-8.23 (m, 2H), 8.09-8.15 (m, 2H), 7.58 (d, J=8.80 Hz, 1H), 7.41 (d, J=8.80 Hz, 1H), 7.10 (br s, 1H), 6.89 (d, J=8.31 Hz, 1H), 5.35 (d, J=4.40 Hz, 1H), 5.11 (dd, J=8.80, 3.42 Hz, 1H), 4.36 (br s, 1H), 1.24 (d, J=5.87 Hz, 3H). LCMS: 383.1 [M+H]$^+$.

Step-8: Preparation of 2-Chloro-4-(((1R,2S)-1-(5-(4-((4-((7-ethyl-6-oxo-5,6-dihydro-1,5-naphthyridin-3-yl)methyl)piperazin-1-yl)methyl)phenyl)-1,3,4-oxadiazol-2-yl)-2-hydroxypropyl)amino)benzonitrile (68)

A flask was charged with 2-chloro-4-(((1R,2S)-1-(5-(4-formylphenyl)-1,3,4-oxadiazol-2-yl)-2-hydroxy propyl)amino)benzonitrile (Int-7, 700 mg, 2.57 mmol, 1.0 eq), 3-ethyl-7-(piperazin-1-ylmethyl)-1,5-naphthyridin-2(1H)-one (SM-3, 786 mg, 2.05 mmol, 0.8 eq, free base), AcOH (3.5 mL, 5 vol) and IPA (7 mL, 10 vol). The reaction mixture was stirred under nitrogen atmosphere at 60° C. for 16 h. The reaction mixture was then cooled down to ambient temperature and NaCNBH$_3$ (818 mg, 3.86 mmol, 1.5 eq) was added. The resulting reaction mixture was stirred at ambient temperature until TLC indicated complete consumption of starting material. Reaction mixture was then quenched with water (100 mL) and extracted with ethyl acetate (2×200 mL). The combined organic layer was washed with brine solution (100 mL), dried over sodium sulfate, filtered and concentrated under reduced pressure. The crude residue was purified by Prep HPLC and the pure fractions were combined and lyophilized to obtain 2-chloro-4-(((1R,2S)-1-(5-(4-((4-((7-ethyl-6-oxo-5,6-dihydro-1,5-naphthyridin-3-yl)methyl)piperazin-1-yl)methyl)phenyl)-1,3,4-oxadiazol-2-yl)-2-hydroxypropyl)amino)-benzonitrile (30.5 mg, 2%).

$^1$H NMR (400 MHz, DMSO-d$_6$) δ 11.82 (s, 1H), 8.35 (s, 1H), 7.91 (d, J=7.83 Hz, 2H), 7.73 (s, 1H), 7.48-7.61 (m, 4H), 7.38 (d, J=8.80 Hz, 1H), 7.08 (s, 1H), 6.87 (d, J=7.83 Hz, 1H), 5.32 (d, J=4.89 Hz, 1H), 5.06 (dd, J=8.31, 3.91 Hz, 1H), 4.31 (dd, J=10.03, 5.14 Hz, 1H), 3.57 (d, J=7.34 Hz, 4H), 3.30 (s, 2H), 2.54 (s, 2H), 2.42 (s, 6H), 1.12-1.30 (m, 6H). LCMS: 639.2 [M+H]$^+$.

Procedure 14: Preparation of 2-Chloro-4-(((1R,2S)-1-(5-(4-((4-((7-ethyl-6-oxo-5,6-dihydro-1,5-naphthyridin-3-yl)methyl)piperazin-1-yl)methyl)phenyl)-1,3,4-oxadiazol-2-yl)-2-hydroxypropyl)amino)-3-methylbenzonitrile (69)

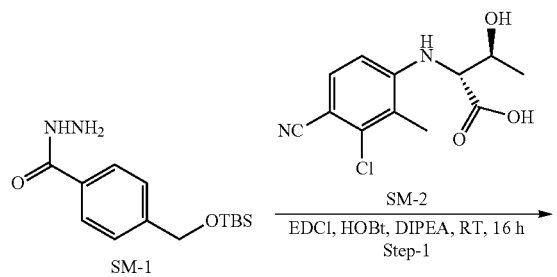

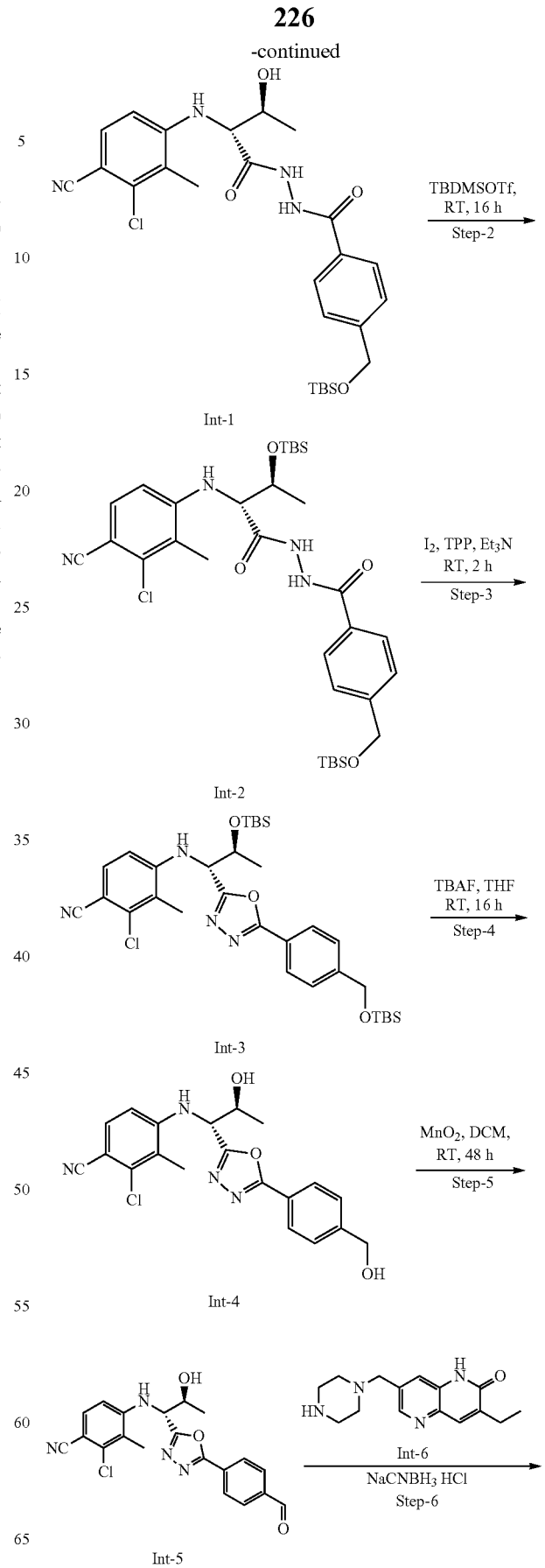

-continued

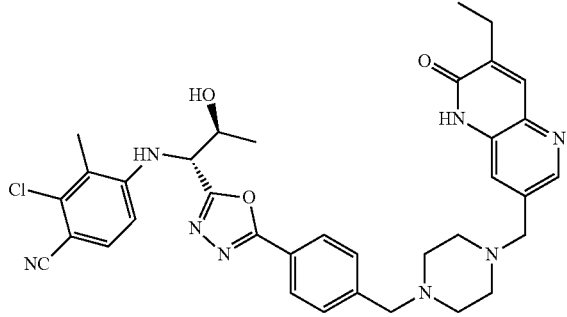

Step-1: Preparation of 4-(((tert-Butyldimethylsilyl)oxy)methyl)-N'-chloro-4-cyano-2-methylphenyl)-D-threonyl)benzohydrazide (Int-1)

A flask was charged with (3-chloro-4-cyano-2-methylphenyl)-D-threonine (SM-2, 5 g, 18.65 mmol, 1.0 eq), 4-(((tert-butyldimethylsilyl)oxy)methyl)benzohydrazide (SM-1, 5.7 g, 20.51 mmol, 1.1 eq), DIPEA (10.3 mL, 55.99 mmol, 3.0 eq), EDC·HCl (5.34 g, 27.97 mmol, 1.5 eq), HOBt (3.77 g, 27.97 mmol, 1.5 eq), DMAP (226 mg, 1.86 mmol, 0.1 eq) and DMF (100 mL, 20 vol). Reaction mixture was allowed to stir under nitrogen atmosphere at ambient temperature until TLC indicated complete consumption of starting material. Reaction mixture was then diluted with water (100 mL), extracted with ethyl acetate (2×200 mL), combined organic layer washed with brine solution (100 mL) and dried over sodium sulfate. The organic layer was filtered, concentrated under reduced pressure and purified by flash column (Silica, 50-60% ethyl acetate in hexane). The pure fractions were combined and concentrated under reduced pressure to obtain 4-(((tert-butyldimethylsilyl)oxy)methyl)-N'-((3-chloro-4-cyano-2-methylphenyl)-D-threonyl)benzohydrazide (5 g, 50%).

$^1$H NMR (400 MHz, DMSO-d$_6$) δ 10.40 (br s, 1H), 10.17 (br s, 2H), 7.84 (d, J=7.83 Hz, 2H), 7.60 (d, J=8.80 Hz, 1H), 7.40 (d, J=7.34 Hz, 2H), 6.66 (d, J=8.80 Hz, 1H), 5.65 (d, J=6.85 Hz, 1H), 5.29 (br s, 1H), 4.77 (s, 2H), 4.12 (br s, 1H), 3.93 (d, J=5.87 Hz, 1H), 2.30 (s, 3H), 1.28 (d, J=5.87 Hz, 3H), 0.91 (s, 9H), 0.08 (s, 6H). LCMS: 531.2 [M+H]$^+$.

Step-2: Preparation of N'—(O-(tert-Butyldimethylsilyl)-N-(3-chloro-4-cyano-2-methylphenyl)-D-threonyl)-4-(((tert-butyldimethylsilyl)oxy)methyl)benzohydrazide (Int-2)

A flask was charged with 4-(((tert-butyldimethylsilyl)oxy)methyl)-N-((3-chloro-4-cyano-2-methylphenyl)-D-threonyl)benzohydrazide (Int-1, 1.2 g, 2.26 mmol, 1.0 eq), tert-butyldimethylsilyl triflate (1.03 mL, 4.52 mmol, 2.0 eq), 2,6-Lutidine (0.52 mL, 4.52 mmol, 2.0 eq) and DCM (24 mL, 20 vol). Reaction mixture was stirred under nitrogen atmosphere at ambient temperature until TLC indicated complete consumption of starting material. Reaction mixture was diluted with water (100 mL), extracted with DCM (2×200 mL) and the combined organic layer was washed with brine solution (100 mL) and dried over sodium sulfate. The organic layer was concentrated under reduced pressure and purified by a flash column (Silica, 20-30% ethyl acetate in hexane). The pure fractions were combined and concentrated under reduced pressure to obtain N'—(O-(tert-butyldimethylsilyl)-N-(3-chloro-4-cyano-2-methylphenyl)-D-threonyl)-4-(((tert-butyldimethylsilyl)oxy)methyl)benzohydrazide (Int-2, 700 mg, 40%).

$^1$H NMR (400 MHz, DMSO-d$_6$) δ 10.37 (br s, 1H), 10.23 (br s, 1H), 7.83 (d, J=8.25 Hz, 2H), 7.60 (d, J=8.76 Hz, 1H), 7.41 (d, J=8.38 Hz, 2H), 6.70 (d, J=8.88 Hz, 1H), 5.61 (d, J=8.75 Hz, 1H), 4.77 (s, 2H), 4.30-4.39 (m, 1H), 4.11 (dd, J=8.76, 5.25 Hz, 1H), 2.26 (s, 3H), 1.30 (s, 3H), 0.91 (s, 9H), 0.82 (s, 9H), 0.08 (m, 12H). LCMS: 645.4 [M+H]$^+$.

Step-3: Preparation of 4-(((1R,2S)-2-((tert-Butyldimethylsilyl)oxy)-1-(5-(4-(((tert-butyldimethylsilyl)oxy)-methyl)phenyl)-1,3,4-oxadiazol-2-yl)propyl)amino)-2-chloro-3-methylbenzonitrile (Int-3)

A flask charged with I$_2$ (1.1 g, 4.96 mmol, 2.0 eq), TPP (1.3 g, 4.96 mmol, 2.0 eq), TEA (1.5 mL, 9.92 mmol, 4.0 eq) and DCM (32 mL, 20 vol) was stirred under nitrogen atmosphere at 0° C. for 30 min., after which time N'—(O-(tert-butyldimethylsilyl)-N-(3-chloro-4-cyano-2-methylphenyl)-D-threonyl)-4-(((tert-butyldimethyl-silyl)oxy)methyl)benzohydrazide (Int-2, 1.6 g, 2.48 mmol, 1.0 eq) was added. Reaction mixture was stirred under nitrogen atmosphere at ambient temperature until TLC indicated complete consumption of starting material. Reaction mixture was diluted with water (100 mL), extracted with DCM (2×200 mL) and the combined organic layer was washed with brine solution (100 mL) and dried over sodium sulfate. The organic layer was filtered, concentrated under reduced pressure and purified by flash column (Silica, 20-30% ethyl acetate in hexane). The pure fractions were combined and concentrated under reduced pressure to afford 4-(((1R,2S)-2-((tert-butyldimethylsilyl)oxy)-1-(5-(4-(((tert-butyldimethylsilyl)oxy)methyl)phenyl)-1,3,4-oxadiazol-2-yl)propyl)amino)-2-chloro-3-methylbenzonitrile (1.5 g, 96%).

$^1$H NMR (400 MHz, DMSO-d$_6$) δ 7.95 (d, J=8.25 Hz, 2H), 7.51-7.58 (m, 3H), 6.86 (d, J=8.88 Hz, 1H), 5.59 (d, J=9.26 Hz, 1H), 5.31 (dd, J=9.13, 2.88 Hz, 1H), 4.79 (s, 2H), 4.61 (dd, J=6.13, 2.88 Hz, 1H), 2.31 (s, 3H), 1.34 (d, J=6.13 Hz, 3H), 0.91 (s, 9H), 0.6 (s, 9H), 0.09 (s, 6H), 0.04 (s, 3H), 0.24 (s, 3H). LCMS: 627.2 [M+H]$^+$.

Step-4: Preparation of 2-Chloro-4-(((1R,2S)-2-hydroxy-1-(5-(4-(hydroxymethyl)phenyl)-1,3,4-oxadiazol-2-yl)propyl)amino)-3-methylbenzonitrile (Int-4)

A flask charged with 4-(((1R,2S)-2-((tert-butyldimethylsilyl)oxy)-1-(5-(4-(((tert-butyldimethyl-silyl)oxy)methyl)phenyl)-1,3,4-oxadiazol-2-yl)propyl)amino)-2-chloro-3-methylbenzonitrile (Int-3, 1.5 g, 2.39 mmol, 1.0 eq) in THF (30 mL, 20 vol), TBAF (9.56 mL, 9.56 mmol, 4.0 eq, 1M in THF) was allowed to stir under nitrogen atmosphere at 0° C. Reaction mixture was stirred under a nitrogen atmosphere at ambient temperature until TLC indicated complete consumption of starting material. Reaction mixture was quenched with water (100 mL), extracted with ethyl acetate (2×200 mL) and the combined organic layer was washed with brine solution (100 mL) and dried over sodium sulfate. The organic layer was concentrated under reduced pressure and purified by a flash column (Silica, 60-80% ethyl acetate in hexane). The pure fractions were combined and concentrated under reduced pressure to obtain 2-chloro-4-(((1R,2S)-2-hydroxy-1-(5-(4-(hydroxymethyl)phenyl)-1,3,4-oxadiazol-2-yl)propyl)amino)-3-methylbenzonitrile (585 mg, 61%).

$^1$H NMR (400 MHz, DMSO-d$_6$) δ 7.92 (d, J=7.83 Hz, 2H), 7.46-7.60 (m, 3H), 6.80 (d, J=8.80 Hz, 1H), 5.87 (d,

J=8.80 Hz, 1H), 5.49 (d, J=5.87 Hz, 1H), 5.39 (t, J=5.62 Hz, 1H), 5.09 (dd, J=7.83, 3.91 Hz, 1H), 4.59 (d, J=5.38 Hz, 2H), 4.35-4.45 (m, 1H), 2.34 (s, 3H), 1.26 (d, J=5.87 Hz, 3H). LCMS: 399.2 [M+H]$^+$.

Step-5: Preparation of 2-Chloro-4-(((1R,2S)-1-(5-(4-formylphenyl)-1,3,4-oxadiazol-2-yl)-2-hydroxy propyl)amino)-3-methylbenzonitrile (Int-5)

A flask was charged with 2-chloro-4-(((1R,2S)-2-hydroxy-1-(5-(4-(hydroxymethyl)phenyl)-1,3,4-oxadiazol-2-yl)propyl)amino)-3-methylbenzonitrile (Int-4, 500 mg, 1.25 mmol, 1.0 eq), MnO$_2$ (1.09 g, 12.5 mmol, 10.0 eq) and DCM (10 mL, 20 vol). Reaction mixture was stirred under nitrogen atmosphere at ambient temperature until TLC indicated complete consumption of starting material. Reaction mixture was filtered through celite pad and the filtrate was concentrated under reduced pressure. The resulting residue was purified by a flash column (Silica, 50-60% ethyl acetate in hexane) and the pure fractions were combined and concentrated under reduced pressure to provide 2-chloro-4-(((1R,2S)-1-(5-(4-formylphenyl)-1,3,4-oxadiazol-2-yl)-2-hydroxypropyl)amino)-3-methylbenzonitrile (440 mg, 88%).

$^1$H NMR (400 MHz, DMSO-d$_6$) δ 10.11 (s, 1H), 8.16-8.22 (m, 2H), 8.08-8.14 (m, 2H), 7.57 (d, J=8.80 Hz, 1H), 6.81 (d, J=8.80 Hz, 1H), 5.88 (d, J=8.80 Hz, 1H), 5.52 (br s, 1H), 5.14 (dd, J=8.31, 3.91 Hz, 1H), 4.43 (br s, 1H), 2.34 (s, 3H), 1.28 (d, J=6.36 Hz, 3H). LCMS: 397.2 [M+H]$^+$.

Step-6: Preparation of 2-Chloro-4-(((1R,2S)-1-(5-(4-((4-((7-ethyl-6-oxo-5,6-dihydro-1,5-naphthyridin-3-yl)methyl)piperazin-1-yl)methyl)phenyl)-1,3,4-oxadiazol-2-yl)-2-hydroxypropyl)amino)-3-methylbenzonitrile (69)

A flask was charged with 2-chloro-4-(((1R,2S)-1-(5-(4-formylphenyl)-1,3,4-oxadiazol-2-yl)-2-hydroxy-propyl) amino)-3-methylbenzonitrile (Int-5, 400 mg, 1.01 mmol, 1.0 eq), 3-ethyl-7-(piperazin-1-ylmethyl)-1,5-naphthyridin-2(1H)-one ((Int-6 free base, prepared in an earlier scheme, 329 mg, 1.21 mmol, 1.2 eq), AcOH (0.2 mL, 0.5 vol) and MeOH (8 mL, 20 vol). Reaction mixture was allowed to stir under nitrogen atmosphere at 60° C. for 16 h. and cool down to ambient temperature. NaCNBH$_3$ (428 mg, 2.02 mmol, 2.0 eq) was then added and the reaction mixture was allowed to stir at ambient temperature until TLC indicated complete consumption of starting material. Reaction mixture was quenched with saturated ammonium chloride (100 mL), extracted with ethyl acetate (2×200 mL) and the combined organic layer was washed with brine solution (100 mL) and dried over sodium sulfate. The organic layer was filtered, concentrated under reduced pressure and purified by Prep HPLC. The pure fractions were combined and lyophilized to obtain 2-chloro-4-(((1R,2S)-1-(5-(44(4-((7-ethyl-6-oxo-5,6-dihydro-1,5-naphthyridin-3-yl)methyl)piperazin-1-yl) methyl)phenyl)-1,3,4-oxadiazol-2-yl)-2-hydroxypropyl) amino)-3-methylbenzonitrile (48 mg, 7.3%).

$^1$H NMR (400 MHz, DMSO-d$_6$) δ 11.81 (s, 1H), 8.35 (s, 1H), 7.91 (d, J=7.83 Hz, 2H), 7.73 (s, 1H), 7.48-7.60 (m, 4H), 6.78 (d, J=8.80 Hz, 1H), 5.87 (d, J=8.31 Hz, 1H), 5.48 (d, J=5.87 Hz, 1H), 5.08 (dd, J=8.07, 3.67 Hz, 1H), 4.34-4.45 (m, 1H), 3.56 (d, J=7.34 Hz, 4H), 2.38-2.42 (m, 8H), 2.34 (s, 3H), 1.26 (d, J=6.36 Hz, 3H), 1.17 (t, J=7.34 Hz, 3H). LCMS: 653.2 [M+H]$^+$.

Procedure 15: Preparation of 7-((4-((1r,4r)-4-((3,5-Difluoro-4-((1R,3R)-2-(2-fluoro-2-methylpropyl)-3-methyl-2,3,4,9-tetrahydro-1H-pyrido[3,4-b]indol-1-yl)phenoxy)methyl)cyclohexane-1-carbonyl) piperazin-1-yl)methyl)-3-ethyl-1,5-naphthyridin-2 (1H)-one (70)

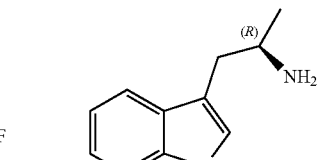

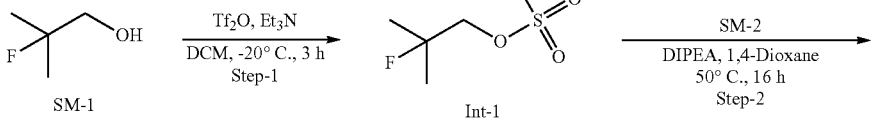

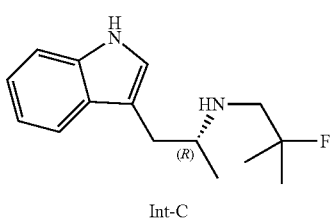

Int-C

-continued
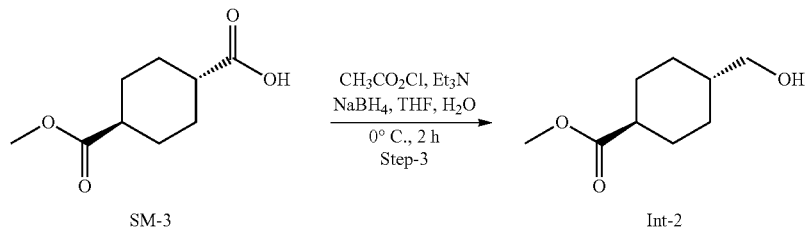
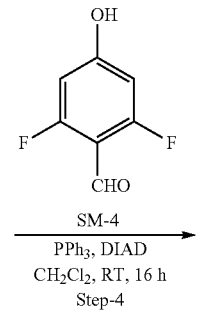
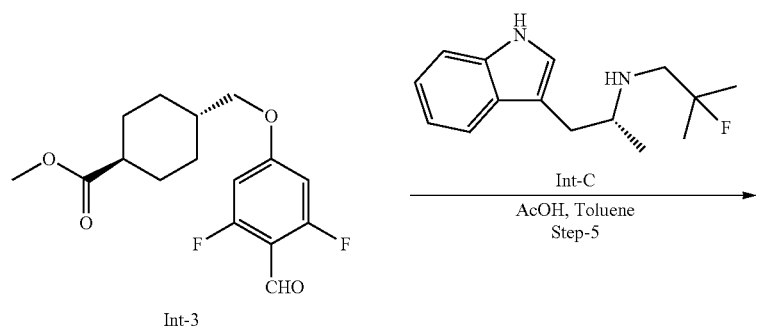
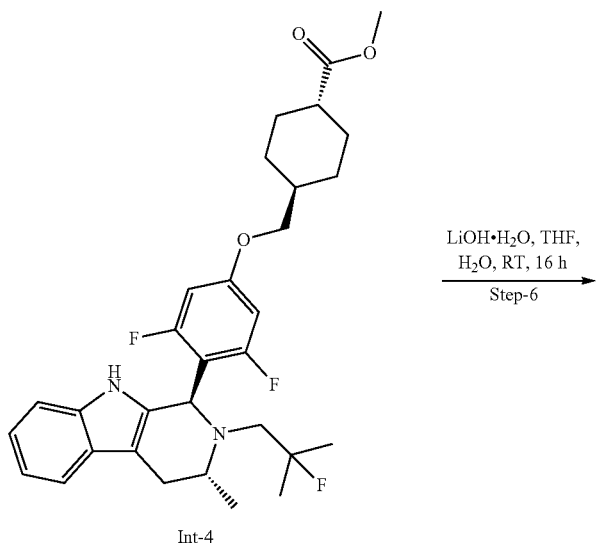

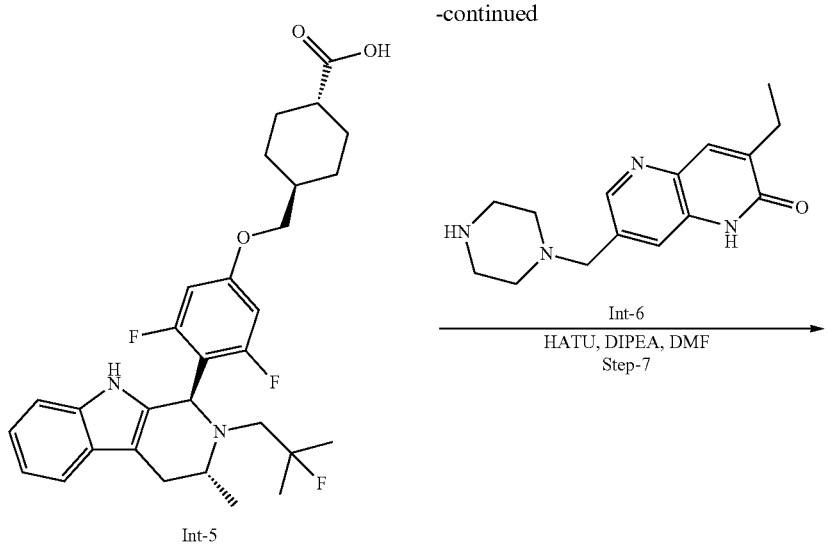

Int-5

Int-6
HATU, DIPEA, DMF
Step-7

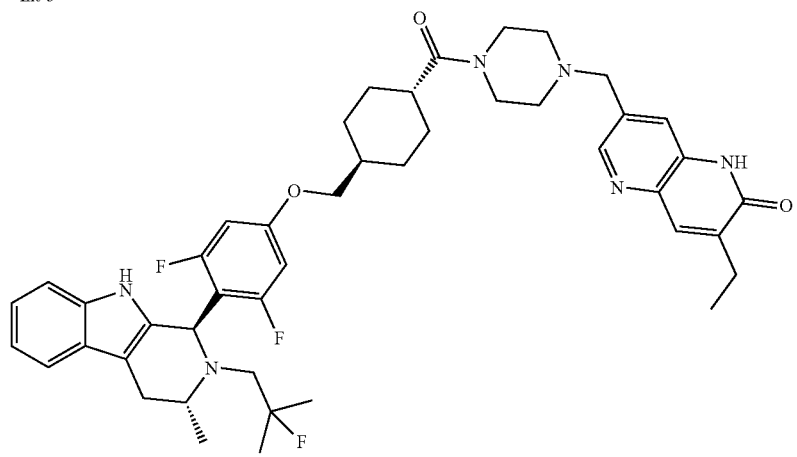

Step-1: Preparation of 2-Fluoro-2-methylpropyl Trifluoromethanesulfonate (Int-1)

To a stirred solution of 2-fluoro-2-methylpropan-1-ol (25 g, 0.271 mol, 1.0 eq) and triethylamine (40 mL, 0.299 mol, 1.1 eq) in DCM (250 mL) was added triflicanhydride (45 mL, 0.271 mol, 1.0 eq) at −20° C. The reaction mixture was allowed to warm up to room temperature and stir for 3 h. Progress of the reaction was monitored by TLC. After completion of the reaction, the reaction mixture was quenched with 1N aq. HCl solution, diluted with water (350 mL) and extracted with dichloromethane (3×300 mL). The combined organic layer was washed with aqueous saturated sodium bicarbonate solution (250 mL), dried over anhydrous sodium sulphate, filtered and concentrated under vacuum to afford the desired product (43.0 g, crude) (used in the next step without further purification).

Step-2: Preparation of (R)—N-(1-(1H-Indol-3-yl)propan-2-yl)-2-fluoro-2-methylpropan-1-amine (Int-C)

To a stirred solution of (R)-1-(1H-indol-3-yl)propan-2-amine (SM-2, 5.0 g, 28.73 mmol, 1.0 eq) in 1,4-dioxane (50 mL) were added DIPEA (15 mL, 86.19 mmol, 3 eq) and 2-fluoro-2-methylpropyl trifluoromethane sulfonate (Int-1, 7.72 g, 34.48 mmol, 1.2 eq) at room temperature. The reaction mixture was heated to 50° C. and stirred for 16 h in a sealed tube. Progress of the reaction was monitored by TLC. After completion of the reaction, solvents were evaporated under reduced pressure to obtain a crude residue. The crude obtained was purified by column chromatography eluting with 30-35% ethyl acetate in heptane to afford the desired product (4.3 g, 60%).

$^1$H NMR (400 MHz, DMSO-$d_6$) δ 10.80 (br s, 1H), 7.52 (d, J=7.83 Hz, 1H), 7.33 (d, J=8.31 Hz, 1H), 7.13 (d, J=1.96 Hz, 1H), 7.05 (t, J=6.85 Hz, 1H), 6.93-6.99 (m, 1H), 2.77-2.93 (m, 2H), 2.57-2.76 (m, 3H), 1.31 (d, J=1.96 Hz, 3H), 1.26 (d, J=2.45 Hz, 3H), 0.98 (d, J=5.87 Hz, 3H). LCMS: 249.4 [M+H]$^+$.

Step-3: Preparation of Methyl (1r,4r)-4-(Hydroxymethyl)cyclohexane-1-carboxylate (Relative trans) (Int-2)

To a stirred solution of (1r,4r)-4-(methoxycarbonyl)cyclohexane-1-carboxylic acid (SM-3, 10 g, 53.7 mmol, 1 eq) in THF (100 mL) were added triethylamine (10.9 mL, 80.5 mmol, 1.5 eq) and methylchloroformate (6.09 g, 6.44 mmol, 1.2 eq) at 0° C. and stirred for 1 h. To this reaction mixture was added dropwise aq. NaBH$_4$ solution (4.06 g, 107 mmol, 2.0 eq) in water (100 mL) over a period of 10 min and stirred for 30 minutes at 0° C. Progress of the reaction was monitored by TLC. After completion of the reaction, the reaction mixture was quenched with saturated NaHCO$_3$ solution (60 mL) and extracted with ethyl acetate (2×100 mL). The combined organic extract was washed with brine (100 mL), dried over anhydrous sodium sulfate, filtered and concentrated under vacuum to obtain the crude product. The crude obtained was purified by column chromatography eluting with 5% acetone in dichloromethane to afford the desired product (6 g, 65%).

$^1$H NMR (400 MHz, CDCl$_3$) δ 3.67 (s, 3H), 3.47 (d, J=6.25 Hz, 2H), 2.28-2.21 (m, 1H), 1.97-2.08 (m, 2H), 1.82-1.93 (m, 2H), 1.38-1.56 (m, 3H), 1.34 (br s, 1H), 0.92-1.07 (m, 2H). LCMS: 173.2 [M+H]$^+$.

Step-4: Preparation of Methyl (1r,4r)-4-((3,5-Difluoro-4-formylphenoxy)methyl)cyclohexane-1-carboxylate (Relative trans) (Int-3)

To a stirred solution of 2,6-difluoro-4-hydroxybenzaldehyde (SM-4, 5 g, 31.6 mmol, 1.0 eq) and methyl (1r,4r)-4-(hydroxymethyl)cyclohexane-1-carboxylate (relative trans) (Int-2, 5.4 g, 31.6 mmol, 1.0 eq) in DCM (100 mL) were added PPh$_3$ (12.4 g, 47.6 mmol, 1.5 eq) and DIAD (9.62 g, 47.6 mmol, 1.5 eq) at room temperature and the reaction mixture was allowed to stir for 16 h. Progress of the reaction was monitored by TLC. After completion of the reaction, solvents were evaporated under reduced pressure to obtain the crude product. The crude obtained was purified by column chromatography eluting with 30% ethyl acetate in heptane to afford the desired product (3.5 g, 35%).

LCMS: 313.2 [M+H]$^+$.

Step-5: Preparation of Methyl (1R,4r)-4-((3,5-Difluoro-4-((1R,3R)-2-(2-fluoro-2-methylpropyl)-3-methyl-2,3,4,9-tetrahydro-1H-pyrido[3,4-b]indol-1-yl)phenoxy)methyl)cyclohexane-1-carboxylate (Int-4)

To a stirred solution of methyl (1r,4r)-4-((3,5-difluoro-4-formylphenoxy)methyl)cyclohexane-1-carboxylate (Int-3, 3.14 g mg, 10.0 mmol, 1.0 eq) and (R)—N-(1-(1H-indol-3-yl)propan-2-yl)-2-fluoro-2-methylpropan-1-amine (Int-C, 2.5 g, 10.0 mmol, 1.0 eq) in toluene (50 mL) was added acetic acid (1.8 g, 30 mmol, 3 eq) at RT. The reaction mixture was heated at 80° C. and allowed to stir for 16 h in a sealed tube. Progress of the reaction was monitored by TLC. After completion of the reaction, solvents were evaporated under reduced pressure to obtain the crude product. The crude obtained was purified by column chromatography eluting with 10% methanol in dichloromethane to afford the desired product (2.7 g, 49%).

$^1$H NMR (400 MHz, DMSO-d$_6$) δ 10.51 (s, 1H), 7.39 (d, J=7.34 Hz, 1H), 7.17 (d, J=7.82 Hz, 1H), 6.89-7.03 (m, 2H), 6.64 (br d, J=11.25 Hz, 2H), 5.76 (s, 1H), 5.11 (s, 1H), 3.79 (d, J=6.36 Hz, 2H), 3.59 (s, 3H), 3.46-3.55 (m, 1H), 3.45-3.46 (m, 1H), 2.74-2.93 (m, 2H), 2.56 (br d, J=4.40 Hz, 1H), 2.20-2.42 (m, 2H), 1.79-1.99 (m, 4H), 1.64-1.76 (m, 1H), 1.28-1.42 (m, 2H), 0.98-1.27 (m, 9H). LCMS: 543 [M+H]$^+$.

Step-6: Preparation of (1R,4r)-4-((3,5-Difluoro-4-((1R,3R)-2-(2-fluoro-2-methylpropyl)-3-methyl-2,3,4,9-tetrahydro-1H-pyrido[3,4-b]indol-1-yl)phenoxy)methyl)cyclohexane-1-carboxylic Acid (Int-6)

To a stirred solution of methyl (1R,4r)-4-((3,5-difluoro-4-((1R,3R)-2-(2-fluoro-2-methylpropyl)-3-methyl-2,3,4,9-tetrahydro-1H-pyrido[3,4-b]indol-1-yl)phenoxy)methyl)cyclohexane-1-carboxylate (Int-4, 2.7 g, 4.98 mmol, 1.0 eq) in THF (27 mL) and water (27 mL) was added lithium hydroxide monohydrate (2.09 g, 4.98 mmol, 10 eq) at room temperature and the resulting reaction mixture was allowed to stir for 16 h. Progress of the reaction was monitored by TLC. After completion of the reaction, volatiles were removed under reduced pressure, diluted with water (50 mL), acidified with 1N HCl until pH~5 and extracted with ethyl acetate (3×50 mL). The combined organic extract was washed with brine (50 mL) and dried over anhydrous sodium sulfate. The organic layer was filtered and concentrate under reduced pressure to afford the desired product (2.2 g, 83%).

$^1$H NMR (400 MHz, DMSO-d$_6$) δ 10.51 (br s, 1H), 7.39 (br d, J=6.85 Hz, 1H), 7.18 (br d, J=7.34 Hz, 1H), 6.96 (br dd, J=12.96, 7.58 Hz, 2H), 6.65 (br d, J=11.25 Hz, 2H), 5.12 (br s, 1H), 4.03 (br d, J=6.85 Hz, 1H), 3.80 (br s, 2H), 3.32-3.56 (m, 4H), 2.76-2.97 (m, 2H), 2.15 (br t, J=11.49 Hz, 1H), 1.74-2.01 (m, 4H), 1.43-1.78 (m, 3H), 0.96-1.40 (m, 9H).

Step-7: Preparation of 7-((4-((1R,4r)-4-((3,5-Difluoro-4-((1R,3R)-2-(2-fluoro-2-methylpropyl)-3-methyl-2,3,4,9-tetrahydro-1H-pyrido[3,4-b]indol-1-yl)phenoxy)methyl)cyclohexane-1-carbonyl)piperazin-1-yl)methyl)-3-ethyl-1,5-naphthyridin-2(1H)-one (70)

To a stirred solution of (1R,4r)-4-((3,5-difluoro-4-((1R,3R)-2-(2-fluoro-2-methylpropyl)-3-methyl-2,3,4,9-tetrahydro-1H-pyrido[3,4-b]indol-1-yl)phenoxy)methyl)cyclohexane-1-carboxylic acid (Int-5, 280 mg, 0.54 mmol, 1.0 eq) and 3-ethyl-7-(piperazin-1-ylmethyl)-1,5-naphthyridin-2(1H)-one (Int-6 free base, prepared in an earlier scheme, 296 mg, 1.09 mmol, 1.5 eq) in DMF (2.8 mL) were added HATU (310 mg, 0.816 mmol, 1.5 eq) and DIPEA (0.142 mL, 0.816 mmol, 1.5 eq) at room temperature and allowed reaction mixture to stir for 16 h. Progress of the reaction was monitored by TLC. After completion of the reaction, the reaction mixture was diluted with water (60 mL), filtered the solid and dried under vacuum to obtain the crude product. The crude obtained was purified by column chromatography eluting with 3-6% methanol in ethyl acetate to afford the titled product (42.5 mg, 8%).

$^1$H NMR (400 MHz, CD$_3$OD) δ 8.46 (d, J=1.63 Hz, 1H), 7.82 (s, 1H), 7.73 (d, J=1.13 Hz, 1H), 7.34-7.42 (m, 1H), 7.12-7.19 (m, 1H), 6.90-7.03 (m, 2H), 6.48 (d, J=10.88 Hz, 2H), 5.17 (s, 1H), 3.78 (d, J=6.13 Hz, 2H), 3.59-3.71 (m, 7H), 3.48 (q, J=7.00 Hz, 1H), 2.97-3.08 (m, 1H), 2.83-2.94 (m, 1H), 2.62-2.69 (m, 3H), 2.54-2.62 (m, 2H), 2.45-2.54 (m, 4H), 2.33-2.41 (m, 1H), 1.89-1.97 (m, 2H), 1.80 (br d, J=12.26 Hz, 3H), 1.48-1.58 (m, 2H), 1.23-1.31 (m, 5H), 1.20-1.12 (m, 7H). HPLC purity: 97.4%. LCMS: 783.8 [M+H]$^+$.

Procedure 16: Preparation of 7-((4-(2-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)ethyl)piperazin-1-yl)methyl)-3-ethyl-1,5-naphthyridin-2(1H)-one (71)

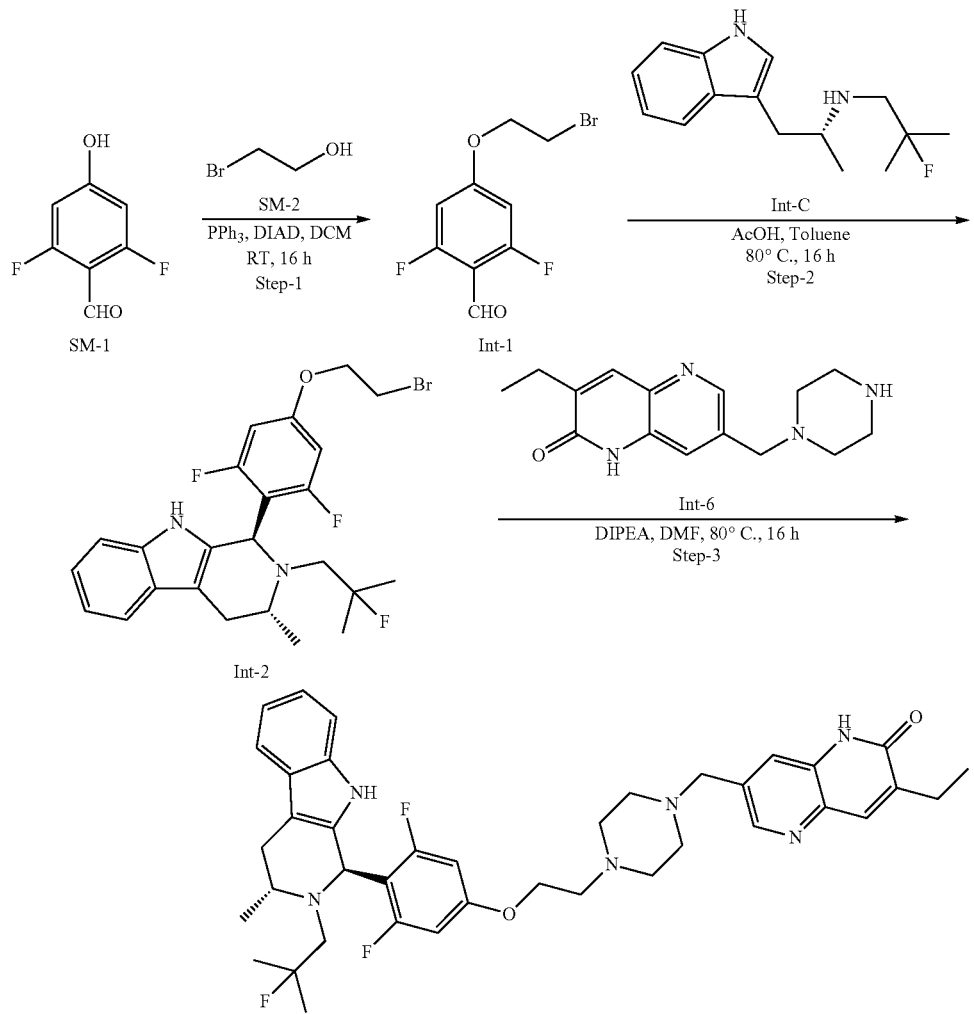

Step-1: Preparation of 4-(2-Bromoethoxy)-2,6-difluorobenzaldehyde (Int-1)

To a stirred solution of 2,6-difluoro-4-hydroxybenzaldehyde (SM-1, 1.0 g, 6.32 mmol, 1.0 eq) and bromoethanol (SM-2, 5 g, 28.73 mmol, 1.0 eq) in DCM (15 mL) were added PPh$_3$ (2.48 g, 9.49 mmol, 1.5 eq) and DIAD (1.8 mL, 9.49 mmol, 1.5 eq) at room temperature and the resulting reaction mixture was allowed to stir for 16 h. Progress of the reaction was monitored by TLC. After completion of the reaction, solvents were evaporated under reduced pressure to obtain the crude product, which was purified by column chromatography eluting with 15-20% ethyl acetate in heptane to afford the titled product (430 mg, 25%).

$^1$H NMR (400 MHz, DMSO-d$_6$) δ 10.07 (s, 1H), 6.95 (d, J=11.25 Hz, 2H), 4.42-4.52 (m, 2H), 3.77-3.88 (m, 2H). LCMS: 265.0 [M+H]$^+$.

Step-2: Preparation of (1R,3R)-1-(4-(2-Bromoethoxy)-2,6-difluorophenyl)-2-(2-fluoro-2-methylpropyl)-3-methyl-2,3,4,9-tetrahydro-1H-pyrido[3,4-b]indole (Int-2)

To a stirred solution of (R)—N-(1-(1H-indol-3-yl)propan-2-yl)-2-fluoro-2-methylpropan-1-amine (Int-C, prepared earlier, 400 mg, 1.60 mmol, 1.0 eq) and 4-(2-bromoethoxy)-2,6-difluorobenzaldehyde (Int-1, 420 mg, 1.60 mmol, 1.0 eq) in toluene (5 mL) was added acetic acid (0.288 mL, 4.81 mmol, 3 eq) at room temperature. The reaction mixture was heated at 80° C. and stirred for 16 h in a sealed tube. Progress of the reaction was monitored by TLC. After completion of the reaction, solvents were evaporated under reduced pressure to obtain crude compound which was purified by column chromatography eluting with 10-13% ethyl acetate in heptane to afford the titled product (550 mg, 69%).

$^1$H NMR (400 MHz, DMSO-d$_6$) δ 10.53 (s, 1H), 7.39 (d, J=7.82 Hz, 1H), 7.18 (d, J=7.82 Hz, 1H), 6.89-7.03 (m, 2H), 6.71 (br d, J=11.25 Hz, 2H), 5.13 (s, 1H), 4.28-4.41 (m, 2H), 3.73-3.86 (m, 2H), 3.43-3.54 (m, 1H), 2.75-2.98 (m, 2H), 2.25-2.43 (m, 2H), 1.09-1.26 (m, 6H), 1.04 (d, J=6.36 Hz, 3H). LCMS: 495.2 [M+H]$^+$.

Step-3: Preparation of 7-((4-(2-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy) ethyl)piperazin-1-yl)methyl)-3-ethyl-1,5-naphthyridin-2(1H)-one (71)

To a stirred solution of (1R,3R)-1-(4-(2-bromoethoxy)-2,6-difluorophenyl)-2-(2-fluoro-2-methylpropyl)-3-methyl-2,3,4,9-tetrahydro-1H-pyrido[3,4-b]indole (Int-2, 250 mg, 0.506 mmol, 1.0 eq) and 3-ethyl-7-(piperazin-1-ylmethyl)-1,5-naphthyridin-2(1H)-one (Int-6 free base, prepared in an earlier scheme, 206 mg, 0.759 mmol, 1.5 eq) in DMF (2.5 mL) was added DIPEA (0.44 mL, 2.530 mmol, 5 eq) at room temperature. The reaction mixture was heated to 80° C. and stirred for 16 h. Progress of the reaction was monitored by TLC. After completion of the reaction, the reaction mixture was diluted with water (60 mL) and extracted with cold ethyl acetate (3×60 mL). The combined organic extract was washed with ice cold water (30 mL), brine (100 mL) and dried over anhydrous sodium sulphate. The organic layer was filtered, concentrated under vacuum to obtain the crude product which was purified by column chromatography eluting with 1-3% methanol in dichloromethane to afford the titled product (55 mg, 15.8%).

$^1$H NMR (400 MHz, DMSO-d$_6$) δ 11.81 (s, 1H), 10.50 (s, 1H), 8.35 (d, J=1.63 Hz, 1H), 7.73 (s, 1H), 7.57 (d, J=0.88 Hz, 1H), 7.39 (d, J=7.50 Hz, 1H), 7.17 (d, J=7.75 Hz, 1H), 6.93-7.0 m, 2H), 6.66 (br d, J=11.26 Hz, 2H), 5.12 (s, 1H), 4.07 (br t, J=5.50 Hz, 2H), 3.44-3.61 (m, 3H), 2.76-2.93 (m, 2H), 2.67 (br t, J=5.38 Hz, 2H), 2.53 (m, 4H), 2.29-2.44 (m, 8H), 1.00-1.25 (m, 12H). HPLC purity: 95.9%. LCMS: 687.4 [M+H]$^+$.

Procedure 17: Preparation of 7-((4-(6-(3,5-Difluoro-44(1R,3R)-2-(2-fluoro-2-methylpropyl)-3-methyl-2,3,4,9-tetrahydro-1H-pyrido[3,4-b]indol-1-yl)phenoxy)hexyl)piperazin-1-yl)methyl)-3-ethyl-1,5-naphthyridin-2(1H)-one (72)

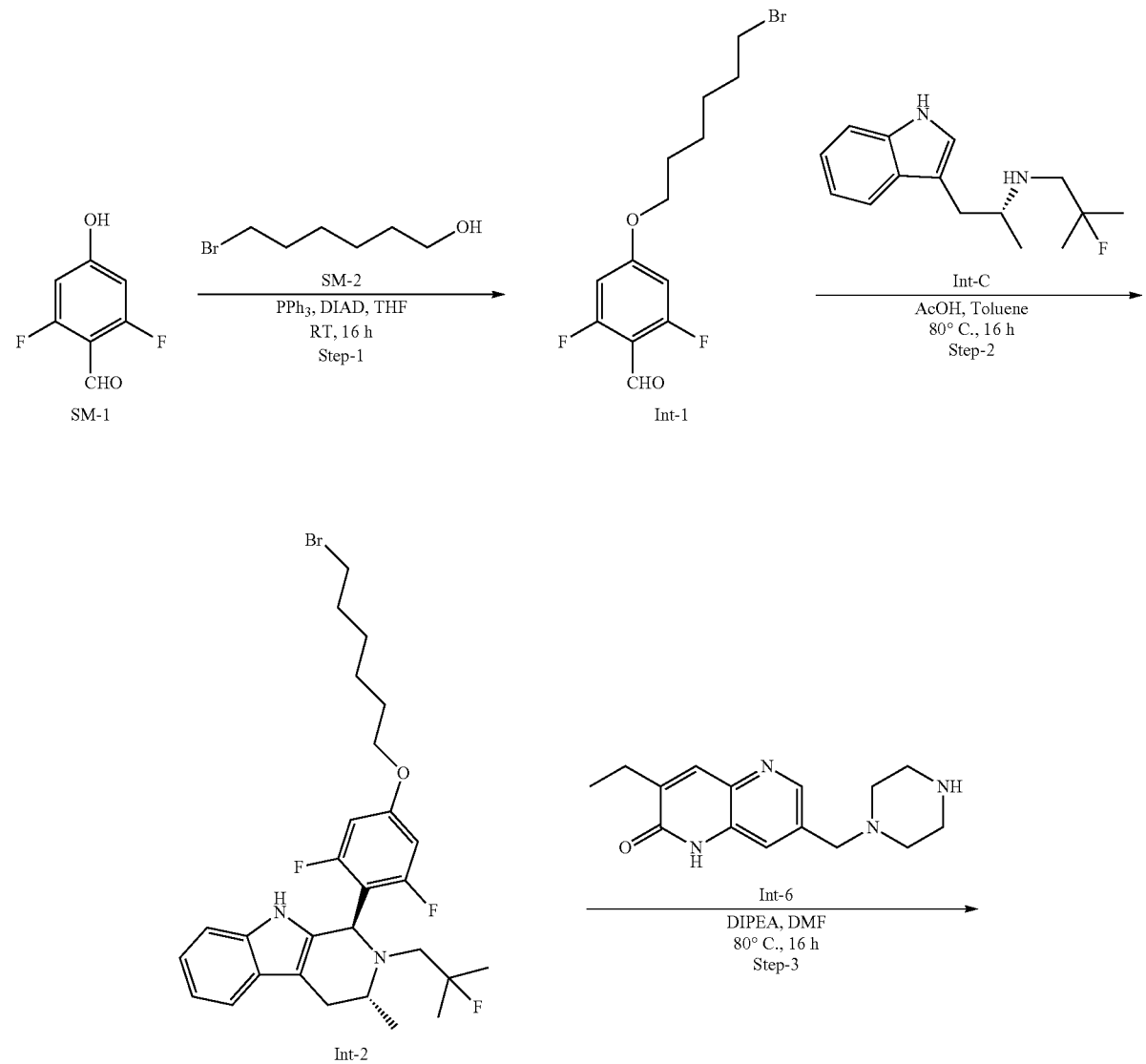

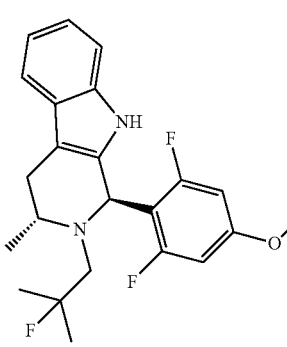

Step-1: Preparation of 4-((6-Bromohexyl)oxy)-2,6-difluorobenzaldehyde (Int-1)

To a stirred solution of 2,6-difluoro-4-hydroxybenzaldehyde (SM-1, 500 mg, 2.0 mmol, 1.0 eq) and 6-bromohexan-1-ol (SM-2, 0.87 mL, 6.32 mmol, 1.0 eq) in DCM (20 mL) were added PPh$_3$ (2.48 g, 9.49 mmol, 1.5 eq) and DIAD (1.8 mL, 9.49 mmol, 1.5 eq) at room temperature and the resulting reaction mixture was allowed to stir for 16 h. Progress of the reaction was monitored by TLC. After completion of the reaction, solvents were evaporated under reduced pressure to obtain the crude product which was purified by column chromatography by eluting with 14-18% ethyl acetate in heptane to afford the titled product (1.0 g, 50%).

$^1$H NMR (400 MHz, DMSO-d$_6$) δ 10.06 (s, 1H), 6.88 (br d, J=11.37 Hz, 2H), 4.11 (t, J=6.42 Hz, 2H), 3.54 (t, J=6.66 Hz, 2H), 1.66-1.86 (m, 4H), 1.34-1.46 (m, 4H).

Step-2: Preparation of (1R,3R)-1-(4-((6-Bromohexyl)oxy)-2,6-difluorophenyl)-2-(2-fluoro-2-methylpropyl)-3-methyl-2,3,4,9-tetrahydro-1H-pyrido[3,4-b]indole (Int-2)

To a stirred solution of (R)—N-(1-(1H-indol-3-yl)propan-2-yl)-2-fluoro-2-methylpropan-1-amine (Int-C, 500 mg, 2.0 mmol, 1.0 eq) and 4-((6-bromohexyl)oxy)-2,6-difluorobenzaldehyde (Int-1, 640 mg, 2.0 mmol, 1.0 eq) in toluene (5 mL) was added acetic acid (0.36 mL, 6.0 mmol, 3 eq) at room temperature. The reaction mixture was heated to 80° C. and allowed to stir for 16 h in a sealed tube. Progress of the reaction was monitored by TLC. After completion of the reaction, solvents were evaporated under reduced pressure to obtained the crude product. The crude obtained was purified by column chromatography eluting with 10-13% ethyl acetate in heptane to afford the titled product (600 mg, 54%).

$^1$H NMR (400 MHz, DMSO-d$_6$) δ 10.50 (s, 1H), 7.39 (d, J=7.34 Hz, 1H), 7.18 (d, J=7.82 Hz, 1H), 6.87-7.03 (m, 2H), 6.64 (br d, J=11.25 Hz, 2H), 5.12 (s, 1H), 3.97 (br t, J=6.11 Hz, 2H), 3.53 (br t, J=6.60 Hz, 3H), 2.75-2.95 (m, 2H), 2.57 (br d, J=4.40 Hz, 1H), 2.24-2.42 (m, 1H), 1.77-1.85 (m, 2H), 1.65-1.74 (m, 2H), 1.36-1.47 (m, 4H), 1.08-1.25 (m, 6H), 1.04 (d, J=6.36 Hz, 3H). LCMS: 549.3 [M–H]$^-$.

Step-3: Preparation of 7-((4-(6-(3,5-Difluoro-4-((1R,3R)-2-(2-fluoro-2-methylpropyl)-3-methyl-2,3,4,9-tetrahydro-1H-1-pyrido[3,4-b]indol-1-yl)phenoxy)hexyl)piperazin-1-yl)methyl)-3-ethyl-1,5-naphthyridin-2(1H)-one (72)

To a stirred solution of (1R,3R)-1-(4-((6-bromohexyl)oxy)-2,6-difluorophenyl)-2-(2-fluoro-2-methylpropyl)-3-methyl-2,3,4,9-tetrahydro-1H-pyrido[3,4-b]indole (Int-2, 400 mg, 0.727 mmol, 1.0 eq) and 3-ethyl-7-(piperazin-1-ylmethyl)-1,5-naphthyridin-2(1H)-one (Int-6 free base, prepared in an earlier scheme, 296 mg, 1.090 mmol, 1.5 eq) in DMF (2.5 mL) was added DIPEA (0.63 mL, 3.635 mmol, 5 eq) at room temperature. The reaction mixture was heated to 80° C. and stirred for 16 h. Progress of the reaction was monitored by TLC. After completion of the reaction, the reaction mixture was diluted with water (60 mL) and extracted with cold ethyl acetate (3×60 mL). The combined organic extract was washed with ice cold water (30 mL), brine (100 mL), dried over anhydrous sodium sulfate, filtered and concentrated under vacuum to obtain the crude product. The crude obtained was purified by column chromatography eluting with 1-3% methanol in dichloromethane to afford the titled product (75 mg, 14%).

$^1$H NMR (400 MHz, DMSO-d$_6$) δ 11.80 (br s, 1H), 10.50 (s, 1H), 8.34 (d, J=1.50 Hz, 1H), 7.73 (s, 1H), 7.57 (s, 1H), 7.38 (d, J=7.63 Hz, 1H), 7.17 (d, J=7.75 Hz, 1H), 6.86-7.05 (m, 2H), 6.63 (br d, J=11.26 Hz, 2H), 5.11 (s, 1H), 3.96 (br t, J=6.32 Hz, 2H), 3.45-3.65 (m, 4H), 2.72-2.98 (m, 3H), 2.52 (br s, 2H), 2.29-2.45 (m, 8H), 2.24 (br t, J=6.94 Hz, 2H), 1.63-1.72 (m, 2H), 1.25-1.47 (m, 6H), 1.12-1.24 (m, 9H), 0.99-1.12 (m, 3H). LCMS: 743.4 [M–H]$^-$.

Procedure 18: Preparation of 7-((4-(2-(3,5-Difluoro-4((1R,3R)-2-(2-fluoro-2-methylpropyl)-3-methyl-2,3,4,9-tetrahydro-1H-pyrido[3,4-b]indol-1-yl)phenoxy)acetyl)piperazin-1-yl)methyl)-3-ethyl-1,5-naphthyridin-2(1H)-one (73)
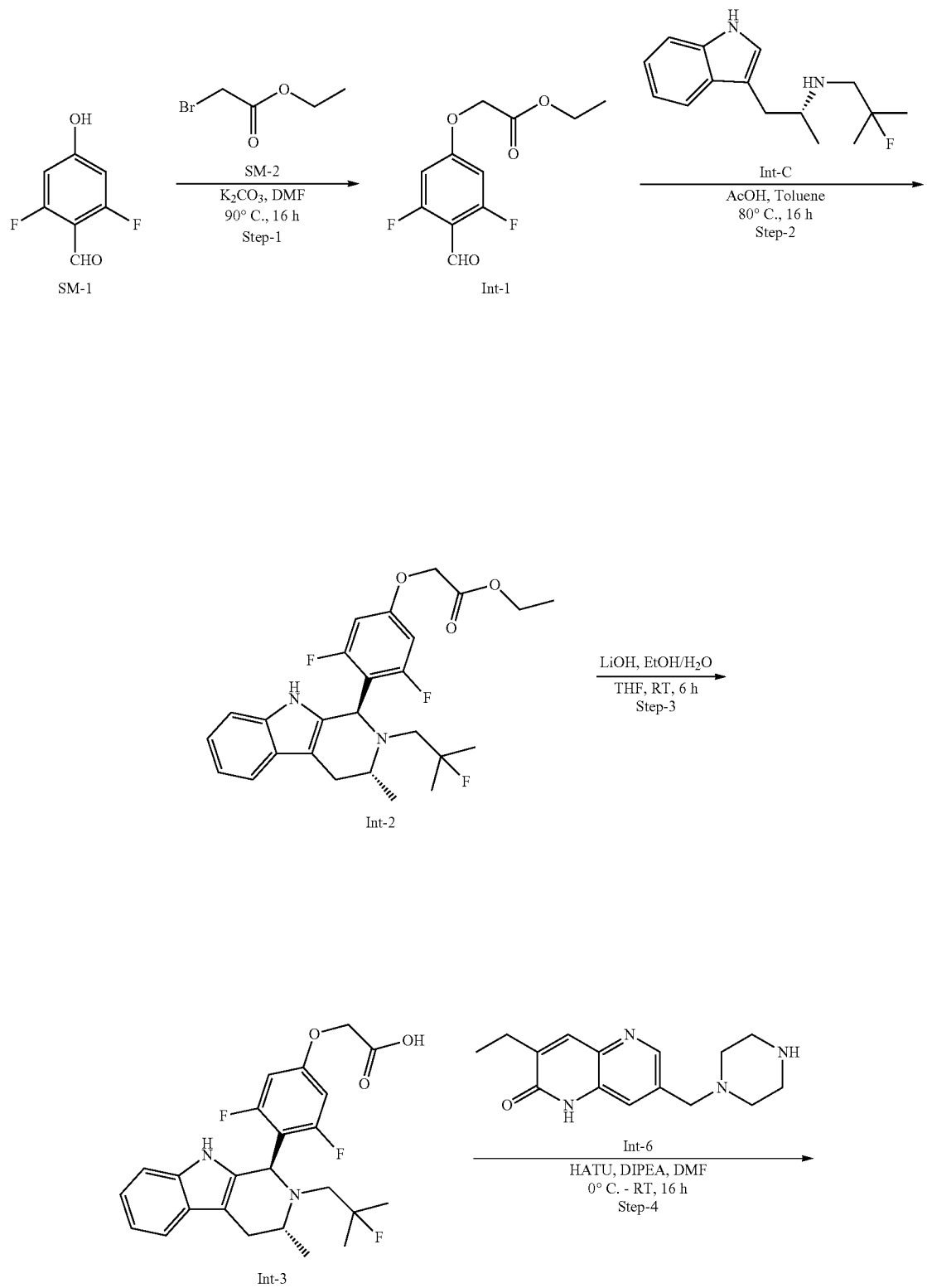

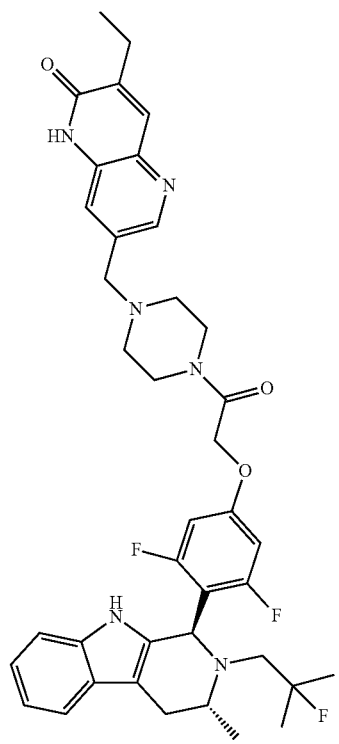

Step-1: Preparation of Ethyl 2-(3,5-Difluoro-4-formylphenoxy)acetate (Int-1)

To a stirred solution of 2,6-difluoro-4-hydroxybenzaldehyde (SM-1, 2.0 g, 12.6 mmol, 1.0 eq) and ethyl 2-bromoacetate (SM-2, 2.53 g, 15.18 mmol, 1.2 eq) in DMF (20 mL) was added $K_2CO_3$ (2.62 g, 18.975 mmol, 1.5 eq) at room temperature. The reaction mixture was heated to 90° C. and stirred for 16 h. Progress of the reaction was monitored by TLC. After completion of the reaction, the reaction mixture was diluted with ice cold water (60 mL) and extracted with cold ethyl acetate (3×30 mL). The combined organic extract was washed with brine (30 mL), dried over anhydrous sodium sulfate, filtered and concentrated under reduced pressure to obtained the crude product, which was purified by column chromatography eluting with 20% ethyl acetate in heptane to afford the titled product (1.567 g, 50.7%).

$^1$H NMR (400 MHz, DMSO-$d_6$) δ 10.07 (s, 1H), 6.95 (d, J=11.25 Hz, 2H), 4.98 (s, 2H), 4.18 (q, J=7.17 Hz, 2H), 1.22 (t, J=7.09 Hz, 3H).

Step-2: Preparation of Ethyl 2-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy) acetate (Int-2)

To a stirred solution of ethyl 2-(3,5-difluoro-4-formylphenoxy)acetate (Int-1, 1.50 g, 6.04 mmol, 1.0 eq) and (R)—N-(1-(1H-indol-3-yl)propan-2-yl)-2-fluoro-2-methylpropan-1-amine (Int-C, prepared earlier, 1.77 g, 7.25 mmol, 1.2 eq) in toluene (15 mL) was added acetic acid (1.1 g, 18.1 mmol, 3 eq) at room temperature. The reaction mixture was heated to 90° C. and stirred for 16 h in a sealed tube. After completion of the reaction, the reaction mixture was diluted with water (60 mL) and extracted with dichloromethane (3×50 mL). The combined organic extract was washed with brine (30 mL), dried over anhydrous sodium sulfate, filtered and concentrated under reduced pressure to obtain the crude product. The crude obtained was purified by column chromatography eluting with 20% ethyl acetate in heptane to afford the desired product (0.986 g, 34%).

$^1$H NMR (400 MHz, DMSO-$d_6$) δ 10.57 (s, 1H), 7.39 (br d, J=7.83 Hz, 1H), 7.18 (br d, J=7.83 Hz, 1H), 6.87-7.05 (m, 2H), 6.70 (br d, J=11.25 Hz, 2H), 5.13 (br s, 1H), 4.83 (s, 2H), 4.16 (q, J=7.34 Hz, 2H), 3.49 (br d, J=5.87 Hz, 1H), 2.73-2.95 (m, 2H), 2.57 (br d, J=4.40 Hz, 1H), 2.24-2.41 (m, 1H), 1.14-1.24 (m, 9H), 1.04 (br d, J=6.36 Hz, 3H). LCMS: 475.2 [M+H]$^+$.

Step-3: Preparation of 2-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)acetic Acid (Int-3)

To a stirred solution of ethyl 2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)acetate (Int-2, 950 mg, 2.0 mmol, 1.0 eq) in THF (7 mL), ethanol (7 mL), water (7 mL) was added lithium hydroxide monohydrate (420 mg, 10 mmol, 5 eq) at room temperature and resulting reaction mixture was allowed to stir for 6 h. Progress of the reaction was monitored by TLC. After completion of the reaction, volatiles were removed under reduced pressure, diluted with water and acidified with 1N HCl until pH~5. The reaction mixture was extracted with DCM (3×50 mL), combined organic extract washed with brine (100 ml), dried over anhydrous sodium sulfate, filtered and concentrated under reduced pressure to afford the titled product (0.764 g, 85%).

$^1$H NMR (400 MHz, DMSO-$d_6$) δ 13.11 (br s, 1H), 10.57 (s, 1H), 7.39 (br d, J=7.34 Hz, 1H), 7.19 (d, J=7.82 Hz, 1H), 6.89-7.04 (m, 2H), 6.67 (br d, J=11.25 Hz, 2H), 5.14 (s, 1H), 4.73 (s, 2H), 3.49 (br dd, J=11.00, 5.14 Hz, 1H), 2.74-2.95

(m, 2H), 2.57 (br d, J=4.89 Hz, 1H), 2.27-2.41 (m, 1H), 0.98-1.29 (m, 9H). HPLC purity: 86.7%. LCMS: 447.2 [M+H]$^+$.

Step-4: Preparation of 7-((4-(2-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy) acetyl)piperazin-1-yl)methyl)-3-ethyl-1,5-naphthyridin-2(1H)-one (73)

To a stirred solution of 2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)acetic acid (Int-3, 375 mg, 0.84 mmol, 1.0 eq) and 3-ethyl-7-(piperazin-1-ylmethyl)-1,5-naphthyridin-2(1H)-one (Int-6 free base, prepared in an earlier scheme, 297 mg, 1.09 mmol, 1.3 eq) in DMF (8 mL) was added HATU (479 mg, 1.26 mmol, 1.5 eq) and DIPEA (543 mg, 4.20 mmol, 5 eq) at 0° C. The reaction mixture was allowed to warm up room temperature and stir for 16 h. Progress of the reaction was monitored by TLC. After completion of the reaction, the reaction mixture was diluted with ice cold water (60 mL) and extracted with cold ethyl acetate (3×20 mL). The combined organic extract was washed with brine (30 mL), dried over anhydrous sodium sulfate, filtered and concentrated under reduced pressure to obtain the crude product. The crude obtained was purified by column chromatography eluting with 6% methanol in dichloromethane to afford the titled product (135 mg, 23%).

$^1$H NMR (400 MHz, DMSO-d$_6$) δ 11.85 (s, 1H), 10.56 (s, 1H), 8.38 (s, 1H), 7.74 (s, 1H), 7.59 (s, 1H), 7.39 (br d, J=7.58 Hz, 1H), 7.18 (br d, J=7.83 Hz, 1H), 6.88-7.04 (m, 2H), 6.65 (br d, J=11.25 Hz, 2H), 5.13 (br s, 1H), 4.88 (s, 2H), 3.61 (s, 2H), 3.37-3.55 (m, 5H), 2.74-2.93 (m, 2H), 2.54 (br d, J=7.34 Hz, 3H), 2.44 (br s, 2H), 2.27-2.40 (m, 3H), 1.13-1.23 (m, 9H), 1.04 (br d, J=6.36 Hz, 3H). HPLC purity: 98.2%. LCMS: 699.2 [M−H]$^−$.

Procedure 19: Preparation of 2-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)-N-(1-((7-ethyl-6-oxo-5,6-dihydro-1,5-naphthyridin-3-yl)methyl)-piperidin-4-yl)-N-methylacetamide (74)

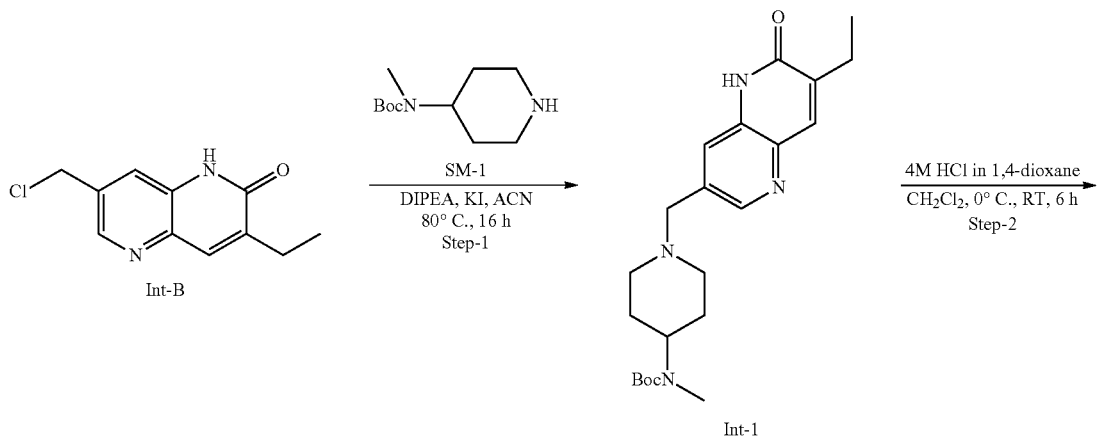

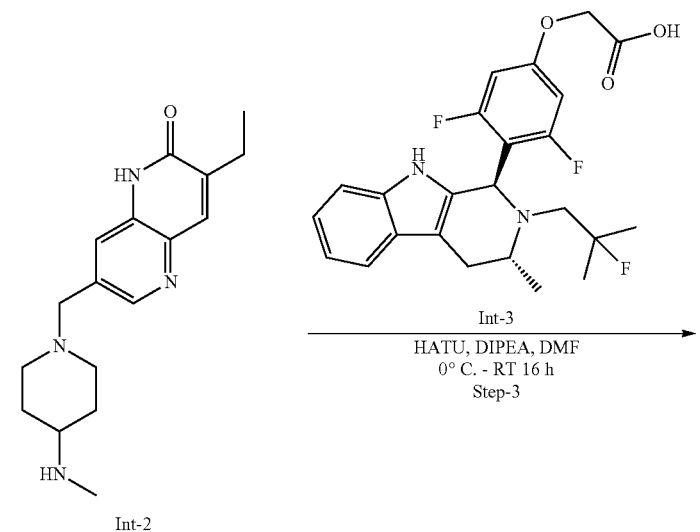

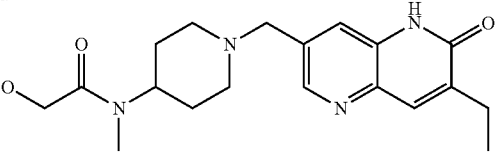

Step-1: Preparation of tert-Butyl (1-((7-Ethyl-6-oxo-5,6-dihydro-1,5-naphthyridin-3-yl)methyl)piperidin-4-yl)(methyl)carbamate (Int-1)

To a stirred solution of 7-(chloromethyl)-3-ethyl-1,5-naphthyridin-2(1H)-one (Int-B, 1 g, 4.49 mmol, 1.0 eq) and tert-butyl methyl(piperidin-4-yl)carbamate (SM-1, 1.15 g, 5.389 mmol, 1.2 eq) in acetonitrile (20 mL) were added potassium iodide (149 mg, 0.898 mmol, 0.2 eq) and DIPEA (2.902 g, 22.45 mmol, 5.0 eq) at room temperature. The reaction mixture was heated to 80° C. and stirred for 16 h. Progress of the reaction was monitored by TLC. After completion of the reaction, solvents were removed under reduced pressure, diluted with water (60 mL) and extracted with ethyl acetate (3×20 mL). The combined organic extract was washed with brine (30 mL), dried over anhydrous sodium sulfate, filtered and concentrated under reduced pressure to obtain the crude product. The crude obtained was purified by column chromatography eluting with 70% ethyl acetate in heptane to afford the desired product (638 mg, 35.48%).

$^1$H NMR (400 MHz, DMSO-d$_6$) δ 11.80 (s, 1H), 8.35 (d, J=1.47 Hz, 1H), 7.73 (s, 1H), 7.57 (s, 1H), 3.56 (s, 2H), 2.86 (br d, J=11.25 Hz, 2H), 2.67 (s, 3H), 2.53 (m, 3H), 2.02 (br t, J=11.25 Hz, 2H), 1.59-1.73 (m, 2H), 1.49 (br d, J=9.29 Hz, 2H), 1.39 (s, 9H), 1.18 (t, J=7.34 Hz, 3H). LCMS: 401.5 [M+H]$^+$.

Step-2: Preparation of 3-Ethyl-7-((4-(methylamino)piperidin-1-yl)methyl)-1,5-naphthyridin-2(1H)-one (Int-2)

To a stirred solution of tert-butyl (14(7-ethyl-6-oxo-5,6-dihydro-1,5-naphthyridin-3-yl)methyl)-piperidin-4-yl) (methyl)carbamate (Int-1, 600 mg, 1.5 mmol, 1.0 eq) in dichloromethane (6 mL) was added 4M HCl in 1,4-dioxane (6 mL, 10 vol) at 0° C. The reaction mixture was allowed to warm up to room temperature and stir for 6 h. Progress of the reaction was monitored by TLC. After completion of the reaction, solvents were removed under reduced pressure to get the crude compound, which was washed with diethyl ether (3×15 mL) and dried under vacuum to afford the titled product (396 mg, 78.6%).

$^1$H NMR (400 MHz, DMSO-d$_6$) δ 12.22 (br s, 1H), 11.11-11.28 (m, 1H), 9.43 (br s, 2H), 8.67 (d, J=1.75 Hz, 1H), 7.87 (d, J=1.00 Hz, 1H), 7.82 (s, 1H), 4.43 (br s, 2H), 3.56 (s, 1H), 3.48 (br d, J=11.76 Hz, 2H), 2.95-3.25 (m, 3H), 2.53-2.61 (m, 3H), 2.23 (br d, J=12.51 Hz, 2H), 1.91-2.06 (m, 2H), 1.19 (t, J=7.44 Hz, 3H).

Step-3: Preparation of 2-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)-N-(1-((7-ethyl-6-oxo-5,6-dihydro-1,5-naphthyridin-3-yl)methyl)piperidin-4-yl)-N-methylacetamide (74)

To a stirred solution 3-ethyl-7-((4-(methylamino)piperidin-1-yl)methyl)-1,5-naphthyridin-2(1H)-one (Int-2, 328 mg, 1.1 mmol, 1.3 eq) and 2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)acetic acid (Int-3 prepared earlier, 375 mg, 0.84 mmol, 1.0 eq) in DMF (8 mL) were added HATU (479 mg, 1.26 mmol, 1.5 eq) and DIPEA (543 mg, 4.20 mmol, 5 eq) at 0° C. The reaction mixture was allowed to warm up to room temperature and stir for 16 h. Progress of the reaction was monitored by TLC. After completion of the reaction, the reaction mixture was diluted with ice cold water (60 mL) and extracted with ethyl acetate (3×20 mL). The combined organic extract was washed with brine (30 mL), dried over anhydrous sodium sulfate, filtered and concentrated under reduced pressure to obtain the crude product. The crude obtained was purified by column chromatography eluting with 2% methanol in dichloromethane to afford the titled product (103 mg, 16.8%).

$^1$H NMR (400 MHz, DMSO-d$_6$) δ 11.82 (s, 1H), 10.56 (s, 1H), 8.36 (s, 1H), 7.74 (s, 1H), 7.57 (s, 1H), 7.39 (br d, J=7.58 Hz, 1H), 7.18 (br d, J=7.83 Hz, 1H), 6.89-7.03 (m, 2H), 6.63 (br dd, J=11.00, 4.65 Hz, 2H), 5.13 (br s, 1H), 4.81-4.95 (m, 2H), 4.19 (br t, J=11.62 Hz, 1H), 3.57 (br d, J=8.56 Hz, 2H), 3.49 (br d, J=4.89 Hz, 1H), 2.76-2.94 (m, 6H), 2.72 (s, 1H), 2.54 (br d, J=7.34 Hz, 3H), 2.24-2.43 (m, 1H), 1.96-2.18 (m, 2H), 1.56-1.86 (m, 3H), 1.44 (br d, J=11.00 Hz, 1H), 1.13-1.26 (m, 9H), 1.04 (br d, J=6.36 Hz, 3H). HPLC purity: 97.9%. LCMS: 727.4 [M−H]$^-$.

Procedure 20: Preparation of 7-((4-(((1R,4r)-4-((3,5-Difluoro-4-((1R,3R)-2-(2-fluoro-2-methylpropyl)-3-methyl-2,3,4,9-tetrahydro-1H-pyrido[3,4-b]indol-1-yl)phenoxy)methyl)cyclohexyl)methyl)piperazin-1-yl)methyl)-3-ethyl-1,5-naphthyridin-2(1H)-one (75)
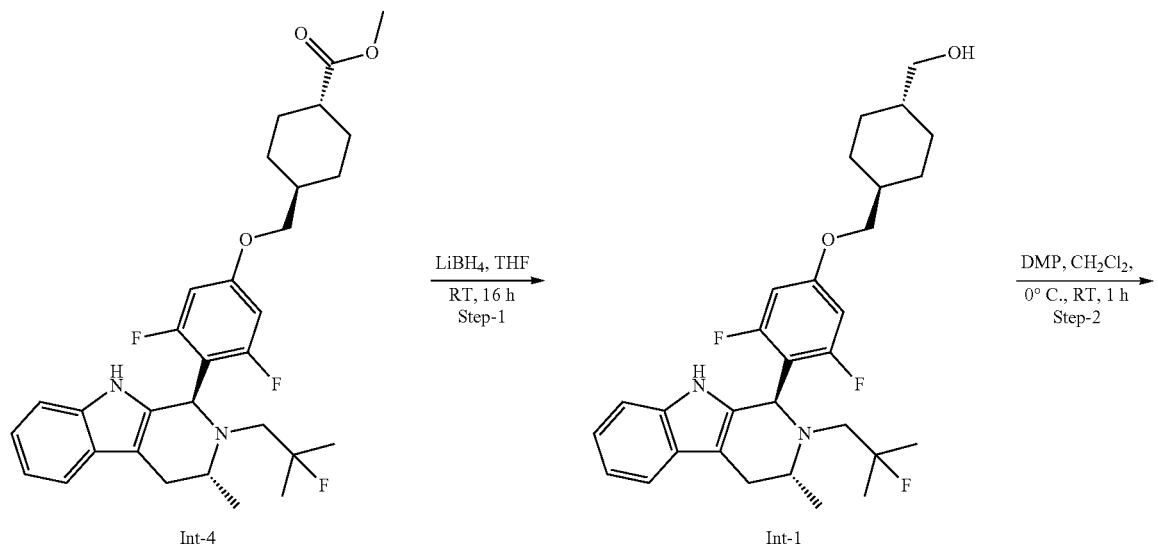
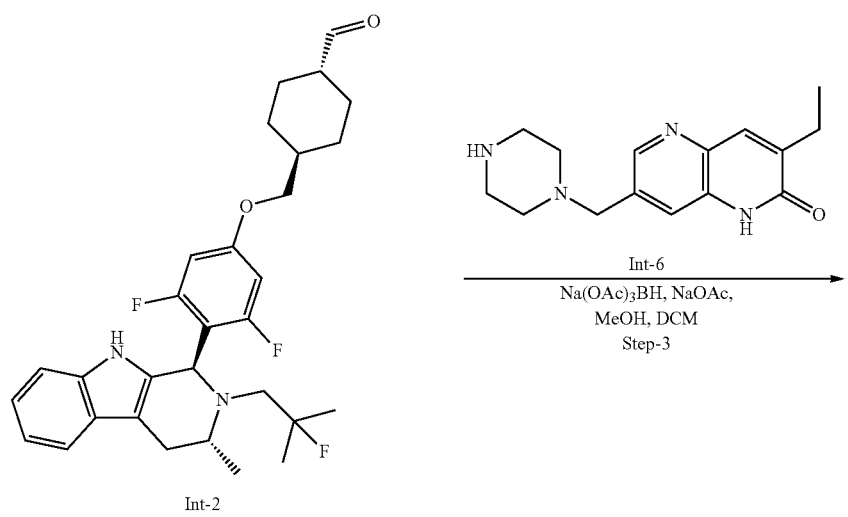

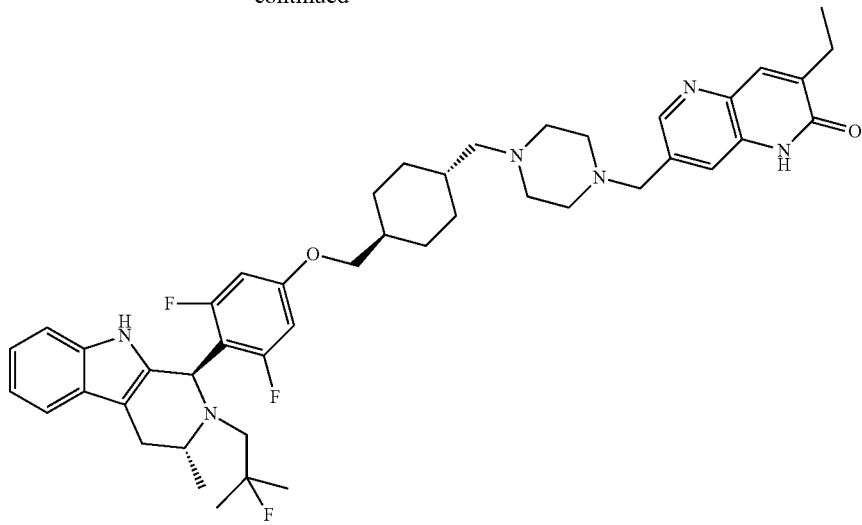

Step-1: Preparation of ((1R,4r)-4-((3,5-Difluoro-4-((1R,3R)-2-(2-fluoro-2-methylpropyl)-3-methyl-2,3,4,9-tetrahydro-1H-pyrido[3,4-b]indol-1-yl)phenoxy)methyl)cyclohexyl)methanol (Int-1)

To a stirred solution of (1R,4r)-4-((3,5-difluoro-4-((1R,3R)-2-(2-fluoro-2-methylpropyl)-3-methyl-2,3,4,9-tetrahydro-1H-pyrido[3,4-b]indol-1-yl)phenoxy)methyl)cyclohexane-1-carboxylic acid (Int-4, prepared above, 700 mg, 1.29 mmol, 1.0 eq) in THF (7 mL) was added 2M LiBH$_4$ in THF (1.29 mL, 2.58 mmol, 2 eq) at 0° C. The reaction mixture was allowed to warm up to room temperature and stir for 16 h. Progress of the reaction was monitored by TLC. After completion of the reaction, the reaction mixture was quenched with ice cold water (60 mL) and extracted with ethyl acetate (3×20 mL). The combined organic extract was washed with brine (30 mL), dried over anhydrous sodium sulfate, filtered and concentrated under vacuum to obtain the crude product. The crude obtained was purified by column chromatography by eluting with 50% ethyl acetate in heptane to afford the desired product (250 mg, 37%).

LCMS: 515.8 [M+H]$^+$.

Step-2: Preparation of (1R,4r)-4-((3,5-Difluoro-4-((1R,3R)-2-(2-fluoro-2-methylpropyl)-3-methyl-2,3,4,9-tetrahydro-1H-pyrido[3,4-b]indol-1-yl)phenoxy)methyl)cyclohexane-1-carbaldehyde (Int-2)

To a stirred solution of (1R,4r)-4-((3,5-difluoro-4-((1R,3R)-2-(2-fluoro-2-methylpropyl)-3-methyl-2,3,4,9-tetrahydro-1H-pyrido[3,4-b]indol-1-yl)phenoxy)methyl)cyclohexane-1-carbaldehyde (Int-1, 150 mg, 0.291 mmol, 1.0 eq) in DCM (1.5 mL) under nitrogen atmosphere was added Dess-Martin periodinane (185 mg, 0.437 mmol, 1.5 eq) at 0° C. The reaction mixture was warmed to room temperature and stirred for 1 h. Progress of the reaction was monitored by TLC. After completion of the reaction, the reaction mixture was quenched with saturated with aq. sodium thiosulfate solution (5 mL) and aq. sodium bicarbonate solution (5 mL) and extracted with dichloromethane (3×10 mL). The combined organic extract was washed with brine (30 mL), dried over anhydrous sodium sulfate, filtered and concentrated under vacuum to afford the desired product (90 mg, 60%) which was used in next step without further purification.

LCMS: 513.6 [M+H]$^+$.

Step-3: Preparation of 7-((4-(((1R,4r)-4-((3,5-Difluoro-4-((1R,3R)-2-(2-fluoro-2-methylpropyl)-3-methyl-2,3,4,9-tetrahydro-1H-pyrido[3,4-b]indol-1-yl)phenoxy)methyl)cyclohexyl)methyl)piperazin-1-yl)methyl)-3-ethyl-1,5-naphthyridin-2(1H)-one (75)

To a stirred solution of 3-ethyl-7-(piperazin-1-ylmethyl)-1,5-naphthyridin-2(1H)-one (Int-6, prepared above, 63 mg, 0.210 mmol, 1.2 eq) in methanol (1 mL) and dichloromethane (1 mL) was added sodium acetate (72 mg, 0.875 mmol, 5 eq) at room temperature and stirred for 10 min. To this solution was added (1R,4 r)-4-((3,5-difluoro-4-((1R,3R)-2-(2-fluoro-2-methylpropyl)-3-methyl-2,3,4,9-tetrahydro-1H-pyrido[3,4-b]indol-1-yl)phenoxy) methyl)cyclohexane-1-carbaldehyde (Int-2, 90 mg, 0.175 mmol, 1.0 eq) and stirred for 1 h at room temperature. To this reaction mixture was added sodium triacetoxyborohydride (74 mg, 0.351 mmol, 2 eq) and the mixture was stirred for 16 h. Progress of the reaction was monitored by TLC. After completion of the reaction, the reaction mixture was concentrated under reduced pressure to obtain the crude product, which was purified by column chromatography eluting with 10% methanol in ethyl acetate to afford the titled product (100 mg, 72%).

$^1$H NMR (400 MHz, DMSO-d$_6$) δ 11.80 (s, 1H), 10.49 (s, 1H), 8.35 (d, J=1.75 Hz, 1H), 7.73 (s, 1H), 7.57 (d, J=1.00 Hz, 1H), 7.38 (d, J=7.63 Hz, 1H), 7.17 (d, J=7.75 Hz, 1H), 6.87-7.04 (m, 2H), 6.63 (br d, J=11.13 Hz, 2H), 5.11 (s, 1H), 3.78 (br d, J=6.25 Hz, 2H), 3.46-3.62 (m, 3H), 2.75-2.95 (m, 2H), 2.52-2.56 (m, 2H), 2.27-2.44 (m, 8H), 2.02-2.11 (m, 2H), 1.79 (br d, J=9.51 Hz, 4H), 1.65 (br dd, J=4.06, 2.31 Hz, 1H), 1.37-1.52 (m, 1H), 1.08-1.26 (m, 10H), 0.94-1.07 (m, 6H). HPLC purity: 95.2%. LCMS: 769.4 [M+H]$^+$.

Procedure 21: Preparation of 7-((4-((1-(3,5-Difluoro-4-(((1R,3R)-2-(2-fluoro-2-methylpropyl)-3-methyl-2,3,4,9-tetrahydro-1H-pyrido[3,4-b]indol-1-yl)phenyl)piperidin-4-yl)methyl)piperazin-1-yl)methyl)-3-ethyl-1,5-naphthyridin-2(1H)-one (76)
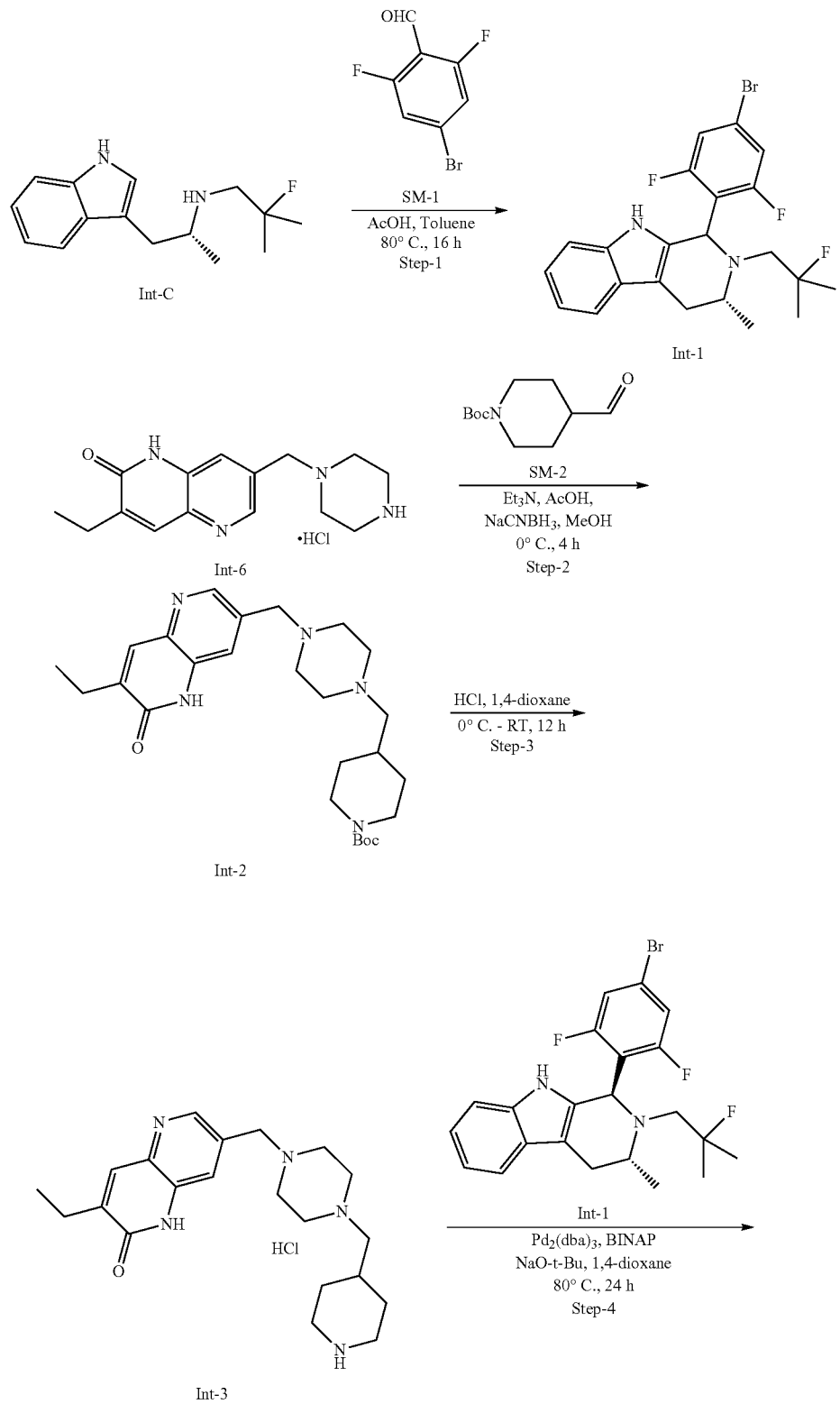

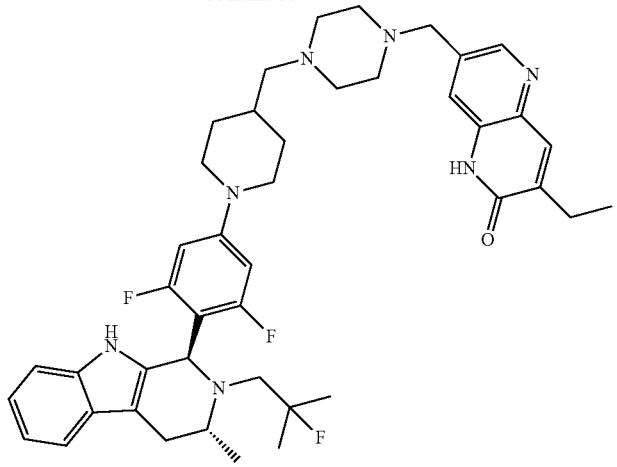 [SMILES: CCc1cc2ncc(CN3CCN(CC4CCN(c5cc(F)c([C@@H]6c7[nH]c8ccccc8c7C[C@@H](C)N6CC(C)(C)F)c(F)c5)CC4)CC3)cc2[nH]c1=O]

Step-1: Preparation of (1R,3R)-1-(4-Bromo-2,6-difluorophenyl)-2-(2-fluoro-2-methylpropyl)-3-methyl-2,3,4,9-tetrahydro-1H-pyrido[3,4-]indole (Int-1)

To a stirred solution of (R)—N-(1-(1H-indol-3-yl)propan-2-yl)-2-fluoro-2-methylpropan-1-amine (Int-C, prepared above, 1.0 g, 4.0 mmol, 1.0 eq) and 4-bromo-2,6-difluorobenzaldehyde (SM-1, 1.68 g, 4.8 mmol, 1.2 eq) in toluene (15 mL) was added acetic acid (0.288 mL, 12 mmol, 3 eq) at room temperature. The reaction mixture was heated to 80° C. and stirred for 16 h in a sealed tube. Progress of the reaction was monitored by TLC. After completion of the reaction, the reaction mixture was diluted with water (120 mL) and extracted with ethyl acetate (3×100 mL). The combined organic extract was dried over anhydrous sodium sulfate and solvents were evaporated under reduced pressure to obtain the crude product, which was purified by column chromatography eluting with 3-6% EtOAc in heptane to afford the titled product (1.2 g, 66%).

LCMS: 451.1 [M+H]+.

Step-2: Preparation of tert-Butyl 4-((4-((7-Ethyl-6-oxo-5,6-dihydro-1,5-naphthyridin-3-yl)methyl)piperazin-1-yl)methyl)piperidine-1-carboxylate (Int-2)

To a stirred solution of 3-ethyl-7-(piperazin-1-ylmethyl)-1,5-naphthyridin-2(1H)-one hydrochloride salt (Int-6, prepared above, 1.0 g, 3.2 mmol, 1.0 eq) in methanol (20 mL) was added triethylamine (323 mg, 3.5 mmol, 1.1 eq) at room temperature and stirred for 15 minutes. To this reaction mixture were added SM-2 (760 mg, 3.5 mmol) and acetic acid (192 mg, 3.2 mmol, 1.0 eq) at room temperature and again stirred for 30 min. To this reaction mixture was added NaCNBH$_3$ (396 mg, 6.4 mmol, 2 eq) at 0° C. The reaction mixture was allowed to warm up to room temperature and stir for 4 h. Progress of the reaction was monitored by TLC. After completion of the reaction, solvents were evaporated under reduced pressure to obtain the crude product which was triturated with diethyl ether (50 mL) and dried under vacuum to afford the desired product (1.1 g, crude) which was used in next step without further purification.

LCMS: 470.2 [M+H]+.

Step-3: Preparation of 3-Ethyl-7-((4-(piperidin-4-ylmethyl) piperazin-1-yl)methyl)-1,5-naphthyridin-2(1H)-one Hydrochloride Salt (Int-3)

To a stirred solution of tert-butyl 4-((4-(((7-ethyl-6-oxo-5,6-dihydro-1,5-naphthyridin-3-yl)methyl)-piperazin-1-yl)methyl)piperidine-1-carboxylate (Int-2, 1.1 g, 2.3 mmol, 1.0 eq) in 1,4-dioxane (10 mL) was added 4M HCl in 1,4-dioxane (3.5 mL, 3.0 eq) at 0° C. The reaction mixture was allowed to warm up to room temperature and stirred for 12 h. Progress of the reaction was monitored by TLC. After completion of the reaction, solvents were removed under reduced pressure to get the crude product. The crude obtained was washed with diethyl ether (3×15 mL) and dried under vacuum to afford the titled product (900 mg, 94%).

LCMS: 370.4 [M+H]+.

Step-4: Preparation of 7-((4-((1-(3,5-Difluoro-4-((1R,3R)-2-(2-fluoro-2-methylpropyl)-3-methyl-2,3,4,9-tetrahydro-1H-pyrido[3,4-b]indol-1-yl)phenyl) piperidin-4-yl)methyl)piperazin-1-yl)methyl)-3-ethyl-1,5-naphthyridin-2(1H)-one (76)

To a stirred solution of 3-ethyl-7-((4-(piperidin-4-ylmethyl)piperazin-1-yl)methyl)-1,5-naphthyridin-2(1H)-one hydrochloride (Int-3, 613 mg, 1.6 mmol, 1.5 eq) in 1,4-dioxane (20 mL) under nitrogen atmosphere was added NaO-t-Bu (528 mg, 5.5 mmol, 5.0 eq) at room temperature and stirred for 20 minutes. To the mixture were added Int-1 (500 mg, 1.1 mmol, 1.0 eq), BINAP (102 mg, 0.22 mmol, 0.2 eq) Pd$_2$(dba)$_3$ (150 mg, 0.16 mmol, 0.15 eq) and the reaction mixture was purged with N$_2$ gas for 30 min. The reaction mixture was heated to 80° C. and stirred for 24 h. Progress of the reaction was monitored by TLC. After completion of the reaction, the reaction mixture was filtered through a pad of celite and the celite bed was washed with ethyl acetate (40 mL). The filtrate was diluted with water (60 mL) and the aqueous layer was extracted with ethyl acetate (2×40 mL). The combined organic extract was dried over anhydrous sodium sulfate, filtered and concentrated under vacuum to obtain the crude product. The crude obtained was purified by Prep. HPLC (ammonium bicarbonate as the modifier) to afford the titled product (145 mg, 17.7%).

$^1$H NMR (400 MHz, DMSO-d$_6$) δ 11.81 (s, 1H), 10.47 (s, 1H), 8.35 (d, J=1.63 Hz, 1H), 7.73 (s, 1H), 7.58 (s, 1H), 7.37 (d, J=7.63 Hz, 1H), 7.17 (d, J=7.75 Hz, 1H), 6.86-7.03 (m,

2H), 6.50 (br d, J=13.26 Hz, 2H), 5.07 (s, 1H), 3.72 (br d, J=12.63 Hz, 2H), 3.56 (s, 3H), 2.78-2.93 (m, 2H), 2.63-2.73 (m, 2H), 2.53 (br d, J=7.50 Hz, 3H), 2.32-2.44 (m, 8H), 2.13 (br d, J=6.88 Hz, 2H), 1.73 (br d, J=12.38 Hz, 3H), 1.00-1.25 (m, 15H). HPLC purity: 95.5%. LCMS: 738.3 [M−H]$^-$.

Biological Assays

Biological Example 1

The following methods are for evaluating the in vitro biology properties of the test articles.

a. RBC HotSpot Poly(ADP-ribose) Polymerases 1 (PARP1) and Poly(ADP-ribose) Polymerases 2 (PARP2) Assays: The assay is conducted at Reaction Biology Corporation (RBC; Malvern, PA). The assay principle is radioisotope-based filter binding assay where incorporation of radioisotope-labeled NAD$^+$ into the substrate captured on filter is detected after washout free NAD$^+$. Data are analyzed using Excel and GraphPad Prism software for IC$_{50}$ curve fits. Each assay is conducted with PJ34 as a positive control.

i. PARP1 assay: Human recombinant PARP1 at a final concentration of 2.5 nM is combined with histone H4 (20 µM) and test articles at various concentrations in reaction buffer (50 mM Tris-HCL, pH 8.0, 50 mM NaCl, 10 mM MgCl$_2$, 1 mM DTT, 1% DMSO, and 20 µg/mL activated DNA). The solution is inoculated for 20 mM at room temperature and the reaction initiated by adding [adenylate-$^{32}$P]-Nicotinamide Adenine Dinucleotide, $^{32}$P-NAD$^+$ at a final concentration of 10 µM. After incubation for 2 hrs at room temperature, the reaction mixture is filtered and washed with 0.75% phosphoric acid for radioactivity detection.

ii. PARP2 assay: Human recombinant PARP2 at a final concentration of 2.5 nM is combined with histone H3 (20 µM) and test articles at various concentrations in reaction buffer (50 mM Tris-HCl, pH 8.0, 50 mM NaCl, 10 mM MgCl$_2$, 1 mM DTT, 1% DMSO, and 20 µg/mL activated DNA). The solution is inoculated for 20 mM at room temperature and the reaction is initiated by adding [adenylate-$^{32}$P]-Nicotinamide Adenine Dinucleotide, $^{32}$P-NAD$^+$ at a final concentration of 10 µM. After incubation for 2 hrs at room temperature, the reaction mixture is filtered and washed with 0.75% phosphoric acid for radioactivity detection.

b. AR binding assay: AR in LNCaP cytosol is used for determining the binding affinity of test articles and the reference compound, progesterone (Sigma, Cat: E2785, St. Louis, MO). IC$_{50}$s are determined using 8 concentrations/compound. Cytosol is plated at 200 µg/well (100 µL) into a 96-well conical polypropylene plate (Agilent, Cat: 5042-1385, Santa Clara, CA) and mixed with 3 µL of test compound. After adding 100 µL of $^3$H-methyltrienolone (PerkinElmer, Cat: NET590250UC, San Jose, CA), the plate is sealed and shaken at 300 rpm at 4° C. for 24 hours. Post incubation, 100 µL of radioligand adsorption buffer containing 10 mM Tris-HCl, pH 7.4; 1.5 mM EDTA; 1 mM DTT; 0.25% charcoal; 0.0025% dextran is added to individual wells. Plate is shaken for 15 mM at 4° C. followed by centrifugation at 3000 rpm for 30 min at 4° C. 150 µL of supernatant is transferred into scint-tube (PerkinElmer, Cat: 6000192) and mixed with 2 mL of Ultima Gold Cocktail (PerkinElmer, Cat: 6013329). Radioactivity is counted using a TriCarb 2910 TR scintillation counter (PerkinElmer). Inhibition of the radioactivity by test articles is calculated using the equation below:

% Inhibition=(1−(Assay well−Average_LC)/(Average_HC−Average_LC))×100%.

IC$_{50}$ values are calculated and graphed using the model "log(inhibitor) vs. response—Variable slope" included in GraphPad Prism 5 (San Diego, CA). The Ki values are further calculated using the equation below where [L] is the radioligand concentration (1 nM) used in this study. Kd value is 0.332 nM.

$Ki=IC_{50}/(1+[L]/Kd)$ c. AR transactivation: Human AR cloned into a CMV vector backbone is used for the transactivation study. HEK-293 cells are plated at 80,000 cells per well of a 24 well plate in DME+5% csFBS. Twenty four hours later, the cells are transfected using Lipofectamine (Invitrogen, Carlsbad, CA) with 0.25 lag GRE-LUC, 0.01 µg CMV-LUC (renilla luciferase) and 25 ng of the AR in OPTIMEM medium. The cells are treated 24 hrs after transfection with various ligands (10$^{-12}$ to 10$^{-5}$ M final concentrations) and luciferase assay performed 48 hours after transfection. Firefly values are normalized to renilla luciferase values and the values represented as relative light units (RLU). Agonist and antagonist assays for the test article are performed in the absence and in the combination with 0.1 nM R1881, respectively. Data are represented as EC$_{50}$ (for agonists) and IC$_{50}$ (for antagonists) values obtained from four parameter logistics curve.

d. Cell culture and proliferation assays: 22RV1 and HT-29 cells are procured from American Type Culture Collection (ATCC). Cells are cultured in medium recommended by the ATCC. Cell culture medium is obtained from Fisher scientific (Waltham, MA) and serum is obtained from Hyclone (San Angelo, TX).

Cells are plated at varying density in the respective growth medium in 96 well plates. 24 hr later, cells are treated, in triplicate or quadruplicate, with test articles prepared in a range of concentrations by series dilution of DMSO stock solutions in growth medium and incubated for three to seven days. The number of viable 22RV1 and HT-29 cells is measured using CellTiter Glo assay (CTG, Promega, Madison, WI) after three days of treatment. Cell viability data are plotted using GraphPad Prism (GraphPad Software, Inc., San Diego, CA). In addition, a nonlinear regression model with a sigmoidal dose response and variable slope within GraphPad Prism is used to calculate the IC$_{50}$ value of individual test articles.

e. Additional cell proliferation assays: Other cancer cell lines can be tested in a cell proliferation assays, such as LnCaP, PC-3, MCF-7, HCC1428, BT474, HCT-116, SK-OV-3 or OVCAR3 cancer cells, by the following method. Cells are cultured in medium recommended by the supplier (e.g., ATCC or JCRB Cell Bank), at 37° C. in a 5% CO$_2$ environment. For the proliferation assay, cells are plated in the growth medium in 96 well plates. Seeding density is adjusted according to the cell type. 24 hr later, cells are treated, in triplicate or quadruplicate, with test articles prepared in a range of concentrations by series dilution of DMSO stock solutions in growth medium, and typically incubated for three to seven days, with test article-containing medium replaced after three or four days. The number of viable cells is measured using CellTiter Glo assay (CTG, Promega, Madison, WI) or similar. Cell viability data are plotted using GraphPad Prism (GraphPad Software, Inc., San Diego, CA). In addition, a nonlinear regression model with a sigmoidal dose response and variable slope within GraphPad Prism is used to calculate the $IC_{50}$ value of individual test articles. Similarly, HEK-293 and HeLa calls can also be tested by methods known in the art.

f. Nuclear translocation: LNCaP cells are plated on coverslips in 24 well plates in growth medium. Twenty-four hours after plating, medium is changed to RPMI+1% csFBS and the cells are maintained in this medium for two days. Medium is replaced again and the cells are treated. Cells are fixed 4 hours after treatment and the AR immunostained using AR N20 antibody (Santa Cruz Biotechnology, Santa Cruz, CA). Nucleus is stained with DAPI. Cells are imaged with a confocal microscope.

g. ER binding assay: ERα binding is assessed by the LanthaScreen® TR-FRET ER Alpha Competitive Binding Assay at Thermo Fisher. In this assay, a terbium-labeled anti-GST antibody is used to indirectly label GST-tagged ER Alpha-ligand binding domain (LBD) by binding to its GST tag. Competitive binding to the ER Alpha-LBD (GST) is detected by a test compound's ability to displace a fluorescent ligand (Fluormone™ ES2 Green tracer) from the ER Alpha-LBD (GST), which results in a loss of FRET signal between the Tb-anti-GST antibody and the tracer. When running the assay, Fluormone™ ES2 Green tracer is added to ligand test compounds or solvent controls followed by addition of a mixture of the ER Alpha-LBD (GST) and terbium anti-GST antibody. After an incubation period at room temperature, the TR-FRET ratio of 520:495 emissions are calculated and used to determine the $IC_{50}$ from a dose response curve of the compound.

h. ER and PR functional assays: COS cells are transfected with 25 ng rat progesterone receptor (PR) and 250 ng GRE-LUC or 50 ng human estrogen receptor a (ER) and 250 ng ERE-LUC. Cells are also transfected with 10 ng CMV-renilla LUC in OptiMEM medium using lipofectamine transfection reagent. Twenty-four hours after transfection medium is changed to DME+5% csFBS w/o and treated with compounds in the presence of 0.1 nM progesterone for PR and estradiol for ER. Twenty four hours after treatment, cells are harvested and luciferase assay is performed using dual luciferase assay kit. The firefly values are normalized to renilla luciferase values and represented as a ratio.

i. Evaluation of test compound in mouse xenograft model: To examine the in vivo antitumor activity of test compound, tumor growth experiments are performed in a cell line xenograft model. Male NOD SCID Gamma (NSG) mice are housed as five animals per cage and are allowed free access to water and commercial rodent chow. 22RV1 cells (grown in RPMI+10% FBS) mixed with 50% matrigel basement membrane are implanted subcutaneously in castrated mice. Alternatively, an antiandrogen resistant cell line other than 22RV1, such as MR49F or VCaP, is used. Once the tumors reach 200-500 mm³, the animals are randomized and treated intraperitoneally with vehicle (DMSO:PEG-300:corn oil 10:30:60 ratio) or test compound. Tumors are measured thrice weekly and the volume is calculated using the formula length*width*width*0.5. Animals are sacrificed at the end of 28 days of treatment and the tumors are weighed and stored for further processing. The tumor growth inhibition (TGI) is calculated by comparing the control group's tumor measurements with the other study groups. TGI is calculated for each group using the formula listed below:

$$TGI\ (\%) = [1 - (TV_{Treatment\_DayN} - TV_{Treatment\_Day0}) / (TV_{Vehicle\_DayN} - TV_{Vehicle\_Day0})] \times 100\%$$

$TV_{Treatment\_DayN}$ is the average tumor volume of a treatment group on a given day, $TV_{Treatment\_Day0}$ is the average tumor volume of the treatment group on the first day of treatment, $TV_{Vehicle\_DayN}$ is the average tumor volume of the vehicle control group on a given day, and $TV_{Vehicle\_Day0}$ is the average tumor volume of the vehicle group on the first day of treatment.

Biological Example 2

AR binding assay: To assess AR binding, test compound (top dose 10 µM, 4 fold serial dilution, 8 point dose response) and control (progesterone) were transferred to the assay plate. Cytosol from LnCaP cells was added to the plate, followed by addition of radiolabeled ³H-R1881 at a final concentration of 1 nM. The plate was sealed, and the reaction was incubated at 300 rpm at 4° C. for 24 hrs. Radioligand absorption buffer (10 mM Tris-HCl, pH 7.4; 1.5 mM EDTA; 1 mM DTT; 0.25% charcoal; 0.0025% dextran) was then added to the plate, mixed, and incubated at 4° C. for 15 minutes. The plate was then centrifuged at 3000 rpm for 30 minutes at 4° C. The supernatant was transferred to the scint-tube and Tri-carb was used for scintillation counting. The data was analyzed using GraphPadPrism v5.0 and binding $IC_{50}$ was determined as the concentration where 50% inhibition of radioligand binding was observed.

GR binding assay: To assess GR binding, test compound (top dose 1 µM, 4 fold serial dilution, 8 point dose response) and control (dexamethasone) were transferred to the assay plate. Cytosol from IM-9 cells was added to the plate, followed by addition of radiolabeled ³H-Dexamethasone at a final concentration of 1.5 nM. The plate was sealed, and the reaction incubated at 300 rpm at 4° C. for 24 hrs. Radioligand absorption buffer (10 mM Tris-HCl, pH 7.4; 1.5 mM EDTA; 1 mM DTT; 0.25% charcoal; 0.0025% dextran) was then added to the plate, mixed, and incubated at 4° C. for 15 minutes. The plate was then centrifuged at 3000 pm for 30 minutes at 4° C. The supernatant was transferred to the scint-tube and Tri-carb was used for scintillation counting. The data was analyzed using GraphPadPrism v5.0 and binding $IC_{50}$ was determined as the concentration where 50% inhibition of radioligand binding is observed.

PR binding assay: Progesterone PR-B receptors from human breast carcinoma T47D cells were used in modified $Na_2HPO_4/NaH_2PO_4$ buffer pH 7.4. Compounds were screened at a range of doses (Top dose 40 nM, 4 fold serial dilution, 8 point dose response) and were dispensed into the assay plate. Supernatant of $1.2 \times 10^5$ cells aliquot was added to the assay plate and was incubated with 0.5 nM [³H] Progesterone for 20 hours at 4° C. Membranes are filtered and washed, the filters were then counted to determine [³H]Progesterone specifically bound. Binding $IC_{50}$ was determined as the concentration where 50% inhibition of radioligand binding was observed.

ER binding assay: ERα binding was assessed using the LanthaScreen® TR-FRET ER Alpha Competitive Binding kit from ThermoFisherScientific. In this assay, a terbium-labeled anti-GST antibody was used to indirectly label GST-tagged ER Alpha-ligand binding domain (LBD) by binding to its GST tag. Competitive binding to the ER Alpha-LBD (GST) was detected by a test compound's ability to displace a fluorescent ligand (Fluormone™ ES2 Green tracer) from the ER Alpha-LBD (GST), which results in a loss of FRET signal between the Tb-anti-GST antibody and the tracer. To assess ER binding, test compound (top dose 10 µM, 4 fold serial dilution, 8 point dose response) and controls (e.g. estradiol) were transferred to the assay plate.

The Fluormone™ ES2 Green tracer (3 nM final concentration with assay buffer) was added to the assay plate. This was followed by addition of a mixture of the ER Alpha-LBD (GST) and terbium anti-GST antibody. After a 2 h incubation period at room temperature, the plate was read on the Envision plate reader and the TR-FRET ratio of 520:495 emissions were calculated and used to determine the $IC_{50}$ from a dose response curve of the compound.

AR antagonism assay: To evaluate AR antagonist activity, test compound was added to the assay plate (top dose 10 μM, 3 fold serial dilution, 10 point dose response). HEK293 cells stably expressing the full-length androgen receptor were seeded at a density of 20000 cells/well in the assay plate. The assay plate was then incubated at room temperature for 10 minutes and at 37° C., 5% $CO_2$ for 20 minutes. Testosterone is added to the assay plate at 1 nM final concentration and the assay plate incubated at 37° C., 5% $CO_2$ for 20 h. After the incubation period, Steady-glo was added to the assay plate and mixed at room temperature for 20 minutes on an orbital shaker, before reading out on the EnVision plate reader.

GR antagonism assay: To evaluate GR antagonist activity, test compound is added to the assay plate (top dose 5 μM, 4 fold serial dilution, 8 point dose response). HEK293 cells stably expressing the ligand binding domain of the glucocorticoid receptor are seeded at a density of 40000 cells/well in the assay plate. The assay plate is then incubated at 37° C., 5% $CO_2$ for 30 minutes. Dexamethasone is added to the assay plate at 1.5 nM final concentration and the assay plate incubated at 37° C., 5% $CO_2$ for 20 h. After the incubation period, Dual-glo luciferase reagent is added to the assay plate and mixed at room temperature for 20 minutes on an orbital shaker, before reading out on the EnVision plate reader. 50 μL of Stop & Glo reagent is added to assay plate, mixed at room temperature for 20 minutes, and read on the Envision plate reader.

PR coactivator antagonist assay: Test compound (Top dose 10 μM, 4 fold serial dilution, 8 point dose response) and/or vehicle is incubated with the 2.5 nM Progesterone Receptor (PR)-LBD and coactivator peptide for 30 minutes at RT. Determination of the amount of complex formed is read spectrofluorimetrically (excitation: 337 nm, emission: 520/490 nm). Test compound-induced inhibition of 10 nM progesterone-induced fluorescence response by 50 percent or more (≥50%) indicates receptor antagonist activity.

ER antagonism assay: To evaluate ER antagonist activity, SK-BR-3 cells were seeded at a density of 30000 cells/well in the assay plate. The assay plate was then incubated at 37° C., 5% $CO_2$ for 24 h. A mixture of ERE plasmid and ER in opti-MEM media was incubated with lipofectamine 3000 in Opti-MEM media and incubated at room temperature for 15 minutes. 10 μL of this transfection mix was added to each well of the assay plate and the assay plate was incubated at 37° C., 5% $CO_2$ for 24 h. 100 nM β-Estradiol in 10 μL medium or 10 μL medium (control wells) was added to corresponding wells of assay plate and incubated at 37° C. 5% $CO_2$ for 24 h. After the incubation period, 50 μL of Dual-glo luciferase reagent was added to the assay plate and mixed at room temperature for 20 mins on an orbital shaker, before reading out on the EnVision plate reader. 50 μL of Stop & Glo reagent was added to assay plate, mixed at room temperature for 20 minutes, and read on the Envision plate reader.

Cell viability assay: LNCap, 22Rv1, MCF7, MDAMB361, T47D, and IEC6 cells were seeded at a density of 500-2000 cells/well in 96 well plates, and a 'T0' (timepoint 0) was included along with the assay plate. The plates were then incubated at 37° C., 5% $CO_2$ in a cell culture incubator overnight. On the next day, the 'T0' plate was assayed using CellTiterGlo (Promega, Inc) according to the manufacturer's instructions. The appropriate compounds were diluted in DMSO and added to the assay plate (final DMSO concentration of 0.1-0.2%) on the next day. The assay plates were incubated for 6 days at 37° C., 5% $CO_2$. After the incubation period, the plates were assayed using CellTiterGlo (Promega, Inc) according to the manufacturer's instructions and luminescence was read on the EnVision plate reader. Inhibition of the tested compounds was determined by the following formula: Inhibition rate (%)=(1−(RLU compound−RLU day0)/(RLU control−RLU day0))*100%. GraphPadPrism was used to analyze the data and determine $GI_{50}/IC_{50}$ values.

Data obtained for certain compounds disclosed herein in the assays described above in Biological Assay 2 are shown in Table 2 and Table 3.

In Table 2, activity is provided as follows: A=$IC_{50}$≤100 nM; B=$IC_{50}$ from >100 nM to ≤1,000 nM; C=$IC_{50}$ from >1,000 nM to ≤10,000 nM; D=$IC_{50}$>10,000 nM; NT=Not tested.

TABLE 2

| No. | AR binding ($IC_{50}$, nM) | AR antagonism ($IC_{50}$, nM) | ER binding ($IC_{50}$, nM) | ER antagonism ($IC_{50}$, nM) |
|---|---|---|---|---|
| 1 | B | D | NT | NT |
| 4 | A | D | NT | NT |
| 13 | A | D | NT | NT |
| 59 | A | D | NT | NT |
| 60 | A | D | NT | NT |
| 61 | NT | NT | A | A |
| 63 | B | D | NT | NT |
| 64 | C | D | NT | NT |
| 65 | D | D | NT | NT |
| 66 | A | D | NT | NT |
| 67 | A | D | NT | NT |
| 68 | D | D | NT | NT |
| 69 | D | D | NT | NT |
| 70 | NT | NT | NT | A |
| 71 | NT | NT | NT | A |
| 72 | NT | NT | NT | A |
| 73 | NT | NT | NT | A |
| 74 | NT | NT | NT | A |

In Table 3, activity is provided as follows: A=$IC_{50}$≤500 nM; B=$IC_{50}$ from >500 nM to ≤5,000 nM; C=$IC_{50}$ from >5,000 nM to ≤30,000 nM; D=$IC_{50}$>30,000 nM; NT=Not tested.

TABLE 3

| No. | LNCap ($GI_{50}$, nM) | 22RV1 ($GI_{50}$, nM) | MCF7 ($GI_{50}$, nM) | MDA-MB-361 ($GI_{50}$, nM) | IEC-6 ($IC_{50}$, nM) |
|---|---|---|---|---|---|
| 4 | A | A | NT | NT | D |
| 59 | B | B | NT | NT | D |
| 60 | B | B | NT | NT | D |
| 1 | A | B | NT | NT | D |
| 61 | NT | NT | A | D | D |
| 63 | B | C | NT | NT | D |
| 64 | B | C | NT | NT | B |
| 13 | B | B | NT | NT | B |
| 65 | C | D | NT | NT | D |
| 66 | A | A | NT | NT | B |
| 67 | A | A | NT | NT | D |
| 68 | B | C | NT | NT | D |
| 69 | B | C | NT | NT | D |
| 70 | NT | NT | C | A | D |
| 71 | NT | NT | A | B | B |
| 72 | NT | NT | A | A | C |

TABLE 3-continued

| No. | LNCap (GI$_{50}$, nM) | 22RV1 (GI$_{50}$, nM) | MCF7 (GI$_{50}$, nM) | MDA-MB-361 (GI$_{50}$, nM) | IEC-6 (IC$_{50}$, nM) |
|---|---|---|---|---|---|
| 73 | NT | NT | A | A | D |
| 74 | NT | NT | A | A | B |
| 75 | NT | NT | NT | NT | C |

What is claimed is:

1. A compound of Formula I, or a tautomer, stereoisomer, mixture of stereoisomers, or pharmaceutically acceptable salt thereof:

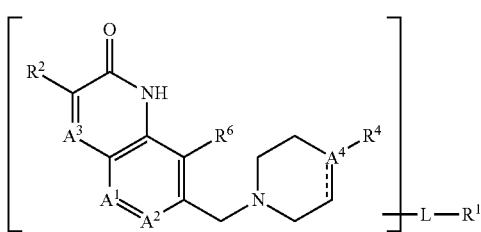

wherein:
$A^1$ is CH or N;
$A^2$ is CH or N;
$A^3$ is N or $CR^3$;
$A^4$ is C and === is a double bond, or $A^4$ is CH and === is a single bond, or $A^4$ is N and === is a single bond;
L is

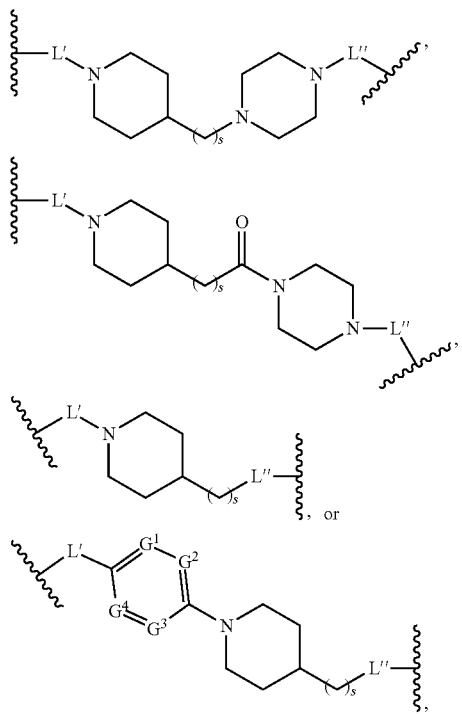

wherein:
s is 1, 2, or 3,
s' is 0 or 1,
$G^1$, $G^2$, $G^3$, and $G^4$ are each independently CH or N, and
L' and L'' are each independently selected from a bond, CH$_2$, CH$_2$CH$_2$, NHC(O), or C=O;
$R^1$ is a nuclear receptor-targeting epitope;
$R^2$ is hydrogen, $C_{1-6}$ alkyl, $C_{1-6}$ haloalkyl, $C_{1-6}$ alkoxy, or $C_{3-6}$ cycloalkyl;
$R^3$ is hydrogen or halo; or
$R^2$ and $R^3$ together with the atoms to which they are attached form a 6-membered heterocyclyl or 6-membered heteroaryl;
$R^4$ is hydrogen, aryl or heteroaryl, wherein the aryl or heteroaryl is optionally substituted with one to five $R^5$;
each $R^5$ is independently halo, cyano, nitro, —OR$^{10}$, —OC(O)R$^{10}$, —C(O)OR$^{10}$, —SR$^{10}$, —NR$^{10}$R$^{11}$, —NR$^{10}$C(O)R$^{11}$, —C(O)NR$^{10}$R$^{11}$, $C_{1-12}$ alkyl, $C_{1-12}$ haloalkyl, $C_{2-12}$ alkenyl, or $C_{2-12}$ alkynyl; wherein each $C_{1-12}$ alkyl, $C_{1-12}$ haloalkyl, $C_{2-12}$ alkenyl, or $C_{2-12}$ alkynyl is independently optionally substituted with one to five halo, hydroxyl, or amino;
$R^6$ is hydrogen, halo, or $C_{1-6}$ alkyl; and
each $R^{10}$ and $R^{11}$ is independently hydrogen or $C_{1-12}$ alkyl optionally substituted with oxo, halo, hydroxyl, or amino as valency permits; or $R^{10}$ and $R^{11}$ are taken together with the atoms to which they are attached to form a heterocyclyl optionally substituted by halo or $C_{1-12}$ alkyl optionally substituted by oxo, halo, hydroxyl, or amino;
wherein any hydrogen atom of the moiety in the brackets is replaced with -L-R$^1$.

2. The compound of claim 1, or a tautomer, stereoisomer, mixture of stereoisomers, or pharmaceutically acceptable salt thereof, wherein $R^6$ is hydrogen.

3. The compound of claim 1, or a tautomer, stereoisomer, mixture of stereoisomers, or pharmaceutically acceptable salt thereof, wherein the compound is represented by Formula IIA:

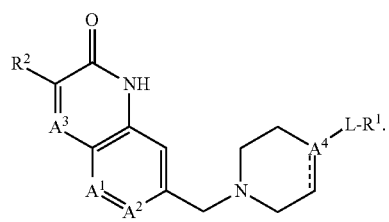

4. The compound of claim 1, or a tautomer, stereoisomer, mixture of stereoisomers, or pharmaceutically acceptable salt thereof, wherein the compound is represented by Formula IIB:

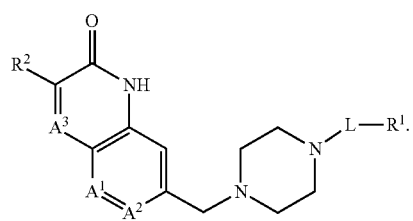

5. The compound of claim 1, or a tautomer, stereoisomer, mixture of stereoisomers, or pharmaceutically acceptable salt thereof, wherein $R^2$ is $C_{1-6}$ alkyl, and $R^3$ is hydrogen.

6. The compound of claim 1, or a tautomer, stereoisomer, mixture of stereoisomers, or pharmaceutically acceptable salt thereof, wherein the compound is represented by Formula IIC:

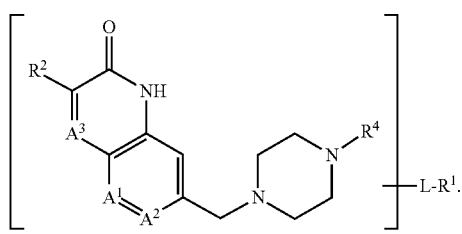

IIC

7. The compound of claim 1, or a tautomer, stereoisomer, mixture of stereoisomers, or pharmaceutically acceptable salt thereof, wherein the compound is represented by Formula IID:

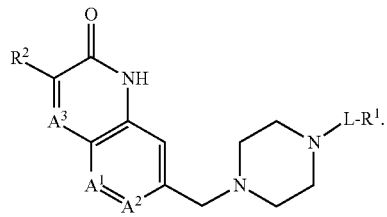

IID

8. The compound of claim 1, or a tautomer, stereoisomer, mixture of stereoisomers, or pharmaceutically acceptable salt thereof, wherein the compound is represented by Formula IIE:

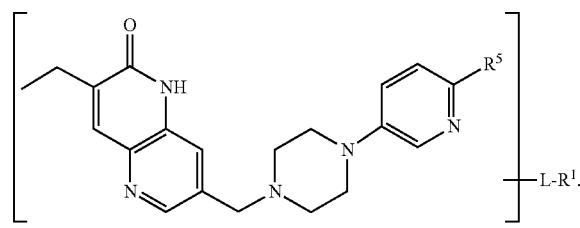

IIE

9. The compound of claim 1, or a tautomer, stereoisomer, mixture of stereoisomers, or pharmaceutically acceptable salt thereof, wherein the compound is represented by Formula IIF:

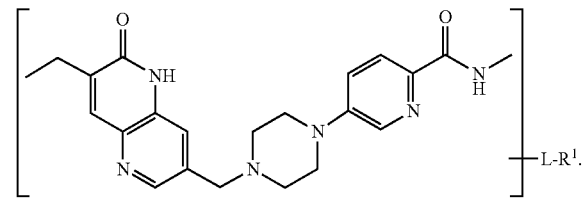

IIF

10. The compound of claim 1, or a tautomer, stereoisomer, mixture of stereoisomers, or pharmaceutically acceptable salt thereof, wherein the compound is represented by Formula IIG:

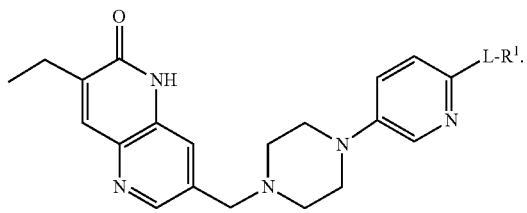

IIG

11. The compound of claim 1, or a tautomer, stereoisomer, mixture of stereoisomers, or pharmaceutically acceptable salt thereof, wherein L is:

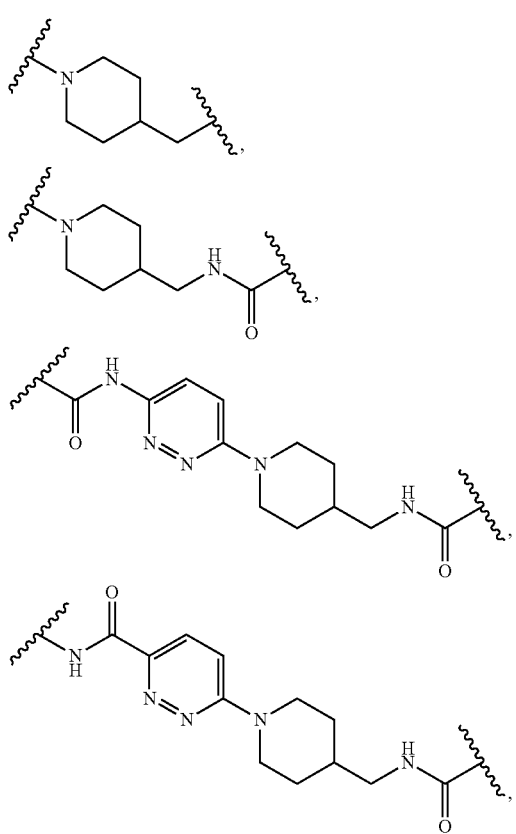

269
-continued
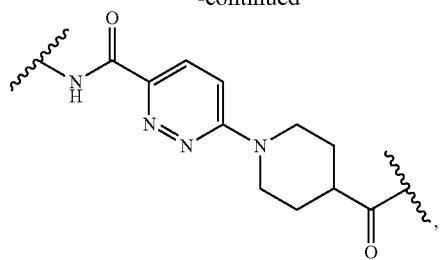
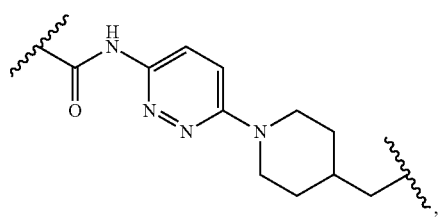
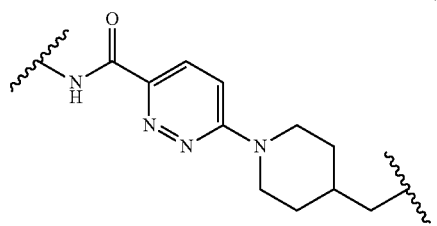
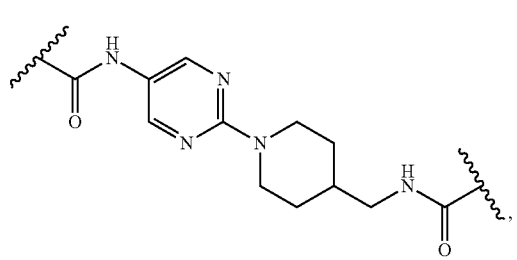
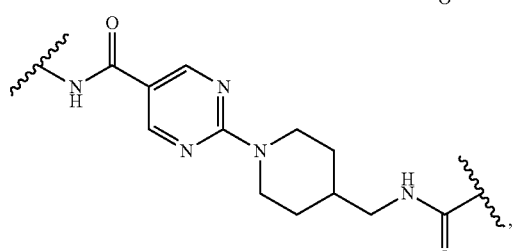
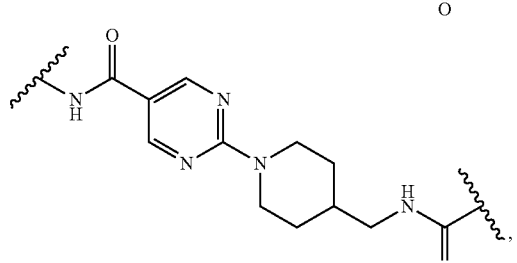
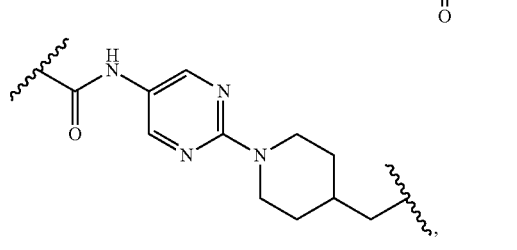
270
-continued
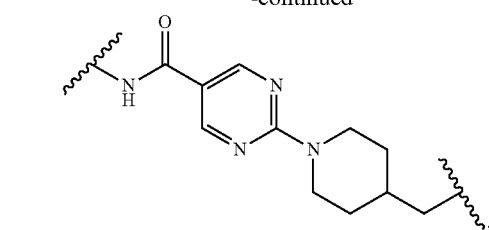
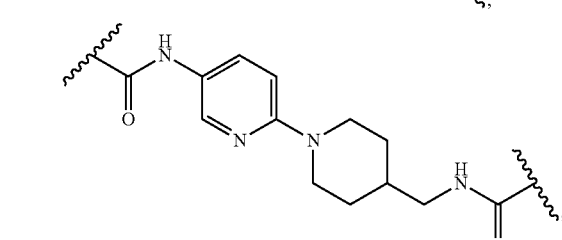
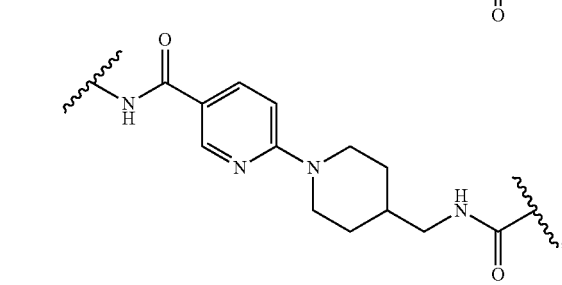
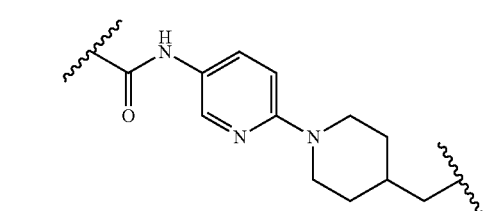
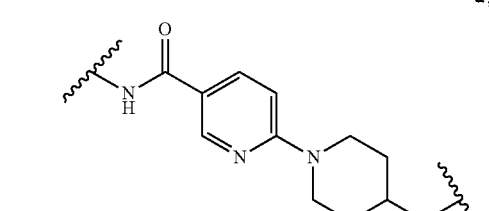
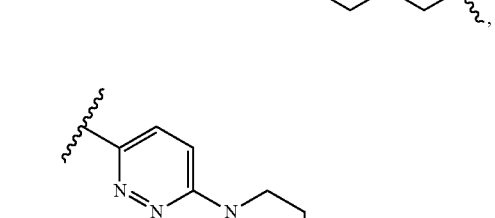
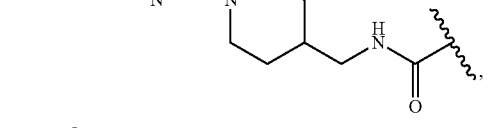
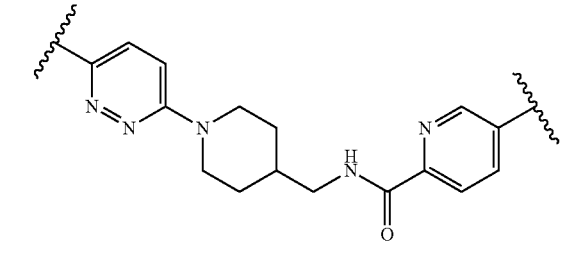

-continued

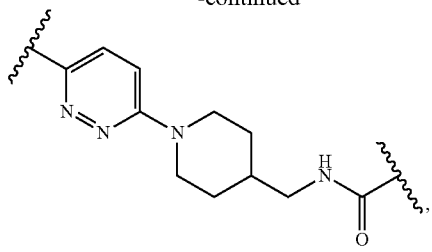

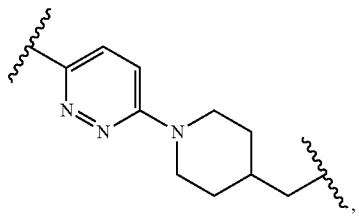

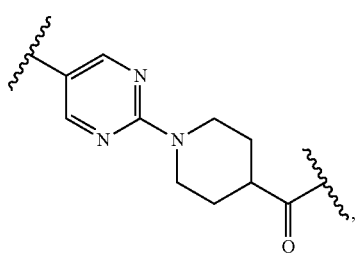

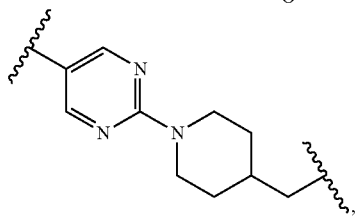

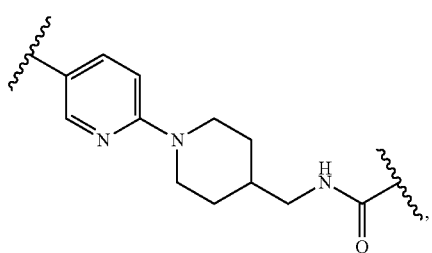

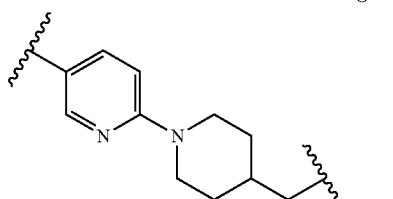

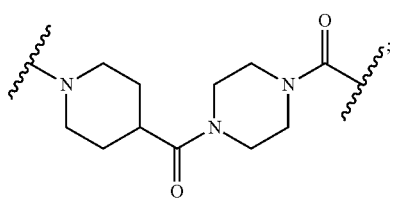

where the "*" and the wavy line represent a covalent bond.

12. The compound of claim 1, or a tautomer, stereoisomer, mixture of stereoisomers, or pharmaceutically acceptable salt thereof, wherein $R^1$ is derived from DHT, testosterone, dienolone, trienolone, drostanolol, stanzolol, JNJ-37654032, LGD-2226, LGD-3303, enzalutamide, apalutamide, darolutamide, bicalutamide, flutamide, nilutamide, enobosarm, BMS-564929, PS178990, LGD-4033 (ligandrol), LGD-2941, JNJ-28330835, JNJ-26146900, LGD-121071, LG-120907, S-40503, RAD-140, acetothiolutamide, andarine (S-4), TFM-4AS-1, YK-11, MK-0773 (PF-05314882), GSK2849466, GSK2881078, GSK8698, GSK4336, ACP-105, TT701, LY2452473, estradiol, fulvestrant, ARN-810 (GDC-810), GW5638, AZD9496, tamoxifen, toremifene, raloxifene, GW7604, bazedoxifene, ospemifene, droloxifene, clomifene, idoxifene, fispemifene, afimoxifene, arzoxifene, zindoxifene, pipendoxifene, GDC9545, lasofoxifene, endoxifen, ormeloxifene, cyclofenil, broparestrol, anordrin, toremifene, mapracorat, flumethasone, loteprednol etabonate, mometasone furoate, methylprednisolone, OP-3633, LLY-2707, CORT-108279, ORIC-101, AL082D06, dagrocorat, fosdagrocorat, megestrol acetate, progesterone, mifepristone (RU-486), telapristone, ulipristal acetate, anordrin, toremifene, or ketodarolutamide, or a stereoisomer or a mixture of stereoisomers thereof, or pharmaceutically acceptable salt thereof.

13. The compound of claim 1, or a tautomer, stereoisomer, mixture of stereoisomers, or pharmaceutically acceptable salt thereof, wherein $R^1$ is

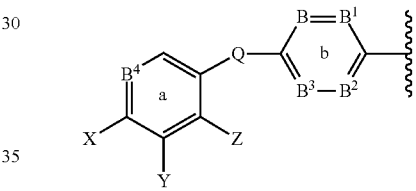

wherein:
Q is

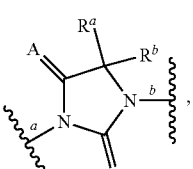 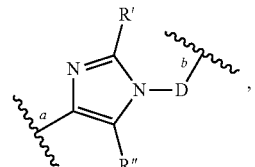

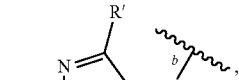 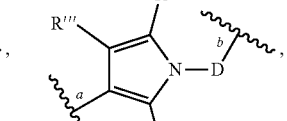

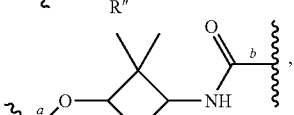

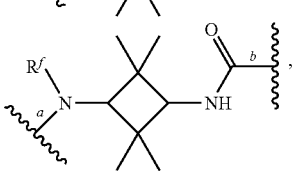

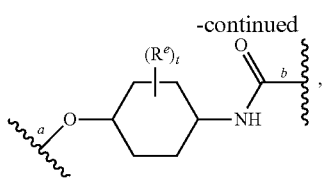

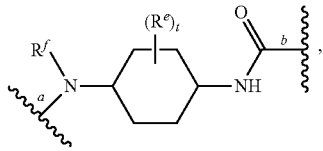

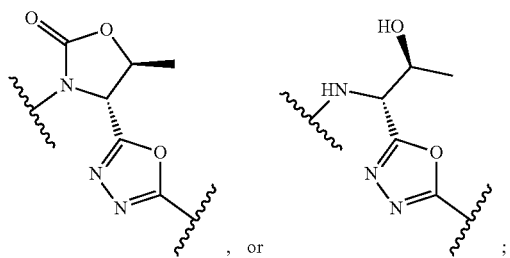, or ;

wherein bond a is attached to ring a and bond b is attached to ring b;

$R^a$ and $R^b$ are each independently $CH_3$ or $CH_2CH_3$; or $R^a$ and $R^b$ together with the atom to which they are attached form a $C_{3-5}$ cycloalkyl, oxiranyl, oxetanyl, or tetrahydrofuranyl;

A and A' are each independently O or S;

B, $B^1$, $B^2$, and $B^3$ are each independently $CR^c$ or N, and each $R^c$ is independently hydrogen, halo, CN, or methyl;

$B^4$ is CF, CH, or N;

D is a bond, $CH_2$, C=O, or (C=O)NH;

D' is NH, O, S, $CH_2$, NH(C=O), C(=O)NH, or C=O;

R', R" and R'" are each independently hydrogen, CN, or $C_{1-2}$ alkyl;

t is 0, 1, 2, 3 or 4;

each $R^e$ is independently halo, cyano, $C_{1-4}$ alkyl, or $C_{1-4}$ haloalkyl;

$R^f$ is hydrogen, $C_{1-4}$ alkyl, or $C_{3-6}$ cycloalkyl;

X is halo, CN, or $NO_2$;

Y is halo, $CH_3$, $CH_2F$, $CHF_2$, or $CF_3$; or

X and Y together form a

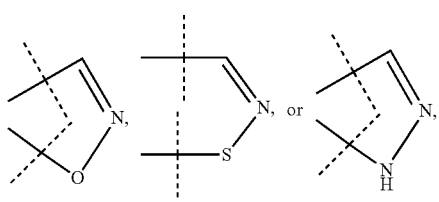

where the broken lines indicate bonds to ring a;

Z is hydrogen, halo, $C_{1-2}$ alkyl, $C_2$ alkenyl, $NO_2$, $CF_3$; or Y and Z together form a

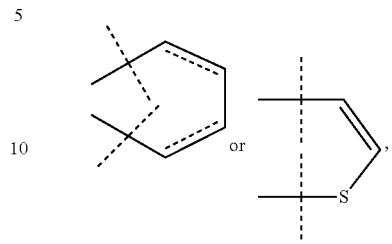

wherein each === is a single or double bond, and where the broken lines indicate bonds to ring a.

14. The compound of claim 1, or a tautomer, stereoisomer, mixture of stereoisomers, or pharmaceutically acceptable salt thereof, wherein $R^1$ is:

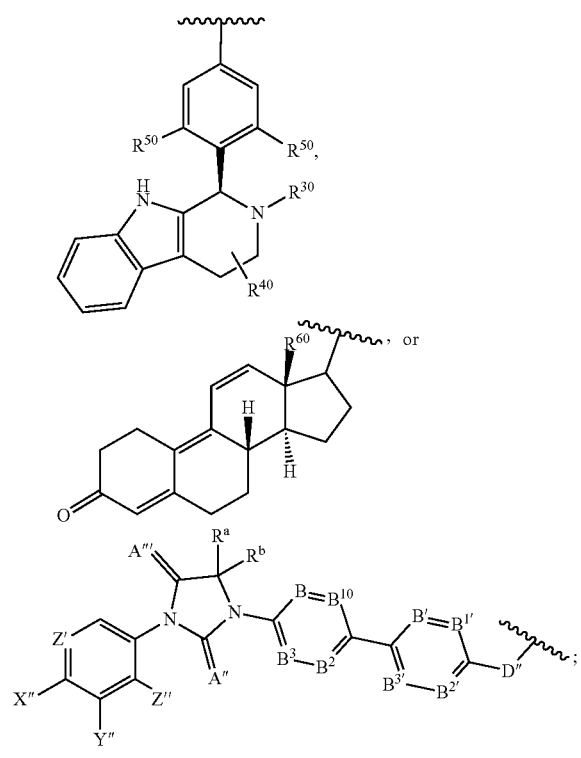

wherein:
$R^{30}$ is hydrogen, $C_{1-2}$ alkyl, $C_{1-12}$ haloalkyl, $C_{2-12}$ alkenyl, $C_{2-12}$ alkynyl, or $C_{3-12}$ cycloalkyl, wherein each $C_{1-12}$ alkyl, $C_{1-12}$ haloalkyl, $C_{2-12}$ alkenyl, $C_{2-12}$ alkynyl, or $C_{3-12}$ cycloalkyl is optionally independently substituted with one to five $R^{100}$ as valency permits;

$R^{40}$ is hydrogen, $C_{1-12}$ alkyl, $C_{1-12}$ haloalkyl, $C_{2-12}$ alkenyl, $C_{2-12}$ alkynyl, or $C_{3-12}$ cycloalkyl, wherein each $C_{1-12}$ alkyl, $C_{1-12}$ haloalkyl, $C_{2-12}$ alkenyl, $C_{2-12}$ alkynyl, or $C_{3-12}$ cycloalkyl is optionally independently substituted with one to five $R^{100}$ as valency permits;

each $R^{50}$ is independently halo, cyano, nitro, $-OR^{170}$, $-SR^{170}$, $-NR^{170}R^{180}$, $C_{1-12}$ alkyl, $C_{1-12}$ haloalkyl, $C_{2-12}$ alkenyl, or $C_{2-12}$ alkynyl; wherein each $C_{1-12}$ alkyl, $C_{1-12}$ haloalkyl, $C_{2-12}$ alkenyl, or $C_{2-12}$ alkynyl is independently optionally substituted with one to five halo, hydroxyl, or amino as valency permits;

$R^{60}$ is hydrogen, $C_{1-12}$ alkyl, $C_{2-12}$ alkenyl, $C_{2-12}$ alkynyl, or $C_{3-12}$ cycloalkyl, wherein each $C_{1-12}$ alkyl, $C_{2-12}$ alkenyl, $C_{2-12}$ alkynyl, or $C_{3-12}$ cycloalkyl is optionally independently substituted with one to five $R^{100}$ as valency permits;

each $R^{100}$ is independently oxo, halo, cyano, nitro, —$OR^{170}$, —$SR^{170}$, —$SF_5$, —$NR^{170}R^{180}$, $C_{1-12}$ alkyl, $C_{2-12}$ alkenyl, $C_{2-12}$ alkynyl, $C_{3-10}$ cycloalkyl, heterocyclyl, aryl, heteroaryl, —C(=O)$R^{170}$, —C(=O)OR$^{170}$, —OC(=O)OR$^{170}$, —OC(=O)R$^{170}$, —C(=O)NR$^{170}R^{180}$, —OC(=O)NR$^{170}R^{180}$, —NR$^{170}$C(=O)NR$^{170}R^{180}$, —S(=O)$_{1-2}R^{170}$, —S(=O)$_{1-2}$NR$^{170}R^{180}$, —NR$^{170}$S(=O)$_{1-2}R^{180}$, —NR$^{170}$S(=O)$_{1-2}$NR$^{170}R^{180}$, —NR$^{170}$C(=O)R$^{180}$, —NR$^{170}$C(=O)OR$^{180}$ or —C=NOR$^{170}$, wherein each $C_{1-12}$ alkyl, $C_{2-12}$ alkenyl, $C_{2-12}$ alkynyl, $C_{3-10}$ cycloalkyl, heterocyclyl, aryl, and heteroaryl of $R^{100}$ are independently optionally substituted with one or more halo or $C_{1-12}$ alkyl optionally substituted by oxo, halo, hydroxyl or amino as valency permits;

each $R^{170}$ and $R^{180}$ is independently hydrogen or $C_{1-12}$ alkyl optionally substituted with oxo, halo, hydroxyl, or amino as valency permits; or $R^{170}$ and $R^{180}$ are taken together with the atoms to which they are attached to form heterocyclyl optionally substituted by halo or $C_{1-12}$ alkyl optionally substituted by oxo, halo, hydroxyl or amino;

A″ and A‴ are each independently O or S;

$R^a$ and $R^b$ are each independently $CH_3$ or $CH_2CH_3$; or $R^a$ and $R^b$ together with the atom to which they are attached form a $C_{3-5}$ cycloalkyl, oxirane, oxetane or tetrahydrofuran;

B, $B^{10}$, $B^2$, $B^3$, B′, B″, $B^{2'}$ and $B^{3'}$ are each independently $CR^c$ or N;

each $R^c$ is independently hydrogen, fluoro, CN, or methyl;

D″ is NH, O, S, $CH_2$ or C=O;

X″ is CN, halo, or $NO_2$;

Y″ is $CH_3$, $CH_2R^d$, $CHF_2$, or $CF_3$;

$R^d$ is halo;

Z″ is H, $C_{1-2}$ alkyl, $C_2$ alkenyl or $NO_2$; or

X″ and Y″ together form a

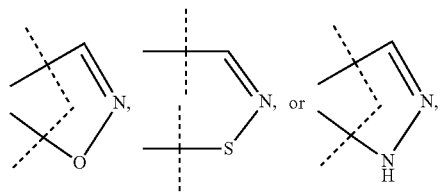

where the broken lines indicate bonds to form a fused ring; or Y″ and Z″ together form a

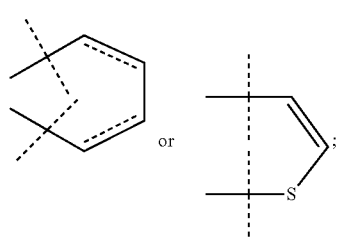

where === is a single or double bond and where the broken lines indicate bonds to form a fused ring;

Z′ is CH or N.

15. The compound of claim 1, or a tautomer, stereoisomer, mixture of stereoisomers, or pharmaceutically acceptable salt thereof, wherein $R^1$ is:

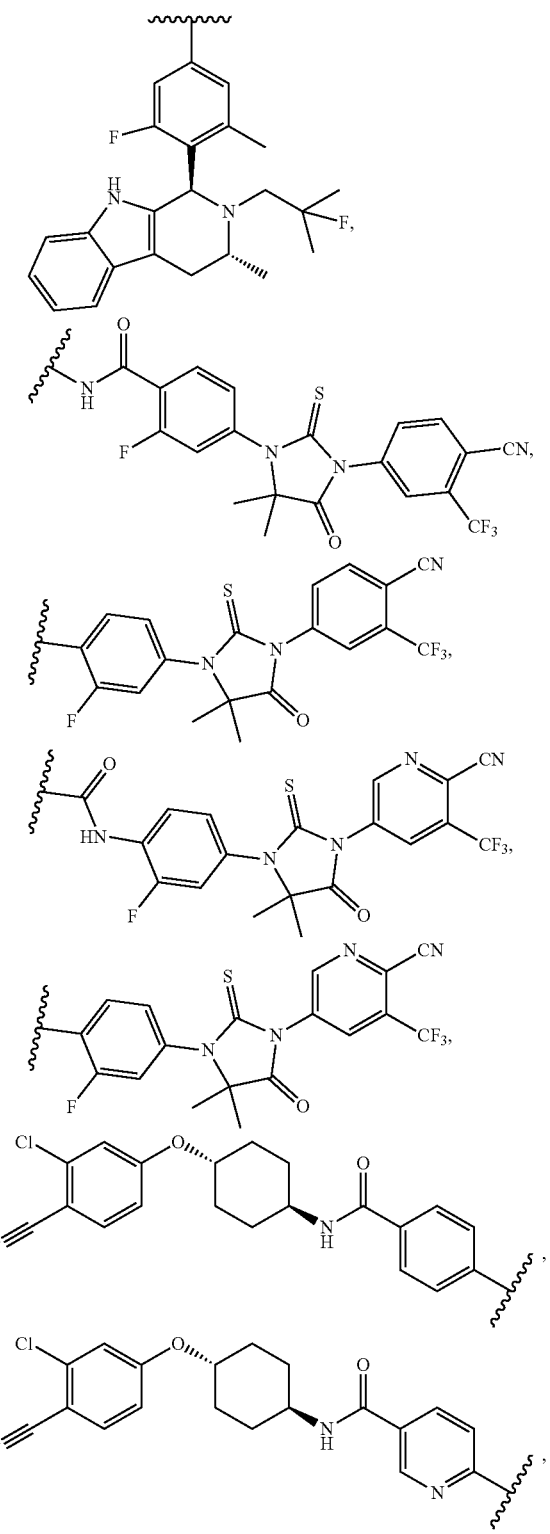

277
-continued
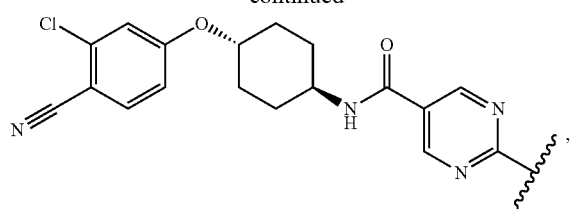,
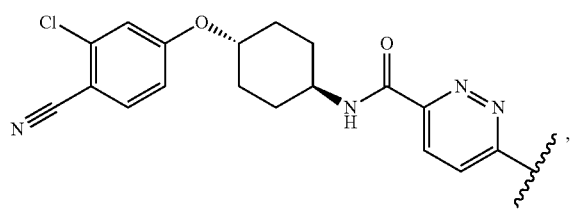,
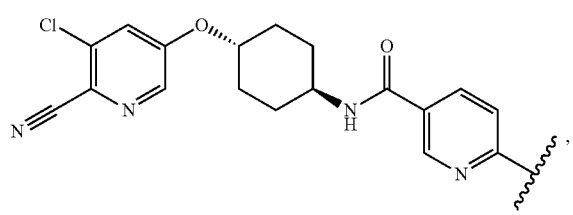,
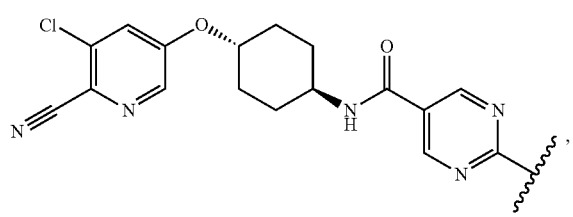,
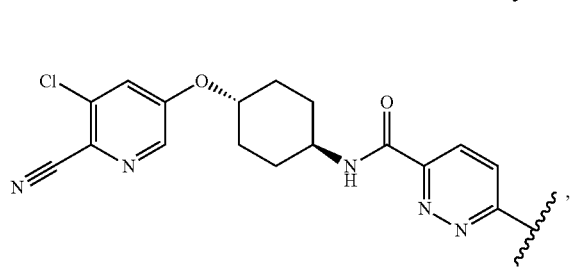,
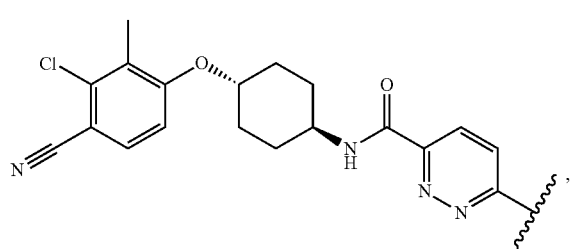,
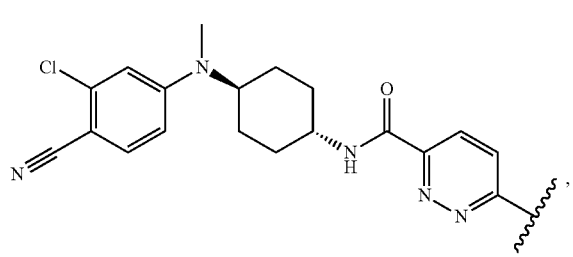,
278
-continued
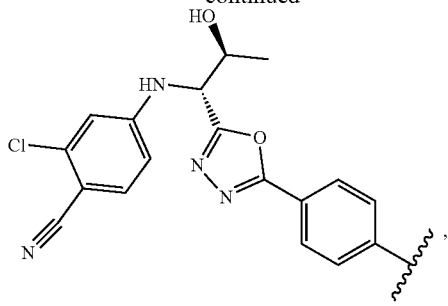,
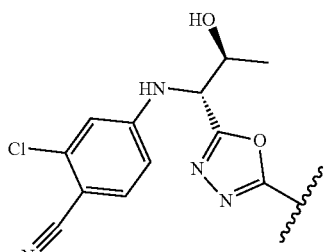,
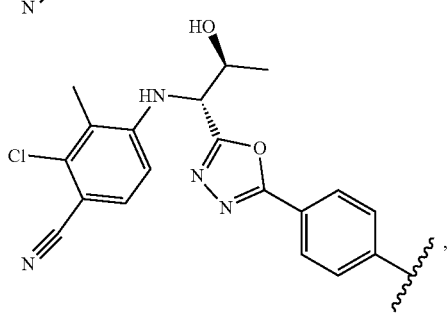,
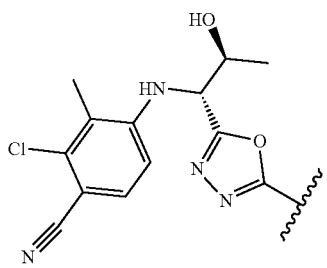,
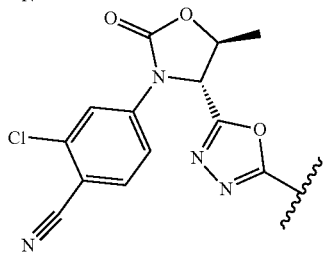, or
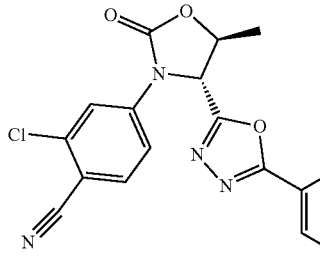,
wherein the wavy bond refers to the point of connection to L.

16. A compound selected from the group consisting of:
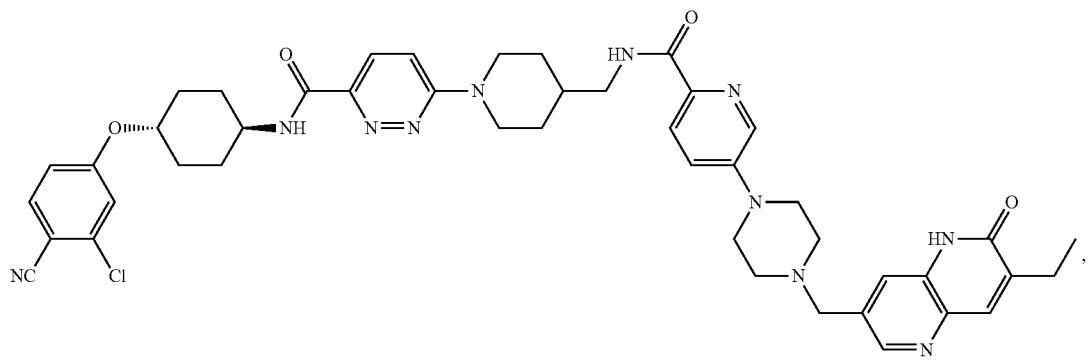
1
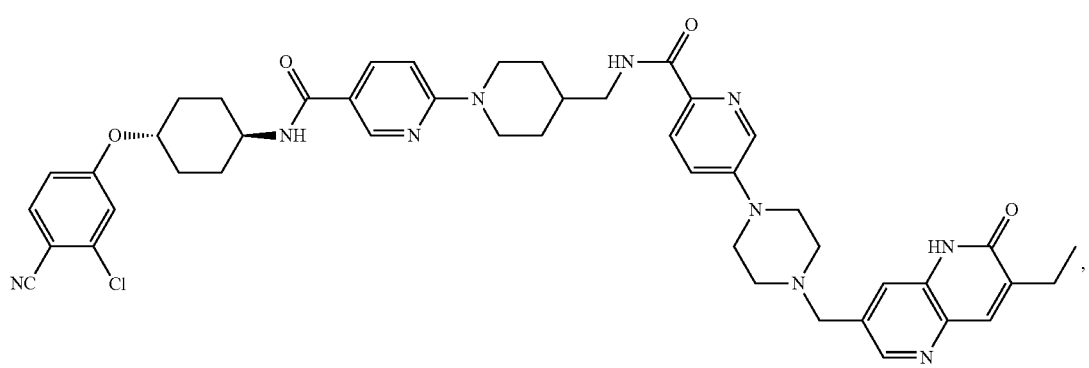
2
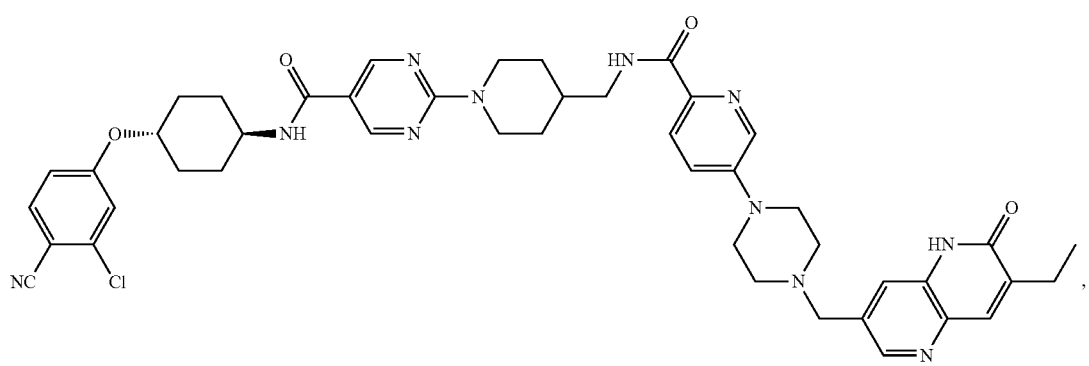
3
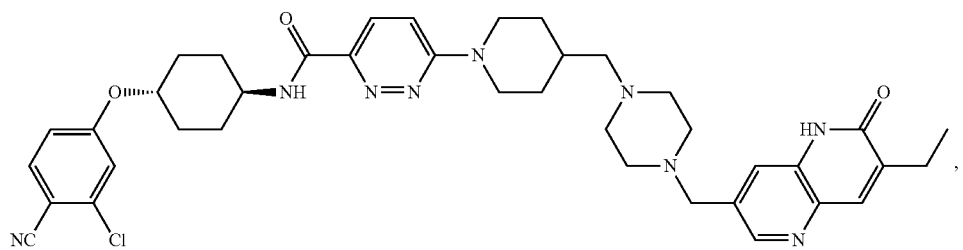
4
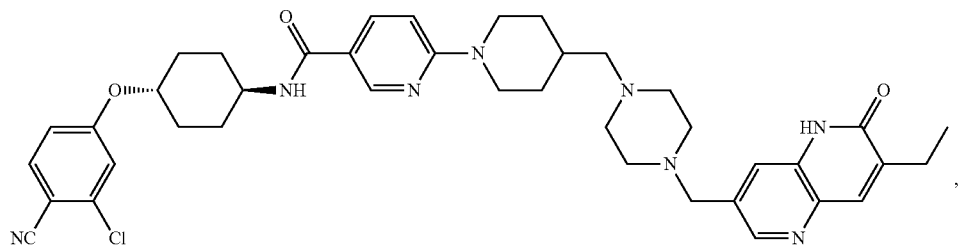
5

-continued
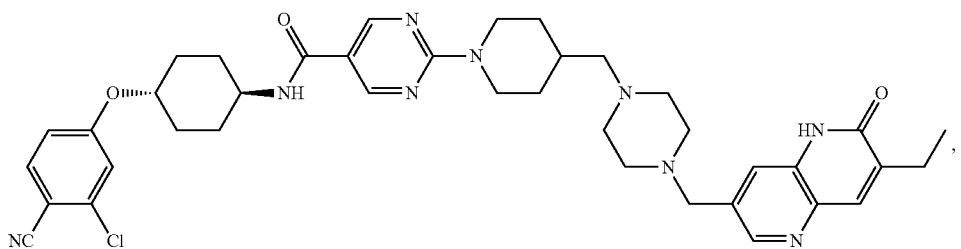
6
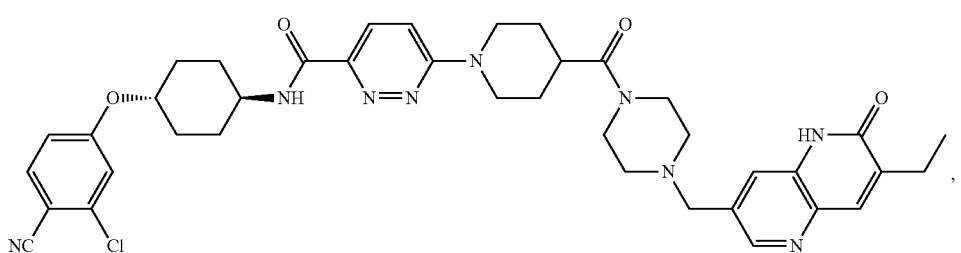
7
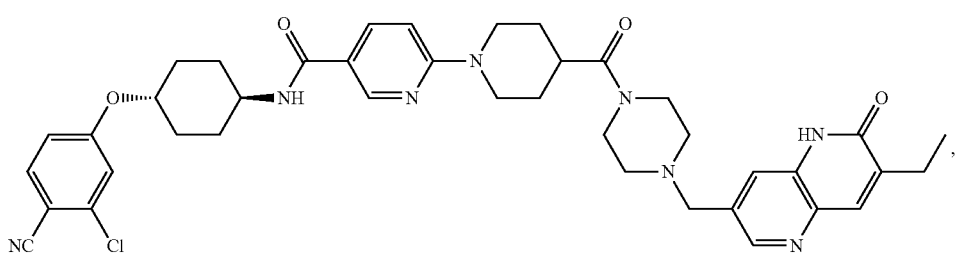
8
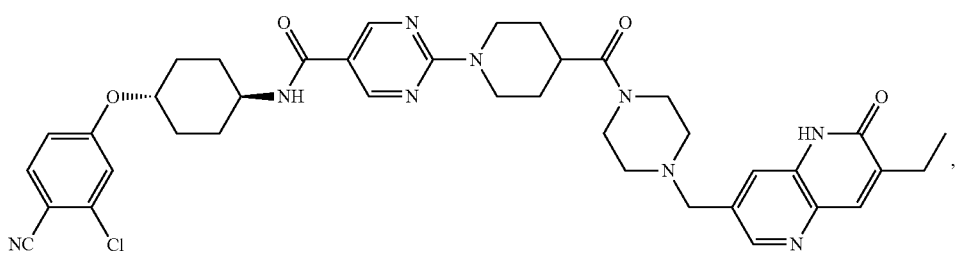
9
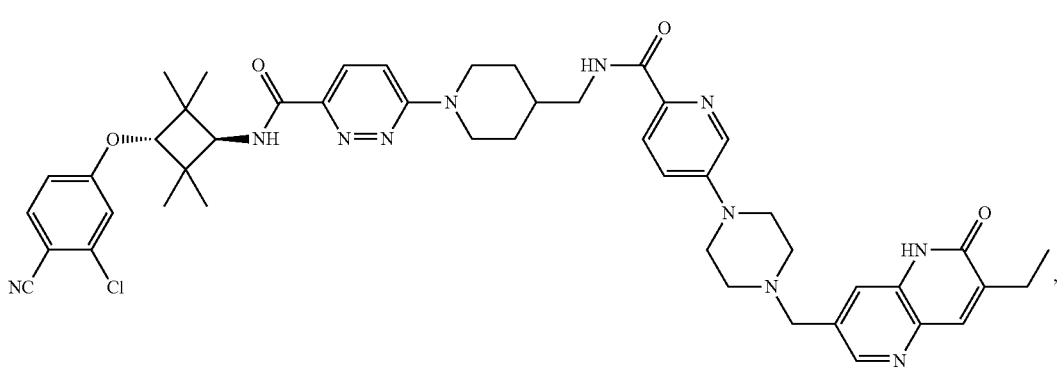
10

-continued
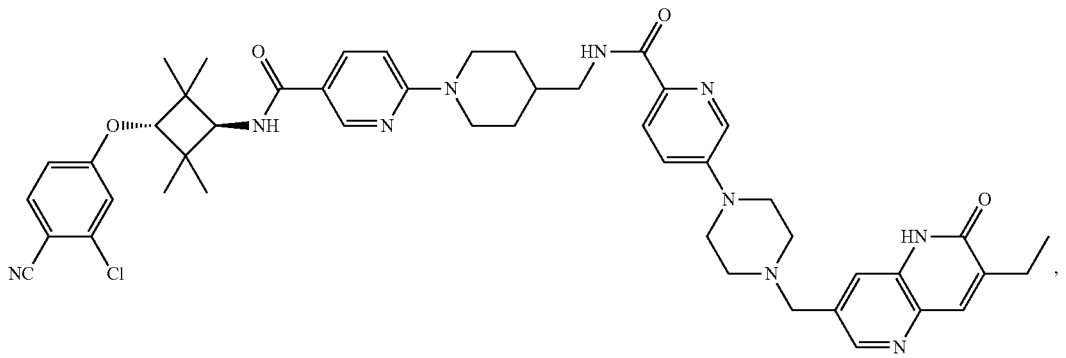
11
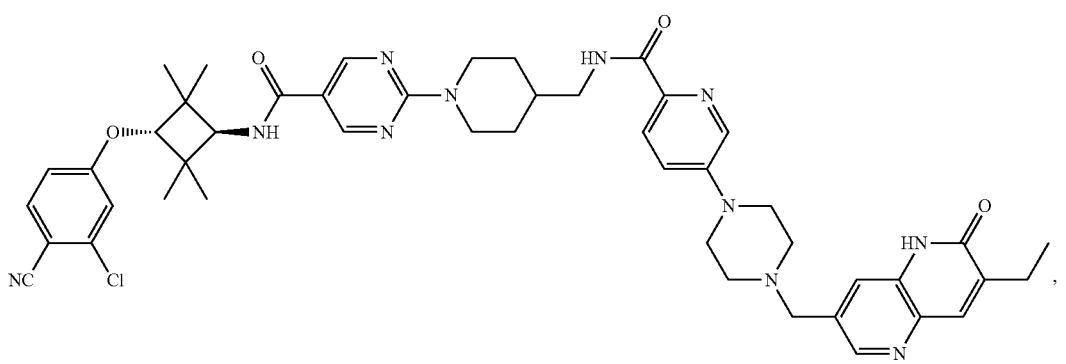
12
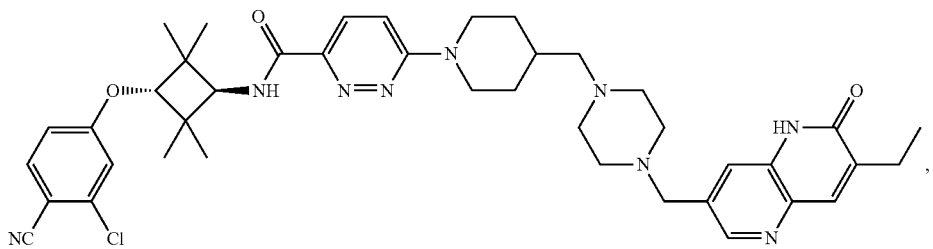
13
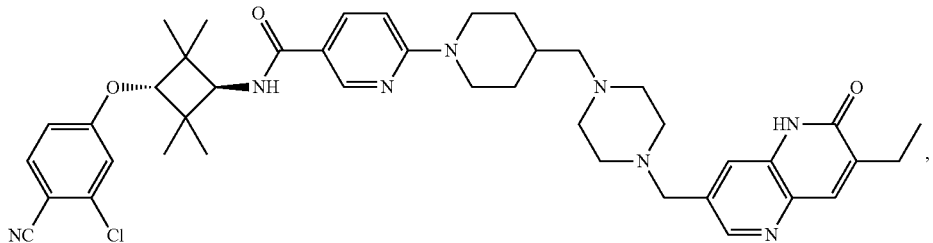
14
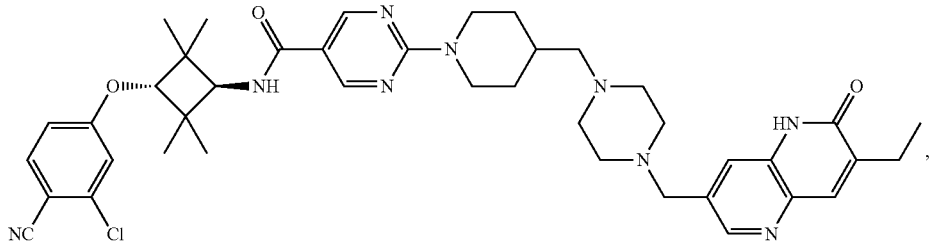
15

-continued
16
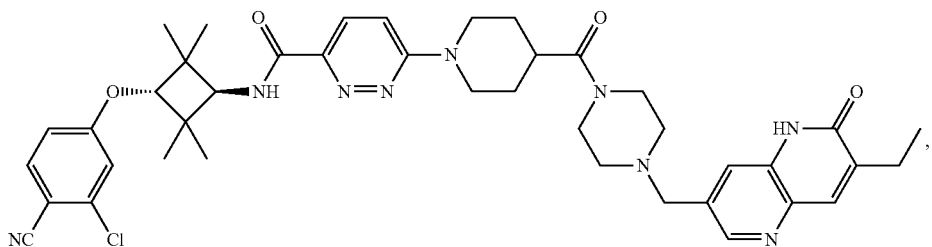
17
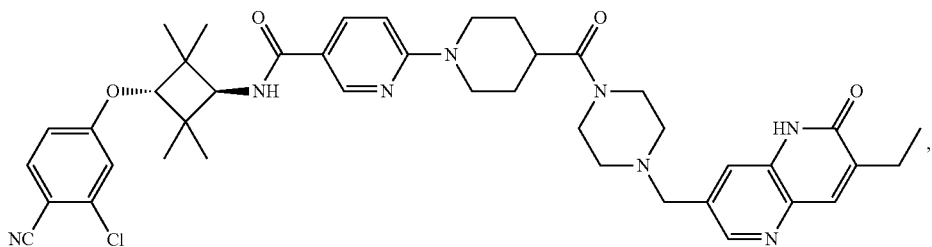
18
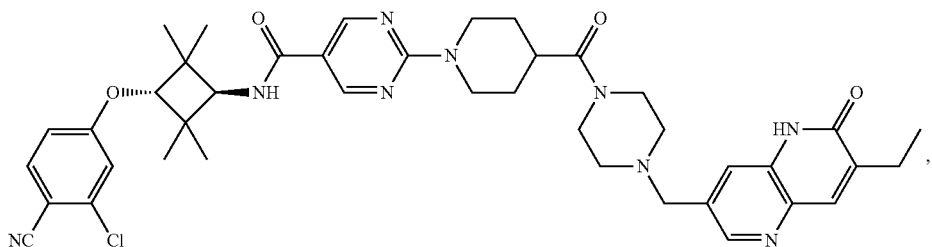
19
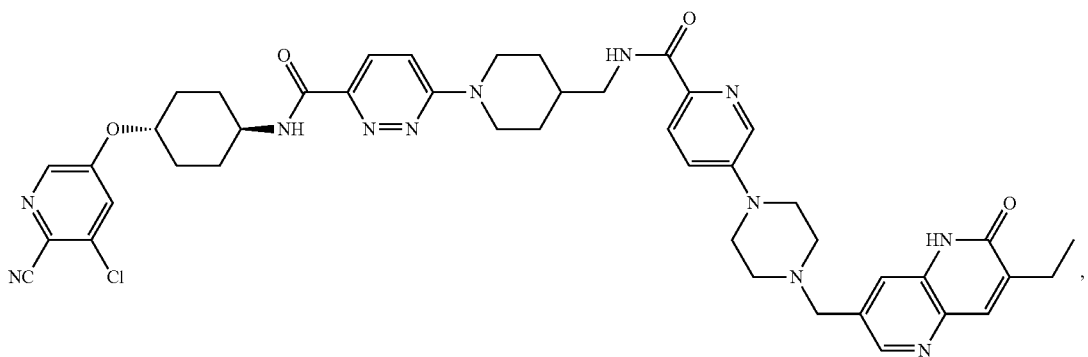
20
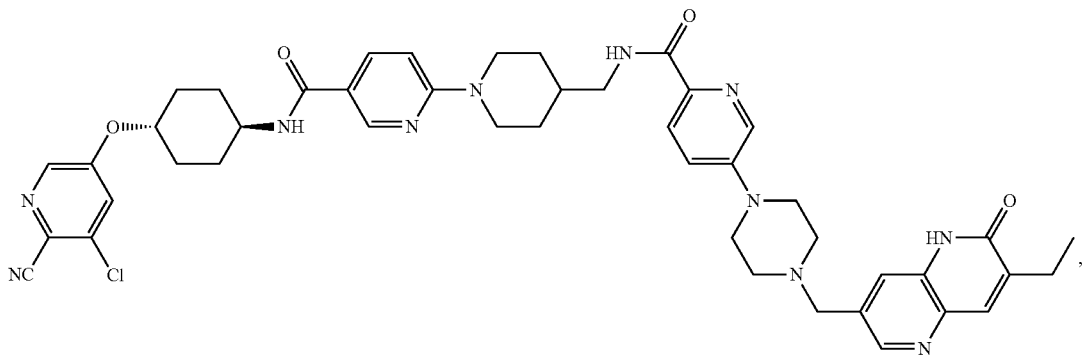

21
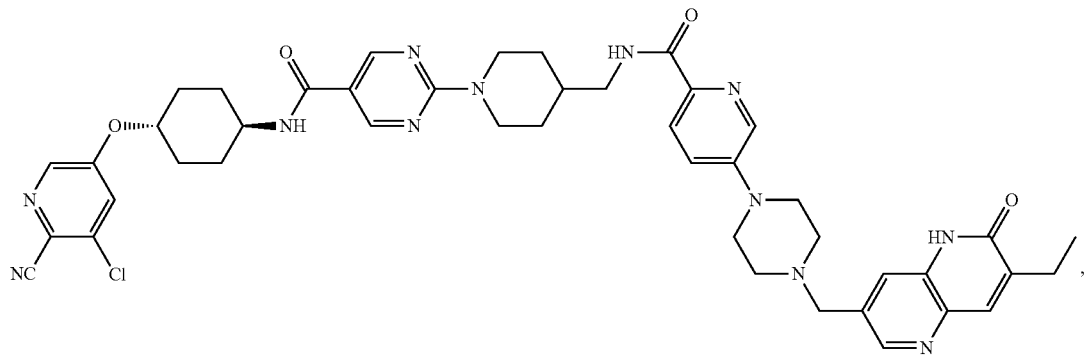
22
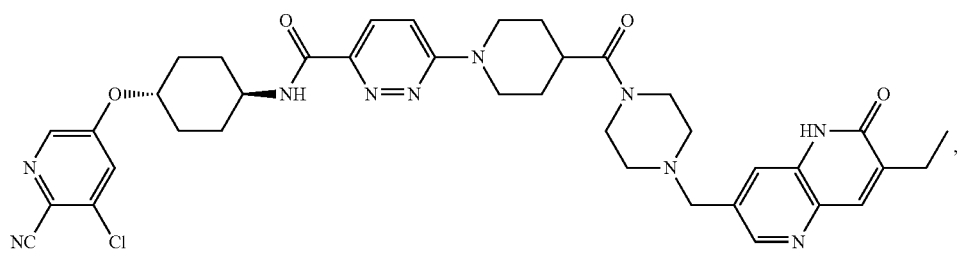
23
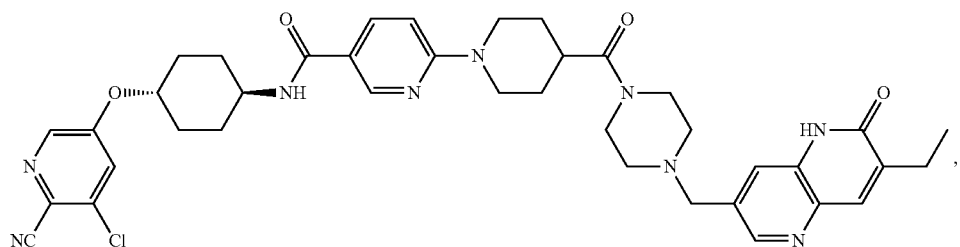
24
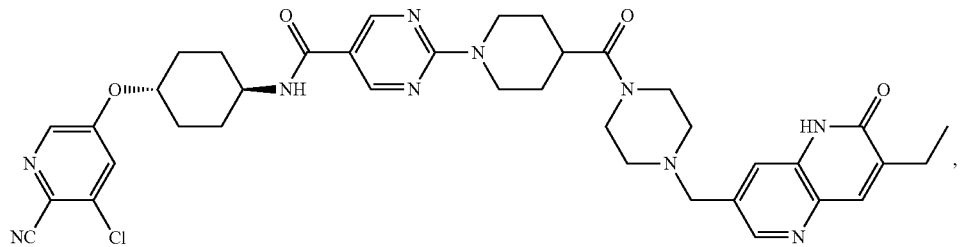
25
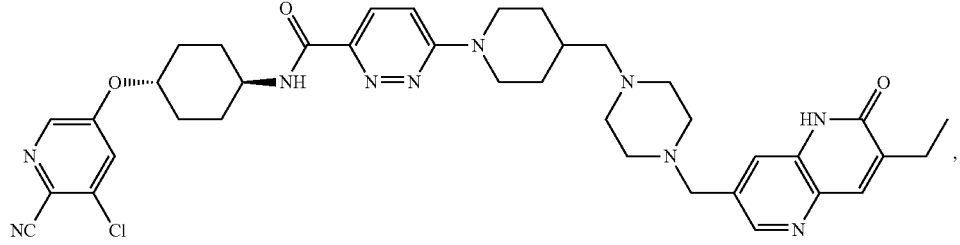
26
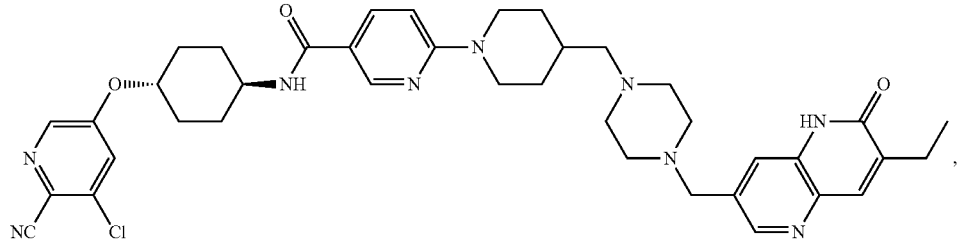

27
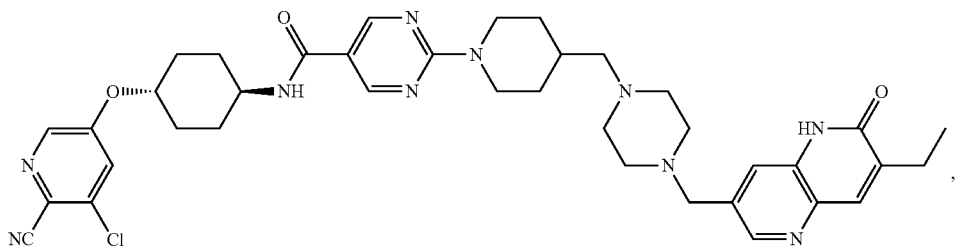
28
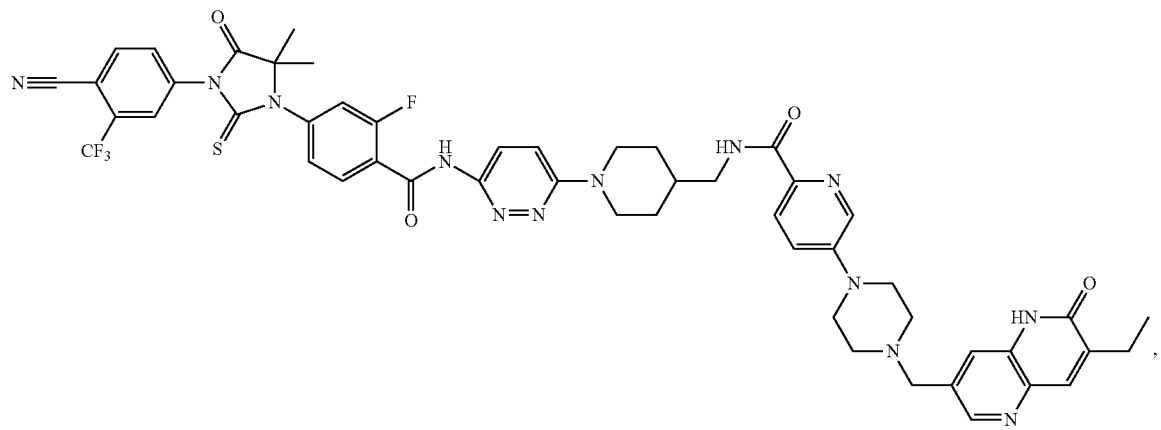
29
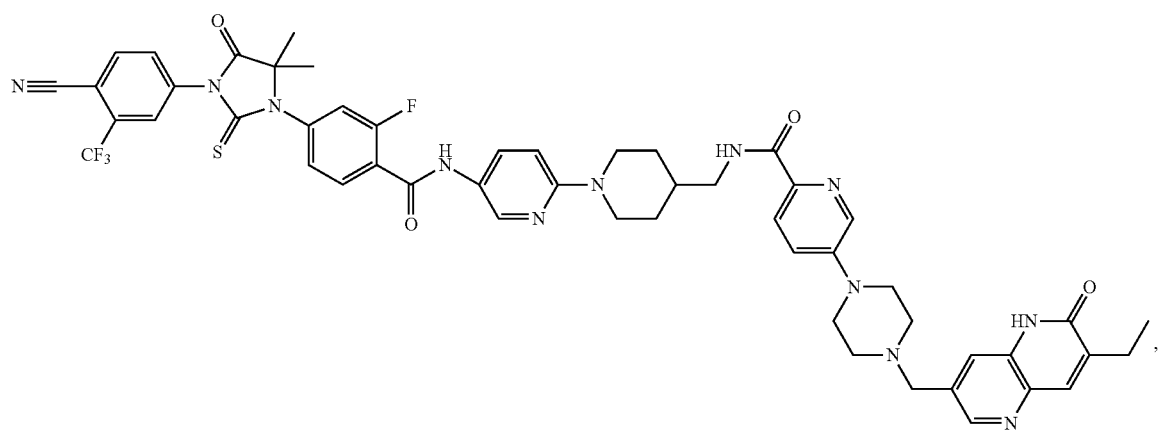
30
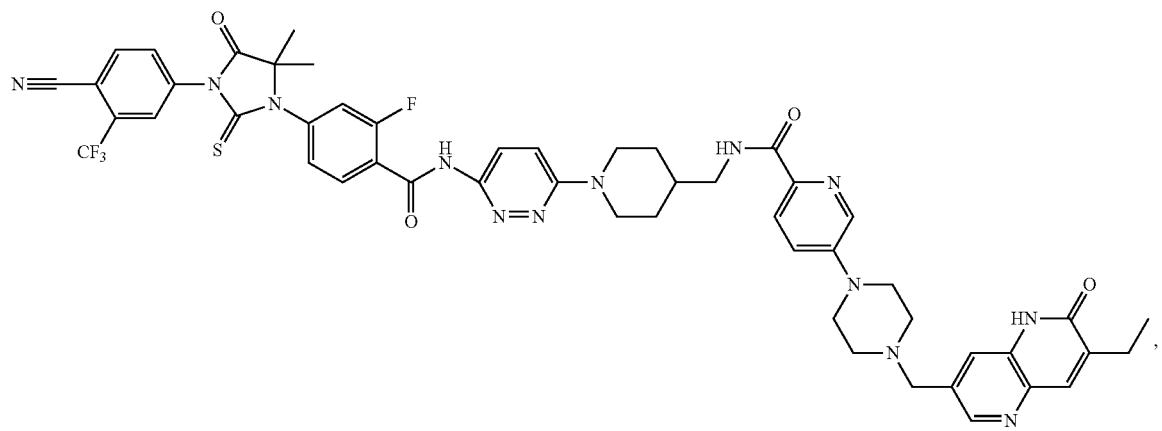

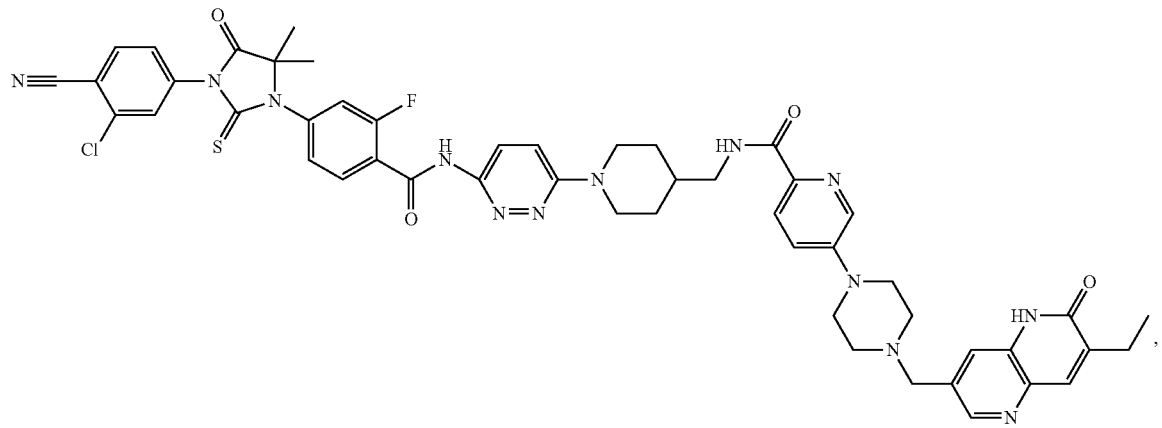
31
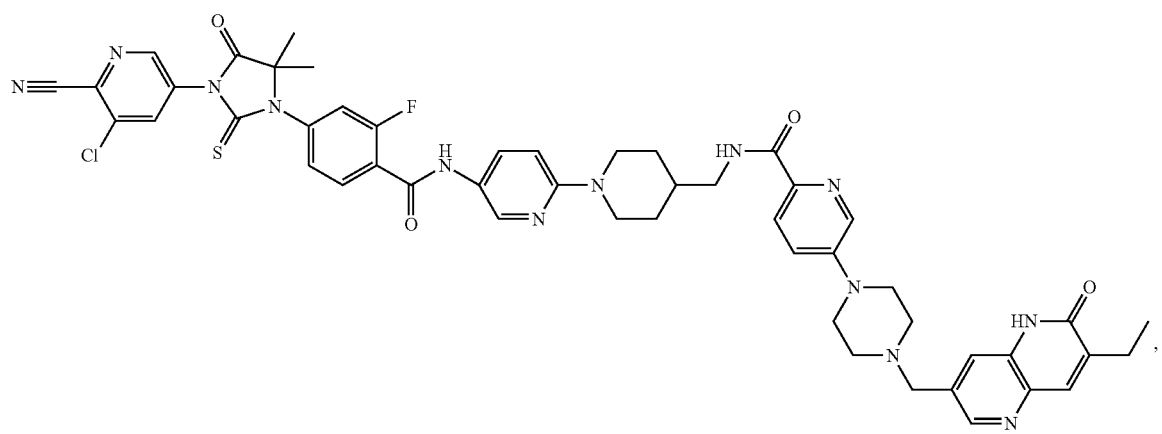
32
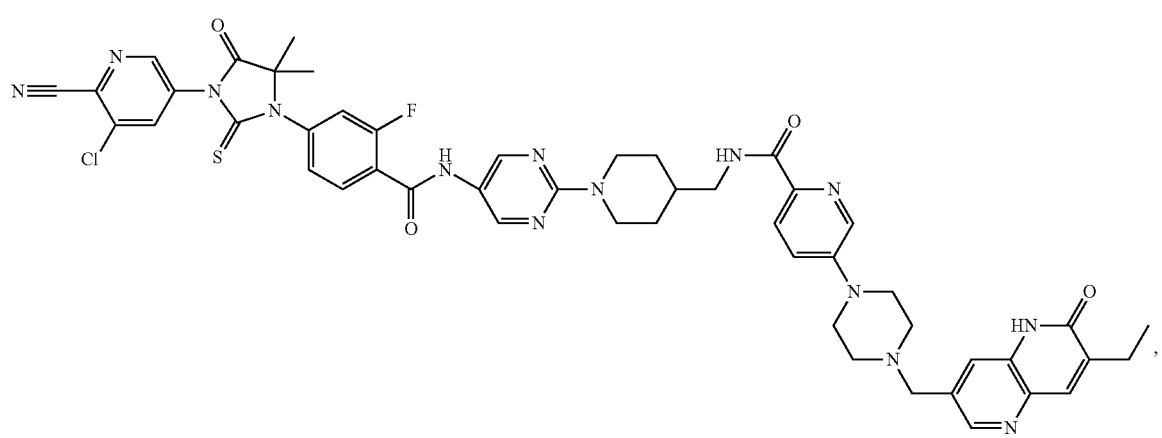
33
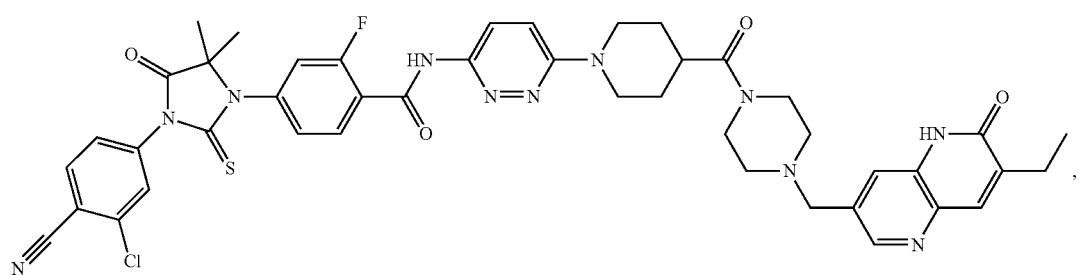
34

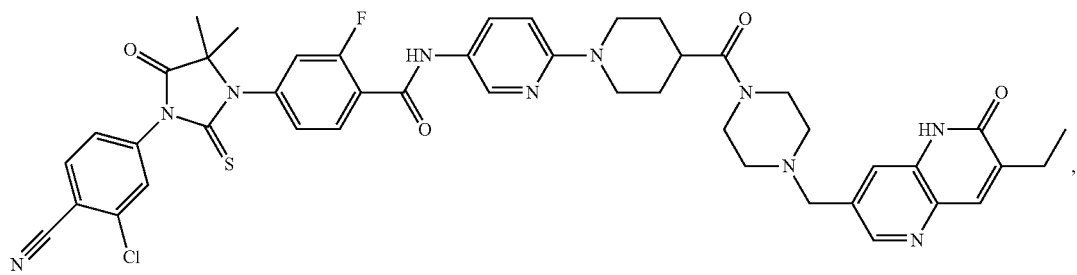
35
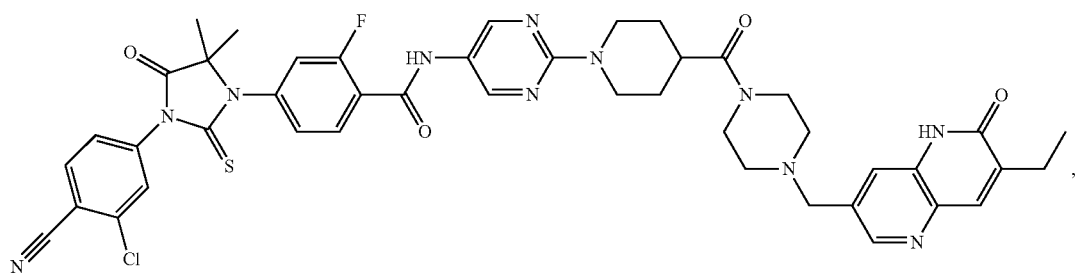
36
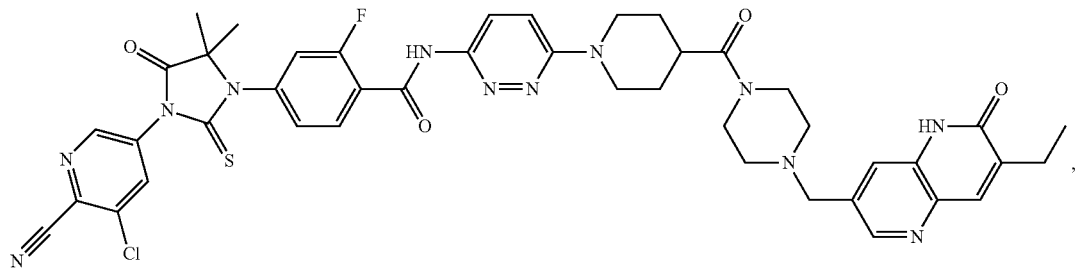
37
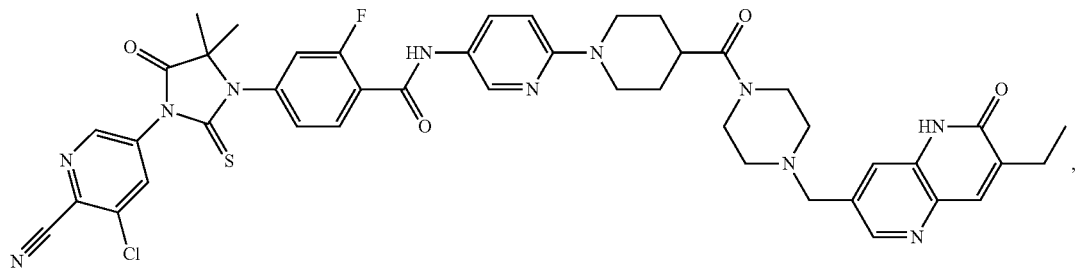
38
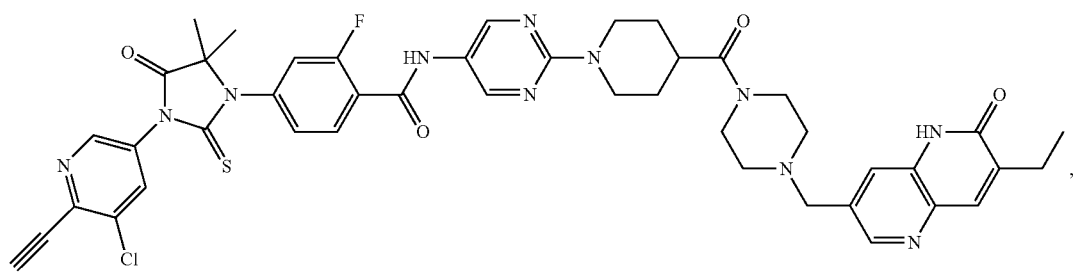
39

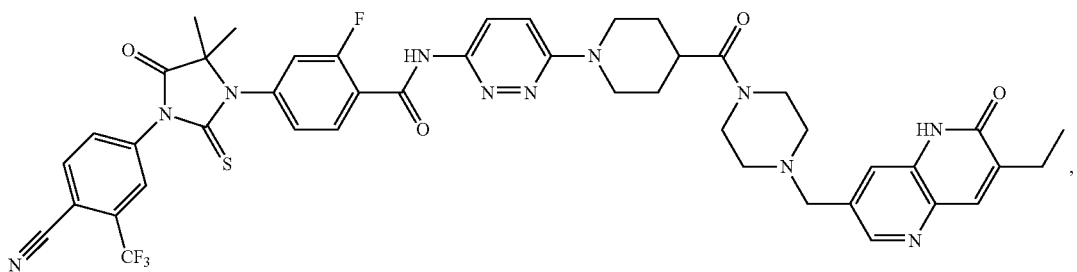
40
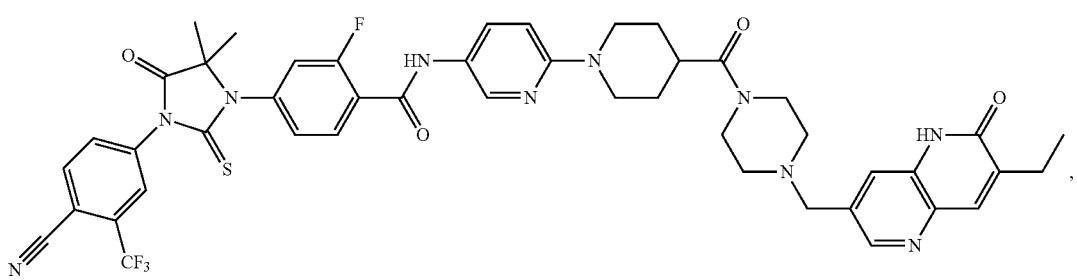
41
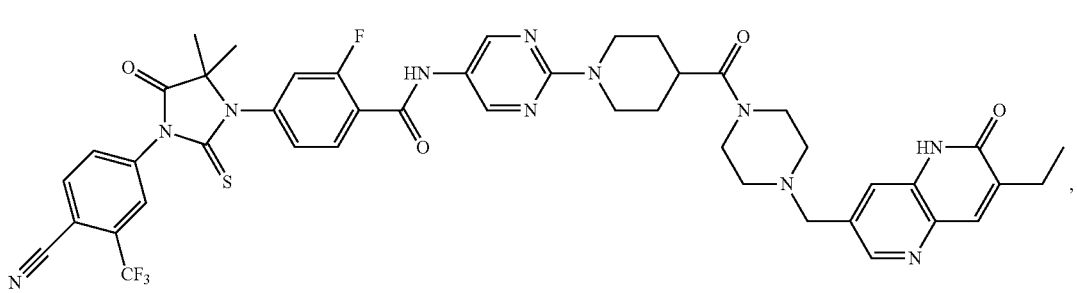
42
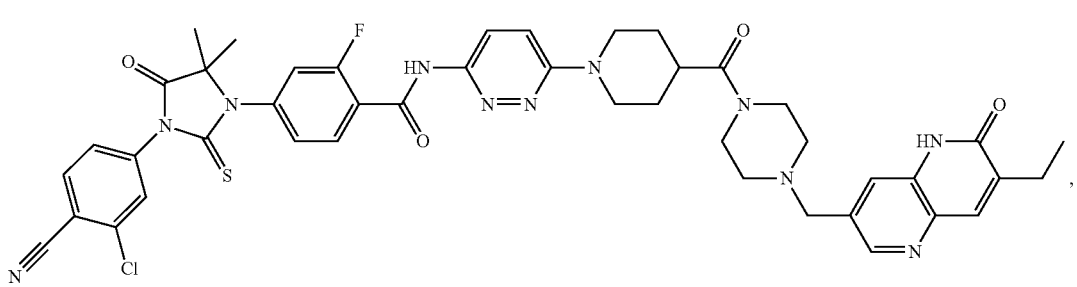
43
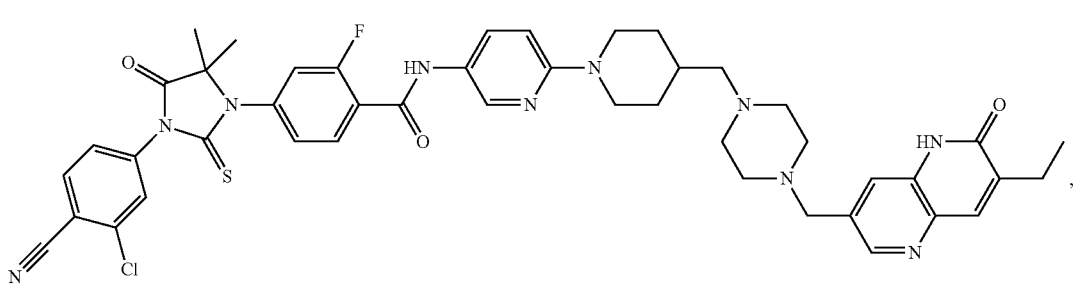
44

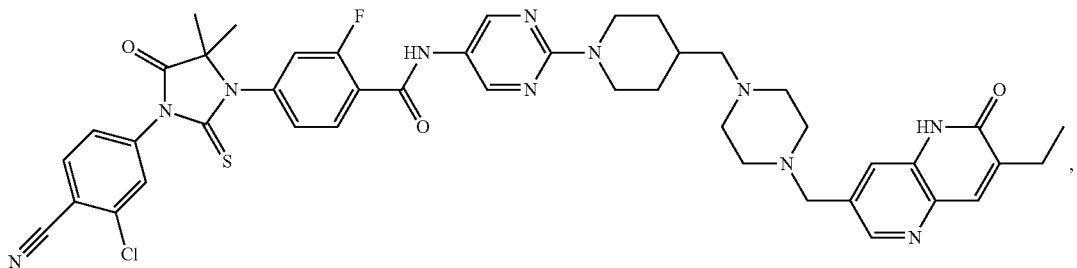
45
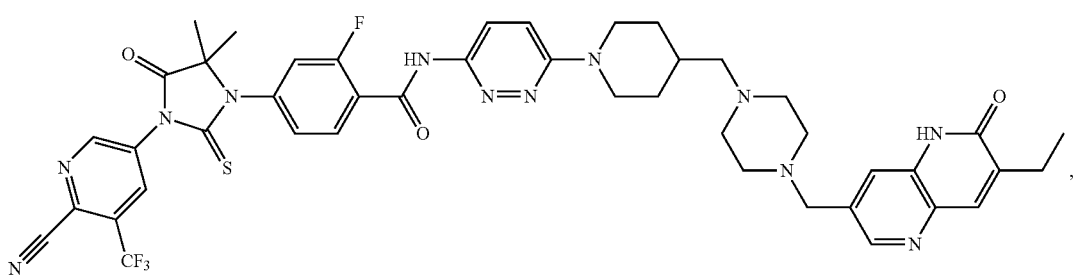
46
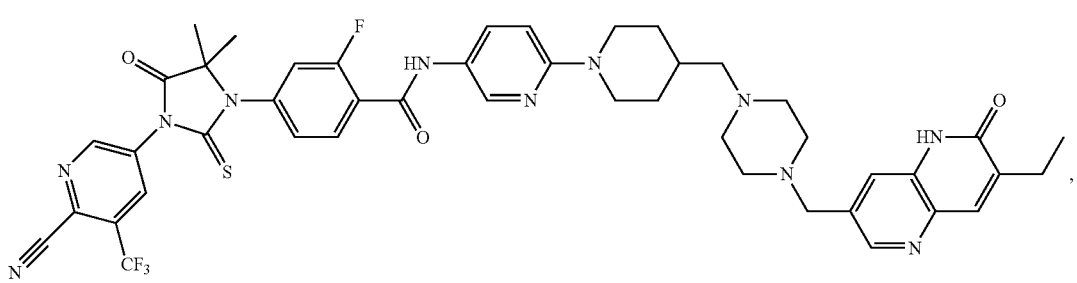
47
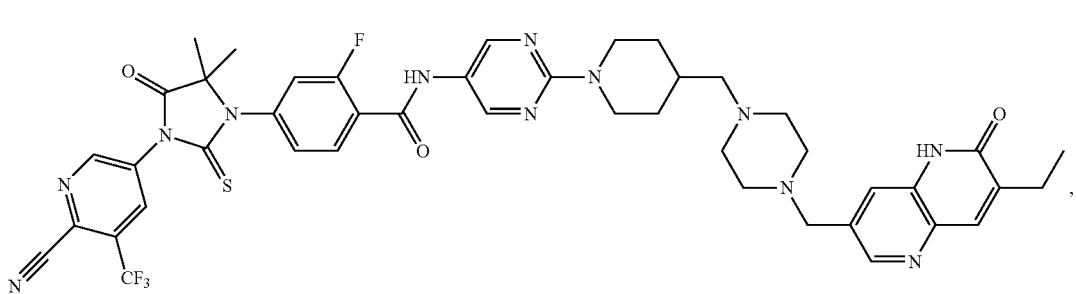
48
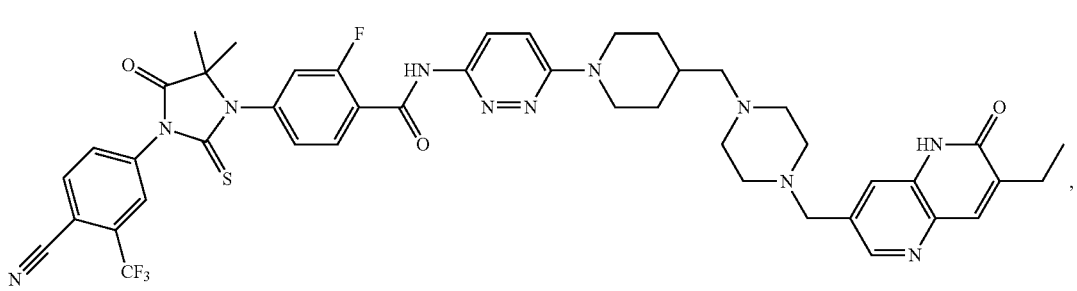
49

-continued
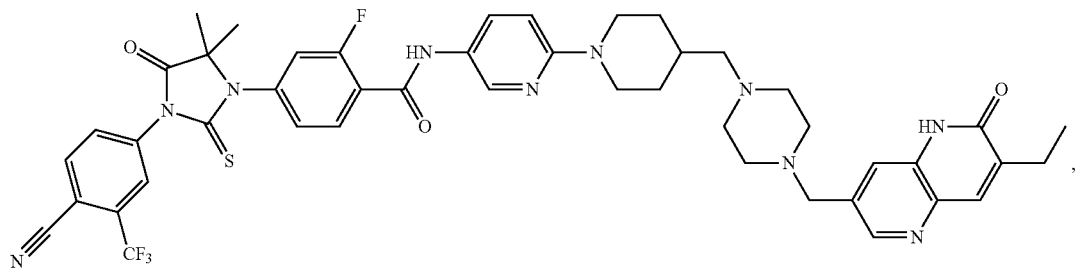 50
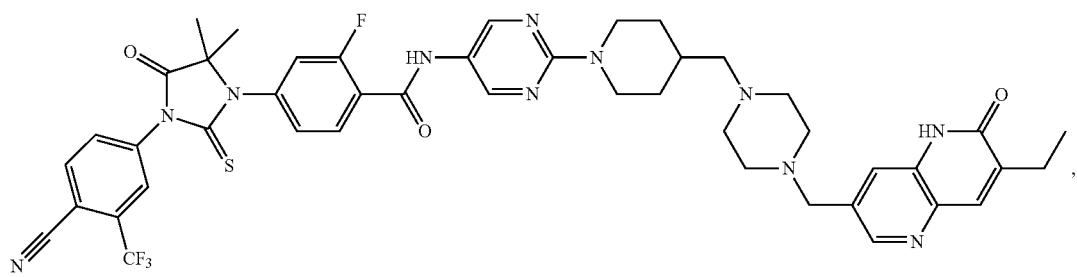 51
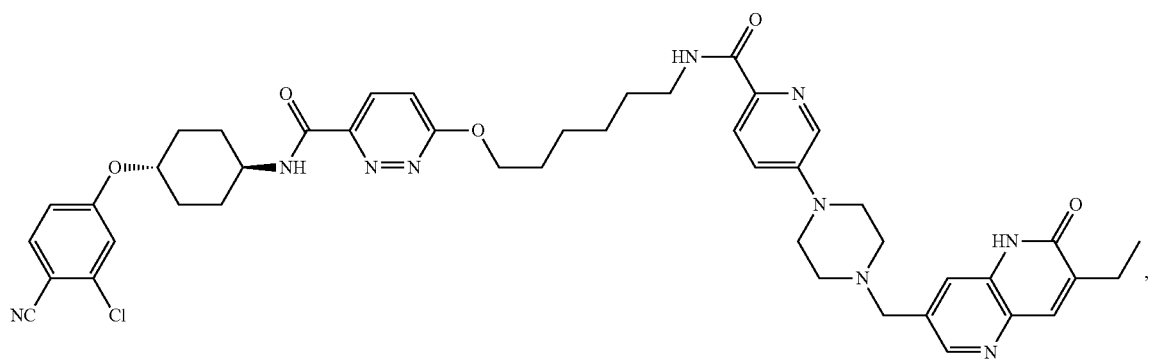 52
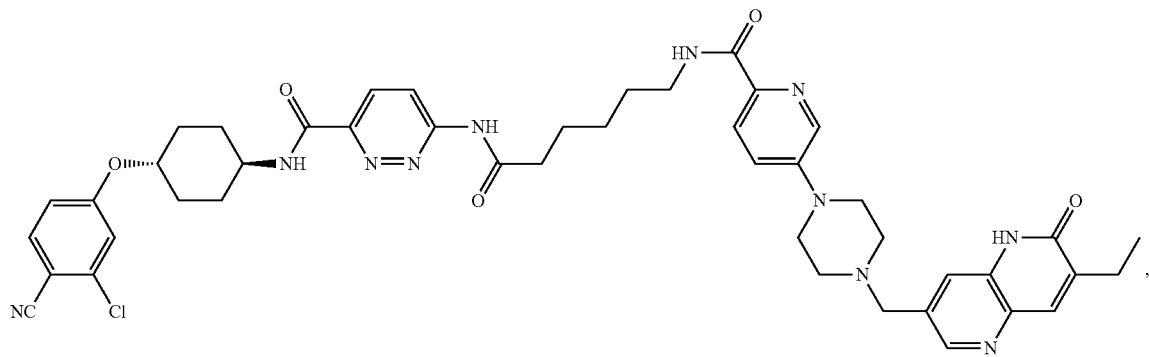 53

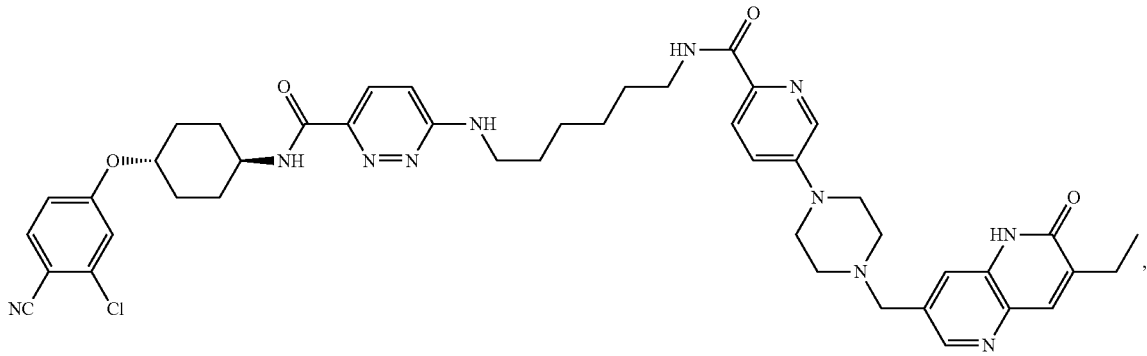
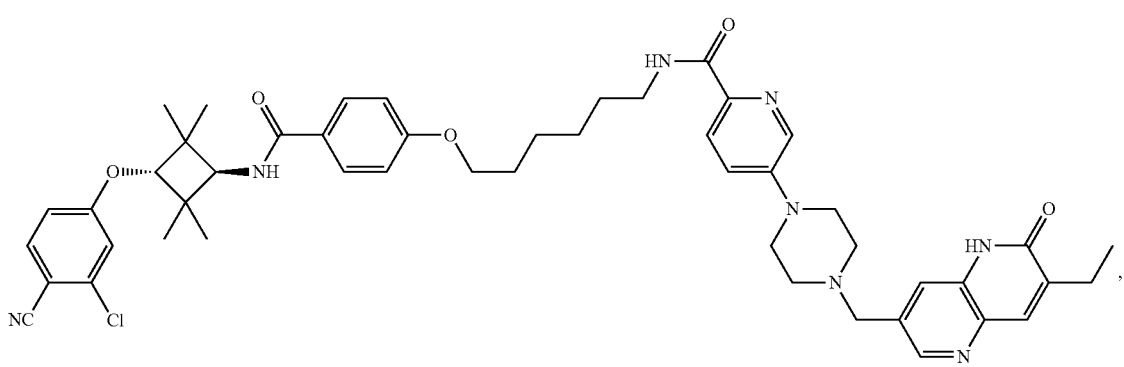
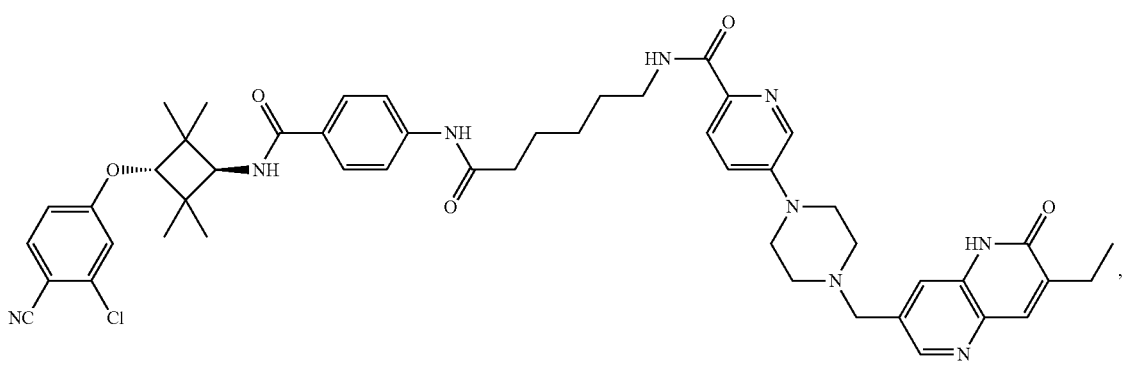
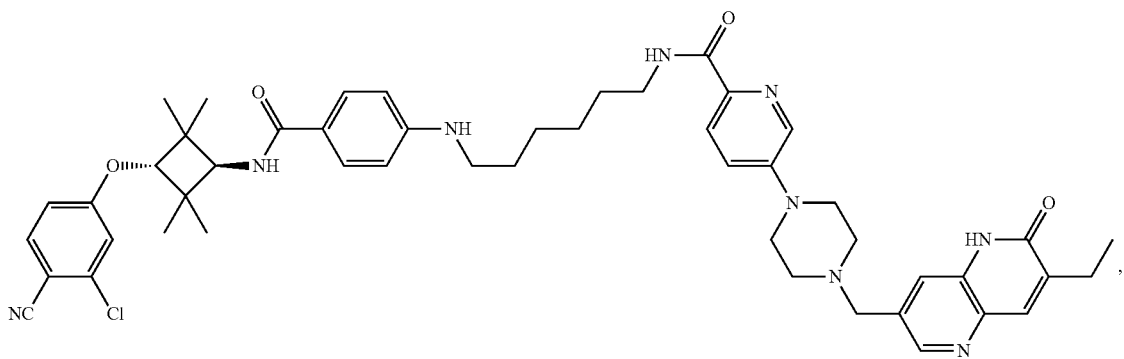

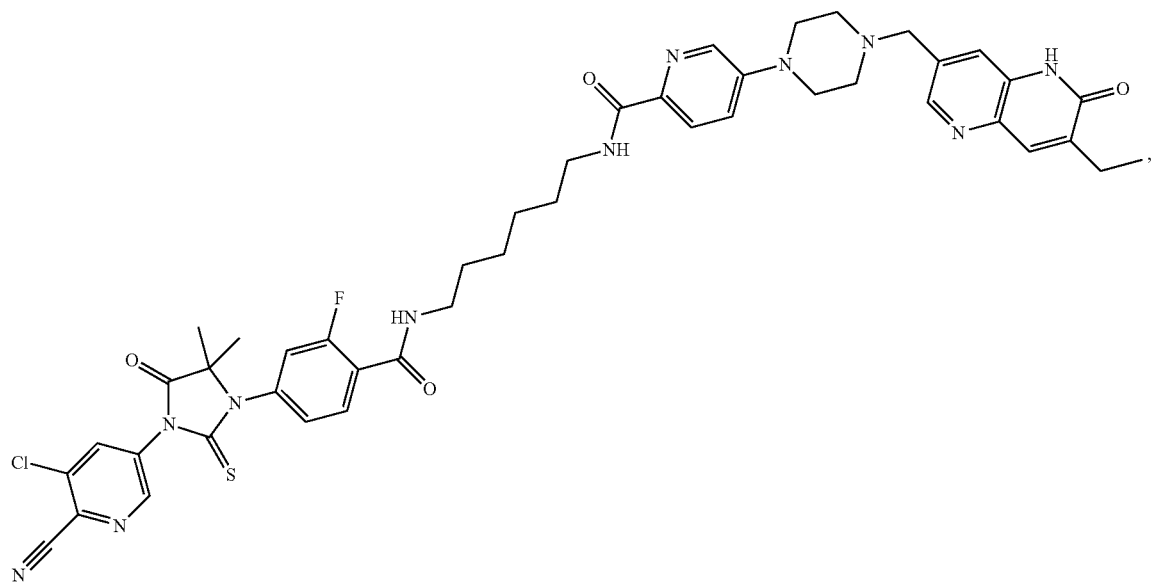
58
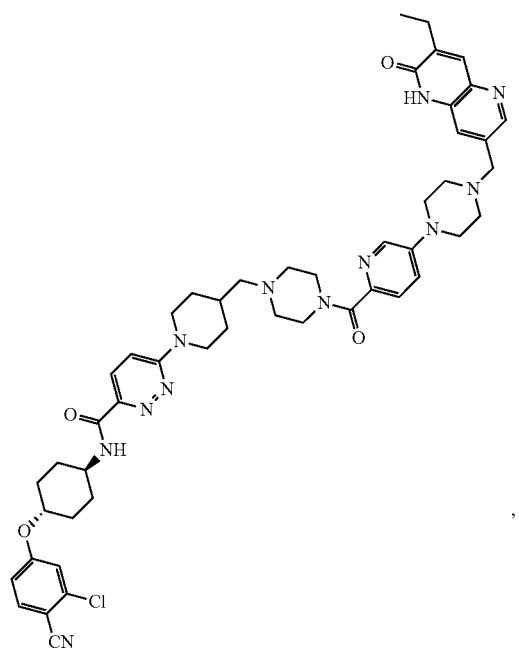
59
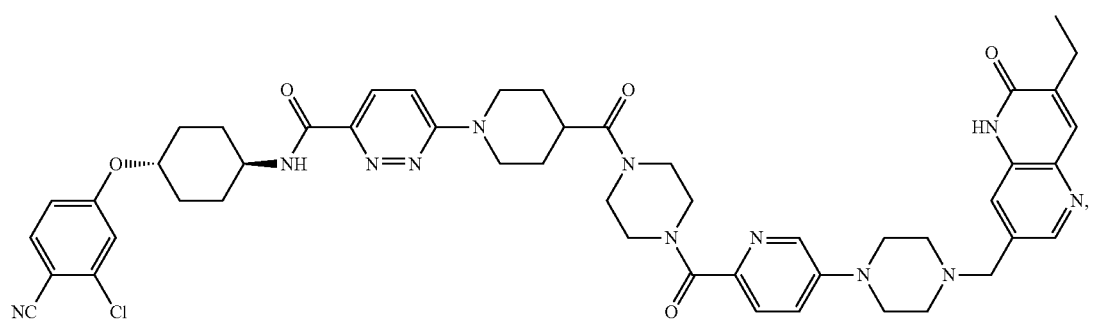
60

61
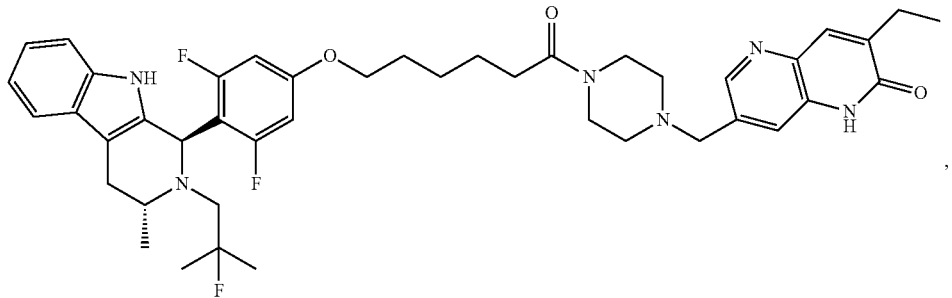
62
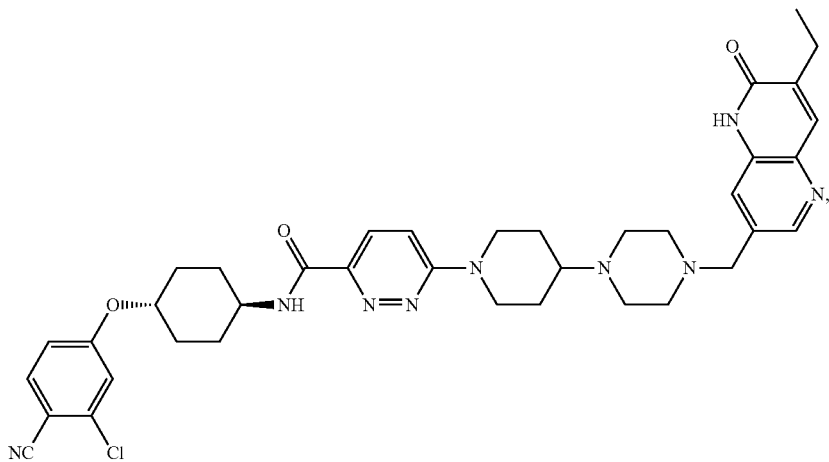
63
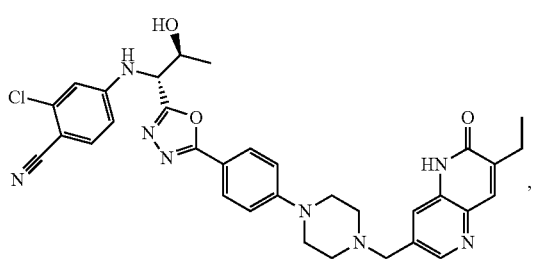
64
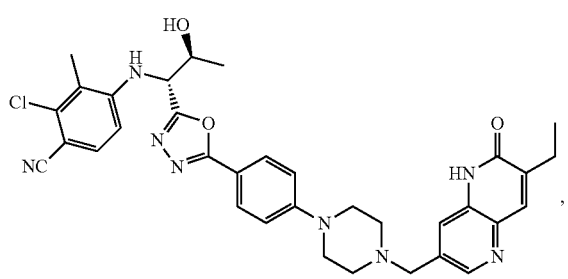
65
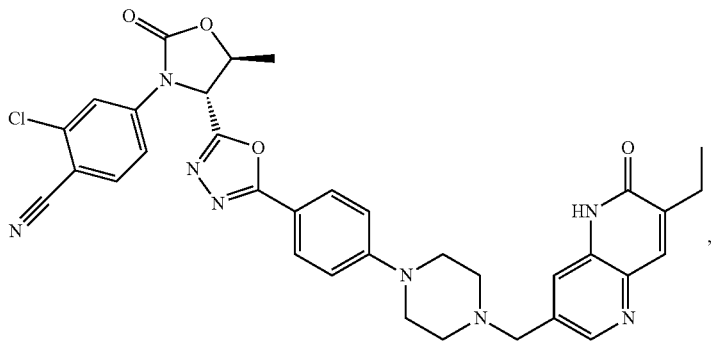

66
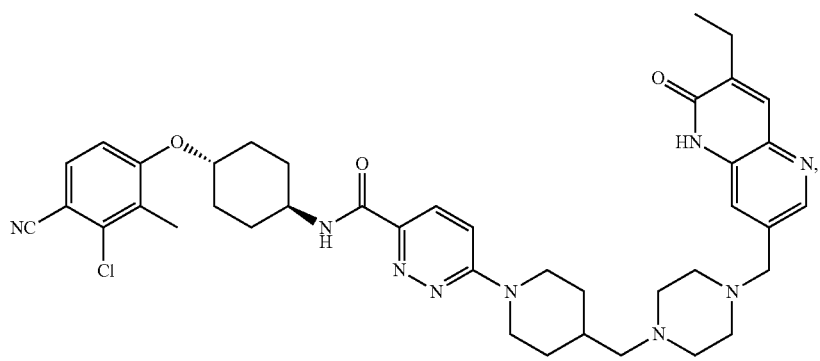
67
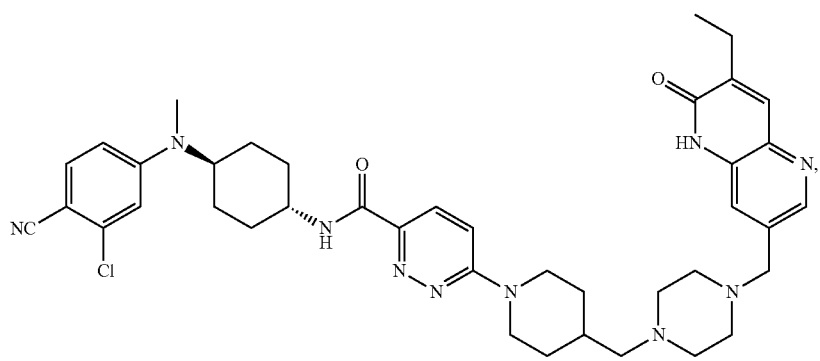
68
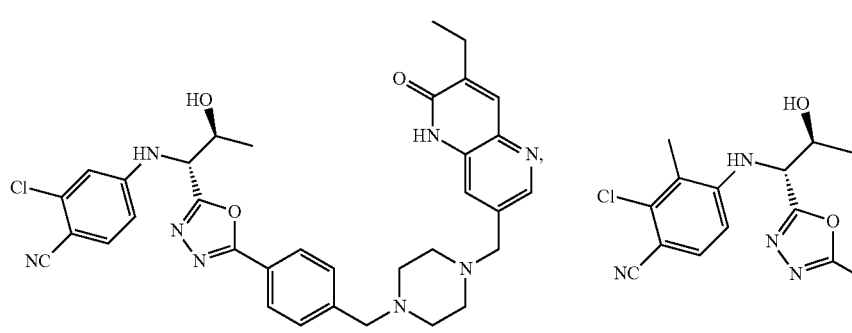
69
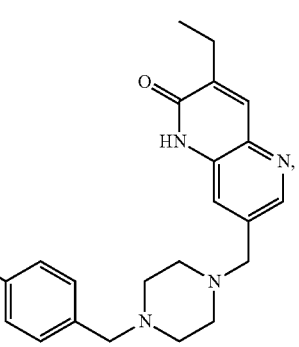
70
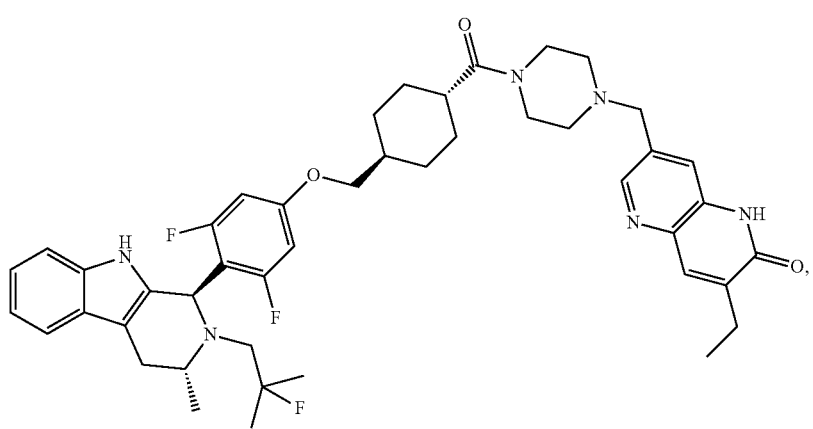

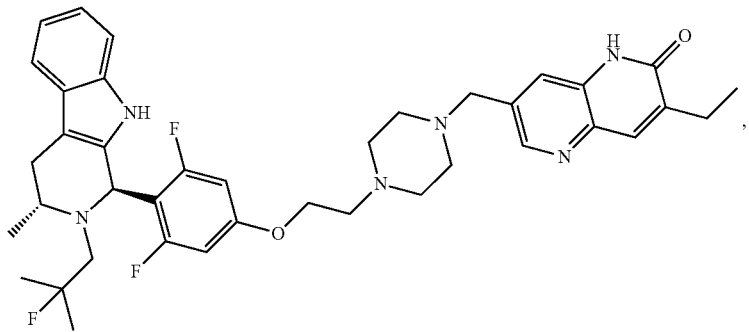
71
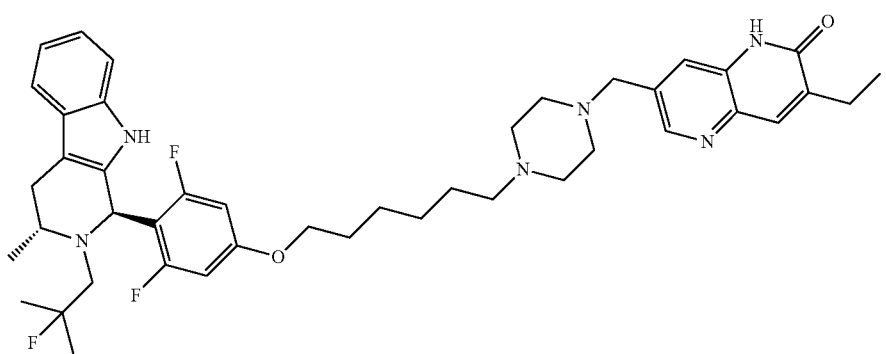
72
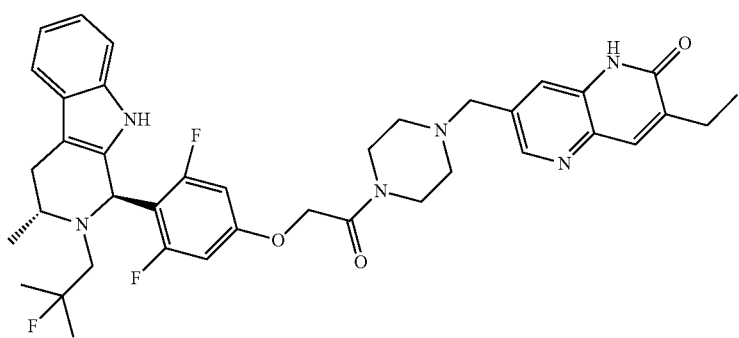
73
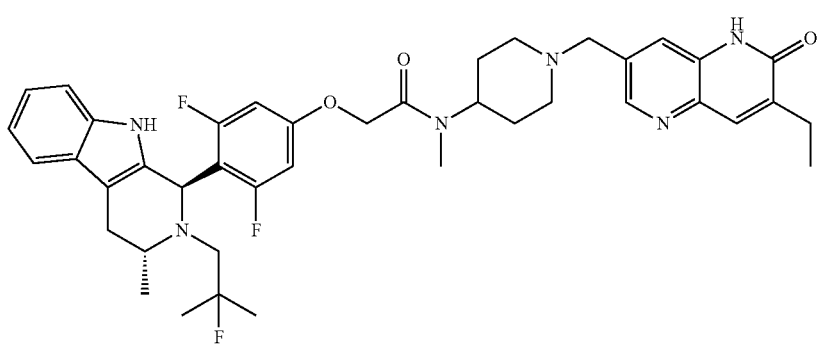
74

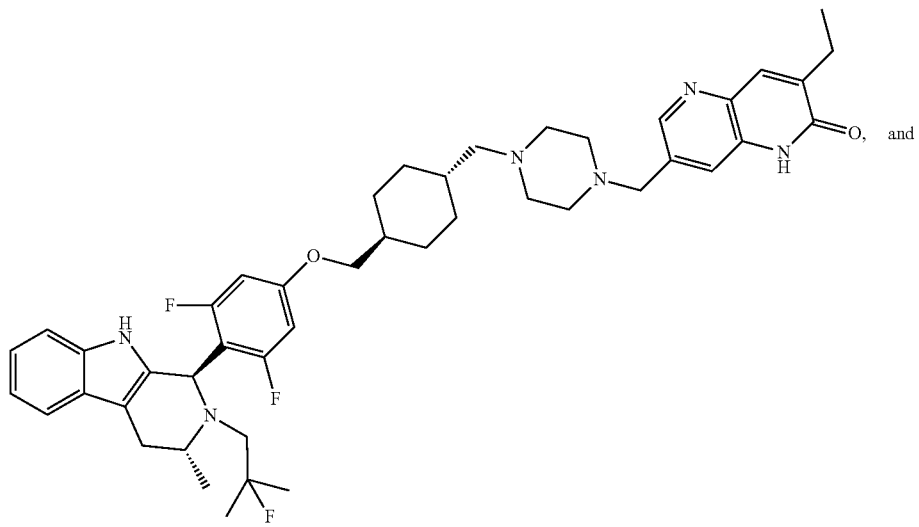
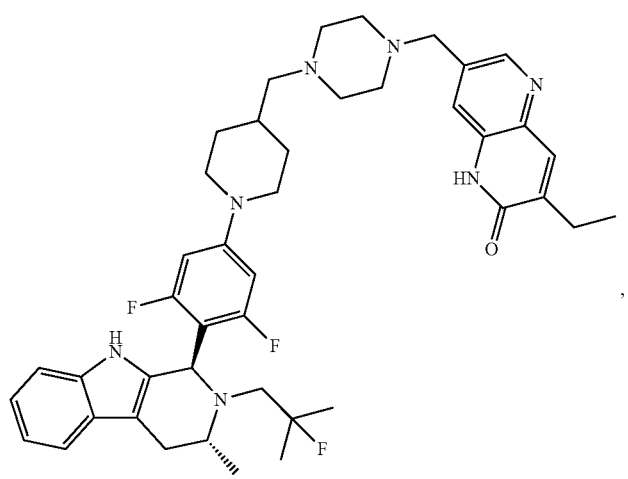
or a pharmaceutically acceptable salt thereof.
17. A pharmaceutical composition comprising a compound as in claim 1, or a tautomer, stereoisomer, mixture of stereoisomers, or pharmaceutically acceptable salt thereof, and a pharmaceutically acceptable excipient.
* * * * *